US012516350B2

(12) United States Patent
Tagliatela et al.

(10) Patent No.: US 12,516,350 B2
(45) Date of Patent: Jan. 6, 2026

(54) COMPOSITIONS AND METHODS FOR SELECTIVE GENE REGULATION

(71) Applicant: Encoded Therapeutics, Inc., South San Francisco, CA (US)

(72) Inventors: Stephanie Tagliatela, San Francisco, CA (US); Anne Tanenhaus, Brisbane, CA (US); Kartik Ramamoorthi, San Francisco, CA (US); Andrew Young, Redwood City, CA (US); David Oberkofler, San Francisco, CA (US)

(73) Assignee: Encoded Therapeutics, Inc., South San Francisco, CA (US)

( * ) Notice: Subject to any disclaimer, the term of this patent is extended or adjusted under 35 U.S.C. 154(b) by 1093 days.

(21) Appl. No.: 17/523,627

(22) Filed: Nov. 10, 2021

(65) Prior Publication Data

US 2022/0136009 A1 May 5, 2022

Related U.S. Application Data

(63) Continuation of application No. PCT/US2020/035431, filed on May 29, 2020.

(60) Provisional application No. 63/008,569, filed on Apr. 10, 2020, provisional application No. 62/857,727, filed on Jun. 5, 2019, provisional application No. 62/854,238, filed on May 29, 2019.

(51) Int. Cl.

| | |
|---|---|
| ***C12N 9/00*** | (2006.01) |
| ***A61P 25/08*** | (2006.01) |
| ***C07K 14/47*** | (2006.01) |
| ***C07K 14/705*** | (2006.01) |
| ***C12N 15/113*** | (2010.01) |
| ***C12N 15/62*** | (2006.01) |
| ***C12N 15/86*** | (2006.01) |

(52) U.S. Cl.

CPC .............. *C12N 15/86* (2013.01); *A61P 25/08* (2018.01); *C07K 14/4705* (2013.01); *C07K 14/705* (2013.01); *C12N 15/1138* (2013.01); *C12N 15/62* (2013.01); *C07K 2319/71* (2013.01); *C07K 2319/81* (2013.01); *C12N 2320/32* (2013.01); *C12N 2710/10343* (2013.01); *C12N 2710/10344* (2013.01); *C12N 2750/14143* (2013.01); *C12N 2750/14152* (2013.01); *C12N 2750/14171* (2013.01); *C12N 2830/008* (2013.01); *C12N 2840/007* (2013.01)

(58) Field of Classification Search

CPC ... C07K 2319/71; C07K 2319/81; C12N 9/00
See application file for complete search history.

(56) References Cited

U.S. PATENT DOCUMENTS

| | | | |
|---|---|---|---|
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,180,613 | B1 | 1/2001 | Kaplitt et al. |
| 6,200,759 | B1 | 3/2001 | Dove et al. |
| 6,303,370 | B1 | 10/2001 | Kappen et al. |
| 6,372,500 | B1 | 4/2002 | Hu et al. |
| 6,436,708 | B1 | 8/2002 | Leone et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,503,888 | B1 | 1/2003 | Kaplitt et al. |
| 6,524,851 | B1 | 2/2003 | Ellis |
| 6,534,261 | B1 | 3/2003 | Cox, III et al. |
| 6,566,118 | B1 | 5/2003 | Atkinson et al. |
| 6,599,692 | B1 | 7/2003 | Case et al. |
| 6,607,882 | B1 | 8/2003 | Cox, III et al. |
| 6,649,371 | B1 | 11/2003 | Jentsch |
| 6,689,558 | B2 | 2/2004 | Case |
| 6,794,136 | B1 | 9/2004 | Eisenberg et al. |
| 6,812,339 | B1 | 11/2004 | Venter et al. |
| 6,903,185 | B2 | 6/2005 | Kim et al. |
| 6,933,113 | B2 | 8/2005 | Case et al. |
| 6,989,264 | B2 | 1/2006 | Atkinson et al. |
| 6,994,993 | B2 | 2/2006 | Qin et al. |
| 6,998,118 | B2 | 2/2006 | Kaspar et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |

(Continued)

FOREIGN PATENT DOCUMENTS

| | | | |
|---|---|---|---|
| CA | 3058189 | A1 | 10/2018 |
| CL | 2014000550 | A1 | 9/2014 |

(Continued)

OTHER PUBLICATIONS

Tanenhaus et al. (2022) "Cell-selective adeno-associated virus-mediated SCN1A gene regulation therapy rescues mortality and seizure phenotypes in a Dravet syndrome mouse model and is well tolerated in nonhuman primates" Human gene therapy, 33(11-12), 579-597. (Year: 2022).*

(Continued)

*Primary Examiner* — James Joseph Graber
(74) *Attorney, Agent, or Firm* — Wilson Sonsini Goodrich & Rosati

(57) ABSTRACT

Provided herein are engineered transcription factors for selective upregulation of SCN1a and uses thereof for treating diseases and disorders, such as, Dravet syndrome. Also provided are microRNA binding sites and uses thereof for selective expression in parvalbumin neurons.

71 Claims, 19 Drawing Sheets

Specification includes a Sequence Listing.

(56) References Cited

U.S. PATENT DOCUMENTS

| | | | |
|---|---|---|---|
| 7,094,600 | B2 | 8/2006 | Wang |
| 7,101,540 | B2 | 9/2006 | Kaspar et al. |
| 7,125,676 | B2 | 10/2006 | George et al. |
| 7,153,949 | B2 | 12/2006 | Kim et al. |
| 7,157,571 | B2 | 1/2007 | Wang et al. |
| 7,220,719 | B2 | 5/2007 | Case et al. |
| 7,253,273 | B2 | 8/2007 | Collingwood |
| 7,262,054 | B2 | 8/2007 | Jamieson et al. |
| 7,358,085 | B2 | 4/2008 | Zhang et al. |
| 7,361,635 | B2 | 4/2008 | Miller et al. |
| 7,534,775 | B2 | 5/2009 | Zhang et al. |
| 7,595,376 | B2 | 9/2009 | Kim et al. |
| 7,655,460 | B2 | 2/2010 | Rouleau et al. |
| 7,943,553 | B2 | 5/2011 | Case et al. |
| 7,947,837 | B2 | 5/2011 | Marks et al. |
| 8,137,948 | B2 | 3/2012 | Qu et al. |
| 8,143,005 | B2 | 3/2012 | Rouleau et al. |
| 8,304,235 | B2 | 11/2012 | Passananti et al. |
| 8,524,874 | B2 | 9/2013 | Liu et al. |
| 8,586,526 | B2 | 11/2013 | Gregory et al. |
| 8,772,453 | B2 | 7/2014 | Paschon et al. |
| 8,927,514 | B2 | 1/2015 | Chatterjee et al. |
| 8,969,077 | B2 | 3/2015 | Head et al. |
| 9,102,949 | B2 | 8/2015 | Gao et al. |
| 9,267,151 | B2 | 2/2016 | Guerrero et al. |
| 9,315,825 | B2 | 4/2016 | Wilson et al. |
| 9,624,498 | B2 | 4/2017 | Froelich et al. |
| 9,845,481 | B2 | 12/2017 | Marengo et al. |
| 10,000,757 | B2 | 6/2018 | Naldini et al. |
| 10,287,607 | B2 | 5/2019 | Tagliatela et al. |
| 10,287,608 | B2 | 5/2019 | Tagliatela et al. |
| 10,519,465 | B2 | 12/2019 | Tagliatela et al. |
| 2002/0115215 | A1 | 8/2002 | Wolffe et al. |
| 2002/0165356 | A1 | 11/2002 | Barbas et al. |
| 2003/0051266 | A1 | 3/2003 | Serafini |
| 2003/0082552 | A1 | 5/2003 | Wolffe et al. |
| 2004/0096885 | A1 | 5/2004 | Rouleau et al. |
| 2004/0191791 | A1 | 9/2004 | Wallace et al. |
| 2004/0258666 | A1 | 12/2004 | Passini et al. |
| 2005/0026169 | A1 | 2/2005 | Cargill et al. |
| 2005/0032219 | A1 | 2/2005 | Aubourg et al. |
| 2005/0064474 | A1 | 3/2005 | Urnov et al. |
| 2005/0228172 | A9 | 10/2005 | Wang |
| 2005/0260576 | A1 | 11/2005 | George et al. |
| 2005/0267061 | A1 | 12/2005 | Martin |
| 2006/0292572 | A1 | 12/2006 | Stuart et al. |
| 2007/0161031 | A1 | 7/2007 | Trinklein et al. |
| 2007/0218528 | A1 | 9/2007 | Miller |
| 2009/0018031 | A1 | 1/2009 | Trinklein et al. |
| 2009/0311222 | A1 | 12/2009 | Baraban et al. |
| 2010/0086532 | A1 | 4/2010 | Barbas, III et al. |
| 2010/0130594 | A1 | 5/2010 | Barkats |
| 2011/0015122 | A1* | 1/2011 | Zimmerman et al. . A61K 38/16 514/4.3 |
| 2011/0065100 | A1 | 3/2011 | Aldred et al. |
| 2011/0135611 | A1 | 6/2011 | Huang et al. |
| 2011/0165129 | A1 | 7/2011 | Kriegstein et al. |
| 2011/0203007 | A1 | 8/2011 | Klein et al. |
| 2011/0268747 | A1 | 11/2011 | Guerrero Martinez et al. |
| 2013/0096183 | A1 | 4/2013 | Collard et al. |
| 2013/0224836 | A1 | 8/2013 | Muramatsu |
| 2013/0254909 | A1 | 9/2013 | Marengo et al. |
| 2014/0037585 | A1 | 2/2014 | Wright et al. |
| 2014/0142160 | A1 | 5/2014 | Lee et al. |
| 2014/0162894 | A1 | 6/2014 | Hatchwell et al. |
| 2015/0035917 | A1 | 2/2015 | Asauchi |
| 2015/0044187 | A1 | 2/2015 | Visel et al. |
| 2015/0071903 | A1 | 3/2015 | Liu et al. |
| 2015/0111955 | A1 | 4/2015 | High et al. |
| 2015/0253339 | A1 | 9/2015 | Shekdar |
| 2015/0353917 | A1 | 12/2015 | Miller |
| 2016/0032319 | A1 | 2/2016 | Wright et al. |
| 2016/0046681 | A1 | 2/2016 | Neutzner et al. |
| 2016/0120960 | A1 | 5/2016 | Mcivor et al. |
| 2017/0166903 | A1 | 6/2017 | Zhang et al. |
| 2017/0218037 | A1 | 8/2017 | Passananti et al. |
| 2018/0126003 | A1 | 5/2018 | Hoerr |
| 2019/0024121 | A1 | 1/2019 | Tagliatela et al. |
| 2020/0165628 | A1 | 5/2020 | Tagliatela et al. |

FOREIGN PATENT DOCUMENTS

| | | | |
|---|---|---|---|
| CN | 106170295 | A | 11/2016 |
| CN | 107759673 | A | 3/2018 |
| EP | 1590467 | B1 | 10/2009 |
| EP | 2130838 | A2 | 12/2009 |
| EP | 1747277 | B1 | 8/2011 |
| EP | 3119878 | A2 | 1/2017 |
| JP | 2018088888 | A | 6/2018 |
| KR | 20120087860 | A | 8/2012 |
| TW | 201514202 | A | 4/2015 |
| TW | 201925474 | A | 7/2019 |
| WO | WO-9519431 | A1 | 7/1995 |
| WO | WO-9606166 | A1 | 2/1996 |
| WO | WO-9853057 | A1 | 11/1998 |
| WO | WO-9853058 | A1 | 11/1998 |
| WO | WO-9853059 | A1 | 11/1998 |
| WO | WO-9853060 | A1 | 11/1998 |
| WO | WO-9854311 | A1 | 12/1998 |
| WO | WO-0027878 | A1 | 5/2000 |
| WO | WO-0130843 | A1 | 5/2001 |
| WO | WO-0138362 | A2 | 5/2001 |
| WO | WO-0160970 | A2 | 8/2001 |
| WO | WO-0185938 | A1 | 11/2001 |
| WO | WO-0188197 | A2 | 11/2001 |
| WO | WO-0216536 | A1 | 2/2002 |
| WO | WO-02057294 | A2 | 7/2002 |
| WO | WO-02066640 | A2 | 8/2002 |
| WO | WO-02099084 | A2 | 12/2002 |
| WO | WO-03016496 | A2 | 2/2003 |
| WO | WO-03066828 | A2 | 8/2003 |
| WO | WO-03076601 | A1 | 9/2003 |
| WO | WO-2005042728 | A2 | 5/2005 |
| WO | WO-2006108846 | A1 | 10/2006 |
| WO | WO-2007069666 | A1 | 6/2007 |
| WO | WO-2007078599 | A2 | 7/2007 |
| WO | WO-2008118820 | A2 | 10/2008 |
| WO | WO-2008129058 | A1 | 10/2008 |
| WO | WO-2008142124 | A1 | 11/2008 |
| WO | WO-2009044383 | A1 | 4/2009 |
| WO | WO-2009060316 | A2 | 5/2009 |
| WO | WO-2010037143 | A1 | 4/2010 |
| WO | WO-2010148143 | A1 | 12/2010 |
| WO | WO-2012087983 | A1 | 6/2012 |
| WO | WO-2014161884 | A2 | 10/2014 |
| WO | WO-2015143046 | A2 | 9/2015 |
| WO | WO-2015153760 | A2 | 10/2015 |
| WO | WO-2016172155 | A1 | 10/2016 |
| WO | WO-2016188112 | A1 | 12/2016 |
| WO | WO-2017048466 | A1 | 3/2017 |
| WO | WO-2017075335 | A1 | 5/2017 |
| WO | WO-2017075338 | A2 | 5/2017 |
| WO | WO-2017106377 | A1 | 6/2017 |
| WO | WO-2017151884 | A1 | 9/2017 |
| WO | WO-2017180915 | A2 | 10/2017 |
| WO | WO-2018049079 | A1 | 3/2018 |
| WO | WO-2018126116 | A1 | 7/2018 |
| WO | WO-2018148256 | A1 | 8/2018 |
| WO | WO-2018187363 | A1 | 10/2018 |
| WO | WO-2018213786 | A1 | 11/2018 |
| WO | WO-2019109051 | A1 | 6/2019 |
| WO | WO-2019224864 | A1 | 11/2019 |
| WO | WO-2020243651 | A1 | 12/2020 |

OTHER PUBLICATIONS

Xie et al. (2011) "MicroRNA-regulated, systemically delivered rAAV9: a step closer to CNS-restricted transgene expression" Molecular therapy, 19(3), 526-535. (Year: 2011).*

Sahenk et al. Systemic delivery of AAVrh74.tMCK.hCAPN3 rescues the phenotype in a mouse model for LGMD2A/R1. Mol Ther Methods Clin Dev 22:401-414 (2021).

(56) References Cited

OTHER PUBLICATIONS

Fenzi Shengwuxue: Chapter 5 Protein Structure and Functions—Transcriptional Factors. Molecular Biology, Ed. Yu Duowei, Gong Zhunan, Liu Ping-Nanjing: Nanjing Normal University Press, College Teaching Materials, pp. 100-107 [English Translation provided] (2007).
Li et al.: The zinc-sensing mechanism of mouse MTF-1 involves linker peptides between the zinc fingers. Mol Cell Biol. 26(15):5580-5587 doi:10.1128/MCB.00471-06 (2006).
EP20815541.6 Supplementary European Search Report dated Jun. 13, 2023.
U.S. Appl. No. 16/670,996 Final Office Action dated Jun. 17, 2022.
Aach et al. CasFinder: Flexible algorithm for identifying specific Cas9 targets in genomes. BioRxiv, Cold Spring Harbor Labs. Posted May 12, 2014. doi: https://doi.org/10.1101/005074. Retrieved Sep. 10, 2020 at URL: https://doi.org/10.1101/005074. 8 pages.
Altschul, et al. Basic local alignment search tool. J Mol Biol. Oct. 5, 1990;215(3):403-410. doi: 10.1016/S0022-2836(05)80360-2.
Altschul, et al. Gapped BLAST and PSI-BLAST: a new generation of protein database search programs. Nucleic Acids Res. Sep. 1, 1997; 25(17):3389-3402. doi: 10.1093/nar/25.17.3389.
Anderson. Human gene therapy. Science. May 8, 1992;256(5058):808-13. doi: 10.1126/science.1589762.
Ayuso et al. Production, purification and characterization of adeno-associated vectors. Curr Gene Ther. Dec. 2010;10(6):423-36. doi: 10.2174/156652310793797685.
Bae et al. Cas-OFFinder: a fast and versatile algorithm that searches for potential off-target sites of Cas9 RNA-guided endonucleases. Bioinformatics, vol. 30, Issue 10, May 15, 2014, pp. 1473-1475, https://doi.org/10.1093/bioinformatics/btu048. Published online Jan. 24, 2014.
Bae et al.: Human zinc fingers as building blocks in the construction of artificial transcription factors. Nat Biotechnol. 21(3):275-280 doi:10.1038/nbt796 (2003).
Bagot et al., Epigenetic signaling in psychiatric disorders: stress and depression, Dialogues Clin Neurosci., 16(3): 281-295 (2014).
Beerli, et al. Engineering polydactyl zinc-finger transcription factors. Nat Biotechnol. Feb. 2002;20(2):135-141. doi: 10.1038/nbt0202-135.
Beerli et al. Positive and negative regulation of endogenous genes by designed transcription factors. PNAS 97(4): 1495-1500 (Feb. 15, 2000).
Bender et al.: SCN1A mutations in Dravet syndrome: impact of interneuron dysfunction on neural networks and cognitive outcome. Epilepsy Behav. 3(3):177-186 doi:10.1016/j.yebeh.2011.11.022 (2012).
Bezzina et al., Early Onset of Hypersynchronous Network Activity and Expression of a Marker of Chronic Seizures in the Tg2576 Mouse Model of Alzheimer's Disease, PLoS ONE 10(3): e0119910 (14 pages) (2015).
Blouin et al. Improving rAAV production and purification: towards the definition of a scaleable process. J Gene Med. Feb. 2004;6 Suppl 1:S223-8. doi: 10.1002/jgm.505.
Büning et a. Recent developments in adeno-associated virus vector technology. J Gene Med. Jul. 2008;10(7):717-33. doi: 10.1002/jgm.1205.
Cermak, et al. Efficient design and assembly of custom TALEN and other TAL effector-based constructs for DNA targeting. Nucleic Acids Res. 39.12 (Jul. 2011): e82. doi: 10.1093/nar/gkr218. Epub Apr. 14, 2011.
Challis et al., Raphe GABAergic Neurons Mediate the Acquisition of Avoidance after Social Defeat, The Journal of Neuroscience, 33(35):13978 -13988 (2013).
Cheah et al., Specific deletion of Nav1.1 sodium channels in inhibitory interneurons causes seizures and premature death in a mouse model of Dravet syndrome, Proc Natl Acad Sci, 109(36): 14646-14651 (2012).
Choo, et al. Advances in zinc finger engineering. Curr Opin Struct Biol. Aug. 2000;10(4):411-416. doi: 10.1016/s0959-440x(00)00107-x.
Colasante, et al. dCas9-Based Scn1a Gene Activation Restores Inhibitory Interneuron Excitability and Attenuates Seizures in Dravet Syndrome Mice. Mol Ther. Jan. 8, 2020;28(1):235-253. doi: 10.1016/j.ymthe.2019.08.018. Epub Sep. 3, 2019.
Connelly. Dravet Syndrome: Diagnosis and Long-Term Course. Can J Neurol Sci. 43: S3-S8 (2016).
Conway et al. Recombinant adeno-associated virus type 2 replication and packaging is entirely supported by a herpes simplex virus type 1 amplicon expressing Rep and Cap. J Virol. Nov. 1997; 71(11): 8780-8789.
CRISPR-Cas9 Epigenome Editing Screen Reveals Regulatory Elements. GenomeWeb. 3 pages. Apr. 3, 2017. Retrieved Nov. 6, 2018 at URL: https://www.genomeweb.com/epigenetics-research/crispr-cas9-epigenome-editing-screen-reveals-regulato . . . .
Desjarlais et al., Use of a Zinc-Finger Consensus Sequence Framework and Specificity Rules to Design Specific DNA Binding Proteins. Proceedings of the National Academy of Sciences of the United States of America, 90.6 (Mar. 1993): 2256-2260.
Dillon. Regulating gene expression in gene therapy. Trends Biotechnol 11(5):167-173 (1993).
Dimidschstein et al. A viral strategy for targeting and manipulating interneurons across vertebrate species. Nat Neurosci. 19(12): 1743-1749 (Dec. 2016). doi:10.1038/nn.4430.
Dingwall et al. The nucleoplasmin nuclear location sequence is larger and more complex than that of SV-40 large T antigen. J Cell Biol. Sep. 1, 1988; 107(3): 841-849. doi: 10.1083/jcb.107.3.841.
Doench et al. Optimized sgrNA design to maximize activity and minimize off-target effects of crisPr-cas9. Nature Biotechnology 34(2):184-191 (Feb. 2016). Advance Online Publication published online Jan. 18, 2016. doi: 10.1038/nbt/3437.
EBI. Emboss Needle. Available at http://www.ebi.ac.uk/Tools/psa/emboss_needle/. Accessed on Dec. 20, 2016.
Eguchi, et al. Reprogramming cell fate with a genome-scale library of artificial transcription factors. Proc Natl Acad Sci USA. Dec. 20, 2016;113(51):E8257-E8266. doi: 10.1073/pnas.1611142114. Epub Dec. 5, 2016.
EMBL-EBI. Emboss Water Pairwise Sequence Alignment. Smith-Waterman algorithm. Accessed on Sep. 30, 2020. 2 pages. Available at https://www.ebi.ac.uk/Tools/psa/emboss_water.
Eriksen, et al. Progranulin: normal function and role in neurodegeneration. J Neurochem. Jan. 2008;104(2):287-97. Epub Oct. 22, 2007.
Feng et al. Imaging Neuronal Subsets in Transgenic Mice Expressing Multiple Spectral Variants of GFP. Neuron 28:41-51 (Oct. 2000).
Frye et al., Neuropathological Mechanisms of Seizures in Autism Spectrum Disorder, Frontiers in Neuroscience, 10:192 (9 pages) (2016).
Geißler, et al. Transcriptional activators of human genes with programmable DNA-specificity. PLoS One. 2011;6(5):e19509. doi: 10.1371/journal.pone.0019509. Epub May 19, 2011.
GenBank Accession No. GCA_000001405.27 (replaced). RefSeq Accession: GCF_000001405.38 (replaced). GRCh38.p12. Date: Dec. 21, 2017. 3 pages. Retrieved Feb. 10, 2021 at URL: https://www.ncbi.nlm.nih.gov/assembly/GCF_000001405.38/.
GenBank Accession No. NC_000017. Version No. NC_000017.11. *Homo sapiens* chromosome 17, GRCh38.p13 Primary Assembly. Record created Aug. 29, 2002. 2 pages. Retrieved Feb. 10, 2021 at URL: https://www.ncbi.nlm.nih.gov/nuccore/NC_000017.
GenBank Accession No. NM_001032221. Version No. NM_001032221.3. *Homo sapiens* syntaxin binding protein 1 (STXBP1), transcript variant 2, mRNA. Record created Aug. 25, 2005. 5 pages. Retrieved Feb. 10, 2021 at URL: https://www.ncbi.nlm.nih.gov/nuccore/NM_001032221.3.
GenBank Accession No. NM_001037 XM_940055. Version No. NM_001037.4. *Homo sapiens* sodium voltage-gated channel beta subunit 1 (SCN1B), transcript variant a, mRNA. Record created Mar. 24, 1999. 4 pages. Retrieved Feb. 10, 2021 at URL: https://www.ncbi.nlm.nih.gov/nuccore/NM_001037.4.
GenBank Accession No. NM_001112741. Version No. NM_001112741.1. *Homo sapiens* potassium voltage-gated channel subfamily C member 1 (KCNC1), transcript variant 1, mRNA. Record created Dec. 20, 2007. 5 pages. Retrieved Feb. 10, 2021 at URL: https://www.ncbi.nlm.nih.gov/nuccore/NM_001112741.1.

(56) References Cited

OTHER PUBLICATIONS

GenBank Accession No. NM_001165963. Version No. NM_001165963.1. *Homo sapiens* sodium voltage-gated channel alpha subunit 1 (SCN1A), transcript variant 1, mRNA. Record created Oct. 1, 2009. 9 pages. Retrieved Feb. 10, 2021 at URL: https://www.ncbi.nlm.nih.gov/nuccore/NM_001165963.1.
GenBank Accession No. NM_002087. Version No. NM_002087.3. *Homo sapiens* granulin precursor (GRN), mRNA. Record created Mar. 24, 1999. 5 pages. Retrieved Feb. 10, 2021 at URL: https://www.ncbi.nlm.nih.gov/nuccore/NM_002087.3.
GenBank Accession No. NM_004588. Version No. NM_004588.4. *Homo sapiens* sodium voltage-gated channel beta subunit 2 (SCN2B), mRNA. Record created May 7, 1999. 5 pages. Retrieved Feb. 10, 2021 at URL: https://www.ncbi.nlm.nih.gov/nuccore/NM_004588.4.
GenBank Accession No. NM_004977. Version No. NM_004977.2. *Homo sapiens* potassium voltage-gated channel subfamily C member 3 (KCNC3), transcript variant 1, mRNA. Record created May 14, 1999. 5 pages. Retrieved Feb. 10, 2021 at URL: https://www.ncbi.nlm.nih.gov/nuccore/NM_004977.2.
GenBank Accession No. XM_005257253. Version No. XM_005257253.1. Predicted: *Homo sapiens* granulin precursor (GRN), transcript variant X1, mRNA. Record created Aug. 13, 2013. 2 pages. Retrieved Feb. 10, 2021 at URL: https://www.ncbi.nlm.nih.gov/nuccore/XM_005257253.1.
Genbank Accession No. AC007405. *Homo sapiens* BAC clone RP11-570C16 from 2, complete sequence. Washington University Genome Sequencing Center. Priority to at least Apr. 30, 2005.
Genome Reference Consortium Accession No. AL589692. Mouse DNA sequence from clone RP23-385C1 on chromosome 15, complete sequence. Wellcome Trust Sanger Institute. Submitted Dec. 13, 2012.
Gersbach et al. Synthetic Zinc Finger Proteins: The Advent of Targeted Gene Regulation and Genome Modification Technologies. Acc Chem Res. Aug. 1, 20149; 47(8): 2309-2318. Published online May 30, 2014. doi: 10.1021/ar500039w.
Ghidoni, et al. Circulating progranulin as a biomarker for neurodegenerative diseases. Am J Neurodegener Dis. 2012;1(2):180-90. Epub Aug. 2, 2012.
Gonzalez, et al. Modular system for the construction of zinc-finger libraries and proteins. Nat Protoc. Apr. 2010;5(4):791-810. doi: 10.1038/nprot.2010.34. Epub Apr. 1, 2010.
Gratz et al. Highly Specific and Efficient CRISPR/Cas9-Catalyzed Homology-Directed Repair in Drosophila. Genetics. Apr. 2014; 196(4): 961-971. Published online Jan. 29, 2014. doi: 10.1534/genetics.113.160713.
Gray et al., Optimizing Promoters for Recombinant Adeno-Associated Virus-Mediated Gene Expression in the Peripheral and Central Nervous System Using Self-Complementary Vectors, Human Gene Therapy, 22:1143-1153 (2011).
Grimm et al. Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.
Haddada, et al. Gene therapy using adenovirus vectors. The Molecular Repertoire of Adenoviruses III. Curr Top Microbiol Immunol. 1995;199 (Pt 3):297-306. doi: 10.1007/978-3-642-79586-2_14.
Han et al., Autistic behavior in Son1a+/−mice and rescue by enhanced GABAergic transmission, Nature, 489(7416): 385-390 (2012).
Han et al., Enhancement of Inhibitory Neurotransmission by GABAA Receptors Having α2,3-Subunits Ameliorates Behavioral Deficits in a Mouse Model of Autism, Neuron, 81(6): 1282-1289 (2014).
Hawkins et al. The synthetic neuroactive steroid SGE-516 reduces seizure burden and improves survival in a Dravet syndrome mouse model. Scientific Reports 7:15327. Published online Nov. 10, 2017. 8 pages. DOI: 10.1038/s41598-017-15609-w.
Hedrich et al., Impaired Action Potential Initiation in GABAergic Interneurons Causes Hyperexcitable Networks in an Epileptic Mouse Model Carrying a Human Nav1.1 Mutation, The Journal of Neuroscience, 34(45): 14874-14889 (2014).
Heigwer et al. E-CRISP: fast CRISPR target site identification. Nat Methods. Feb. 2014;11(2):122-3. doi: 10.1038/nmeth.2812.
Heilbronn, et al. Viral vectors for gene transfer: current status of gene therapeutics. Handb Exp Pharmacol. 2010;(197):143-170. doi: 10.1007/978-3-642-00477-3_5.
Hocquemiller et al. Adeno-Associated Virus-Based Gene Therapy for CNS Diseases. Human Gene Therapy 27(7):478-496 (2016).
Hossain et al.: Artificial zinc finger DNA binding domains: versatile tools for genome engineering and modulation of gene expression. J Cell Biochem. 116(11):2435-2444 doi:10.1002/jcb.25226 (2015).
International search report with written opinion dated Feb. 14, 2019 for PCT/US2018/063498.
International search report with written opinion dated Aug. 28, 2020 for PCT/US2020/035431.
Irizarry et al., Incidence of New-Onset Seizures in Mild to Moderate Alzheimer Disease, Arch Neurol., 69(3): 368-372 (2012).
Isalan, et al. A rapid, generally applicable method to engineer zinc fingers illustrated by targeting the HIV-1 promoter. Nat Biotechnol. Jul. 2001;19(7):656-660. doi: 10.1038/90264.
Karlin, et al. Applications and statistics for multiple high-scoring segments in molecular sequences. Proc Natl Acad Sci USA. Jun. 15, 1993; 90(12):5873-5877. doi: 10.1073/pnas.90.12.5873.
Karlin, et al. Methods for assessing the statistical significance of molecular sequence features by using general scoring schemes. Proc Natl Acad Sci USA. Mar. 1990; 87(6): 2264-2268. doi: 10.1073/pnas.87.6.2264.
Khan et al. Computational tools and resources for prediction and analysis of gene regulatory regions in the chick genome. Genesis 51(5):311-324 (May 2013).
Kovacs et al., Alzheimer's secretases regulate voltage-gated sodium channels, Neurosci Lett., 486(2): 68-72 (2010).
Kremer et al. Adenovirus and adeno-associated virus mediated gene transfer. Br Med Bull. 51(1):31-44 (1995).
Kurien, et al. A brief review of other notable protein detection methods on acrylamide gels. Methods Mol Biol. 2012;869:617-620. doi: 10.1007/978-1-61779-821-4_56.
Lambert et al. The Human Transcription Factors. Cell 172:650-665 (Feb. 8, 2018).
Ledri et al. Global Optogenetic Activation of Inhibitory Interneurons during Epileptiform Activity. Journal of Neuroscience 34(9):3364-3377 (Feb. 26, 2014). DOI: https://doi.org/10.1523/JNEUROSCI.2734-13.2014.
Lee et al. Transcriptional Regulation and its Misregulation in Disease. Cell 152(6):1237-1251. doi: 10.1016/j.cell.2013.02.014.
Lee et al. The Largest Group of Superficial Neocortical GABAergic Interneurons Expresses Ionotropic Serotonin Receptors. Journal of Neuroscience 30(50):16796-16808 (Dec. 15, 2010). DOI: https://doi.org/10.1523/JNEUROSCI.1869-10.2010.
Li et al. Modularly assembled designer TAL effector nucleases for targeted gene knockout and gene replacement in eukaryotes. Nucleic Acids Res. Aug. 2011; 39(14): 6315-6325. Published online Mar. 31, 2011. doi: 10.1093/nar/gkr188.
Liu, et al. CRISPR-ERA: a comprehensive design tool for CRISPR-mediated gene editing, repression and activation. Bioinformatics. 31 (22). 2015. pp. 3676-3678.
Liu et al. Design of polydactyl zinc-finger proteins for unique addressing within complex genomes. Proc Natl Acad Sci U S A. May 27, 1997;94(11):5525-30. doi: 10.1073/pnas.94.11.5525.
Lock et al. Absolute determination of single-stranded and self-complementary adeno-associated viral vector genome titers by droplet digital PCR. Hum Gene Ther Methods 25(2):115-125 (2014).
Lock et al. Characterization of a recombinant adeno-associated virus type 2 Reference Standard Material. Hum Gene Ther. Oct. 2010;21(10):1273-85. doi: 10.1089/hum.2009.223.
Ma, et al. A guide RNA sequence design platform for the CRISPR/Cas9 system for model organism genomes. Biomed Res Int. 2013;2013:270805. doi: 10.1155/2013/270805. Epub Oct. 3, 2013. 4 pages.
Maguire et al. Gene Therapy for the Nervous System: Challenges and New Strategies. Neurotherapeutics 11:817-839 (Aug. 27, 2014). DOI: 10.1007/s13311-014-0299-5.

(56) References Cited

OTHER PUBLICATIONS

Makkerh et al.: Comparative mutagenesis of nuclear localization signals reveals the importance of neutral and acidic amino acids. Curr Biol. Aug. 1, 1996;6(8):1025-1027. doi: 10.1016/s0960-9822(02)00648-6.
Mandell, et al. Zinc Finger Tools: custom DNA-binding domains for transcription factors and nucleases. Nucleic Acids Res. Jul. 1, 2006;34(Web Server issue):W516-W523. doi: 10.1093/nar/gkl209.
Marini et al. The genetics of Dravet syndrome. Epilepsia 52(Suppl. 2):24-29 (2011).
McLean et al., Widespread neuron-specific transgene expression in brain and spinalcord following synapsin promoter-driven AAV9 neonatalintracerebroventricular injection, Neuroscience Letters, 576: 73-78 (2014).
Meyer et al. In vivo labeling of parvalbumin-positive interneurons and analysis of electrical coupling in identified neurons. J Neurosci 22(16):7055-7064 (Aug. 15, 2002).
Miller, et al. From Gene Replacement to Gene Regulation: Developing a Disease-Modifying AAV Gene Therapy Vector for SCN1A-Positive (SCN1A+) Pediatric Epilepsy. American Epilepsy Association Annual Meeting Abstracts. Abstract 1.091. Published Nov. 2019. (online journal) Retrieved from the internet on Feb. 10, 2021. URL: https://www.aesnet.org/meetings_events/annual_meeting_abstracts/view/2421087.
Miller et al. Mapping genetic modifiers of survival in a mouse model of Dravet syndrome. Genes, Brain and Behavior 13:163-172 (Feb. 2014). First published Oct. 23, 2013. doi: 10.1111/gbb.12099.
Miller. Human gene therapy comes of age. Nature 357:455-460 (1992).
Mitani et al. Delivering therapeutic genes-matching approach and application Trends Biotechnol 11:162-166 (1993).
Mo et al. Epigenomic Signatures of Neuronal Diversity in the Mammalian Brain. Neuron 86:1369-1384 (Jun. 17, 2015).
Mo et al. Supplemental Information: Epigenomic Signatures of Neuronal Diversity in the Mammalian Brain. Neuron 86(6) (Jun. 17, 2015). 30 pages.
Montague et al. CHOPCHOP: a CRISPR/Cas9 and TALEN web tool for genome editing. Nucleic Acids Res. Jul. 1, 2014; 42(Web Server issue): W401-W407. Published online May 26, 2014. doi: 10.1093/nar/gku410.
Morbitzer et al. Assembly of custom TALE-type DNA binding domains by modular cloning. Nucleic Acids Res. Jul. 2011; 39(13): 5790-5799. Published online Mar. 18, 2011. doi: 10.1093/nar/gkr151.
Nabel, et al. Direct gene transfer for immunotherapy and immunization. Trends Biotechnol. May 1993;11(5):211-215. doi: 10.1016/0167-7799(93)90117-R.
Narlikar et al. Identifying regulatory elements in eukaryotic genomes. Briefings in Functional Genomics and Proteomics 8(4):215-230 (Jun. 4, 2009).
Nathanson et al., Short promoters in viral vectors drive selective expression in mammalian inhibitory neurons, but do not restrict activity to specifi c inhibitory cell-types, Frontiers in Neural Circuits, 3(19): 1-24 (2009).
NCBI. Basic Local Alignment Search Tool. BLAST algorithm. Available at https://blast.ncbi.nlm.nih.gov/Blast.cgi. Accessed on Jan. 3, 2017.
Nguyen, et al. Progranulin: at the interface of neurodegenerative and metabolic diseases. Trends Endocrinol Metab. Dec. 2013;24(12):597-606. doi: 10.1016/j.tem.2013.08.003. Epub Sep. 10, 2013.
Niels Van Tol et al. Artificial transcription factor-mediated regulation of gene expression. Plant Science 225:58-67 (2014).
Oakley, et al. Temperature- and age-dependent seizures in a mouse model of severe myoclonic epilepsy in infancy. Proc Natl Acad Sci USA. Mar. 10, 2009;106(10):3994-9. doi: 10.1073/pnas.0813330106. Epub Feb. 20, 2009.
Ogiwara et al., Nav1.1 haploinsufficiency in excitatory neurons ameliorates seizure-associated sudden death in a mouse model of Dravet syndrome, Human Molecular Genetics, 22(23): 4784-4804 (2013).
Ogiwara et al. Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).
Oliva Jr. et al. Novel Hippocampal Interneuronal Subtypes Identified Using Transgenic Mice That Express Green Fluorescent Protein in GABAergic Interneurons. The Journal of Neuroscience 20(9):3354-3368 (May 1, 2000).
Onori et al. UtroUp is a novel six zinc finger artificial transcription factor that recognises 18 base pairs of the utrophin promoter and efficiently drives utrophin upregulation. BMC Molecular Biology 14:3 (2013). 9 pages.
Pabo, et al. Design and selection of novel Cys2His2 zinc finger proteins. Annu Rev Biochem. 2001;70:313-340. doi: 10.1146/annurev.biochem.70.1.313.
Palop et al., Aberrant Excitatory Neuronal Activity and CompensatoryRemodelingof InhibitoryHippocampal Circuits in MouseModels of Alzheimer's Disease, Neuron, 55: 697-711 (2007).
Palop et al., Epilepsy and Cognitive Impairments in Alzheimer Disease, Arch Neurol., 66(4): 435 (11 pages) (2009).
Papworth et al. Designer zinc-finger proteins and their applications. Gene 366:27-38 (2006).
PCT/US2018/025940 International Search Report and Written Opinion dated Aug. 23, 2018.
Pelkey et al. Hippocampal GABAergic Inhibitory Interneurons. Physiol Rev 97(4): 1619-1747 (Oct. 1, 2017). DOI: 10.1152/physrev.00007.2017.
Puts et al., Reduced GABA and Altered Somatosensory Function in Children with Autism Spectrum Disorder, Autism Res., 10(4): 608-619 (2017).
PVALB (main page). The Human Protein Atlas. Available at https://www.proteinatlas.org/ENSG00000100362-PVALB/tissue. Accessed on Sep. 27, 2018.
Radde et al. Aβ42-driven cerebral amyloidosis in transgenic mice reveals early and robust pathology. EMBO reports 7(9):940-946 (Sep. 1, 2006). Published online Aug. 11, 2006. DOI 10.1038/sj.embor.7400784.
Ran et al. In vivo genome editing using *Staphylococcus aureus* Cas9. Nature. 520(7546):186-191 (2015).
Ray et al. Quantitative tracking of protein trafficking to the nucleus using cytosolic protein delivery by nanoparticle-stabilized nanocapsules. Bioconjug Chem. Jun. 17, 2015; 26(6): 1004-1007. Published online Jun. 2, 2015. doi: 10.1021/acs.bioconjchem.5b00141.
Reetz et al., Development of Adenoviral Delivery Systems to Target Hepatic Stellate Cells In Vivo, PLoS ONE 8(6): e67091, 14 pages (2013).
Ritter et al., Lentiviral expression of GAD67 and CCK promoterdriven opsins to target interneurons in vitro and in vivo, J Gene Med, 18: 27-37 (2016).
Sander, et al. Zinc Finger Targeter (ZiFIT): an engineered zinc finger/target site design tool. Nucleic Acids Res. Jul. 2007;35(Web Server issue):W599-W605. doi: 10.1093/nar/gkm349. Epub May 25, 2007.
Schleef et al. The structure of the mouse parvalbumin gene. Mammalian Genome 3:217-225 (1992).
Scott et al. Targeted genome regulation and modification using transcription activator-like effectors. FEBS Journal 281:4583-4597 (2014). doi: 10.1111/febs.12973.
Segal, et al. Custom DNA-binding proteins come of age: polydactyl zinc-finger proteins. Curr Opin Biotechnol. Dec. 2001;12(6):632-637. doi: 10.1016/s0958-1669(01)00272-5.
Shevtsova et al., Promoters and serotypes: targeting of adeno-associated virus vectors for gene transfer in the rat central nervous system in vitro and in vivo, Exp Physiol 90.1 pp. 53-59 (2004).
Snowden, et al. Progranulin gene mutations associated with frontotemporal dementia and progressive non-fluent aphasia. Brain. Nov. 2006;129(Pt 11):3091-102. Epub Sep. 26, 2006.

(56) References Cited

OTHER PUBLICATIONS

Sohn et al., A Single Vector Platform for High-Level Gene Transduction of Central Neurons: Adeno-Associated Virus Vector Equipped with the Tet-Off System, PLoS ONE 12(1): e0169611, 22 pages, (2017).
Soukupova et al., Impairment of GABA release in the hippocampus at the time of the first spontaneous seizure in the pilocarpine model of temporal lobe epilepsy, Experimental Neurology, 257: 39-49 (2014).
Strimpakos et al. Novel Adeno-Associated Viral Vector Delivering the Utrophin Gene Regulator Jazz Counteracts Dystrophic Pathology in mdx Mice. J Cell Physiol 229:1283-1291 (2014).
Sun et al., SCN1A, SCN1B, and GABRG2 gene mutation analysis in Chinese families with generalized epilepsy with febrile seizures plus, J Hum Genet, 53:769-774 (2008).
Tai et al., Impaired excitability of somatostatin- and parvalbumin-expressing cortical interneurons in a mouse model of Dravet Syndrome, Proc Natl Acad Sci, 111(30): E3139-3148 (2014).
Tamamaki et al. Green flourescent protein expression and colocalization with calretinin, parvalbumin, and somatostatin in the GAD67-GFP knock-in mouse. J Comp Neurol 467(1):60-79 (Dec. 1, 2003).
Taniguchi et al., A Resource of Cre Driver Lines for Genetic Targeting of GABAergic Neurons in Cerebral Cortex, Neuron, 71: 995-1013 (2011).
Taniguchi, Genetic dissection of GABAergic neural circuits in mouse neocortex. Front Cell Neurosci vol. 8, Article 8 (Jan. 27, 2014). 22 pages. DOI: .https://doi.org/10.3389/fncel.2014.00008.
Uil et al. Therapeutic modulation of endogenous gene function by agents with designed DNA-sequence specificities. Nucleic Acids Research 31(21):6064-6078 (2003). DOI: 10.1093/nar/gkg815.
Urabe et al. Insect cells as a factory to produce adeno-associated virus type 2 vectors. Hum Gene Ther. Nov. 1, 2002;13(16):1935-43. doi: 10.1089/10430340260355347.
U.S. Appl. No. 16/670,996 Non-Final Office Action mailed Dec. 8, 2021.
U.S. Appl. No. 16/153,401 Office Action dated Jan. 11, 2019.
U.S. Appl. No. 16/153,420 Office Action dated Dec. 14, 2018.
U.S. Appl. No. 16/153,433 Office Action dated Dec. 31, 2018.
U.S. Appl. No. 16/153,433 Office Action dated Jul. 1, 2019.
U.S. Appl. No. 16/153,443 Office Action dated Jan. 11, 2019.
U.S. Appl. No. 16/153,443 Office Action dated Jul. 29, 2019.
U.S. Appl. No. 16/153,443 Office Action dated Mar. 5, 2020.
Van Brunt. Molecular Farming: Transgenic Animals as Bioreactors. Biotechnology (NY). 1988;6(10):1149-1154. doi: 10.1038/nbt1088-1149.
Van Den Pol et al. Selective neuronal expression of green fluorescent protein with cytomegalovirus promoter reveals entire neuronal arbor in transgenic mice. J Neurosci 18(24):10640-10651 (Dec. 15, 1998).
Verret et al., Inhibitory Interneuron Deficit Links Altered Network Activity and Cognitive Dysfunction in Alzheimer Model, Cell, 149(3): 708-721 (2012).
Vigne et al. Third-generation adenovectors for gene therapy. Restor Neurol Neurosci 8(1):35-36 (1995).
Weber, et al. Assembly of Designer TAL Effectors by Golden Gate Cloning, PLoS ONE, 6:e19722 (2001).
Wootton et al. Statistics of local complexity in amino acid sequences and sequence databases. Computers & Chemistry 17(2):149-163 (Jun. 1993).
Wright et al. Standardized reagents and protocols for engineering zinc finger nucleases by modular assembly. Nat Protoc. 2006;1(3):1637-52. doi: 10.1038/nprot.2006.259.
Wu et al. Target specificity of the CRISPR-Cas9 system. Quantitative Biology, vol. 2, pp. 59-70 (2014). Published: Aug. 26, 2014. DOI 10.1007/s40484-014-0030-x.
Xiao et al. CasOT: a genome-wide Cas9/gRNA off-target searching tool. Bioinformatics. Apr. 15, 2014;30(8):1180-1182.
Xiao, et al. Production of high-titer recombinant adeno-associated virus vectors in the absence of helper adenovirus. J Virol. Mar. 1998;72(3):2224-2232.
Xie et al., MicroRNA-regulated, Systemically Delivered rAAV9: A Step Closer to CNS-restricted Transgene Expression, Mol Ther., 19(3):526-535 (2011).
Xu et al. Immunochemical characterization of inhibitory mouse cortical neurons: Three chemically distinct classes of inhibitory cells. J Comp Neurol 518(3):389-404 (Feb. 1, 2010). doi: 10.1002/cne.22229.
Yan et al., Targeting the β secretase BACE1 for Alzheimer's disease therapy, Lancet Neurol., 13(3): 319-329 (2014).
Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).
Young, et al. A GABA-Selective AAV Vector Upregulates Endogenous SCN1A Expression and Reverses Multiple Phenotypes in a Mouse Model of Dravet Syndrome. American Epilepsy Association Annual Meeting Abstracts. Abstract 3.1. Published Nov. 2019. (online journal) Retrieved from the Internet on Feb. 10, 2021. URL: https://www.aesnet.org/meetings_events/annual_meeting_abstracts/view/2421999.
Yu et al. Progress towards gene therapy for HIV infection. Gene Ther 1(1):13-26 (1994).
Yu, et al. The spectrum of mutations in progranulin: a collaborative study screening 545 cases of neurodegeneration. Arch Neurol. Feb. 2010;67(2):161-70. doi: 10.1001/archneurol.2009.328.
Zetsche, et al. Cpf1 is a single RNA-guided endonuclease of a class 2 CRISPR-Cas system. Cell. Oct. 22, 2015;163(3):759-771. doi: 10.1016/j.cell.2015.09.038. Epub Sep. 25, 2015.
Zhang et al. Efficient construction of sequence-specific TAL effectors for modulating mammalian transcription. Nature Biotechnology vol. 29, pp. 149-153 (Jan. 19, 2011).
Zuris et al., Efficient Delivery of Genome-Editing Proteins In Vitro and In Vivo, Nat Biotechnol., 33(1): 73-80 (Jan. 2015).
Hsiao, J. et al., "Upregulation of Haploinsufficient Gene Expression in the Brain by Targeting a Long Non-coding RNA Improves Seizure Phenotype in a Model of Dravet Syndrome," EBioMedicine, 2016, vol. 9, pp. 257-277.
Grieger et al.: Production of Recombinant Adeno-associated Virus Vectors Using Suspension HEK293 Cells and Continuous Harvest of Vector From the Culture Media for Gmp FIX and FLT1 Clinical Vector. Mol. Ther. 24(2):287-297 (2016).

* cited by examiner

EF1a

RE 2

RE 2 + m1
GFP
A
B
C

PV
D
E
F
100 µm

GFP
High Resolution
G
H
I

PV
High Resolution
J
K
L
25 µm

SEQUENCE LISTING

```
<160> NUMBER OF SEQ ID NOS: 226

<210> SEQ ID NO 1
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gtgatgcggt tttggcagta catcaatggg cgtggatagc ggtttgactc acggggattt      60

ccaagtctcc accccattga cgtcaatggg agtttgtttt ggcaccaaaa tcaacgggac     120

tttccaaaat gtcgtaacaa ctccgcccca ttgacgcaaa tgggcggtag gcgtgtacgg     180

tgggaggtct atataagcag agctggtacc gtgtgtatgc tcaggggctg ggaaaggagg     240

ggagggagct ccggctcag                                                  259


<210> SEQ ID NO 2
<211> LENGTH: 2051
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2

```
ggaggaagcc atcaactaaa ctacaatgac tgtaagatac aaaattggga atggtaacat     60
attttgaagt tctgttgaca taaagaatca tgatattaat gcccatggaa atgaaagggc    120
gatcaacact atggtttgaa aagggggaaa ttgtagagca cagatgtgtt cgtgtggcag    180
tgtgctgtct ctagcaatac tcagagaaga gagagaacaa tgaaattctg attggcccca    240
gtgtgagccc agatgaggtt cagctgccaa ctttctcttt cacatcttat gaaagtcatt    300
taagcacaac taactttttt tttttttttt tttttttgag acagagtctt gctctgttgc    360
ccaggacaga gtgcagtagt gactcaatct cggctcactg cagcctccac ctcctaggct    420
caaacggtcc tcctgcatca gcctcccaag tagctggaat tacaggagtg gcccaccatg    480
cccagctaat ttttgtattt ttaatagata cggggggtttc accatatcac ccaggctggt    540
ctcgaactcc tggcctcaag tgatccacct gcctcggcct cccaaagtgc tgggattata    600
ggcgtcagcc actatgccca acccgaccaa cctttttttaa aataaatatt taaaaaattg    660
gtatttcaca tatatactag tatttacatt tatccacaca aaacggacgg gcctccgctg    720
aaccagtgag gccccagacg tgcgcataaa taacccctgc gtgctgcacc acctggggag    780
agggggagga ccacggtaaa tggagcgagc gcatagcaaa agggacgcgg ggtccttttc    840
tctgccggtg gcactgggta gctgtggcca ggtgtggtac tttgatgggg cccagggctg    900
gagctcaagg aagcgtcgca gggtcacaga tctgggggaa ccccggggaa aagcactgag    960
gcaaaaccgc cgctcgtctc ctacaatata tgggaggggg aggttgagta cgttctggat   1020
tactcataag accttttttt tttccttccg ggcgcaaaac cgtgagctgg atttataatc   1080
gccctataaa gctccagagg cggtcaggca cctgcagagg agccccgccg ctccgccgac   1140
tagctgcccc cgcgagcaac ggcctcgtga tttccccgcc gatccggtcc ccgcctcccc   1200
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag gggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct g                                                        2051
```

<210> SEQ ID NO 3
<211> LENGTH: 1878
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
tcaacagggg gacacttggg aaagaaggat ggggacagag ccgagaggac tgttacacat 60
tagagaaaca tcagtgactg tgccagcttt ggggtagact gcacaaaagc cctgaggcag 120
cacaggcagg atccagtctg ctggtcccag gaagctaacc gtctcagaca gagcacaaag 180
caccgagaca tgtgccacaa ggcttgtgta gagaggtcag aggacagcgt acaggtccca 240
gagatcaaac tcaacctcac caggcttggc agcaagcctt taccaaccca cccccacccc 300
acccaccctg cacgcgcccc tctcccctcc ccatggtctc ccatggctat ctcacttggc 360
cctaaaatgt ttaaggatga cactggctgc tgagtggaaa tgagacagca gaagtcaaca 420
gtagatttta ggaaagccag agaaaaaggc ttgtgctgtt tttagaaagc caagggacaa 480
gctaagatag ggcccaagta atgctagtat ttacatttat ccacacaaaa cggacgggcc 540
tccgctgaac cagtgaggcc ccagacgtgc gcataaataa cccctgcgtg ctgcaccacc 600
tggggagagg gggaggacca cggtaaatgg agcgagcgca tagcaaaagg gacgcggggt 660
ccttttctct gccggtggca ctgggtagct gtggccaggt gtggtacttt gatggggccc 720
agggctggag ctcaaggaag cgtcgcaggg tcacagatct gggggaaccc cggggaaaag 780
cactgaggca aaaccgccgc tcgtctccta caatatatgg gagggggagg ttgagtacgt 840
tctggattac tcataagacc ttttttttt ccttccgggc gcaaaaccgt gagctggatt 900
tataatcgcc ctataaagct ccagaggcgg tcaggcacct gcagaggagc cccgccgctc 960
cgccgactag ctgcccccgc gagcaacggc ctcgtgattt ccccgccgat ccggtccccg 1020
cctccccact ctgcccccgc ctaccccgga gccgtgcagc cgcctctccg aatctctctc 1080
ttctcctggc gctcgcgtgc gagagggaac tagcgagaac gaggaagcag ctggaggtga 1140
cgccgggcag attacgcctg tcagggccga gccgagcgga tcgctgggcg ctgtgcagag 1200
gaaaggcggg agtgcccggc tcgctgtcgc agagccgagg tgggtaagct agcgaccacc 1260
tggacttccc agcgcccaac cgtggctttt cagccaggtc ctctcctccc gcggcttctc 1320
aaccaacccc atcccagcgc cggccaccca acctcccgaa atgagtgctt cctgccccag 1380
cagccgaagg cgctactagg aacggtaacc tgttactttt ccaggggccg tagtcgaccc 1440
gctgcccgag ttgctgtgcg actgcgcgcg cggggctaga gtgcaaggtg actgtggttc 1500
ttctctggcc aagtccgagg gagaacgtaa agatatgggc ctttttcccc ctctcacctt 1560
gtctcaccaa agtccctagt ccccggagca gttagcctct ttctttccag ggaattagcc 1620
agacacaaca acgggaacca gacaccgaac cagacatgcc cgccccgtgc gccctccccg 1680
ctcgctgcct ttcctccctc ttgtctctcc agagccggat cttcaagggg agcctccgtg 1740
cccccggctg ctcagtccct ccggtgtgca ggaccccgga agtcctcccc gcacagctct 1800
cgcttctctt tgcagcctgt ttctgcgccg gaccagtcga ggactctgga cagtagaggc 1860
cccgggacga ccgagctg 1878

<210> SEQ ID NO 4
<211> LENGTH: 509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gccctctagg ccacctgacc aggtcccctc agtccccccc ttcccacact cccacactca     60

gccccccctcc cccccccccg accccctgcag gattatcctg tctgtgttcc tgactcagcc    120

tgggagccac ctgggcagca ggggccaagg gtgtcctaga agggacctgg agtccacgct    180

gggccaagcc tgccctttct ccctctgtct tccgtccctg cttgcggttc tgctgaatgt    240

ggttatttct ctggctcctt ttacagagaa tgctgctgct aattttatgt ggagctctga    300

ggcagtgtaa ttggaagcca gacaccctgt cagcagtggg ctcccgtcct gagctgccat    360

gcttcctgct ctcctcccgt cccggctcct catttcatgc agccacctgt cccagggaga    420

gaggagtcac ccaggcccct cagtccgccc cttaaataag aaagcctccg ttgctcggca    480

cacataccaa gcagccgctg gtgcaatct                                       509
```

<210> SEQ ID NO 5
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catgggtcga ggtgagcccc acgttctgct tcactctccc catctccccc ccctccccac    360

ccccaatttt gtatttattt atttttaat tattttgtgc agcgatgggg gcggggggg    420

gggggcgcg cgccaggcgg ggcggggcgg ggcgaggggc ggggcggggc gaggcggaga    480

ggtgcggcgg cagccaatca gagcggcgcg ctccgaaagt ttccttttat ggcgaggcgg    540

cggcggcggc ggccctataa aaagcgaagc gcgcggcggg cgggagtcgc tgcgttgcct    600

tcgccccgtg ccccgctccg cgccgcctcg cgccgcccgc cccggctctg actgaccgcg    660

ttactcccac aggtgagcgg gcgggacggc ccttctcctc cgggctgtaa ttagcgcttg    720

gtttaatgac ggctcgtttc ttttctgtgg ctgcgtgaaa gccttaaagg gctccgggag    780

ggccctttgt gcgggggga gcggctcggg gggtgcgtgc gtgtgtgtgt gcgtggggag    840

cgccgcgtgc ggcccgcgct gcccggcggc tgtgagcgct gcgggcgcgg cgcggggctt    900

tgtgcgctcc gcgtgtgcgc gaggggagcg cggccggggg cggtgccccg cggtgcgggg    960

gggctgcgag gggaacaaag gctgcgtgcg ggtgtgtgc gtgggggggt gagcaggggg   1020

tgtgggcgcg gcggtcgggc tgtaaccccc ccctgcaccc ccctccccga gttgctgagc   1080

acggcccggc ttcgggtgcg gggctccgtg cggggcgtgg cgcggggctc gccgtgccgg   1140

gcgggggtg gcggcaggtg ggggtgccgg gcggggcggg gccgcctcgg gccggggagg   1200

gctcggggga ggggcgcggc ggccccggag cgccggcggc tgtcgaggcg cggcgagccg   1260

cagccattgc cttttatggt aatcgtgcga gagggcgcag ggacttcctt tgtcccaaat   1320
```

```
ctggcggagc cgaaatctgg gaggcgccgc cgcacccccct ctagcgggcg cgggcgaagc   1380

ggtgcggcgc cggcaggaag gaaatgggcg gggagggcct tcgtgcgtcg ccgcgccgcc   1440

gtccccttct ccatctccag cctcggggct gccgcagggg gacggctgcc ttcggggggg   1500

acggggcagg gcggggttcg gcttctggcg tgtgaccggc ggctctagag cctctgctaa   1560

ccatgttcat gccttcttct ttttcctaca gctcctgggc aacgtgctgg ttgttgtgct   1620

gtctcatcat tttggcaaag aatt                                           1644
```

<210> SEQ ID NO 6
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gagtaattca tacaaaagga ctcgcccctg ccttggggaa tcccagggac cgtcgttaaa     60

ctcccactaa cgtagaaccc agagatcgct gcgttcccgc cccctcaccc gcccgctctc    120

gtcatcactg aggtggagaa gagcatgcgt gaggctccgg tgcccgtcag tgggcagagc    180

gcacatcgcc cacagtcccc gagaagttgg ggggaggggt cggcaattga accggtgcct    240

agagaaggtg gcgcggggta aactgggaaa gtgatgtcgt gtactggctc cgcctttttc    300

ccgagggtgg gggagaaccg tatataagtg cagtagtcgc cgtgaacgtt ctttttcgca    360

acgggtttgc cgccagaaca caggtaagtg ccgtgtgtgg ttcccgcggg cctggcctct    420

ttacgggtta tggcccttgc gtgccttgaa ttacttccac gcccctggct gcagtacgtg    480

attcttgatc ccgagcttcg ggttggaagt gggtgggaga gttcgaggcc ttgcgcttaa    540

ggagcccctt cgcctcgtgc ttgagttgag gcctggcttg ggcgctgggg ccgccgcgtg    600

cgaatctggt ggcaccttcg cgcctgtctc gctgctttcg ataagtctct agccatttaa    660

aatttttgat gacctgctgc gacgcttttt ttctggcaag atagtcttgt aaatgcgggc    720

caagatctgc acactggtat ttcggttttt ggggccgcgg gcggcgacgg ggcccgtgcg    780

tcccagcgca catgttcggc gaggcggggc ctgcgagcgc ggccaccgag aatcggacgg    840

gggtagtctc aagctggccg gcctgctctg gtgcctggcc tcgcgccgcc gtgtatcgcc    900

ccgccctggg cggcaaggct ggcccggtcg gcaccagttg cgtgagcgga aagatggccg    960

cttcccggcc ctgctgcagg gagctcaaaa tggaggacgc ggcgctcggg agagcgggcg   1020

ggtgagtcac ccacacaaag gaaaagggcc tttccgtcct cagccgtcgc ttcatgtgac   1080

tccacggagt accgggcgcc gtccaggcac ctcgattagt tctcgagctt ttggagtacg   1140

tcgtctttag gttgggggga ggggttttat gcgatggagt ttccccacac tgagtgggtg   1200

gagactgaag ttaggccagc ttggcacttg atgtaattct ccttggaatt tgcccttttt   1260

gagtttggat cttggttcat tctcaagcct cagacagtgg ttcaaagttt ttttcttcca   1320

tttcaggtgt cgtga                                                     1335
```

<210> SEQ ID NO 7
<211> LENGTH: 214
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
aaagagaccg gttcactgtg acagtaaaag agaccggttc actgtgagaa tgaaagagac     60

cggttcactg tgatcggaaa agagaccggt tcactgtgag cggccttgaa acccagcaga    120

caatgtagct cagtagaaac ccagcagaca atgtagctga atggaaaccc agcagacaat    180

gtagcttcgg agaaacccag cagacaatgt agct                                214


<210> SEQ ID NO 8
<211> LENGTH: 21
<212> TYPE: RNA
<213> ORGANISM: Homo sapiens

<400> SEQUENCE: 8

ucacagugaa ccggucucuu u                                               21


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

aaagagaccg gttcactgtg a                                               21


<210> SEQ ID NO 10
<211> LENGTH: 23
<212> TYPE: RNA
<213> ORGANISM: Homo sapiens

<400> SEQUENCE: 10

agcuacauug ucugcugggu uuc                                             23


<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

gaaacccagc agacaatgta gct                                             23


<210> SEQ ID NO 12
<211> LENGTH: 23
<212> TYPE: RNA
<213> ORGANISM: Homo sapiens

<400> SEQUENCE: 12

agcuacaucu ggcuacuggg ucu                                             23


<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

agacccagta gccagatgta gct                                             23
```

```
<210> SEQ ID NO 14
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

gaaacccagc agacaatgta gctagaccca gtagccagat gtagctaaag agaccggttc     60

actgtga                                                               67


<210> SEQ ID NO 15
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

gaaacccagc agacaatgta gctagaccca gtagccagat gtagctaaag agaccggttc     60

actgtgagaa acccagcaga caatgtagct agacccagta gccagatgta gctaaagaga    120

ccggttcact gtga                                                      134


<210> SEQ ID NO 16
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

aataaaagat ctttattttc attagatctg tgtgttggtt ttttgtgtgc ggaccgcacg     60

tg                                                                    62


<210> SEQ ID NO 17
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

gggtggcatc cctgtgaccc ctccccagtg cctctcctgg ccctggaagt tgccactcca     60

gtgcccacca gccttgtcct aataaaatta agttgcatca ttttgtctga ctaggtgtcc    120

ttctataata ttatggggtg gaggggggtg gtatggagca aggggcaagt tgggaagaca    180

acctgtaggg cctgcggggt ctattgggaa ccaagctgga gtgcagtggc acaatcttgg    240

ctcactgcaa tctccgcctc ctgggttcaa gcgattctcc tgcctcagcc tcccgagttg    300

ttgggattcc aggcatgcat gaccaggctc agctaatttt tgttttttttg gtagagacgg    360

ggtttcacca tattggccag gctggtctcc aactcctaat ctcaggtgat ctacccacct    420

tggcctccca aattgctggg attacaggcg tgaaccactg ctcccttccc tgtcctt       477


<210> SEQ ID NO 18
<211> LENGTH: 18
<212> TYPE: DNA
<213> ORGANISM: Homo sapiens
```

<400> SEQUENCE: 18
ctaggtcaag tgtaggag 18

<210> SEQ ID NO 19
<211> LENGTH: 18
<212> TYPE: DNA
<213> ORGANISM: Homo sapiens

<400> SEQUENCE: 19
acttgaccta gacagcct 18

<210> SEQ ID NO 20
<211> LENGTH: 18
<212> TYPE: DNA
<213> ORGANISM: Homo sapiens

<400> SEQUENCE: 20
tgaataactc attagtga 18

<210> SEQ ID NO 21
<211> LENGTH: 18
<212> TYPE: DNA
<213> ORGANISM: Homo sapiens

<400> SEQUENCE: 21
aaagtacatt aggctaat 18

<210> SEQ ID NO 22
<211> LENGTH: 18
<212> TYPE: DNA
<213> ORGANISM: Homo sapiens

<400> SEQUENCE: 22
ccagcactgg tgcttcgt 18

<210> SEQ ID NO 23
<211> LENGTH: 18
<212> TYPE: DNA
<213> ORGANISM: Homo sapiens

<400> SEQUENCE: 23
aaggctgtct aggtcaag 18

<210> SEQ ID NO 24
<211> LENGTH: 24
<212> TYPE: DNA
<213> ORGANISM: Homo sapiens

<400> SEQUENCE: 24
ctaggtcaag tgtaggagac acac 24

<210> SEQ ID NO 25
<211> LENGTH: 18
<212> TYPE: DNA
<213> ORGANISM: Homo sapiens

<400> SEQUENCE: 25
ggtcaagtgt aggagaca 18

<210> SEQ ID NO 26
<211> LENGTH: 18
<212> TYPE: DNA
<213> ORGANISM: Homo sapiens

<400> SEQUENCE: 26
caagtgtagg agacacac 18

<210> SEQ ID NO 27
<211> LENGTH: 24
<212> TYPE: DNA
<213> ORGANISM: Homo sapiens

<400> SEQUENCE: 27
agtgtaggag acacactgct ggcc 24

<210> SEQ ID NO 28
<211> LENGTH: 18
<212> TYPE: DNA
<213> ORGANISM: Homo sapiens

<400> SEQUENCE: 28
agtgtaggag acacactg 18

<210> SEQ ID NO 29
<211> LENGTH: 21
<212> TYPE: DNA
<213> ORGANISM: Homo sapiens

<400> SEQUENCE: 29
aggagacaca ctgctggcct g 21

<210> SEQ ID NO 30
<211> LENGTH: 18
<212> TYPE: DNA
<213> ORGANISM: Homo sapiens

<400> SEQUENCE: 30
taggtaccat agagtgag 18

<210> SEQ ID NO 31
<211> LENGTH: 18
<212> TYPE: DNA
<213> ORGANISM: Homo sapiens

<400> SEQUENCE: 31
gaggatactg cagaggtc 18

<210> SEQ ID NO 32
<211> LENGTH: 27
<212> TYPE: DNA
<213> ORGANISM: Homo sapiens

<400> SEQUENCE: 32
taggtaccat agagtgaggc gaggatg 27

<210> SEQ ID NO 33
<211> LENGTH: 27
<212> TYPE: DNA
<213> ORGANISM: Homo sapiens

<400> SEQUENCE: 33
atagagtgag gcgaggatga agccgag 27

<210> SEQ ID NO 34
<211> LENGTH: 27
<212> TYPE: DNA

<213> ORGANISM: Homo sapiens

<400> SEQUENCE: 34
tgaagccgag aggatactgc agaggtc 27

<210> SEQ ID NO 35
<211> LENGTH: 21
<212> TYPE: DNA
<213> ORGANISM: Homo sapiens

<400> SEQUENCE: 35
aaggctgtct aggtcaagtg t 21

<210> SEQ ID NO 36
<211> LENGTH: 21
<212> TYPE: DNA
<213> ORGANISM: Homo sapiens

<400> SEQUENCE: 36
tgttcctcca gattaacact t 21

<210> SEQ ID NO 37
<211> LENGTH: 21
<212> TYPE: DNA
<213> ORGANISM: Homo sapiens

<400> SEQUENCE: 37
gatgaagccg agaggatact g 21

<210> SEQ ID NO 38
<211> LENGTH: 21
<212> TYPE: DNA
<213> ORGANISM: Homo sapiens

<400> SEQUENCE: 38
gctgatttgt attaggtacc a 21

<210> SEQ ID NO 39
<211> LENGTH: 21
<212> TYPE: DNA
<213> ORGANISM: Homo sapiens

<400> SEQUENCE: 39
agaaagctga tacagataca a 21

<210> SEQ ID NO 40
<211> LENGTH: 21
<212> TYPE: DNA
<213> ORGANISM: Homo sapiens

<400> SEQUENCE: 40
ggtacgggca aagatttctt g 21

<210> SEQ ID NO 41
<211> LENGTH: 21
<212> TYPE: DNA
<213> ORGANISM: Homo sapiens

<400> SEQUENCE: 41
agaaagctga tacagataca a 21

<210> SEQ ID NO 42
<211> LENGTH: 21

<212> TYPE: DNA
<213> ORGANISM: Homo sapiens

<400> SEQUENCE: 42
acacaatgag ccacctacaa g 21

<210> SEQ ID NO 43
<211> LENGTH: 21
<212> TYPE: DNA
<213> ORGANISM: Homo sapiens

<400> SEQUENCE: 43
gtggctcatt gtgtgtgtgc c 21

<210> SEQ ID NO 44
<211> LENGTH: 21
<212> TYPE: DNA
<213> ORGANISM: Homo sapiens

<400> SEQUENCE: 44
catatccctg caggttcaga a 21

<210> SEQ ID NO 45
<211> LENGTH: 21
<212> TYPE: DNA
<213> ORGANISM: Homo sapiens

<400> SEQUENCE: 45
agagagagag agagagagag a 21

<210> SEQ ID NO 46
<211> LENGTH: 21
<212> TYPE: DNA
<213> ORGANISM: Homo sapiens

<400> SEQUENCE: 46
ttctcagttt tgaaattaaa a 21

<210> SEQ ID NO 47
<211> LENGTH: 21
<212> TYPE: DNA
<213> ORGANISM: Homo sapiens

<400> SEQUENCE: 47
tggattctct tctgaacctg c 21

<210> SEQ ID NO 48
<211> LENGTH: 21
<212> TYPE: DNA
<213> ORGANISM: Homo sapiens

<400> SEQUENCE: 48
tgctgaggca ggacacagtg t 21

<210> SEQ ID NO 49
<211> LENGTH: 21
<212> TYPE: DNA
<213> ORGANISM: Homo sapiens

<400> SEQUENCE: 49
atcatctgta accatcaagg a 21

<210> SEQ ID NO 50

<211> LENGTH: 21
<212> TYPE: DNA
<213> ORGANISM: Homo sapiens

<400> SEQUENCE: 50
tcctgcctac ttagtttcaa g 21

<210> SEQ ID NO 51
<211> LENGTH: 21
<212> TYPE: DNA
<213> ORGANISM: Homo sapiens

<400> SEQUENCE: 51
attacagttc tgtcagcatg c 21

<210> SEQ ID NO 52
<211> LENGTH: 21
<212> TYPE: DNA
<213> ORGANISM: Homo sapiens

<400> SEQUENCE: 52
tggtctcatt ctttttgtgg g 21

<210> SEQ ID NO 53
<211> LENGTH: 21
<212> TYPE: DNA
<213> ORGANISM: Homo sapiens

<400> SEQUENCE: 53
cgatattttc atggattcct t 21

<210> SEQ ID NO 54
<211> LENGTH: 21
<212> TYPE: DNA
<213> ORGANISM: Homo sapiens

<400> SEQUENCE: 54
ctgacactta ctttgtctaa a 21

<210> SEQ ID NO 55
<211> LENGTH: 21
<212> TYPE: DNA
<213> ORGANISM: Homo sapiens

<400> SEQUENCE: 55
aaaactggaa ccgcattccc a 21

<210> SEQ ID NO 56
<211> LENGTH: 21
<212> TYPE: DNA
<213> ORGANISM: Homo sapiens

<400> SEQUENCE: 56
acaaagtaag tgtcagtgtg g 21

<210> SEQ ID NO 57
<211> LENGTH: 21
<212> TYPE: DNA
<213> ORGANISM: Homo sapiens

<400> SEQUENCE: 57
ataatagttg tgtctttata a 21

<210> SEQ ID NO 58
<211> LENGTH: 21
<212> TYPE: DNA
<213> ORGANISM: Homo sapiens

<400> SEQUENCE: 58
tgtacaagca gggctgcaaa g 21

<210> SEQ ID NO 59
<211> LENGTH: 21
<212> TYPE: DNA
<213> ORGANISM: Homo sapiens

<400> SEQUENCE: 59
gttaacaaat acactaaaca c 21

<210> SEQ ID NO 60
<211> LENGTH: 21
<212> TYPE: DNA
<213> ORGANISM: Homo sapiens

<400> SEQUENCE: 60
ttcaacaagc tcccaagaag t 21

<210> SEQ ID NO 61
<211> LENGTH: 21
<212> TYPE: DNA
<213> ORGANISM: Homo sapiens

<400> SEQUENCE: 61
atgttcaagg tgcagaagga a 21

<210> SEQ ID NO 62
<211> LENGTH: 21
<212> TYPE: DNA
<213> ORGANISM: Homo sapiens

<400> SEQUENCE: 62
tgtttgctca aacgtgcacc a 21

<210> SEQ ID NO 63
<211> LENGTH: 21
<212> TYPE: DNA
<213> ORGANISM: Homo sapiens

<400> SEQUENCE: 63
aaataagaca tgaaaacaag a 21

<210> SEQ ID NO 64
<211> LENGTH: 21
<212> TYPE: DNA
<213> ORGANISM: Homo sapiens

<400> SEQUENCE: 64
aaatatgtac cacaagaaat g 21

<210> SEQ ID NO 65
<211> LENGTH: 21
<212> TYPE: DNA
<213> ORGANISM: Homo sapiens

<400> SEQUENCE: 65
tatctggttt ctctcactgc t 21

<210> SEQ ID NO 66
<211> LENGTH: 21
<212> TYPE: DNA
<213> ORGANISM: Homo sapiens

<400> SEQUENCE: 66
attgcaaagc ataatttgga t 21

<210> SEQ ID NO 67
<211> LENGTH: 3585
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
ggaggaagcc atcaactaaa ctacaatgac tgtaagatac aaaattggga atggtaacat 60
attttgaagt tctgttgaca taaagaatca tgatattaat gcccatggaa atgaaagggc 120
gatcaacact atggtttgaa aagggggaaa ttgtagagca cagatgtgtt cgtgtggcag 180
tgtgctgtct ctagcaatac tcagagaaga gagagaacaa tgaaattctg attggcccca 240
gtgtgagccc agatgaggtt cagctgccaa ctttctcttt cacatcttat gaaagtcatt 300
taagcacaac taactttttt tttttttttt tttttttgag acagagtctt gctctgttgc 360
ccaggacaga gtgcagtagt gactcaatct cggctcactg cagcctccac ctcctaggct 420
caaacggtcc tcctgcatca gcctcccaag tagctggaat tacaggagtg gcccaccatg 480
cccagctaat ttttgtattt ttaatagata cgggggtttc accatatcac ccaggctggt 540
ctcgaactcc tggcctcaag tgatccacct gcctcggcct cccaaagtgc tgggattata 600
ggcgtcagcc actatgccca acccgaccaa cctttttttaa aataaatatt taaaaaattg 660
gtatttcaca tatatactag tatttacatt tatccacaca aaacggacgg gcctccgctg 720
aaccagtgag gccccagacg tgcgcataaa taacccctgc gtgctgcacc acctggggag 780
agggggagga ccacggtaaa tggagcgagc gcatagcaaa agggacgcgg ggtccttttc 840
tctgccggtg gcactgggta gctgtggcca ggtgtggtac tttgatgggg cccagggctg 900
gagctcaagg aagcgtcgca gggtcacaga tctgggggaa ccccggggaa aagcactgag 960
gcaaaaccgc cgctcgtctc ctacaatata tgggaggggg aggttgagta cgttctggat 1020
tactcataag accttttttt tttccttccg ggcgcaaaac cgtgagctgg atttataatc 1080
gccctataaa gctccagagg cggtcaggca cctgcagagg agccccgccg ctccgccgac 1140
tagctgcccc cgcgagcaac ggcctcgtga tttccccgcc gatccggtcc ccgcctcccc 1200
actctgcccc cgcctacccc ggagccgtgc agccgcctct ccgaatctct ctcttctcct 1260
ggcgctcgcg tgcgagaggg aactagcgag aacgaggaag cagctggagg tgacgccggg 1320
cagattacgc ctgtcagggc cgagccgagc ggatcgctgg gcgctgtgca gaggaaaggc 1380
gggagtgccc ggctcgctgt cgcagagccg aggtgggtaa gctagcgacc acctggactt 1440
cccagcgccc aaccgtggct tttcagccag gtcctctcct cccgcggctt ctcaaccaac 1500
cccatcccag cgccggccac ccaacctccc gaaatgagtg cttcctgccc cagcagccga 1560
aggcgctact aggaacggta acctgttact tttccagggg ccgtagtcga cccgctgccc 1620
gagttgctgt gcgactgcgc gcgcggggct agagtgcaag gtgactgtgg ttcttctctg 1680
gccaagtccg agggagaacg taaagatatg ggcctttttc cccctctcac cttgtctcac 1740

-continued

```
caaagtccct agtccccgga gcagttagcc tctttctttc cagggaatta gccagacaca   1800

acaacgggaa ccagacaccg aaccagacat gcccgccccg tgcgccctcc ccgctcgctg   1860

cctttcctcc ctcttgtctc tccagagccg gatcttcaag gggagcctcc gtgcccccgg   1920

ctgctcagtc cctccggtgt gcaggacccc ggaagtcctc cccgcacagc tctcgcttct   1980

ctttgcagcc tgtttctgcg ccggaccagt cgaggactct ggacagtaga ggccccggga   2040

cgaccgagct ggaattcgcc accatggccc caaagaagaa gcggaaggtc ggtatccacg   2100

gagtcccagc agccctcgaa ccaggtgaaa aaccttacaa atgtcctgaa tgtgggaaat   2160

cattcagtcg cagcgacaac ctggtgagac atcaacgcac ccatacagga gaaaaacctt   2220

ataaatgtcc agaatgtgga aagtccttct cacgagagga taacttgcac actcatcaac   2280

gaacacatac tggtgaaaaa ccatacaagt gtcccgaatg tggtaaaagt tttagccgga   2340

gcgatgaact tgtccgacac caacgaaccc atacaggcga gaagccttac aaatgtcccg   2400

agtgtggcaa gagcttctca caatcaggga atctgactga gcatcaacga actcataccg   2460

gggaaaaacc ttacaagtgt ccagagtgtg ggaagagctt ttccacaagt ggacatctgg   2520

tacgccacca gaggacacat acaggggaga agccctacaa atgccccgaa tgcggtaaaa   2580

gtttctctca gaatagtacc ctgaccgaac accagcgaac acacactggg aaaaaaacga   2640

gtaaaaggcc ggcggccacg aaaaaggccg gccaggcaaa aaagaaaaag ggatcctacc   2700

catacgacgt accagattac gctctcgagg acgcgctgga cgatttcgat ctcgacatgc   2760

tgggttctga tgccctcgat gactttgacc tggatatgtt gggaagcgac gcattggatg   2820

actttgatct ggacatgctc ggctccgatg ctctggacga tttcgatctc gatatgttat   2880

aaactagtaa agagaccggt tcactgtgac agtaaaagag accggttcac tgtgagaatg   2940

aaagagaccg gttcactgtg atcggaaaag agaccggttc actgtgagcg gccttgaaac   3000

ccagcagaca atgtagctca gtagaaaccc agcagacaat gtagctgaat ggaaacccag   3060

cagacaatgt agcttcggag aaacccagca gacaatgtag ctaagcttgg gtggcatccc   3120

tgtgacccct ccccagtgcc tctcctggcc ctggaagttg ccactccagt gcccaccagc   3180

cttgtcctaa taaaattaag ttgcatcatt ttgtctgact aggtgtcctt ctataatatt   3240

atggggtgga ggggggtggt atggagcaag gggcaagttg ggaagacaac ctgtagggcc   3300

tgcggggtct attgggaacc aagctggagt gcagtggcac aatcttggct cactgcaatc   3360

tccgcctcct gggttcaagc gattctcctg cctcagcctc ccgagttgtt gggattccag   3420

gcatgcatga ccaggctcag ctaatttttg tttttttggt agagacgggg tttcaccata   3480

ttggccaggc tggtctccaa ctcctaatct caggtgatct acccaccttg gcctcccaaa   3540

ttgctgggat tacaggcgtg aaccactgct cccttccctg tcctt                    3585
```

<210> SEQ ID NO 68
<211> LENGTH: 3371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
ggaggaagcc atcaactaaa ctacaatgac tgtaagatac aaaattggga atggtaacat     60

attttgaagt tctgttgaca taaagaatca tgatattaat gcccatggaa atgaaagggc    120

gatcaacact atggtttgaa aagggggaaa ttgtagagca cagatgtgtt cgtgtggcag    180
```

-continued

```
tgtgctgtct ctagcaatac tcagagaaga gagagaacaa tgaaattctg attggcccca    240
gtgtgagccc agatgaggtt cagctgccaa ctttctcttt cacatcttat gaaagtcatt    300
taagcacaac taactttttt tttttttttt tttttttgag acagagtctt gctctgttgc    360
ccaggacaga gtgcagtagt gactcaatct cggctcactg cagcctccac ctcctaggct    420
caaacggtcc tcctgcatca gcctcccaag tagctggaat tacaggagtg gcccaccatg    480
cccagctaat ttttgtattt ttaatagata cggggggtttc accatatcac ccaggctggt   540
ctcgaactcc tggcctcaag tgatccacct gcctcggcct cccaaagtgc tgggattata    600
ggcgtcagcc actatgccca acccgaccaa cctttttttaa aataaatatt taaaaaattg   660
gtatttcaca tatatactag tatttacatt tatccacaca aaacggacgg gcctccgctg    720
aaccagtgag gccccagacg tgcgcataaa taacccctgc gtgctgcacc acctggggag    780
agggggagga ccacggtaaa tggagcgagc gcatagcaaa agggacgcgg ggtccttttc    840
tctgccggtg gcactgggta gctgtggcca ggtgtggtac tttgatgggg cccagggctg    900
gagctcaagg aagcgtcgca gggtcacaga tctgggggaa ccccggggaa aagcactgag    960
gcaaaaccgc cgctcgtctc ctacaatata tgggaggggg aggttgagta cgttctggat   1020
tactcataag acctttttttt tttccttccg ggcgcaaaac cgtgagctgg atttataatc  1080
gccctataaa gctccagagg cggtcaggca cctgcagagg agccccgccg ctccgccgac   1140
tagctgcccc cgcgagcaac ggcctcgtga tttccccgcc gatccggtcc ccgcctcccc   1200
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag gggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccc caaagaagaa gcggaaggtc ggtatccacg   2100
gagtcccagc agccctcgaa ccaggtgaaa aaccttacaa atgtcctgaa tgtgggaaat   2160
cattcagtcg cagcgacaac ctggtgagac atcaacgcac ccatacagga gaaaaacctt   2220
ataaatgtcc agaatgtgga aagtccttct cacgagagga taacttgcac actcatcaac   2280
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
```

```
gtttctctca gaatagtacc ctgaccgaac accagcgaac acacactggg aaaaaaacga   2640

gtaaaaggcc ggcggccacg aaaaaggccg gccaggcaaa aaagaaaaag ggatcctacc   2700

catacgacgt accagattac gctctcgagg acgcgctgga cgatttcgat ctcgacatgc   2760

tgggttctga tgccctcgat gactttgacc tggatatgtt gggaagcgac gcattggatg   2820

actttgatct ggacatgctc ggctccgatg ctctggacga tttcgatctc gatatgttat   2880

aaactagtaa gcttgggtgg catccctgtg acccctcccc agtgcctctc ctggccctgg   2940

aagttgccac tccagtgccc accagccttg tcctaataaa attaagttgc atcattttgt   3000

ctgactaggt gtccttctat aatattatgg ggtggagggg ggtggtatgg agcaaggggc   3060

aagttgggaa gacaacctgt agggcctgcg ggtctattg ggaaccaagc tggagtgcag    3120

tggcacaatc ttggctcact gcaatctccg cctcctgggt tcaagcgatt ctcctgcctc   3180

agcctcccga gttgttggga ttccaggcat gcatgaccag gctcagctaa tttttgtttt   3240

tttggtagag acggggtttc accatattgg ccaggctggt ctccaactcc taatctcagg   3300

tgatctaccc accttggcct cccaaattgc tgggattaca ggcgtgaacc actgctccct   3360

tccctgtcct t                                                       3371
```

```
<210> SEQ ID NO 69
<211> LENGTH: 4380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
```

```
ggaggaagcc atcaactaaa ctacaatgac tgtaagatac aaaattggga atggtaacat     60

attttgaagt tctgttgaca taaagaatca tgatattaat gcccatggaa atgaaagggc    120

gatcaacact atggtttgaa aagggggaaa ttgtagagca cagatgtgtt cgtgtggcag    180

tgtgctgtct ctagcaatac tcagagaaga gagagaacaa tgaaattctg attggcccca    240

gtgtgagccc agatgaggtt cagctgccaa ctttctcttt cacatcttat gaaagtcatt    300

taagcacaac taactttttt tttttttttt tttttttgag acagagtctt gctctgttgc    360

ccaggacaga gtgcagtagt gactcaatct cggctcactg cagcctccac ctcctaggct    420

caaacggtcc tcctgcatca gcctcccaag tagctggaat tacaggagtg gcccaccatg    480

cccagctaat ttttgtattt ttaatagata cgggggtttc accatatcac ccaggctggt    540

ctcgaactcc tggcctcaag tgatccacct gcctcggcct cccaaagtgc tgggattata    600

ggcgtcagcc actatgccca acccgaccaa cctttttttaa aataaatatt taaaaaattg    660

gtatttcaca tatatactag tatttacatt tatccacaca aaacggacgg gcctccgctg    720

aaccagtgag gccccagacg tgcgcataaa taacccctgc gtgctgcacc acctggggag    780

agggggagga ccacggtaaa tggagcgagc gcatagcaaa agggacgcgg ggtccttttc    840

tctgccggtg gcactgggta gctgtggcca ggtgtggtac tttgatgggg cccagggctg    900

gagctcaagg aagcgtcgca gggtcacaga tctgggggaa ccccggggaa aagcactgag    960

gcaaaaccgc cgctcgtctc ctacaatata tgggaggggg aggttgagta cgttctggat   1020

tactcataag acctttttt tttccttccg ggcgcaaaac cgtgagctgg atttataatc    1080

gccctataaa gctccagagg cggtcaggca cctgcagagg agccccgccg ctccgccgac   1140

tagctgcccc cgcgagcaac ggcctcgtga tttccccgcc gatccggtcc ccgcctcccc   1200
```

-continued

```
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag ggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccc caaagaagaa gcggaaggtc ggtatccacg   2100
gagtcccagc agccctcgaa ccaggtgaaa aaccttacaa atgtcctgaa tgtgggaaat   2160
cattcagtcg cagcgacaac ctggtgagac atcaacgcac ccatacagga gaaaaacctt   2220
ataaatgtcc agaatgtgga aagtccttct cacgagagga taacttgcac actcatcaac   2280
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
gtttctctca gaatagtacc ctgaccgaac accagcgaac acacactggg aaaaaaacga   2640
gtaaaaggcc ggcggccacg aaaaaggccg gccaggcaaa aaagaaaaag ggatcctacc   2700
catacgacgt accagattac gctctcgagg aggccagcgg ttccggacgg gctgacgcat   2760
tggacgattt tgatctggat atgctgggaa gtgacgccct cgatgatttt gaccttgaca   2820
tgcttggttc ggatgccctt gatgactttg acctcgacat gctcggcagt gacgcccttg   2880
atgatttcga cctggacatg ctgattaact ctagaagttc cggatctccg aaaaagaaac   2940
gcaaagttgg tagccagtac ctgcccgaca ccgacgaccg gcaccggatc gaggaaaagc   3000
ggaagcggac ctacgagaca ttcaagagca tcatgaagaa gtccccctc agcggcccca   3060
ccgaccctag acctccacct agaagaatcg ccgtgcccag cagatccagc gccagcgtgc   3120
caaaacctgc cccccagcct tacccccttca ccagcagcct gagcaccatc aactacgacg   3180
agttccctac catggtgttc cccagcggcc agatctctca ggcctctgct ctggctccag   3240
cccctcctca ggtgctgcct caggctcctg ctcctgcacc agctccagcc atggtgtctg   3300
cactggctca ggcaccagca cccgtgcctg tgctggctcc tggacctcca caggctgtgg   3360
ctccaccagc ccctaaacct acacaggccg gcgagggcac actgtctgaa gctctgctgc   3420
agctgcagtt cgacgacgag gatctgggag ccctgctggg aaacagcacc gatcctgccg   3480
tgttcaccga cctggccagc gtggacaaca gcgagttcca gcagctgctg aaccagggca   3540
```

tccctgtggc cctcacacc accgagccca tgctgatgga ataccccgag gccatcaccc 3600
ggctcgtgac aggcgctcag aggcctcctg atccagctcc tgcccctctg ggagcaccag 3660
gcctgcctaa tggactgctg tctggcgacg aggacttcag ctctatcgcc gatatggatt 3720
tctcagcctt gctgggctct ggcagcggca gccgggattc cagggaaggg atgtttttgc 3780
cgaagcctga ggccggctcc gctattagtg acgtgtttga gggccgcgag gtgtgccagc 3840
caaaacgaat ccggccattt catcctccag gaagtccatg ggccaaccgc ccactccccg 3900
ccagcctcgc accaacacca accggtccag tacatgagcc agtcgggtca ctgaccccgg 3960
caccagtccc tcagccactg gatccagcgc ccgcagtgac tcccgaggcc agtcacctgt 4020
tggaggatcc cgatgaagag acgagccagg ctgtcaaagc ccttcgggag atggccgata 4080
ctgtgattcc ccagaaggaa gaggctgcaa tctgtggcca aatggacctt tcccatccgc 4140
ccccaagggg ccatctggat gagctgacaa ccacacttga gtccatgacc gaggatctga 4200
acctggactc acccctgacc ccggaattga acgagattct ggataccttc ctgaacgacg 4260
agtgcctctt gcatgccatg catatcagca caggactgtc catcttcgac acatctctgt 4320
tttaaactag taataaaaga tctttatttt cattagatct gtgtgttggt tttttgtgtg 4380

<210> SEQ ID NO 70
<211> LENGTH: 3332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
ggaggaagcc atcaactaaa ctacaatgac tgtaagatac aaaattggga atggtaacat 60
attttgaagt tctgttgaca taaagaatca tgatattaat gcccatggaa atgaaagggc 120
gatcaacact atggtttgaa aagggggaaa ttgtagagca cagatgtgtt cgtgtggcag 180
tgtgctgtct ctagcaatac tcagagaaga gagagaacaa tgaaattctg attggcccca 240
gtgtgagccc agatgaggtt cagctgccaa ctttctcttt cacatcttat gaaagtcatt 300
taagcacaac taactttttt tttttttttt tttttttgag acagagtctt gctctgttgc 360
ccaggacaga gtgcagtagt gactcaatct cggctcactg cagcctccac ctcctaggct 420
caaacggtcc tcctgcatca gcctcccaag tagctggaat tacaggagtg gcccaccatg 480
cccagctaat ttttgtattt ttaatagata cggggggtttc accatatcac ccaggctggt 540
ctcgaactcc tggcctcaag tgatccacct gcctcggcct cccaaagtgc tgggattata 600
ggcgtcagcc actatgccca acccgaccaa cctttttttaa aataaatatt taaaaaattg 660
gtatttcaca tatatactag tatttacatt tatccacaca aaacggacgg gcctccgctg 720
aaccagtgag gccccagacg tgcgcataaa taacccctgc gtgctgcacc acctggggag 780
agggggagga ccacggtaaa tggagcgagc gcatagcaaa agggacgcgg ggtccttttc 840
tctgccggtg gcactgggta gctgtggcca ggtgtggtac tttgatgggg cccagggctg 900
gagctcaagg aagcgtcgca gggtcacaga tctgggggaa ccccggggaa aagcactgag 960
gcaaaaccgc cgctcgtctc ctacaatata tgggaggggg aggttgagta cgttctggat 1020
tactcataag accttttttt tttccttccg ggcgcaaaac cgtgagctgg atttataatc 1080
gccctataaa gctccagagg cggtcaggca cctgcagagg agccccgccg ctccgccgac 1140
tagctgcccc cgcgagcaac ggcctcgtga tttccccgcc gatccggtcc ccgcctcccc 1200

```
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag ggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccc caaagaagaa gcggaaggtc ggtatccacg   2100
gagtcccagc agccctcgaa ccaggtgaaa aaccttacaa atgtcctgaa tgtgggaaat   2160
cattcagtcg cagcgacaac ctggtgagac atcaacgcac ccatacagga gaaaaacctt   2220
ataaatgtcc agaatgtgga aagtccttct cacgagagga taacttgcac actcatcaac   2280
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
gtttctctca gaatagtacc ctgaccgaac accagcgaac acacactggg aaaaaaacga   2640
gtaaaaggcc ggcggccacg aaaaaggccg gccaggcaaa aaagaaaaag ggatccgacg   2700
cgctggacga tttcgatctc gacatgctgg gttctgatgc cctcgatgac tttgacctgg   2760
atatgttggg aagcgacgca ttggatgact ttgatctgga catgctcggc tccgatgctc   2820
tggacgattt cgatctcgat atgttataaa agcttgggtg gcatccctgt gacccctccc   2880
cagtgcctct cctggccctg gaagttgcca ctccagtgcc caccagcctt gtcctaataa   2940
aattaagttg catcattttg tctgactagg tgtccttcta taatattatg gggtggaggg   3000
gggtggtatg gagcaagggg caagttggga agacaacctg tagggcctgc ggggtctatt   3060
gggaaccaag ctggagtgca gtggcacaat cttggctcac tgcaatctcc gcctcctggg   3120
ttcaagcgat tctcctgcct cagcctcccg agttgttggg attccaggca tgcatgacca   3180
ggctcagcta atttttgttt ttttggtaga gacggggttt caccatattg gccaggctgg   3240
tctccaactc ctaatctcag gtgatctacc caccttggcc tcccaaattg ctgggattac   3300
aggcgtgaac cactgctccc ttccctgtcc tt                                  3332
```

<210> SEQ ID NO 71
<211> LENGTH: 3546
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71
ggaggaagcc atcaactaaa ctacaatgac tgtaagatac aaaattggga atggtaacat 60
attttgaagt tctgttgaca taaagaatca tgatattaat gcccatggaa atgaaagggc 120
gatcaacact atggtttgaa aagggggaaa ttgtagagca cagatgtgtt cgtgtggcag 180
tgtgctgtct ctagcaatac tcagagaaga gagagaacaa tgaaattctg attggcccca 240
gtgtgagccc agatgaggtt cagctgccaa ctttctcttt cacatcttat gaaagtcatt 300
taagcacaac taactttttt tttttttttt tttttttgag acagagtctt gctctgttgc 360
ccaggacaga gtgcagtagt gactcaatct cggctcactg cagcctccac ctcctaggct 420
caaacggtcc tcctgcatca gcctcccaag tagctggaat tacaggagtg gcccaccatg 480
cccagctaat ttttgtattt ttaatagata cgggggtttc accatatcac ccaggctggt 540
ctcgaactcc tggcctcaag tgatccacct gcctcggcct cccaaagtgc tgggattata 600
ggcgtcagcc actatgccca acccgaccaa cctttttttaa aataaatatt taaaaaattg 660
gtatttcaca tatatactag tatttacatt tatccacaca aaacggacgg gcctccgctg 720
aaccagtgag gccccagacg tgcgcataaa taacccctgc gtgctgcacc acctggggag 780
agggggagga ccacggtaaa tggagcgagc gcatagcaaa agggacgcgg ggtccttttc 840
tctgccggtg gcactgggta gctgtggcca ggtgtggtac tttgatgggg cccagggctg 900
gagctcaagg aagcgtcgca gggtcacaga tctgggggaa ccccggggaa aagcactgag 960
gcaaaaccgc cgctcgtctc ctacaatata tgggaggggg aggttgagta cgttctggat 1020
tactcataag accttttttt tttccttccg ggcgcaaaac cgtgagctgg atttataatc 1080
gccctataaa gctccagagg cggtcaggca cctgcagagg agccccgccg ctccgccgac 1140
tagctgcccc cgcgagcaac ggcctcgtga tttccccgcc gatccggtcc ccgcctcccc 1200
actctgcccc cgcctacccc ggagccgtgc agccgcctct ccgaatctct ctcttctcct 1260
ggcgctcgcg tgcgagaggg aactagcgag aacgaggaag cagctggagg tgacgccggg 1320
cagattacgc ctgtcagggc cgagccgagc ggatcgctgg gcgctgtgca gaggaaaggc 1380
gggagtgccc ggctcgctgt cgcagagccg aggtgggtaa gctagcgacc acctggactt 1440
cccagcgccc aaccgtggct tttcagccag gtcctctcct cccgcggctt ctcaaccaac 1500
cccatcccag cgccggccac ccaacctccc gaaatgagtg cttcctgccc cagcagccga 1560
aggcgctact aggaacggta acctgttact tttccagggg ccgtagtcga cccgctgccc 1620
gagttgctgt gcgactgcgc gcgcggggct agagtgcaag gtgactgtgg ttcttctctg 1680
gccaagtccg agggagaacg taaagatatg ggcctttttc cccctctcac cttgtctcac 1740
caaagtccct agtccccgga gcagttagcc tctttctttc cagggaatta gccagacaca 1800
acaacgggaa ccagacaccg aaccagacat gcccgccccg tgcgccctcc ccgctcgctg 1860
cctttcctcc ctcttgtctc tccagagccg gatcttcaag gggagcctcc gtgcccccgg 1920
ctgctcagtc cctccggtgt gcaggacccc ggaagtcctc cccgcacagc tctcgcttct 1980
ctttgcagcc tgtttctgcg ccggaccagt cgaggactct ggacagtaga ggccccggga 2040
cgaccgagct ggaattcgcc accatggccc caaagaagaa gcggaaggtc ggtatccacg 2100
gagtcccagc agccctcgaa ccaggtgaaa aaccttacaa atgtcctgaa tgtgggaaat 2160
cattcagtcg cagcgacaac ctggtgagac atcaacgcac ccatacagga gaaaaacctt 2220
ataaatgtcc agaatgtgga aagtccttct cacgagagga taacttgcac actcatcaac 2280

```
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
gtttctctca gaatagtacc ctgaccgaac accagcgaac acacactggg aaaaaaacga   2640
gtaaaaggcc ggcggccacg aaaaaggccg gccaggcaaa aaagaaaaag ggatccgacg   2700
cgctggacga tttcgatctc gacatgctgg gttctgatgc cctcgatgac tttgacctgg   2760
atatgttggg aagcgacgca ttggatgact ttgatctgga catgctcggc tccgatgctc   2820
tggacgattt cgatctcgat atgttataaa aagagaccgg ttcactgtga cagtaaaaga   2880
gaccggttca ctgtgagaat gaaagagacc ggttcactgt gatcggaaaa gagaccggtt   2940
cactgtgagc ggccttgaaa cccagcagac aatgtagctc agtagaaacc cagcagacaa   3000
tgtagctgaa tggaaaccca gcagacaatg tagcttcgga gaaacccagc agacaatgta   3060
gctaagcttg ggtggcatcc ctgtgacccc tccccagtgc ctctcctggc cctggaagtt   3120
gccactccag tgcccaccag ccttgtccta ataaaattaa gttgcatcat tttgtctgac   3180
taggtgtcct tctataatat tatggggtgg aggggggtgg tatggagcaa ggggcaagtt   3240
gggaagacaa cctgtagggc ctgcggggtc tattgggaac caagctggag tgcagtggca   3300
caatcttggc tcactgcaat ctccgcctcc tgggttcaag cgattctcct gcctcagcct   3360
cccgagttgt tgggattcca ggcatgcatg accaggctca gctaattttt gtttttttgg   3420
tagagacggg gtttcaccat attggccagg ctggtctcca actcctaatc tcaggtgatc   3480
tacccacctt ggcctcccaa attgctggga ttacaggcgt gaaccactgc tcccttccct   3540
gtcctt                                                              3546
```

<210> SEQ ID NO 72
<211> LENGTH: 1707
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atggccgcag atcacctgat gctggctgaa ggctacagac tggtgcagcg gcctccatct     60
gccgctgccg cccacggccc ccacgccctg agaacactgc ccccctacgc cggccctggt    120
cttgatagcg gactcagacc tagaggcgcc cctctgggcc ctccacctcc aagacagcct    180
ggagccctgg cctacggcgc cttcggccct ccttctagct tccagccctt ccccgccgtg    240
cctcctccag ccgctggcat cgcccacctg cagcctgtgg ccacccctta ccccggaaga    300
gccgccgccc ctccaaacgc ccctggcgga cctcctggcc cccagcctgc tccaagcgcc    360
gctgcccctc cacctcctgc tcatgccctg ggcggcatgg acgccgagct gatcgacgag    420
gaagccctga ccagcctgga actggaactg ggcctgcaca gagtgcggga actgcctgag    480
ctgttcctgg gacagagcga gttcgactgc ttcagcgacc tgggcagcgc ccctcctgcc    540
ggctctgtgt cctgcgccga ccacctgatg ctcgccgagg gctaccgcct ggtgcagagg    600
ccgccgtccg ccgccgccgc ccatggccct catgcgctcc ggactctgcc gccgtacgcg    660
ggcccgggcc tggacagtgg gctgaggccg cggggggctc cgctggggcc gccgccgccc    720
```

```
cgccaacccg gggccctggc gtacggggcc ttcgggccgc cgtcctcctt ccagcccttt    780
ccggccgtgc ctccgccggc cgcgggcatc gcgcacctgc agcctgtggc gacgccgtac    840
cccggccgcg ccgccgcgcc ccccaacgct ccgggaggcc ccccgggccc gcagccggcc    900
ccaagcgccg cagccccgcc gccgcccgcg cacgccctgg gcggcatgga cgccgaactc    960
atcgacgagg aggcgctgac gtcgctggag ctggagctgg ggctgcaccg cgtgcgcgag   1020
ctgcccgagc tgttcctggg ccagagcgag ttcgactgct tctcggactt ggggtccgcg   1080
ccgcccgccg gctccgtgag ctgccagtcc cagctcatca aacccagccg catgcgcaag   1140
taccccaacc ggcccagcaa gacgcccccc cacgaacgcc cttacgcttg cccagtggag   1200
tcctgtgatc gccgcttctc ccgcagcgac aacctggtga gacacatccg catccacaca   1260
ggccagaagc ccttccagtg ccgcatctgc atgagaaact tcagccgaga ggataacttg   1320
cacactcaca tccgcaccca cacaggcgaa aagcccttcg cctgcgacat ctgtggaaga   1380
aagtttgccc ggagcgatga acttgtccga cataccaaga tccacttgcg gcagaaggac   1440
cgcccttacg cttgcccagt ggagtcctgt gatcgccgct tctcccaatc agggaatctg   1500
actgagcaca tccgcatcca cacaggccag aagcccttcc agtgccgcat ctgcatgaga   1560
aacttcagca caagtggaca tctggtacgc cacatccgca cccacacagg cgaaaagccc   1620
ttcgcctgcg acatctgtgg aagaaagttt gcccagaata gtaccctgac cgaacatacc   1680
aagatccact tgcggcagaa ggacaag                                       1707
```

```
<210> SEQ ID NO 73
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
```

```
atggccgcag atcacctgat gctggctgaa ggctacagac tggtgcagcg gcctccatct     60
gccgctgccg cccacggccc ccacgccctg agaacactgc ccccctacgc cggccctggt    120
cttgatagcg gactcagacc tagaggcgcc cctctgggcc ctccacctcc aagacagcct    180
ggagccctgg cctacggcgc cttcggccct ccttctagct tccagccctt ccccgccgtg    240
cctcctccag ctgctggcat cgcccacctg cagcctgtgg ccacccctta ccccggaaga    300
gccgccgccc ctccaaacgc ccctggcgga cctcctggcc cccagcctgc tccaagcgcc    360
gctgcccctc cacctcctgc tcatgccctg ggcggcatgg acgccgagct gatcgacgag    420
gaagccctga ccagcctgga actggaactg ggcctgcaca gagtgcggga actgcctgag    480
ctgttcctgg gacagagcga gttcgactgc ttcagcgacc tgggcagcgc ccctcctgcc    540
ggctctgtgt cctgcggcgg cagcggcggc ggaagcggcg ccgaccacct gatgctcgcc    600
gagggctacc gcctggtgca gaggccgccg tccgccgccg ccgcccatgg ccctcatgcg    660
ctccggactc tgccgccgta cgcgggcccg ggcctggaca gtgggctgag gccgcggggg    720
gctccgctgg ggccgccgcc gccccgccaa cccggggccc tggcgtacgg ggccttcggg    780
ccgccgtcct ccttccagcc ctttccggcc gtgcctccgc cggccgcggg catcgcgcac    840
ctgcagcctg tggcgacgcc gtaccccggc cgcgcggccg cgcccccaa cgctccggga     900
ggcccccggg gcccgcagcc ggccccaagc gccgcagccc cgccgccgcc cgcgcacgcc    960
ctgggcggca tggacgccga actcatcgac gaggaggcgc tgacgtcgct ggagctggag   1020
```

```
ctggggctgc accgcgtgcg cgagctgccc gagctgttcc tgggccagag cgagttcgac   1080

tgcttctcgg acttggggtc cgcgccgccc gccggctccg tgagctgcgg tggttctggt   1140

ggtggttctg gtcagtccca gctcatcaaa cccagccgca tgcgcaagta ccccaaccgg   1200

cccagcaaga cgcccccca cgaacgccct tacgcttgcc cagtggagtc ctgtgatcgc   1260

cgcttctccc gcagcgacaa cctggtgaga cacatccgca tccacacagg ccagaagccc   1320

ttccagtgcc gcatctgcat gagaaacttc agccgagagg ataacttgca cactcacatc   1380

cgcacccaca caggcgaaaa gcccttcgcc tgcgacatct gtggaagaaa gtttgcccgg   1440

agcgatgaac ttgtccgaca taccaagatc cacttgcggc agaaggaccg cccttacgct   1500

tgcccagtgg agtcctgtga tcgccgcttc tcccaatcag ggaatctgac tgagcacatc   1560

cgcatccaca caggccagaa gcccttccag tgccgcatct gcatgagaaa cttcagcaca   1620

agtggacatc tggtacgcca catccgcacc cacacaggcg aaaagccctt cgcctgcgac   1680

atctgtggaa gaaagtttgc ccagaatagt accctgaccg aacataccaa gatccacttg   1740

cggcagaagg acaag                                                    1755
```

<210> SEQ ID NO 74
<211> LENGTH: 3438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
ggaggaagcc atcaactaaa ctacaatgac tgtaagatac aaaattggga atggtaacat     60

attttgaagt tctgttgaca taaagaatca tgatattaat gcccatggaa atgaaagggc    120

gatcaacact atggtttgaa aagggggaaa ttgtagagca cagatgtgtt cgtgtggcag    180

tgtgctgtct ctagcaatac tcagagaaga gagagaacaa tgaaattctg attggcccca    240

gtgtgagccc agatgaggtt cagctgccaa ctttctcttt cacatcttat gaaagtcatt    300

taagcacaac taactttttt tttttttttt tttttttgag acagagtctt gctctgttgc    360

ccaggacaga gtgcagtagt gactcaatct cggctcactg cagcctccac ctcctaggct    420

caaacggtcc tcctgcatca gcctcccaag tagctggaat tacaggagtg gcccaccatg    480

cccagctaat ttttgtattt ttaatagata cggggggtttc accatatcac ccaggctggt    540

ctcgaactcc tggcctcaag tgatccacct gcctcggcct cccaaagtgc tgggattata    600

ggcgtcagcc actatgccca acccgaccaa cctttttttaa aataaatatt taaaaaaattg    660

gtatttcaca tatatactag tatttacatt tatccacaca aaacggacgg gcctccgctg    720

aaccagtgag gccccagacg tgcgcataaa taacccctgc gtgctgcacc acctggggag    780

agggggagga ccacggtaaa tggagcgagc gcatagcaaa agggacgcgg ggtccttttc    840

tctgccggtg gcactgggta gctgtggcca ggtgtggtac tttgatgggg cccagggctg    900

gagctcaagg aagcgtcgca gggtcacaga tctgggggaa ccccggggaa aagcactgag    960

gcaaaaccgc cgctcgtctc ctacaatata tgggaggggg aggttgagta cgttctggat   1020

tactcataag acctttttttt tttccttccg ggcgcaaaac cgtgagctgg atttataatc   1080

gccctataaa gctccagagg cggtcaggca cctgcagagg agccccgccg ctccgccgac   1140

tagctgcccc cgcgagcaac ggcctcgtga tttccccgcc gatccggtcc ccgcctcccc   1200

actctgcccc cgcctacccc ggagccgtgc agccgcctct ccgaatctct ctcttctcct   1260
```

```
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag gggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccc caaagaagaa gcggaaggtc ggtatccacg   2100
gagtcccagc agccctcgaa ccaggtgaaa aaccttacaa atgtcctgaa tgtgggaaat   2160
cattcagtcg cagcgacaac ctggtgagac atcaacgcac ccatacagga gaaaaacctt   2220
ataaatgtcc agaatgtgga aagtccttct cacgagagga taacttgcac actcatcaac   2280
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
gtttctctca gaatagtacc ctgaccgaac accagcgaac acacactggg aaaaaaacga   2640
gtaaaaggcc ggcggccacg aaaaaggccg gccaggcaaa aaagaaaaag ggatcctacc   2700
catacgacgt accagattac gctctcgagg acgcgctgga cgatttcgat ctcgacatgc   2760
tgggttctga tgccctcgat gactttgacc tggatatgtt gggaagcgac gcattggatg   2820
actttgatct ggacatgctc ggctccgatg ctctggacga tttcgatctc gatatgttat   2880
aaactagtga aacccagcag acaatgtagc tagacccagt agccagatgt agctaaagag   2940
accggttcac tgtgaaagct tgggtggcat ccctgtgacc cctccccagt gcctctcctg   3000
gccctggaag ttgccactcc agtgcccacc agccttgtcc taataaaatt aagttgcatc   3060
attttgtctg actaggtgtc cttctataat attatggggt ggaggggggt ggtatggagc   3120
aaggggcaag ttgggaagac aacctgtagg gcctgcgggg tctattggga accaagctgg   3180
agtgcagtgg cacaatcttg gctcactgca atctccgcct cctgggttca agcgattctc   3240
ctgcctcagc ctcccgagtt gttgggattc caggcatgca tgaccaggct cagctaattt   3300
ttgttttttt ggtagagacg gggtttcacc atattggcca ggctggtctc caactcctaa   3360
tctcaggtga tctacccacc ttggcctccc aaattgctgg gattacaggc gtgaaccact   3420
gctcccttcc ctgtcctt                                                 3438
```

<210> SEQ ID NO 75
<211> LENGTH: 3505
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 75
ggaggaagcc atcaactaaa ctacaatgac tgtaagatac aaaattggga atggtaacat 60
attttgaagt tctgttgaca taaagaatca tgatattaat gcccatggaa atgaaagggc 120
gatcaacact atggtttgaa aagggggaaa ttgtagagca cagatgtgtt cgtgtggcag 180
tgtgctgtct ctagcaatac tcagagaaga gagagaacaa tgaaattctg attggcccca 240
gtgtgagccc agatgaggtt cagctgccaa ctttctcttt cacatcttat gaaagtcatt 300
taagcacaac taactttttt tttttttttt ttttttgag acagagtctt gctctgttgc 360
ccaggacaga gtgcagtagt gactcaatct cggctcactg cagcctccac ctcctaggct 420
caaacggtcc tcctgcatca gcctcccaag tagctggaat tacaggagtg gcccaccatg 480
cccagctaat ttttgtattt ttaatagata cgggggtttc accatatcac ccaggctggt 540
ctcgaactcc tggcctcaag tgatccacct gcctcggcct cccaaagtgc tgggattata 600
ggcgtcagcc actatgccca acccgaccaa cctttttttaa aataaatatt taaaaaattg 660
gtatttcaca tatatactag tatttacatt tatccacaca aaacggacgg gcctccgctg 720
aaccagtgag gccccagacg tgcgcataaa taacccctgc gtgctgcacc acctggggag 780
agggggagga ccacggtaaa tggagcgagc gcatagcaaa agggacgcgg ggtccttttc 840
tctgccggtg gcactgggta gctgtggcca ggtgtggtac tttgatgggg cccagggctg 900
gagctcaagg aagcgtcgca gggtcacaga tctgggggaa ccccggggaa aagcactgag 960
gcaaaaccgc cgctcgtctc ctacaatata tgggaggggg aggttgagta cgttctggat 1020
tactcataag accttttttt tttccttccg ggcgcaaaac cgtgagctgg atttataatc 1080
gccctataaa gctccagagg cggtcaggca cctgcagagg agccccgccg ctccgccgac 1140
tagctgcccc cgcgagcaac ggcctcgtga tttccccgcc gatccggtcc ccgcctcccc 1200
actctgcccc cgcctacccc ggagccgtgc agccgcctct ccgaatctct ctcttctcct 1260
ggcgctcgcg tgcgagaggg aactagcgag aacgaggaag cagctggagg tgacgccggg 1320
cagattacgc ctgtcagggc cgagccgagc ggatcgctgg gcgctgtgca gaggaaaggc 1380
gggagtgccc ggctcgctgt cgcagagccg aggtgggtaa gctagcgacc acctggactt 1440
cccagcgccc aaccgtggct tttcagccag gtcctctcct cccgcggctt ctcaaccaac 1500
cccatcccag cgccggccac ccaacctccc gaaatgagtg cttcctgccc cagcagccga 1560
aggcgctact aggaacggta acctgttact tttccagggg ccgtagtcga cccgctgccc 1620
gagttgctgt gcgactgcgc gcgcggggct agagtgcaag gtgactgtgg ttcttctctg 1680
gccaagtccg agggagaacg taaagatatg ggcctttttc cccctctcac cttgtctcac 1740
caaagtccct agtccccgga gcagttagcc tctttctttc cagggaatta gccagacaca 1800
acaacgggaa ccagacaccg aaccagacat gcccgccccg tgcgccctcc ccgctcgctg 1860
cctttcctcc ctcttgtctc tccagagccg gatcttcaag gggagcctcc gtgccccgg 1920 ctgctcagtc cctccggtgt gcaggacccc ggaagtcctc cccgcacagc tctcgcttct 1980
ctttgcagcc tgtttctgcg ccggaccagt cgaggactct ggacagtaga ggccccggga 2040
cgaccgagct ggaattcgcc accatggccc caaagaagaa gcggaaggtc ggtatccacg 2100
gagtcccagc agccctcgaa ccaggtgaaa aaccttacaa atgtcctgaa tgtgggaaat 2160

```
cattcagtcg cagcgacaac ctggtgagac atcaacgcac ccatacagga gaaaaacctt   2220
ataaatgtcc agaatgtgga aagtccttct cacgagagga taacttgcac actcatcaac   2280
gaacacatac tggtgaaaaa ccatacaagt gtcccgaatg tggtaaaagt tttagccgga   2340
gcgatgaact tgtccgacac caacgaaccc atacaggcga gaagccttac aaatgtcccg   2400
agtgtggcaa gagcttctca caatcaggga atctgactga gcatcaacga actcataccg   2460
gggaaaaacc ttacaagtgt ccagagtgtg ggaagagctt ttccacaagt ggacatctgg   2520
tacgccacca gaggacacat acaggggaga agccctacaa atgccccgaa tgcggtaaaa   2580
gtttctctca gaatagtacc ctgaccgaac accagcgaac acacactggg aaaaaaacga   2640
gtaaaaggcc ggcggccacg aaaaaggccg gccaggcaaa aaagaaaaag ggatcctacc   2700
catacgacgt accagattac gctctcgagg acgcgctgga cgatttcgat ctcgacatgc   2760
tgggttctga tgccctcgat gactttgacc tggatatgtt gggaagcgac gcattggatg   2820
actttgatct ggacatgctc ggctccgatg ctctggacga tttcgatctc gatatgttat   2880
aaactagtga aacccagcag acaatgtagc tagacccagt agccagatgt agctaaagag   2940
accggttcac tgtgagaaac ccagcagaca atgtagctag acccagtagc cagatgtagc   3000
taaagagacc ggttcactgt gaaagcttgg gtggcatccc tgtgacccct ccccagtgcc   3060
tctcctggcc ctggaagttg ccactccagt gcccaccagc cttgtcctaa taaaattaag   3120
ttgcatcatt ttgtctgact aggtgtcctt ctataatatt atggggtgga ggggggtggt   3180
atggagcaag gggcaagttg ggaagacaac ctgtagggcc tgcggggtct attgggaacc   3240
aagctggagt gcagtggcac aatcttggct cactgcaatc tccgcctcct gggttcaagc   3300
gattctcctg cctcagcctc ccgagttgtt gggattccag gcatgcatga ccaggctcag   3360
ctaatttttg tttttttggt agagacgggg tttcaccata ttggccaggc tggtctccaa   3420
ctcctaatct caggtgatct acccaccttg gcctcccaaa ttgctgggat tacaggcgtg   3480
aaccactgct cccttccctg tcctt                                         3505
```

<210> SEQ ID NO 76
<211> LENGTH: 3804
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76

```
ggaggaagcc atcaactaaa ctacaatgac tgtaagatac aaaattggga atggtaacat     60
attttgaagt tctgttgaca taaagaatca tgatattaat gcccatggaa atgaaagggc    120
gatcaacact atggtttgaa aagggggaaa ttgtagagca cagatgtgtt cgtgtggcag    180
tgtgctgtct ctagcaatac tcagagaaga gagagaacaa tgaaattctg attggcccca    240
gtgtgagccc agatgaggtt cagctgccaa ctttctcttt cacatcttat gaaagtcatt    300
taagcacaac taactttttt tttttttttt tttttttgag acagagtctt gctctgttgc    360
ccaggacaga gtgcagtagt gactcaatct cggctcactg cagcctccac ctcctaggct    420
caaacggtcc tcctgcatca gcctcccaag tagctggaat tacaggagtg gcccaccatg    480
cccagctaat ttttgtattt ttaatagata cgggggtttc accatatcac ccaggctggt    540
ctcgaactcc tggcctcaag tgatccacct gcctcggcct cccaaagtgc tgggattata    600
ggcgtcagcc actatgccca acccgaccaa cctttttttaa aataaatatt taaaaaattg    660
```

```
gtatttcaca tatatactag tatttacatt tatccacaca aaacggacgg gcctccgctg    720
aaccagtgag gccccagacg tgcgcataaa taacccctgc gtgctgcacc acctggggag    780
agggggagga ccacggtaaa tggagcgagc gcatagcaaa agggacgcgg ggtccttttc    840
tctgccggtg gcactgggta gctgtggcca ggtgtggtac tttgatgggg cccagggctg    900
gagctcaagg aagcgtcgca gggtcacaga tctgggggaa ccccggggaa aagcactgag    960
gcaaaaccgc cgctcgtctc ctacaatata tgggaggggg aggttgagta cgttctggat   1020
tactcataag accttttttt tttccttccg ggcgcaaaac cgtgagctgg atttataatc   1080
gccctataaa gctccagagg cggtcaggca cctgcagagg agccccgccg ctccgccgac   1140
tagctgcccc cgcgagcaac ggcctcgtga tttccccgcc gatccggtcc ccgcctcccc   1200
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag gggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccg ccgaccacct gatgctcgcc gagggctacc   2100
gcctggtgca gaggccgccg tccgccgccg ccgcccatgg ccctcatgcg ctccggactc   2160
tgccgccgta cgcgggcccg ggcctggaca gtgggctgag gccgcggggg gctccgctgg   2220
ggccgccgcc gccccgccaa cccggggccc tggcgtacgg ggccttcggg ccgccgtcct   2280
ccttccagcc ctttccggcc gtgcctccgc cggccgcggg catcgcgcac ctgcagcctg   2340
tggcgacgcc gtaccccggc cgcgcggccg cgccccccaa cgctccggga ggcccccggg   2400
gcccgcagcc ggccccaagc gccgcagccc cgccgccgcc cgcgcacgcc ctgggcggca   2460
tggacgccga actcatcgac gaggaggcgc tgacgtcgct ggagctggag ctggggctgc   2520
accgcgtgcg cgagctgccc gagctgttcc tgggccagag cgagttcgac tgcttctcgg   2580
acttggggtc cgcgccgccc gccggctccg tgagctgcgg tggttctggt ggtggttctg   2640
gtcagtccca gctcatcaaa cccagccgca tgcgcaagta ccccaaccgg cccagcaaga   2700
cgcccccccca cgaacgccct tacgcttgcc cagtggagtc ctgtgatcgc cgcttctccc   2760
gcagcgacaa cctggtgaga cacatccgca tccacacagg ccagaagccc ttccagtgcc   2820
gcatctgcat gagaaacttc agccgagagg ataacttgca cactcacatc cgcacccaca   2880
caggcgaaaa gcccttcgcc tgcgacatct gtggaagaaa gtttgcccgg agcgatgaac   2940
ttgtccgaca taccaagatc cacttgcggc agaaggaccg cccttacgct tgcccagtgg   3000
agtcctgtga tcgccgcttc tcccaatcag ggaatctgac tgagcacatc cgcatccaca   3060
```

```
caggccagaa gcccttccag tgccgcatct gcatgagaaa cttcagcaca agtggacatc   3120

tggtacgcca catccgcacc cacacaggcg aaaagccctt cgcctgcgac atctgtggaa   3180

gaaagtttgc ccagaatagt accctgaccg aacataccaa gatccacttg cggcagaagg   3240

acaagtaact cgaggaaacc cagcagacaa tgtagctaga cccagtagcc agatgtagct   3300

aaagagaccg gttcactgtg aaagcttggg tggcatccct gtgacccctc cccagtgcct   3360

ctcctggccc tggaagttgc cactccagtg cccaccagcc ttgtcctaat aaaattaagt   3420

tgcatcattt tgtctgacta ggtgtccttc tataatatta tggggtggag gggggtggta   3480

tggagcaagg ggcaagttgg gaagacaacc tgtagggcct gcggggtcta ttgggaacca   3540

agctggagtg cagtggcaca atcttggctc actgcaatct ccgcctcctg ggttcaagcg   3600

attctcctgc ctcagcctcc cgagttgttg ggattccagg catgcatgac caggctcagc   3660

taatttttgt ttttttggta gagacggggt ttcaccatat tggccaggct ggtctccaac   3720

tcctaatctc aggtgatcta cccaccttgg cctcccaaat tgctgggatt acaggcgtga   3780

accactgctc ccttccctgt cctt                                          3804
```

```
<210> SEQ ID NO 77
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Glu Pro Gly Glu Lys Pro Tyr Lys Cys Pro Glu Cys Gly Lys Ser
1               5                   10                  15

Phe Ser Arg Ser Asp Asn Leu Val Arg His Gln Arg Thr His Thr Gly
            20                  25                  30

Glu Lys Pro Tyr Lys Cys Pro Glu Cys Gly Lys Ser Phe Ser Arg Glu
        35                  40                  45

Asp Asn Leu His Thr His Gln Arg Thr His Thr Gly Glu Lys Pro Tyr
    50                  55                  60

Lys Cys Pro Glu Cys Gly Lys Ser Phe Ser Arg Ser Asp Glu Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Gln Ser Gly Asn Leu Thr Glu His Gln Arg
            100                 105                 110

Thr His Thr Gly Glu Lys Pro Tyr Lys Cys Pro Glu Cys Gly Lys Ser
        115                 120                 125

Phe Ser Thr Ser Gly His Leu Val Arg His Gln Arg Thr His Thr Gly
    130                 135                 140

Glu Lys Pro Tyr Lys Cys Pro Glu Cys Gly Lys Ser Phe Ser Gln Asn
145                 150                 155                 160

Ser Thr Leu Thr Glu His Gln Arg Thr His Thr Gly Lys Lys Thr Ser
                165                 170                 175


<210> SEQ ID NO 78
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 78

Leu Glu Pro Gly Glu Lys Pro Tyr Lys Cys Pro Glu Cys Gly Lys Ser
1 5 10 15

Phe Ser Thr Lys Asn Ser Leu Thr Glu His Gln Arg Thr His Thr Gly
20 25 30

Glu Lys Pro Tyr Lys Cys Pro Glu Cys Gly Lys Ser Phe Ser Arg Ala
35 40 45

Asp Asn Leu Thr Glu His Gln Arg Thr His Thr Gly Glu Lys Pro Tyr
50 55 60

Lys Cys Pro Glu Cys Gly Lys Ser Phe Ser Gln Leu Ala His Leu Arg
65 70 75 80

Ala His Gln Arg Thr His Thr Gly Glu Lys Pro Tyr Lys Cys Pro Glu
85 90 95

Cys Gly Lys Ser Phe Ser Thr Lys Asn Ser Leu Thr Glu His Gln Arg
100 105 110

Thr His Thr Gly Glu Lys Pro Tyr Lys Cys Pro Glu Cys Gly Lys Ser
115 120 125

Phe Ser Gln Ala Gly His Leu Ala Ser His Gln Arg Thr His Thr Gly
130 135 140

Glu Lys Pro Tyr Lys Cys Pro Glu Cys Gly Lys Ser Phe Ser Thr His
145 150 155 160

Leu Asp Leu Ile Arg His Gln Arg Thr His Thr Gly Lys Lys Thr Ser
165 170 175

<210> SEQ ID NO 79
<211> LENGTH: 176
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Leu Glu Pro Gly Glu Lys Pro Tyr Lys Cys Pro Glu Cys Gly Lys Ser
1 5 10 15

Phe Ser Gln Ala Gly His Leu Ala Ser His Gln Arg Thr His Thr Gly
20 25 30

Glu Lys Pro Tyr Lys Cys Pro Glu Cys Gly Lys Ser Phe Ser Arg Glu
35 40 45

Asp Asn Leu His Thr His Gln Arg Thr His Thr Gly Glu Lys Pro Tyr
50 55 60

Lys Cys Pro Glu Cys Gly Lys Ser Phe Ser Thr Ser Gly Asn Leu Thr
65 70 75 80

Glu His Gln Arg Thr His Thr Gly Glu Lys Pro Tyr Lys Cys Pro Glu
85 90 95

Cys Gly Lys Ser Phe Ser Thr His Leu Asp Leu Ile Arg His Gln Arg
100 105 110

Thr His Thr Gly Glu Lys Pro Tyr Lys Cys Pro Glu Cys Gly Lys Ser
115 120 125

Phe Ser Gln Lys Ser Ser Leu Ile Ala His Gln Arg Thr His Thr Gly
130 135 140

Glu Lys Pro Tyr Lys Cys Pro Glu Cys Gly Lys Ser Phe Ser Gln Ala
145 150 155 160

Gly His Leu Ala Ser His Gln Arg Thr His Thr Gly Lys Lys Thr Ser
165 170 175

<210> SEQ ID NO 80
<211> LENGTH: 176
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Leu Glu Pro Gly Glu Lys Pro Tyr Lys Cys Pro Glu Cys Gly Lys Ser
1 5 10 15

Phe Ser Thr Thr Gly Asn Leu Thr Val His Gln Arg Thr His Thr Gly
20 25 30

Glu Lys Pro Tyr Lys Cys Pro Glu Cys Gly Lys Ser Phe Ser Thr Ser
35 40 45

Gly Glu Leu Val Arg His Gln Arg Thr His Thr Gly Glu Lys Pro Tyr
50 55 60

Lys Cys Pro Glu Cys Gly Lys Ser Phe Ser Arg Glu Asp Asn Leu His
65 70 75 80

Thr His Gln Arg Thr His Thr Gly Glu Lys Pro Tyr Lys Cys Pro Glu
85 90 95

Cys Gly Lys Ser Phe Ser Thr Ser Gly Asn Leu Thr Glu His Gln Arg
100 105 110

Thr His Thr Gly Glu Lys Pro Tyr Lys Cys Pro Glu Cys Gly Lys Ser
115 120 125

Phe Ser Gln Ser Ser Ser Leu Val Arg His Gln Arg Thr His Thr Gly
130 135 140

Glu Lys Pro Tyr Lys Cys Pro Glu Cys Gly Lys Ser Phe Ser Gln Arg
145 150 155 160

Ala Asn Leu Arg Ala His Gln Arg Thr His Thr Gly Lys Lys Thr Ser
165 170 175

<210> SEQ ID NO 81
<211> LENGTH: 176
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Leu Glu Pro Gly Glu Lys Pro Tyr Lys Cys Pro Glu Cys Gly Lys Ser
1 5 10 15

Phe Ser Ser Arg Arg Thr Cys Arg Ala His Gln Arg Thr His Thr Gly
20 25 30

Glu Lys Pro Tyr Lys Cys Pro Glu Cys Gly Lys Ser Phe Ser Thr Thr
35 40 45

Gly Ala Leu Thr Glu His Gln Arg Thr His Thr Gly Glu Lys Pro Tyr
50 55 60

Lys Cys Pro Glu Cys Gly Lys Ser Phe Ser Arg Ser Asp Glu Leu Val
65 70 75 80

Arg His Gln Arg Thr His Thr Gly Glu Lys Pro Tyr Lys Cys Pro Glu
85 90 95

Cys Gly Lys Ser Phe Ser Arg Asn Asp Ala Leu Thr Glu His Gln Arg
100 105 110

Thr His Thr Gly Glu Lys Pro Tyr Lys Cys Pro Glu Cys Gly Lys Ser
115 120 125

```
Phe Ser Gln Ser Gly Asp Leu Arg Arg His Gln Arg Thr His Thr Gly
    130                 135                 140

Glu Lys Pro Tyr Lys Cys Pro Glu Cys Gly Lys Ser Phe Ser Thr Ser
145                 150                 155                 160

His Ser Leu Thr Glu His Gln Arg Thr His Thr Gly Lys Lys Thr Ser
                165                 170                 175


<210> SEQ ID NO 82
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Leu Glu Pro Gly Glu Lys Pro Tyr Lys Cys Pro Glu Cys Gly Lys Ser
1               5                   10                  15

Phe Ser Arg Lys Asp Asn Leu Lys Asn His Gln Arg Thr His Thr Gly
            20                  25                  30

Glu Lys Pro Tyr Lys Cys Pro Glu Cys Gly Lys Ser Phe Ser Asp Pro
        35                  40                  45

Gly Ala Leu Val Arg His Gln Arg Thr His Thr Gly Glu Lys Pro Tyr
    50                  55                  60

Lys Cys Pro Glu Cys Gly Lys Ser Phe Ser Arg Glu Asp Asn Leu His
65                  70                  75                  80

Thr His Gln Arg Thr His Thr Gly Glu Lys Pro Tyr Lys Cys Pro Glu
                85                  90                  95

Cys Gly Lys Ser Phe Ser Asp Pro Gly Ala Leu Val Arg His Gln Arg
            100                 105                 110

Thr His Thr Gly Glu Lys Pro Tyr Lys Cys Pro Glu Cys Gly Lys Ser
        115                 120                 125

Phe Ser Thr Ser Gly Glu Leu Val Arg His Gln Arg Thr His Thr Gly
    130                 135                 140

Glu Lys Pro Tyr Lys Cys Pro Glu Cys Gly Lys Ser Phe Ser Arg Lys
145                 150                 155                 160

Asp Asn Leu Lys Asn His Gln Arg Thr His Thr Gly Lys Lys Thr Ser
                165                 170                 175


<210> SEQ ID NO 83
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Glu Pro Gly Glu Lys Pro Tyr Lys Cys Pro Glu Cys Gly Lys Ser
1               5                   10                  15

Phe Ser Ser Lys Lys Ala Leu Thr Glu His Gln Arg Thr His Thr Gly
            20                  25                  30

Glu Lys Pro Tyr Lys Cys Pro Glu Cys Gly Lys Ser Phe Ser Ser Pro
        35                  40                  45

Ala Asp Leu Thr Arg His Gln Arg Thr His Thr Gly Glu Lys Pro Tyr
    50                  55                  60

Lys Cys Pro Glu Cys Gly Lys Ser Phe Ser Arg Ser Asp Asn Leu Val
65                  70                  75                  80
```

Arg His Gln Arg Thr His Thr Gly Glu Lys Pro Tyr Lys Cys Pro Glu
85 90 95

Cys Gly Lys Ser Phe Ser Arg Glu Asp Asn Leu His Thr His Gln Arg
100 105 110

Thr His Thr Gly Glu Lys Pro Tyr Lys Cys Pro Glu Cys Gly Lys Ser
115 120 125

Phe Ser Arg Ser Asp Glu Leu Val Arg His Gln Arg Thr His Thr Gly
130 135 140

Glu Lys Pro Tyr Lys Cys Pro Glu Cys Gly Lys Ser Phe Ser Gln Ser
145 150 155 160

Gly Asn Leu Thr Glu His Gln Arg Thr His Thr Gly Glu Lys Pro Tyr
165 170 175

Lys Cys Pro Glu Cys Gly Lys Ser Phe Ser Thr Ser Gly His Leu Val
180 185 190

Arg His Gln Arg Thr His Thr Gly Glu Lys Pro Tyr Lys Cys Pro Glu
195 200 205

Cys Gly Lys Ser Phe Ser Gln Asn Ser Thr Leu Thr Glu His Gln Arg
210 215 220

Thr His Thr Gly Lys Lys Thr Ser
225 230

<210> SEQ ID NO 84
<211> LENGTH: 176
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Leu Glu Pro Gly Glu Lys Pro Tyr Lys Cys Pro Glu Cys Gly Lys Ser
1 5 10 15

Phe Ser Ser Pro Ala Asp Leu Thr Arg His Gln Arg Thr His Thr Gly
20 25 30

Glu Lys Pro Tyr Lys Cys Pro Glu Cys Gly Lys Ser Phe Ser Arg Ser
35 40 45

Asp Asn Leu Val Arg His Gln Arg Thr His Thr Gly Glu Lys Pro Tyr
50 55 60

Lys Cys Pro Glu Cys Gly Lys Ser Phe Ser Arg Glu Asp Asn Leu His
65 70 75 80

Thr His Gln Arg Thr His Thr Gly Glu Lys Pro Tyr Lys Cys Pro Glu
85 90 95

Cys Gly Lys Ser Phe Ser Arg Ser Asp Glu Leu Val Arg His Gln Arg
100 105 110

Thr His Thr Gly Glu Lys Pro Tyr Lys Cys Pro Glu Cys Gly Lys Ser
115 120 125

Phe Ser Gln Ser Gly Asn Leu Thr Glu His Gln Arg Thr His Thr Gly
130 135 140

Glu Lys Pro Tyr Lys Cys Pro Glu Cys Gly Lys Ser Phe Ser Thr Ser
145 150 155 160

Gly His Leu Val Arg His Gln Arg Thr His Thr Gly Lys Lys Thr Ser
165 170 175

<210> SEQ ID NO 85
<211> LENGTH: 176
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 85

Leu Glu Pro Gly Glu Lys Pro Tyr Lys Cys Pro Glu Cys Gly Lys Ser
1               5                   10                  15

Phe Ser Ser Lys Lys Ala Leu Thr Glu His Gln Arg Thr His Thr Gly
            20                  25                  30

Glu Lys Pro Tyr Lys Cys Pro Glu Cys Gly Lys Ser Phe Ser Ser Pro
        35                  40                  45

Ala Asp Leu Thr Arg His Gln Arg Thr His Thr Gly Glu Lys Pro Tyr
    50                  55                  60

Lys Cys Pro Glu Cys Gly Lys Ser Phe Ser Arg Ser Asp Asn Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Arg Glu Asp Asn Leu His Thr His Gln Arg
            100                 105                 110

Thr His Thr Gly Glu Lys Pro Tyr Lys Cys Pro Glu Cys Gly Lys Ser
        115                 120                 125

Phe Ser Arg Ser Asp Glu Leu Val Arg His Gln Arg Thr His Thr Gly
    130                 135                 140

Glu Lys Pro Tyr Lys Cys Pro Glu Cys Gly Lys Ser Phe Ser Gln Ser
145                 150                 155                 160

Gly Asn Leu Thr Glu His Gln Arg Thr His Thr Gly Lys Lys Thr Ser
                165                 170                 175


<210> SEQ ID NO 86
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Leu Glu Pro Gly Glu Lys Pro Tyr Lys Cys Pro Glu Cys Gly Lys Ser
1               5                   10                  15

Phe Ser Asp Cys Arg Asp Leu Ala Arg His Gln Arg Thr His Thr Gly
            20                  25                  30

Glu Lys Pro Tyr Lys Cys Pro Glu Cys Gly Lys Ser Phe Ser Arg Asn
        35                  40                  45

Asp Ala Leu Thr Glu His Gln Arg Thr His Thr Gly Glu Lys Pro Tyr
    50                  55                  60

Lys Cys Pro Glu Cys Gly Lys Ser Phe Ser Arg Asn Asp Ala Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Ser Pro Ala Asp Leu Thr Arg His Gln Arg
            100                 105                 110

Thr His Thr Gly Glu Lys Pro Tyr Lys Cys Pro Glu Cys Gly Lys Ser
        115                 120                 125

Phe Ser Asp Pro Gly Asn Leu Val Arg His Gln Arg Thr His Thr Gly
    130                 135                 140

Glu Lys Pro Tyr Lys Cys Pro Glu Cys Gly Lys Ser Phe Ser Gln Arg
```

```
145                 150                 155                 160

Ala His Leu Glu Arg His Gln Arg Thr His Thr Gly Glu Lys Pro Tyr
                165                 170                 175

Lys Cys Pro Glu Cys Gly Lys Ser Phe Ser Gln Ser Ser Ser Leu Val
            180                 185                 190

Arg His Gln Arg Thr His Thr Gly Glu Lys Pro Tyr Lys Cys Pro Glu
        195                 200                 205

Cys Gly Lys Ser Phe Ser His Arg Thr Thr Leu Thr Asn His Gln Arg
    210                 215                 220

Thr His Thr Gly Lys Lys Thr Ser
225                 230


<210> SEQ ID NO 87
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Leu Glu Pro Gly Glu Lys Pro Tyr Lys Cys Pro Glu Cys Gly Lys Ser
1               5                   10                  15

Phe Ser Arg Asn Asp Ala Leu Thr Glu His Gln Arg Thr His Thr Gly
            20                  25                  30

Glu Lys Pro Tyr Lys Cys Pro Glu Cys Gly Lys Ser Phe Ser Ser Pro
        35                  40                  45

Ala Asp Leu Thr Arg His Gln Arg Thr His Thr Gly Glu Lys Pro Tyr
    50                  55                  60

Lys Cys Pro Glu Cys Gly Lys Ser Phe Ser Asp Pro Gly Asn Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Gln Arg Ala His Leu Glu Arg His Gln Arg
            100                 105                 110

Thr His Thr Gly Glu Lys Pro Tyr Lys Cys Pro Glu Cys Gly Lys Ser
        115                 120                 125

Phe Ser Gln Ser Ser Ser Leu Val Arg His Gln Arg Thr His Thr Gly
    130                 135                 140

Glu Lys Pro Tyr Lys Cys Pro Glu Cys Gly Lys Ser Phe Ser His Arg
145                 150                 155                 160

Thr Thr Leu Thr Asn His Gln Arg Thr His Thr Gly Lys Lys Thr Ser
                165                 170                 175


<210> SEQ ID NO 88
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Glu Pro Gly Glu Lys Pro Tyr Lys Cys Pro Glu Cys Gly Lys Ser
1               5                   10                  15

Phe Ser Arg Asn Asp Ala Leu Thr Glu His Gln Arg Thr His Thr Gly
            20                  25                  30

Glu Lys Pro Tyr Lys Cys Pro Glu Cys Gly Lys Ser Phe Ser Asp Pro
```

```
        35                  40                  45

Gly His Leu Val Arg His Gln Arg Thr His Thr Gly Glu Lys Pro Tyr
    50                  55                  60

Lys Cys Pro Glu Cys Gly Lys Ser Phe Ser Thr Ser Gly Glu Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Thr His Leu Asp Leu Ile Arg His Gln Arg
            100                 105                 110

Thr His Thr Gly Glu Lys Pro Tyr Lys Cys Pro Glu Cys Gly Lys Ser
        115                 120                 125

Phe Ser Ser Lys Lys Ala Leu Thr Glu His Gln Arg Thr His Thr Gly
    130                 135                 140

Glu Lys Pro Tyr Lys Cys Pro Glu Cys Gly Lys Ser Phe Ser Gln Leu
145                 150                 155                 160

Ala His Leu Arg Ala His Gln Arg Thr His Thr Gly Glu Lys Pro Tyr
                165                 170                 175

Lys Cys Pro Glu Cys Gly Lys Ser Phe Ser Arg Ser Asp His Leu Thr
            180                 185                 190

Asn His Gln Arg Thr His Thr Gly Lys Lys Thr Ser
        195                 200


<210> SEQ ID NO 89
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Leu Glu Pro Gly Glu Lys Pro Tyr Lys Cys Pro Glu Cys Gly Lys Ser
1               5                   10                  15

Phe Ser Arg Ser Asp Asn Leu Val Arg His Gln Arg Thr His Thr Gly
            20                  25                  30

Glu Lys Pro Tyr Lys Cys Pro Glu Cys Gly Lys Ser Phe Ser His Arg
        35                  40                  45

Thr Thr Leu Thr Asn His Gln Arg Thr His Thr Gly Glu Lys Pro Tyr
    50                  55                  60

Lys Cys Pro Glu Cys Gly Lys Ser Phe Ser Arg Glu Asp Asn Leu His
65                  70                  75                  80

Thr His Gln Arg Thr His Thr Gly Glu Lys Pro Tyr Lys Cys Pro Glu
                85                  90                  95

Cys Gly Lys Ser Phe Ser Thr Ser His Ser Leu Thr Glu His Gln Arg
            100                 105                 110

Thr His Thr Gly Glu Lys Pro Tyr Lys Cys Pro Glu Cys Gly Lys Ser
        115                 120                 125

Phe Ser Gln Ser Ser Ser Leu Val Arg His Gln Arg Thr His Thr Gly
    130                 135                 140

Glu Lys Pro Tyr Lys Cys Pro Glu Cys Gly Lys Ser Phe Ser Arg Glu
145                 150                 155                 160

Asp Asn Leu His Thr His Gln Arg Thr His Thr Gly Lys Lys Thr Ser
                165                 170                 175


<210> SEQ ID NO 90
<211> LENGTH: 176
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

```
Leu Glu Pro Gly Glu Lys Pro Tyr Lys Cys Pro Glu Cys Gly Lys Ser
1               5                   10                  15

Phe Ser Asp Pro Gly Ala Leu Val Arg His Gln Arg Thr His Thr Gly
            20                  25                  30

Glu Lys Pro Tyr Lys Cys Pro Glu Cys Gly Lys Ser Phe Ser Arg Ser
        35                  40                  45

Asp Asn Leu Val Arg His Gln Arg Thr His Thr Gly Glu Lys Pro Tyr
    50                  55                  60

Lys Cys Pro Glu Cys Gly Lys Ser Phe Ser Gln Ser Gly Asp Leu Arg
65                  70                  75                  80

Arg His Gln Arg Thr His Thr Gly Glu Lys Pro Tyr Lys Cys Pro Glu
                85                  90                  95

Cys Gly Lys Ser Phe Ser Thr His Leu Asp Leu Ile Arg His Gln Arg
            100                 105                 110

Thr His Thr Gly Glu Lys Pro Tyr Lys Cys Pro Glu Cys Gly Lys Ser
        115                 120                 125

Phe Ser Thr Ser Gly Asn Leu Val Arg His Gln Arg Thr His Thr Gly
    130                 135                 140

Glu Lys Pro Tyr Lys Cys Pro Glu Cys Gly Lys Ser Phe Ser Arg Ser
145                 150                 155                 160

Asp Asn Leu Val Arg His Gln Arg Thr His Thr Gly Lys Lys Thr Ser
                165                 170                 175
```

<210> SEQ ID NO 91
<211> LENGTH: 260
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

```
Leu Glu Pro Gly Glu Lys Pro Tyr Lys Cys Pro Glu Cys Gly Lys Ser
1               5                   10                  15

Phe Ser Arg Arg Asp Glu Leu Asn Val His Gln Arg Thr His Thr Gly
            20                  25                  30

Glu Lys Pro Tyr Lys Cys Pro Glu Cys Gly Lys Ser Phe Ser Arg Ser
        35                  40                  45

Asp His Leu Thr Asn His Gln Arg Thr His Thr Gly Glu Lys Pro Tyr
    50                  55                  60

Lys Cys Pro Glu Cys Gly Lys Ser Phe Ser Arg Ser Asp Asp Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Arg Ser Asp Asn Leu Val Arg His Gln Arg
            100                 105                 110

Thr His Thr Gly Glu Lys Pro Tyr Lys Cys Pro Glu Cys Gly Lys Ser
        115                 120                 125

Phe Ser His Arg Thr Thr Leu Thr Asn His Gln Arg Thr His Thr Gly
    130                 135                 140
```

```
Glu Lys Pro Tyr Lys Cys Pro Glu Cys Gly Lys Ser Phe Ser Arg Glu
145                 150                 155                 160

Asp Asn Leu His Thr His Gln Arg Thr His Thr Gly Glu Lys Pro Tyr
                165                 170                 175

Lys Cys Pro Glu Cys Gly Lys Ser Phe Ser Thr Ser His Ser Leu Thr
            180                 185                 190

Glu His Gln Arg Thr His Thr Gly Glu Lys Pro Tyr Lys Cys Pro Glu
        195                 200                 205

Cys Gly Lys Ser Phe Ser Gln Ser Ser Ser Leu Val Arg His Gln Arg
    210                 215                 220

Thr His Thr Gly Glu Lys Pro Tyr Lys Cys Pro Glu Cys Gly Lys Ser
225                 230                 235                 240

Phe Ser Arg Glu Asp Asn Leu His Thr His Gln Arg Thr His Thr Gly
                245                 250                 255

Lys Lys Thr Ser
            260
```

<210> SEQ ID NO 92
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Arg Pro Tyr Ala Cys Pro Val Glu Ser Cys Asp Arg Arg Phe Ser Arg
1               5                   10                  15

Ser Asp Asn Leu Val Arg His Ile Arg Ile His Thr Gly Gln Lys Pro
            20                  25                  30

Phe Gln Cys Arg Ile Cys Met Arg Asn Phe Ser Arg Glu Asp Asn Leu
        35                  40                  45

His Thr His Ile Arg Thr His Thr Gly Glu Lys Pro Phe Ala Cys Asp
    50                  55                  60

Ile Cys Gly Arg Lys Phe Ala Arg Ser Asp Glu Leu Val Arg His Thr
65                  70                  75                  80

Lys Ile His Leu Arg Gln Lys Asp Arg Pro Tyr Ala Cys Pro Val Glu
                85                  90                  95

Ser Cys Asp Arg Arg Phe Ser Gln Ser Gly Asn Leu Thr Glu His Ile
            100                 105                 110

Arg Ile His Thr Gly Gln Lys Pro Phe Gln Cys Arg Ile Cys Met Arg
        115                 120                 125

Asn Phe Ser Thr Ser Gly His Leu Val Arg His Ile Arg Thr His Thr
    130                 135                 140

Gly Glu Lys Pro Phe Ala Cys Asp Ile Cys Gly Arg Lys Phe Ala Gln
145                 150                 155                 160

Asn Ser Thr Leu Thr Glu His Thr Lys Ile His Leu Arg Gln Lys Asp
                165                 170                 175

Lys
```

<210> SEQ ID NO 93
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Arg Pro Tyr Ala Cys Pro Val Glu Ser Cys Asp Arg Arg Phe Ser Arg
1 5 10 15

Ser Asp Asn Leu Val Arg His Ile Arg Ile His Thr Gly Gln Lys Pro
20 25 30

Phe Gln Cys Arg Ile Cys Met Arg Asn Phe Ser His Arg Thr Thr Leu
35 40 45

Thr Asn His Ile Arg Thr His Thr Gly Glu Lys Pro Phe Ala Cys Asp
50 55 60

Ile Cys Gly Arg Lys Phe Ala Arg Glu Asp Asn Leu His Thr His Thr
65 70 75 80

Lys Ile His Leu Arg Gln Lys Asp Arg Pro Tyr Ala Cys Pro Val Glu
85 90 95

Ser Cys Asp Arg Arg Phe Ser Thr Ser His Ser Leu Thr Glu His Ile
100 105 110

Arg Ile His Thr Gly Gln Lys Pro Phe Gln Cys Arg Ile Cys Met Arg
115 120 125

Asn Phe Ser Gln Ser Ser Ser Leu Val Arg His Ile Arg Thr His Thr
130 135 140

Gly Glu Lys Pro Phe Ala Cys Asp Ile Cys Gly Arg Lys Phe Ala Arg
145 150 155 160

Glu Asp Asn Leu His Thr His Thr Lys Ile His Leu Arg Gln Lys Asp
165 170 175

Lys

<210> SEQ ID NO 94
<211> LENGTH: 264
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Arg Pro Tyr Ala Cys Pro Val Glu Ser Cys Asp Arg Arg Phe Ser Arg
1 5 10 15

Arg Asp Glu Leu Asn Val His Ile Arg Ile His Thr Gly Gln Lys Pro
20 25 30

Phe Gln Cys Arg Ile Cys Met Arg Asn Phe Ser Arg Ser Asp His Leu
35 40 45

Thr Asn His Ile Arg Thr His Thr Gly Glu Lys Pro Phe Ala Cys Asp
50 55 60

Ile Cys Gly Arg Lys Phe Ala Arg Ser Asp Asp Leu Val Arg His Thr
65 70 75 80

Lys Ile His Leu Arg Gln Lys Asp Arg Pro Tyr Ala Cys Pro Val Glu
85 90 95

Ser Cys Asp Arg Arg Phe Ser Arg Ser Asp Asn Leu Val Arg His Ile
100 105 110

Arg Ile His Thr Gly Gln Lys Pro Phe Gln Cys Arg Ile Cys Met Arg
115 120 125

Asn Phe Ser His Arg Thr Thr Leu Thr Asn His Ile Arg Thr His Thr
130 135 140

Gly Glu Lys Pro Phe Ala Cys Asp Ile Cys Gly Arg Lys Phe Ala Arg
145 150 155 160

Glu Asp Asn Leu His Thr His Thr Lys Ile His Leu Arg Gln Lys Asp

```
                165                 170                 175

Arg Pro Tyr Ala Cys Pro Val Glu Ser Cys Asp Arg Arg Phe Ser Thr
            180                 185                 190

Ser His Ser Leu Thr Glu His Ile Arg Ile His Thr Gly Gln Lys Pro
        195                 200                 205

Phe Gln Cys Arg Ile Cys Met Arg Asn Phe Ser Gln Ser Ser Ser Leu
    210                 215                 220

Val Arg His Ile Arg Thr His Thr Gly Glu Lys Pro Phe Ala Cys Asp
225                 230                 235                 240

Ile Cys Gly Arg Lys Phe Ala Arg Glu Asp Asn Leu His Thr His Thr
                245                 250                 255

Lys Ile His Leu Arg Gln Lys Asp
            260


<210> SEQ ID NO 95
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Arg Pro Tyr Ala Cys Pro Val Glu Ser Cys Asp Arg Arg Phe Ser Asp
1               5                   10                  15

Pro Gly Ala Leu Val Arg His Ile Arg Ile His Thr Gly Gln Lys Pro
            20                  25                  30

Phe Gln Cys Arg Ile Cys Met Arg Asn Phe Ser Arg Ser Asp Asn Leu
        35                  40                  45

Val Arg His Ile Arg Thr His Thr Gly Glu Lys Pro Phe Ala Cys Asp
    50                  55                  60

Ile Cys Gly Arg Lys Phe Ala Gln Ser Gly Asp Leu Arg Arg His Thr
65                  70                  75                  80

Lys Ile His Leu Arg Gln Lys Asp Arg Pro Tyr Ala Cys Pro Val Glu
                85                  90                  95

Ser Cys Asp Arg Arg Phe Ser Thr His Leu Asp Leu Ile Arg His Ile
            100                 105                 110

Arg Ile His Thr Gly Gln Lys Pro Phe Gln Cys Arg Ile Cys Met Arg
        115                 120                 125

Asn Phe Ser Thr Ser Gly Asn Leu Val Arg His Ile Arg Thr His Thr
    130                 135                 140

Gly Glu Lys Pro Phe Ala Cys Asp Ile Cys Gly Arg Lys Phe Ala Arg
145                 150                 155                 160

Ser Asp Asn Leu Val Arg His Thr Lys Ile His Leu Arg Gln Lys Asp
                165                 170                 175

Arg Pro Tyr Ala Cys Pro Val Glu Ser Cys Asp Arg Arg Phe Ser Gln
            180                 185                 190

Ser Gly His Leu Thr Glu His Ile Arg Ile His Thr Gly Gln Lys Pro
        195                 200                 205

Phe Gln Cys Arg Ile Cys Met Arg Asn Phe Ser Glu Arg Ser His Leu
    210                 215                 220

Arg Glu His Ile Arg Thr His Thr Gly Glu Lys Pro Phe Ala Cys Asp
225                 230                 235                 240

Ile Cys Gly Arg Lys Phe Ala Gln Ala Gly His Leu Ala Ser His Thr
                245                 250                 255
```

Lys Ile His Leu Arg Gln Lys Asp
260

<210> SEQ ID NO 96
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Arg Pro His Ala Cys Pro Ala Glu Gly Cys Asp Arg Arg Phe Ser Arg
1 5 10 15

Ser Asp Asn Leu Val Arg His Leu Arg Ile His Thr Gly His Lys Pro
20 25 30

Phe Gln Cys Arg Ile Cys Met Arg Ser Phe Ser Arg Glu Asp Asn Leu
35 40 45

His Thr His Ile Arg Thr His Thr Gly Glu Lys Pro Phe Ala Cys Glu
50 55 60

Phe Cys Gly Arg Lys Phe Ala Arg Ser Asp Glu Leu Val Arg His Ala
65 70 75 80

Lys Ile His Leu Lys Gln Lys Glu His Ala Cys Pro Ala Glu Gly Cys
85 90 95

Asp Arg Arg Phe Ser Gln Ser Gly Asn Leu Thr Glu His Leu Arg Ile
100 105 110

His Thr Gly His Lys Pro Phe Gln Cys Arg Ile Cys Met Arg Ser Phe
115 120 125

Ser Thr Ser Gly His Leu Val Arg His Ile Arg Thr His Thr Gly Glu
130 135 140

Lys Pro Phe Ala Cys Glu Phe Cys Gly Arg Lys Phe Ala Gln Asn Ser
145 150 155 160

Thr Leu Thr Glu His Ala Lys Ile His Leu Lys Gln Lys Glu Lys
165 170 175

<210> SEQ ID NO 97
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Arg Pro His Ala Cys Pro Ala Glu Gly Cys Asp Arg Arg Phe Ser Arg
1 5 10 15

Ser Asp Asn Leu Val Arg His Leu Arg Ile His Thr Gly His Lys Pro
20 25 30

Phe Gln Cys Arg Ile Cys Met Arg Ser Phe Ser His Arg Thr Thr Leu
35 40 45

Thr Asn His Ile Arg Thr His Thr Gly Glu Lys Pro Phe Ala Cys Glu
50 55 60

Phe Cys Gly Arg Lys Phe Ala Arg Glu Asp Asn Leu His Thr His Ala
65 70 75 80

Lys Ile His Leu Lys Gln Lys Glu His Ala Cys Pro Ala Glu Gly Cys
85 90 95

Asp Arg Arg Phe Ser Thr Ser His Ser Leu Thr Glu His Leu Arg Ile
100 105 110

```
His Thr Gly His Lys Pro Phe Gln Cys Arg Ile Cys Met Arg Ser Phe
        115                 120                 125

Ser Gln Ser Ser Ser Leu Val Arg His Ile Arg Thr His Thr Gly Glu
    130                 135                 140

Lys Pro Phe Ala Cys Glu Phe Cys Gly Arg Lys Phe Ala Arg Glu Asp
145                 150                 155                 160

Asn Leu His Thr His Ala Lys Ile His Leu Lys Gln Lys Glu Lys
                165                 170                 175


<210> SEQ ID NO 98
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Arg Pro His Ala Cys Pro Ala Glu Gly Cys Asp Arg Arg Phe Ser Arg
1               5                   10                  15

Arg Asp Glu Leu Asn Val His Leu Arg Ile His Thr Gly His Lys Pro
            20                  25                  30

Phe Gln Cys Arg Ile Cys Met Arg Ser Phe Ser Arg Ser Asp His Leu
        35                  40                  45

Thr Asn His Ile Arg Thr His Thr Gly Glu Lys Pro Phe Ala Cys Glu
    50                  55                  60

Phe Cys Gly Arg Lys Phe Ala Arg Ser Asp Asp Leu Val Arg His Ala
65                  70                  75                  80

Lys Ile His Leu Lys Gln Lys Glu His Ala Cys Pro Ala Glu Gly Cys
                85                  90                  95

Asp Arg Arg Phe Ser Arg Ser Asp Asn Leu Val Arg His Leu Arg Ile
            100                 105                 110

His Thr Gly His Lys Pro Phe Gln Cys Arg Ile Cys Met Arg Ser Phe
        115                 120                 125

Ser His Arg Thr Thr Leu Thr Asn His Ile Arg Thr His Thr Gly Glu
    130                 135                 140

Lys Pro Phe Ala Cys Glu Phe Cys Gly Arg Lys Phe Ala Arg Glu Asp
145                 150                 155                 160

Asn Leu His Thr His Ala Lys Ile His Leu Lys Gln Lys Glu His Ala
                165                 170                 175

Cys Pro Ala Glu Gly Cys Asp Arg Arg Phe Ser Thr Ser His Ser Leu
            180                 185                 190

Thr Glu His Leu Arg Ile His Thr Gly His Lys Pro Phe Gln Cys Arg
        195                 200                 205

Ile Cys Met Arg Ser Phe Ser Gln Ser Ser Ser Leu Val Arg His Ile
    210                 215                 220

Arg Thr His Thr Gly Glu Lys Pro Phe Ala Cys Glu Phe Cys Gly Arg
225                 230                 235                 240

Lys Phe Ala Arg Glu Asp Asn Leu His Thr His Ala Lys Ile His Leu
                245                 250                 255

Lys Gln Lys Glu Lys
            260


<210> SEQ ID NO 99
<211> LENGTH: 753
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 99

Met Ala Pro Lys Lys Lys Arg Lys Val Gly Ile His Gly Val Pro Ala
1               5                   10                  15

Ala Leu Glu Pro Gly Glu Lys Pro Tyr Lys Cys Pro Glu Cys Gly Lys
            20                  25                  30

Ser Phe Ser Arg Ser Asp Asn Leu Val Arg His Gln Arg Thr His Thr
        35                  40                  45

Gly Glu Lys Pro Tyr Lys Cys Pro Glu Cys Gly Lys Ser Phe Ser His
    50                  55                  60

Arg Thr Thr Leu Thr Asn His Gln Arg Thr His Thr Gly Glu Lys Pro
65                  70                  75                  80

Tyr Lys Cys Pro Glu Cys Gly Lys Ser Phe Ser Arg Glu Asp Asn Leu
                85                  90                  95

His Thr His Gln Arg Thr His Thr Gly Glu Lys Pro Tyr Lys Cys Pro
            100                 105                 110

Glu Cys Gly Lys Ser Phe Ser Thr Ser His Ser Leu Thr Glu His Gln
        115                 120                 125

Arg Thr His Thr Gly Glu Lys Pro Tyr Lys Cys Pro Glu Cys Gly Lys
    130                 135                 140

Ser Phe Ser Gln Ser Ser Ser Leu Val Arg His Gln Arg Thr His Thr
145                 150                 155                 160

Gly Glu Lys Pro Tyr Lys Cys Pro Glu Cys Gly Lys Ser Phe Ser Arg
                165                 170                 175

Glu Asp Asn Leu His Thr His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Tyr Pro Tyr Asp Val Pro Asp Tyr Ala Leu Glu Glu Ala
    210                 215                 220

Ser Gly Ser Gly Arg Ala Asp Ala Leu Asp Asp Phe Asp Leu Asp Met
225                 230                 235                 240

Leu Gly Ser Asp Ala Leu Asp Asp Phe Asp Leu Asp Met Leu Gly Ser
                245                 250                 255

Asp Ala Leu Asp Asp Phe Asp Leu Asp Met Leu Gly Ser Asp Ala Leu
            260                 265                 270

Asp Asp Phe Asp Leu Asp Met Leu Ile Asn Ser Arg Ser Ser Gly Ser
        275                 280                 285

Pro Lys Lys Lys Arg Lys Val Gly Ser Gln Tyr Leu Pro Asp Thr Asp
    290                 295                 300

Asp Arg His Arg Ile Glu Glu Lys Arg Lys Arg Thr Tyr Glu Thr Phe
305                 310                 315                 320

Lys Ser Ile Met Lys Lys Ser Pro Phe Ser Gly Pro Thr Asp Pro Arg
                325                 330                 335

Pro Pro Pro Arg Arg Ile Ala Val Pro Ser Arg Ser Ser Ala Ser Val
            340                 345                 350

Pro Lys Pro Ala Pro Gln Pro Tyr Pro Phe Thr Ser Ser Leu Ser Thr
        355                 360                 365

Ile Asn Tyr Asp Glu Phe Pro Thr Met Val Phe Pro Ser Gly Gln Ile
    370                 375                 380

Ser Gln Ala Ser Ala Leu Ala Pro Ala Pro Pro Gln Val Leu Pro Gln
```

```
385                 390                 395                 400

Ala Pro Ala Pro Ala Pro Ala Pro Ala Met Val Ser Ala Leu Ala Gln
                405                 410                 415

Ala Pro Ala Pro Val Pro Val Leu Ala Pro Gly Pro Pro Gln Ala Val
            420                 425                 430

Ala Pro Pro Ala Pro Lys Pro Thr Gln Ala Gly Glu Gly Thr Leu Ser
        435                 440                 445

Glu Ala Leu Leu Gln Leu Gln Phe Asp Asp Glu Asp Leu Gly Ala Leu
    450                 455                 460

Leu Gly Asn Ser Thr Asp Pro Ala Val Phe Thr Asp Leu Ala Ser Val
465                 470                 475                 480

Asp Asn Ser Glu Phe Gln Gln Leu Leu Asn Gln Gly Ile Pro Val Ala
                485                 490                 495

Pro His Thr Thr Glu Pro Met Leu Met Glu Tyr Pro Glu Ala Ile Thr
            500                 505                 510

Arg Leu Val Thr Gly Ala Gln Arg Pro Pro Asp Pro Ala Pro Ala Pro
        515                 520                 525

Leu Gly Ala Pro Gly Leu Pro Asn Gly Leu Leu Ser Gly Asp Glu Asp
    530                 535                 540

Phe Ser Ser Ile Ala Asp Met Asp Phe Ser Ala Leu Leu Gly Ser Gly
545                 550                 555                 560

Ser Gly Ser Arg Asp Ser Arg Glu Gly Met Phe Leu Pro Lys Pro Glu
                565                 570                 575

Ala Gly Ser Ala Ile Ser Asp Val Phe Glu Gly Arg Glu Val Cys Gln
            580                 585                 590

Pro Lys Arg Ile Arg Pro Phe His Pro Pro Gly Ser Pro Trp Ala Asn
        595                 600                 605

Arg Pro Leu Pro Ala Ser Leu Ala Pro Thr Pro Thr Gly Pro Val His
    610                 615                 620

Glu Pro Val Gly Ser Leu Thr Pro Ala Pro Val Pro Gln Pro Leu Asp
625                 630                 635                 640

Pro Ala Pro Ala Val Thr Pro Glu Ala Ser His Leu Leu Glu Asp Pro
                645                 650                 655

Asp Glu Glu Thr Ser Gln Ala Val Lys Ala Leu Arg Glu Met Ala Asp
            660                 665                 670

Thr Val Ile Pro Gln Lys Glu Glu Ala Ala Ile Cys Gly Gln Met Asp
        675                 680                 685

Leu Ser His Pro Pro Pro Arg Gly His Leu Asp Glu Leu Thr Thr Thr
    690                 695                 700

Leu Glu Ser Met Thr Glu Asp Leu Asn Leu Asp Ser Pro Leu Thr Pro
705                 710                 715                 720

Glu Leu Asn Glu Ile Leu Asp Thr Phe Leu Asn Asp Glu Cys Leu Leu
                725                 730                 735

His Ala Met His Ile Ser Thr Gly Leu Ser Ile Phe Asp Thr Ser Leu
            740                 745                 750

Phe
```

<210> SEQ ID NO 100
<211> LENGTH: 753
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 100

Met Ala Pro Lys Lys Lys Arg Lys Val Gly Ile His Gly Val Pro Ala
1               5                   10                  15

Ala Leu Glu Pro Gly Glu Lys Pro Tyr Lys Cys Pro Glu Cys Gly Lys
            20                  25                  30

Ser Phe Ser Arg Ser Asp Asn Leu Val Arg His Gln Arg Thr His Thr
        35                  40                  45

Gly Glu Lys Pro Tyr Lys Cys Pro Glu Cys Gly Lys Ser Phe Ser Arg
    50                  55                  60

Glu Asp Asn Leu His Thr His Gln Arg Thr His Thr Gly Glu Lys Pro
65                  70                  75                  80

Tyr Lys Cys Pro Glu Cys Gly Lys Ser Phe Ser Arg Ser Asp Glu Leu
                85                  90                  95

Val Arg His Gln Arg Thr His Thr Gly Glu Lys Pro Tyr Lys Cys Pro
            100                 105                 110

Glu Cys Gly Lys Ser Phe Ser Gln Ser Gly Asn Leu Thr Glu His Gln
        115                 120                 125

Arg Thr His Thr Gly Glu Lys Pro Tyr Lys Cys Pro Glu Cys Gly Lys
    130                 135                 140

Ser Phe Ser Thr Ser Gly His Leu Val Arg His Gln Arg Thr His Thr
145                 150                 155                 160

Gly Glu Lys Pro Tyr Lys Cys Pro Glu Cys Gly Lys Ser Phe Ser Gln
                165                 170                 175

Asn Ser Thr Leu Thr Glu His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Tyr Pro Tyr Asp Val Pro Asp Tyr Ala Leu Glu Glu Ala
    210                 215                 220

Ser Gly Ser Gly Arg Ala Asp Ala Leu Asp Asp Phe Asp Leu Asp Met
225                 230                 235                 240

Leu Gly Ser Asp Ala Leu Asp Asp Phe Asp Leu Asp Met Leu Gly Ser
                245                 250                 255

Asp Ala Leu Asp Asp Phe Asp Leu Asp Met Leu Gly Ser Asp Ala Leu
            260                 265                 270

Asp Asp Phe Asp Leu Asp Met Leu Ile Asn Ser Arg Ser Ser Gly Ser
        275                 280                 285

Pro Lys Lys Lys Arg Lys Val Gly Ser Gln Tyr Leu Pro Asp Thr Asp
    290                 295                 300

Asp Arg His Arg Ile Glu Glu Lys Arg Lys Arg Thr Tyr Glu Thr Phe
305                 310                 315                 320

Lys Ser Ile Met Lys Lys Ser Pro Phe Ser Gly Pro Thr Asp Pro Arg
                325                 330                 335

Pro Pro Pro Arg Arg Ile Ala Val Pro Ser Arg Ser Ser Ala Ser Val
            340                 345                 350

Pro Lys Pro Ala Pro Gln Pro Tyr Pro Phe Thr Ser Ser Leu Ser Thr
        355                 360                 365

Ile Asn Tyr Asp Glu Phe Pro Thr Met Val Phe Pro Ser Gly Gln Ile
    370                 375                 380

Ser Gln Ala Ser Ala Leu Ala Pro Ala Pro Pro Gln Val Leu Pro Gln
385                 390                 395                 400

Ala Pro Ala Pro Ala Pro Ala Pro Ala Met Val Ser Ala Leu Ala Gln
                405                 410                 415

```
Ala Pro Ala Pro Val Pro Val Leu Ala Pro Gly Pro Pro Gln Ala Val
            420                 425                 430

Ala Pro Pro Ala Pro Lys Pro Thr Gln Ala Gly Glu Gly Thr Leu Ser
        435                 440                 445

Glu Ala Leu Leu Gln Leu Gln Phe Asp Asp Glu Asp Leu Gly Ala Leu
    450                 455                 460

Leu Gly Asn Ser Thr Asp Pro Ala Val Phe Thr Asp Leu Ala Ser Val
465                 470                 475                 480

Asp Asn Ser Glu Phe Gln Gln Leu Leu Asn Gln Gly Ile Pro Val Ala
                485                 490                 495

Pro His Thr Thr Glu Pro Met Leu Met Glu Tyr Pro Glu Ala Ile Thr
            500                 505                 510

Arg Leu Val Thr Gly Ala Gln Arg Pro Pro Asp Pro Ala Pro Ala Pro
        515                 520                 525

Leu Gly Ala Pro Gly Leu Pro Asn Gly Leu Leu Ser Gly Asp Glu Asp
    530                 535                 540

Phe Ser Ser Ile Ala Asp Met Asp Phe Ser Ala Leu Leu Gly Ser Gly
545                 550                 555                 560

Ser Gly Ser Arg Asp Ser Arg Glu Gly Met Phe Leu Pro Lys Pro Glu
                565                 570                 575

Ala Gly Ser Ala Ile Ser Asp Val Phe Glu Gly Arg Glu Val Cys Gln
            580                 585                 590

Pro Lys Arg Ile Arg Pro Phe His Pro Pro Gly Ser Pro Trp Ala Asn
        595                 600                 605

Arg Pro Leu Pro Ala Ser Leu Ala Pro Thr Pro Thr Gly Pro Val His
    610                 615                 620

Glu Pro Val Gly Ser Leu Thr Pro Ala Pro Val Pro Gln Pro Leu Asp
625                 630                 635                 640

Pro Ala Pro Ala Val Thr Pro Glu Ala Ser His Leu Leu Glu Asp Pro
                645                 650                 655

Asp Glu Glu Thr Ser Gln Ala Val Lys Ala Leu Arg Glu Met Ala Asp
            660                 665                 670

Thr Val Ile Pro Gln Lys Glu Glu Ala Ala Ile Cys Gly Gln Met Asp
        675                 680                 685

Leu Ser His Pro Pro Pro Arg Gly His Leu Asp Glu Leu Thr Thr Thr
    690                 695                 700

Leu Glu Ser Met Thr Glu Asp Leu Asn Leu Asp Ser Pro Leu Thr Pro
705                 710                 715                 720

Glu Leu Asn Glu Ile Leu Asp Thr Phe Leu Asn Asp Glu Cys Leu Leu
                725                 730                 735

His Ala Met His Ile Ser Thr Gly Leu Ser Ile Phe Asp Thr Ser Leu
            740                 745                 750

Phe
```

<210> SEQ ID NO 101
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Met Ala Pro Lys Lys Lys Arg Lys Val Gly Ile His Gly Val Pro Ala
1               5                   10                  15
```

```
Ala Leu Glu Pro Gly Glu Lys Pro Tyr Lys Cys Pro Glu Cys Gly Lys
            20                  25                  30

Ser Phe Ser Arg Ser Asp Asn Leu Val Arg His Gln Arg Thr His Thr
        35                  40                  45

Gly Glu Lys Pro Tyr Lys Cys Pro Glu Cys Gly Lys Ser Phe Ser His
    50                  55                  60

Arg Thr Thr Leu Thr Asn His Gln Arg Thr His Thr Gly Glu Lys Pro
65                  70                  75                  80

Tyr Lys Cys Pro Glu Cys Gly Lys Ser Phe Ser Arg Glu Asp Asn Leu
                85                  90                  95

His Thr His Gln Arg Thr His Thr Gly Glu Lys Pro Tyr Lys Cys Pro
            100                 105                 110

Glu Cys Gly Lys Ser Phe Ser Thr Ser His Ser Leu Thr Glu His Gln
        115                 120                 125

Arg Thr His Thr Gly Glu Lys Pro Tyr Lys Cys Pro Glu Cys Gly Lys
    130                 135                 140

Ser Phe Ser Gln Ser Ser Ser Leu Val Arg His Gln Arg Thr His Thr
145                 150                 155                 160

Gly Glu Lys Pro Tyr Lys Cys Pro Glu Cys Gly Lys Ser Phe Ser Arg
                165                 170                 175

Glu Asp Asn Leu His Thr His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Tyr Pro Tyr Asp Val Pro Asp Tyr Ala Leu Glu Asp Ala
    210                 215                 220

Leu Asp Asp Phe Asp Leu Asp Met Leu Gly Ser Asp Ala Leu Asp Asp
225                 230                 235                 240

Phe Asp Leu Asp Met Leu Gly Ser Asp Ala Leu Asp Asp Phe Asp Leu
                245                 250                 255

Asp Met Leu Gly Ser Asp Ala Leu Asp Asp Phe Asp Leu Asp Met Leu
            260                 265                 270


<210> SEQ ID NO 102
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Ala Pro Lys Lys Lys Arg Lys Val Gly Ile His Gly Val Pro Ala
1               5                   10                  15

Ala Leu Glu Pro Gly Glu Lys Pro Tyr Lys Cys Pro Glu Cys Gly Lys
            20                  25                  30

Ser Phe Ser Arg Ser Asp Asn Leu Val Arg His Gln Arg Thr His Thr
        35                  40                  45

Gly Glu Lys Pro Tyr Lys Cys Pro Glu Cys Gly Lys Ser Phe Ser Arg
    50                  55                  60

Glu Asp Asn Leu His Thr His Gln Arg Thr His Thr Gly Glu Lys Pro
65                  70                  75                  80

Tyr Lys Cys Pro Glu Cys Gly Lys Ser Phe Ser Arg Ser Asp Glu Leu
                85                  90                  95

Val Arg His Gln Arg Thr His Thr Gly Glu Lys Pro Tyr Lys Cys Pro
```

```
            100                 105                 110

Glu Cys Gly Lys Ser Phe Ser Gln Ser Gly Asn Leu Thr Glu His Gln
        115                 120                 125

Arg Thr His Thr Gly Glu Lys Pro Tyr Lys Cys Pro Glu Cys Gly Lys
    130                 135                 140

Ser Phe Ser Thr Ser Gly His Leu Val Arg His Gln Arg Thr His Thr
145                 150                 155                 160

Gly Glu Lys Pro Tyr Lys Cys Pro Glu Cys Gly Lys Ser Phe Ser Gln
                165                 170                 175

Asn Ser Thr Leu Thr Glu His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Tyr Pro Tyr Asp Val Pro Asp Tyr Ala Leu Glu Asp Ala
    210                 215                 220

Leu Asp Asp Phe Asp Leu Asp Met Leu Gly Ser Asp Ala Leu Asp Asp
225                 230                 235                 240

Phe Asp Leu Asp Met Leu Gly Ser Asp Ala Leu Asp Asp Phe Asp Leu
                245                 250                 255

Asp Met Leu Gly Ser Asp Ala Leu Asp Asp Phe Asp Leu Asp Met Leu
            260                 265                 270


<210> SEQ ID NO 103
<211> LENGTH: 580
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190
```

```
Gly Gln Ser Gln Leu Ile Lys Pro Ser Arg Met Arg Lys Tyr Pro Asn
        195                 200                 205

Arg Pro Ser Lys Thr Pro Pro His Glu Arg Pro Tyr Ala Cys Pro Val
    210                 215                 220

Glu Ser Cys Asp Arg Arg Phe Ser Arg Ser Asp Asn Leu Val Arg His
225                 230                 235                 240

Ile Arg Ile His Thr Gly Gln Lys Pro Phe Gln Cys Arg Ile Cys Met
                245                 250                 255

Arg Asn Phe Ser His Arg Thr Thr Leu Thr Asn His Ile Arg Thr His
            260                 265                 270

Thr Gly Glu Lys Pro Phe Ala Cys Asp Ile Cys Gly Arg Lys Phe Ala
        275                 280                 285

Arg Glu Asp Asn Leu His Thr His Thr Lys Ile His Leu Arg Gln Lys
    290                 295                 300

Asp Arg Pro Tyr Ala Cys Pro Val Glu Ser Cys Asp Arg Arg Phe Ser
305                 310                 315                 320

Thr Ser His Ser Leu Thr Glu His Ile Arg Ile His Thr Gly Gln Lys
                325                 330                 335

Pro Phe Gln Cys Arg Ile Cys Met Arg Asn Phe Ser Gln Ser Ser Ser
            340                 345                 350

Leu Val Arg His Ile Arg Thr His Thr Gly Glu Lys Pro Phe Ala Cys
        355                 360                 365

Asp Ile Cys Gly Arg Lys Phe Ala Arg Glu Asp Asn Leu His Thr His
    370                 375                 380

Thr Lys Ile His Leu Arg Gln Lys Asp Lys Leu Glu Met Ala Asp His
385                 390                 395                 400

Leu Met Leu Ala Glu Gly Tyr Arg Leu Val Gln Arg Pro Pro Ser Ala
                405                 410                 415

Ala Ala Ala His Gly Pro His Ala Leu Arg Thr Leu Pro Pro Tyr Ala
            420                 425                 430

Gly Pro Gly Leu Asp Ser Gly Leu Arg Pro Arg Gly Ala Pro Leu Gly
        435                 440                 445

Pro Pro Pro Pro Arg Gln Pro Gly Ala Leu Ala Tyr Gly Ala Phe Gly
    450                 455                 460

Pro Pro Ser Ser Phe Gln Pro Phe Pro Ala Val Pro Pro Pro Ala Ala
465                 470                 475                 480

Gly Ile Ala His Leu Gln Pro Val Ala Thr Pro Tyr Pro Gly Arg Ala
                485                 490                 495

Ala Ala Pro Pro Asn Ala Pro Gly Gly Pro Pro Gly Pro Gln Pro Ala
            500                 505                 510

Pro Ser Ala Ala Ala Pro Pro Pro Pro Ala His Ala Leu Gly Gly Met
        515                 520                 525

Asp Ala Glu Leu Ile Asp Glu Glu Ala Leu Thr Ser Leu Glu Leu Glu
    530                 535                 540

Leu Gly Leu His Arg Val Arg Glu Leu Pro Glu Leu Phe Leu Gly Gln
545                 550                 555                 560

Ser Glu Phe Asp Cys Phe Ser Asp Leu Gly Ser Ala Pro Pro Ala Gly
                565                 570                 575

Ser Val Ser Cys
            580
```

<210> SEQ ID NO 104
<211> LENGTH: 394
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 104

```
Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190

Gly Gln Ser Gln Leu Ile Lys Pro Ser Arg Met Arg Lys Tyr Pro Asn
        195                 200                 205

Arg Pro Ser Lys Thr Pro Pro His Glu Arg Pro Tyr Ala Cys Pro Val
    210                 215                 220

Glu Ser Cys Asp Arg Arg Phe Ser Arg Ser Asp Asn Leu Val Arg His
225                 230                 235                 240

Ile Arg Ile His Thr Gly Gln Lys Pro Phe Gln Cys Arg Ile Cys Met
                245                 250                 255

Arg Asn Phe Ser His Arg Thr Thr Leu Thr Asn His Ile Arg Thr His
            260                 265                 270

Thr Gly Glu Lys Pro Phe Ala Cys Asp Ile Cys Gly Arg Lys Phe Ala
        275                 280                 285

Arg Glu Asp Asn Leu His Thr His Thr Lys Ile His Leu Arg Gln Lys
    290                 295                 300

Asp Arg Pro Tyr Ala Cys Pro Val Glu Ser Cys Asp Arg Arg Phe Ser
305                 310                 315                 320

Thr Ser His Ser Leu Thr Glu His Ile Arg Ile His Thr Gly Gln Lys
                325                 330                 335

Pro Phe Gln Cys Arg Ile Cys Met Arg Asn Phe Ser Gln Ser Ser Ser
            340                 345                 350

Leu Val Arg His Ile Arg Thr His Thr Gly Glu Lys Pro Phe Ala Cys
        355                 360                 365

Asp Ile Cys Gly Arg Lys Phe Ala Arg Glu Asp Asn Leu His Thr His
    370                 375                 380
```

```
Thr Lys Ile His Leu Arg Gln Lys Asp Lys
385                 390


<210> SEQ ID NO 105
<211> LENGTH: 580
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190

Gly Gln Ser Gln Leu Ile Lys Pro Ser Arg Met Arg Lys Tyr Pro Asn
        195                 200                 205

Arg Pro Ser Lys Thr Pro Pro His Glu Arg Pro Tyr Ala Cys Pro Val
    210                 215                 220

Glu Ser Cys Asp Arg Arg Phe Ser Arg Ser Asp Asn Leu Val Arg His
225                 230                 235                 240

Ile Arg Ile His Thr Gly Gln Lys Pro Phe Gln Cys Arg Ile Cys Met
                245                 250                 255

Arg Asn Phe Ser Arg Glu Asp Asn Leu His Thr His Ile Arg Thr His
            260                 265                 270

Thr Gly Glu Lys Pro Phe Ala Cys Asp Ile Cys Gly Arg Lys Phe Ala
        275                 280                 285

Arg Ser Asp Glu Leu Val Arg His Thr Lys Ile His Leu Arg Gln Lys
    290                 295                 300

Asp Arg Pro Tyr Ala Cys Pro Val Glu Ser Cys Asp Arg Arg Phe Ser
305                 310                 315                 320

Gln Ser Gly Asn Leu Thr Glu His Ile Arg Ile His Thr Gly Gln Lys
                325                 330                 335

Pro Phe Gln Cys Arg Ile Cys Met Arg Asn Phe Ser Thr Ser Gly His
            340                 345                 350
```

Leu Val Arg His Ile Arg Thr His Thr Gly Glu Lys Pro Phe Ala Cys
355 360 365

Asp Ile Cys Gly Arg Lys Phe Ala Gln Asn Ser Thr Leu Thr Glu His
370 375 380

Thr Lys Ile His Leu Arg Gln Lys Asp Lys Leu Glu Met Ala Asp His
385 390 395 400

Leu Met Leu Ala Glu Gly Tyr Arg Leu Val Gln Arg Pro Pro Ser Ala
405 410 415

Ala Ala Ala His Gly Pro His Ala Leu Arg Thr Leu Pro Pro Tyr Ala
420 425 430

Gly Pro Gly Leu Asp Ser Gly Leu Arg Pro Arg Gly Ala Pro Leu Gly
435 440 445

Pro Pro Pro Pro Arg Gln Pro Gly Ala Leu Ala Tyr Gly Ala Phe Gly
450 455 460

Pro Pro Ser Ser Phe Gln Pro Phe Pro Ala Val Pro Pro Pro Ala Ala
465 470 475 480

Gly Ile Ala His Leu Gln Pro Val Ala Thr Pro Tyr Pro Gly Arg Ala
485 490 495

Ala Ala Pro Pro Asn Ala Pro Gly Gly Pro Pro Gly Pro Gln Pro Ala
500 505 510

Pro Ser Ala Ala Ala Pro Pro Pro Pro Ala His Ala Leu Gly Gly Met
515 520 525

Asp Ala Glu Leu Ile Asp Glu Glu Ala Leu Thr Ser Leu Glu Leu Glu
530 535 540

Leu Gly Leu His Arg Val Arg Glu Leu Pro Glu Leu Phe Leu Gly Gln
545 550 555 560

Ser Glu Phe Asp Cys Phe Ser Asp Leu Gly Ser Ala Pro Pro Ala Gly
565 570 575

Ser Val Ser Cys
580

<210> SEQ ID NO 106
<211> LENGTH: 394
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

Met Ala Ala Asp His Leu Met Leu Ala Glu Gly Tyr Arg Leu Val Gln
1 5 10 15

Arg Pro Pro Ser Ala Ala Ala Ala His Gly Pro His Ala Leu Arg Thr
20 25 30

Leu Pro Pro Tyr Ala Gly Pro Gly Leu Asp Ser Gly Leu Arg Pro Arg
35 40 45

Gly Ala Pro Leu Gly Pro Pro Pro Pro Arg Gln Pro Gly Ala Leu Ala
50 55 60

Tyr Gly Ala Phe Gly Pro Pro Ser Ser Phe Gln Pro Phe Pro Ala Val
65 70 75 80

Pro Pro Pro Ala Ala Gly Ile Ala His Leu Gln Pro Val Ala Thr Pro
85 90 95

Tyr Pro Gly Arg Ala Ala Ala Pro Pro Asn Ala Pro Gly Gly Pro Pro
100 105 110

Gly Pro Gln Pro Ala Pro Ser Ala Ala Ala Pro Pro Pro Pro Ala His 115 120 125

Ala Leu Gly Gly Met Asp Ala Glu Leu Ile Asp Glu Glu Ala Leu Thr
130 135 140

Ser Leu Glu Leu Glu Leu Gly Leu His Arg Val Arg Glu Leu Pro Glu
145 150 155 160

Leu Phe Leu Gly Gln Ser Glu Phe Asp Cys Phe Ser Asp Leu Gly Ser
165 170 175

Ala Pro Pro Ala Gly Ser Val Ser Cys Gly Gly Ser Gly Gly Gly Ser
180 185 190

Gly Gln Ser Gln Leu Ile Lys Pro Ser Arg Met Arg Lys Tyr Pro Asn
195 200 205

Arg Pro Ser Lys Thr Pro Pro His Glu Arg Pro Tyr Ala Cys Pro Val
210 215 220

Glu Ser Cys Asp Arg Arg Phe Ser Arg Ser Asp Asn Leu Val Arg His
225 230 235 240

Ile Arg Ile His Thr Gly Gln Lys Pro Phe Gln Cys Arg Ile Cys Met
245 250 255

Arg Asn Phe Ser Arg Glu Asp Asn Leu His Thr His Ile Arg Thr His
260 265 270

Thr Gly Glu Lys Pro Phe Ala Cys Asp Ile Cys Gly Arg Lys Phe Ala
275 280 285

Arg Ser Asp Glu Leu Val Arg His Thr Lys Ile His Leu Arg Gln Lys
290 295 300

Asp Arg Pro Tyr Ala Cys Pro Val Glu Ser Cys Asp Arg Arg Phe Ser
305 310 315 320

Gln Ser Gly Asn Leu Thr Glu His Ile Arg Ile His Thr Gly Gln Lys
325 330 335

Pro Phe Gln Cys Arg Ile Cys Met Arg Asn Phe Ser Thr Ser Gly His
340 345 350

Leu Val Arg His Ile Arg Thr His Thr Gly Glu Lys Pro Phe Ala Cys
355 360 365

Asp Ile Cys Gly Arg Lys Phe Ala Gln Asn Ser Thr Leu Thr Glu His
370 375 380

Thr Lys Ile His Leu Arg Gln Lys Asp Lys
385 390

<210> SEQ ID NO 107
<211> LENGTH: 388
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Met Gln Ser Gln Leu Ile Lys Pro Ser Arg Met Arg Lys Tyr Pro Asn
1 5 10 15

Arg Pro Ser Lys Thr Pro Pro His Glu Arg Pro Tyr Ala Cys Pro Val
20 25 30

Glu Ser Cys Asp Arg Arg Phe Ser Arg Ser Asp Asn Leu Val Arg His
35 40 45

Ile Arg Ile His Thr Gly Gln Lys Pro Phe Gln Cys Arg Ile Cys Met
50 55 60

Arg Asn Phe Ser Arg Glu Asp Asn Leu His Thr His Ile Arg Thr His
65 70 75 80

```
Thr Gly Glu Lys Pro Phe Ala Cys Asp Ile Cys Gly Arg Lys Phe Ala
                85                  90                  95

Arg Ser Asp Glu Leu Val Arg His Thr Lys Ile His Leu Arg Gln Lys
            100                 105                 110

Asp Arg Pro Tyr Ala Cys Pro Val Glu Ser Cys Asp Arg Arg Phe Ser
        115                 120                 125

Gln Ser Gly Asn Leu Thr Glu His Ile Arg Ile His Thr Gly Gln Lys
    130                 135                 140

Pro Phe Gln Cys Arg Ile Cys Met Arg Asn Phe Ser Thr Ser Gly His
145                 150                 155                 160

Leu Val Arg His Ile Arg Thr His Thr Gly Glu Lys Pro Phe Ala Cys
                165                 170                 175

Asp Ile Cys Gly Arg Lys Phe Ala Gln Asn Ser Thr Leu Thr Glu His
            180                 185                 190

Thr Lys Ile His Leu Arg Gln Lys Asp Lys Leu Glu Met Ala Asp His
        195                 200                 205

Leu Met Leu Ala Glu Gly Tyr Arg Leu Val Gln Arg Pro Pro Ser Ala
    210                 215                 220

Ala Ala Ala His Gly Pro His Ala Leu Arg Thr Leu Pro Pro Tyr Ala
225                 230                 235                 240

Gly Pro Gly Leu Asp Ser Gly Leu Arg Pro Arg Gly Ala Pro Leu Gly
                245                 250                 255

Pro Pro Pro Pro Arg Gln Pro Gly Ala Leu Ala Tyr Gly Ala Phe Gly
            260                 265                 270

Pro Pro Ser Ser Phe Gln Pro Phe Pro Ala Val Pro Pro Pro Ala Ala
        275                 280                 285

Gly Ile Ala His Leu Gln Pro Val Ala Thr Pro Tyr Pro Gly Arg Ala
    290                 295                 300

Ala Ala Pro Pro Asn Ala Pro Gly Gly Pro Pro Gly Pro Gln Pro Ala
305                 310                 315                 320

Pro Ser Ala Ala Ala Pro Pro Pro Pro Ala His Ala Leu Gly Gly Met
                325                 330                 335

Asp Ala Glu Leu Ile Asp Glu Glu Ala Leu Thr Ser Leu Glu Leu Glu
            340                 345                 350

Leu Gly Leu His Arg Val Arg Glu Leu Pro Glu Leu Phe Leu Gly Gln
        355                 360                 365

Ser Glu Phe Asp Cys Phe Ser Asp Leu Gly Ser Ala Pro Pro Ala Gly
    370                 375                 380

Ser Val Ser Cys
385


<210> SEQ ID NO 108
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Gln Ser Gln Leu Ile Lys Pro Ser Arg Met Arg Lys Tyr Pro Asn
1               5                   10                  15

Arg Pro Ser Lys Thr Pro Pro His Glu Arg Pro Tyr Ala Cys Pro Val
            20                  25                  30

Glu Ser Cys Asp Arg Arg Phe Ser Arg Ser Asp Asn Leu Val Arg His
        35                  40                  45
```

```
Ile Arg Ile His Thr Gly Gln Lys Pro Phe Gln Cys Arg Ile Cys Met
    50                  55                  60

Arg Asn Phe Ser Arg Glu Asp Asn Leu His Thr His Ile Arg Thr His
65                  70                  75                  80

Thr Gly Glu Lys Pro Phe Ala Cys Asp Ile Cys Gly Arg Lys Phe Ala
                85                  90                  95

Arg Ser Asp Glu Leu Val Arg His Thr Lys Ile His Leu Arg Gln Lys
            100                 105                 110

Asp Arg Pro Tyr Ala Cys Pro Val Glu Ser Cys Asp Arg Arg Phe Ser
        115                 120                 125

Gln Ser Gly Asn Leu Thr Glu His Ile Arg Ile His Thr Gly Gln Lys
    130                 135                 140

Pro Phe Gln Cys Arg Ile Cys Met Arg Asn Phe Ser Thr Ser Gly His
145                 150                 155                 160

Leu Val Arg His Ile Arg Thr His Thr Gly Glu Lys Pro Phe Ala Cys
                165                 170                 175

Asp Ile Cys Gly Arg Lys Phe Ala Gln Asn Ser Thr Leu Thr Glu His
            180                 185                 190

Thr Lys Ile His Leu Arg Gln Lys Asp Lys Leu Glu Met Ser Gly Leu
        195                 200                 205

Glu Met Ala Asp His Met Met Ala Met Asn His Gly Arg Phe Pro Asp
    210                 215                 220

Gly Thr Asn Gly Leu His His His Pro Ala His Arg Met Gly Met Gly
225                 230                 235                 240

Gln Phe Pro Ser Pro His His His Gln Gln Gln Gln Pro Gln His Ala
                245                 250                 255

Phe Asn Ala Leu Met Gly Glu His Ile His Tyr Gly Ala Gly Asn Met
            260                 265                 270

Asn Ala Thr Ser Gly Ile Arg His Ala Met Gly Pro Gly Thr Val Asn
        275                 280                 285

Gly Gly His Pro Pro Ser Ala Leu Ala Pro Ala Ala Arg Phe Asn Asn
    290                 295                 300

Ser Gln Phe Met Gly Pro Pro Val Ala Ser Gln Gly Gly Ser Leu Pro
305                 310                 315                 320

Ala Ser Met Gln Leu Gln Lys Leu Asn Asn Gln Tyr Phe Asn His His
                325                 330                 335

Pro Tyr Pro His Asn His Tyr Met Pro Asp Leu His Pro Ala Ala Gly
            340                 345                 350

His Gln Met Asn Gly Thr Asn Gln His Phe Arg Asp Cys Asn Pro Lys
        355                 360                 365

His Ser Gly Gly Ser Ser Thr Pro Gly Gly Ser Gly Gly Ser Ser Thr
    370                 375                 380

Pro Gly Gly Ser Gly Ser Ser Ser Gly Gly Gly Ala Gly Ser Ser Asn
385                 390                 395                 400

Ser Gly Gly Gly Ser Gly Ser Gly Asn Met Pro Ala Ser Val Ala His
                405                 410                 415

Val Pro Ala Ala Met Leu Pro Pro Asn Val Ile Asp Thr Asp Phe Ile
            420                 425                 430

Asp Glu Glu Val Leu Met Ser Leu Val Ile Glu Met Gly Leu Asp Arg
        435                 440                 445

Ile Lys Glu Leu Pro Glu Leu Trp Leu Gly Gln Asn Glu Phe Asp Phe
    450                 455                 460
```

```
Met Thr Asp Phe Val Cys Lys Gln Gln Pro Ser Arg Val Ser Cys
465                 470                 475


<210> SEQ ID NO 109
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Ser Gly Leu Glu Met Ala Asp His Met Met Ala Met Asn His Gly
1               5                   10                  15

Arg Phe Pro Asp Gly Thr Asn Gly Leu His His His Pro Ala His Arg
            20                  25                  30

Met Gly Met Gly Gln Phe Pro Ser Pro His His His Gln Gln Gln Gln
        35                  40                  45

Pro Gln His Ala Phe Asn Ala Leu Met Gly Glu His Ile His Tyr Gly
    50                  55                  60

Ala Gly Asn Met Asn Ala Thr Ser Gly Val Arg His Ala Met Gly Pro
65                  70                  75                  80

Gly Thr Val Asn Gly Gly His Pro Pro Ser Ala Leu Ala Pro Ala Ala
                85                  90                  95

Arg Phe Asn Asn Ser Gln Phe Met Gly Pro Pro Val Ala Ser Gln Gly
            100                 105                 110

Gly Ser Leu Pro Ala Ser Met Gln Leu Gln Lys Leu Asn Asn Gln Tyr
        115                 120                 125

Phe Asn His His Pro Tyr Pro His Asn His Tyr Met Pro Asp Leu His
    130                 135                 140

Pro Ala Ala Gly His Gln Met Asn Gly Thr Asn Gln His Phe Arg Asp
145                 150                 155                 160

Cys Asn Pro Lys His Ser Gly Gly Ser Ser Thr Pro Gly Gly Ser Gly
                165                 170                 175

Gly Ser Ser Thr Pro Gly Gly Ser Gly Ser Ser Ser Gly Gly Gly Ala
            180                 185                 190

Gly Ser Ser Asn Ser Gly Gly Gly Ser Gly Ser Gly Asn Met Pro Ala
        195                 200                 205

Ser Val Ala His Val Pro Ala Ala Met Leu Pro Pro Asn Val Ile Asp
    210                 215                 220

Thr Asp Phe Ile Asp Glu Glu Val Leu Met Ser Leu Val Ile Glu Met
225                 230                 235                 240

Gly Leu Asp Arg Ile Lys Glu Leu Pro Glu Leu Trp Leu Gly Gln Asn
                245                 250                 255

Glu Phe Asp Phe Met Thr Asp Phe Val Cys Lys Gln Gln Pro Ser Arg
            260                 265                 270

Val Ser Cys Gln Ser Gln Leu Ile Lys Pro Ser Arg Met Arg Lys Tyr
        275                 280                 285

Pro Asn Arg Pro Ser Lys Thr Pro Pro His Glu Arg Pro Tyr Ala Cys
    290                 295                 300

Pro Val Glu Ser Cys Asp Arg Arg Phe Ser Arg Ser Asp Asn Leu Val
305                 310                 315                 320

Arg His Ile Arg Ile His Thr Gly Gln Lys Pro Phe Gln Cys Arg Ile
                325                 330                 335

Cys Met Arg Asn Phe Ser Arg Glu Asp Asn Leu His Thr His Ile Arg
            340                 345                 350
```

Thr His Thr Gly Glu Lys Pro Phe Ala Cys Asp Ile Cys Gly Arg Lys
355 360 365

Phe Ala Arg Ser Asp Glu Leu Val Arg His Thr Lys Ile His Leu Arg
370 375 380

Gln Lys Asp Arg Pro Tyr Ala Cys Pro Val Glu Ser Cys Asp Arg Arg
385 390 395 400

Phe Ser Gln Ser Gly Asn Leu Thr Glu His Ile Arg Ile His Thr Gly
405 410 415

Gln Lys Pro Phe Gln Cys Arg Ile Cys Met Arg Asn Phe Ser Thr Ser
420 425 430

Gly His Leu Val Arg His Ile Arg Thr His Thr Gly Glu Lys Pro Phe
435 440 445

Ala Cys Asp Ile Cys Gly Arg Lys Phe Ala Gln Asn Ser Thr Leu Thr
450 455 460

Glu His Thr Lys Ile His Leu Arg Gln Lys Asp Lys
465 470 475

<210> SEQ ID NO 110
<211> LENGTH: 554
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Met Ala Ala Asp His Leu Met Leu Ala Glu Gly Tyr Arg Leu Val Gln
1 5 10 15

Arg Pro Pro Ser Ala Ala Ala Ala His Gly Pro His Ala Leu Arg Thr
20 25 30

Leu Pro Pro Tyr Ala Gly Pro Gly Leu Asp Ser Gly Leu Arg Pro Arg
35 40 45

Gly Ala Pro Leu Gly Pro Pro Pro Pro Arg Gln Pro Gly Ala Leu Ala
50 55 60

Tyr Gly Ala Phe Gly Pro Pro Ser Ser Phe Gln Pro Phe Pro Ala Val
65 70 75 80

Pro Pro Pro Ala Ala Gly Ile Ala His Leu Gln Pro Val Ala Thr Pro
85 90 95

Tyr Pro Gly Arg Ala Ala Ala Pro Pro Asn Ala Pro Gly Gly Pro Pro
100 105 110

Gly Pro Gln Pro Ala Pro Ser Ala Ala Ala Pro Pro Pro Pro Ala His
115 120 125

Ala Leu Gly Gly Met Asp Ala Glu Leu Ile Asp Glu Glu Ala Leu Thr
130 135 140

Ser Leu Glu Leu Glu Leu Gly Leu His Arg Val Arg Glu Leu Pro Glu
145 150 155 160

Leu Phe Leu Gly Gln Ser Glu Phe Asp Cys Phe Ser Asp Leu Gly Ser
165 170 175

Ala Pro Pro Ala Gly Ser Val Ser Cys Gly Gly Ser Gly Gly Gly Ser
180 185 190

Gly Arg Pro His Ala Cys Pro Ala Glu Gly Cys Asp Arg Arg Phe Ser
195 200 205

Arg Ser Asp Asn Leu Val Arg His Leu Arg Ile His Thr Gly His Lys
210 215 220

Pro Phe Gln Cys Arg Ile Cys Met Arg Ser Phe Ser Arg Glu Asp Asn

```
225                 230                 235                 240

Leu His Thr His Ile Arg Thr His Thr Gly Glu Lys Pro Phe Ala Cys
                245                 250                 255

Glu Phe Cys Gly Arg Lys Phe Ala Arg Ser Asp Glu Leu Val Arg His
            260                 265                 270

Ala Lys Ile His Leu Lys Gln Lys Glu His Ala Cys Pro Ala Glu Gly
        275                 280                 285

Cys Asp Arg Arg Phe Ser Gln Ser Gly Asn Leu Thr Glu His Leu Arg
    290                 295                 300

Ile His Thr Gly His Lys Pro Phe Gln Cys Arg Ile Cys Met Arg Ser
305                 310                 315                 320

Phe Ser Thr Ser Gly His Leu Val Arg His Ile Arg Thr His Thr Gly
                325                 330                 335

Glu Lys Pro Phe Ala Cys Glu Phe Cys Gly Arg Lys Phe Ala Gln Asn
            340                 345                 350

Ser Thr Leu Thr Glu His Ala Lys Ile His Leu Lys Gln Lys Glu Lys
        355                 360                 365

Leu Glu Met Ala Asp His Leu Met Leu Ala Glu Gly Tyr Arg Leu Val
    370                 375                 380

Gln Arg Pro Pro Ser Ala Ala Ala Ala His Gly Pro His Ala Leu Arg
385                 390                 395                 400

Thr Leu Pro Pro Tyr Ala Gly Pro Gly Leu Asp Ser Gly Leu Arg Pro
                405                 410                 415

Arg Gly Ala Pro Leu Gly Pro Pro Pro Pro Arg Gln Pro Gly Ala Leu
            420                 425                 430

Ala Tyr Gly Ala Phe Gly Pro Pro Ser Ser Phe Gln Pro Phe Pro Ala
        435                 440                 445

Val Pro Pro Pro Ala Ala Gly Ile Ala His Leu Gln Pro Val Ala Thr
    450                 455                 460

Pro Tyr Pro Gly Arg Ala Ala Ala Pro Pro Asn Ala Pro Gly Gly Pro
465                 470                 475                 480

Pro Gly Pro Gln Pro Ala Pro Ser Ala Ala Ala Pro Pro Pro Pro Ala
                485                 490                 495

His Ala Leu Gly Gly Met Asp Ala Glu Leu Ile Asp Glu Glu Ala Leu
            500                 505                 510

Thr Ser Leu Glu Leu Glu Leu Gly Leu His Arg Val Arg Glu Leu Pro
        515                 520                 525

Glu Leu Phe Leu Gly Gln Ser Glu Phe Asp Cys Phe Ser Asp Leu Gly
    530                 535                 540

Ser Ala Pro Pro Ala Gly Ser Val Ser Cys
545                 550
```

<210> SEQ ID NO 111
<211> LENGTH: 362
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Met Arg Pro His Ala Cys Pro Ala Glu Gly Cys Asp Arg Arg Phe Ser
1               5                   10                  15

Arg Ser Asp Asn Leu Val Arg His Leu Arg Ile His Thr Gly His Lys
            20                  25                  30
```

```
Pro Phe Gln Cys Arg Ile Cys Met Arg Ser Phe Ser Arg Glu Asp Asn
        35                  40                  45

Leu His Thr His Ile Arg Thr His Thr Gly Glu Lys Pro Phe Ala Cys
    50                  55                  60

Glu Phe Cys Gly Arg Lys Phe Ala Arg Ser Asp Glu Leu Val Arg His
65                  70                  75                  80

Ala Lys Ile His Leu Lys Gln Lys Glu His Ala Cys Pro Ala Glu Gly
                85                  90                  95

Cys Asp Arg Arg Phe Ser Gln Ser Gly Asn Leu Thr Glu His Leu Arg
            100                 105                 110

Ile His Thr Gly His Lys Pro Phe Gln Cys Arg Ile Cys Met Arg Ser
        115                 120                 125

Phe Ser Thr Ser Gly His Leu Val Arg His Ile Arg Thr His Thr Gly
    130                 135                 140

Glu Lys Pro Phe Ala Cys Glu Phe Cys Gly Arg Lys Phe Ala Gln Asn
145                 150                 155                 160

Ser Thr Leu Thr Glu His Ala Lys Ile His Leu Lys Gln Lys Glu Lys
                165                 170                 175

Leu Glu Met Ala Asp His Leu Met Leu Ala Glu Gly Tyr Arg Leu Val
            180                 185                 190

Gln Arg Pro Pro Ser Ala Ala Ala Ala His Gly Pro His Ala Leu Arg
        195                 200                 205

Thr Leu Pro Pro Tyr Ala Gly Pro Gly Leu Asp Ser Gly Leu Arg Pro
    210                 215                 220

Arg Gly Ala Pro Leu Gly Pro Pro Pro Pro Arg Gln Pro Gly Ala Leu
225                 230                 235                 240

Ala Tyr Gly Ala Phe Gly Pro Pro Ser Ser Phe Gln Pro Phe Pro Ala
                245                 250                 255

Val Pro Pro Pro Ala Ala Gly Ile Ala His Leu Gln Pro Val Ala Thr
            260                 265                 270

Pro Tyr Pro Gly Arg Ala Ala Ala Pro Pro Asn Ala Pro Gly Gly Pro
        275                 280                 285

Pro Gly Pro Gln Pro Ala Pro Ser Ala Ala Ala Pro Pro Pro Pro Ala
    290                 295                 300

His Ala Leu Gly Gly Met Asp Ala Glu Leu Ile Asp Glu Glu Ala Leu
305                 310                 315                 320

Thr Ser Leu Glu Leu Glu Leu Gly Leu His Arg Val Arg Glu Leu Pro
                325                 330                 335

Glu Leu Phe Leu Gly Gln Ser Glu Phe Asp Cys Phe Ser Asp Leu Gly
            340                 345                 350

Ser Ala Pro Pro Ala Gly Ser Val Ser Cys
        355                 360
```

<210> SEQ ID NO 112
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Met Arg Pro His Ala Cys Pro Ala Glu Gly Cys Asp Arg Arg Phe Ser
1               5                   10                  15

Arg Ser Asp Asn Leu Val Arg His Leu Arg Ile His Thr Gly His Lys
            20                  25                  30
```

```
Pro Phe Gln Cys Arg Ile Cys Met Arg Ser Phe Ser Arg Glu Asp Asn
        35                  40                  45

Leu His Thr His Ile Arg Thr His Thr Gly Glu Lys Pro Phe Ala Cys
    50                  55                  60

Glu Phe Cys Gly Arg Lys Phe Ala Arg Ser Asp Glu Leu Val Arg His
65                  70                  75                  80

Ala Lys Ile His Leu Lys Gln Lys Glu His Ala Cys Pro Ala Glu Gly
                85                  90                  95

Cys Asp Arg Arg Phe Ser Gln Ser Gly Asn Leu Thr Glu His Leu Arg
            100                 105                 110

Ile His Thr Gly His Lys Pro Phe Gln Cys Arg Ile Cys Met Arg Ser
        115                 120                 125

Phe Ser Thr Ser Gly His Leu Val Arg His Ile Arg Thr His Thr Gly
    130                 135                 140

Glu Lys Pro Phe Ala Cys Glu Phe Cys Gly Arg Lys Phe Ala Gln Asn
145                 150                 155                 160

Ser Thr Leu Thr Glu His Ala Lys Ile His Leu Lys Gln Lys Glu Lys
                165                 170                 175

Lys Ala Glu Lys Gly Gly Ala Pro Ser Ala Ser Ser Ala Pro Pro Val
            180                 185                 190

Ser Leu Ala Pro Val Val Thr Thr Cys Ala Leu Glu Met Ser Gly Leu
        195                 200                 205

Glu Met Ala Asp His Met Met Ala Met Asn His Gly Arg Phe Pro Asp
    210                 215                 220

Gly Thr Asn Gly Leu His His His Pro Ala His Arg Met Gly Met Gly
225                 230                 235                 240

Gln Phe Pro Ser Pro His His His Gln Gln Gln Gln Pro Gln His Ala
                245                 250                 255

Phe Asn Ala Leu Met Gly Glu His Ile His Tyr Gly Ala Gly Asn Met
            260                 265                 270

Asn Ala Thr Ser Gly Ile Arg His Ala Met Gly Pro Gly Thr Val Asn
        275                 280                 285

Gly Gly His Pro Pro Ser Ala Leu Ala Pro Ala Ala Arg Phe Asn Asn
    290                 295                 300

Ser Gln Phe Met Gly Pro Pro Val Ala Ser Gln Gly Gly Ser Leu Pro
305                 310                 315                 320

Ala Ser Met Gln Leu Gln Lys Leu Asn Asn Gln Tyr Phe Asn His His
                325                 330                 335

Pro Tyr Pro His Asn His Tyr Met Pro Asp Leu His Pro Ala Ala Gly
            340                 345                 350

His Gln Met Asn Gly Thr Asn Gln His Phe Arg Asp Cys Asn Pro Lys
        355                 360                 365

His Ser Gly Gly Ser Ser Thr Pro Gly Gly Ser Gly Gly Ser Ser Thr
    370                 375                 380

Pro Gly Gly Ser Gly Ser Ser Ser Gly Gly Gly Ala Gly Ser Ser Asn
385                 390                 395                 400

Ser Gly Gly Gly Ser Gly Ser Gly Asn Met Pro Ala Ser Val Ala His
                405                 410                 415

Val Pro Ala Ala Met Leu Pro Pro Asn Val Ile Asp Thr Asp Phe Ile
            420                 425                 430

Asp Glu Glu Val Leu Met Ser Leu Val Ile Glu Met Gly Leu Asp Arg
        435                 440                 445
```

```
Ile Lys Glu Leu Pro Glu Leu Trp Leu Gly Gln Asn Glu Phe Asp Phe
    450                 455                 460

Met Thr Asp Phe Val Cys Lys Gln Gln Pro Ser Arg Val Ser Cys
465                 470                 475


<210> SEQ ID NO 113
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Ser Gly Leu Glu Met Ala Asp His Met Met Ala Met Asn His Gly
1               5                   10                  15

Arg Phe Pro Asp Gly Thr Asn Gly Leu His His His Pro Ala His Arg
            20                  25                  30

Met Gly Met Gly Gln Phe Pro Ser Pro His His His Gln Gln Gln Gln
        35                  40                  45

Pro Gln His Ala Phe Asn Ala Leu Met Gly Glu His Ile His Tyr Gly
    50                  55                  60

Ala Gly Asn Met Asn Ala Thr Ser Gly Val Arg His Ala Met Gly Pro
65                  70                  75                  80

Gly Thr Val Asn Gly Gly His Pro Pro Ser Ala Leu Ala Pro Ala Ala
                85                  90                  95

Arg Phe Asn Asn Ser Gln Phe Met Gly Pro Pro Val Ala Ser Gln Gly
            100                 105                 110

Gly Ser Leu Pro Ala Ser Met Gln Leu Gln Lys Leu Asn Asn Gln Tyr
        115                 120                 125

Phe Asn His His Pro Tyr Pro His Asn His Tyr Met Pro Asp Leu His
    130                 135                 140

Pro Ala Ala Gly His Gln Met Asn Gly Thr Asn Gln His Phe Arg Asp
145                 150                 155                 160

Cys Asn Pro Lys His Ser Gly Gly Ser Ser Thr Pro Gly Gly Ser Gly
                165                 170                 175

Gly Ser Ser Thr Pro Gly Gly Ser Gly Ser Ser Ser Gly Gly Gly Ala
            180                 185                 190

Gly Ser Ser Asn Ser Gly Gly Gly Ser Gly Ser Gly Asn Met Pro Ala
        195                 200                 205

Ser Val Ala His Val Pro Ala Ala Met Leu Pro Pro Asn Val Ile Asp
    210                 215                 220

Thr Asp Phe Ile Asp Glu Glu Val Leu Met Ser Leu Val Ile Glu Met
225                 230                 235                 240

Gly Leu Asp Arg Ile Lys Glu Leu Pro Glu Leu Trp Leu Gly Gln Asn
                245                 250                 255

Glu Phe Asp Phe Met Thr Asp Phe Val Cys Lys Gln Gln Pro Ser Arg
            260                 265                 270

Val Ser Cys Arg Pro His Ala Cys Pro Ala Glu Gly Cys Asp Arg Arg
        275                 280                 285

Phe Ser Arg Ser Asp Asn Leu Val Arg His Leu Arg Ile His Thr Gly
    290                 295                 300

His Lys Pro Phe Gln Cys Arg Ile Cys Met Arg Ser Phe Ser Arg Glu
305                 310                 315                 320

Asp Asn Leu His Thr His Ile Arg Thr His Thr Gly Glu Lys Pro Phe
                325                 330                 335
```

```
Ala Cys Glu Phe Cys Gly Arg Lys Phe Ala Arg Ser Asp Glu Leu Val
            340                 345                 350

Arg His Ala Lys Ile His Leu Lys Gln Lys Glu His Ala Cys Pro Ala
        355                 360                 365

Glu Gly Cys Asp Arg Arg Phe Ser Gln Ser Gly Asn Leu Thr Glu His
    370                 375                 380

Leu Arg Ile His Thr Gly His Lys Pro Phe Gln Cys Arg Ile Cys Met
385                 390                 395                 400

Arg Ser Phe Ser Thr Ser Gly His Leu Val Arg His Ile Arg Thr His
                405                 410                 415

Thr Gly Glu Lys Pro Phe Ala Cys Glu Phe Cys Gly Arg Lys Phe Ala
            420                 425                 430

Gln Asn Ser Thr Leu Thr Glu His Ala Lys Ile His Leu Lys Gln Lys
        435                 440                 445

Glu Lys Lys Ala Glu Lys Gly Gly Ala Pro Ser Ala Ser Ser Ala Pro
    450                 455                 460

Pro Val Ser Leu Ala Pro Val Val Thr Thr Cys Ala
465                 470                 475


<210> SEQ ID NO 114
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Thr Gly Lys Leu Ala Glu Lys Leu Pro Val Thr Met Ser Ser Leu
1               5                   10                  15

Leu Asn Gln Leu Pro Asp Asn Leu Tyr Pro Glu Glu Ile Pro Ser Ala
            20                  25                  30

Leu Asn Leu Phe Ser Gly Ser Ser Asp Ser Val Val His Tyr Asn Gln
        35                  40                  45

Met Ala Thr Glu Asn Val Met Asp Ile Gly Leu Thr Asn Glu Lys Pro
    50                  55                  60

Asn Pro Glu Leu Ser Tyr Ser Gly Ser Phe Gln Pro Ala Pro Gly Asn
65                  70                  75                  80

Lys Thr Val Thr Tyr Leu Gly Lys Phe Ala Phe Asp Ser Pro Ser Asn
                85                  90                  95

Trp Cys Gln Asp Asn Ile Ile Ser Leu Met Ser Ala Gly Ile Leu Gly
            100                 105                 110

Val Pro Pro Ala Ser Gly Ala Leu Ser Thr Gln Thr Ser Thr Ala Ser
        115                 120                 125

Met Val Gln Pro Pro Gln Gly Asp Val Glu Ala Met Tyr Pro Ala Leu
    130                 135                 140

Pro Pro Tyr Ser Asn Cys Gly Asp Leu Tyr Ser Glu Pro Val Ser Phe
145                 150                 155                 160

His Asp Pro Gln Gly Asn Pro Gly Leu Ala Tyr Ser Pro Gln Asp Tyr
                165                 170                 175

Gln Ser Ala Lys Pro Ala Leu Asp Ser Asn Leu Phe Pro Met Ile Pro
            180                 185                 190

Asp Tyr Asn Leu Tyr His His Pro Asn Asp Met Gly Ser Ile Pro Glu
        195                 200                 205

His Lys Pro Phe Gln Gly Met Asp Pro Ile Arg Val Asn Pro Pro Pro
```

```
    210                 215                 220

Ile Thr Pro Leu Glu Thr Ile Lys Ala Phe Lys Asp Lys Gln Ile His
225                 230                 235                 240

Pro Gly Phe Gly Ser Leu Pro Gln Pro Pro Leu Thr Leu Lys Pro Ile
                245                 250                 255

Arg Pro Arg Lys Tyr Pro Asn Arg Pro Ser Lys Thr Pro Leu His Glu
            260                 265                 270

Arg Pro His Ala Cys Pro Ala Glu Gly Cys Asp Arg Arg Phe Ser Arg
        275                 280                 285

Arg Asp Glu Leu Asn Val His Leu Arg Ile His Thr Gly His Lys Pro
    290                 295                 300

Phe Gln Cys Arg Ile Cys Met Arg Ser Phe Ser Arg Ser Asp His Leu
305                 310                 315                 320

Thr Asn His Ile Arg Thr His Thr Gly Glu Lys Pro Phe Ala Cys Glu
                325                 330                 335

Phe Cys Gly Arg Lys Phe Ala Arg Ser Asp Asp Leu Val Arg His Ala
            340                 345                 350

Lys Ile His Leu Lys Gln Lys Glu His Ala Cys Pro Ala Glu Gly Cys
        355                 360                 365

Asp Arg Arg Phe Ser Arg Ser Asp Asn Leu Val Arg His Leu Arg Ile
    370                 375                 380

His Thr Gly His Lys Pro Phe Gln Cys Arg Ile Cys Met Arg Ser Phe
385                 390                 395                 400

Ser His Arg Thr Thr Leu Thr Asn His Ile Arg Thr His Thr Gly Glu
                405                 410                 415

Lys Pro Phe Ala Cys Glu Phe Cys Gly Arg Lys Phe Ala Arg Glu Asp
            420                 425                 430

Asn Leu His Thr His Ala Lys Ile His Leu Lys Gln Lys Glu His Ala
        435                 440                 445

Cys Pro Ala Glu Gly Cys Asp Arg Arg Phe Ser Thr Ser His Ser Leu
    450                 455                 460

Thr Glu His Leu Arg Ile His Thr Gly His Lys Pro Phe Gln Cys Arg
465                 470                 475                 480

Ile Cys Met Arg Ser Phe Ser Gln Ser Ser Ser Leu Val Arg His Ile
                485                 490                 495

Arg Thr His Thr Gly Glu Lys Pro Phe Ala Cys Glu Phe Cys Gly Arg
            500                 505                 510

Lys Phe Ala Arg Glu Asp Asn Leu His Thr His Ala Lys Ile His Leu
        515                 520                 525

Lys Gln Lys Glu Lys Lys Ala Glu Lys Gly Gly Ala Pro Ser Ala Ser
    530                 535                 540

Ser Ala Pro Pro Val Ser Leu Ala Pro Val Val Thr Thr Cys Ala
545                 550                 555
```

<210> SEQ ID NO 115
<211> LENGTH: 631
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Met Ala Ala Ala Lys Ala Glu Met Gln Leu Met Ser Pro Leu Gln Ile
1               5                   10                  15
```

```
Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Val Arg His Ile Arg Ile His Thr Gly Gln Lys Pro Phe
        355                 360                 365

Gln Cys Arg Ile Cys Met Arg Asn Phe Ser His Arg Thr Thr Leu Thr
    370                 375                 380

Asn His Ile Arg Thr His Thr Gly Glu Lys Pro Phe Ala Cys Asp Ile
385                 390                 395                 400

Cys Gly Arg Lys Phe Ala Arg Glu Asp Asn Leu His Thr His Thr Lys
                405                 410                 415

Ile His Leu Arg Gln Lys Asp Arg Pro Tyr Ala Cys Pro Val Glu Ser
            420                 425                 430

Cys Asp Arg Arg Phe Ser Thr Ser His Ser Leu Thr Glu His Ile Arg
```

```
        435                 440                 445

Ile His Thr Gly Gln Lys Pro Phe Gln Cys Arg Ile Cys Met Arg Asn
    450                 455                 460

Phe Ser Gln Ser Ser Ser Leu Val Arg His Ile Arg Thr His Thr Gly
465                 470                 475                 480

Glu Lys Pro Phe Ala Cys Asp Ile Cys Gly Arg Lys Phe Ala Arg Glu
                485                 490                 495

Asp Asn Leu His Thr His Thr Lys Ile His Leu Arg Gln Lys Asp Lys
            500                 505                 510

Lys Ala Asp Lys Ser Val Val Ala Ser Ser Ala Thr Ser Ser Leu Ser
        515                 520                 525

Ser Tyr Pro Ser Pro Val Ala Thr Ser Tyr Pro Ser Pro Val Thr Thr
    530                 535                 540

Ser Tyr Pro Ser Pro Ala Thr Thr Ser Tyr Pro Ser Pro Val Pro Thr
545                 550                 555                 560

Ser Phe Ser Ser Pro Gly Ser Ser Thr Tyr Pro Ser Pro Val His Ser
                565                 570                 575

Gly Phe Pro Ser Pro Ser Val Ala Thr Thr Tyr Ser Ser Val Pro Pro
            580                 585                 590

Ala Phe Pro Ala Gln Val Ser Ser Phe Pro Ser Ser Ala Val Thr Asn
        595                 600                 605

Ser Phe Ser Ala Ser Thr Gly Leu Ser Asp Met Thr Ala Thr Phe Ser
    610                 615                 620

Pro Arg Thr Ile Glu Ile Cys
625                 630


<210> SEQ ID NO 116
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160
```

```
Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Arg
            340                 345                 350

Asp Glu Leu Asn Val His Ile Arg Ile His Thr Gly Gln Lys Pro Phe
        355                 360                 365

Gln Cys Arg Ile Cys Met Arg Asn Phe Ser Arg Ser Asp His Leu Thr
    370                 375                 380

Asn His Ile Arg Thr His Thr Gly Glu Lys Pro Phe Ala Cys Asp Ile
385                 390                 395                 400

Cys Gly Arg Lys Phe Ala Arg Ser Asp Asp Leu Val Arg His Thr Lys
                405                 410                 415

Ile His Leu Arg Gln Lys Asp Arg Pro Tyr Ala Cys Pro Val Glu Ser
            420                 425                 430

Cys Asp Arg Arg Phe Ser Arg Ser Asp Asn Leu Val Arg His Ile Arg
        435                 440                 445

Ile His Thr Gly Gln Lys Pro Phe Gln Cys Arg Ile Cys Met Arg Asn
    450                 455                 460

Phe Ser His Arg Thr Thr Leu Thr Asn His Ile Arg Thr His Thr Gly
465                 470                 475                 480

Glu Lys Pro Phe Ala Cys Asp Ile Cys Gly Arg Lys Phe Ala Arg Glu
                485                 490                 495

Asp Asn Leu His Thr His Thr Lys Ile His Leu Arg Gln Lys Asp Arg
            500                 505                 510

Pro Tyr Ala Cys Pro Val Glu Ser Cys Asp Arg Arg Phe Ser Thr Ser
        515                 520                 525

His Ser Leu Thr Glu His Ile Arg Ile His Thr Gly Gln Lys Pro Phe
    530                 535                 540

Gln Cys Arg Ile Cys Met Arg Asn Phe Ser Gln Ser Ser Ser Leu Val
545                 550                 555                 560

Arg His Ile Arg Thr His Thr Gly Glu Lys Pro Phe Ala Cys Asp Ile
                565                 570                 575

Cys Gly Arg Lys Phe Ala Arg Glu Asp Asn Leu His Thr His Thr Lys
```

```
            580                 585                 590

Ile His Leu Arg Gln Lys Asp Lys Lys Ala Asp Lys Ser Val Val Ala
        595                 600                 605

Ser Ser Ala Thr Ser Ser Leu Ser Ser Tyr Pro Ser Pro Val Ala Thr
    610                 615                 620

Ser Tyr Pro Ser Pro Val Thr Thr Ser Tyr Pro Ser Pro Ala Thr Thr
625                 630                 635                 640

Ser Tyr Pro Ser Pro Val Pro Thr Ser Phe Ser Ser Pro Gly Ser Ser
                645                 650                 655

Thr Tyr Pro Ser Pro Val His Ser Gly Phe Pro Ser Pro Ser Val Ala
            660                 665                 670

Thr Thr Tyr Ser Ser Val Pro Pro Ala Phe Pro Ala Gln Val Ser Ser
        675                 680                 685

Phe Pro Ser Ser Ala Val Thr Asn Ser Phe Ser Ala Ser Thr Gly Leu
    690                 695                 700

Ser Asp Met Thr Ala Thr Phe Ser Pro Arg Thr Ile Glu Ile Cys
705                 710                 715


<210> SEQ ID NO 117
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220
```

```
Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Val Arg His Ile Arg Ile His Thr Gly Gln Lys Pro Phe
        355                 360                 365

Gln Cys Arg Ile Cys Met Arg Asn Phe Ser His Arg Thr Thr Leu Thr
    370                 375                 380

Asn His Ile Arg Thr His Thr Gly Glu Lys Pro Phe Ala Cys Asp Ile
385                 390                 395                 400

Cys Gly Arg Lys Phe Ala Arg Glu Asp Asn Leu His Thr His Ile Arg
                405                 410                 415

Thr His Thr Gly Glu Lys Pro Phe Ala Cys Asp Ile Cys Gly Arg Lys
            420                 425                 430

Phe Ser Thr Ser His Ser Leu Thr Glu His Ile Arg Ile His Thr Gly
        435                 440                 445

Gln Lys Pro Phe Gln Cys Arg Ile Cys Met Arg Asn Phe Ser Gln Ser
    450                 455                 460

Ser Ser Leu Val Arg His Ile Arg Thr His Thr Gly Glu Lys Pro Phe
465                 470                 475                 480

Ala Cys Asp Ile Cys Gly Arg Lys Phe Ala Arg Glu Asp Asn Leu His
                485                 490                 495

Thr His Thr Lys Ile His Leu Arg Gln Lys Asp Lys Lys Ala Asp Lys
            500                 505                 510

Ser Val Val Ala Ser Ser Ala Thr Ser Ser Leu Ser Ser Tyr Pro Ser
        515                 520                 525

Pro Val Ala Thr Ser Tyr Pro Ser Pro Val Thr Thr Ser Tyr Pro Ser
    530                 535                 540

Pro Ala Thr Thr Ser Tyr Pro Ser Pro Val Pro Thr Ser Phe Ser Ser
545                 550                 555                 560

Pro Gly Ser Ser Thr Tyr Pro Ser Pro Val His Ser Gly Phe Pro Ser
                565                 570                 575

Pro Ser Val Ala Thr Thr Tyr Ser Ser Val Pro Pro Ala Phe Pro Ala
            580                 585                 590

Gln Val Ser Ser Phe Pro Ser Ser Ala Val Thr Asn Ser Phe Ser Ala
        595                 600                 605

Ser Thr Gly Leu Ser Asp Met Thr Ala Thr Phe Ser Pro Arg Thr Ile
    610                 615                 620

Glu Ile Cys
625
```

```
<210> SEQ ID NO 118
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Val Arg His Ile Arg Ile His Thr Gly Gln Lys Pro Phe
        355                 360                 365
```

```
Gln Cys Arg Ile Cys Met Arg Asn Phe Ser Arg Glu Asp Asn Leu His
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Leu Val Arg His Thr Lys
                405                 410                 415

Ile His Leu Arg Gln Lys Asp Arg Pro Tyr Ala Cys Pro Val Glu Ser
            420                 425                 430

Cys Asp Arg Arg Phe Ser Gln Ser Gly Asn Leu Thr Glu His Ile Arg
        435                 440                 445

Ile His Thr Gly Gln Lys Pro Phe Gln Cys Arg Ile Cys Met Arg Asn
    450                 455                 460

Phe Ser Thr Ser Gly His Leu Val Arg His Ile Arg Thr His Thr Gly
465                 470                 475                 480

Glu Lys Pro Phe Ala Cys Asp Ile Cys Gly Arg Lys Phe Ala Gln Asn
                485                 490                 495

Ser Thr Leu Thr Glu His Thr Lys Ile His Leu Arg Gln Lys Asp Lys
            500                 505                 510

Lys Ala Asp Lys Ser Val Val Ala Ser Ser Ala Thr Ser Ser Leu Ser
        515                 520                 525

Ser Tyr Pro Ser Pro Val Ala Thr Ser Tyr Pro Ser Pro Val Thr Thr
    530                 535                 540

Ser Tyr Pro Ser Pro Ala Thr Thr Ser Tyr Pro Ser Pro Val Pro Thr
545                 550                 555                 560

Ser Phe Ser Ser Pro Gly Ser Ser Thr Tyr Pro Ser Pro Val His Ser
                565                 570                 575

Gly Phe Pro Ser Pro Ser Val Ala Thr Thr Tyr Ser Ser Val Pro Pro
            580                 585                 590

Ala Phe Pro Ala Gln Val Ser Ser Phe Pro Ser Ser Ala Val Thr Asn
        595                 600                 605

Ser Phe Ser Ala Ser Thr Gly Leu Ser Asp Met Thr Ala Thr Phe Ser
    610                 615                 620

Pro Arg Thr Ile Glu Ile Cys
625                 630


<210> SEQ ID NO 119
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Thr Gly Lys Leu Ala Glu Lys Leu Pro Val Thr Met Ser Ser Leu
1               5                   10                  15

Leu Asn Gln Leu Pro Asp Asn Leu Tyr Pro Glu Glu Ile Pro Ser Ala
            20                  25                  30

Leu Asn Leu Phe Ser Gly Ser Ser Asp Ser Val Val His Tyr Asn Gln
        35                  40                  45

Met Ala Thr Glu Asn Val Met Asp Ile Gly Leu Thr Asn Glu Lys Pro
    50                  55                  60

Asn Pro Glu Leu Ser Tyr Ser Gly Ser Phe Gln Pro Ala Pro Gly Asn
65                  70                  75                  80

Lys Thr Val Thr Tyr Leu Gly Lys Phe Ala Phe Asp Ser Pro Ser Asn
                85                  90                  95
```

```
Trp Cys Gln Asp Asn Ile Ile Ser Leu Met Ser Ala Gly Ile Leu Gly
            100                 105                 110

Val Pro Pro Ala Ser Gly Ala Leu Ser Thr Gln Thr Ser Thr Ala Ser
        115                 120                 125

Met Val Gln Pro Pro Gln Gly Asp Val Glu Ala Met Tyr Pro Ala Leu
    130                 135                 140

Pro Pro Tyr Ser Asn Cys Gly Asp Leu Tyr Ser Glu Pro Val Ser Phe
145                 150                 155                 160

His Asp Pro Gln Gly Asn Pro Gly Leu Ala Tyr Ser Pro Gln Asp Tyr
                165                 170                 175

Gln Ser Ala Lys Pro Ala Leu Asp Ser Asn Leu Phe Pro Met Ile Pro
            180                 185                 190

Asp Tyr Asn Leu Tyr His His Pro Asn Asp Met Gly Ser Ile Pro Glu
        195                 200                 205

His Lys Pro Phe Gln Gly Met Asp Pro Ile Arg Val Asn Pro Pro Pro
    210                 215                 220

Ile Thr Pro Leu Glu Thr Ile Lys Ala Phe Lys Asp Lys Gln Ile His
225                 230                 235                 240

Pro Gly Phe Gly Ser Leu Pro Gln Pro Pro Leu Thr Leu Lys Pro Ile
                245                 250                 255

Arg Pro Arg Lys Tyr Pro Asn Arg Pro Ser Lys Thr Pro Leu His Glu
            260                 265                 270

Arg Pro His Ala Cys Pro Ala Glu Gly Cys Asp Arg Arg Phe Ser Arg
        275                 280                 285

Ser Asp Asn Leu Val Arg His Leu Arg Ile His Thr Gly His Lys Pro
    290                 295                 300

Phe Gln Cys Arg Ile Cys Met Arg Ser Phe Ser His Arg Thr Thr Leu
305                 310                 315                 320

Thr Asn His Ile Arg Thr His Thr Gly Glu Lys Pro Phe Ala Cys Glu
                325                 330                 335

Phe Cys Gly Arg Lys Phe Ala Arg Glu Asp Asn Leu His Thr His Ala
            340                 345                 350

Lys Ile His Leu Lys Gln Lys Glu His Ala Cys Pro Ala Glu Gly Cys
        355                 360                 365

Asp Arg Arg Phe Ser Thr Ser His Ser Leu Thr Glu His Leu Arg Ile
    370                 375                 380

His Thr Gly His Lys Pro Phe Gln Cys Arg Ile Cys Met Arg Ser Phe
385                 390                 395                 400

Ser Gln Ser Ser Ser Leu Val Arg His Ile Arg Thr His Thr Gly Glu
                405                 410                 415

Lys Pro Phe Ala Cys Glu Phe Cys Gly Arg Lys Phe Ala Arg Glu Asp
            420                 425                 430

Asn Leu His Thr His Ala Lys Ile His Leu Lys Gln Lys Glu Lys Lys
        435                 440                 445

Ala Glu Lys Gly Gly Ala Pro Ser Ala Ser Ser Ala Pro Pro Val Ser
    450                 455                 460

Leu Ala Pro Val Val Thr Thr Cys Ala
465                 470
```

<210> SEQ ID NO 120
<211> LENGTH: 719
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 120

```
Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Asp Pro
            340                 345                 350

Gly Ala Leu Val Arg His Ile Arg Ile His Thr Gly Gln Lys Pro Phe
        355                 360                 365

Gln Cys Arg Ile Cys Met Arg Asn Phe Ser Arg Ser Asp Asn Leu Val
    370                 375                 380

Arg His Ile Arg Thr His Thr Gly Glu Lys Pro Phe Ala Cys Asp Ile
385                 390                 395                 400
```

Cys Gly Arg Lys Phe Ala Gln Ser Gly Asp Leu Arg Arg His Thr Lys
405 410 415

Ile His Leu Arg Gln Lys Asp Arg Pro Tyr Ala Cys Pro Val Glu Ser
420 425 430

Cys Asp Arg Arg Phe Ser Thr His Leu Asp Leu Ile Arg His Ile Arg
435 440 445

Ile His Thr Gly Gln Lys Pro Phe Gln Cys Arg Ile Cys Met Arg Asn
450 455 460

Phe Ser Thr Ser Gly Asn Leu Val Arg His Ile Arg Thr His Thr Gly
465 470 475 480

Glu Lys Pro Phe Ala Cys Asp Ile Cys Gly Arg Lys Phe Ala Arg Ser
485 490 495

Asp Asn Leu Val Arg His Thr Lys Ile His Leu Arg Gln Lys Asp Arg
500 505 510

Pro Tyr Ala Cys Pro Val Glu Ser Cys Asp Arg Arg Phe Ser Gln Ser
515 520 525

Gly His Leu Thr Glu His Ile Arg Ile His Thr Gly Gln Lys Pro Phe
530 535 540

Gln Cys Arg Ile Cys Met Arg Asn Phe Ser Glu Arg Ser His Leu Arg
545 550 555 560

Glu His Ile Arg Thr His Thr Gly Glu Lys Pro Phe Ala Cys Asp Ile
565 570 575

Cys Gly Arg Lys Phe Ala Gln Ala Gly His Leu Ala Ser His Thr Lys
580 585 590

Ile His Leu Arg Gln Lys Asp Lys Lys Ala Asp Lys Ser Val Val Ala
595 600 605

Ser Ser Ala Thr Ser Ser Leu Ser Ser Tyr Pro Ser Pro Val Ala Thr
610 615 620

Ser Tyr Pro Ser Pro Val Thr Thr Ser Tyr Pro Ser Pro Ala Thr Thr
625 630 635 640

Ser Tyr Pro Ser Pro Val Pro Thr Ser Phe Ser Ser Pro Gly Ser Ser
645 650 655

Thr Tyr Pro Ser Pro Val His Ser Gly Phe Pro Ser Pro Ser Val Ala
660 665 670

Thr Thr Tyr Ser Ser Val Pro Pro Ala Phe Pro Ala Gln Val Ser Ser
675 680 685

Phe Pro Ser Ser Ala Val Thr Asn Ser Phe Ser Ala Ser Thr Gly Leu
690 695 700

Ser Asp Met Thr Ala Thr Phe Ser Pro Arg Thr Ile Glu Ile Cys
705 710 715

<210> SEQ ID NO 121
<211> LENGTH: 627
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Met Ala Ala Ala Lys Ala Glu Met Gln Leu Met Ser Pro Leu Gln Ile
1 5 10 15

Ser Asp Pro Phe Gly Ser Phe Pro His Ser Pro Thr Met Asp Asn Tyr
20 25 30

Pro Lys Leu Glu Glu Met Met Leu Leu Ser Asn Gly Ala Pro Gln Phe

```
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Thr Arg His Ile Arg Ile His Thr Gly Gln Lys Pro Phe
        355                 360                 365

Gln Cys Arg Ile Cys Met Arg Asn Phe Ser His Ser Thr Thr Leu Thr
    370                 375                 380

Asn His Ile Arg Thr His Thr Gly Glu Lys Pro Phe Ala Cys Asp Ile
385                 390                 395                 400

Cys Gly Arg Lys Phe Ala Arg Ser Asp Asn Arg Lys Thr His Ile Arg
                405                 410                 415

Thr His Thr Gly Glu Lys Pro Phe Ala Cys Asp Ile Cys Gly Arg Lys
            420                 425                 430

Phe Ser Thr Ser His Ser Leu Thr Glu His Ile Arg Ile His Thr Gly
        435                 440                 445

Gln Lys Pro Phe Gln Cys Arg Ile Cys Met Arg Asn Phe Ser Gln Ser
    450                 455                 460
```

Ser Ser Leu Thr Arg His Ile Arg Thr His Thr Gly Glu Lys Pro Phe
465 470 475 480

Ala Cys Asp Ile Cys Gly Arg Lys Phe Ala Arg Ser Asp Asn Arg Lys
485 490 495

Thr His Thr Lys Ile His Leu Arg Gln Lys Asp Lys Lys Ala Asp Lys
500 505 510

Ser Val Val Ala Ser Ser Ala Thr Ser Ser Leu Ser Ser Tyr Pro Ser
515 520 525

Pro Val Ala Thr Ser Tyr Pro Ser Pro Val Thr Thr Ser Tyr Pro Ser
530 535 540

Pro Ala Thr Thr Ser Tyr Pro Ser Pro Val Pro Thr Ser Phe Ser Ser
545 550 555 560

Pro Gly Ser Ser Thr Tyr Pro Ser Pro Val His Ser Gly Phe Pro Ser
565 570 575

Pro Ser Val Ala Thr Thr Tyr Ser Ser Val Pro Pro Ala Phe Pro Ala
580 585 590

Gln Val Ser Ser Phe Pro Ser Ser Ala Val Thr Asn Ser Phe Ser Ala
595 600 605

Ser Thr Gly Leu Ser Asp Met Thr Ala Thr Phe Ser Pro Arg Thr Ile
610 615 620

Glu Ile Cys
625

<210> SEQ ID NO 122
<211> LENGTH: 473
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Met Thr Gly Lys Leu Ala Glu Lys Leu Pro Val Thr Met Ser Ser Leu
1 5 10 15

Leu Asn Gln Leu Pro Asp Asn Leu Tyr Pro Glu Glu Ile Pro Ser Ala
20 25 30

Leu Asn Leu Phe Ser Gly Ser Ser Asp Ser Val Val His Tyr Asn Gln
35 40 45

Met Ala Thr Glu Asn Val Met Asp Ile Gly Leu Thr Asn Glu Lys Pro
50 55 60

Asn Pro Glu Leu Ser Tyr Ser Gly Ser Phe Gln Pro Ala Pro Gly Asn
65 70 75 80

Lys Thr Val Thr Tyr Leu Gly Lys Phe Ala Phe Asp Ser Pro Ser Asn
85 90 95

Trp Cys Gln Asp Asn Ile Ile Ser Leu Met Ser Ala Gly Ile Leu Gly
100 105 110

Val Pro Pro Ala Ser Gly Ala Leu Ser Thr Gln Thr Ser Thr Ala Ser
115 120 125

Met Val Gln Pro Pro Gln Gly Asp Val Glu Ala Met Tyr Pro Ala Leu
130 135 140

Pro Pro Tyr Ser Asn Cys Gly Asp Leu Tyr Ser Glu Pro Val Ser Phe
145 150 155 160

His Asp Pro Gln Gly Asn Pro Gly Leu Ala Tyr Ser Pro Gln Asp Tyr
165 170 175

Gln Ser Ala Lys Pro Ala Leu Asp Ser Asn Leu Phe Pro Met Ile Pro

```
            180                 185                 190

Asp Tyr Asn Leu Tyr His His Pro Asn Asp Met Gly Ser Ile Pro Glu
        195                 200                 205

His Lys Pro Phe Gln Gly Met Asp Pro Ile Arg Val Asn Pro Pro Pro
    210                 215                 220

Ile Thr Pro Leu Glu Thr Ile Lys Ala Phe Lys Asp Lys Gln Ile His
225                 230                 235                 240

Pro Gly Phe Gly Ser Leu Pro Gln Pro Pro Leu Thr Leu Lys Pro Ile
                245                 250                 255

Arg Pro Arg Lys Tyr Pro Asn Arg Pro Ser Lys Thr Pro Leu His Glu
            260                 265                 270

Arg Pro His Ala Cys Pro Ala Glu Gly Cys Asp Arg Arg Phe Ser Arg
        275                 280                 285

Ser Asp Asn Leu Val Arg His Leu Arg Ile His Thr Gly His Lys Pro
    290                 295                 300

Phe Gln Cys Arg Ile Cys Met Arg Ser Phe Ser Arg Glu Asp Asn Leu
305                 310                 315                 320

His Thr His Ile Arg Thr His Thr Gly Glu Lys Pro Phe Ala Cys Glu
                325                 330                 335

Phe Cys Gly Arg Lys Phe Ala Arg Ser Asp Glu Leu Val Arg His Ala
            340                 345                 350

Lys Ile His Leu Lys Gln Lys Glu His Ala Cys Pro Ala Glu Gly Cys
        355                 360                 365

Asp Arg Arg Phe Ser Gln Ser Gly Asn Leu Thr Glu His Leu Arg Ile
    370                 375                 380

His Thr Gly His Lys Pro Phe Gln Cys Arg Ile Cys Met Arg Ser Phe
385                 390                 395                 400

Ser Thr Ser Gly His Leu Val Arg His Ile Arg Thr His Thr Gly Glu
                405                 410                 415

Lys Pro Phe Ala Cys Glu Phe Cys Gly Arg Lys Phe Ala Gln Asn Ser
            420                 425                 430

Thr Leu Thr Glu His Ala Lys Ile His Leu Lys Gln Lys Glu Lys Lys
        435                 440                 445

Ala Glu Lys Gly Gly Ala Pro Ser Ala Ser Ser Ala Pro Pro Val Ser
    450                 455                 460

Leu Ala Pro Val Val Thr Thr Cys Ala
465                 470
```

<210> SEQ ID NO 123
<211> LENGTH: 627
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60
```

```
Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Thr Arg His Ile Arg Ile His Thr Gly Gln Lys Pro Phe
        355                 360                 365

Gln Cys Arg Ile Cys Met Arg Asn Phe Ser Arg Ser Asp Asn Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Ile Arg
                405                 410                 415

Thr His Thr Gly Glu Lys Pro Phe Ala Cys Asp Ile Cys Gly Arg Lys
            420                 425                 430

Phe Ser Gln Ser Gly Asn Leu Thr Glu His Ile Arg Ile His Thr Gly
        435                 440                 445

Gln Lys Pro Phe Gln Cys Arg Ile Cys Met Arg Asn Phe Ser Thr Ser
    450                 455                 460

Gly His Leu Thr Arg His Ile Arg Thr His Thr Gly Glu Lys Pro Phe
465                 470                 475                 480

Ala Cys Asp Ile Cys Gly Arg Lys Phe Ala Gln Ser Ser Thr Arg Lys
```

```
                485                 490                 495

Glu His Thr Lys Ile His Leu Arg Gln Lys Asp Lys Lys Ala Asp Lys
            500                 505                 510

Ser Val Val Ala Ser Ser Ala Thr Ser Ser Leu Ser Ser Tyr Pro Ser
        515                 520                 525

Pro Val Ala Thr Ser Tyr Pro Ser Pro Val Thr Thr Ser Tyr Pro Ser
    530                 535                 540

Pro Ala Thr Thr Ser Tyr Pro Ser Pro Val Pro Thr Ser Phe Ser Ser
545                 550                 555                 560

Pro Gly Ser Ser Thr Tyr Pro Ser Pro Val His Ser Gly Phe Pro Ser
                565                 570                 575

Pro Ser Val Ala Thr Thr Tyr Ser Ser Val Pro Pro Ala Phe Pro Ala
            580                 585                 590

Gln Val Ser Ser Phe Pro Ser Ser Ala Val Thr Asn Ser Phe Ser Ala
        595                 600                 605

Ser Thr Gly Leu Ser Asp Met Thr Ala Thr Phe Ser Pro Arg Thr Ile
    610                 615                 620

Glu Ile Cys
625


<210> SEQ ID NO 124
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205
```

-continued

```
Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Asn Leu Val Arg His Ile Arg Ile His Thr Gly Gln Lys Pro Phe
        355                 360                 365

Gln Cys Arg Ile Cys Met Arg Asn Phe Ser Arg Glu Asp Asn Leu His
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Leu Val Arg His Ile Arg
                405                 410                 415

Thr His Thr Gly Glu Lys Pro Phe Ala Cys Asp Ile Cys Gly Arg Lys
            420                 425                 430

Phe Ser Gln Ser Gly Asn Leu Thr Glu His Ile Arg Ile His Thr Gly
        435                 440                 445

Gln Lys Pro Phe Gln Cys Arg Ile Cys Met Arg Asn Phe Ser Thr Ser
    450                 455                 460

Gly His Leu Val Arg His Ile Arg Thr His Thr Gly Glu Lys Pro Phe
465                 470                 475                 480

Ala Cys Asp Ile Cys Gly Arg Lys Phe Ala Gln Asn Ser Thr Leu Thr
                485                 490                 495

Glu His Thr Lys Ile His Leu Arg Gln Lys Asp Lys Lys Ala Asp Lys
            500                 505                 510

Ser Val Val Ala Ser Ser Ala Thr Ser Ser Leu Ser Ser Tyr Pro Ser
        515                 520                 525

Pro Val Ala Thr Ser Tyr Pro Ser Pro Val Thr Thr Ser Tyr Pro Ser
    530                 535                 540

Pro Ala Thr Thr Ser Tyr Pro Ser Pro Val Pro Thr Ser Phe Ser Ser
545                 550                 555                 560

Pro Gly Ser Ser Thr Tyr Pro Ser Pro Val His Ser Gly Phe Pro Ser
                565                 570                 575

Pro Ser Val Ala Thr Thr Tyr Ser Ser Val Pro Pro Ala Phe Pro Ala
            580                 585                 590

Gln Val Ser Ser Phe Pro Ser Ser Ala Val Thr Asn Ser Phe Ser Ala
        595                 600                 605

Ser Thr Gly Leu Ser Asp Met Thr Ala Thr Phe Ser Pro Arg Thr Ile
    610                 615                 620

Glu Ile Cys
```

625

<210> SEQ ID NO 125
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Met Ala Pro Lys Lys Lys Arg Lys Val Gly Ile His Gly Val Pro Ala
1 5 10 15

Ala Leu Glu Pro Gly Glu Lys Pro Tyr Lys Cys Pro Glu Cys Gly Lys
20 25 30

Ser Phe Ser Ser Pro Ala Asp Leu Thr Arg His Gln Arg Thr His Thr
35 40 45

Gly Glu Lys Pro Tyr Lys Cys Pro Glu Cys Gly Lys Ser Phe Ser Arg
50 55 60

Ser Asp Asn Leu Val Arg His Gln Arg Thr His Thr Gly Glu Lys Pro
65 70 75 80

Tyr Lys Cys Pro Glu Cys Gly Lys Ser Phe Ser Arg Glu Asp Asn Leu
85 90 95

His Thr His Gln Arg Thr His Thr Gly Glu Lys Pro Tyr Lys Cys Pro
100 105 110

Glu Cys Gly Lys Ser Phe Ser Arg Ser Asp Glu Leu Val Arg His Gln
115 120 125

Arg Thr His Thr Gly Glu Lys Pro Tyr Lys Cys Pro Glu Cys Gly Lys
130 135 140

Ser Phe Ser Gln Ser Gly Asn Leu Thr Glu His Gln Arg Thr His Thr
145 150 155 160

Gly Glu Lys Pro Tyr Lys Cys Pro Glu Cys Gly Lys Ser Phe Ser Thr
165 170 175

Ser Gly His Leu Val Arg His Gln Arg Thr His Thr Gly Lys Lys Thr
180 185 190

Ser Lys Arg Pro Ala Ala Thr Lys Lys Ala Gly Gln Ala Lys Lys Lys
195 200 205

Lys Gly Ser Tyr Pro Tyr Asp Val Pro Asp Tyr Ala Leu Glu Asp Ala
210 215 220

Leu Asp Asp Phe Asp Leu Asp Met Leu Gly Ser Asp Ala Leu Asp Asp
225 230 235 240

Phe Asp Leu Asp Met Leu Gly Ser Asp Ala Leu Asp Asp Phe Asp Leu
245 250 255

Asp Met Leu Gly Ser Asp Ala Leu Asp Asp Phe Asp Leu Asp Met Leu
260 265 270

<210> SEQ ID NO 126
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Met Ala Pro Lys Lys Lys Arg Lys Val Gly Ile His Gly Val Pro Ala
1 5 10 15

Ala Leu Glu Pro Gly Glu Lys Pro Tyr Lys Cys Pro Glu Cys Gly Lys

```
            20                  25                  30

Ser Phe Ser Asp Pro Gly Ala Leu Val Arg His Gln Arg Thr His Thr
        35                  40                  45

Gly Glu Lys Pro Tyr Lys Cys Pro Glu Cys Gly Lys Ser Phe Ser Arg
    50                  55                  60

Ser Asp Asn Leu Val Arg His Gln Arg Thr His Thr Gly Glu Lys Pro
65                  70                  75                  80

Tyr Lys Cys Pro Glu Cys Gly Lys Ser Phe Ser Gln Ser Gly Asp Leu
                85                  90                  95

Arg Arg His Gln Arg Thr His Thr Gly Glu Lys Pro Tyr Lys Cys Pro
            100                 105                 110

Glu Cys Gly Lys Ser Phe Ser Thr His Leu Asp Leu Ile Arg His Gln
        115                 120                 125

Arg Thr His Thr Gly Glu Lys Pro Tyr Lys Cys Pro Glu Cys Gly Lys
    130                 135                 140

Ser Phe Ser Thr Ser Gly Asn Leu Val Arg His Gln Arg Thr His Thr
145                 150                 155                 160

Gly Glu Lys Pro Tyr Lys Cys Pro Glu Cys Gly Lys Ser Phe Ser Arg
                165                 170                 175

Ser Asp Asn Leu Val Arg His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Tyr Pro Tyr Asp Val Pro Asp Tyr Ala Leu Glu Asp Ala
    210                 215                 220

Leu Asp Asp Phe Asp Leu Asp Met Leu Gly Ser Asp Ala Leu Asp Asp
225                 230                 235                 240

Phe Asp Leu Asp Met Leu Gly Ser Asp Ala Leu Asp Asp Phe Asp Leu
                245                 250                 255

Asp Met Leu Gly Ser Asp Ala Leu Asp Asp Phe Asp Leu Asp Met Leu
            260                 265                 270


<210> SEQ ID NO 127
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Pro Lys Lys Lys Arg Lys Val Gly Ile His Gly Val Pro Ala
1               5                   10                  15

Ala Leu Glu Pro Gly Glu Lys Pro Tyr Lys Cys Pro Glu Cys Gly Lys
            20                  25                  30

Ser Phe Ser Arg Ser Asp Asn Leu Val Arg His Gln Arg Thr His Thr
        35                  40                  45

Gly Glu Lys Pro Tyr Lys Cys Pro Glu Cys Gly Lys Ser Phe Ser Arg
    50                  55                  60

Glu Asp Asn Leu His Thr His Gln Arg Thr His Thr Gly Glu Lys Pro
65                  70                  75                  80

Tyr Lys Cys Pro Glu Cys Gly Lys Ser Phe Ser Arg Ser Asp Glu Leu
                85                  90                  95

Val Arg His Gln Arg Thr His Thr Gly Glu Lys Pro Tyr Lys Cys Pro
            100                 105                 110
```

```
Glu Cys Gly Lys Ser Phe Ser Gln Ser Gly Asn Leu Thr Glu His Gln
        115                 120                 125

Arg Thr His Thr Gly Glu Lys Pro Tyr Lys Cys Pro Glu Cys Gly Lys
    130                 135                 140

Ser Phe Ser Thr Ser Gly His Leu Val Arg His Gln Arg Thr His Thr
145                 150                 155                 160

Gly Glu Lys Pro Tyr Lys Cys Pro Glu Cys Gly Lys Ser Phe Ser Gln
                165                 170                 175

Asn Ser Thr Leu Thr Glu His Gln Arg Thr His Thr Gly Lys Lys Thr
            180                 185                 190

Ser Lys Arg Pro Ala Ala Thr Lys Lys Ala Gly Gln Ala Lys Lys Lys
        195                 200                 205

Lys Gly Ser Asp Ala Leu Asp Asp Phe Asp Leu Asp Met Leu Gly Ser
    210                 215                 220

Asp Ala Leu Asp Asp Phe Asp Leu Asp Met Leu Gly Ser Asp Ala Leu
225                 230                 235                 240

Asp Asp Phe Asp Leu Asp Met Leu Gly Ser Asp Ala Leu Asp Asp Phe
                245                 250                 255

Asp Leu Asp Met Leu
            260


<210> SEQ ID NO 128
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gln Ser Gln Leu Ile Lys Pro
            180                 185                 190

Ser Arg Met Arg Lys Tyr Pro Asn Arg Pro Ser Lys Thr Pro Pro His
        195                 200                 205
```

```
Glu Arg Pro Tyr Ala Cys Pro Val Glu Ser Cys Asp Arg Arg Phe Ser
    210                 215                 220

Arg Ser Asp Asn Leu Val Arg His Ile Arg Ile His Thr Gly Gln Lys
225                 230                 235                 240

Pro Phe Gln Cys Arg Ile Cys Met Arg Asn Phe Ser Arg Glu Asp Asn
                245                 250                 255

Leu His Thr His Ile Arg Thr His Thr Gly Glu Lys Pro Phe Ala Cys
            260                 265                 270

Asp Ile Cys Gly Arg Lys Phe Ala Arg Ser Asp Glu Leu Val Arg His
        275                 280                 285

Thr Lys Ile His Leu Arg Gln Lys Asp Arg Pro Tyr Ala Cys Pro Val
    290                 295                 300

Glu Ser Cys Asp Arg Arg Phe Ser Gln Ser Gly Asn Leu Thr Glu His
305                 310                 315                 320

Ile Arg Ile His Thr Gly Gln Lys Pro Phe Gln Cys Arg Ile Cys Met
                325                 330                 335

Arg Asn Phe Ser Thr Ser Gly His Leu Val Arg His Ile Arg Thr His
            340                 345                 350

Thr Gly Glu Lys Pro Phe Ala Cys Asp Ile Cys Gly Arg Lys Phe Ala
        355                 360                 365

Gln Asn Ser Thr Leu Thr Glu His Thr Lys Ile His Leu Arg Gln Lys
    370                 375                 380

Asp Lys
385


<210> SEQ ID NO 129
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
```

```
                165                 170                 175

Ala Pro Pro Ala Gly Ser Val Ser Cys Gly Gly Ser Gly Gly Gly Ser
            180                 185                 190

Gly Gly Gly Ser Gly Gly Gly Ser Gly Gln Ser Gln Leu Ile Lys Pro
        195                 200                 205

Ser Arg Met Arg Lys Tyr Pro Asn Arg Pro Ser Lys Thr Pro Pro His
    210                 215                 220

Glu Arg Pro Tyr Ala Cys Pro Val Glu Ser Cys Asp Arg Arg Phe Ser
225                 230                 235                 240

Arg Ser Asp Asn Leu Val Arg His Ile Arg Ile His Thr Gly Gln Lys
                245                 250                 255

Pro Phe Gln Cys Arg Ile Cys Met Arg Asn Phe Ser Arg Glu Asp Asn
            260                 265                 270

Leu His Thr His Ile Arg Thr His Thr Gly Glu Lys Pro Phe Ala Cys
        275                 280                 285

Asp Ile Cys Gly Arg Lys Phe Ala Arg Ser Asp Glu Leu Val Arg His
    290                 295                 300

Thr Lys Ile His Leu Arg Gln Lys Asp Arg Pro Tyr Ala Cys Pro Val
305                 310                 315                 320

Glu Ser Cys Asp Arg Arg Phe Ser Gln Ser Gly Asn Leu Thr Glu His
                325                 330                 335

Ile Arg Ile His Thr Gly Gln Lys Pro Phe Gln Cys Arg Ile Cys Met
            340                 345                 350

Arg Asn Phe Ser Thr Ser Gly His Leu Val Arg His Ile Arg Thr His
        355                 360                 365

Thr Gly Glu Lys Pro Phe Ala Cys Asp Ile Cys Gly Arg Lys Phe Ala
    370                 375                 380

Gln Asn Ser Thr Leu Thr Glu His Thr Lys Ile His Leu Arg Gln Lys
385                 390                 395                 400

Asp Lys


<210> SEQ ID NO 130
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
```

```
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Ala Asp His Leu Met Leu Ala
            180                 185                 190

Glu Gly Tyr Arg Leu Val Gln Arg Pro Pro Ser Ala Ala Ala Ala His
        195                 200                 205

Gly Pro His Ala Leu Arg Thr Leu Pro Pro Tyr Ala Gly Pro Gly Leu
    210                 215                 220

Asp Ser Gly Leu Arg Pro Arg Gly Ala Pro Leu Gly Pro Pro Pro Pro
225                 230                 235                 240

Arg Gln Pro Gly Ala Leu Ala Tyr Gly Ala Phe Gly Pro Pro Ser Ser
                245                 250                 255

Phe Gln Pro Phe Pro Ala Val Pro Pro Pro Ala Ala Gly Ile Ala His
            260                 265                 270

Leu Gln Pro Val Ala Thr Pro Tyr Pro Gly Arg Ala Ala Ala Pro Pro
        275                 280                 285

Asn Ala Pro Gly Gly Pro Pro Gly Pro Gln Pro Ala Pro Ser Ala Ala
    290                 295                 300

Ala Pro Pro Pro Pro Ala His Ala Leu Gly Gly Met Asp Ala Glu Leu
305                 310                 315                 320

Ile Asp Glu Glu Ala Leu Thr Ser Leu Glu Leu Glu Leu Gly Leu His
                325                 330                 335

Arg Val Arg Glu Leu Pro Glu Leu Phe Leu Gly Gln Ser Glu Phe Asp
            340                 345                 350

Cys Phe Ser Asp Leu Gly Ser Ala Pro Pro Ala Gly Ser Val Ser Cys
        355                 360                 365

Gln Ser Gln Leu Ile Lys Pro Ser Arg Met Arg Lys Tyr Pro Asn Arg
    370                 375                 380

Pro Ser Lys Thr Pro Pro His Glu Arg Pro Tyr Ala Cys Pro Val Glu
385                 390                 395                 400

Ser Cys Asp Arg Arg Phe Ser Arg Ser Asp Asn Leu Val Arg His Ile
                405                 410                 415

Arg Ile His Thr Gly Gln Lys Pro Phe Gln Cys Arg Ile Cys Met Arg
            420                 425                 430

Asn Phe Ser Arg Glu Asp Asn Leu His Thr His Ile Arg Thr His Thr
        435                 440                 445

Gly Glu Lys Pro Phe Ala Cys Asp Ile Cys Gly Arg Lys Phe Ala Arg
    450                 455                 460

Ser Asp Glu Leu Val Arg His Thr Lys Ile His Leu Arg Gln Lys Asp
465                 470                 475                 480

Arg Pro Tyr Ala Cys Pro Val Glu Ser Cys Asp Arg Arg Phe Ser Gln
                485                 490                 495

Ser Gly Asn Leu Thr Glu His Ile Arg Ile His Thr Gly Gln Lys Pro
            500                 505                 510

Phe Gln Cys Arg Ile Cys Met Arg Asn Phe Ser Thr Ser Gly His Leu
        515                 520                 525

Val Arg His Ile Arg Thr His Thr Gly Glu Lys Pro Phe Ala Cys Asp
    530                 535                 540
```

```
Ile Cys Gly Arg Lys Phe Ala Gln Asn Ser Thr Leu Thr Glu His Thr
545                 550                 555                 560

Lys Ile His Leu Arg Gln Lys Asp Lys
                565


<210> SEQ ID NO 131
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190

Gly Ala Asp His Leu Met Leu Ala Glu Gly Tyr Arg Leu Val Gln Arg
        195                 200                 205

Pro Pro Ser Ala Ala Ala Ala His Gly Pro His Ala Leu Arg Thr Leu
    210                 215                 220

Pro Pro Tyr Ala Gly Pro Gly Leu Asp Ser Gly Leu Arg Pro Arg Gly
225                 230                 235                 240

Ala Pro Leu Gly Pro Pro Pro Pro Arg Gln Pro Gly Ala Leu Ala Tyr
                245                 250                 255

Gly Ala Phe Gly Pro Pro Ser Ser Phe Gln Pro Phe Pro Ala Val Pro
            260                 265                 270

Pro Pro Ala Ala Gly Ile Ala His Leu Gln Pro Val Ala Thr Pro Tyr
        275                 280                 285

Pro Gly Arg Ala Ala Ala Pro Pro Asn Ala Pro Gly Gly Pro Pro Gly
    290                 295                 300

Pro Gln Pro Ala Pro Ser Ala Ala Ala Pro Pro Pro Pro Ala His Ala
305                 310                 315                 320

Leu Gly Gly Met Asp Ala Glu Leu Ile Asp Glu Glu Ala Leu Thr Ser
```

```
                325                 330                 335

Leu Glu Leu Glu Leu Gly Leu His Arg Val Arg Glu Leu Pro Glu Leu
            340                 345                 350

Phe Leu Gly Gln Ser Glu Phe Asp Cys Phe Ser Asp Leu Gly Ser Ala
        355                 360                 365

Pro Pro Ala Gly Ser Val Ser Cys Gly Gly Ser Gly Gly Gly Ser Gly
    370                 375                 380

Gln Ser Gln Leu Ile Lys Pro Ser Arg Met Arg Lys Tyr Pro Asn Arg
385                 390                 395                 400

Pro Ser Lys Thr Pro Pro His Glu Arg Pro Tyr Ala Cys Pro Val Glu
                405                 410                 415

Ser Cys Asp Arg Arg Phe Ser Arg Ser Asp Asn Leu Val Arg His Ile
            420                 425                 430

Arg Ile His Thr Gly Gln Lys Pro Phe Gln Cys Arg Ile Cys Met Arg
        435                 440                 445

Asn Phe Ser Arg Glu Asp Asn Leu His Thr His Ile Arg Thr His Thr
    450                 455                 460

Gly Glu Lys Pro Phe Ala Cys Asp Ile Cys Gly Arg Lys Phe Ala Arg
465                 470                 475                 480

Ser Asp Glu Leu Val Arg His Thr Lys Ile His Leu Arg Gln Lys Asp
                485                 490                 495

Arg Pro Tyr Ala Cys Pro Val Glu Ser Cys Asp Arg Arg Phe Ser Gln
            500                 505                 510

Ser Gly Asn Leu Thr Glu His Ile Arg Ile His Thr Gly Gln Lys Pro
        515                 520                 525

Phe Gln Cys Arg Ile Cys Met Arg Asn Phe Ser Thr Ser Gly His Leu
    530                 535                 540

Val Arg His Ile Arg Thr His Thr Gly Glu Lys Pro Phe Ala Cys Asp
545                 550                 555                 560

Ile Cys Gly Arg Lys Phe Ala Gln Asn Ser Thr Leu Thr Glu His Thr
                565                 570                 575

Lys Ile His Leu Arg Gln Lys Asp Lys
            580                 585
```

<210> SEQ ID NO 132
<211> LENGTH: 523
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ile Asn Ser Arg Ser Ser Gly Ser Pro Lys Lys Lys Arg Lys
    50                  55                  60

Val Gly Ser Gln Tyr Leu Pro Asp Thr Asp Asp Arg His Arg Ile Glu
65                  70                  75                  80

Glu Lys Arg Lys Arg Thr Tyr Glu Thr Phe Lys Ser Ile Met Lys Lys
                85                  90                  95
```

-continued

```
Ser Pro Phe Ser Gly Pro Thr Asp Pro Arg Pro Pro Pro Arg Arg Ile
            100                 105                 110

Ala Val Pro Ser Arg Ser Ser Ala Ser Val Pro Lys Pro Ala Pro Gln
        115                 120                 125

Pro Tyr Pro Phe Thr Ser Ser Leu Ser Thr Ile Asn Tyr Asp Glu Phe
    130                 135                 140

Pro Thr Met Val Phe Pro Ser Gly Gln Ile Ser Gln Ala Ser Ala Leu
145                 150                 155                 160

Ala Pro Ala Pro Pro Gln Val Leu Pro Gln Ala Pro Ala Pro Ala Pro
                165                 170                 175

Ala Pro Ala Met Val Ser Ala Leu Ala Gln Ala Pro Ala Pro Val Pro
            180                 185                 190

Val Leu Ala Pro Gly Pro Pro Gln Ala Val Ala Pro Pro Ala Pro Lys
        195                 200                 205

Pro Thr Gln Ala Gly Glu Gly Thr Leu Ser Glu Ala Leu Leu Gln Leu
    210                 215                 220

Gln Phe Asp Asp Glu Asp Leu Gly Ala Leu Leu Gly Asn Ser Thr Asp
225                 230                 235                 240

Pro Ala Val Phe Thr Asp Leu Ala Ser Val Asp Asn Ser Glu Phe Gln
                245                 250                 255

Gln Leu Leu Asn Gln Gly Ile Pro Val Ala Pro His Thr Thr Glu Pro
            260                 265                 270

Met Leu Met Glu Tyr Pro Glu Ala Ile Thr Arg Leu Val Thr Gly Ala
        275                 280                 285

Gln Arg Pro Pro Asp Pro Ala Pro Ala Pro Leu Gly Ala Pro Gly Leu
    290                 295                 300

Pro Asn Gly Leu Leu Ser Gly Asp Glu Asp Phe Ser Ser Ile Ala Asp
305                 310                 315                 320

Met Asp Phe Ser Ala Leu Leu Gly Ser Gly Ser Gly Ser Arg Asp Ser
                325                 330                 335

Arg Glu Gly Met Phe Leu Pro Lys Pro Glu Ala Gly Ser Ala Ile Ser
            340                 345                 350

Asp Val Phe Glu Gly Arg Glu Val Cys Gln Pro Lys Arg Ile Arg Pro
        355                 360                 365

Phe His Pro Pro Gly Ser Pro Trp Ala Asn Arg Pro Leu Pro Ala Ser
    370                 375                 380

Leu Ala Pro Thr Pro Thr Gly Pro Val His Glu Pro Val Gly Ser Leu
385                 390                 395                 400

Thr Pro Ala Pro Val Pro Gln Pro Leu Asp Pro Ala Pro Ala Val Thr
                405                 410                 415

Pro Glu Ala Ser His Leu Leu Glu Asp Pro Asp Glu Glu Thr Ser Gln
            420                 425                 430

Ala Val Lys Ala Leu Arg Glu Met Ala Asp Thr Val Ile Pro Gln Lys
        435                 440                 445

Glu Glu Ala Ala Ile Cys Gly Gln Met Asp Leu Ser His Pro Pro Pro
    450                 455                 460

Arg Gly His Leu Asp Glu Leu Thr Thr Thr Leu Glu Ser Met Thr Glu
465                 470                 475                 480

Asp Leu Asn Leu Asp Ser Pro Leu Thr Pro Glu Leu Asn Glu Ile Leu
                485                 490                 495

Asp Thr Phe Leu Asn Asp Glu Cys Leu Leu His Ala Met His Ile Ser
            500                 505                 510

Thr Gly Leu Ser Ile Phe Asp Thr Ser Leu Phe
```

515 520

<210> SEQ ID NO 133
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Asp Ala Leu Asp Asp Phe Asp Leu Asp Met Leu Gly Ser Asp Ala Leu
1 5 10 15

Asp Asp Phe Asp Leu Asp Met Leu Gly Ser Asp Ala Leu Asp Asp Phe
20 25 30

Asp Leu Asp Met Leu Gly Ser Asp Ala Leu Asp Asp Phe Asp Leu Asp
35 40 45

Met Leu
50

<210> SEQ ID NO 134
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Met Ser Gly Leu Glu Met Ala Asp His Met Met Ala Met Asn His Gly
1 5 10 15

Arg Phe Pro Asp Gly Thr Asn Gly Leu His His His Pro Ala His Arg
20 25 30

Met Gly Met Gly Gln Phe Pro Ser Pro His His His Gln Gln Gln Gln
35 40 45

Pro Gln His Ala Phe Asn Ala Leu Met Gly Glu His Ile His Tyr Gly
50 55 60

Ala Gly Asn Met Asn Ala Thr Ser Gly Ile Arg His Ala Met Gly Pro
65 70 75 80

Gly Thr Val Asn Gly Gly His Pro Pro Ser Ala Leu Ala Pro Ala Ala
85 90 95

Arg Phe Asn Asn Ser Gln Phe Met Gly Pro Pro Val Ala Ser Gln Gly
100 105 110

Gly Ser Leu Pro Ala Ser Met Gln Leu Gln Lys Leu Asn Asn Gln Tyr
115 120 125

Phe Asn His His Pro Tyr Pro His Asn His Tyr Met Pro Asp Leu His
130 135 140

Pro Ala Ala Gly His Gln Met Asn Gly Thr Asn Gln His Phe Arg Asp
145 150 155 160

Cys Asn Pro Lys His Ser Gly Gly Ser Ser Thr Pro Gly Gly Ser Gly
165 170 175

Gly Ser Ser Thr Pro Gly Gly Ser Gly Ser Ser Ser Gly Gly Gly Ala
180 185 190

Gly Ser Ser Asn Ser Gly Gly Gly Ser Gly Ser Gly Asn Met Pro Ala
195 200 205

Ser Val Ala His Val Pro Ala Ala Met Leu Pro Pro Asn Val Ile Asp
210 215 220

Thr Asp Phe Ile Asp Glu Glu Val Leu Met Ser Leu Val Ile Glu Met

```
225                 230                 235                 240

Gly Leu Asp Arg Ile Lys Glu Leu Pro Glu Leu Trp Leu Gly Gln Asn
                245                 250                 255

Glu Phe Asp Phe Met Thr Asp Phe Val Cys Lys Gln Gln Pro Ser Arg
            260                 265                 270

Val Ser Cys
        275


<210> SEQ ID NO 135
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Asp His Leu Met Leu Ala Glu Gly Tyr Arg Leu Val Gln Arg Pro
1               5                   10                  15

Pro Ser Ala Ala Ala Ala His Gly Pro His Ala Leu Arg Thr Leu Pro
            20                  25                  30

Pro Tyr Ala Gly Pro Gly Leu Asp Ser Gly Leu Arg Pro Arg Gly Ala
        35                  40                  45

Pro Leu Gly Pro Pro Pro Pro Arg Gln Pro Gly Ala Leu Ala Tyr Gly
    50                  55                  60

Ala Phe Gly Pro Pro Ser Ser Phe Gln Pro Phe Pro Ala Val Pro Pro
65                  70                  75                  80

Pro Ala Ala Gly Ile Ala His Leu Gln Pro Val Ala Thr Pro Tyr Pro
                85                  90                  95

Gly Arg Ala Ala Ala Pro Pro Asn Ala Pro Gly Gly Pro Pro Gly Pro
            100                 105                 110

Gln Pro Ala Pro Ser Ala Ala Ala Pro Pro Pro Pro Ala His Ala Leu
        115                 120                 125

Gly Gly Met Asp Ala Glu Leu Ile Asp Glu Glu Ala Leu Thr Ser Leu
    130                 135                 140

Glu Leu Glu Leu Gly Leu His Arg Val Arg Glu Leu Pro Glu Leu Phe
145                 150                 155                 160

Leu Gly Gln Ser Glu Phe Asp Cys Phe Ser Asp Leu Gly Ser Ala Pro
                165                 170                 175

Pro Ala Gly Ser Val Ser Cys
            180


<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
```

<400> SEQUENCE: 136

Cys Xaa Cys Xaa His Xaa His
1 5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 137

Cys Xaa Cys Xaa Cys Xaa His Xaa Xaa Xaa Cys Xaa Cys Xaa Cys Xaa
1 5 10 15

Cys

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 138

Cys Xaa Cys Xaa Cys Xaa Cys Xaa Xaa Xaa His Xaa Cys Xaa Cys Xaa
1               5                   10                  15

Cys

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Cys, His, or Asp

<400> SEQUENCE: 139

Cys Xaa Cys Xaa His Xaa Cys Xaa Cys Xaa Cys Xaa Cys Xaa Xaa
1               5                   10                  15

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)

<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 140

Cys Xaa Cys Xaa Cys Xaa Cys Xaa Xaa Xaa Cys Xaa Cys Xaa Cys Xaa
1               5                   10                  15

Cys

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 141

Cys Xaa Cys Xaa Cys Xaa His
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 142

Cys Xaa Cys Xaa His Xaa Cys
1               5

<210> SEQ ID NO 143

<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 143

```
Cys Xaa Cys Xaa His Xaa Cys Xaa Xaa Xaa Cys Xaa Cys Xaa His Xaa
1               5                   10                  15

Cys
```

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 144

Cys Xaa Cys Xaa Cys Xaa Cys Xaa Xaa Xaa Cys Xaa Cys Xaa His Xaa
1 5 10 15

Cys

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 145

Cys Xaa Cys Xaa Cys Xaa Cys
1 5

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 146

Cys Xaa Cys Xaa Cys Xaa Cys Xaa Xaa Xaa Cys Xaa His Xaa His Xaa
1 5 10 15

Cys

<210> SEQ ID NO 147

```
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (8)..(322)
<223> OTHER INFORMATION: This region may encompass 1-15 "Tyr Lys Cys Pro
      Glu Cys Gly Lys Ser Phe Ser His Gln Arg Thr His Thr Gly Glu Lys
      Pro" repeating units
<220> FEATURE:
<221> NAME/KEY: NON_CONS
<222> LOCATION: (18)..(19)
<220> FEATURE:
<221> NAME/KEY: NON_CONS
<222> LOCATION: (39)..(40)
<220> FEATURE:
<221> NAME/KEY: NON_CONS
<222> LOCATION: (60)..(61)
<220> FEATURE:
<221> NAME/KEY: NON_CONS
<222> LOCATION: (81)..(82)
<220> FEATURE:
<221> NAME/KEY: NON_CONS
<222> LOCATION: (102)..(103)
<220> FEATURE:
<221> NAME/KEY: NON_CONS
<222> LOCATION: (123)..(124)
<220> FEATURE:
<221> NAME/KEY: NON_CONS
<222> LOCATION: (144)..(145)
<220> FEATURE:
<221> NAME/KEY: NON_CONS
<222> LOCATION: (165)..(166)
<220> FEATURE:
<221> NAME/KEY: NON_CONS
<222> LOCATION: (186)..(187)
<220> FEATURE:
<221> NAME/KEY: NON_CONS
<222> LOCATION: (207)..(208)
<220> FEATURE:
<221> NAME/KEY: NON_CONS
<222> LOCATION: (228)..(229)
<220> FEATURE:
<221> NAME/KEY: NON_CONS
<222> LOCATION: (249)..(250)
<220> FEATURE:
<221> NAME/KEY: NON_CONS
<222> LOCATION: (270)..(271)
<220> FEATURE:
<221> NAME/KEY: NON_CONS
<222> LOCATION: (291)..(292)
<220> FEATURE:
<221> NAME/KEY: NON_CONS
<222> LOCATION: (312)..(313)
<220> FEATURE:
<221> NAME/KEY: NON_CONS
<222> LOCATION: (333)..(334)
<220> FEATURE:
<223> OTHER INFORMATION: See specification as filed for detailed
      description of substitutions and preferred embodiments

<400> SEQUENCE: 147

Leu Glu Pro Gly Glu Lys Pro Tyr Lys Cys Pro Glu Cys Gly Lys Ser
1               5                   10                  15

Phe Ser His Gln Arg Thr His Thr Gly Glu Lys Pro Tyr Lys Cys Pro
            20                  25                  30

Glu Cys Gly Lys Ser Phe Ser His Gln Arg Thr His Thr Gly Glu Lys
        35                  40                  45

Pro Tyr Lys Cys Pro Glu Cys Gly Lys Ser Phe Ser His Gln Arg Thr
    50                  55                  60

His Thr Gly Glu Lys Pro Tyr Lys Cys Pro Glu Cys Gly Lys Ser Phe
```

```
65                  70                  75                  80

Ser His Gln Arg Thr His Thr Gly Glu Lys Pro Tyr Lys Cys Pro Glu
                85                  90                  95

Cys Gly Lys Ser Phe Ser His Gln Arg Thr His Thr Gly Glu Lys Pro
            100                 105                 110

Tyr Lys Cys Pro Glu Cys Gly Lys Ser Phe Ser His Gln Arg Thr His
        115                 120                 125

Thr Gly Glu Lys Pro Tyr Lys Cys Pro Glu Cys Gly Lys Ser Phe Ser
    130                 135                 140

His Gln Arg Thr His Thr Gly Glu Lys Pro Tyr Lys Cys Pro Glu Cys
145                 150                 155                 160

Gly Lys Ser Phe Ser His Gln Arg Thr His Thr Gly Glu Lys Pro Tyr
                165                 170                 175

Lys Cys Pro Glu Cys Gly Lys Ser Phe Ser His Gln Arg Thr His Thr
            180                 185                 190

Gly Glu Lys Pro Tyr Lys Cys Pro Glu Cys Gly Lys Ser Phe Ser His
        195                 200                 205

Gln Arg Thr His Thr Gly Glu Lys Pro Tyr Lys Cys Pro Glu Cys Gly
    210                 215                 220

Lys Ser Phe Ser His Gln Arg Thr His Thr Gly Glu Lys Pro Tyr Lys
225                 230                 235                 240

Cys Pro Glu Cys Gly Lys Ser Phe Ser His Gln Arg Thr His Thr Gly
                245                 250                 255

Glu Lys Pro Tyr Lys Cys Pro Glu Cys Gly Lys Ser Phe Ser His Gln
            260                 265                 270

Arg Thr His Thr Gly Glu Lys Pro Tyr Lys Cys Pro Glu Cys Gly Lys
        275                 280                 285

Ser Phe Ser His Gln Arg Thr His Thr Gly Glu Lys Pro Tyr Lys Cys
    290                 295                 300

Pro Glu Cys Gly Lys Ser Phe Ser His Gln Arg Thr His Thr Gly Glu
305                 310                 315                 320

Lys Pro Tyr Lys Cys Pro Glu Cys Gly Lys Ser Phe Ser His Gln Arg
                325                 330                 335

Thr His Thr Gly Lys Lys Thr Ser
            340
```

<210> SEQ ID NO 148
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: This region may encompass 1-50 residues
<220> FEATURE:
<221> NAME/KEY: MOD_RES
<222> LOCATION: (65)..(114)
<223> OTHER INFORMATION: Any amino acid
<220> FEATURE:
<221> NAME/KEY: MISC_FEATURE
<222> LOCATION: (65)..(114)
<223> OTHER INFORMATION: This region may encompass 1-50 residues
<220> FEATURE:
<221> NAME/KEY: MOD_RES

```
<222> LOCATION: (122)..(171)
<223> OTHER INFORMATION: Any amino acid
<220> FEATURE:
<221> NAME/KEY: MISC_FEATURE
<222> LOCATION: (122)..(171)
<223> OTHER INFORMATION: This region may encompass 1-50 residues
<220> FEATURE:
<221> NAME/KEY: MOD_RES
<222> LOCATION: (179)..(228)
<223> OTHER INFORMATION: Any amino acid
<220> FEATURE:
<221> NAME/KEY: MISC_FEATURE
<222> LOCATION: (179)..(228)
<223> OTHER INFORMATION: This region may encompass 1-50 residues
<220> FEATURE:
<221> NAME/KEY: MOD_RES
<222> LOCATION: (236)..(285)
<223> OTHER INFORMATION: Any amino acid
<220> FEATURE:
<221> NAME/KEY: MISC_FEATURE
<222> LOCATION: (236)..(285)
<223> OTHER INFORMATION: This region may encompass 1-50 residues

<400> SEQUENCE: 148

Arg Ser Asp Asn Leu Val Arg Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Arg Glu Asp Asn Leu His Thr
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Arg Ser Asp Glu Leu Val Arg Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Gln Ser Gly Asn Leu
                165                 170                 175

Thr Glu Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Thr Ser Gly His Leu Val Arg Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Gln Asn Ser
        275                 280                 285
```

```
Thr Leu Thr Glu
    290


<210> SEQ ID NO 149
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: This region may encompass 1-50 residues
<220> FEATURE:
<221> NAME/KEY: MOD_RES
<222> LOCATION: (65)..(114)
<223> OTHER INFORMATION: Any amino acid
<220> FEATURE:
<221> NAME/KEY: MISC_FEATURE
<222> LOCATION: (65)..(114)
<223> OTHER INFORMATION: This region may encompass 1-50 residues
<220> FEATURE:
<221> NAME/KEY: MOD_RES
<222> LOCATION: (122)..(171)
<223> OTHER INFORMATION: Any amino acid
<220> FEATURE:
<221> NAME/KEY: MISC_FEATURE
<222> LOCATION: (122)..(171)
<223> OTHER INFORMATION: This region may encompass 1-50 residues
<220> FEATURE:
<221> NAME/KEY: MOD_RES
<222> LOCATION: (179)..(228)
<223> OTHER INFORMATION: Any amino acid
<220> FEATURE:
<221> NAME/KEY: MISC_FEATURE
<222> LOCATION: (179)..(228)
<223> OTHER INFORMATION: This region may encompass 1-50 residues
<220> FEATURE:
<221> NAME/KEY: MOD_RES
<222> LOCATION: (236)..(285)
<223> OTHER INFORMATION: Any amino acid
<220> FEATURE:
<221> NAME/KEY: MISC_FEATURE
<222> LOCATION: (236)..(285)
<223> OTHER INFORMATION: This region may encompass 1-50 residues

<400> SEQUENCE: 149

Arg Ser Asp Asn Leu Val Arg Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa His Arg Thr Thr Leu Thr Asn
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Arg Glu Asp Asn Leu His Thr Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
```

```
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Thr Ser His Ser Leu
                165                 170                 175

Thr Glu Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Gln Ser Ser Ser Leu Val Arg Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Arg Glu Asp
        275                 280                 285

Asn Leu His Thr
    290
```

<210> SEQ ID NO 150
<211> LENGTH: 292
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: This region may encompass 1-50 residues
<220> FEATURE:
<221> NAME/KEY: MOD_RES
<222> LOCATION: (65)..(114)
<223> OTHER INFORMATION: Any amino acid
<220> FEATURE:
<221> NAME/KEY: MISC_FEATURE
<222> LOCATION: (65)..(114)
<223> OTHER INFORMATION: This region may encompass 1-50 residues
<220> FEATURE:
<221> NAME/KEY: MOD_RES
<222> LOCATION: (122)..(171)
<223> OTHER INFORMATION: Any amino acid
<220> FEATURE:
<221> NAME/KEY: MISC_FEATURE
<222> LOCATION: (122)..(171)
<223> OTHER INFORMATION: This region may encompass 1-50 residues
<220> FEATURE:
<221> NAME/KEY: MOD_RES
<222> LOCATION: (179)..(228)
<223> OTHER INFORMATION: Any amino acid
<220> FEATURE:
<221> NAME/KEY: MISC_FEATURE
<222> LOCATION: (179)..(228)
<223> OTHER INFORMATION: This region may encompass 1-50 residues
<220> FEATURE:
<221> NAME/KEY: MOD_RES
<222> LOCATION: (236)..(285)
<223> OTHER INFORMATION: Any amino acid
<220> FEATURE:
<221> NAME/KEY: MISC_FEATURE
<222> LOCATION: (236)..(285)

```
<223> OTHER INFORMATION: This region may encompass 1-50 residues

<400> SEQUENCE: 150

Asp Pro Gly Ala Leu Val Arg Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Arg Ser Asp Asn Leu Val Arg
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Gln Ser Gly Asp Leu Arg Arg Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Thr His Leu Asp Leu
                165                 170                 175

Ile Arg Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Thr Ser Gly Asn Leu Val Arg Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Arg Ser Asp
        275                 280                 285

Asn Leu Val Arg
    290


<210> SEQ ID NO 151
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: This region may encompass 1-50 residues
<220> FEATURE:
<221> NAME/KEY: MOD_RES
```

<222> LOCATION: (65)..(114)
<223> OTHER INFORMATION: Any amino acid
<220> FEATURE:
<221> NAME/KEY: MISC_FEATURE
<222> LOCATION: (65)..(114)
<223> OTHER INFORMATION: This region may encompass 1-50 residues
<220> FEATURE:
<221> NAME/KEY: MOD_RES
<222> LOCATION: (122)..(171)
<223> OTHER INFORMATION: Any amino acid
<220> FEATURE:
<221> NAME/KEY: MISC_FEATURE
<222> LOCATION: (122)..(171)
<223> OTHER INFORMATION: This region may encompass 1-50 residues
<220> FEATURE:
<221> NAME/KEY: MOD_RES
<222> LOCATION: (179)..(228)
<223> OTHER INFORMATION: Any amino acid
<220> FEATURE:
<221> NAME/KEY: MISC_FEATURE
<222> LOCATION: (179)..(228)
<223> OTHER INFORMATION: This region may encompass 1-50 residues
<220> FEATURE:
<221> NAME/KEY: MOD_RES
<222> LOCATION: (236)..(285)
<223> OTHER INFORMATION: Any amino acid
<220> FEATURE:
<221> NAME/KEY: MISC_FEATURE
<222> LOCATION: (236)..(285)
<223> OTHER INFORMATION: This region may encompass 1-50 residues
<220> FEATURE:
<221> NAME/KEY: MOD_RES
<222> LOCATION: (293)..(342)
<223> OTHER INFORMATION: Any amino acid
<220> FEATURE:
<221> NAME/KEY: MISC_FEATURE
<222> LOCATION: (293)..(342)
<223> OTHER INFORMATION: This region may encompass 1-50 residues
<220> FEATURE:
<221> NAME/KEY: MOD_RES
<222> LOCATION: (350)..(399)
<223> OTHER INFORMATION: Any amino acid
<220> FEATURE:
<221> NAME/KEY: MISC_FEATURE
<222> LOCATION: (350)..(399)
<223> OTHER INFORMATION: This region may encompass 1-50 residues
<220> FEATURE:
<221> NAME/KEY: MOD_RES
<222> LOCATION: (407)..(456)
<223> OTHER INFORMATION: Any amino acid
<220> FEATURE:
<221> NAME/KEY: MISC_FEATURE
<222> LOCATION: (407)..(456)
<223> OTHER INFORMATION: This region may encompass 1-50 residues

<400> SEQUENCE: 151

```
Arg Arg Asp Glu Leu Asn Val Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Arg Ser Asp His Leu Thr Asn
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Arg Ser Asp Asp Leu Val Arg Xaa Xaa Xaa Xaa Xaa Xaa Xaa
```

```
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Arg Ser Asp Asn Leu
                165                 170                 175

Val Arg Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa His Arg Thr Thr Leu Thr Asn Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Arg Glu Asp
        275                 280                 285

Asn Leu His Thr Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Thr Ser His Ser Leu Thr Glu Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Gln
385                 390                 395                 400

Ser Ser Ser Leu Val Arg Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Arg Glu Asp Asn Leu His Thr
    450                 455                 460
```

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

```
Arg Ser Asp Asn Leu Val Arg
1               5
```

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Arg Glu Asp Asn Leu His Thr
1 5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Arg Ser Asp Glu Leu Val Arg
1 5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Gln Ser Gly Asn Leu Thr Glu
1 5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Thr Ser Gly His Leu Val Arg
1 5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Gln Asn Ser Thr Leu Thr Glu
1 5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Asp Pro Gly Ala Leu Val Arg
1 5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

His Arg Thr Thr Leu Thr Asn
1 5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Gln Ser Gly Asp Leu Arg Arg
1 5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Thr Ser His Ser Leu Thr Glu
1 5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Thr His Leu Asp Leu Ile Arg
1 5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Gln Ser Ser Ser Leu Val Arg
1 5

<210> SEQ ID NO 164
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 164

Thr Ser Gly Asn Leu Val Arg
1 5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Arg Arg Asp Glu Leu Asn Val
1 5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Arg Ser Asp Asp Leu Val Arg
1 5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Arg Ser Asp His Leu Thr Asn
1 5

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Leu Ile Lys Pro Ser Arg Met Arg Lys Tyr Pro Asn Arg Pro Ser Lys
1 5 10 15

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Pro Lys Lys Lys Arg Lys Val
1 5

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

```
Lys Arg Pro Ala Ala Thr Lys Lys Ala Gly Gln Ala Lys Lys Lys Lys
1               5                   10                  15
```

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

```
Tyr Pro Tyr Asp Val Pro Asp Tyr Ala
1               5
```

<210> SEQ ID NO 172
<211> LENGTH: 2009
<212> TYPE: PRT
<213> ORGANISM: Homo sapiens

<400> SEQUENCE: 172

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220
```

```
Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
```

```
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                1015                1020

Ala Tyr  Val Lys Arg Lys Ile  Tyr Glu Phe Ile Gln  Gln Ser Phe
    1025                1030                1035

Ile Arg  Lys Gln Lys Ile Leu  Asp Glu Ile Lys Pro  Leu Asp Asp
    1040                1045                1050

Leu Asn  Asn Lys Lys Asp Ser  Cys Met Ser Asn His  Thr Ala Glu
    1055                1060                1065
```

```
Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455
```

```
Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
    1475                 1480                 1485

Gln Lys  Lys Lys Phe Gly Gly  Gln Asp Ile Phe Met  Thr Glu Glu
    1490                 1495                 1500

Gln Lys  Lys Tyr Tyr Asn Ala  Met Lys Lys Leu Gly  Ser Lys Lys
    1505                 1510                 1515

Pro Gln  Lys Pro Ile Pro Arg  Pro Gly Asn Lys Phe  Gln Gly Met
    1520                 1525                 1530

Val Phe  Asp Phe Val Thr Arg  Gln Val Phe Asp Ile  Ser Ile Met
    1535                 1540                 1545

Ile Leu  Ile Cys Leu Asn Met  Val Thr Met Met Val  Glu Thr Asp
    1550                 1555                 1560

Asp Gln  Ser Glu Tyr Val Thr  Thr Ile Leu Ser Arg  Ile Asn Leu
    1565                 1570                 1575

Val Phe  Ile Val Leu Phe Thr  Gly Glu Cys Val Leu  Lys Leu Ile
    1580                 1585                 1590

Ser Leu  Arg His Tyr Tyr Phe  Thr Ile Gly Trp Asn  Ile Phe Asp
    1595                 1600                 1605

Phe Val  Val Val Ile Leu Ser  Ile Val Gly Met Phe  Leu Ala Glu
    1610                 1615                 1620

Leu Ile  Glu Lys Tyr Phe Val  Ser Pro Thr Leu Phe  Arg Val Ile
    1625                 1630                 1635

Arg Leu  Ala Arg Ile Gly Arg  Ile Leu Arg Leu Ile  Lys Gly Ala
    1640                 1645                 1650

Lys Gly  Ile Arg Thr Leu Leu  Phe Ala Leu Met Met  Ser Leu Pro
    1655                 1660                 1665

Ala Leu  Phe Asn Ile Gly Leu  Leu Leu Phe Leu Val  Met Phe Ile
    1670                 1675                 1680

Tyr Ala  Ile Phe Gly Met Ser  Asn Phe Ala Tyr Val  Lys Arg Glu
    1685                 1690                 1695

Val Gly  Ile Asp Asp Met Phe  Asn Phe Glu Thr Phe  Gly Asn Ser
    1700                 1705                 1710

Met Ile  Cys Leu Phe Gln Ile  Thr Thr Ser Ala Gly  Trp Asp Gly
    1715                 1720                 1725

Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Ser
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
```

```
    1850                1855                1860

Cys Leu  Asp Ile Leu Phe Ala  Phe Thr Lys Arg Val  Leu Gly Glu
    1865                1870                1875

Ser Gly  Glu Met Asp Ala Leu  Arg Ile Gln Met Glu  Glu Arg Phe
    1880                1885                1890

Met Ala  Ser Asn Pro Ser Lys  Val Ser Tyr Gln Pro  Ile Thr Thr
    1895                1900                1905

Thr Leu  Lys Arg Lys Gln Glu  Glu Val Ser Ala Val  Ile Ile Gln
    1910                1915                1920

Arg Ala  Tyr Arg Arg His Leu  Leu Lys Arg Thr Val  Lys Gln Ala
    1925                1930                1935

Ser Phe  Thr Tyr Asn Lys Asn  Lys Ile Lys Gly Gly  Ala Asn Leu
    1940                1945                1950

Leu Ile  Lys Glu Asp Met Ile  Ile Asp Arg Ile Asn  Glu Asn Ser
    1955                1960                1965

Ile Thr  Glu Lys Thr Asp Leu  Thr Met Ser Thr Ala  Ala Cys Pro
    1970                1975                1980

Pro Ser  Tyr Asp Arg Val Thr  Lys Pro Ile Val Glu  Lys His Glu
    1985                1990                1995

Gln Glu  Gly Lys Asp Glu Lys  Ala Lys Gly Lys
    2000                2005


<210> SEQ ID NO 173
<211> LENGTH: 1052
<212> TYPE: PRT
<213> ORGANISM: Homo sapiens

<400> SEQUENCE: 173

Lys Arg Asn Tyr Ile Leu Gly Leu Ala Ile Gly Ile Thr Ser Val Gly
1               5                   10                  15

Tyr Gly Ile Ile Asp Tyr Glu Thr Arg Asp Val Ile Asp Ala Gly Val
            20                  25                  30

Arg Leu Phe Lys Glu Ala Asn Val Glu Asn Asn Glu Gly Arg Arg Ser
        35                  40                  45

Lys Arg Gly Ala Arg Arg Leu Lys Arg Arg Arg Arg His Arg Ile Gln
    50                  55                  60

Arg Val Lys Lys Leu Leu Phe Asp Tyr Asn Leu Leu Thr Asp His Ser
65                  70                  75                  80

Glu Leu Ser Gly Ile Asn Pro Tyr Glu Ala Arg Val Lys Gly Leu Ser
                85                  90                  95

Gln Lys Leu Ser Glu Glu Glu Phe Ser Ala Ala Leu Leu His Leu Ala
            100                 105                 110

Lys Arg Arg Gly Val His Asn Val Asn Glu Val Glu Glu Asp Thr Gly
        115                 120                 125

Asn Glu Leu Ser Thr Lys Glu Gln Ile Ser Arg Asn Ser Lys Ala Leu
    130                 135                 140

Glu Glu Lys Tyr Val Ala Glu Leu Gln Leu Glu Arg Leu Lys Lys Asp
145                 150                 155                 160

Gly Glu Val Arg Gly Ser Ile Asn Arg Phe Lys Thr Ser Asp Tyr Val
                165                 170                 175

Lys Glu Ala Lys Gln Leu Leu Lys Val Gln Lys Ala Tyr His Gln Leu
            180                 185                 190

Asp Gln Ser Phe Ile Asp Thr Tyr Ile Asp Leu Leu Glu Thr Arg Arg
        195                 200                 205
```

```
Thr Tyr Tyr Glu Gly Pro Gly Glu Gly Ser Pro Phe Gly Trp Lys Asp
    210                 215                 220

Ile Lys Glu Trp Tyr Glu Met Leu Met Gly His Cys Thr Tyr Phe Pro
225                 230                 235                 240

Glu Glu Leu Arg Ser Val Lys Tyr Ala Tyr Asn Ala Asp Leu Tyr Asn
                245                 250                 255

Ala Leu Asn Asp Leu Asn Asn Leu Val Ile Thr Arg Asp Glu Asn Glu
            260                 265                 270

Lys Leu Glu Tyr Tyr Glu Lys Phe Gln Ile Ile Glu Asn Val Phe Lys
        275                 280                 285

Gln Lys Lys Lys Pro Thr Leu Lys Gln Ile Ala Lys Glu Ile Leu Val
    290                 295                 300

Asn Glu Glu Asp Ile Lys Gly Tyr Arg Val Thr Ser Thr Gly Lys Pro
305                 310                 315                 320

Glu Phe Thr Asn Leu Lys Val Tyr His Asp Ile Lys Asp Ile Thr Ala
                325                 330                 335

Arg Lys Glu Ile Ile Glu Asn Ala Glu Leu Leu Asp Gln Ile Ala Lys
            340                 345                 350

Ile Leu Thr Ile Tyr Gln Ser Ser Glu Asp Ile Gln Glu Glu Leu Thr
        355                 360                 365

Asn Leu Asn Ser Glu Leu Thr Gln Glu Glu Ile Glu Gln Ile Ser Asn
    370                 375                 380

Leu Lys Gly Tyr Thr Gly Thr His Asn Leu Ser Leu Lys Ala Ile Asn
385                 390                 395                 400

Leu Ile Leu Asp Glu Leu Trp His Thr Asn Asp Asn Gln Ile Ala Ile
                405                 410                 415

Phe Asn Arg Leu Lys Leu Val Pro Lys Lys Val Asp Leu Ser Gln Gln
            420                 425                 430

Lys Glu Ile Pro Thr Thr Leu Val Asp Asp Phe Ile Leu Ser Pro Val
        435                 440                 445

Val Lys Arg Ser Phe Ile Gln Ser Ile Lys Val Ile Asn Ala Ile Ile
    450                 455                 460

Lys Lys Tyr Gly Leu Pro Asn Asp Ile Ile Ile Glu Leu Ala Arg Glu
465                 470                 475                 480

Lys Asn Ser Lys Asp Ala Gln Lys Met Ile Asn Glu Met Gln Lys Arg
                485                 490                 495

Asn Arg Gln Thr Asn Glu Arg Ile Glu Glu Ile Ile Arg Thr Thr Gly
            500                 505                 510

Lys Glu Asn Ala Lys Tyr Leu Ile Glu Lys Ile Lys Leu His Asp Met
        515                 520                 525

Gln Glu Gly Lys Cys Leu Tyr Ser Leu Glu Ala Ile Pro Leu Glu Asp
    530                 535                 540

Leu Leu Asn Asn Pro Phe Asn Tyr Glu Val Asp His Ile Ile Pro Arg
545                 550                 555                 560

Ser Val Ser Phe Asp Asn Ser Phe Asn Asn Lys Val Leu Val Lys Gln
                565                 570                 575

Glu Glu Ala Ser Lys Lys Gly Asn Arg Thr Pro Phe Gln Tyr Leu Ser
            580                 585                 590

Ser Ser Asp Ser Lys Ile Ser Tyr Glu Thr Phe Lys Lys His Ile Leu
        595                 600                 605

Asn Leu Ala Lys Gly Lys Gly Arg Ile Ser Lys Thr Lys Lys Glu Tyr
    610                 615                 620

Leu Leu Glu Glu Arg Asp Ile Asn Arg Phe Ser Val Gln Lys Asp Phe
```

```
625                 630                 635                 640

Ile Asn Arg Asn Leu Val Asp Thr Arg Tyr Ala Thr Arg Gly Leu Met
                645                 650                 655

Asn Leu Leu Arg Ser Tyr Phe Arg Val Asn Asn Leu Asp Val Lys Val
            660                 665                 670

Lys Ser Ile Asn Gly Gly Phe Thr Ser Phe Leu Arg Arg Lys Trp Lys
        675                 680                 685

Phe Lys Lys Glu Arg Asn Lys Gly Tyr Lys His His Ala Glu Asp Ala
    690                 695                 700

Leu Ile Ile Ala Asn Ala Asp Phe Ile Phe Lys Glu Trp Lys Lys Leu
705                 710                 715                 720

Asp Lys Ala Lys Lys Val Met Glu Asn Gln Met Phe Glu Glu Lys Gln
                725                 730                 735

Ala Glu Ser Met Pro Glu Ile Glu Thr Glu Gln Glu Tyr Lys Glu Ile
            740                 745                 750

Phe Ile Thr Pro His Gln Ile Lys His Ile Lys Asp Phe Lys Asp Tyr
        755                 760                 765

Lys Tyr Ser His Arg Val Asp Lys Lys Pro Asn Arg Glu Leu Ile Asn
    770                 775                 780

Asp Thr Leu Tyr Ser Thr Arg Lys Asp Asp Lys Gly Asn Thr Leu Ile
785                 790                 795                 800

Val Asn Asn Leu Asn Gly Leu Tyr Asp Lys Asp Asn Asp Lys Leu Lys
                805                 810                 815

Lys Leu Ile Asn Lys Ser Pro Glu Lys Leu Leu Met Tyr His His Asp
            820                 825                 830

Pro Gln Thr Tyr Gln Lys Leu Lys Leu Ile Met Glu Gln Tyr Gly Asp
        835                 840                 845

Glu Lys Asn Pro Leu Tyr Lys Tyr Tyr Glu Glu Thr Gly Asn Tyr Leu
    850                 855                 860

Thr Lys Tyr Ser Lys Lys Asp Asn Gly Pro Val Ile Lys Lys Ile Lys
865                 870                 875                 880

Tyr Tyr Gly Asn Lys Leu Asn Ala His Leu Asp Ile Thr Asp Asp Tyr
                885                 890                 895

Pro Asn Ser Arg Asn Lys Val Val Lys Leu Ser Leu Lys Pro Tyr Arg
            900                 905                 910

Phe Asp Val Tyr Leu Asp Asn Gly Val Tyr Lys Phe Val Thr Val Lys
        915                 920                 925

Asn Leu Asp Val Ile Lys Lys Glu Asn Tyr Tyr Glu Val Asn Ser Lys
    930                 935                 940

Cys Tyr Glu Glu Ala Lys Lys Leu Lys Lys Ile Ser Asn Gln Ala Glu
945                 950                 955                 960

Phe Ile Ala Ser Phe Tyr Asn Asn Asp Leu Ile Lys Ile Asn Gly Glu
                965                 970                 975

Leu Tyr Arg Val Ile Gly Val Asn Asn Asp Leu Leu Asn Arg Ile Glu
            980                 985                 990

Val Asn Met Ile Asp Ile Thr Tyr  Arg Glu Tyr Leu Glu  Asn Met Asn
        995                 1000                 1005

Asp Lys  Arg Pro Pro Arg Ile  Ile Lys Thr Ile Ala  Ser Lys Thr
    1010                 1015                 1020

Gln Ser  Ile Lys Lys Tyr Ser  Thr Asp Ile Leu Gly  Asn Leu Tyr
    1025                 1030                 1035

Glu Val  Lys Ser Lys Lys His  Pro Gln Ile Ile Lys  Lys Gly
    1040                 1045                 1050
```

<210> SEQ ID NO 174
<211> LENGTH: 1148
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 174

Met Ala Pro Lys Lys Lys Arg Lys Val Gly Ile His Gly Val Pro Ala
1 5 10 15

Ala Lys Arg Asn Tyr Ile Leu Gly Leu Ala Ile Gly Ile Thr Ser Val
20 25 30

Gly Tyr Gly Ile Ile Asp Tyr Glu Thr Arg Asp Val Ile Asp Ala Gly
35 40 45

Val Arg Leu Phe Lys Glu Ala Asn Val Glu Asn Asn Glu Gly Arg Arg
50 55 60

Ser Lys Arg Gly Ala Arg Arg Leu Lys Arg Arg Arg Arg His Arg Ile
65 70 75 80

Gln Arg Val Lys Lys Leu Leu Phe Asp Tyr Asn Leu Leu Thr Asp His
85 90 95

Ser Glu Leu Ser Gly Ile Asn Pro Tyr Glu Ala Arg Val Lys Gly Leu
100 105 110

Ser Gln Lys Leu Ser Glu Glu Glu Phe Ser Ala Ala Leu Leu His Leu
115 120 125

Ala Lys Arg Arg Gly Val His Asn Val Asn Glu Val Glu Glu Asp Thr
130 135 140

Gly Asn Glu Leu Ser Thr Lys Glu Gln Ile Ser Arg Asn Ser Lys Ala
145 150 155 160

Leu Glu Glu Lys Tyr Val Ala Glu Leu Gln Leu Glu Arg Leu Lys Lys
165 170 175

Asp Gly Glu Val Arg Gly Ser Ile Asn Arg Phe Lys Thr Ser Asp Tyr
180 185 190

Val Lys Glu Ala Lys Gln Leu Leu Lys Val Gln Lys Ala Tyr His Gln
195 200 205

Leu Asp Gln Ser Phe Ile Asp Thr Tyr Ile Asp Leu Leu Glu Thr Arg
210 215 220

Arg Thr Tyr Tyr Glu Gly Pro Gly Glu Gly Ser Pro Phe Gly Trp Lys
225 230 235 240

Asp Ile Lys Glu Trp Tyr Glu Met Leu Met Gly His Cys Thr Tyr Phe
245 250 255

Pro Glu Glu Leu Arg Ser Val Lys Tyr Ala Tyr Asn Ala Asp Leu Tyr
260 265 270

Asn Ala Leu Asn Asp Leu Asn Asn Leu Val Ile Thr Arg Asp Glu Asn
275 280 285

Glu Lys Leu Glu Tyr Tyr Glu Lys Phe Gln Ile Ile Glu Asn Val Phe
290 295 300

Lys Gln Lys Lys Lys Pro Thr Leu Lys Gln Ile Ala Lys Glu Ile Leu
305 310 315 320

Val Asn Glu Glu Asp Ile Lys Gly Tyr Arg Val Thr Ser Thr Gly Lys
325 330 335

Pro Glu Phe Thr Asn Leu Lys Val Tyr His Asp Ile Lys Asp Ile Thr
340 345 350

Ala Arg Lys Glu Ile Ile Glu Asn Ala Glu Leu Leu Asp Gln Ile Ala 355 360 365

Lys Ile Leu Thr Ile Tyr Gln Ser Ser Glu Asp Ile Gln Glu Glu Leu
370 375 380

Thr Asn Leu Asn Ser Glu Leu Thr Gln Glu Glu Ile Glu Gln Ile Ser
385 390 395 400

Asn Leu Lys Gly Tyr Thr Gly Thr His Asn Leu Ser Leu Lys Ala Ile
405 410 415

Asn Leu Ile Leu Asp Glu Leu Trp His Thr Asn Asp Asn Gln Ile Ala
420 425 430

Ile Phe Asn Arg Leu Lys Leu Val Pro Lys Lys Val Asp Leu Ser Gln
435 440 445

Gln Lys Glu Ile Pro Thr Thr Leu Val Asp Asp Phe Ile Leu Ser Pro
450 455 460

Val Val Lys Arg Ser Phe Ile Gln Ser Ile Lys Val Ile Asn Ala Ile
465 470 475 480

Ile Lys Lys Tyr Gly Leu Pro Asn Asp Ile Ile Ile Glu Leu Ala Arg
485 490 495

Glu Lys Asn Ser Lys Asp Ala Gln Lys Met Ile Asn Glu Met Gln Lys
500 505 510

Arg Asn Arg Gln Thr Asn Glu Arg Ile Glu Glu Ile Ile Arg Thr Thr
515 520 525

Gly Lys Glu Asn Ala Lys Tyr Leu Ile Glu Lys Ile Lys Leu His Asp
530 535 540

Met Gln Glu Gly Lys Cys Leu Tyr Ser Leu Glu Ala Ile Pro Leu Glu
545 550 555 560

Asp Leu Leu Asn Asn Pro Phe Asn Tyr Glu Val Asp His Ile Ile Pro
565 570 575

Arg Ser Val Ser Phe Asp Asn Ser Phe Asn Asn Lys Val Leu Val Lys
580 585 590

Gln Glu Glu Ala Ser Lys Lys Gly Asn Arg Thr Pro Phe Gln Tyr Leu
595 600 605

Ser Ser Ser Asp Ser Lys Ile Ser Tyr Glu Thr Phe Lys Lys His Ile
610 615 620

Leu Asn Leu Ala Lys Gly Lys Gly Arg Ile Ser Lys Thr Lys Lys Glu
625 630 635 640

Tyr Leu Leu Glu Glu Arg Asp Ile Asn Arg Phe Ser Val Gln Lys Asp
645 650 655

Phe Ile Asn Arg Asn Leu Val Asp Thr Arg Tyr Ala Thr Arg Gly Leu
660 665 670

Met Asn Leu Leu Arg Ser Tyr Phe Arg Val Asn Asn Leu Asp Val Lys
675 680 685

Val Lys Ser Ile Asn Gly Gly Phe Thr Ser Phe Leu Arg Arg Lys Trp
690 695 700

Lys Phe Lys Lys Glu Arg Asn Lys Gly Tyr Lys His His Ala Glu Asp
705 710 715 720

Ala Leu Ile Ile Ala Asn Ala Asp Phe Ile Phe Lys Glu Trp Lys Lys
725 730 735

Leu Asp Lys Ala Lys Lys Val Met Glu Asn Gln Met Phe Glu Glu Lys
740 745 750

Gln Ala Glu Ser Met Pro Glu Ile Glu Thr Glu Gln Glu Tyr Lys Glu
755 760 765

Ile Phe Ile Thr Pro His Gln Ile Lys His Ile Lys Asp Phe Lys Asp
770 775 780

Tyr Lys Tyr Ser His Arg Val Asp Lys Lys Pro Asn Arg Glu Leu Ile
785 790 795 800

Asn Asp Thr Leu Tyr Ser Thr Arg Lys Asp Asp Lys Gly Asn Thr Leu
805 810 815

Ile Val Asn Asn Leu Asn Gly Leu Tyr Asp Lys Asp Asn Asp Lys Leu
820 825 830

Lys Lys Leu Ile Asn Lys Ser Pro Glu Lys Leu Leu Met Tyr His His
835 840 845

Asp Pro Gln Thr Tyr Gln Lys Leu Lys Leu Ile Met Glu Gln Tyr Gly
850 855 860

Asp Glu Lys Asn Pro Leu Tyr Lys Tyr Tyr Glu Glu Thr Gly Asn Tyr
865 870 875 880

Leu Thr Lys Tyr Ser Lys Lys Asp Asn Gly Pro Val Ile Lys Lys Ile
885 890 895

Lys Tyr Tyr Gly Asn Lys Leu Asn Ala His Leu Asp Ile Thr Asp Asp
900 905 910

Tyr Pro Asn Ser Arg Asn Lys Val Val Lys Leu Ser Leu Lys Pro Tyr
915 920 925

Arg Phe Asp Val Tyr Leu Asp Asn Gly Val Tyr Lys Phe Val Thr Val
930 935 940

Lys Asn Leu Asp Val Ile Lys Lys Glu Asn Tyr Tyr Glu Val Asn Ser
945 950 955 960

Lys Cys Tyr Glu Glu Ala Lys Lys Leu Lys Lys Ile Ser Asn Gln Ala
965 970 975

Glu Phe Ile Ala Ser Phe Tyr Asn Asn Asp Leu Ile Lys Ile Asn Gly
980 985 990

Glu Leu Tyr Arg Val Ile Gly Val Asn Asn Asp Leu Leu Asn Arg Ile
995 1000 1005

Glu Val Asn Met Ile Asp Ile Thr Tyr Arg Glu Tyr Leu Glu Asn
1010 1015 1020

Met Asn Asp Lys Arg Pro Pro Arg Ile Ile Lys Thr Ile Ala Ser
1025 1030 1035

Lys Thr Gln Ser Ile Lys Lys Tyr Ser Thr Asp Ile Leu Gly Asn
1040 1045 1050

Leu Tyr Glu Val Lys Ser Lys Lys His Pro Gln Ile Ile Lys Lys
1055 1060 1065

Gly Lys Arg Pro Ala Ala Thr Lys Lys Ala Gly Gln Ala Lys Lys
1070 1075 1080

Lys Lys Gly Ser Tyr Pro Tyr Asp Val Pro Asp Tyr Ala Leu Glu
1085 1090 1095

Asp Ala Leu Asp Asp Phe Asp Leu Asp Met Leu Gly Ser Asp Ala
1100 1105 1110

Leu Asp Asp Phe Asp Leu Asp Met Leu Gly Ser Asp Ala Leu Asp
1115 1120 1125

Asp Phe Asp Leu Asp Met Leu Gly Ser Asp Ala Leu Asp Asp Phe
1130 1135 1140

Asp Leu Asp Met Leu
1145

<210> SEQ ID NO 175
<211> LENGTH: 387
<212> TYPE: PRT
<213> ORGANISM: Homo sapiens

<400> SEQUENCE: 175

```
Met Thr Gly Lys Leu Ala Glu Lys Leu Pro Val Thr Met Ser Ser Leu
1               5                   10                  15

Leu Asn Gln Leu Pro Asp Asn Leu Tyr Pro Glu Glu Ile Pro Ser Ala
            20                  25                  30

Leu Asn Leu Phe Ser Gly Ser Ser Asp Ser Val Val His Tyr Asn Gln
        35                  40                  45

Met Ala Thr Glu Asn Val Met Asp Ile Gly Leu Thr Asn Glu Lys Pro
    50                  55                  60

Asn Pro Glu Leu Ser Tyr Ser Gly Ser Phe Gln Pro Ala Pro Gly Asn
65                  70                  75                  80

Lys Thr Val Thr Tyr Leu Gly Lys Phe Ala Phe Asp Ser Pro Ser Asn
                85                  90                  95

Trp Cys Gln Asp Asn Ile Ile Ser Leu Met Ser Ala Gly Ile Leu Gly
            100                 105                 110

Val Pro Pro Ala Ser Gly Ala Leu Ser Thr Gln Thr Ser Thr Ala Ser
        115                 120                 125

Met Val Gln Pro Pro Gln Gly Asp Val Glu Ala Met Tyr Pro Ala Leu
    130                 135                 140

Pro Pro Tyr Ser Asn Cys Gly Asp Leu Tyr Ser Glu Pro Val Ser Phe
145                 150                 155                 160

His Asp Pro Gln Gly Asn Pro Gly Leu Ala Tyr Ser Pro Gln Asp Tyr
                165                 170                 175

Gln Ser Ala Lys Pro Ala Leu Asp Ser Asn Leu Phe Pro Met Ile Pro
            180                 185                 190

Asp Tyr Asn Leu Tyr His His Pro Asn Asp Met Gly Ser Ile Pro Glu
        195                 200                 205

His Lys Pro Phe Gln Gly Met Asp Pro Ile Arg Val Asn Pro Pro Pro
    210                 215                 220

Ile Thr Pro Leu Glu Thr Ile Lys Ala Phe Lys Asp Lys Gln Ile His
225                 230                 235                 240

Pro Gly Phe Gly Ser Leu Pro Gln Pro Pro Leu Thr Leu Lys Pro Ile
                245                 250                 255

Arg Pro Arg Lys Tyr Pro Asn Arg Pro Ser Lys Thr Pro Leu His Glu
            260                 265                 270

Arg Pro His Ala Cys Pro Ala Glu Gly Cys Asp Arg Arg Phe Ser Arg
        275                 280                 285

Ser Asp Glu Leu Thr Arg His Leu Arg Ile His Thr Gly His Lys Pro
    290                 295                 300

Phe Gln Cys Arg Ile Cys Met Arg Ser Phe Ser Arg Ser Asp His Leu
305                 310                 315                 320

Thr Thr His Ile Arg Thr His Thr Gly Glu Lys Pro Phe Ala Cys Glu
                325                 330                 335

Phe Cys Gly Arg Lys Phe Ala Arg Ser Asp Glu Arg Lys Arg His Ala
            340                 345                 350

Lys Ile His Leu Lys Gln Lys Glu Lys Lys Ala Glu Lys Gly Gly Ala
        355                 360                 365

Pro Ser Ala Ser Ser Ala Pro Pro Val Ser Leu Ala Pro Val Val Thr
    370                 375                 380

Thr Cys Ala
385
```

<210> SEQ ID NO 176

<211> LENGTH: 543
<212> TYPE: PRT
<213> ORGANISM: Homo sapiens

<400> SEQUENCE: 176

```
Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
        355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
```

385 390 395 400

Cys Gly Arg Lys Phe Ala Arg Ser Asp Glu Arg Lys Arg His Thr Lys
405 410 415

Ile His Leu Arg Gln Lys Asp Lys Lys Ala Asp Lys Ser Val Val Ala
420 425 430

Ser Ser Ala Thr Ser Ser Leu Ser Ser Tyr Pro Ser Pro Val Ala Thr
435 440 445

Ser Tyr Pro Ser Pro Val Thr Thr Ser Tyr Pro Ser Pro Ala Thr Thr
450 455 460

Ser Tyr Pro Ser Pro Val Pro Thr Ser Phe Ser Ser Pro Gly Ser Ser
465 470 475 480

Thr Tyr Pro Ser Pro Val His Ser Gly Phe Pro Ser Pro Ser Val Ala
485 490 495

Thr Thr Tyr Ser Ser Val Pro Pro Ala Phe Pro Ala Gln Val Ser Ser
500 505 510

Phe Pro Ser Ser Ala Val Thr Asn Ser Phe Ser Ala Ser Thr Gly Leu
515 520 525

Ser Asp Met Thr Ala Thr Phe Ser Pro Arg Thr Ile Glu Ile Cys
530 535 540

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Gly Gly Ser Gly Gly Gly Ser Gly
1 5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Gly Gly Ser Gly Gly Gly Ser Gly Gly Gly Ser Gly Gly Gly Ser Gly
1 5 10 15

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments

<400> SEQUENCE: 179

Gly Gly Gly Ser
1

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: See specification as filed for detailed
description of substitutions and preferred embodiments

<400> SEQUENCE: 180

Gly Gly Gly Gly Ser
1 5

<210> SEQ ID NO 181
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: See specification as filed for detailed
description of substitutions and preferred embodiments

<400> SEQUENCE: 181

Gly Gly Ser Gly
1

<210> SEQ ID NO 182
<211> LENGTH: 9
<212> TYPE: DNA
<213> ORGANISM: Homo sapiens

<400> SEQUENCE: 182 gcgkgggcg 9

<210> SEQ ID NO 183
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
gttttagtac tctggaaaca gaatctacta aaacaaggca aaatgccgtg tttatctcgt 60
caacttgttg gcgaga 76

<210> SEQ ID NO 184
<211> LENGTH: 3871
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184
ggaggaagcc atcaactaaa ctacaatgac tgtaagatac aaaattggga atggtaacat 60
attttgaagt tctgttgaca taaagaatca tgatattaat gcccatggaa atgaaagggc 120
gatcaacact atggtttgaa aagggggaaa ttgtagagca cagatgtgtt cgtgtggcag 180
tgtgctgtct ctagcaatac tcagagaaga gagagaacaa tgaaattctg attggcccca 240
gtgtgagccc agatgaggtt cagctgccaa ctttctcttt cacatcttat gaaagtcatt 300
taagcacaac taactttttt tttttttttt tttttttgag acagagtctt gctctgttgc 360
ccaggacaga gtgcagtagt gactcaatct cggctcactg cagcctccac ctcctaggct 420

```
caaacggtcc tcctgcatca gcctcccaag tagctggaat tacaggagtg gcccaccatg    480
cccagctaat ttttgtattt ttaatagata cgggggtttc accatatcac ccaggctggt    540
ctcgaactcc tggcctcaag tgatccacct gcctcggcct cccaaagtgc tgggattata    600
ggcgtcagcc actatgccca acccgaccaa cctttttaa aataaatatt taaaaaattg    660
gtatttcaca tatatactag tatttacatt tatccacaca aaacggacgg gcctccgctg    720
aaccagtgag gccccagacg tgcgcataaa taacccctgc gtgctgcacc acctggggag    780
agggggagga ccacggtaaa tggagcgagc gcatagcaaa agggacgcgg ggtccttttc    840
tctgccggtg gcactgggta gctgtggcca ggtgtggtac tttgatgggg cccagggctg    900
gagctcaagg aagcgtcgca gggtcacaga tctgggggaa ccccggggaa aagcactgag    960
gcaaaaccgc cgctcgtctc ctacaatata tgggaggggg aggttgagta cgttctggat   1020
tactcataag accttttttt tttccttccg ggcgcaaaac cgtgagctgg atttataatc   1080
gccctataaa gctccagagg cggtcaggca cctgcagagg agccccgccg ctccgccgac   1140
tagctgcccc cgcgagcaac ggcctcgtga tttccccgcc gatccggtcc ccgcctcccc   1200
actctgcccc cgcctacccc ggagccgtgc agccgcctct ccgaatctct ctcttctcct   1260
ggcgctcgcg tgcgagaggg aactagcgag aacgaggaag cagctggagg tgacgccggg   1320
cagattacgc ctgtcagggc cgagccgagc ggatcgctgg gcgctgtgca gaggaaaggc   1380
gggagtgccc ggctcgctgt cgcagagccg aggtgggtaa gctagcgacc acctggactt   1440
cccagcgccc aaccgtggct tttcagccag gtcctctcct cccgcggctt ctcaaccaac   1500
cccatcccag cgccggccac ccaacctccc gaaatgagtg cttcctgccc cagcagccga   1560
aggcgctact aggaacggta acctgttact tttccagggg ccgtagtcga cccgctgccc   1620
gagttgctgt gcgactgcgc gcgcggggct agagtgcaag gtgactgtgg ttcttctctg   1680
gccaagtccg agggagaacg taaagatatg ggcctttttc cccctctcac cttgtctcac   1740
caaagtccct agtccccgga gcagttagcc tctttctttc cagggaatta gccagacaca   1800
acaacgggaa ccagacaccg aaccagacat gcccgccccg tgcgccctcc ccgctcgctg   1860
cctttcctcc ctcttgtctc tccagagccg gatcttcaag gggagcctcc gtgcccccgg   1920
ctgctcagtc cctccggtgt gcaggacccc ggaagtcctc cccgcacagc tctcgcttct   1980
ctttgcagcc tgtttctgcg ccggaccagt cgaggactct ggacagtaga ggccccggga   2040
cgaccgagct ggaattcgcc accatggccg ccgaccacct gatgctcgcc gagggctacc   2100
gcctggtgca gaggccgccg tccgccgccg ccgcccatgg ccctcatgcg ctccggactc   2160
tgccgccgta cgcgggcccg ggcctggaca gtgggctgag gccgcggggg gctccgctgg   2220
ggccgccgcc gccccgccaa cccggggccc tggcgtacgg ggccttcggg ccgccgtcct   2280
ccttccagcc ctttccggcc gtgcctccgc cggccgcggg catcgcgcac ctgcagcctg   2340
tggcgacgcc gtaccccggc cgcgcggccg cgccccccaa cgctccggga ggcccccggg   2400
gcccgcagcc ggccccaagc gccgcagccc cgccgccgcc cgcgcacgcc ctgggcggca   2460
tggacgccga actcatcgac gaggaggcgc tgacgtcgct ggagctggag ctggggctgc   2520
accgcgtgcg cgagctgccc gagctgttcc tgggccagag cgagttcgac tgcttctcgg   2580
acttggggtc cgcgccgccc gccggctccg tgagctgcgg tggttctggt ggtggttctg   2640
gtcagtccca gctcatcaaa cccagccgca tgcgcaagta ccccaaccgg cccagcaaga   2700
cgccccccca cgaacgccct tacgcttgcc cagtggagtc ctgtgatcgc cgcttctccc   2760
gcagcgacaa cctggtgaga cacatccgca tccacacagg ccagaagccc ttccagtgcc   2820
```

```
gcatctgcat gagaaacttc agccgagagg ataacttgca cactcacatc cgcacccaca   2880

caggcgaaaa gcccttcgcc tgcgacatct gtggaagaaa gtttgcccgg agcgatgaac   2940

ttgtccgaca taccaagatc cacttgcggc agaaggaccg cccttacgct tgcccagtgg   3000

agtcctgtga tcgccgcttc tcccaatcag ggaatctgac tgagcacatc cgcatccaca   3060

caggccagaa gcccttccag tgccgcatct gcatgagaaa cttcagcaca agtggacatc   3120

tggtacgcca catccgcacc cacacaggcg aaaagccctt cgcctgcgac atctgtggaa   3180

gaaagtttgc ccagaatagt accctgaccg aacataccaa gatccacttg cggcagaagg   3240

acaagtaact cgaggaaacc cagcagacaa tgtagctaga cccagtagcc agatgtagct   3300

aaagagaccg gttcactgtg agaaacccag cagacaatgt agctagaccc agtagccaga   3360

tgtagctaaa gagaccggtt cactgtgaaa gcttgggtgg catccctgtg acccctcccc   3420

agtgcctctc ctggccctgg aagttgccac tccagtgccc accagccttg tcctaataaa   3480

attaagttgc atcattttgt ctgactaggt gtccttctat aatattatgg ggtggagggg   3540

ggtggtatgg agcaaggggc aagttgggaa gacaacctgt agggcctgcg ggtctattg   3600

ggaaccaagc tggagtgcag tggcacaatc ttggctcact gcaatctccg cctcctgggt   3660

tcaagcgatt ctcctgcctc agcctcccga gttgttggga ttccaggcat gcatgaccag   3720

gctcagctaa tttttgtttt tttggtagag acggggtttc accatattgg ccaggctggt   3780

ctccaactcc taatctcagg tgatctaccc accttggcct cccaaattgc tgggattaca   3840

ggcgtgaacc actgctccct tccctgtcct t                                  3871
```

```
<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185

tgtctcggca ttgagaacat tc                                              22


<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186

attggtggga ggccattgta t                                               21


<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187

accacagtcc atgccatcac                                                 20


<210> SEQ ID NO 188
<211> LENGTH: 20
```

<212> TYPE: DNA
<213> ORGANISM: Artificial Sequence
<220> FEATURE:
<223> OTHER INFORMATION: Description of Artificial Sequence: Synthetic
primer

<400> SEQUENCE: 188
tccaccaccc tgttgctgta 20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 189
caaaaaagcc acaaaagcct 20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 190
ttagctccgc aagaaacatc 20

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 191
ccatggaact ggctcgattt cac 23

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 192
attggtggga ggccactgta t 21

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 193
aggcctgaaa accattgtgg gagccct 27

<210> SEQ ID NO 194
<211> LENGTH: 24
<212> TYPE: DNA

<213> ORGANISM: Artificial Sequence
<220> FEATURE:
<223> OTHER INFORMATION: Description of Artificial Sequence: Synthetic
primer

<400> SEQUENCE: 194
gaatgtggga aatcattcag tcgc 24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 195
gcaagttatc ctctcgtgag aagg 24

<210> SEQ ID NO 196
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 196
gcgacaacct ggtgagacat caacgcacc 29

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 197
gctgttatct cttgtgggct gt 22

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 198
aaactcatgg gagctgccgg tt 22

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 199
ccacacaaat ctctccctgg cattg 25

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 200
gaatgtggga aatcattcag tcgc 24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 201
gcaagttatc ctctcgtgag aagg 24

<210> SEQ ID NO 202
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 202
gcgacaacct ggtgagacat caacgcacc 29

<210> SEQ ID NO 203
<211> LENGTH: 1182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203
atggccgccg accacctgat gctcgccgag ggctaccgcc tggtgcagag gccgccgtcc 60
gccgccgccg cccatggccc tcatgcgctc cggactctgc cgccgtacgc gggcccgggc 120
ctggacagtg ggctgaggcc gcggggggct ccgctggggc cgccgccgcc ccgccaaccc 180
ggggccctgg cgtacggggc cttcgggccg ccgtcctcct tccagccctt tccggccgtg 240
cctccgccgg ccgcgggcat cgcgcacctg cagcctgtgg cgacgccgta ccccggccgc 300
gcggccgcgc cccccaacgc tccgggaggc cccccgggcc cgcagccggc cccaagcgcc 360
gcagccccgc cgccgccccgc gcacgccctg ggcggcatgg acgccgaact catcgacgag 420
gaggcgctga cgtcgctgga gctggagctg gggctgcacc gcgtgcgcga gctgcccgag 480
ctgttcctgg gccagagcga gttcgactgc ttctcggact tggggtccgc gccgcccgcc 540
ggctccgtga gctgcggtgg ttctggtggt ggttctggtc agtcccagct catcaaaccc 600
agccgcatgc gcaagtaccc caaccggccc agcaagacgc ccccccacga acgcccttac 660
gcttgcccag tggagtcctg tgatcgccgc ttctcccgca gcgacaacct ggtgagacac 720
atccgcatcc acacaggcca gaagcccttc cagtgccgca tctgcatgag aaacttcagc 780
cgagaggata acttgcacac tcacatccgc acccacacag gcgaaaagcc cttcgcctgc 840
gacatctgtg gaagaaagtt tgcccggagc gatgaacttg tccgacatac caagatccac 900
ttgcggcaga aggaccgccc ttacgcttgc ccagtggagt cctgtgatcg ccgcttctcc 960
caatcaggga atctgactga gcacatccgc atccacacag gccagaagcc cttccagtgc 1020

```
cgcatctgca tgagaaactt cagcacaagt ggacatctgg tacgccacat ccgcacccac   1080

acaggcgaaa agcccttcgc ctgcgacatc tgtggaagaa agtttgccca gaatagtacc   1140

ctgaccgaac ataccaagat ccacttgcgg cagaaggaca ag                      1182


<210> SEQ ID NO 204
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204

atggccgccg accacctgat gctcgccgag ggctaccgcc tggtgcagag gccgccgtcc     60

gccgccgccg cccatggccc tcatgcgctc cggactctgc cgccgtacgc gggcccgggc    120

ctggacagtg ggctgaggcc gcggggggct ccgctggggc cgccgccgcc ccgccaaccc    180

ggggccctgg cgtacggggc cttcgggccg ccgtcctcct tccagccctt tccggccgtg    240

cctccgccgg ccgcgggcat cgcgcacctg cagcctgtgg cgacgccgta ccccggccgc    300

gcggccgcgc cccccaacgc tccgggaggc cccccgggcc cgcagccggc cccaagcgcc    360

gcagccccgc cgccgcccgc gcacgccctg ggcggcatgg acgccgaact catcgacgag    420

gaggcgctga cgtcgctgga gctggagctg gggctgcacc gcgtgcgcga gctgcccgag    480

ctgttcctgg gccagagcga gttcgactgc ttctcggact tggggtccgc gccgcccgcc    540

ggctccgtga gctgcggtgg ttctggtggt ggttctggtg gtggcagcgg gggaggttct    600

ggtcagtccc agctcatcaa acccagccgc atgcgcaagt accccaaccg gcccagcaag    660

acgccccccc acgaacgccc ttacgcttgc ccagtggagt cctgtgatcg ccgcttctcc    720

cgcagcgaca acctggtgag acacatccgc atccacacag gccagaagcc cttccagtgc    780

cgcatctgca tgagaaactt cagccgagag gataacttgc acactcacat ccgcacccac    840

acaggcgaaa agcccttcgc ctgcgacatc tgtggaagaa agtttgcccg gagcgatgaa    900

cttgtccgac ataccaagat ccacttgcgg cagaaggacc gcccttacgc ttgcccagtg    960

gagtcctgtg atcgccgctt ctcccaatca gggaatctga ctgagcacat ccgcatccac   1020

acaggccaga agcccttcca gtgccgcatc tgcatgagaa acttcagcac aagtggacat   1080

ctggtacgcc acatccgcac ccacacaggc gaaaagccct tcgcctgcga catctgtgga   1140

agaaagtttg cccagaatag taccctgacc gaacatacca agatccactt gcggcagaag   1200

gacaag                                                              1206


<210> SEQ ID NO 205
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45
```

```
Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190

Gly Gly Gly Ser Gly Gly Gly Ser Gly Gln Ser Gln Leu Ile Lys Pro
        195                 200                 205

Ser Arg Met Arg Lys Tyr Pro Asn Arg Pro Ser Lys Thr Pro Pro His
    210                 215                 220

Glu Arg Pro Tyr Ala Cys Pro Val Glu Ser Cys Asp Arg Arg Phe Ser
225                 230                 235                 240

Arg Ser Asp Asn Leu Val Arg His Ile Arg Ile His Thr Gly Gln Lys
                245                 250                 255

Pro Phe Gln Cys Arg Ile Cys Met Arg Asn Phe Ser Arg Glu Asp Asn
            260                 265                 270

Leu His Thr His Ile Arg Thr His Thr Gly Glu Lys Pro Phe Ala Cys
        275                 280                 285

Asp Ile Cys Gly Arg Lys Phe Ala Arg Ser Asp Glu Leu Val Arg His
    290                 295                 300

Thr Lys Ile His Leu Arg Gln Lys Asp Arg Pro Tyr Ala Cys Pro Val
305                 310                 315                 320

Glu Ser Cys Asp Arg Arg Phe Ser Gln Ser Gly Asn Leu Thr Glu His
                325                 330                 335

Ile Arg Ile His Thr Gly Gln Lys Pro Phe Gln Cys Arg Ile Cys Met
            340                 345                 350

Arg Asn Phe Ser Thr Ser Gly His Leu Val Arg His Ile Arg Thr His
        355                 360                 365

Thr Gly Glu Lys Pro Phe Ala Cys Asp Ile Cys Gly Arg Lys Phe Ala
    370                 375                 380

Gln Asn Ser Thr Leu Thr Glu His Thr Lys Ile His Leu Arg Gln Lys
385                 390                 395                 400

Asp Lys
```

<210> SEQ ID NO 206
<211> LENGTH: 1707
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206

```
atggccgcag atcacctgat gctggctgaa ggctacagac tggtgcagcg gcctccatct      60
gccgctgccg cccacggccc ccacgccctg agaacactgc ccccctacgc cggccctggt     120
cttgatagcg gactcagacc tagaggcgcc cctctgggcc ctccacctcc aagacagcct     180
ggagccctgg cctacggcgc cttcggccct ccttctagct tccagccctt ccccgccgtg     240
cctcctccag ccgctggcat cgcccacctg cagcctgtgg ccacccctta ccccggaaga     300
gccgccgccc ctccaaacgc ccctggcgga cctcctggcc cccagcctgc tccaagcgcc     360
gctgcccctc cacctcctgc tcatgccctg ggcggcatgg acgccgagct gatcgacgag     420
gaagccctga ccagcctgga actggaactg ggcctgcaca gagtgcggga actgcctgag     480
ctgttcctgg gacagagcga gttcgactgc ttcagcgacc tgggcagcgc ccctcctgcc     540
ggctctgtgt cctgcgccga ccacctgatg ctcgccgagg gctaccgcct ggtgcagagg     600
ccgccgtccg ccgccgccgc ccatggccct catgcgctcc ggactctgcc gccgtacgcg     660
ggcccgggcc tggacagtgg gctgaggccg cggggggctc cgctggggcc gccgccgccc     720
cgccaacccg ggccctggc gtacggggcc ttcgggccgc cgtcctcctt ccagcccttt     780
ccggccgtgc ctccgccggc cgcgggcatc gcgcacctgc agcctgtggc gacgccgtac     840
cccggccgcg ccgccgcgcc ccccaacgct ccgggaggcc ccccgggccc gcagccggcc     900
ccaagcgccg cagccccgcc gccgcccgcg cacgccctgg gcggcatgga cgccgaactc     960
atcgacgagg aggcgctgac gtcgctggag ctggagctgg ggctgcaccg cgtgcgcgag    1020
ctgcccgagc tgttcctggg ccagagcgag ttcgactgct tctcggactt ggggtccgcg    1080
ccgcccgccg gctccgtgag ctgccagtcc cagctcatca aacccagccg catgcgcaag    1140
taccccaacc ggcccagcaa gacgcccccc cacgaacgcc cttacgcttg cccagtggag    1200
tcctgtgatc gccgcttctc ccgcagcgac aacctggtga gacacatccg catccacaca    1260
ggccagaagc ccttccagtg ccgcatctgc atgagaaact tcagccgaga ggataacttg    1320
cacactcaca tccgcaccca cacaggcgaa aagcccttcg cctgcgacat ctgtggaaga    1380
aagtttgccc ggagcgatga acttgtccga cataccaaga tccacttgcg gcagaaggac    1440
cgcccttacg cttgcccagt ggagtcctgt gatcgccgct tctcccaatc agggaatctg    1500
actgagcaca tccgcatcca cacaggccag aagcccttcc agtgccgcat ctgcatgaga    1560
aacttcagca caagtggaca tctggtacgc cacatccgca cccacacagg cgaaaagccc    1620
ttcgcctgcg acatctgtgg aagaaagttt gcccagaata gtaccctgac cgaacatacc    1680
aagatccact tgcggcagaa ggacaag                                        1707
```

```
<210> SEQ ID NO 207
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
```

```
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Ala Asp His Leu Met Leu Ala
            180                 185                 190

Glu Gly Tyr Arg Leu Val Gln Arg Pro Pro Ser Ala Ala Ala Ala His
        195                 200                 205

Gly Pro His Ala Leu Arg Thr Leu Pro Pro Tyr Ala Gly Pro Gly Leu
    210                 215                 220

Asp Ser Gly Leu Arg Pro Arg Gly Ala Pro Leu Gly Pro Pro Pro Pro
225                 230                 235                 240

Arg Gln Pro Gly Ala Leu Ala Tyr Gly Ala Phe Gly Pro Pro Ser Ser
                245                 250                 255

Phe Gln Pro Phe Pro Ala Val Pro Pro Pro Ala Ala Gly Ile Ala His
            260                 265                 270

Leu Gln Pro Val Ala Thr Pro Tyr Pro Gly Arg Ala Ala Ala Pro Pro
        275                 280                 285

Asn Ala Pro Gly Gly Pro Pro Gly Pro Gln Pro Ala Pro Ser Ala Ala
    290                 295                 300

Ala Pro Pro Pro Pro Ala His Ala Leu Gly Gly Met Asp Ala Glu Leu
305                 310                 315                 320

Ile Asp Glu Glu Ala Leu Thr Ser Leu Glu Leu Glu Leu Gly Leu His
                325                 330                 335

Arg Val Arg Glu Leu Pro Glu Leu Phe Leu Gly Gln Ser Glu Phe Asp
            340                 345                 350

Cys Phe Ser Asp Leu Gly Ser Ala Pro Pro Ala Gly Ser Val Ser Cys
        355                 360                 365

Gln Ser Gln Leu Ile Lys Pro Ser Arg Met Arg Lys Tyr Pro Asn Arg
    370                 375                 380

Pro Ser Lys Thr Pro Pro His Glu Arg Pro Tyr Ala Cys Pro Val Glu
385                 390                 395                 400

Ser Cys Asp Arg Arg Phe Ser Arg Ser Asp Asn Leu Val Arg His Ile
                405                 410                 415

Arg Ile His Thr Gly Gln Lys Pro Phe Gln Cys Arg Ile Cys Met Arg
            420                 425                 430

Asn Phe Ser Arg Glu Asp Asn Leu His Thr His Ile Arg Thr His Thr
        435                 440                 445

Gly Glu Lys Pro Phe Ala Cys Asp Ile Cys Gly Arg Lys Phe Ala Arg
    450                 455                 460

Ser Asp Glu Leu Val Arg His Thr Lys Ile His Leu Arg Gln Lys Asp
465                 470                 475                 480
```

```
Arg Pro Tyr Ala Cys Pro Val Glu Ser Cys Asp Arg Arg Phe Ser Gln
                485                 490                 495

Ser Gly Asn Leu Thr Glu His Ile Arg Ile His Thr Gly Gln Lys Pro
            500                 505                 510

Phe Gln Cys Arg Ile Cys Met Arg Asn Phe Ser Thr Ser Gly His Leu
        515                 520                 525

Val Arg His Ile Arg Thr His Thr Gly Glu Lys Pro Phe Ala Cys Asp
    530                 535                 540

Ile Cys Gly Arg Lys Phe Ala Gln Asn Ser Thr Leu Thr Glu His Thr
545                 550                 555                 560

Lys Ile His Leu Arg Gln Lys Asp Lys
                565
```

<210> SEQ ID NO 208
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208

```
atggccgcag atcacctgat gctggctgaa ggctacagac tggtgcagcg gcctccatct     60

gccgctgccg cccacggccc ccacgccctg agaacactgc cccccctacgc cggccctggt    120

cttgatagcg gactcagacc tagaggcgcc cctctgggcc ctccacctcc aagacagcct    180

ggagccctgg cctacggcgc cttcggccct ccttctagct tccagccctt ccccgccgtg    240

cctcctccag ctgctggcat cgcccacctg cagcctgtgg ccaccccctta ccccggaaga    300

gccgccgccc ctccaaacgc ccctggcgga cctcctggcc cccagcctgc tccaagcgcc    360

gctgcccctc cacctcctgc tcatgccctg ggcggcatgg acgccgagct gatcgacgag    420

gaagccctga ccagcctgga actggaactg ggcctgcaca gagtgcggga actgcctgag    480

ctgttcctgg gacagagcga gttcgactgc ttcagcgacc tgggcagcgc ccctcctgcc    540

ggctctgtgt cctgcggcgg cagcggcggc ggaagcggcg ccgaccacct gatgctcgcc    600

gagggctacc gcctggtgca gaggccgccg tccgccgccg ccgcccatgg ccctcatgcg    660

ctccggactc tgccgccgta cgcgggcccg ggcctggaca gtgggctgag gccgcggggg    720

gctccgctgg ggccgccgcc gccccgccaa cccggggccc tggcgtacgg ggccttcggg    780

ccgccgtcct ccttccagcc ctttccggcc gtgcctccgc cggccgcggg catcgcgcac    840

ctgcagcctg tggcgacgcc gtaccccggc cgcgcggccg cgccccccaa cgctccggga    900

ggcccccgg gcccgcagcc ggccccaagc gccgcagccc cgccgccgcc cgcgcacgcc    960

ctgggcggca tggacgccga actcatcgac gaggaggcgc tgacgtcgct ggagctggag   1020

ctggggctgc accgcgtgcg cgagctgccc gagctgttcc tgggccagag cgagttcgac   1080

tgcttctcgg acttggggtc cgcgccgccc gccggctccg tgagctgcgg tggttctggt   1140

ggtggttctg gtcagtccca gctcatcaaa cccagccgca tgcgcaagta ccccaaccgg   1200

cccagcaaga cgcccccccca cgaacgccct tacgcttgcc cagtggagtc ctgtgatcgc   1260

cgcttctccc gcagcgacaa cctggtgaga cacatccgca tccacacagg ccagaagccc   1320

ttccagtgcc gcatctgcat gagaaacttc agccgagagg ataacttgca cactcacatc   1380

cgcacccaca caggcgaaaa gcccttcgcc tgcgacatct gtggaagaaa gtttgcccgg   1440

agcgatgaac ttgtccgaca taccaagatc cacttgcggc agaaggaccg cccttacgct   1500
```

```
tgcccagtgg agtcctgtga tcgccgcttc tcccaatcag ggaatctgac tgagcacatc   1560

cgcatccaca caggccagaa gcccttccag tgccgcatct gcatgagaaa cttcagcaca   1620

agtggacatc tggtacgcca catccgcacc cacacaggcg aaaagccctt cgcctgcgac   1680

atctgtggaa gaaagtttgc ccagaatagt accctgaccg aacataccaa gatccacttg   1740

cggcagaagg acaag                                                    1755
```

```
<210> SEQ ID NO 209
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Ala Ala Asp His Leu Met Leu Ala Glu Gly Tyr Arg Leu Val Gln
1               5                   10                  15

Arg Pro Pro Ser Ala Ala Ala Ala His Gly Pro His Ala Leu Arg Thr
            20                  25                  30

Leu Pro Pro Tyr Ala Gly Pro Gly Leu Asp Ser Gly Leu Arg Pro Arg
        35                  40                  45

Gly Ala Pro Leu Gly Pro Pro Pro Pro Arg Gln Pro Gly Ala Leu Ala
    50                  55                  60

Tyr Gly Ala Phe Gly Pro Pro Ser Ser Phe Gln Pro Phe Pro Ala Val
65                  70                  75                  80

Pro Pro Pro Ala Ala Gly Ile Ala His Leu Gln Pro Val Ala Thr Pro
                85                  90                  95

Tyr Pro Gly Arg Ala Ala Ala Pro Pro Asn Ala Pro Gly Gly Pro Pro
            100                 105                 110

Gly Pro Gln Pro Ala Pro Ser Ala Ala Ala Pro Pro Pro Pro Ala His
        115                 120                 125

Ala Leu Gly Gly Met Asp Ala Glu Leu Ile Asp Glu Glu Ala Leu Thr
    130                 135                 140

Ser Leu Glu Leu Glu Leu Gly Leu His Arg Val Arg Glu Leu Pro Glu
145                 150                 155                 160

Leu Phe Leu Gly Gln Ser Glu Phe Asp Cys Phe Ser Asp Leu Gly Ser
                165                 170                 175

Ala Pro Pro Ala Gly Ser Val Ser Cys Gly Gly Ser Gly Gly Gly Ser
            180                 185                 190

Gly Ala Asp His Leu Met Leu Ala Glu Gly Tyr Arg Leu Val Gln Arg
        195                 200                 205

Pro Pro Ser Ala Ala Ala Ala His Gly Pro His Ala Leu Arg Thr Leu
    210                 215                 220

Pro Pro Tyr Ala Gly Pro Gly Leu Asp Ser Gly Leu Arg Pro Arg Gly
225                 230                 235                 240

Ala Pro Leu Gly Pro Pro Pro Pro Arg Gln Pro Gly Ala Leu Ala Tyr
                245                 250                 255

Gly Ala Phe Gly Pro Pro Ser Ser Phe Gln Pro Phe Pro Ala Val Pro
            260                 265                 270

Pro Pro Ala Ala Gly Ile Ala His Leu Gln Pro Val Ala Thr Pro Tyr
        275                 280                 285

Pro Gly Arg Ala Ala Ala Pro Pro Asn Ala Pro Gly Gly Pro Pro Gly
    290                 295                 300
```

```
Pro Gln Pro Ala Pro Ser Ala Ala Ala Pro Pro Pro Pro Ala His Ala
305                 310                 315                 320

Leu Gly Gly Met Asp Ala Glu Leu Ile Asp Glu Glu Ala Leu Thr Ser
                325                 330                 335

Leu Glu Leu Glu Leu Gly Leu His Arg Val Arg Glu Leu Pro Glu Leu
            340                 345                 350

Phe Leu Gly Gln Ser Glu Phe Asp Cys Phe Ser Asp Leu Gly Ser Ala
        355                 360                 365

Pro Pro Ala Gly Ser Val Ser Cys Gly Gly Ser Gly Gly Gly Ser Gly
    370                 375                 380

Gln Ser Gln Leu Ile Lys Pro Ser Arg Met Arg Lys Tyr Pro Asn Arg
385                 390                 395                 400

Pro Ser Lys Thr Pro Pro His Glu Arg Pro Tyr Ala Cys Pro Val Glu
                405                 410                 415

Ser Cys Asp Arg Arg Phe Ser Arg Ser Asp Asn Leu Val Arg His Ile
            420                 425                 430

Arg Ile His Thr Gly Gln Lys Pro Phe Gln Cys Arg Ile Cys Met Arg
        435                 440                 445

Asn Phe Ser Arg Glu Asp Asn Leu His Thr His Ile Arg Thr His Thr
    450                 455                 460

Gly Glu Lys Pro Phe Ala Cys Asp Ile Cys Gly Arg Lys Phe Ala Arg
465                 470                 475                 480

Ser Asp Glu Leu Val Arg His Thr Lys Ile His Leu Arg Gln Lys Asp
                485                 490                 495

Arg Pro Tyr Ala Cys Pro Val Glu Ser Cys Asp Arg Arg Phe Ser Gln
            500                 505                 510

Ser Gly Asn Leu Thr Glu His Ile Arg Ile His Thr Gly Gln Lys Pro
        515                 520                 525

Phe Gln Cys Arg Ile Cys Met Arg Asn Phe Ser Thr Ser Gly His Leu
    530                 535                 540

Val Arg His Ile Arg Thr His Thr Gly Glu Lys Pro Phe Ala Cys Asp
545                 550                 555                 560

Ile Cys Gly Arg Lys Phe Ala Gln Asn Ser Thr Leu Thr Glu His Thr
                565                 570                 575

Lys Ile His Leu Arg Gln Lys Asp Lys
            580                 585
```

<210> SEQ ID NO 210
<211> LENGTH: 1113
<212> TYPE: DNA
<213> ORGANISM: Homo sapiens

<400> SEQUENCE: 210

```
atggagctgg aattggatgc tggtgaccaa gacctgctgg ccttcctgct agaggaaagt     60

ggagatttgg ggacggcacc cgatgaggcc gtgagggccc cactggactg ggcgctgccg    120

ctttctgagg tgccgagcga ctgggaagta gatgatttgc tgtgctccct gctgagtccc    180

ccagcgtcgt tgaacattct cagctcctcc aacccctgcc ttgtccacca tgaccacacc    240

tactccctcc cacgggaaac tgtctctatg gatctagaga gtgagagctg tagaaaagag    300

gggacccaga tgactccaca gcatatggag gagctggcag agcaggagat tgctaggcta    360

gtactgacag atgaggagaa gagtctattg gagaaggagg ggcttattct gcctgagaca    420

cttcctctca ctaagacaga ggaacaaatt ctgaaacgtg tgcggaggaa gattcgaaat    480

aaaagatctg ctcaagagag ccgcaggaaa aagaaggtgt acgttggggg tttagagagc    540
```

```
cgggtcttga aatacacagc ccagaatatg gagcttcaga acaaagtaca gcttctggag    600

gaacagaatt tgtcccttct agatcaactg aggaaactcc aggccatggt gattgagatc    660

tcaaacaaaa ccagcagcag cagcacctgc atcttggtcc tgctagtctc cttctgcctc    720

ctccttgtac ctgctatgta ctcctctgac acaaggggga gcctgccagc tgagcatgga    780

gtgttgtccc gccagcttcg tgccctcccc agtgaggacc cttaccagct ggagctgcct    840

gccctgcagt cagaagtgcc gaaagacagc acacaccagt ggttggacgg ctcagactgt    900

gtactccagg cccctggcaa cacttcctgc ctgctgcatt acatgcctca ggctcccagt    960

gcagagcctc ccctggagtg gcccttccct gacctcttct cagagcctct ctgccgaggt   1020

cccatcctcc ccctgcaggc aaatctcaca aggaagggag gatggcttcc tactggtagc   1080

ccctctgtca ttttgcagga cagatactca ggc                                1113
```

<210> SEQ ID NO 211
<211> LENGTH: 371
<212> TYPE: PRT
<213> ORGANISM: Homo sapiens

<400> SEQUENCE: 211

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Lys Ile Arg Asn
145                 150                 155                 160

Lys Arg Ser Ala Gln Glu Ser Arg Arg Lys Lys Lys Val Tyr Val Gly
                165                 170                 175

Gly Leu Glu Ser Arg Val Leu Lys Tyr Thr Ala Gln Asn Met Glu Leu
            180                 185                 190

Gln Asn Lys Val Gln Leu Leu Glu Glu Gln Asn Leu Ser Leu Leu Asp
        195                 200                 205

Gln Leu Arg Lys Leu Gln Ala Met Val Ile Glu Ile Ser Asn Lys Thr
    210                 215                 220

Ser Ser Ser Ser Thr Cys Ile Leu Val Leu Leu Val Ser Phe Cys Leu
225                 230                 235                 240

Leu Leu Val Pro Ala Met Tyr Ser Ser Asp Thr Arg Gly Ser Leu Pro
                245                 250                 255

Ala Glu His Gly Val Leu Ser Arg Gln Leu Arg Ala Leu Pro Ser Glu
            260                 265                 270
```

```
Asp Pro Tyr Gln Leu Glu Leu Pro Ala Leu Gln Ser Glu Val Pro Lys
        275                 280                 285

Asp Ser Thr His Gln Trp Leu Asp Gly Ser Asp Cys Val Leu Gln Ala
    290                 295                 300

Pro Gly Asn Thr Ser Cys Leu Leu His Tyr Met Pro Gln Ala Pro Ser
305                 310                 315                 320

Ala Glu Pro Pro Leu Glu Trp Pro Phe Pro Asp Leu Phe Ser Glu Pro
                325                 330                 335

Leu Cys Arg Gly Pro Ile Leu Pro Leu Gln Ala Asn Leu Thr Arg Lys
            340                 345                 350

Gly Gly Trp Leu Pro Thr Gly Ser Pro Ser Val Ile Leu Gln Asp Arg
        355                 360                 365

Tyr Ser Gly
    370


<210> SEQ ID NO 212
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

atggagctgg aattggatgc tggtgaccaa gacctgctgg ccttcctgct agaggaaagt      60

ggagatttgg ggacggcacc cgatgaggcc gtgagggccc cactggactg ggcgctgccg     120

ctttctgagg tgccgagcga ctgggaagta gatgatttgc tgtgctccct gctgagtccc     180

ccagcgtcgt tgaacattct cagctcctcc aacccctgcc ttgtccacca tgaccacacc     240

tactccctcc cacgggaaac tgtctctatg gatctagaga gtgagagctg tagaaaagag     300

gggacccaga tgactccaca gcatatggag gagctggcag agcaggagat tgctaggcta     360

gtactgacag atgaggagaa gagtctattg gagaaggagg ggcttattct gcctgagaca     420

cttcctctca ctaagacaga ggaacaaatt ctgaaacgtg tgcggctcga accaggtgaa     480

aaaccttaca aatgtcctga atgtgggaaa tcattcagtc gcagcgacaa cctggtgaga     540

catcaacgca cccatacagg agaaaaacct tataaatgtc cagaatgtgg aaagtccttc     600

tcacgagagg ataacttgca cactcatcaa cgaacacata ctggtgaaaa accatacaag     660

tgtcccgaat gtggtaaaag ttttagccgg agcgatgaac ttgtccgaca ccaacgaacc     720

catacaggcg agaagcctta caaatgtccc gagtgtggca agagcttctc acaatcaggg     780

aatctgactg agcatcaacg aactcatacc ggggaaaaac cttacaagtg tccagagtgt     840

gggaagagct tttccacaag tggacatctg gtacgccacc agaggacaca tacaggggag     900

aagccctaca aatgccccga atgcggtaaa agtttctctc agaatagtac cctgaccgaa     960

caccagcgaa cacacactgg gaaaaaaacg agtgtgtacg ttgggggttt agagagccgg    1020

gtcttgaaat acacagccca gaatatggag cttcagaaca aagtacagct tctggaggaa    1080

cagaatttgt cccttctaga tcaactgagg aaactccagg ccatggtgat tgagatctca    1140

aacaaaacca gcagcagcag cacctgcatc ttggtcctgc tagtctcctt ctgcctcctc    1200

cttgtacctg ctatgtactc ctctgacaca agggggagcc tgccagctga gcatggagtg    1260

ttgtcccgcc agcttcgtgc cctccccagt gaggaccctt accagctgga gctgcctgcc    1320

ctgcagtcag aagtgccgaa agacagcaca caccagtggt tggacggctc agactgtgta    1380
```

```
ctccaggccc ctggcaacac ttcctgcctg ctgcattaca tgcctcaggc tcccagtgca   1440

gagcctcccc tggagtggcc cttccctgac ctcttctcag agcctctctg ccgaggtccc   1500

atcctccccc tgcaggcaaa tctcacaagg aagggaggat ggcttcctac tggtagcccc   1560

tctgtcattt tgcaggacag atactcaggc                                     1590


<210> SEQ ID NO 213
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Leu Glu Pro Gly Glu
145                 150                 155                 160

Lys Pro Tyr Lys Cys Pro Glu Cys Gly Lys Ser Phe Ser Arg Ser Asp
                165                 170                 175

Asn Leu Val Arg His Gln Arg Thr His Thr Gly Glu Lys Pro Tyr Lys
            180                 185                 190

Cys Pro Glu Cys Gly Lys Ser Phe Ser Arg Glu Asp Asn Leu His Thr
        195                 200                 205

His Gln Arg Thr His Thr Gly Glu Lys Pro Tyr Lys Cys Pro Glu Cys
    210                 215                 220

Gly Lys Ser Phe Ser Arg Ser Asp Glu Leu Val Arg His Gln Arg Thr
225                 230                 235                 240

His Thr Gly Glu Lys Pro Tyr Lys Cys Pro Glu Cys Gly Lys Ser Phe
                245                 250                 255

Ser Gln Ser Gly Asn Leu Thr Glu His Gln Arg Thr His Thr Gly Glu
            260                 265                 270

Lys Pro Tyr Lys Cys Pro Glu Cys Gly Lys Ser Phe Ser Thr Ser Gly
        275                 280                 285

His Leu Val Arg His Gln Arg Thr His Thr Gly Glu Lys Pro Tyr Lys
    290                 295                 300

Cys Pro Glu Cys Gly Lys Ser Phe Ser Gln Asn Ser Thr Leu Thr Glu
305                 310                 315                 320
```

```
His Gln Arg Thr His Thr Gly Lys Lys Thr Ser Val Tyr Val Gly Gly
                325                 330                 335

Leu Glu Ser Arg Val Leu Lys Tyr Thr Ala Gln Asn Met Glu Leu Gln
            340                 345                 350

Asn Lys Val Gln Leu Leu Glu Glu Gln Asn Leu Ser Leu Leu Asp Gln
        355                 360                 365

Leu Arg Lys Leu Gln Ala Met Val Ile Glu Ile Ser Asn Lys Thr Ser
    370                 375                 380

Ser Ser Ser Thr Cys Ile Leu Val Leu Leu Val Ser Phe Cys Leu Leu
385                 390                 395                 400

Leu Val Pro Ala Met Tyr Ser Ser Asp Thr Arg Gly Ser Leu Pro Ala
                405                 410                 415

Glu His Gly Val Leu Ser Arg Gln Leu Arg Ala Leu Pro Ser Glu Asp
            420                 425                 430

Pro Tyr Gln Leu Glu Leu Pro Ala Leu Gln Ser Glu Val Pro Lys Asp
        435                 440                 445

Ser Thr His Gln Trp Leu Asp Gly Ser Asp Cys Val Leu Gln Ala Pro
    450                 455                 460

Gly Asn Thr Ser Cys Leu Leu His Tyr Met Pro Gln Ala Pro Ser Ala
465                 470                 475                 480

Glu Pro Pro Leu Glu Trp Pro Phe Pro Asp Leu Phe Ser Glu Pro Leu
                485                 490                 495

Cys Arg Gly Pro Ile Leu Pro Leu Gln Ala Asn Leu Thr Arg Lys Gly
            500                 505                 510

Gly Trp Leu Pro Thr Gly Ser Pro Ser Val Ile Leu Gln Asp Arg Tyr
        515                 520                 525

Ser Gly
    530
```

<210> SEQ ID NO 214
<211> LENGTH: 1590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 214

```
atggagctgg aattggatgc tggtgaccaa gacctgctgg ccttcctgct agaggaaagt      60

ggagatttgg ggacggcacc cgatgaggcc gtgagggccc cactggactg ggcgctgccg     120

ctttctgagg tgccgagcga ctgggaagta gatgatttgc tgtgctccct gctgagtccc     180

ccagcgtcgt tgaacattct cagctcctcc aacccctgcc ttgtccacca tgaccacacc     240

tactccctcc cacgggaaac tgtctctatg gatctagaga gtgagagctg tagaaaagag     300

gggacccaga tgactccaca gcatatggag gagctggcag agcaggagat tgctaggcta     360

gtactgacag atgaggagaa gagtctattg gagaaggagg ggcttattct gcctgagaca     420

cttcctctca ctaagacaga ggaacaaatt ctgaaacgtg tgcggcttga gcccggagag     480

aagccgtaca agtgccctga gtgcggcaag tcttttagca gaagagacga acttaatgtc     540

caccagcgaa cgcatactgg tgaaaagccc tataaatgtc ctgaatgtgg gaaatcattc     600

tccagccgca gaacctgtag ggctcaccag cgaacacaca ccggcgaaaa accatacaaa     660

tgtccagaat gcgggaaatc cttttctcag tcatccaact tggtgagaca tcaacgcacg     720

cacactggag aaaagcctta caaatgcccg gaatgtggaa agtctttttc ccaattggcc     780
```

```
catttgcgag cccatcagag gactcacacg ggcgagaaac cttacaaatg cccggaatgc    840

gggaaatctt tttcaacgag tggcaacctc gtaagacacc aaagaacgca tacaggcgaa    900

aagccatata agtgtcctga gtgtggtaaa tcattctcac acaggaccac cctgacaaat    960

caccagcgca cgcacaccgg caagaagaca agcgtgtacg ttgggggttt agagagccgg   1020

gtcttgaaat acacagccca gaatatggag cttcagaaca aagtacagct tctggaggaa   1080

cagaatttgt cccttctaga tcaactgagg aaactccagg ccatggtgat tgagatctca   1140

aacaaaacca gcagcagcag cacctgcatc ttggtcctgc tagtctcctt ctgcctcctc   1200

cttgtacctg ctatgtactc ctctgacaca agggggagcc tgccagctga gcatggagtg   1260

ttgtcccgcc agcttcgtgc cctccccagt gaggaccctt accagctgga gctgcctgcc   1320

ctgcagtcag aagtgccgaa agacagcaca caccagtggt tggacggctc agactgtgta   1380

ctccaggccc ctggcaacac ttcctgcctg ctgcattaca tgcctcaggc tcccagtgca   1440

gagcctcccc tggagtggcc cttccctgac ctcttctcag agcctctctg ccgaggtccc   1500

atcctccccc tgcaggcaaa tctcacaagg aagggaggat ggcttcctac tggtagcccc   1560

tctgtcattt tgcaggacag atactcaggc                                    1590
```

```
<210> SEQ ID NO 215
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Leu Glu Pro Gly Glu
145                 150                 155                 160

Lys Pro Tyr Lys Cys Pro Glu Cys Gly Lys Ser Phe Ser Arg Arg Asp
                165                 170                 175

Glu Leu Asn Val His Gln Arg Thr His Thr Gly Glu Lys Pro Tyr Lys
            180                 185                 190

Cys Pro Glu Cys Gly Lys Ser Phe Ser Ser Arg Arg Thr Cys Arg Ala
        195                 200                 205

His Gln Arg Thr His Thr Gly Glu Lys Pro Tyr Lys Cys Pro Glu Cys
```

```
    210                 215                 220

Gly Lys Ser Phe Ser Gln Ser Ser Asn Leu Val Arg His Gln Arg Thr
225                 230                 235                 240

His Thr Gly Glu Lys Pro Tyr Lys Cys Pro Glu Cys Gly Lys Ser Phe
                245                 250                 255

Ser Gln Leu Ala His Leu Arg Ala His Gln Arg Thr His Thr Gly Glu
            260                 265                 270

Lys Pro Tyr Lys Cys Pro Glu Cys Gly Lys Ser Phe Ser Thr Ser Gly
        275                 280                 285

Asn Leu Val Arg His Gln Arg Thr His Thr Gly Glu Lys Pro Tyr Lys
    290                 295                 300

Cys Pro Glu Cys Gly Lys Ser Phe Ser His Arg Thr Thr Leu Thr Asn
305                 310                 315                 320

His Gln Arg Thr His Thr Gly Lys Lys Thr Ser Val Tyr Val Gly Gly
                325                 330                 335

Leu Glu Ser Arg Val Leu Lys Tyr Thr Ala Gln Asn Met Glu Leu Gln
            340                 345                 350

Asn Lys Val Gln Leu Leu Glu Glu Gln Asn Leu Ser Leu Leu Asp Gln
        355                 360                 365

Leu Arg Lys Leu Gln Ala Met Val Ile Glu Ile Ser Asn Lys Thr Ser
    370                 375                 380

Ser Ser Ser Thr Cys Ile Leu Val Leu Leu Val Ser Phe Cys Leu Leu
385                 390                 395                 400

Leu Val Pro Ala Met Tyr Ser Ser Asp Thr Arg Gly Ser Leu Pro Ala
                405                 410                 415

Glu His Gly Val Leu Ser Arg Gln Leu Arg Ala Leu Pro Ser Glu Asp
            420                 425                 430

Pro Tyr Gln Leu Glu Leu Pro Ala Leu Gln Ser Glu Val Pro Lys Asp
        435                 440                 445

Ser Thr His Gln Trp Leu Asp Gly Ser Asp Cys Val Leu Gln Ala Pro
    450                 455                 460

Gly Asn Thr Ser Cys Leu Leu His Tyr Met Pro Gln Ala Pro Ser Ala
465                 470                 475                 480

Glu Pro Pro Leu Glu Trp Pro Phe Pro Asp Leu Phe Ser Glu Pro Leu
                485                 490                 495

Cys Arg Gly Pro Ile Leu Pro Leu Gln Ala Asn Leu Thr Arg Lys Gly
            500                 505                 510

Gly Trp Leu Pro Thr Gly Ser Pro Ser Val Ile Leu Gln Asp Arg Tyr
        515                 520                 525

Ser Gly
    530
```

<210> SEQ ID NO 216
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216

```
atggagctgg aattggatgc tggtgaccaa gacctgctgg ccttcctgct agaggaaagt      60

ggagatttgg ggacggcacc cgatgaggcc gtgagggccc cactggactg ggcgctgccg     120

ctttctgagg tgccgagcga ctgggaagta gatgatttgc tgtgctccct gctgagtccc     180
```

```
ccagcgtcgt tgaacattct cagctcctcc aacccctgcc ttgtccacca tgaccacacc    240

tactccctcc cacgggaaac tgtctctatg gatctagaga gtgagagctg tagaaaagag    300

gggacccaga tgactccaca gcatatggag gagctggcag agcaggagat tgctaggcta    360

gtactgacag atgaggagaa gagtctattg gagaaggagg ggcttattct gcctgagaca    420

cttcctctca ctaagacaga ggaacaaatt ctgaaacgtg tgcggcgccc ttacgcttgc    480

ccagtggagt cctgtgatcg ccgcttctcc cgcagcgaca acctggtgag acacatccgc    540

atccacacag gccagaagcc cttccagtgc cgcatctgca tgagaaactt cagccgagag    600

gataacttgc acactcacat ccgcacccac acaggcgaaa agcccttcgc ctgcgacatc    660

tgtggaagaa agtttgcccg gagcgatgaa cttgtccgac ataccaagat ccacttgcgg    720

cagaaggacc gcccttacgc ttgcccagtg gagtcctgtg atcgccgctt ctcccaatca    780

gggaatctga ctgagcacat ccgcatccac acaggccaga agcccttcca gtgccgcatc    840

tgcatgagaa acttcagcac aagtggacat ctggtacgcc acatccgcac ccacacaggc    900

gaaaagccct tcgcctgcga catctgtgga agaaagtttg cccagaatag taccctgacc    960

gaacatacca agatccactt gcggcagaag gacgtgtacg ttggggggttt agagagccgg   1020

gtcttgaaat acacagccca gaatatggag cttcagaaca aagtacagct tctggaggaa   1080

cagaatttgt cccttctaga tcaactgagg aaactccagg ccatggtgat tgagatctca   1140

aacaaaacca gcagcagcag cacctgcatc ttggtcctgc tagtctcctt ctgcctcctc   1200

cttgtacctg ctatgtactc ctctgacaca aggggggagcc tgccagctga gcatggagtg   1260

ttgtcccgcc agcttcgtgc cctccccagt gaggaccctt accagctgga gctgcctgcc   1320

ctgcagtcag aagtgccgaa agacagcaca caccagtggt tggacggctc agactgtgta   1380

ctccaggccc ctggcaacac ttcctgcctg ctgcattaca tgcctcaggc tcccagtgca   1440

gagcctcccc tggagtggcc cttccctgac ctcttctcag agcctctctg ccgaggtccc   1500

atcctccccc tgcaggcaaa tctcacaagg aagggaggat ggcttcctac tggtagcccc   1560

tctgtcattt tgcaggacag atactcaggc                                     1590
```

<210> SEQ ID NO 217
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110
```

```
Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Pro Tyr Ala Cys
145                 150                 155                 160

Pro Val Glu Ser Cys Asp Arg Arg Phe Ser Arg Ser Asp Asn Leu Val
                165                 170                 175

Arg His Ile Arg Ile His Thr Gly Gln Lys Pro Phe Gln Cys Arg Ile
            180                 185                 190

Cys Met Arg Asn Phe Ser Arg Glu Asp Asn Leu His Thr His Ile Arg
        195                 200                 205

Thr His Thr Gly Glu Lys Pro Phe Ala Cys Asp Ile Cys Gly Arg Lys
    210                 215                 220

Phe Ala Arg Ser Asp Glu Leu Val Arg His Thr Lys Ile His Leu Arg
225                 230                 235                 240

Gln Lys Asp Arg Pro Tyr Ala Cys Pro Val Glu Ser Cys Asp Arg Arg
                245                 250                 255

Phe Ser Gln Ser Gly Asn Leu Thr Glu His Ile Arg Ile His Thr Gly
            260                 265                 270

Gln Lys Pro Phe Gln Cys Arg Ile Cys Met Arg Asn Phe Ser Thr Ser
        275                 280                 285

Gly His Leu Val Arg His Ile Arg Thr His Thr Gly Glu Lys Pro Phe
    290                 295                 300

Ala Cys Asp Ile Cys Gly Arg Lys Phe Ala Gln Asn Ser Thr Leu Thr
305                 310                 315                 320

Glu His Thr Lys Ile His Leu Arg Gln Lys Asp Val Tyr Val Gly Gly
                325                 330                 335

Leu Glu Ser Arg Val Leu Lys Tyr Thr Ala Gln Asn Met Glu Leu Gln
            340                 345                 350

Asn Lys Val Gln Leu Leu Glu Glu Gln Asn Leu Ser Leu Leu Asp Gln
        355                 360                 365

Leu Arg Lys Leu Gln Ala Met Val Ile Glu Ile Ser Asn Lys Thr Ser
    370                 375                 380

Ser Ser Ser Thr Cys Ile Leu Val Leu Leu Val Ser Phe Cys Leu Leu
385                 390                 395                 400

Leu Val Pro Ala Met Tyr Ser Ser Asp Thr Arg Gly Ser Leu Pro Ala
                405                 410                 415

Glu His Gly Val Leu Ser Arg Gln Leu Arg Ala Leu Pro Ser Glu Asp
            420                 425                 430

Pro Tyr Gln Leu Glu Leu Pro Ala Leu Gln Ser Glu Val Pro Lys Asp
        435                 440                 445

Ser Thr His Gln Trp Leu Asp Gly Ser Asp Cys Val Leu Gln Ala Pro
    450                 455                 460

Gly Asn Thr Ser Cys Leu Leu His Tyr Met Pro Gln Ala Pro Ser Ala
465                 470                 475                 480

Glu Pro Pro Leu Glu Trp Pro Phe Pro Asp Leu Phe Ser Glu Pro Leu
                485                 490                 495

Cys Arg Gly Pro Ile Leu Pro Leu Gln Ala Asn Leu Thr Arg Lys Gly
            500                 505                 510

Gly Trp Leu Pro Thr Gly Ser Pro Ser Val Ile Leu Gln Asp Arg Tyr
        515                 520                 525
```

Ser Gly
530

<210> SEQ ID NO 218
<211> LENGTH: 1590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 218
atggagctgg aattggatgc tggtgaccaa gacctgctgg ccttcctgct agaggaaagt 60
ggagatttgg ggacggcacc cgatgaggcc gtgagggccc cactggactg ggcgctgccg 120
ctttctgagg tgccgagcga ctgggaagta gatgatttgc tgtgctccct gctgagtccc 180
ccagcgtcgt tgaacattct cagctcctcc aacccctgcc ttgtccacca tgaccacacc 240
tactccctcc cacgggaaac tgtctctatg gatctagaga gtgagagctg tagaaaagag 300
gggacccaga tgactccaca gcatatggag gagctggcag agcaggagat tgctaggcta 360
gtactgacag atgaggagaa gagtctattg gagaaggagg ggcttattct gcctgagaca 420
cttcctctca ctaagacaga ggaacaaatt ctgaaacgtg tgcggcgccc ttacgcttgc 480
ccagtggagt cctgtgatcg ccgcttctcc cgctcagaca acctcgttcg acacatccgc 540
atccacacag gccagaagcc cttccagtgc cgcatctgca tgagaaactt cagccaccgg 600
actacactca cgaaccacat ccgcacccac acaggcgaaa agcccttcgc ctgcgacatc 660
tgtggaagaa agtttgccag agaagacaat ctccatactc ataccaagat ccacttgcgg 720
cagaaggacc gcccttacgc ttgcccagtg gagtcctgtg atcgccgctt ctccaccagc 780
cattctctca ctgaacacat ccgcatccac acaggccaga agcccttcca gtgccgcatc 840
tgcatgagaa acttcagcca gtctagctca ctggtgaggc acatccgcac ccacacaggc 900
gaaaagccct tcgcctgcga catctgtgga agaaagtttg ccagggagga taacctgcat 960
acgcatacca agatccactt gcggcagaag gacgtgtacg ttgggggttt agagagccgg 1020
gtcttgaaat acacagccca gaatatggag cttcagaaca aagtacagct tctggaggaa 1080
cagaatttgt cccttctaga tcaactgagg aaactccagg ccatggtgat tgagatctca 1140
aacaaaacca gcagcagcag cacctgcatc ttggtcctgc tagtctcctt ctgcctcctc 1200
cttgtacctg ctatgtactc ctctgacaca agggggagcc tgccagctga gcatggagtg 1260
ttgtcccgcc agcttcgtgc cctccccagt gaggaccctt accagctgga gctgcctgcc 1320
ctgcagtcag aagtgccgaa agacagcaca caccagtggt tggacggctc agactgtgta 1380
ctccaggccc ctggcaacac ttcctgcctg ctgcattaca tgcctcaggc tcccagtgca 1440
gagcctcccc tggagtggcc cttccctgac ctcttctcag agcctctctg ccgaggtccc 1500
atcctccccc tgcaggcaaa tctcacaagg aagggaggat ggcttcctac tggtagcccc 1560
tctgtcattt tgcaggacag atactcaggc 1590

<210> SEQ ID NO 219
<211> LENGTH: 530
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Pro Tyr Ala Cys
145                 150                 155                 160

Pro Val Glu Ser Cys Asp Arg Arg Phe Ser Arg Ser Asp Asn Leu Val
                165                 170                 175

Arg His Ile Arg Ile His Thr Gly Gln Lys Pro Phe Gln Cys Arg Ile
            180                 185                 190

Cys Met Arg Asn Phe Ser His Arg Thr Thr Leu Thr Asn His Ile Arg
        195                 200                 205

Thr His Thr Gly Glu Lys Pro Phe Ala Cys Asp Ile Cys Gly Arg Lys
    210                 215                 220

Phe Ala Arg Glu Asp Asn Leu His Thr His Thr Lys Ile His Leu Arg
225                 230                 235                 240

Gln Lys Asp Arg Pro Tyr Ala Cys Pro Val Glu Ser Cys Asp Arg Arg
                245                 250                 255

Phe Ser Thr Ser His Ser Leu Thr Glu His Ile Arg Ile His Thr Gly
            260                 265                 270

Gln Lys Pro Phe Gln Cys Arg Ile Cys Met Arg Asn Phe Ser Gln Ser
        275                 280                 285

Ser Ser Leu Val Arg His Ile Arg Thr His Thr Gly Glu Lys Pro Phe
    290                 295                 300

Ala Cys Asp Ile Cys Gly Arg Lys Phe Ala Arg Glu Asp Asn Leu His
305                 310                 315                 320

Thr His Thr Lys Ile His Leu Arg Gln Lys Asp Val Tyr Val Gly Gly
                325                 330                 335

Leu Glu Ser Arg Val Leu Lys Tyr Thr Ala Gln Asn Met Glu Leu Gln
            340                 345                 350

Asn Lys Val Gln Leu Leu Glu Glu Gln Asn Leu Ser Leu Leu Asp Gln
        355                 360                 365

Leu Arg Lys Leu Gln Ala Met Val Ile Glu Ile Ser Asn Lys Thr Ser
    370                 375                 380

Ser Ser Ser Thr Cys Ile Leu Val Leu Leu Val Ser Phe Cys Leu Leu
385                 390                 395                 400

Leu Val Pro Ala Met Tyr Ser Ser Asp Thr Arg Gly Ser Leu Pro Ala
                405                 410                 415

Glu His Gly Val Leu Ser Arg Gln Leu Arg Ala Leu Pro Ser Glu Asp
```

```
            420                 425                 430

Pro Tyr Gln Leu Glu Leu Pro Ala Leu Gln Ser Glu Val Pro Lys Asp
        435                 440                 445

Ser Thr His Gln Trp Leu Asp Gly Ser Asp Cys Val Leu Gln Ala Pro
    450                 455                 460

Gly Asn Thr Ser Cys Leu Leu His Tyr Met Pro Gln Ala Pro Ser Ala
465                 470                 475                 480

Glu Pro Pro Leu Glu Trp Pro Phe Pro Asp Leu Phe Ser Glu Pro Leu
                485                 490                 495

Cys Arg Gly Pro Ile Leu Pro Leu Gln Ala Asn Leu Thr Arg Lys Gly
            500                 505                 510

Gly Trp Leu Pro Thr Gly Ser Pro Ser Val Ile Leu Gln Asp Arg Tyr
        515                 520                 525

Ser Gly
    530
```

<210> SEQ ID NO 220
<211> LENGTH: 1140
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 220

```
atggagctgg aattggatgc tggtgaccaa gacctgctgg ccttcctgct agaggaaagt     60

ggagatttgg ggacggcacc cgatgaggcc gtgagggccc cactggactg ggcgctgccg    120

ctttctgagg tgccgagcga ctgggaagta gatgatttgc tgtgctccct gctgagtccc    180

ccagcgtcgt tgaacattct cagctcctcc aacccctgcc ttgtccacca tgaccacacc    240

tactccctcc cacgggaaac tgtctctatg gatctagaga gtgagagctg tagaaaagag    300

gggacccaga tgactccaca gcatatggag gagctggcag agcaggagat tgctaggcta    360

gtactgacag atgaggagaa gagtctattg gagaaggagg ggcttattct gcctgagaca    420

cttcctctca ctaagacaga ggaacaaatt ctgaaacgtg tgcggctcga accaggtgaa    480

aaaccttaca aatgtcctga atgtgggaaa tcattcagtc gcagcgacaa cctggtgaga    540

catcaacgca cccatacagg agaaaaacct tataaatgtc cagaatgtgg aaagtccttc    600

tcacgagagg ataacttgca cactcatcaa cgaacacata ctggtgaaaa accatacaag    660

tgtcccgaat gtggtaaaag ttttagccgg agcgatgaac ttgtccgaca ccaacgaacc    720

catacaggcg agaagcctta caaatgtccc gagtgtggca agagcttctc acaatcaggg    780

aatctgactg agcatcaacg aactcatacc ggggaaaaac cttacaagtg tccagagtgt    840

gggaagagct tttccacaag tggacatctg gtacgccacc agaggacaca tacaggggag    900

aagccctaca aatgccccga atgcggtaaa agtttctctc agaatagtac cctgaccgaa    960

caccagcgaa cacacactgg gaaaaaaacg agtgtgtacg ttgggggttt agagagccgg   1020

gtcttgaaat acacagccca gaatatggag cttcagaaca aagtacagct tctggaggaa   1080

cagaatttgt cccttctaga tcaactgagg aaactccagg ccatggtgat tgagatatca   1140
```

<210> SEQ ID NO 221
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 221

Met Glu Leu Glu Leu Asp Ala Gly Asp Gln Asp Leu Leu Ala Phe Leu
1 5 10 15

Leu Glu Glu Ser Gly Asp Leu Gly Thr Ala Pro Asp Glu Ala Val Arg
20 25 30

Ala Pro Leu Asp Trp Ala Leu Pro Leu Ser Glu Val Pro Ser Asp Trp
35 40 45

Glu Val Asp Asp Leu Leu Cys Ser Leu Leu Ser Pro Pro Ala Ser Leu
50 55 60

Asn Ile Leu Ser Ser Ser Asn Pro Cys Leu Val His His Asp His Thr
65 70 75 80

Tyr Ser Leu Pro Arg Glu Thr Val Ser Met Asp Leu Glu Ser Glu Ser
85 90 95

Cys Arg Lys Glu Gly Thr Gln Met Thr Pro Gln His Met Glu Glu Leu
100 105 110

Ala Glu Gln Glu Ile Ala Arg Leu Val Leu Thr Asp Glu Glu Lys Ser
115 120 125

Leu Leu Glu Lys Glu Gly Leu Ile Leu Pro Glu Thr Leu Pro Leu Thr
130 135 140

Lys Thr Glu Glu Gln Ile Leu Lys Arg Val Arg Leu Glu Pro Gly Glu
145 150 155 160

Lys Pro Tyr Lys Cys Pro Glu Cys Gly Lys Ser Phe Ser Arg Ser Asp
165 170 175

Asn Leu Val Arg His Gln Arg Thr His Thr Gly Glu Lys Pro Tyr Lys
180 185 190

Cys Pro Glu Cys Gly Lys Ser Phe Ser Arg Glu Asp Asn Leu His Thr
195 200 205

His Gln Arg Thr His Thr Gly Glu Lys Pro Tyr Lys Cys Pro Glu Cys
210 215 220

Gly Lys Ser Phe Ser Arg Ser Asp Glu Leu Val Arg His Gln Arg Thr
225 230 235 240

His Thr Gly Glu Lys Pro Tyr Lys Cys Pro Glu Cys Gly Lys Ser Phe
245 250 255

Ser Gln Ser Gly Asn Leu Thr Glu His Gln Arg Thr His Thr Gly Glu
260 265 270

Lys Pro Tyr Lys Cys Pro Glu Cys Gly Lys Ser Phe Ser Thr Ser Gly
275 280 285

His Leu Val Arg His Gln Arg Thr His Thr Gly Glu Lys Pro Tyr Lys
290 295 300

Cys Pro Glu Cys Gly Lys Ser Phe Ser Gln Asn Ser Thr Leu Thr Glu
305 310 315 320

His Gln Arg Thr His Thr Gly Lys Lys Thr Ser Val Tyr Val Gly Gly
325 330 335

Leu Glu Ser Arg Val Leu Lys Tyr Thr Ala Gln Asn Met Glu Leu Gln
340 345 350

Asn Lys Val Gln Leu Leu Glu Glu Gln Asn Leu Ser Leu Leu Asp Gln
355 360 365

Leu Arg Lys Leu Gln Ala Met Val Ile Glu Ile Ser
370 375 380

<210> SEQ ID NO 222
<211> LENGTH: 1140

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 222
atggagctgg aattggatgc tggtgaccaa gacctgctgg ccttcctgct agaggaaagt 60
ggagatttgg ggacggcacc cgatgaggcc gtgagggccc cactggactg ggcgctgccg 120
ctttctgagg tgccgagcga ctgggaagta gatgatttgc tgtgctccct gctgagtccc 180
ccagcgtcgt tgaacattct cagctcctcc aacccctgcc ttgtccacca tgaccacacc 240
tactccctcc cacgggaaac tgtctctatg gatctagaga gtgagagctg tagaaaagag 300
gggacccaga tgactccaca gcatatggag gagctggcag agcaggagat tgctaggcta 360
gtactgacag atgaggagaa gagtctattg gagaaggagg ggcttattct gcctgagaca 420
cttcctctca ctaagacaga ggaacaaatt ctgaaacgtg tgcggcgccc ttacgcttgc 480
ccagtggagt cctgtgatcg ccgcttctcc cgcagcgaca acctggtgag acacatccgc 540
atccacacag gccagaagcc cttccagtgc cgcatctgca tgagaaactt cagccgagag 600
gataacttgc acactcacat ccgcacccac acaggcgaaa agcccttcgc ctgcgacatc 660
tgtggaagaa agtttgcccg gagcgatgaa cttgtccgac ataccaagat ccacttgcgg 720
cagaaggacc gcccttacgc ttgcccagtg gagtcctgtg atcgccgctt ctcccaatca 780
gggaatctga ctgagcacat ccgcatccac acaggccaga agcccttcca gtgccgcatc 840
tgcatgagaa acttcagcac aagtggacat ctggtacgcc acatccgcac ccacacaggc 900
gaaaagccct tcgcctgcga catctgtgga agaaagtttg cccagaatag taccctgacc 960
gaacatacca agatccactt gcggcagaag gacgtgtacg ttgggggttt agagagccgg 1020
gtcttgaaat acacagccca gaatatggag cttcagaaca aagtacagct tctggaggaa 1080
cagaatttgt cccttctaga tcaactgagg aaactccagg ccatggtgat tgagatctca 1140

<210> SEQ ID NO 223
<211> LENGTH: 380
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 223

Met Glu Leu Glu Leu Asp Ala Gly Asp Gln Asp Leu Leu Ala Phe Leu
1 5 10 15

Leu Glu Glu Ser Gly Asp Leu Gly Thr Ala Pro Asp Glu Ala Val Arg
20 25 30

Ala Pro Leu Asp Trp Ala Leu Pro Leu Ser Glu Val Pro Ser Asp Trp
35 40 45

Glu Val Asp Asp Leu Leu Cys Ser Leu Leu Ser Pro Pro Ala Ser Leu
50 55 60

Asn Ile Leu Ser Ser Ser Asn Pro Cys Leu Val His His Asp His Thr
65 70 75 80

Tyr Ser Leu Pro Arg Glu Thr Val Ser Met Asp Leu Glu Ser Glu Ser
85 90 95

Cys Arg Lys Glu Gly Thr Gln Met Thr Pro Gln His Met Glu Glu Leu
100 105 110

Ala Glu Gln Glu Ile Ala Arg Leu Val Leu Thr Asp Glu Glu Lys Ser

```
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Pro Tyr Ala Cys
145                 150                 155                 160

Pro Val Glu Ser Cys Asp Arg Arg Phe Ser Arg Ser Asp Asn Leu Val
                165                 170                 175

Arg His Ile Arg Ile His Thr Gly Gln Lys Pro Phe Gln Cys Arg Ile
            180                 185                 190

Cys Met Arg Asn Phe Ser Arg Glu Asp Asn Leu His Thr His Ile Arg
        195                 200                 205

Thr His Thr Gly Glu Lys Pro Phe Ala Cys Asp Ile Cys Gly Arg Lys
    210                 215                 220

Phe Ala Arg Ser Asp Glu Leu Val Arg His Thr Lys Ile His Leu Arg
225                 230                 235                 240

Gln Lys Asp Arg Pro Tyr Ala Cys Pro Val Glu Ser Cys Asp Arg Arg
                245                 250                 255

Phe Ser Gln Ser Gly Asn Leu Thr Glu His Ile Arg Ile His Thr Gly
            260                 265                 270

Gln Lys Pro Phe Gln Cys Arg Ile Cys Met Arg Asn Phe Ser Thr Ser
        275                 280                 285

Gly His Leu Val Arg His Ile Arg Thr His Thr Gly Glu Lys Pro Phe
    290                 295                 300

Ala Cys Asp Ile Cys Gly Arg Lys Phe Ala Gln Asn Ser Thr Leu Thr
305                 310                 315                 320

Glu His Thr Lys Ile His Leu Arg Gln Lys Asp Val Tyr Val Gly Gly
                325                 330                 335

Leu Glu Ser Arg Val Leu Lys Tyr Thr Ala Gln Asn Met Glu Leu Gln
            340                 345                 350

Asn Lys Val Gln Leu Leu Glu Glu Gln Asn Leu Ser Leu Leu Asp Gln
        355                 360                 365

Leu Arg Lys Leu Gln Ala Met Val Ile Glu Ile Ser
    370                 375                 380
```

<210> SEQ ID NO 224
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95
```

Cys Arg Lys Glu Gly Thr Gln Met Thr Pro Gln His Met Glu Glu Leu
100 105 110

Ala Glu Gln Glu Ile Ala Arg Leu Val Leu Thr Asp Glu Glu Lys Ser
115 120 125

Leu Leu Glu Lys Glu Gly Leu Ile Leu Pro Glu Thr Leu Pro Leu Thr
130 135 140

Lys Thr Glu Glu Gln Ile Leu Lys Arg Val Arg
145 150 155

<210> SEQ ID NO 225
<211> LENGTH: 199
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 225

Val Tyr Val Gly Gly Leu Glu Ser Arg Val Leu Lys Tyr Thr Ala Gln
1 5 10 15

Asn Met Glu Leu Gln Asn Lys Val Gln Leu Leu Glu Glu Gln Asn Leu
20 25 30

Ser Leu Leu Asp Gln Leu Arg Lys Leu Gln Ala Met Val Ile Glu Ile
35 40 45

Ser Asn Lys Thr Ser Ser Ser Ser Thr Cys Ile Leu Val Leu Leu Val
50 55 60

Ser Phe Cys Leu Leu Leu Val Pro Ala Met Tyr Ser Ser Asp Thr Arg
65 70 75 80

Gly Ser Leu Pro Ala Glu His Gly Val Leu Ser Arg Gln Leu Arg Ala
85 90 95

Leu Pro Ser Glu Asp Pro Tyr Gln Leu Glu Leu Pro Ala Leu Gln Ser
100 105 110

Glu Val Pro Lys Asp Ser Thr His Gln Trp Leu Asp Gly Ser Asp Cys
115 120 125

Val Leu Gln Ala Pro Gly Asn Thr Ser Cys Leu Leu His Tyr Met Pro
130 135 140

Gln Ala Pro Ser Ala Glu Pro Pro Leu Glu Trp Pro Phe Pro Asp Leu
145 150 155 160

Phe Ser Glu Pro Leu Cys Arg Gly Pro Ile Leu Pro Leu Gln Ala Asn
165 170 175

Leu Thr Arg Lys Gly Gly Trp Leu Pro Thr Gly Ser Pro Ser Val Ile
180 185 190

Leu Gln Asp Arg Tyr Ser Gly
195

<210> SEQ ID NO 226
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

Val Tyr Val Gly Gly Leu Glu Ser Arg Val Leu Lys Tyr Thr Ala Gln
1 5 10 15

Asn Met Glu Leu Gln Asn Lys Val Gln Leu Leu Glu Glu Gln Asn Leu
20 25 30

-continued

```
Ser Leu Leu Asp Gln Leu Arg Lys Leu Gln Ala Met Val Ile Glu Ile
        35                  40                  45

Ser
```

COMPOSITIONS AND METHODS FOR SELECTIVE GENE REGULATION

CROSS-REFERENCE

This application is a continuation of International Application No. PCT/US2020/035431, filed May 29, 2020, which claims the benefit of U.S. Provisional Patent Application No. 62/854,238, filed May 29, 2019; U.S. Provisional Patent Application No. 62/857,727, filed Jun. 5, 2019; and U.S. Provisional Patent Application No. 63/008,569, filed Apr. 10, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 28, 2020, is named 46482-724_301_SL.txt and is 418.550 bytes in size.

BACKGROUND

A broad range of human diseases are associated with abnormal expression of genes. In some cases, a genetic mutation in a gene causes it to be dysregulated, downregulated, or not expressed at all, resulting in haploinsufficiency. In some cases, a genetic mutation in a gene causes it to be upregulated, resulting in overexpression of the gene. Many challenges exist in treating genetic disorders or diseases. One approach is gene therapy, which involves therapeutic delivery of a nucleic acid into a patient's cells. However, various challenges associated with gene therapy remain unsolved, such as unwanted immune response elicited by gene therapy, off-target effects, limitations on cloning capacity of gene therapy vehicles (e.g., viruses), sustaining the therapeutic effect over a longer period of time, etc. The central nervous system (CNS) poses many unique challenges for the development of a therapy that addresses the underlying impairment in a gene and/or protein expression. While there are drugs that help to manage symptoms of CNS diseases/disorders, many CNS diseases/disorders, e.g, Dravet syndrome, lack specific treatments or a cure. Thus, there is a need for novel compositions and methods capable of modulating the expression of any endogenous gene to help reverse the effects of a disease or disorder, in particular, a therapy with reduced immunogenicity, reduced off-target effects, increased specificity for a target gene, and/or increased therapeutic efficacy.

SUMMARY

In one aspect, the application provides an expression cassette comprising a sequence encoding a non-naturally occurring transcription factor which increases expression of the SCN1A gene in a cell, wherein the non-naturally occurring transcription factor comprises a DNA binding domain (DBD) operably linked to at least two transcription activating domains (TAD) in the following manner: TAD1-TAD2-DBD, DBD-TAD3-TAD4, or TAD1-TAD2-DBD-TAD3-TAD4. In certain embodiments, TAD1, TAD2, TAD3 and TAD4 are independently selected from the following: VP16, VP64, Viper, CITED2, CITED4, CREB3 or functional fragments thereof. In certain embodiments, TAD1 and TAD2 are the same TAD. In certain embodiments, TAD1 and TAD2 are CITED2, or a functional fragment thereof in certain embodiments, TAD1 and TAD2 are CITED4, or a functional fragment thereof. In certain embodiments, TAD3 and TAD4 are the same TAD. In certain embodiments, TAD3 and TAD4 are CITED2, or a functional fragment thereof. In certain embodiments, TAD3 and TAD4 are CITED4, or a functional fragment thereof. In certain embodiments, TAD1, TAD2, TAD3 and TAD4 are the same TAD. In certain embodiments, TAD1, TAD2, TAD3 and TAD4 are CITED2, or a functional fragment thereof. In certain embodiments, TAD1, TAD2, TAD3 and TAD4 are CITED4, or a functional fragment thereof.

In certain embodiments, there is no linker between the at least two TAD domains.

In certain embodiments, there is a linker between the at least two TAD domains. In certain embodiments, the linker comprises or consists of GGSGGGSG (SEQ ID NO: 177) or GGSGGGSGGGSGGGSG (SEQ ID NO: 178).

In certain embodiments, the DBD binds to a genomic region having 18-27 nucleotides.

In certain embodiments, the DBD comprises at least 80% sequence identity to its closest human counterpart. In certain embodiments, the DBD comprises at least 90% sequence identity to its closest human counterpart. In certain embodiments, the DBD and the at least two TAD each comprise at least 80% sequence identity to their closest human counterparts. In certain embodiments, the DBD and the at least two TAD each comprise at least 90% sequence identity to their closest human counterparts.

In certain embodiments, the DBD comprises a guide RNA and a nuclease inactivated Cas protein. In certain embodiments, the nuclease inactivated Cas protein is a nuclease inactivated Cas9.

In certain embodiments, the DBD comprises a zinc finger domain. In certain embodiments, the DBD comprises six to nine zinc finger domains. In certain embodiments, the DBD comprises six zinc fingers. In certain embodiments, the DBD binds to a genomic region having 18 nucleotides. In certain embodiments, the DBD comprises nine zinc fingers, in certain embodiments, the DBD binds to a genomic region having 27 nucleotides.

In certain embodiments, the DBD comprises a sequence having at least 95% sequence identity to any of SEQ ID NOs: 148-151. In certain embodiments, the DBD comprises a sequence having any one of SEQ ID NOs: 148-151.

In certain embodiments, the DBD is derived from human EGR1 or human EGR3.

In certain embodiments, the DBD comprises a sequence having at least 90% identity to any one of SEQ ID NOs: 77-98. In certain embodiments, the DBD comprises SEQ ID NOs: 77-98.

In certain embodiments, the DBD comprises a sequence having at least 90% identity to SEQ II) NO: 92. In certain embodiments, the DBD comprises SEQ ID NO: 92.

In certain embodiments, the non-naturally occurring transcription factor comprises a sequence having at least 90% identity to SEQ ID NO: 130 or 131. In certain embodiments, the non-naturally occurring transcription factor comprises SEQ ID NO: 130 or 131.

In certain embodiments, the expression cassette comprises a nucleotide sequence having at least 90% identity to any one of SEQ ID NOs: 72 or 73. In certain embodiments, the expression cassette comprises a nucleotide sequence of any one of SEQ ID NOs: 72 or 73.

In certain embodiments, the expression cassette further comprises a regulatory element that drives expression of the transcription factor at a higher level in PV neurons than in other cell types. In certain embodiments, the regulatory element comprises any one of SEQ ID NOs: 1-4. In certain embodiments, the regulatory element comprises SEQ ID NO: 2 or 3.

In certain embodiments, the expression cassette further comprises a PV selective microRNA binding site. In certain embodiments, the PV selective microRNA binding site comprises at least 90% identity to any one of SEQ ID NOs: 7, 14 or 15. In certain embodiments, the PV selective microRNA binding site comprises any one of SEQ NOs: 7, 14, or 15.

In certain embodiments, the expression cassette is a part of a viral vector. In certain embodiments, the viral vector is an AAV virus. In certain embodiments, the AAV virus is an AAV9 virus or a scAAV9 virus. In certain embodiments, the viral vector is a Lentivirus.

In another aspect, the application provides an expression cassette comprising a sequence encoding a non-naturally occurring transcription factor which increases expression of the SCN1A gene in a cell, wherein the non-naturally occurring transcription factor comprises a DNA binding domain operably linked to a transcription activating domain, wherein the DNA binding domain is a zinc finger protein comprising the sequence LEPGEKP-[YKCPECGKSFS X HQRTH TGEKP]n-YKCPECGKSFS X HQRTH-TGKKTS (SEQ ID NO: 147), and wherein there is no HA tag (SEQ ID NO: 303) between the DNA binding domain and the transcription activating domain. In certain embodiments, the transcription activating domain comprises a VP16, VPR or VP64 sequence, or a functional fragment thereof. In certain embodiments, the transcription activating domain comprises VP64.

In certain embodiments, the DNA binding domain binds to a genomic region having 18-27 nucleotides. In certain embodiments, the DNA binding domain is a zinc finger domain comprising SEQ ID NO: 147 wherein n=6 to 9. In certain embodiments, the DNA binding domain is a zinc finger domain comprising SEQ ID NO: 147 wherein n=6. In certain embodiments, the DNA binding domain binds to a genomic region having 18 nucleotides. In certain embodiments, the DNA binding domain is a zinc finger domain comprising SEQ ID NO: 147 wherein n=9. In certain embodiments, the DNA binding domain binds to a genomic region having 27 nucleotides.

In certain embodiments, the DNA binding domain comprises a sequence having at least 95% sequence identity to any of SEQ ID NOs: 148-151. In certain embodiments, the DNA binding domain comprises a sequence having any one of SEQ ID NOs: 148-151.

In certain embodiments, the DNA binding domain comprises a sequence having at least 90% identity to any one of SEQ ID NOs: 77-91. In certain embodiments, the DNA binding domain comprises any one of SEQ ID NOs: 77-91.

In certain embodiments, the expression cassette further comprises a regulatory element that drives expression of the transcription factor at a higher level in PV neurons than in other cell types. In certain embodiments, the regulatory element comprises any one of SEQ ID NOs: 1-4. In certain embodiments, the regulatory element comprises SEQ ID NO: 2 or 3.

In certain embodiments, the non-naturally occurring transcription factor comprises a sequence having at least 90% identity to SEQ ID NO: 127. In certain embodiments, the non-naturally occurring transcription factor comprises SEQ ID NO: 127.

In certain embodiments, the expression cassette comprises a nucleotide sequence having at least 90% identity to any one of SEQ ID NOs: 93 or 71. In certain embodiments, the expression cassette comprises a nucleotide sequence of any one of SEQ ID NOs: 93 or 71.

In certain embodiments, the expression cassette further comprises a PV selective microRNA binding site. In certain embodiments, the PV selective microRNA binding site comprises at least 90% identity to any one of SEQ ID NOs: 7, 14 or 15. In certain embodiments, the PV selective microRNA binding site comprises any one of SEQ ID NOs: 7, 14, or 15.

In certain embodiments, the expression cassette is a part of a viral vector. In certain embodiments, the viral vector is an AAV virus. In certain embodiments, the AAV virus is an AAV9 virus or a scAAV9 virus. In certain embodiments, the viral vector is a Lentivirus. In another aspect, the application provides a polynucleotide comprising a PV selective microRNA binding site comprising a sequence having at least 80% sequence identity to SEQ ID NO: 14 or 15, wherein the microRNA binding site reduces expression of the transgene in excitatory neurons. In certain embodiments, the PV selective microRNA binding site comprises SEQ ID NO: 14. In certain embodiments, the PV selective microRNA binding site comprises SEQ ID NO: 15. In another aspect, the application provides an expression cassette comprising the PV selective microRNA binding site and a promoter and/or enhancer. In certain embodiments, the promoter and/or enhancer is a PV selective regulatory element that drives expression of the transgene at a higher level in parvalbumin (PV) neurons than in other cell types. In certain embodiments, the PV selective regulatory element is operably linked to a transgene.

In another aspect, the application provides an expression cassette comprising a regulatory element operably linked to a transgene and at least one microRNA binding site, wherein the regulatory element drives expression of the transgene at a higher level in parvalbumin (PV) neurons than in other cell types, and wherein the microRNA binding site reduces expression of the transgene in excitatory neurons. In certain embodiments, the expression cassette does not comprise SEQ ID NO: 67. In certain embodiments, the microRNA binding site comprises at least one binding site for MIR128 (SEQ ID NO: 9). In certain embodiments, the microRNA binding site comprises at least one binding site for MIR221 (SEQ ID NO: 11). In certain embodiments, the microRNA binding site comprises at least one binding site for MIR222 (SEQ ID NO: 13). In certain embodiments, the microRNA binding site comprises at least one binding site for MIR128 (SEQ ID NO: 9) and at least one binding site for MIR221 (SEQ ID NO: 11). In certain embodiments, the microRNA binding site comprises at least one binding site for MIR128 (SEQ ID NO: 9), at least one binding site for MIR221 (SEQ ID NO: 11), and at least one binding site for MIR222 (SEQ ID NO: 13). In certain embodiments, the microRNA binding site comprises a sequence having at least 90% identity to any one of SEQ ID NOs: 7, 14 or 15. In certain embodiments, the microRNA binding site comprises SEQ ID NO: 7, 14 or 15.

In certain embodiments, the transgene encodes a polypeptide comprising a non-naturally occurring transcription factor which increases expression of the SCN1A gene in a cell. In certain embodiments, the transcription factor binds to a genomic region having 18-27 nucleotides. In certain embodiments, the transcription factor comprises a DNA binding domain. In certain embodiments, the transcription factor comprises a DNA binding domain and a transcription activating domain.

In certain embodiments, the DNA binding domain comprises at least 80% sequence identity to its closest human counterpart. In certain embodiments, the DNA binding domain comprises at least 90% sequence identity to its closest human counterpart. In certain embodiments, the DNA binding domain and the transcription activating domain both comprise at least 80% sequence identity to their closest human counterparts. In certain embodiments, the DNA binding domain and the transcription activating domain both comprise at least 90% sequence identity to their closest human counterparts.

In certain embodiments, the DNA binding domain comprises a guide RNA and a nuclease inactivated. Cas protein. In certain embodiments, the nuclease inactivated Cas protein is a nuclease inactivated Cas9.

In certain embodiments, the DNA binding domain comprises a zinc finger domain. In certain embodiments, the DNA binding domain comprises six to nine zinc finger domains. In certain embodiments, the DNA binding domain comprises six zinc fingers. In certain embodiments, the DNA binding domain binds to a genomic region having 18 nucleotides. In certain embodiments, the DNA binding domain comprises nine zinc fingers. In certain embodiments, the DNA binding domain binds to a genomic region having 27 nucleotides.

In certain embodiments, the DNA binding domain comprises a sequence having at least 95% sequence identity to any of SEQ ID NOs: 148-151. In certain embodiments, the DNA binding domain comprises a sequence having any one of SEQ ID NOs: 148-151. In certain embodiments, the DNA binding domain comprises a sequence having at least 90% identity to any one of SEQ ID NOs: 92-98. In certain embodiments, the DNA binding domain comprises any one of SEQ ID NOs: 92-98.

In certain embodiments, the DNA binding domain is a zinc finger protein comprising the sequence LEPGEKP-[YKCPECGKSFS X HQRTH TGEKP]n-YKCPECGKSFS X HQRTH-TGKKTS (SEQ ID NO. 147).

In certain embodiments, the DNA binding domain comprises a sequence having at least 90% identity to any one of SEQ ID NOs: 77-91, In certain embodiments, the DNA binding domain comprises any one of SEQ ID NOs: 77-91.

In certain embodiments, the DNA binding domain is derived from human EGR1 or human EGR3.

In certain embodiments, the transcription activating domain comprises a VP16, VPR, VP64, CITED2, CITED4, or CREB3 sequence, or a functional fragment thereof. In certain embodiments, the transcription activating domain comprises a human CITED2, CITED4, or CREB3 sequence, or a functional fragment thereof.

In certain embodiments, the regulatory element comprises a sequence having any one of SEQ ID NOs: 1-4. In certain embodiments, the regulatory element comprises a sequence having SEQ ID NO: 2 or 3.

In certain embodiments, the non-naturally occurring transcription factor comprises a sequence having at least 90% identity to any one of SEQ ID NOs: 105, 106, and 127-129. In certain embodiments, the non-naturally occurring transcription factor comprises any one of SEQ ID NOs: 105, 106, and 127-129.

In certain embodiments, the transgene comprises a nucleotide sequence having at least 90% identity to any one of SEQ NOs: 71, 74, 75, 76 or 184. In certain embodiments, the transgene comprises any one of SEQ NOs: 71, 74, 75, 76 or 184.

In certain embodiments, the expression cassette is a part of a viral vector. In certain embodiments, the viral vector is an AAV virus. In certain embodiments, AAV virus is an AAV9 virus or a scAAV9 virus. In certain embodiments, the viral vector is a Lentivirus.

In another aspect, the application provides a method for selective expression of a transgene in parvalbumin (PV) neurons of a primate comprising administering to a primate a viral vector comprising a transgene and at least one microRNA binding site, wherein the microRNA binding site reduces expression of the transgene in excitatory neurons.

In certain embodiments, the viral vector further comprises a regulatory element operably linked to the transgene, wherein the regulatory element drives expression of the transgene at a higher level in parvalbumin (PV) neurons than in other cell types.

In certain embodiments, the microRNA binding site comprises at least one binding site for MIR128 (SEQ ID NO: 9). In certain embodiments, the microRNA binding site comprises at least one binding site for MIR221 (SEQ ID NO: 11). In certain embodiments, the microRNA binding site comprises at least one binding site for MIR222 (SEQ ID NO: 13). In certain embodiments, the microRNA binding site comprises at least one binding site for MIR128 (SEQ ID NO: 9) and at least one binding site for MIR221 (SEQ ID NO: 11). In certain embodiments, the microRNA binding site comprises at least one binding site for MIR128 (SEQ ID NO: 9), at least one binding site for MIR221 (SEQ ID NO: 11), and at least one binding site for MIR222 (SEQ ID NO: 13). In certain embodiments, the microRNA binding site comprises a sequence having at least 90% identity to any one of SEQ ID NOs: 7, 14 or 15. In certain embodiments, the microRNA binding site comprises SEQ ID NO: 7, 14 or 15.

In certain embodiments, the transgene comprises a sequence encoding a non-naturally occurring transcription factor which increases expression of the SCN1A gene in a cell.

In certain embodiments, the transcription factor binds to a genomic region having 18-27 nucleotides.

In certain embodiments, the transcription factor comprises a DNA binding domain.

In certain embodiments, the transcription factor comprises a DNA binding domain and a transcription activating domain.

In certain embodiments, the DNA binding domain comprises at least 80% sequence identity to its closest human counterpart. In certain embodiments, the DNA binding domain comprises at least 90% sequence identity to its closest human counterpart. In certain embodiments, the DNA binding domain and the transcription activating domain both comprise at least 80% sequence identity to their closest human counterparts. In certain embodiments, the DNA binding domain and the transcription activating domain both comprise at least 90% sequence identity to their closest human counterparts.

In certain embodiments, the DNA binding domain comprises a guide RNA and a nuclease inactivated Cas protein. In certain embodiments, the nuclease inactivated Cas protein is a nuclease inactivated Cas9.

In certain embodiments, the DNA binding domain comprises a zinc finger domain. In certain embodiments, the DNA binding domain comprises six to nine zinc finger domains. In certain embodiments, the DNA binding domain comprises six zinc fingers. In certain embodiments, the DNA binding domain binds to a genomic region having 18 nucleotides. In certain embodiments, the DNA binding domain comprises nine zinc fingers. In certain embodiments, the DNA binding domain binds to a genomic region having 27 nucleotides.

In certain embodiments, the DNA binding domain comprises a sequence having at least 95% sequence identity to any of SEQ ID NOs: 148-151. In certain embodiments, the DNA binding domain comprises a sequence having any one of SEQ ID NOs: 148-151.

In certain embodiments, the DNA binding domain is derived from human EGR1 or human EGR3.

In certain embodiments, the DNA binding domain comprises a sequence having at least 90% identity to any one of SEQ ID NOs: 92-98. In certain embodiments, the DNA binding domain comprises any one of SEQ ID NOs: 92-98.

In certain embodiments, the DNA binding domain is a zinc finger protein comprising the sequence LEPGEKP-[YKCPECGKSFS X HQRTH TGEKP]n-YKCPECGKSFS X HQRTH-TGKKTS (SEQ ID NO: 147).

In certain embodiments, the DNA binding domain comprises a sequence having at least 90% identity to any one of SEQ ID NOs: 77-91. In certain embodiments, the DNA binding domain comprises any one of SEQ ID NOs: 77-91.

In certain embodiments, the transcription activating domain comprises a VP16, VPR, VP64, CITED2, CITED4, or CREB3 sequence, or a functional fragment thereof. In certain embodiments, the transcription activating domain comprises a human CITED2, CITED4, or CREB3 sequence, or a functional fragment thereof.

In certain embodiments, the regulatory element comprises a sequence having any one of SEQ ID NOs: 1-4. In certain embodiments, the regulatory element comprises a sequence having SEQ ID NO: 2 or 3.

In certain embodiments, the non-naturally occurring transcription factor comprises a sequence having at least 90% identity to any one of SEQ ID NOs: 105, 106, and 127-129. In certain embodiments, the non-naturally occurring transcription factor comprises any one of SEQ NOs: 105, 106, and 127-129.

In certain embodiments, the transgene comprises a nucleotide sequence having at least 90% identity to any one of SEQ ID NOs: 71, 74, 75, 76 or 184. In certain embodiments, the transgene comprises any one of SEQ ID NOs: 71, 74, 75, 76 or 184.

In certain embodiments, the viral vector is an AAV virus. In certain embodiments, the AAV virus is an AAV9 virus or a scAAV9 virus. In certain embodiments, the viral vector is a Lentivirus.

In certain embodiments, the primate is a human. In certain embodiments, the primate is a non-human primate. In certain embodiments, the non-human primate is an old world monkey, an orangutan, a gorilla, a chimpanzee, a marmoset, a crab-eating macaque, a rhesus macaque or a pig-tailed macaque.

In another aspect, the application provides an expression cassette comprising a sequence encoding a non-naturally occurring transcription factor which increases expression of the SCN1A gene in a cell, wherein the non-naturally occurring transcription factor comprises a sequence having at least 90% identity to SEQ ID NO: 128 or 129. In certain embodiments, the non-naturally occurring transcription factor comprises SEQ ID NO: 128 or 129.

In another aspect, the application provides a method of increasing expression of SCN1A in a cell by administering any of the expression cassettes provided herein. In certain embodiments, the cell is a neuronal cell. In certain embodiments, the neuronal cell is selected from the group consisting of unipolar, bipolar, multipolar, or pseudounipolar neurons. In certain embodiments, the cell is GABAergic neuron. In certain embodiments, the cell is a PV neuron. In certain embodiments, the cell is a non-neuronal cell. In certain embodiments, the cell is a glial cell. In certain embodiments, the glial cell is selected from the group consisting of astrocytes, oligodendrocytes, ependymal cells, Schwann cells, and satellite cells. In certain embodiments, the cell is within a subject. In certain embodiments, the subject is a mammal. In certain embodiments, the subject is a human. In certain embodiments, increasing expression of SCN1A treats a disease, disorder or symptom. In certain embodiments, the disorder is a central nervous system disorder. In certain embodiments, the disorder is epilepsy associated with SCN1A haploinsufficiency. In certain embodiments, the haploinsufficiency is the result of the subject being heterozygous for a loss of function mutation of the SCN1A gene. In certain embodiments, the disorder is epilepsy associated with an insertion, deletion, or substitution in the SCN1A gene. In certain embodiments, the disorder is epilepsy associated with a point mutation in the SCN1A gene. In certain embodiments, the disorder is Dravet Syndrome. In certain embodiments, a symptom of the central nervous system disorder is neuronal hyperactivity. In certain embodiments, treating the central nervous system disorder comprises reducing neuronal hyperactivity. In certain embodiments, a symptom of the central nervous system disorder is seizures. In certain embodiments, treating the central nervous system disorder comprises reducing the frequency of seizures. In certain embodiments, treating the central nervous system disorder comprises reducing the severity of seizures.

In another aspect, the application provides a method of increasing expression of SCN1A in the CNS by administering any one of the expression cassettes provided herein. In certain embodiments, the expression cassette is administered via unilateral intracerebroventricular (ICV) administration. In certain embodiments, the expression cassette is administered via bilateral intracerebroventricular (ICV) administration. In certain embodiments, the increased expression of SCN1A occurs in the brain. In certain embodiments, the increased expression of SCN1A occurs in the frontal cortex, parietal cortex, temporal cortex, hippocampus, medulla, and/or occipital cortex. In certain embodiments, the increased expression of SCN1A occurs in the spine. In certain embodiments, the increased expression of SCN1A occurs in the spinal cord and/or dorsal root ganglion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative cases, in which the principles of the invention are utilized, and the accompanying drawings of which:

FIG. 5A illustrates the relative expression of SCN1A gene in mice with injected with either control eGFP or Construct 4 comprising an SCN1A transcriptional activator. FIG. 5B illustrates the change in SCN1A expression in terms of percentage mean eGFP. These experiments indicate transcriptional activation by Construct 4 resulted in about 20-30% upregulation of SCN1A expression.

FIG. 6D shows a direct comparison between Construct 32, which contains an HA tag located between the DBD and TAD, and Construct 34, which does not contain an HA tag. FIG. 6E shows a direct comparison between Construct 31, which contains the ml microRNA binding site located between the coding region and polyA tail, and Construct 32, which does not contain the ml microRNA binding site.

FIG. 7A illustrates the comparison between wild-type (PBS WT) and Scn1a+/−mice (PBS HET) in a survival assay. P1 Scn1a+/− (N=53) and Scn1a+/+(N=54) mice were infused with PBS. Mice were observed in their home cage daily and in the case of any mortality, the date was recorded. There was a significant difference in survival between Scn1a+/− and Scn1a+/+ animals (P<0.0001). FIGS. 7B-D illustrate the effect on survival in a mouse model of Dravet syndrome for mice treated with various SCN1A specific transcription factors as compared to a control. P1 Scn1a+/−mice were infused with either PBS or an AAV9 vector expressing an SCN1A specific transcription factor (Constructs 31 or 33). Mice were observed in their home cage daily and in the case of any mortality, the date was recorded. FIG. 7D shows a direct comparison between Construct 31, which contains the ml microRNA binding site located between the coding region and polyA tail, and Construct 33, which does not contain the ml microRNA binding site.

In FIG. 9A (EF1a treatment) the hippocampus CA4 hylus region is outlined in yellow and the arrows point to the dentate cell granule cell body layer (DG). FIG. 9B and FIG. 9C are centered on the same region. The CA4 region, which is a mixture of excitatory and inhibitory interneurons, is highlighted as it was the only region of significant expression in the RE 2+ml condition. With EF1a and RE 2 driven transgene expression, GFP expression was more widespread and included other regions of the hippocampus. The DG cell layer is thought to contain primarily excitatory neurons. GFP expression driven by EF1a and RE 2 is visible in the DG cell layer (FIG. 9D and FIG. 9E) yet is not present in RE 2+ml treated animals (FIG. 9F) (white arrowheads).

DETAILED DESCRIPTION OF THE DISCLOSURE

Figure 1:
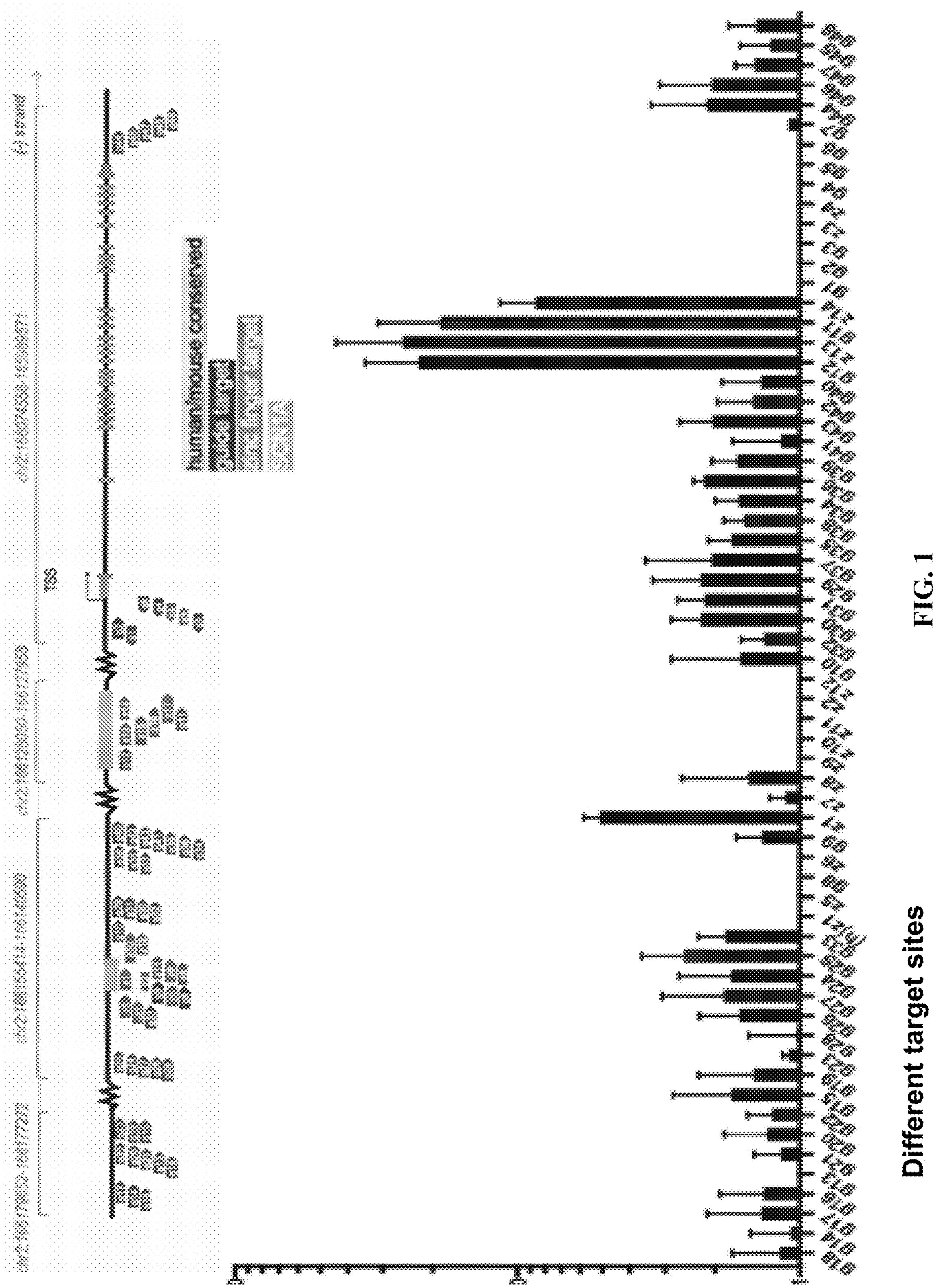
FIG. 1 illustrates upregulation of endogenous SCN1A using engineered transcription factors that bind to various regions on chromosome 2 (with reference to GRCh38.p12). Data are presented as fold change in SCN1A expression with respect to control (EGFP-KASH) condition.

Provided herein are engineered transcription factors, or eTFs, that are non-naturally occurring and have been designed to bind to a genomic target site and modulate expression of an endogenous gene of interest. Such eTFs may be designed to either upregulate or downregulate expression (RNA and/or protein expression) of a gene of interest. Also provided herein are microRNA binding sites that may be incorporated into a viral vector and provide selective expression of a transgene in parvalbumin (PV) neurons.

In one aspect, the application provides eTFs that are capable of upregulating expression of the sodium voltage gated channel alpha subunit 1 (SCN1A) gene and increasing expression of its corresponding protein product Nav1.1 and methods of use thereof for treating diseases or disorders associated with a deficiency in Nav1.1, such as, for example, Dravet syndrome.

In another aspect, the application provides microRNA binding sites that reduce expression of a mRNA containing the microRNA binding site in excitatory neurons thereby leading to selective expression of the gene in GABAergic or parvalbumin (PV) neurons and methods of use thereof for selective expression of a gene of interest in PV neurons.

Definitions

As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising”.

The term “about” or “approximately” means within an acceptable error range for the particular value as determined by one of ordinary skill in the art, which will depend in part on how the value is measured or determined, i.e., the limitations of the measurement system. For example, “about” can mean within one or more than one standard deviation, per the practice in the art. Alternatively, “about” can mean a range of up to 20%, up to 15%, up to 10%, up to 5%, or up to 1% of a given value.

The terms “determining”, “measuring”, “evaluating”, “assessing”, “assaying”, “analyzing”, and their grammatical equivalents can be used interchangeably herein to refer to any form of measurement, and include determining if an element is present or not (for example, detection). These terms can include both quantitative and/or qualitative determinations. Assessing may be relative or absolute.

The term “expression” refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as “gene product.” If the polynucleotide is derived from genomic DNA, expression may include splicing of the mRNA in a eukaryotic cell.

As used herein, “operably linked”, “operable linkage”, “operatively linked”, or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

A “vector” as used herein refers to a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target.

As used herein, “an expression cassette” and “a nucleic acid cassette” are used interchangeably to refer to a combination of nucleic acid sequences or elements that are expressed together or are operably linked for expression. In some cases, an expression cassette refers to the combination of regulatory elements and a gene or genes to which they are operably linked for expression.

The term “AAV” is an abbreviation for adeno-associated virus, and may be used to refer to the virus itself or a derivative thereof. The term covers all serotypes, subtypes, and both naturally occurring and recombinant forms, except where required otherwise. The abbreviation “rAAV” refers to recombinant adeno-associated virus, also referred to as a recombinant AAV vector (or “rAAV vector”). The term “AAV” includes AAV1, AAV2, AAV3, AAV4, AAV5, AAV6, AAV7, AAV8, AAV9, AAV10, AAV11, AAV12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). An rAAV vector may either be single-stranded (ssAAV) or self-complementary (scAAV). An "AAV virus" or "AAV viral particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV vector particle" or simply an "rAAV particle". Thus, production of rAAV particle necessarily includes production of rAAV vector, as such a vector is contained within an rAAV particle.

As used herein, the terms "treat", "treatment", "therapy" and the like refer to alleviating, delaying or slowing the progression, prophylaxis, attenuation, reducing the effects or symptoms, preventing onset, inhibiting, or ameliorating the onset of the diseases or disorders. The methods of the present disclosure may be used with any mammal. Exemplary mammals include, but are not limited to rats, cats, dogs, horses, cows, sheep, pigs, and more preferably humans. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, a therapeutic may be administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms (e.g., a reduction in the frequency, duration and/or severity of seizures). A prophylactic effect includes delaying or eliminating the appearance of a disease or condition, delaying or eliminating the onset of symptoms of a disease or condition, slowing, halting, or reversing the progression of a disease or condition, or any combination thereof.

The term "effective amount" or "therapeutically effective amount" refers to that amount of a composition described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

A "fragment" of a nucleotide or peptide sequence refers to a sequence that is shorter than a reference or "full-length" sequence.

A "variant" of a molecule refers to allelic variations of such sequences, that is, a sequence substantially similar in structure and biological activity to either the entire molecule, or to a fragment thereof.

A "functional fragment" of a DNA or protein sequence refers to a fragment that retains a biological activity (either functional or structural) that is substantially similar to a biological activity of the full-length DNA or protein sequence. A biological activity of a DNA sequence can be its ability to influence expression in a manner known to be attributed to the full-length sequence.

The terms "subject" and "individual" are used interchangeably herein to refer to a vertebrate, preferably a mammal, more preferably a human. The methods described herein can be useful in human therapeutics, veterinary applications, and/or preclinical studies in animal models of a disease or condition.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

In general, "sequence identity" or "sequence homology", which can be used interchangeably, refer to an exact nucleotide-to-nucleotide or amino acid-to-amino acid correspondence of two polynucleotides or polypeptide sequences, respectively. Typically, techniques for determining sequence identity include comparing two nucleotide or amino acid sequences and the determining their percent identity. Sequence comparisons, such as for the purpose of assessing identities, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings), the BLAST algorithm (see, e.g., the BLAST alignment tool available at blast.ncbi.nlm-.nih.gov/Blast.cgi, optionally with default settings), and the Smith-Waterman algorithm (see, e.g., the EMBOSS Water aligner available at www.ebi.ac.uk/Tools/psa/emboss_water/, optionally with default settings). Optimal alignment may be assessed using any suitable parameters of a chosen algorithm, including default parameters. The "percent identity", also referred to as "percent homology", between two sequences may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). High sequence identity generally includes ranges of sequence identity of approximately 80% to 100% and integer values there between.

As used herein, "engineered" with reference to a protein refers to a non-naturally occurring protein, including, but not limited to, a protein that is derived from a naturally occurring protein, or where a naturally occurring protein has been modified or reprogrammed to have a certain property.

As used herein, "synthetic" and "artificial" are used interchangeably to refer to a protein or a domain thereof that has low sequence identity (e.g., less than 50% sequence identity) to a naturally occurring human protein. For example, VPR and VP64 domains are synthetic transactivation domains.

As used herein, an "engineered transcription factor" or "eTF" refers to as a non-naturally occurring DNA binding protein or a non-naturally occurring transcription modulator that has been modified or reprogrammed to bind to a specific target binding site and/or to include a modified or replaced transcription effector domain.

As used herein, a "DNA binding domain" can be used to refer to one or more DNA binding motifs, such as a zinc finger or a basic helix-loop-helix (bHLH) motif, individually or collectively as part of a DNA binding protein.

The terms "transcription activation domain", "transcriptional activation domain", "transactivation domain", "transactivating domain" and "TAD" are used interchangeably herein and refer to a domain of a protein which in conjunction with a DNA binding domain can activate transcription from a promoter by contacting transcriptional machinery (e.g., general transcription factors and/or RNA polymerase) either directly or through other proteins known as co-activators.

The terms "transcriptional repressor domain", "transcription repressor domain" and "TRD" are used interchangeably herein and refer to a domain of a protein which in conjunction with a DNA binding domain can repress transcription from a promoter by contacting transcriptional machinery (e.g., general transcription factors and/or RNA polymerase) either directly or through other proteins known as co-repressors.

The term "GRCh38.p12" refers to Genome Reference Consortium Human Build 38 patch release 12 (GRCh38.p12) having GenBank Assembly Accession No. GCA_000001405.27 and dated 2017 Dec. 21.

Unless otherwise indicated, all terms used herein have the same meaning as they would to one skilled in the art and the practice of the present invention will employ, conventional techniques of molecular biology, microbiology, and recombinant DNA technology, which are within the knowledge of those of skill of the art.

Engineered Transcription Factors (eTFs) that Upregulate SCN1A

In one aspect, the application provides eTFs that are capable of upregulating expression of the sodium voltage gated channel alpha subunit 1 (SCN1A) gene and increasing expression of its corresponding protein product Nav1.1. The SCN1A gene belongs to a family of genes that code for subunits used for assembling sodium channels. These channels, which transport positively charged sodium ions into cells, play a key role in a cell's ability to generate and transmit electrical signals. The SCN1A gene encodes one part (the alpha subunit) of a sodium channel called Nav1.1. These channels are primarily found in the brain, where they control the flow of sodium ions into cells. Nav1.1 channels are involved in transmitting signals from one nerve cell (or neuron) to another. Several mutations in the SCN1A gene have been found to cause genetic epilepsy with febrile seizures plus (GEFS+), which is a spectrum of seizure disorders of varying severity. These conditions include simple febrile (fever-associated) seizures, which start in infancy and usually stop by age 5, and febrile seizures plus (FS+). FS+ involves febrile and other types of seizures, including those not related to fevers (afebrile seizures), that continue beyond childhood. The GEFS+ spectrum also includes other conditions, such as Dravet syndrome (also known as severe myoclonic epilepsy of infancy or SMEI), that cause more serious seizures that last longer and may be difficult to control. These recurrent seizures (epilepsy) can worsen over time and are often accompanied by a decline in brain function. Many other mutations have been associated with familial hemiplegic migraine, a form of migraine headache that runs in families and at least one mutation has been associated with the effectiveness of certain anti-seizure medications. Thus, an eTF provided herein that increases expression of SCN1A can be used to treat a variety of disease or disorders associated with mutations in the Nav1.1 channel.

Transcription factors (TFs) are proteins that bind specific sequences in the genome and control the expression of genes. The engineered transcription factors or eTFs provided herein that upregulate SCN1A are non-naturally occurring proteins that comprise a DNA binding domain (DBD) and at least one domain that is a transcriptional modulator, e.g., either a transcriptional activation domain (TAD) or a transcriptional repressor domain (TRD). In one embodiment, an eTF that upregulates SCN1A may comprise a DBD and a TAD (e.g., TAD-DBD or DBD-TAD), wherein the DBD and TAD may be derived from the same protein or from different proteins. In another embodiment, an eTF that upregulates SCN1A may comprise a DBD and two TADs, wherein the DBD and TADs are derived from the same protein, the DBD is derived from a first protein and both TADs are derived from a second protein, the DBD and one TAD are derived from a first protein and the second TAD is derived from a second protein, or the DBD is derived from a first protein, one TAD is derived from a second protein, and the second TAD is derived from a third protein (e.g., TAD1-DBD-TAD1, TAD1-DBD-TAD2, TAD1-TAD1-DBD, TAD1-TAD2-DBD, DBD-TAD1-TAD1, or DBD-TAD1-TAD2). In another embodiment, an eTF that upregulates SCN1A may comprise a DBD and three TADs, wherein the DBD and TADs are derived from the same protein, the DBD is derived from a first protein and the TADs are derived from one or more different proteins, or wherein the DBD and all of the TADs are all derived from different proteins e.g., TADx-TADx-TADx-DBD, TADx-TADx-DBD-TADx, TADx-DBD-TADx-TADx, or DBD-TADx-TADx-TADx, wherein each X is independently selected and may be the same or different from one or all of the other TADs. Examples include, for example, TAD1-TAD1-DBD-TAD1, TAD1-TAD1-DBD-TAD2, TAD1-TAD2-DBD-TAD1, TAD1-TAD2-DBD-TAD2, TAD1-TAD2-DBD-TAD3, TAD1-DBD-TAD1-TAD1, TAD1-DBD-TAD2-TAD2, TAD1-DBD-TAD1-TAD2, TAD2-DBD-TAD1-TAD2, TAD1-DBD-TAD2-TAD3, TAD1-TAD1-TAD1-DBD, TAD1-TAD2-TAD2-DBD, TAD1-TAD2-TAD2-DBD, TAD1-TAD2-TAD3-DBD, DBD-TAD1-TAD1-TAD1, DBD-TAD1-TAD1-TAD2, DBD-TAD1-TAD2-TAD2, or DBD-TAD1-TAD2-TAD3, etc. In another embodiment, an eTF that upregulates SCN1A may comprise a DBD and four TADs, wherein the DBD and TADs are derived from the same protein, the DBD is derived from a first protein and the TADs are derived from one or more different proteins, or wherein the DBD and all of the TADs are all derived from different proteins e.g., TADx-TADx-TADx-TADx-DBD, TADx-TADx-TADx-DBD-TADx, TADx-TADx-DBD-TADx-TADx, TADx-DBD-TADx-TADx-TADx or DBD-TADx-TADx-TADx-TADx, wherein each X is independently selected and may be the same or different from one or all of the other TADs. Examples include, for examples, TAD1-TAD1-DBD-TAD1-TAD1, TAD1-TAD1-DBD-TAD2-TAD2, TAD1-TAD2-DBD-TAD1-TAD2, TAD1-TAD2-DBD-TAD2-TAD1, TAD1-TAD2-DBD-TAD1-TAD3, TAD1-TAD3-DBD-TAD1-TAD2, TAD1-TAD2-DBD-TAD3-TAD4, TAD1-TAD1-TAD1-DBD-TAD2, TAD1-TAD2-TAD3-DBD-TAD4, TAD1-DBD-TAD1-TAD1-TAD2, TAD1-DBD-TAD2-TAD3-TAD4, TAD1-DBD-TAD1-TAD2-TAD3, TAD2-DBD-TAD1-TAD2-TAD3, TAD1-DBD-TAD2-TAD3-TAD4, TAD1-TAD1-TAD1-TAD1-DBD, TAD1-TAD2-TAD2-TAD3-DBD, TAD1-TAD2-TAD3-TAD4-DBD, DBD-TAD1-TAD1-TAD1-TAD1, DBD-TAD1-TAD1-TAD2-TAD2, DBD-TAD1-TAD2-TAD3-TAD4, or DBD-TAD1-TAD2-TAD3-TAD3, etc. In one embodiment, an eTF that upregulates SCN1A comprises a DBD and two TADs that are located at the same terminus of the DBD (e.g., N-terminus or C-terminus) wherein the DBD is derived from a first protein and both TADs are derived from a second protein, or the DBD is derived from a first protein, one TAD is derived from a second protein, and the second TAD is derived from a third protein (e.g., TAD1-TAD1-DBD, TAD1-TAD2-DBD, DBD-TAD1-TAD1, or DBD-TAD1-TAD2). In certain embodiments, the DBD may be a synthetic construct that contains domains from multiple proteins.

In certain embodiments, a DBD and a TAD and/or two TADs may be directly conjugated, e.g. with no intervening amino acid sequence, a DBD and a TAD and/or two TADs may be conjugated using a peptide linker, or combinations thereof. In certain embodiments, a DBD is conjugated to a TAD and/or one TAD is conjugated to a second TAD via a linker having 1, 2, 3, 4, 5, 6, 7, 8, 9, 10, 11, 12, 13, 14, 15, 16, 17, 18, 19, 20, 25, 30, 35, 40, 50, 60, 70, 75, 80, 90, or 100 amino acids, or from 1-5, 1-10, 1-20, 1-30, 1-40, 1-50, 1-75, 1-100, 5-10, 5-20, 5-30, 5-40, 5-50, 5-75, 5-100, 10-20, 10-30, 10-40, 10-50, 10-75, 10-100, 20-30, 20-40, 20-50, 20-75, or 20-100 amino acids. In some cases, the DBD and the TAD and/or two TADs are conjugated via naturally occurring intervening residues found in the naturally occurring proteins from which the domains are derived. In other embodiments, the DBD and TAD and/or two TADs are conjugated via a synthetic or exogenous linker sequence. Suitable linkers can be flexible, cleavable, non-cleavable, hydrophilic and/or hydrophobic. In certain embodiments, a DBD and a TAD and/or two TADs may be fused together via a linker comprising a plurality of glycine and/or serine residues. Examples of glycine/serine peptide linkers include [GS]n, [GGGS]n (SEQ ID NO: 179), [GGGGS]n (SEQ ID NO: 180), [GGSG]n (SEQ ID NO: 181), wherein n is an integer equal to or greater than 1. In certain embodiments, a linker useful for conjugating a DBD and a TAD and/or two TADs is GGSGGGSG (SEQ ID NO: 177). In certain embodiments, a linker useful for conjugating a DBD and a TAD and/or two TADs is GGSGGGSGGGSGGGSG (SEQ ID NO: 178). In certain embodiments, when a DBD is conjugated to two TADs, the first and second TADs may be conjugated to the DBD with the same or different linkers, or one TAD may be conjugated to the DBD with a linker and the other TAD is directly conjugated to the DBD (e.g., without an intervening linker sequence), or both TADs may be directly conjugated to the DBD (e.g., without intervening linker sequences). In certain embodiments, when a DBD is conjugated to two TADs on the same terminus (e.g., N-terminus or C-terminus), the linker connecting the two TADs may be the same or different from the linker connecting the TADs to the DBD, or the TADs may be conjugated to each other with a linker but the TADs are directly conjugated to the DBD (e.g., without an intervening linker sequence), or the TADs may be directly conjugated to each other (e.g., without intervening linker sequences) but the TADs are conjugated to the DBD with a linker. In certain embodiments, the eTFs provided herein that upregulate SCN1A do not comprise one or more HA tag(s) (e.g., SEQ ID NO: 171) located between the DBD and the one or more TADs.

The eTFs provided herein that upregulate SCN1A have different properties than naturally occurring transcription factors. In certain embodiments, an eTF that upregulates SCN1A comprises a DBD derived from a naturally occurring protein that has been modified such that the DBD binds to a different target site as compared to the naturally occurring protein from which it was derived and the eTF comprising such modified DBD modulates expression from a different gene (e.g., SCN1A) as compared to the naturally occurring protein from which the DBD was derived (e.g., a gene other than SCN1A). In other embodiments, an eTF provided herein that upregulates SCN1A comprises a TAD derived from a naturally occurring protein that has been modified such that the eTF comprising such modified TAD modulates expression from a different gene (e.g., SCN1A) as compared to the naturally occurring protein from which the TAD was derived (e.g., a gene other than SCN1A), and/or the eTF comprising such modified TAD differently modulates expression of SCN1A (e.g., upregulates vs. downregulates) as compared to the naturally occurring protein from which the TAD was derived. In certain embodiments, an eTF provided herein that upregulates SCN1A comprises a DBD derived from a naturally occurring protein and a TAD derived from a naturally occurring protein (either the same or different proteins), wherein both the DBD and TAD have been modified. In such embodiments, the DBD may bind to a different target site as compared to the naturally occurring protein from which it was derived, the eTF comprising such modified DBD and TAD modulates expression from a different gene (e.g., SCN1A) as compared to the naturally occurring proteins from which the domains were derived (e.g., gene(s) other than SCN1A), and/or the eTF comprising such modified DBD and TAD differently modulates expression of SCN1A (e.g., upregulates vs. downregulates) as compared to the naturally occurring proteins from which the DBD and TAD domains were derived.

DNA Binding Domains (DBDs)

The eTFs provided herein that upregulate SCN1A may comprise any suitable DBD that binds to a target site of interest (e.g., a target site that results in upregulation of SCN1A when bound by an eTF provided herein). In certain embodiments, the DBD may be a synthetically designed DBD. In other embodiments, the DBD may be derived from a naturally occurring protein. DBD families include basic helix-loop-helix (bHLH) (e.g., c-Myc), basic-leucine zipper (e.g., C/EBP), helix-turn-helix (e.g., Oct-1), and zinc fingers (e.g., EGR1 or EGR3). These families exhibit a wide range of DNA binding specificities and gene targets. As contemplated herein, any one of the known human transcription factor proteins can serve as a protein platform for engineering and/or reprogramming a DBD to recognize a specific target site resulting in modulation of expression of an endogenous SCN1A gene. In exemplary embodiments, a DBD provided herein comprises a zinc finger domain, a TALEN binding domain, or a gRNA/Cas complex.

The DBD provided herein may be designed to recognize any target site that results in upregulation of SCN1A. In exemplary embodiments, a DBD is designed to recognize a genomic location and upregulate expression of an endogenous SCN1A gene when bound by an eTF. Binding sites capable of modulating expression of an endogenous SCN1A gene when bound by an eTF provided herein may be located anywhere in the genome that results in modulation of gene expression of SCN1A. In various embodiments, the binding site may be located on a different chromosome from SCN1A, on the same chromosome as SCN1A, upstream of the transcriptional start site (TSS) of the SCN1A gene, downstream of the TSS of the SCN1A gene, proximal to the TSS of the SCN1A gene, distal to the SCN1A gene, within the coding region of the SCN1A gene, within an intron of the SCN1A gene, downstream of the polyA tail of the SCN1A gene, within a promoter sequence that regulates the SCN1A gene, or within an enhancer sequence that regulates the SCN1A gene.

The DBD may be designed to bind to a target binding site of any length so long as it provides specific recognition of the target binding site sequence by the DBD, e.g., with minimal or no off target binding. In certain embodiments, the target binding site may modulate expression of SCN1A when bound by an eTF at a level that is at least 2-fold, 5-fold, 10-fold, 20-fold, 50-fold, 75-fold, 100-fold, 150-fold, 200-fold, 250-fold, 500-fold, or greater as compared to all other genes. In certain embodiments, the target binding site may modulate expression of SCN1A when bound by an eTF at a level that is at least 2-fold, 5-fold, 10-fold, 20-fold, 50-fold, 75-fold, 100-fold, 150-fold, 200-fold, 250-fold, 500-fold, or greater as compared to the 40 nearest neighbor genes (e.g., the 40 genes located closest on the chromosome, either upstream or downstream, of the coding sequence of SCN1A). In certain embodiments, the target binding site may be at least 5 bp, 10 bp, 15 bp, 20 bp, 25 bp, 30 bp, 35 bp, 40 bp, 45 bp or 50 bp, or more. The specific length of the binding site will be informed by the type of DBD in the eTF. In general, the longer the length of the binding site, the greater the specificity for binding and modulation of gene expression (e.g., longer binding sites have fewer off target effects). In certain embodiments, an eTF having a DBD recognizing a longer target binding site has fewer off-target effects associated with non-specific binding (such as, for example, modulation of expression of an off-target gene or gene other than SCN1A) relative to the off-target effects observed with an eTF having a DBD that binds to a shorter target site. In some cases, the reduction in off-target binding is at least 1.2, 1.3, 1.4, 1.5, 2, 3, 4, 5, 6, 7, 8, 9, or 10 fold lower as compared to a comparable eTF having a DBD that recognizes a shorter target binding site.

In certain embodiments, a DBD provided herein can be modified to have increased binding affinity such that it binds to a target binding site for a longer period of time such that a TAD conjugated to the DBD is able to recruit more transcription factors and/or recruit such transcription factor for a longer period of time to exert a greater effect on the expression level of the endogenous SCN1A gene. In certain embodiments, a DBD may be modified to increase its specific binding (or on-target binding) to a desired target site and/or modified to decrease its non-specific or off-target binding.

In various embodiments, binding between a DBD or eTF and a target binding site may be determined using various methods. In certain embodiments, specific binding between a DBD or eTF and a target binding site may be determined using a mobility shift assay, DNase protection assay, or any other in vitro method known in the art for assaying protein-DNA binding. In other embodiments, specific binding between an eTF and a target binding site may be determined using a functional assay, e.g., by measuring expression (RNA or protein) of a gene (e.g., SCN1A) when the target binding site is bound by the eTF. For example, a target binding site may be positioned upstream of a reporter gene (such as, for example, eGFP) or the SCN1A gene on a vector contained in a cell or integrated into the genome of the cell, wherein the cell expresses the eTF. Alternatively, a vector expressing the eTF may be introduced into a cell type that naturally contains the SCN1A gene. Greater levels of expression of the reporter gene (or SCN1A) in the presence of the eTF as compared to a control (e.g., no eTF or an eTF that recognizes a different target site) indicate that the DBD of the eTF binds to the target site. Suitable in vitro (e.g., non cell based) transcriptional and translational systems may also be used in a similar manner. In certain embodiments, an eTF that binds to a target site may have at least 2-fold, 3-fold, 5-fold, 10-fold, 15-fold, 20-fold, 30-fold, 50-fold, 75-fold, 100-fold, 150-fold, or greater expression of the reporter gene or SCN1A as compared to a control (e.g., no eTF or an eTF that recognizes a different target site).

In certain embodiments, an eTF disclosed herein that upregulates SCN1A recognizes a target binding site that is at least 9 bp, 12 bp, 15 bp, 18 bp, 21 bp, 24 bp, 27 bp, 30 bp, 33 bp, or 36 bp in size; more than 9 bp, 12 bp, 15 bp, 18 bp, 21 bp, 24 bp, 27 bp, or 30 bp; or from 9-33 bp, 9-30 bp, 9-27 bp, 9-24 bp, 9-21 bp, 9-18 bp, 9-15 bp, 9-12 bp, 12-33 bp, 12-30 bp, 12-27 bp, 12-24 bp, 12-21 bp, 12-18 bp, 12-15 bp, 15-33 bp, 15-30 bp, 15-27 bp, 15-24 bp, 15-21 bp, 15-18 bp, 18-33 bp, 18-30 bp, 18-27 bp, 18-24 bp, 18-21 bp, 21-33 bp, 21-30 bp, 21-27 bp, 21-24 bp, 24-33 bp, 24-30 bp, 24-27 bp, 27-33 bp, 27-30 bp, or 30-33 bp. In exemplary embodiments, an eTF disclosed herein that upregulates SCN1A recognizes a target binding site that is 18-27 bp, 18 bp, or 27 bp.

In certain embodiments, an eTF disclosed herein that upregulates SCN1A recognizes a target binding site that is located on chromosome 2. In certain embodiments, an eTF disclosed herein that upregulates SCN1A recognizes a target binding site that is located on chromosome 2 within 110 kb, 100 kb, 90 kb, 80 kb, 70 kb, 60 kb, 50 kb, 40 kb, 30 kb, 20 kb, 10 kb, 5 kb, 4 kb, 3 kb, 2 kb, or 1 kb upstream or downstream of the TSS of SCN1A. In certain embodiments, an eTF disclosed herein that upregulates SCN1A recognizes a target binding site that is located on chromosome 2 within 110 kb upstream of the TSS of SCN1A. In certain embodiments, an eTF disclosed herein that upregulates SCN1A recognizes a target binding site that is located on chromosome 2 within 110 kb downstream of the TSS of SCN1A. In exemplary embodiments, such target binding sites are 18-27 bp, 18 bp, or 27 bp.

In certain embodiments, an eTF disclosed herein that upregulates SCN1A recognizes a target binding site that is located on chromosome 2 within positions 166179652-165989571, within positions 166128050-166127958, within positions 166155414-166140590, within positions 166179652-1661777272, or within positions 1659990246-165989592 (all with reference to GRCh38.p12). In exemplary embodiments, such target binding sites are 18-27 bp, 18 bp, or 27 bp.

In certain embodiments, an eTF disclosed herein that upregulates SCN1A recognizes a target binding site that is (i) 18-27 bp, 18 bp, or 27 bp, (ii) overlaps with a position on chromosome 2 selected from 166178880, 166177369, 166177362, 166177299, 166177299, 166155393, 166155264, 166149373, 166149176, 166149165, 166149118, 166148953, 166148565, 166142396, 166142391, 166142344, 166142239, 166141162, 166140928, 166140590, 165990076, 165989684, 165989571, 166155255, 166155099, 166148843, 166148361, 166142219, 166141090, 165990246, 165990193, 166149168, 166127991, 166128002, 166128037, or 166128025 (all with reference to GRCh38.p12), and (iii) is capable of producing at least a 1.2 fold increase in expression of SCN1A when bound by an eTF disclosed herein.

In certain embodiments, an eTF disclosed herein that upregulates SCN1A (i) binds to a target site comprising or consisting of any of SEQ ID NOs: 18, 25, 30, 31, or 35-66, and (ii) is capable of producing at least a 1.2 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, (ii) overlaps with a position on chromosome 2 selected from 166155255, 166155099, 166148843, 166148361, 166142219, 166141090, 165990246, 165990193, 166149168, 166127991, 166128002, 166128037, or 166128025 (all with reference to GRCh38.p12), and (iii) is capable of producing at least a 2 fold increase in expression of SCN1A when bound by an eTF disclosed herein.

In certain embodiments, an eTF disclosed herein that upregulates SCN1A (i) binds to a target site comprising or consisting of any of SEQ ID NOs: 18, 30, 31, 37, 38, 45, 47, 48, 49, 55, 61, 62, or 64, and (ii) is capable of producing at least a 2 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, and (ii) overlaps with a position on chromosome 2 selected from 166149168, 166127991, 166128002, 166128037 or 166128025 (all with reference to GRCh38.p12), and (iii) is capable of producing at least a 5 fold increase in expression of SCN1A when bound by an eTF disclosed herein.

In certain embodiments, an eTF disclosed herein that upregulates SCN1A (i) binds to a target site comprising or consisting of any of SEQ ID NOs: 18, 30, 31, 37, or 38, and (ii) is capable of producing at least a 5 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, (ii) overlaps with a position on chromosome 2 selected from 166128002, 166128037, or 166128025 (all with reference to GRCh38.p12), and (iii) is capable of producing at least a 15 fold increase in expression of SCN1A when bound by an eTF disclosed herein.

In certain embodiments, an eTF disclosed herein that upregulates SCN1A (i) binds to a target site comprising or consisting of any of SEQ ID NOs: 30, 37, or 38, and (ii) is capable of producing at least a 15 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, (ii) overlaps with a position on chromosome 2 selected from 166128037 or 166128025 (all with reference to GRCh38.p12), and (iii) is capable of producing at least a 20 fold increase in expression of SCN1A when bound by an eTF disclosed herein.

In certain embodiments, an eTF disclosed herein that upregulates SCN1A (i) binds to a target site comprising or consisting of any of SEQ ID NOs: 30 or 38, and (ii) is capable of producing at least a 20 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, (ii) overlaps with a position on chromosome 2 at position 166128025, and (iii) is capable of producing at least a 25 fold increase in expression of SCN1A when bound by an eTF disclosed herein.

In certain embodiments, an eTF disclosed herein that upregulates SCN1A (i) binds to a target site comprising or consisting of SEQ ID NO: 30, and (ii) is capable of producing at least a 25 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, and (ii) binds to a genomic region that is within at least 1 kb, 750 bp, 500 bp, 400 bp, 300 bp, 200 bp, 100 bp, or 50 bp of a genomic location having a sequence of any one of SEQ ID NOs: 18, 25, 30, 31, or 35-66. In certain embodiments, the target binding site is capable of producing at least a 1.2 fold, 2 fold, 5 fold, 15 fold, 20 fold, or 25 fold increase in expression of SCN1A when bound by an eTF disclosed herein.

In certain embodiments, an eTF disclosed herein that upregulates SCN1A recognizes a target binding site that is (i) 18-27 bp, 18 bp, or 27 bp, and (ii) binds to a genomic region that is at least partially overlapping with a genomic location having a sequence of any one of SEQ ID NOs: 18, 25, 30, 31, or 35-66. In certain embodiments, the target binding site is capable of producing at least a 1.2 fold, 2 fold, 5 fold, 15 fold, 20 fold, or 25 fold increase in expression of SCN1A when bound by an eTF disclosed herein.

In certain embodiments, an eTF disclosed herein that upregulates SCN1A recognizes a target binding site having any one of the following sequences: SEQ ID NOs: 18, 25, 30, 31, or 35-66. In certain embodiments, the target binding site is capable of producing at least a 1.2 fold, 2 fold, 5 fold, 15 fold, 20 fold, or 25 fold increase in expression of SCN1A when bound by an eTF disclosed herein.

In certain embodiments, an eTF disclosed herein that upregulates SCN1A results in at least 1.5 fold, 2 fold, 3 fold, 4 fold, 5 fold, 6 fold, 7 fold, 8 fold, 9 fold, 10 fold, 15 fold, 20 fold, 25 fold, 50 fold, 100 fold, or greater, or at least a 50%, 60%, 70%, 75%, 80%, 90%, 100%, 125%, 150%, 200%, 250%, 300%, 400%, or 500% or greater upregulation of SCN1A expression (SCN1A RNA and/or Nav1.1 protein) in a cell or in vivo as compared to a control (e.g., no eTF or an eTF that does not recognize the target site). In various embodiments, upregulation of SCN1A expression can be detected using PCR methods, Western blot, or immunoassays.

In certain embodiments, an eTF disclosed herein that upregulates SCN1A binds to a target site that is capable of increasing SCN1A expression by at least 1.2 fold, 1.3 fold, 1.4 fold, 1.5 fold, 1.6 fold, 1.7 fold, 1.8 fold, 1.9 fold, 2 fold, 3 fold, 4 fold, 5 fold, 8 fold, 10 fold, 12 fold, 15 fold, 18 fold, 20 fold, 25 fold, 30 fold, 40 fold, 50 fold, 75 fold, 100 fold, or greater or by at least 20%, 30%, 40%, 50%, 60%, 70%, 75%, 80%, 90%, 100%, 125%, 150%, 200%, 250%, 300%, 400%, or 500% or greater relative to a control in a transcriptional activation assay. An exemplary SCN1A transcriptional activation assay is provided herein in Example 3. Briefly, HEK293 are transfected with a plasmid carrying an eTF or a control eGFP reporter construct. 48 h following transfection, cells are collected, RNA is isolated, and reverse transcribed and the resulting cDNA samples are analyzed by qPCR (for example, using primers having SEQ ID NOs: 185 and 186) to quantify levels of endogenous SCN1A transcript. GAPDH may be used as a reference gene to determine relative levels of SCN1A expression.

In certain embodiments, an eTF disclosed herein that upregulates SCN1A has minimal off target effects, e.g., off-target effects associated with non-specific binding such as, for example, modulation of expression of an off-target gene or gene other than SCN1A. In one embodiment, an eTF disclosed herein that upregulates SCN1A specifically upregulates SCN1A as compared to a control by at least 5 fold, 10 fold, 15 fold, 20 fold, 25 fold, 30 fold, 40 fold, or 50 fold greater than the expression produced by the eTF for one or more off target genes as compared to a control. In an exemplary embodiment, an eTF disclosed herein that upregulates SCN1A specifically upregulates transcription from the SCN1A gene as compared to a control by at least 15 fold greater than the transcription of the 40 nearest neighbor genes (e.g., the 40 nearest genes located to the coding sequence of SCN1A on chromosome 2) produced by the eTF relative to a control, e.g., PLA2R1, ITGB6, RBMS1, TANK, PSMD14, TBR1, SLC4A10, DPP4, FAP, IFIH1, GCA, FIGN, GRB14, COBLL1, SLC38A11, SCN3A, SCN2A, CSRNP3, GALNT3, TTC21B, SCN9A, SCN7A, B3GALT1, STK39, CERS6, NOSTRIN, SPC25, ABCB11, DHRS9, BBSS, KLHL41, FASTKD1, PPIG, CCDC173, PHOSPHO2, KLHL23, SSB, METTL5, UBR3, and MYO3B (see TABLE 14). In various embodiments, upregulation of transcription from the SCN1A gene can be detected using PCR methods.

In certain embodiments, an eTF disclosed herein that upregulates SCN1A is capable of reducing the frequency of seizures in a hyperthermic seizure (HTS) assay in the Scn1a$^{tm1kea}$ mouse model of Dravet syndrome. In certain embodiments, an eTF disclosed herein is able to reduce the frequency of seizures at 42.6° C. in an HTS assay by at least 1.2 fold, 1.3 fold, 1.4 fold, 1.5 fold, 1.6 fold, 1.7 fold, 1.8 fold, 1.9 fold, 2.0 fold, or more or by at least 20%, 30% 40%, 50%, 55%, 60%, 65%, 70%, 75%, 80%, 85%, 90%, 95%, 100% or more as compared to a control (e.g., PBS treated or treatment with an AAV vector comprising a sequence encoding eGFP). In certain embodiments, an eTF disclosed herein is able to reduce the frequency of seizures at 42.6° C. in an HTS assay so that at least 60%, 62%, 65%, 70%, 75%, 76%, 80%, 85%, 86%, 87%, 88%, 89%, 90%, 91%, 92%, 93%, 94%, 95%, 96%, 97%, 98% or 99% of the mice run in the assay are seizure free at 42.6° C. An exemplary HTS assay is described herein in Example 6. Briefly, litters of pups produced from male Scn1a+/−mice crossed with female C57Bl/6J mice may be dosed with an AAV9 vector encoding an eTF that upregulates SCN1A as provided herein or a control vector encoding eGFP via bilateral ICV at P1. Mice may be dosed with ~1.0 E10-5.0 E12 gc/mouse. The HTS assay is performed in P26-P28 SCN1A heterozygous mice and SCN1A wild-type mice in a mixed 129Stac X C57BL/6 background by increasing the body temperature of the mice (under controlled conditions and with body temperature monitoring) by ~0.5° C. every 2 minutes until the onset of the first tonic-clonic seizure accompanied by loss of posture or until a body temperature of 43° C. is reached. A mouse is considered to be seizure free if no seizure with loss of posture is detected over the full course of the experiment.

In certain embodiments, an eTF disclosed herein that upregulates SCN1A is capable of increasing the survival of a mouse that is heterozygous for SCN1A, e.g., an Scn1a$^{tm1kea}$ mouse line. In certain embodiments, an eTF disclosed herein is able to increase the survival rate of SCN1A heterozygous mice at P100 by at least 1.2 fold, 1.3 fold, 1.4 fold, 1.5 fold, 1.6 fold, 1.7 fold, 1.8 fold, 1.9 fold, 2.0 fold, or more or by at least 20%, 30% 40%, 50%, 55%, 60%, 65%, 70%, 75%, 80%, 85%, 90%, 95%, 100% or more as compared to a control (e.g., PBS treated or treatment with an AAV vector comprising a sequence encoding eGFP). In certain embodiments, an eTF disclosed herein is able to increase the survival rate of SCN1A heterozygous mice at P100 so that at least 65%, 70%, 75%, 80%, 85%, 86%, 87%, 88%, 89%, 90%, 91%, 92%, 93%, 94%, 95%, 96%, 97%, 98%, 99% or 100% of the mice run in the assay are still alive at P100. An exemplary survival assay is described herein in Example 7. Briefly, litters of pups produced from male Scn1a+/−mice crossed with female C57Bl/6J mice may be dosed with AAV9 vector via bilateral ICV at P1. Mice may be dosed with ~1.0 E10-5.0 E12 gc/mouse. The number of mice that have survived to P100 is determined.

In certain embodiments, an eTF provided herein that upregulates SCN1A may comprise a DBD from a zinc finger protein, derived from a zinc finger protein, or that is a nuclease is inactivated zinc finger protein. A zinc finger is a small protein structural motif that is characterized by the coordination of one or more zinc ions ($Zn^{2+}$) in order to stabilize the fold. Zinc finger (Znf) domains are relatively small protein motifs that contain multiple finger-like protrusions that make tandem contacts with a DNA target site. The modular nature of the zinc finger motif allows for a large number of combinations of DNA sequences to be bound with high degree of affinity and specificity, and is therefore ideally suited for engineering protein that can be targeted to and bind specific DNA sequences. Many engineered zinc finger arrays are based on the zinc finger domain of the murine transcription factor Zif268. Zif268 has three individual zinc finger motifs that collectively bind a 9 by sequence with high affinity. A wide variety of zinc fingers proteins have been identified and are characterized into different types based on structure as further described herein. Any such zinc finger protein is useful in connection with the DBDs described herein.

Various methods for designing zinc finger proteins are available. For example, methods for designing zinc finger proteins to bind to a target DNA sequence of interest are described, see e.g., Liu Q, et al., Design of polydactyl zinc-finger proteins for unique addressing within complex genomes, Proc Natl Acad Sci USA. 94 (11): 5525-30 (1997); Wright D A et al., Standardized reagents and protocols for engineering zinc finger nucleases by modular assembly, Nat Protoc. Nat Protoc. 2006; 1(3):1637-52; and CA Gersbach and T Gaj, Synthetic Zinc Finger Proteins: The Advent of Targeted Gene Regulation and Genome Modification Technologies, Am Chem Soc 47: 2309-2318 (2014). In addition, various web based tools for designing zinc finger proteins to bind to a DNA target sequence of interest are publicly available, see e.g., the Zinc Finger Nuclease Design Software Tools and Genome Engineering Data. Analysis website from OmicX available on the world wide web at omictools- .com/zfns-category; and the Zinc Finger Tools design website from Scripps available on the world wide web at scripps.edu/barbas/zfdesign/zfdesignhome.php. In addition, various commercially available services for designing zinc finger proteins to bind to a DNA target sequence of interest are available, see e.g., the commercially available services or kits offered by Creative Biolabs (world wide web at creative-biolabs.com/Design-and-Synthesis-of-Artificial-Zinc-Finger-Proteins.html), the Zinc Finger Consortium Modular Assembly Kit available from Addgene (world wide web at addgene.org/kits/zfc-modular-assembly/), or the CompoZr Custom ZFN Service from Sigma Aldrich (world wide web at sigmaaldrich.com/life-science/zinc-finger-nuclease-technology/custom-zfn.html).

In certain embodiments, the eTFs provided herein that upregulate SCN1A comprise a DBD comprising one or more zinc fingers or is derived from a DBD of a zinc finger protein. In some cases, the DBD comprises multiple zinc fingers, wherein each zinc finger is linked to another zinc finger or another domain either at its N-terminus or C-terminus, or both via an amino acid linker. In some cases, a DBD provided herein comprises one or more zinc fingers from one or more of the zinc finger types described in TABLE 9. In some cases, a DBD provided herein comprises a plurality of zinc finger structures or motifs, or a plurality of zinc fingers having one or more of SEQ ID NOs: 152-167, or any combination thereof. In certain embodiments, a DBD comprises X-[ZF-X]n and/or [X-ZF]n-X, wherein ZF is a zinc finger domain having any one of the motifs listed in TABLE 9 (e.g., any one of SEQ ID NOs: 136-146), X is an amino acid linker comprising 1-50 amino acids, and n is an integer from 1-15, e.g., 1, 2, 3, 4, 5, 6, 7, 8, 9, 10, 11, 12, 13, 14, or 15, wherein each ZF can independently have the same sequence or a different sequence from the other ZF sequences in the DBD, and wherein each linker X can independently have the same sequence or a different sequence from the other X sequences in the DBD. Each zinc finger can be linked to another sequence, zinc finger, or domain at its C-terminus, N-terminus, or both. In a DBD, each linker X can be identical in sequence, length, and/or property (e.g., flexibility or charge), or be different in sequence, length, and/or property. In some cases, two or more linkers may be identical, while other linkers are different. In exemplary embodiments, the linker may be obtained or derived from the sequences connecting the zinc fingers found in one or more naturally occurring zinc finger proteins provided in TABLE 9. In other embodiments, suitable linker sequences, include, for example, linkers of 5 or more amino acids in length. See, also, U.S. Pat. Nos. 6,479,626; 6,903,185; and 7,153,949 for exemplary linker sequences of 6 or more amino acids in length, each of which is incorporated herein in their entireties. The DBD proteins provided herein may include any combination of suitable linkers between the individual zinc fingers of the protein. The DBD proteins described herein may include any combination of suitable linkers between the individual zinc fingers of the protein.

In certain embodiments, the eTFs provided herein that upregulate SCN1A comprise a DBD comprising one or more classic zinc fingers. A classical C2H2 zinc-finger has two cysteines in one chain and two histidine residues in another chain, coordinated by a zinc ion. A classical zinc-finger domain has two β-sheets and one α-helix, wherein the α-helix interacts with a DNA molecule and forms the basis of the DBD binding to a target site and may be referred to as the "recognition helix". In exemplary embodiments, the recognition helix of a zinc fingers comprises at least one amino acid substitution at position −1, 2, 3 or 6 thereby changing the binding specificity of the zinc finger domain. In other embodiments, an DBD provided herein comprises one or more non-classical zinc-fingers, e.g., C2-H2, C2-CH, and C2-C2.

In another embodiment, an eTF provided herein that upregulates SCN1A comprises a DBD comprising a zinc finger motif having the following structure: LEPGEKP-[YKCPECGKSFS X HQRTH TGEKP]n-YKCPECGKSFS X HQRTH-TGKKTS (SEQ ID NO: 147), wherein n is an integer from 1-15, e.g., 1, 2, 3, 4, 5, 6, 7, 8, 9, 10, 11, 12, 13, 14, or 15, and each X independently is a recognition sequence (e.g., a recognition helix) capable of binding to 3 bp of the target sequence. In exemplary embodiments, n is 3, 6 or 9. In a particularly preferred embodiment, n is 6. In various embodiments, each X may independently have the same amino acid sequence or a different amino acid sequence as compared to other X sequences in the DBD. In an exemplary embodiment, each X is a sequence comprising 7 amino acids that has been designed to interact with 3 bp of the target binding site of interest using the Zinger Finger Design Tool from Scripps located on world wide web at scripps.edu/barbas/zfdesign/zfdesignhome.php.

Since each zinc finger within a DBD recognizes 3 bp, the number of zinc fingers included in the DBD informs the length of the binding site recognized by the DBD, e.g., a DBD with 1 zinc finger will recognize a target binding site having 3 bp, a DBD with 2 zinc fingers will recognize a target binding site having 6 bp, a DBD with 3 zinc fingers will recognize a target binding site having 9 bp, a DBD with 4 zinc fingers will recognize a target binding site having 12 bp, a DBD with 5 zinc fingers will recognize a target binding site having 15 bp, a DBD with 6 zinc fingers will recognize a target binding site having 18 bp, a DBD with 9 zinc fingers will recognize a target binding site having 27 bp, etc. In general, DBD that recognize longer target binding sites will exhibit greater binding specificity (e.g., less off target or non-specific binding).

In other embodiments, an eTF provided herein that upregulates SCN1A comprises a DBD that is derived from a naturally occurring zinc finger protein by making one or more amino acid substitutions in one or more of the recognition helices of the zinc finger domains so as to change the binding specificity of the DBD (e.g., changing the target site recognized by the DBD). DBD provided herein may be derived from any naturally occurring zinc finger protein. In various embodiments, such DBD may be derived from a zinc finger protein of any species, e.g., a mouse, rat, human, etc. In an exemplary embodiment, a DBD provided herein is derived from a human zinc finger protein. In certain embodiments, a DBD provided herein is derived from a naturally occurring protein listed in TABLE 9. In an exemplary embodiment, a DBD protein provided herein is derived from a human EGR zinc finger protein, e.g., EGR1, EGR2, EGR3, or EGR4.

In certain embodiments, an eTF provided herein that upregulates SCN1A comprises a DBD that is derived from a naturally occurring protein by modifying the DBD to increase the number of zinc finger domains in the DBD protein by repeating one or more zinc fingers within the DBD of the naturally occurring protein. In certain embodiments, such modifications include duplication, triplication, quadruplication, or further multiplication of the zinc fingers within the DBD of the naturally occurring protein. In some cases, one zinc finger from a DBD of a human protein is multiplied, e.g., 2, 3, 4, 5, 6, 7, 8, 9, 10, 11, 12, or more copies of the same zinc finger motif is repeated in the DBD of the eTF. In some cases, a set of zinc fingers from a DBD of a naturally occurring protein is multiplied, e.g., a set of 3 zinc fingers from a DBD of a naturally occurring protein is duplicated to yield an eTF having a DBD with 6 zinc fingers, is triplicated to yield a DBD of an eTF with 9 zinc fingers, or is quadruplicated to yield a DBD of an eTF with 12 zinc fingers, etc. In some cases, a set of zinc fingers from a DBD of a naturally occurring protein is partially replicated to form a DBD of an eTF having a greater number of zinc fingers, e.g., a DBD of an eTF comprises four zinc fingers wherein the zinc fingers represent one copy of the first zinc finger, one copy of the second zinc finger, and two copies of a third zinc finger from a naturally occurring protein for a total of four zinc fingers in the DBD of the eTF. Such DBD are then further modified by making one or more amino acid substitutions in one or more of the recognition helices of the zinc finger domains so as to change the binding specificity of the DBD (e.g., changing the target site recognized by the DBD). In exemplary embodiments, the DBD is derived from a naturally occurring human protein, such as a human EGR zinc finger protein, e.g., EGR1, EGR2, EGR3, or EGR4.

Human EGR1 and EGR3 are characterized by a three-finger C2H2 zinc finger DBD. The generic binding rules for zinc fingers provide that all three fingers interact with its cognate DNA sequence with similar geometry, using the same amino acids in the alpha helix of each zinc finger to determine the specificity or recognition of the target binding site sequence. Such binding rules allow one to modify the DBD of EGR1 or EGR3 to engineer a DBD that recognizes a desired target binding site. In some cases, the 7-amino acid DNA recognition helix in a zinc finger motif of EGR1 or EGR3 is modified according to published zinc finger design rules. In certain embodiments, each zinc finger in the three-finger DBD of EGR1 or EGR3 is modified, e.g., by altering the sequence of one or more recognition helices and/or by increasing the number of zinc fingers in the DBD. In certain embodiments, EGR1 or EGR3 is reprogrammed to recognize a target binding site of at least 9, 12, 15, 18, 21, 24, 27, 30, 33, 36 or more base pairs at a desired target site. In certain embodiments, such DBD derived from ERG1 or EGR3 comprises at least 3, 4, 5, 6, 7, 8, 9, 10, 11, 12, or more zinc fingers. In exemplary embodiment, one or more of the zinc fingers in the DBD comprises at least one amino acid substitution at position −1, 2, 3 or 6 of the recognition helix.

In various embodiments, an eTF that upregulates SCN1A comprising a DBD derived from EGR1 or EGR3 has a DNA binding specificity that is different from the binding specificity of naturally occurring EGR1 or EGR3, e.g., the DBD recognizes a target binding site having a sequence different from the sequence of the binding site recognized by unmodified EGR1 or EGR3: (GCG(T/G)GGGCG) (SEQ ID NO: 182).

In other embodiments, an eTF provided herein that upregulates SCN1A comprises a DBD that is a gRNA/Cas complex. CRISPR (clustered regularly interspaced short palindromic repeats)/Cas9 is a genome editing tools that allows for site-specific genomic targeting. The type II CRISPR/Cas system is a prokaryotic adaptive immune response system that uses noncoding RNAs to guide the Cas9 nuclease to induce site-specific DNA cleavage. The CRISPR/Cas9 system has been harnessed to create a simple, RNA-programmable method to mediate genome editing in mammalian cells. A single guide RNA (sgRNA) may be generated to direct the Cas9 nuclease to a specific genomic location that is then bound by the gRNA/Cas9 complex. A gRNA may be designed to bind to a target site of interest using various methods and tools. For example, methods for designing gRNAs to bind to a target DNA sequence of interest are described in Aach, et al. Flexible algorithm for identifying specific Cas9 targets in genomes. BioRxiv, Cold Spring Harbor Labs. doi: dx.doi.org/10.1101/005074 (2014); Bae, et al. Cas-OFFinder: a fast and versatile algorithm that searches for potential off-target sites of Cas9 RNA-guided endonucleases. Bioinformatics. 30(10):1473-1475 (2014); Doench, J. G. et al. Optimized sgRNA design to maximize activity and minimize off-target effects of CRISPR-Cas9. Nat Biotech 34, 184-191 (2016); Gratz, et al. Highly specific and efficient CRISPR/Cas9-catalyzed homology-directed repair in *Drosophila*. Genetics. 196(4): 961-971 (2014); Heigwer, et al. E-CRISP: fast CRISPR target site identification. Nat Methods. 11(2):122-123 (2014); Ma, et al. A guide RNA sequence design platform for the CRISPR/Cas9 system for model organism genomes. Biomed Res Int. doi: doi.org/10.1155/2013/270805 (2013); Montague, et al. CHOPCHOP: a CRISPR/Cas9 and TALEN web tool for genome editing. Nucleic Acids Res. 42(W1): W401-W407 (2014); Liu, et al. CRISPR-ERA: a comprehensive design tool for CRISPR-mediated gene editing, repression and activation. Bioinformatics. 31(22):3676-3678 (2015); Ran, et al. In vivo genome editing using *Staphylococcus aureus* Cas9. Nature. 520(7546):186-191 (2015); Wu, et al. Target specificity of the CRISPR-Cas9 system. Quant Biol. 2(2):59-70 (2015); Xiao, et al. CasOT: a genome-wide Cas9/gRNA off-target searching tool. Bioinformatics. 30(8):1180-1182 (2014); Zetsche, et al. Cpf1 is a single RNA-guided endonuclease of a Class 2 CRISPR-Cas System. Cell. 163(3):759-771 (2015). In addition, various web based tools for designing gRNAs to bind to a DNA target sequence of interest are publicly available, see e.g., the CRISPR gRNA Design tool available from AUTM on world wide web at atum.bio/eCommerce/cas9/input?multipleContacts=false; the CRISPRa/i gRNA design tool available from the Broad Institute on the world wide web at portals.broadinstitute.org/gpp/public/analysis-tools/sgrna-design-crisprai; the E-CRISP design tool available from DKFZ German Cancer Research Center available on the world wide web at e-crisp.org/E-CRISP/; and the Knock-out Guide Design tool available from Synthego on the world wide web at design.synthego.com/#/. In addition, various commercially available services for designing gRNAs to bind to a DNA target sequence of interest are available, see e.g., the commercially available services offered by IDT (world wide web at idtdna.com/site/order/designtool/index/CRISPR_SEQUENCE), ThermoFisher (world wide web at thermofisher.com/order/custom-oligo/crispr), and GenScript (world wide web at genscript.com/gRNA-design-tool.html).

In exemplary embodiments, a DBD that is a gRNA/Cas complex comprises a nuclease deactivated Cas protein or dCas, such as for example, a dCas9, such as nuclease deactivated *Staphylococcus aureus* (dSaCas9) or nuclease deactivated *Streptococcus pyogenes* Cas9 (dSpCas9). The gRNA is provided as a sequence comprising a targeting region, which targets the gRNA/Cas complex to a desired target site, and scaffold region, that facilitates the interaction with the Cas protein. Any suitable gRNA scaffold may be used in connection with the gRNAs provided herein. In an exemplary embodiment, the gRNA is a single gRNA or sgRNA and comprises the following scaffold sequence: 5'-GTTTTAGTACTCTGGAAACAGAATC-TACTAAAACAAGGCAAAATGCCGTGTTTATCT CGT-CAACTTGTTGGCGAGA-3' (SEQ ID NO: 183). The targeting region of the guide RNA is attached to the 5' end of the scaffold sequence to form the complete sgRNA. In certain embodiments, a gRNA and dCas protein may be expressed from the same expression cassette. In certain embodiments, a U6 promoter is used to express the gRNA. In other embodiments, a gRNA may be expressed in a cell that has been engineered to stably express the dCas-TAD protein, e.g., either by stably integrating the dCas into the genome or on a plasmid that is stably maintained extrachromosomally.

In other embodiments, an eTF provided herein that upregulates SCN1A may comprise a DBD from a TALEN, derived from a TALEN, or that is a nuclease inactivated TALEN. Transcription activator-like effector nucleases (TALEN) are restriction enzymes that contain a DBD and a nuclease domain that can be engineered to cut specific sequences of DNA. TALENs are created by conjugating a TAL effector DNA binding domain to a DNA cleavage domain (e.g., a nuclease). Transcription activator-like effectors (TALEs) can be engineered to bind to a desired target DNA sequence thereby directing the nuclease domain to a specific location.

TAL effectors are bacterial proteins from *Xanthomonas* bacteria. The DNA binding domain contains a repeated highly conserved 33-34 amino acid sequence with divergent 12th and 13th amino acids. These two positions, referred to as the Repeat Variable Diresidue (RVD), are highly variable and show a strong correlation with specific nucleotide recognition. This straightforward relationship between amino acid sequence and DNA recognition allows the engineering of DBDs that specifically target a desired sequence by selecting a combination of repeat segments containing the appropriate RVDs.

Various methods for designing TALEs are available. For example, methods for designing TALEs to bind to a target DNA sequence of interest are described in T. Cermak et al., *Nucleic Acids Research.* 39 (12): e82 (2011); F. Zhang F et al., *Nature Biotechnology.* 29 (2): 149-53 (2011); R. Morbitzer et al., *Nucleic Acids Research.* 39 (13): 5790-9 (2011); T. Li et al., *Nucleic Acids Research.* 39 (14): 6315-25 (2011); R. Geissler et al., *PLOS One.* 6(5): e19509 (2011); and E. Weber et al., *PLOS One.* 6 (5): e19722 (2011). In addition, various web based tools for designing TALEs to bind to a DNA target sequence of interest are publicly available, see e.g., the E-Talen available on the world wide web at e-talen.org/E-TALEN/TAL and the Effector Nucleotide Targeter 2.0 tool available on the world wide web at tale-nt.cac.cornell.edu/node/add/single-tale. In addition, various commercially available services for designing TALEs to bind to a DNA target sequence of interest are available, see e.g., the commercially available services offered by OmicX (world wide web at omictools.com/), Addgene (world wide web at addgene.org/talen/guide/), or ThermoFisher (world wide web at thermofisher.com/us/en/home/life-science/genome-editing/geneart-tals/tal-design-tool.html). In addition, the publicly available software program (DNAWorks) may be used to design oligonucleotides suitable for assembly of TALEs, see e.g., D. Hoover D *Methods in Molecular Biology.* 852: 215-23 (2012).

Transcriptional Modulation Domains

The eTFs provided herein that upregulate SCN1A may comprise any suitable domain that is capable of recruiting one or more protein factors that can modulate transcription (e.g., RNA polymerase II, CBP/p300, CREB or KRAB) or the level of gene expression from a gene of interest when the eTF is bound to a target site via the DBD (e.g., a zinc finger DBD, gRNA/Cas DBD, or TALE DBD). In certain embodiments, such a domain recruits protein factors that increase the level of transcription or gene expression of a gene of interest and is a transcriptional activation domain (TAD). In other embodiments, such a domain recruits protein factors that decrease the level of transcription or gene expression from a gene of interest and is a transcriptional repressor domain (TRD). In certain embodiments, the transcriptional modulation domain (TAD or TRD) may be a synthetically designed domain. In other embodiments, the transcriptional modulation domain (TAD or TRD) may be derived from a naturally occurring protein, e.g., a transcription factor, a transcriptional co-activator, a transcriptional co-repressor, or a silencer protein. In various embodiments, the transcriptional modulation domain (TAD or TRD) may be derived from a protein of any species, e.g., a mouse, rat, monkey, virus, or human.

In one exemplary embodiment, a TAD suitable for use in the eTFs provided herein that upregulate SNC1A is derived from a viral protein. Exemplary TADs derived from viral proteins include, for example, a TAD domain of VP64 (SEQ ID NO: 133), VPR (SEQ ID NO: 132), VP16, VP128, p65, p300, or any functional fragment or variant thereof, or a sequence having at least 80%, 85%, 90%, 91%, 92%, 93%, 94%, 95%, 96%, 97%, 98%, or 99% sequence identity thereto.

In another exemplary embodiment, a TAD suitable for use in the eTFs provided herein that upregulate SCN1A is derived from a human protein. Exemplary TADs derived from human proteins include, for example, a TAD domain of CBP/p300-interacting transactivator 2 (CITED2) (SEQ ID NO: 134), CBP/p300-interacting transactivator 4 (CITED4) (SEQ ID NO: 135), EGR1 (SEQ ID NO: 176), CREB3 (SEQ ID NO: 224), or EGR3 (SEQ ID NO: 175), or any functional fragment or variant thereof, or a sequence having at least 80%, 85%, 90%, 91%, 92%, 93%, 94%, 95%, 96%, 97%, 98%, or 99% sequence identity thereto.

In certain embodiments, an eTF that upregulates SCN1A comprises a zinc finger DBD that is conjugated to a transcriptional activation domain or TAD. In various embodiments, the zinc finger DBD may be conjugated to a TAD from a viral protein, such as VP64 or VPR, or a TAD from a human protein, such as CITED2, CITED4, or CREB3. In certain embodiments, a zinc finger DBD derived from a human protein, e.g., EGR1 or EGR3, is conjugated to a TAD derived from a human protein, e.g., CITED2, CITED4, or CREB3. In certain embodiments, a zinc finger DBD derived from a human protein, e.g., EGR1 or EGR3, is conjugated to a VP64 or VPR TAD. In certain embodiments, a synthetic zinc finger DBD or zinc finger DBD having less than 75% sequence identity to a human protein, e.g., EGR1 or EGR3, is conjugated to a TAD derived from a human protein, e.g., CITED2, CITED4, or CREB3. In certain embodiments, a synthetic zinc finger DBD or zinc finger DBD having less than 75% sequence identity to a human protein, e.g., EGR1 or EGR3, is conjugated to a VP64 or VPR TAD.

In certain embodiments, a dCas protein is conjugated to a TAD. In various embodiments, the dCas9 may be conjugated to a TAD from a viral protein, such as VP64 or VPR, or a TAD from a human protein, such as CITED2, CITED4, or CREB3. In exemplary embodiments, a dCas9 is conjugated to a VP64 or VPR TAD.

In certain embodiments, a TALE protein is conjugated to a TAD. In various embodiments, the TALE may be conjugated to a TAD from a viral protein, such as VP64 or VPR, or a TAD from a human protein, such as CITED2, CITED4, or CREB3. In exemplary embodiments, a TALE is conjugated to a VP64 or VPR TAD.

eTFs that Upregulate SCN1A and are Highly Homologous to Human Proteins

In certain embodiments, an eTF disclosed herein that upregulates SCN1A has a high percent identity to one or more human proteins (as further described below). In certain embodiments, such eTFs have at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibit reduced immunogenicity as compared to an eTF having a lower overall percent sequence identity to one or more human proteins. In various embodiments, a reduction in immunogenicity can be measured using an elispot assay, an immunoassay, or an in silico method. In certain embodiments, such eTFs may comprise a DBD derived from human EGR1 or EGR3 and a TAD derived from human EGR1, EGR3, CITED2, CITED4, or CREB3. Such eTFs have little to no immunogenicity when administered to a subject or have reduced immunogenicity as compared to eTFs having lower percent identity to human protein sequences.

In certain embodiments, an eTF provided herein that upregulates SNC1A has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to one or more human proteins. When an eTF provided herein that upregulates SCN1A comprises a DBD and a TAD derived from the same protein, the percent identity to a human protein may be determined by calculating the total number of amino acid residues in the eTF that match the human protein from which it was derived (e.g., EGR1 or EGR3), divided by the total number of amino acid residues in the eTF. When an eTF provided that upregulates SCN1A comprises a DBD from one human protein and a TAD derived from a different human protein, the percent identity to human may be determined by separately calculating the percent identity to human of each domain and summing the two together, e.g., (i) calculating the total number of amino acid residues in the DBD that match the human protein from which it was derived (e.g., EGR1 or EGR3), divided by the total number of amino acid residues in the eTF; (ii) calculating the total number of amino acid residues in the TAD that match the human protein from which it was derived (e.g., CITED2, CITED4, or CREB3), divided by the total number of amino acid residues in the eTF; and (iii) summing the total of (i) and (ii). In such an embodiment, the domains are divided as follows: the first domain runs from the N-terminus of the eTF through the start of the coding sequence for the second domain, and the second domain runs from the start of the coding sequence for the second domain through the C-terminus of the eTF (e.g., for an eTF having the configuration NLS-DBD-linker-NLS-TAD, the first domain would be NLS-DBD-linker and the second domain would be NLS-TAD). When an eTF provided herein that upregulates SNC1A comprises a DBD from one human protein and two TADs derived from one or more different human protein, the percent identity to human may be determined by separately calculating the percent identity to human of each domain and summing all the three together, e.g., (i) calculating the total number of amino acid residues in the DBD that match the human protein from which it was derived (e.g., EGR1 or EGR3), divided by the total number of amino acid residues in the eTF; (ii) calculating the total number of amino acid residues in the first TAD that match the human protein from which it was derived (e.g., CITED2, CITED4, or CREB3), divided by the total number of amino acid residues in the eTF; (iii) calculating the total number of amino acid residues in the second TAD that match the human protein from which it was derived (e.g., CITED2, CITED4, or CREB3), divided by the total number of amino acid residues in the eTF; and (iv) summing the total of (i), (ii) and (iii). In such an embodiment, the domains are divided as follows: the first domain runs from the N-terminus of the eTF through the start of the coding sequence for the second domain, the second domain runs from the start of the coding sequence for the second domain through the start of the coding sequence for the third domain, and the third domain runs from the start of the coding sequence for the third domain through the C-terminus of the eTF (e.g., for an eTF having the configuration NLS-TAD1-linker-NLS-DBD-linker-NLS-TAD2, the first domain would be NLS-TAD1-linker, the second domain would be NLS-DBD-linker, and the third domain would be NLS-TAD2). The percent identity to one or more human proteins as described in this section may be determined using the percent identity output obtained using the standard protein BLAST tool available from the NCBI (e.g., the blastp suite alignment tool, using the blastp (protein→protein) algorithm with default parameters) available on the world wide web from the NCBI website at blast.ncbi.nlm.nih.gov/.

In certain embodiments, an eTF provided herein that upregulates SCN1A has the benefit of eliciting little, minimal, or no adverse immune response in a human subject due to a high degree of sequence identity to naturally occurring human proteins. In certain embodiments, an eTF provided herein that upregulates SCN1A elicits reduced immunogenicity, e.g., at least a 0.5, 1, 1.5, 2, 2.5, 3, 3.5, 4, 4.5, 5, 10, 15, 20, 25, 30, 35, 40, 45, or 50 fold or greater fold reduction in immunogenicity as compared to the immunogenicity observed with an eTF comprising a lower percent identity to one or more human proteins, e.g., an eTF comprising less than 50%, 55%, 65%, or 70% sequence identity to one or more human proteins. In some cases, reduction in immunogenicity can be measured using an elispot assay, an immunoassay, or an in silico method. A gene therapy having a low or minimal immunogenicity has several advantages, including improved patient tolerance, decreased dosage needed to achieve a therapeutic effect, prolonged therapeutic effects after one administration, ability to be administered multiple times or in multiple doses as needed, sustained therapeutic efficacy over a longer period of time per administration, increased safety, and/or increased effectiveness of a gene therapy.

In certain embodiments, the eTFs provided herein that upregulate SCN1A and have a high percent sequence identity to one or more human proteins comprise a DBD and a TAD derived from one or more naturally occurring human proteins. In certain embodiments, such eTFs may comprise a DBD derived from any naturally occurring human protein comprising a DBD. In exemplary embodiments, an eTF provided herein that upregulates SCN1A and has a high percent sequence identity to one or more human proteins comprises a DBD derived from a naturally occurring zinc finger protein, such as, for example, any one of Constructs 5-27, 36-41, or 44-53 listed in TABLE 1. In certain embodiments, an eTF provided herein that upregulates SCN1A and has a high percent sequence identity to one or more human proteins comprises a DBD derived from a human EGR protein, such as EGR1, EGR2, EGR3, or EGR4. In exemplary embodiments, an eTF provided herein that upregulates SCN1A and has a high percent sequence identity to one or more human proteins comprises a DBD derived from a human EGR1 or EGR3. In various embodiments, an eTF provided herein that upregulates SCN1A and has a high percent sequence identity to one or more human proteins comprises a DBD derived from a human zinc finger protein wherein minimal amino acid changes (e.g., 1, 2, 3, 4, 5, 6, 7, or 1-2, 1-3, 1-4, 1-5, 1-6, 1-7, 2-3, 2-4, 2-5, 2-6, 2-7, 3-4, 3-5, 36, or 3-7 amino acid changes) have been made in one or more zinc finger domains of the DBD to alter the binding specificity of the DBD to recognize a target binding site of interest. Such sequence modifications are preferably made in the recognition helices of the zinc finger domains of the DBD, while the rest of the human zinc finger DBD or protein (including the TAD) remains unmodified so as to preserve as much sequence identity to the naturally occurring human protein as possible.

In certain embodiments, the eTFs provided herein that upregulate SCN1A and have a high percent sequence identity to one or more human proteins comprises one or more transcriptional modulation domains (e.g., a TAD) derived from a human protein conjugated to a DBD derived from a human protein. In various embodiments, the transcriptional modulation domain may be derived from any naturally occurring human protein having a domain capable of recruiting one or more protein factors that can modulate transcription (e.g., RNA polymerase II, a co-activator protein, or a co-repressor protein) or the level of gene expression from a gene of interest when the eTF is bound to a target site via the DBD. In exemplary embodiments, the TAD is derived from a human EGR protein, such as for example, human EGR1, EGR2, EGR3 or EGR4, or a human cited protein, such as for example, a human CITED2 or CITED4 protein. In an exemplary embodiment, an eTF provided herein that upregulates SCN1A and has a high percent sequence identity to one or more human proteins comprises a TAD from a human EGR1 or EGR3 protein. In another exemplary embodiment, an eTF provided herein that upregulates SCN1A and has a high percent sequence identity to one or more human proteins comprises a TAD from a human CITED2 or CITED4 protein.

In one embodiment, an eTF provided herein that upregulates SCN1A and having a high percent sequence identity to one or more human proteins may comprise a human DBD (hDBD) and a human TAD (hTAD) (e.g., hTAD-hDBD or hDBD-hTAD), wherein the hDBD and hTAD may be derived from the same human protein or from human different proteins. In another embodiment, an eTF provided herein having a high percent sequence identity to one or more human proteins may comprise a hDBD and two hTADs, wherein the hDBD and hTADs are derived from the same human protein, the hDBD is derived from a first human protein and both hTADs are derived from a second human protein, the hDBD and one hTAD are derived from a first human protein and the second hTAD is derived from a second human protein, or the hDBD is derived from a first human protein, one hTAD is derived from a second human protein, and the second hTAD is derived from a third human protein (e.g., hTAD1-hDBD-hTAD1, hTAD1-hDBD-hTAD2, hTAD1-hTAD1-hDBD, hTAD1-hTAD2-hDBD, hDBD-hTAD1-hTAD1, or hDBD-hTAD1-hTAD2).

In exemplary embodiments, an eTF provided herein having a high percent sequence identity to one or more human proteins comprises any one of the following configurations: (i) a hDBD and a hTAD both derived from human EGR1; (ii) a hDBD and a hTAD both derived from human EGR3; (iii) a hDBD derived from human EGR1 and a hTAD derived from CITED2 (e.g., hEGR1 DBD-hCITED2 TAD or hCITED2 TAD-hEGR1 DBD); (iv) a hDBD derived from human EGR1 and a hTAD derived from human CITED4 (e.g., hEGR1 DBD-hCITED4 TAD or hCITED4 TAD-hEGR1 DBD); (v) a hDBD derived from human EGR3 and a hTAD derived from CITED2 (e.g., hEGR3 DBD-hCITED2 TAD or hCITED2 TAD-hEGR3 DBD); (vi) a hDBD derived from human EGR3 and a hTAD derived from human CITED4 (e.g., hEGR3 DBD-hCITED4 TAD or hCITED4 TAD-hEGR3 DBD); (vii) a hDBD derived from human EGR1 and two hTADs derived from CITED2 (e.g., hCITED2 TAD-hEGR1 DBD-hCITED2 TAD, hCITED2 TAD-hCITED2 TAD-hEGR1 DBD, or hEGR1 DBD-hCITED2 TAD-hCITED2 TAD); (viii) a hDBD derived from human EGR1 and two hTADs derived from human CITED4 (e.g., hCITED4 TAD-hEGR1 DBD-hCITED4 TAD, hCITED4 TAD-hCITED4 TAD-hEGR1 DBD, or hEGR1 DBD-hCITED4 TAD-hCITED4 TAD); (ix) a hDBD derived from human EGR3 and two hTADs derived from human CITED2 (e.g., hCITED2 TAD-hEGR3 DBD-hCITED2 TAD, hCITED2 TAD-hCITED2 TAD-hEGR3 DBD, or hEGR3 DBD-hCITED2 TAD-hCITED2 TAD); (x) a hDBD derived from human EGR3 and two hTADs derived from human CITED4 (e.g., hCITED4 TAD-hEGR3 DBD-hCITED4 TAD, hCITED4 TAD-hCITED4 TAD-hEGR3 DBD, or hEGR3 DBD-hCITED4 TAD-hCITED4 TAD); (xi) a hDBD derived from human EGR1, a first hTAD derived from human CITED2, a second hTAD derived from human CITED4 (e.g., hCITED2 TAD-hEGR1 DBD-hCITED4 TAD, hCITED4 TAD-hEGR1 DBD-hCITED2 TAD, hCITED2 TAD-hCITED4 TAD-hEGR1 DBD, hCITED4 TAD-hCITED2 TAD-hEGR1 DBD, hEGR1 DBD-hCITED4 TAD-hCITED2 TAD, or hEGR1 DBD-hCITED2 TAD-hCITED4 TAD); or (xii) a hDBD derived from human EGR3, a first hTAD derived from human CITED2, a second hTAD derived from human CITED4 (e.g., hCITED2 TAD-hEGR3 DBD-hCITED4 TAD, hCITED4 TAD-hEGR3 DBD-hCITED2 TAD, hCITED2 TAD-hCITED4 TAD-hEGR3 DBD, hCITED4 TAD-hCITED2 TAD-hEGR3 DBD, hEGR3 DBD-hCITED4 TAD-hCITED2 TAD, or hEGR3 DBD-hCITED2 TAD-hCITED4 TAD).

In certain embodiments, an eTF provided herein that upregulates SCN1A and has a high percent sequence identity to one or more human proteins comprises any one of: (i) a sequence comprising any one of SEQ ID NOs: 103-124, 128-131, 205, 207, 209, 213, 217, 219, 221, or 223; (ii) a sequence comprising any one of SEQ ID NOs: 92-98; (iii) a sequence comprising at least 80%, 85%, 86%, 87%, 88%, 89%, 90%, 91%, 92%, 93%, 94%, 95%, 96%, 97%, 98% or 99% sequence identity to any of the sequences of (i) or (ii); or (iv) a functional fragment or variant of any of the sequences of (i), (ii) or (iii). In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF provided herein that upregulates SCN1A and has a high percent sequence identity to one or more human proteins may additional comprise one or more amino acid sequences or domains in addition to the DBD and TAD domains, such as a nuclear localization signal or a linker, etc. In addition, a polynucleotide encoding an eTF provided herein having a high percent sequence identity to one or more human proteins may additional comprise one or more nucleic acid sequences in addition to the coding sequence for the eTF such as a promoter, enhancer, polyA tail, etc. In such embodiments, one or more of the additional amino acid sequences and/or nucleic acid sequences are preferably human sequences, derived from human sequences, or have at least 75%, 80%, 85%, 86%, 87%, 88%, 89%, 90%, 91%, 92%, 93%, 94%, 95%, 96%, 97%, 98% or 99% sequence identity to a human protein.

Exemplary SCN1A eTFs

In certain embodiments, an eTF disclosed herein that upregulates SCN1A comprises a DNA binding domain having one or more zinc finger domains comprising a recognition helix comprising any one of SEQ ID NOs: 152-167. In certain embodiments, an eTF disclosed herein that upregulates SCN1A comprises a DNA binding domain having at least one, two, three, four, five, six, seven, eight, nine, ten, eleven or twelve zinc finger domains, wherein each zinger finger domain independently comprises a recognition helix comprising any one of SEQ ID NOs: 152-167. In certain embodiments, an eTF disclosed herein that upregulates SCN1A comprises a DNA binding domain having six zinc finger domains, wherein each zinger finger domain independently comprises a recognition helix comprising any one of SEQ ID NOs: 152-167. In certain embodiments, an eTF disclosed herein that upregulates SCN1A comprises a DNA binding domain having nine zinc finger domains, wherein each zinger finger domain independently comprises a recognition helix comprising any one of SEQ ID NOs: 152-167. In exemplary embodiments, such eTFs comprise a DNA binding domain having SEQ ID NO: 147, wherein each X is independently selected from any one of SEQ ID NOs: 152-167, and n is 6 or 9.

In certain embodiments, an eTF disclosed herein that upregulates SCN1A comprises a DNA binding domain having any one of: (i) a sequence comprising RSDNLVR x REDNLHT x RSDELVR x QSGNLTE x TSGHLVR x QNSTLTE (SEQ ID NO: 148), wherein x can be a linker of 1-50 amino acids, (ii) a sequence having at least 80%, 85%, 90%, 95%, 96%, 97%, 98%, or 99% sequence identity to SEQ ID NO: 148, or (ii) a functional fragment of (i) or (ii). In certain embodiments, such an eTF further comprises one or more TADs selected from VP64, VPR, CITED2, CITED4, or CREB3. In one embodiment, such an eTF comprises a VPR TAD domain conjugated to the C-terminus of the DBD. In certain embodiments, such an eTF comprises a CITED2 TAD conjugated to the N-terminus, the C-terminus, or the N-terminus and C-terminus of the DBD. In certain embodiments, such an eTF comprises a CITED4 TAD conjugated to the N-terminus, the C-terminus, or the N-terminus and C-terminus of the DBD. In certain embodiments, such an eTF comprises two CITED4 TADs conjugated to the N-terminus or the C-terminus of the DBD. In certain embodiments, such an eTF is capable of binding to a target site having SEQ ID NO: 18 and upregulating expression of SCN1A by at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises a DNA binding domain having any one of: (i) a sequence comprising RSDNLVR x HRTTLTN x REDNLHT x TSHSLTE x QSSSLVR x REDNLHT (SEQ ID NO: 149), wherein x can be a linker of 1-50 amino acids, (ii) a sequence having at least 80%, 85%, 90%, 95%, 96%, 97%, 98%, or 99% sequence identity to SEQ ID NO: 149, or (ii) a functional fragment of (i) or (ii). In certain embodiments, such an eTF further comprises one or more TADs selected from VP64, VPR, CITED2, CITED4, or CREB3. In one embodiment, such an eTF comprises a VPR TAD domain conjugated to the C-terminus of the DBD. In certain embodiments, such an eTF comprises a CITED2 TAD conjugated to the N-terminus, the C-terminus, or the N-terminus and C-terminus of the DBD. In certain embodiments, such an eTF comprises a CITED4 TAD conjugated to the N-terminus, the C-terminus, or the N-terminus and C-terminus of the DBD. In certain embodiments, such an eTF comprises two CITED4 TADs conjugated to the N-terminus or the C-terminus of the DBD. In certain embodiments, such an eTF is capable of binding to a target site having SEQ ID NO: 30 and upregulating expression of SCN1A by at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises a DNA binding domain having any one of: (i) a sequence comprising RRDELNV x RSDHLTN x RSDDLVR x RSDNLVR x HRTTLTN x REDNLHT x TSHSLTE x QSSSLVR x REDNLHT (SEQ ID NO: 151), (ii) a sequence having at least 80%, 85%, 90%, 95%, 96%, 97%, 98%, or 99% sequence identity to SEQ ID NO: 151, or (ii) a functional fragment of (i) or (ii). In certain embodiments, such an eTF further comprises one or more TADs selected from VP64, VPR, CITED2, CITED4, or CREB3. In one embodiment, such an eTF comprises a VPR TAD domain conjugated to the C-terminus of the DBD. In certain embodiments, such an eTF comprises a CITED2 TAD conjugated to the N-terminus, the C-terminus, or the N-terminus and C-terminus of the DBD. In certain embodiments, such an eTF comprises a CITED4 TAD conjugated to the N-terminus, the C-terminus, or the N-terminus and C-terminus of the DBD. In certain embodiments, such an eTF comprises two CITED4 TADs conjugated to the N-terminus or the C-terminus of the DBD. In certain embodiments, such an eTF is capable of binding to a target site having SEQ ID NO: 32 and upregulating expression of SCN1A by at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises a DNA binding domain having any one of: (i) a sequence comprising DPGALVR x RSDNLVR x QSGDLRR x THLDLIR x TSGNLVR x RSDNLVR (SEQ ID NO: 150), (ii) a sequence having at least 89%, 85%, 90%, 95%, 96%, 97%, 98%, or 99% sequence identity to SEQ ID NO: 150, or (ii) a functional fragment of (i) or (ii). In certain embodiments, such an eTF further comprises one or more TADs selected from VP64, VPR, CITED2, CITED4, or CREB3. In one embodiment, such an eTF comprises a VPR TAD domain conjugated to the C-terminus of the DBD. In certain embodiments, such an eTF comprises a CITED2 TAD conjugated to the N-terminus, the C-terminus, or the N-terminus and C-terminus of the DBD. In certain embodiments, such an eTF comprises a CITED4 TAD conjugated to the N-terminus, the C-terminus, or the N-terminus and C-terminus of the DBD. In certain embodiments, such an eTF comprises two CITED4 TADs conjugated to the N-terminus or the C-terminus of the DBD. In certain embodiments, such an eTF is capable of binding to a target site having SEQ ID NO: 31 and upregulating expression of SCN1A by at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises any one of: (i) a sequence comprising any one of SEQ ID NOs: 99-131, 205, 207, 209, 213, 217, 219, 221, or 223; (ii) a sequence comprising any one of SEQ ID NOs: 77-98; (iii) a sequence comprising at least 80%, 85%, 86%, 87%, 88%, 89%, 90%, 91%, 92%, 93%, 94%, 95%, 96%, 97%, 98% or 99% sequence identity to any of the sequences of (i) or (ii); or (iv) a functional fragment or variant of any of the sequences of (i), (ii) or (iii). In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises any one of: (i) a sequence comprising any one of SEQ ID NOs: 99-102 or 125-127; (ii) a sequence comprising any one of SEQ ID NOs: 77-91; (iii) a sequence comprising at least 80%, 85%, 86%, 87%, 88%, 89%, 90%, 91%, 92%, 93%, 94%, 95%, 96%, 97%, 98% or 99% sequence identity to any of the sequences of (i) or (ii); or (iv) a functional fragment or variant of any of the sequences of (i), (ii) or (iii). In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises any one of: (i) a sequence comprising any one of SEQ ID NOs: 103-124, 128-131, 205, 207, 209, 213, 217, 219, 221, or 223; (ii) a sequence comprising any one of SEQ ID NOs: 92-98; (iii) a sequence comprising at least 80%, 85%, 86%, 87%, 88%, 89%, 90%, 91%, 92%, 93%, 94%, 95%, 96%, 97%, 98% or 99% sequence identity to any of the sequences of (i) or (ii); or (iv) a functional fragment or variant of any of the sequences of (i), (ii) or (iii). In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF disclosed herein that upregulates SCN1A comprises any one of: (i) a sequence comprising SEQ ID NO: 127; (ii) a sequence comprising at least 80%, 85%, 86%, 87%, 88%, 89%, 90%, 91%, 92%, 93%, 94%, 95%, 96%, 97%, 98% or 99% sequence identity to SEQ ID NO: 127; or (iii) a functional fragment or variant of any of the sequences of (i) or (ii). In exemplary embodiments, such eTFs comprise SEQ ID NO: 77 and bind to a target site having SEQ ID NO: 18. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control.

In certain embodiments, an eTF disclosed herein that upregulates SCN1A comprises any one of: (i) a sequence comprising SEQ ID NO: 128; (ii) a sequence comprising at least 80%, 85%, 86%, 87%, 88%, 89%, 90%, 91%, 92%, 93%, 94%, 95%, 96%, 97%, 98% or 99% sequence identity to SEQ ID NO: 128; or (iii) a functional fragment or variant of any of the sequences of (i) or (ii). In exemplary embodiments, such eTFs comprise SEQ ID NO: 92 and bind to a target site having SEQ ID NO: 18. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF disclosed herein that upregulates SCN1A comprises any one of: (i) a sequence comprising SEQ ID NO: 129; (ii) a sequence comprising at least 80%, 85%, 86%, 87%, 88%, 89%, 90%, 91%, 92%, 93%, 94%, 95%, 96%, 97%, 98% or 99% sequence identity to SEQ ID NO: 129; or (iii) a functional fragment or variant of any of the sequences of (i) or (ii). In exemplary embodiments, such eTFs comprise SEQ m NO: 92 and bind to a target site having SEQ ID NO: 18. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF disclosed herein that upregulates SCN1A comprises any one of: (i) a sequence comprising SEQ ID NO: 130; (ii) a sequence comprising at least 80%, 85%, 86%, 87%, 88%, 89%, 90%, 91%, 92%, 93%, 94%, 95%, 96%, 97%, 98% or 99% sequence identity to SEQ ID NO: 130; or (iii) a functional fragment or variant of any of the sequences of (i) or (ii). In exemplary embodiments, such eTFs comprise SEQ ID NO: 92 and bind to a target site having SEQ ID NO: 18. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF disclosed herein that upregulates SCN1A comprises any one of: (i) a sequence comprising SEQ ID NO: 131; (ii) a sequence comprising at least 80%, 85%, 86%, 87%, 88%, 89%, 90%, 91%, 92%, 93%, 94%, 95%, 96%, 97%, 98% or 99% sequence identity to SEQ ID NO: 131; or (iii) a functional fragment or variant of any of the sequences of (i) or (ii). In exemplary embodiments, such eTFs comprise SEQ ID NO: 92 and bind to a target site having SEQ ID NO: 18. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control, or by at least 20%, 30%, 40%, 50%, 60%, 70%, 75%, 80%, 90%, 100%, 125%, 150%, 200%, 250%, 300%, 400%, or 500% or greater as compared to a control. In exemplary embodiments, such eTFs have at least at least 75%, 80%, 85%, 86%, 87%, 88%, 89%, 90%, 91%, 92%, 93%, 94%, 95%, 96%, 97%, 98% or 99% overall sequence identity to one or more human proteins. In certain embodiments, such eTFs exhibits reduced immunogenicity as compared to an eTF having a lower overall percent sequence identity to one or more human proteins. In various embodiments, a reduction in immunogenicity can be measured using an elispot assay, an immunoassay, or an in silico method.

In certain embodiments, an eTF disclosed herein that upregulates SCN1A comprises a DBD comprising a gRNA/Cas complex, wherein the gRNA comprises a targeting sequence comprising any one of SEQ ID NOs: 35-66. The target sequence of the gRNA is attached to the 5' end of a scaffold sequence having the sequence: 5'-GTTTTAGTACTCTGGAAACAGAATCTACTAAAACAAGGCAAAATGCCGTGTTTATCT CGTCAACTTGTTGGCGAGA-3' (SEQ ID NO: 183). In exemplary embodiments, the Cas protein is a nuclease deactivated Cas9 protein. In certain embodiments, such an eTF further comprises one or more TADs conjugated to the Cas protein, wherein the TAD is selected from VP64, VPR, CITED2, CITED4, or CREB3. In one embodiment, such an eTF comprises a VPR TAD domain conjugated to the C-terminus of the Cas protein. In certain embodiments, such an eTF comprises a CITED2 TAD conjugated to the N-terminus, the C-terminus, or the N-terminus and C-terminus of the Cas protein. In certain embodiments, such an eTF comprises a CITED4 TAD conjugated to the N-terminus, the C-terminus, or the N-terminus and C-terminus of the Cas protein. In exemplary embodiments, such eTFs are capable of upregulating SCN1A expression by at least at least 2 fold, 5 fold, 10 fold, 15 fold, 20 fold, 25 fold, 30 fold, 40 fold, 50 fold, or greater as compared to a control.

Polynucleotides

In another aspect, the application provides polynucleotides encoding any of the eTFs that upregulate SNC1A disclosed herein. In another aspect the application provides polynucleotides comprising a PV selective microRNA binding site. In certain embodiments, the application provides polynucleotides comprising a PV selective regulatory element operably linked to a transgene and a PV selective microRNA binding site. In certain embodiments, the application provides polynucleotides comprising a sequence encoding an eTF that upregulates SCN1A as disclosed herein and a PV selective microRNA binding site. In certain embodiments, the application provides a PV selective regulatory element operably linked to a transgene encoding an eTF that upregulates SCN1A and a PV selective regulatory element.

Polynucleotides Encoding eTFs that Upregulate SCN1A

In certain embodiments, the application provides a polynucleotide comprising any one of the following: (i) a nucleic acid sequence encoding an eTF that upregulates SCN1A comprising any one of SEQ ID NOs: 77-131, 205, 207, 209, 213, 217, 219, 221, or 223, or a variant or a functional fragment thereof; (ii) a nucleic acid encoding a functional fragment of an eTF that upregulates SCN1A having any one of SEQ ID NOs: 77-131, 205, 207, 209, 213, 217, 219, 221, or 223; or (iii) a nucleic acid encoding an eTF that upregulates SCN1A having at least 70%, 75%, 80%, 85%, 86%, 87%, 88%, 89%, 90%, 91%, 92%, 93%, 94%, 95%, 96%, 97%, 98%, 99% or greater sequence identity to an eTF that upregulates SCN1A having any one of SEQ ID NOs: 77-131, 205, 207, 209, 213, 217, 219, 221, or 223, or a variant or a functional fragment thereof.

In certain embodiments, the application provides a polynucleotide comprising any one of the following: (i) a nucleic acid sequence encoding a DBD comprising any one of SEQ ID NOs: 92-98, or a variant or functional fragment thereof; (ii) a nucleic acid encoding a functional fragment of a DBD having any one of SEQ ID NOs: 92-98; or (iii) a nucleic acid encoding a DBD having at least 70%, 75%, 80%, 85%, 86%, 87%, 88%, 89%, 90%, 91%, 92%, 93%, 94%, 95%, 96%, 97%, 98%, 99% or greater sequence identity to a DBD having any one of SEQ ID NOs: 92-98, or a variant or functional fragment thereof, wherein the DBD is capable of binding to a target site bound by any one of SEQ ID NOs: 92-98.

In certain embodiments, the application provides a polynucleotide encoding an eTF that upregulates endogenous SCN1A, wherein the polynucleotide comprises any one of the following: (i) a nucleic acid sequence encoding an eTF comprising any one of SEQ ID NOs: 103-124, 128-131, 205, 207, 209, 213, 217, 219, 221, or 223; (ii) a nucleic acid encoding a functional fragment of an eTF having any one of SEQ ID NOs: 103-124, 128-131, 205, 207, 209, 213, 217, 219, 221, or 223; or (iii) a nucleic acid encoding an eTF having at least 70%, 75%, 80%, 85%, 86%, 87%, 88%, 89%, 90%, 91%, 92%, 93%, 94%, 95%, 96%, 97%, 98%, 99% or greater sequence identity to an eTF having any one of SEQ ID NOs: 103-124, 128-131, 205, 207, 209, 213, 217, 219, 221, or 223, wherein the eTF is capable of upregulating SCN1A.

In certain embodiments, the application provides a polynucleotide encoding a DBD that binds to a genomic target site capable of upregulating endogenous SCN1A when bound by an eTF disclosed herein, wherein the polynucleotide comprises any one of the following: (i) a nucleic acid sequence encoding a DBD comprising any one of SEQ ID NOs: 77-98; (ii) a nucleic acid encoding a functional fragment of a DBD having any one of SEQ ID NOs: 77-98; or (iii) a nucleic acid encoding an eTF having at least 70%, 75%, 80%, 85%, 86%, 87%, 88%, 89%, 90%, 91%, 92%, 93%, 94%, 95%, 96%, 97%, 98%, 99% or greater sequence identity to a DBD having any one of SEQ ID NOs: 77-98, wherein the DBD is capable of binding to a target site bound by any one of SEQ ID NOs: 77-98.

In certain embodiments, the application provides a polynucleotide encoding a DBD that binds to a genomic target site capable of upregulating endogenous SCN1A when bound by an eTF disclosed herein, wherein the polynucleotide comprises any one of the following: (i) a nucleic acid sequence encoding a DBD comprising any one of SEQ ID NOs: 148-151; (ii) a nucleic acid encoding a functional fragment of a DBD having any one of SEQ ID NOs: 148-151; or (iii) a nucleic acid encoding an eTF having at least 70%, 75%, 80%, 85%, 86%, 87%, 88%, 89%, 90%, 91%, 92%, 93%, 94%, 95%, 96%, 97%, 98%, 99% or greater sequence identity to a DBD having any one of SEQ ID NOs: 148-151, wherein the DBD is capable of binding to a target site bound by any one of SEQ ID NOs: 92-98.

In certain embodiments, the application provides a polynucleotide encoding an eTF capable of regulating endogenous SCN1A, wherein the polynucleotide comprises any one of the following: (i) a nucleic acid sequence having any of SEQ ID NOs: 70-76 or 184; (ii) a nucleic acid having a functional fragment of any one of the sequences of (i); or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii), wherein the polynucleotide encodes an eTF that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 70; (ii) a nucleic acid having a functional fragment of SEQ ID NO: 70; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 127, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 71; (ii) a nucleic acid having a functional fragment of SEQ ID NO: 71; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 127, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 72; (ii) a nucleic acid having a functional fragment of SEQ ID NO: 72; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 130, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 73; (ii) a nucleic acid sequence having a functional fragment of SEQ ID NO: 73; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 131, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 74; (ii) a nucleic acid sequence having a functional fragment of SEQ ID NO: 74; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 127, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 75; (ii) a nucleic acid sequence having a functional fragment of SEQ ID NO: 75; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 127, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 76; (ii) a nucleic acid sequence having a functional fragment of SEQ ID NO: 76; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 106, or a functional fragment or variant thereof that is capable of upregulating SCN1A.

In certain embodiments, the application provides a polynucleotide encoding an eTF capable of regulating endogenous SCN1A, wherein the polynucleotide comprises any one of the following: (i) a nucleic acid sequence having SEQ ID NO: 184; (ii) a nucleic acid sequence having a functional fragment of SEQ ID NO: 184; or (iii) a nucleic acid having at least 70%, 75%, 80%, 85%, 86%, 87%, 88%, 89%, 90%, 91%, 92%, 93%, 94%, 95%, 96%, 97%, 98%, 99% or greater sequence identity to any one of the sequences of (i) or (ii). In exemplary embodiments, such polynucleotides encode an eTF having SEQ ID NO: 106, or a functional fragment or variant thereof that is capable of upregulating SCN1A.

Polynucleotides Comprising MicroRNA Binding Sites for Selective Expression in PV Neurons In another aspect, the application provides polynucleotides comprising microRNA binding sites that lead to selective expression of a gene of interest in parvalbumin (PV) neurons. MicroRNAs or miRNAs are small non-coding RNAs (~20 nucleotides) that regulate gene expression post-transcriptionally by hybridizing to complementary recognition sites within an mRNA molecule and lead to inhibition of gene expression by promoting degradation of the mRNA transcript or by repressing translation of the protein encoded by the mRNA. The microRNA binding sites provided herein inhibit expression of a gene of interest in excitatory neurons thereby promoting selective expression of a gene of interest in PV neurons (e.g., PV selective microRNA binding sites). In certain embodiments, excitatory neurons are neurons that express one or more of STAC, Slc17a7, Car12 Syt17, ITPKA, Col6a1, CamKII, Sv2b, INHBA, and/or DKK3. In an exemplary embodiment, excitatory neurons are neurons that express CamKII.

In certain embodiments, the application provides polynucleotides comprising one or more microRNA binding sites for one or more microRNAs that promote PV selective expression, e.g., promote degradation of an mRNA comprising the microRNA binding site in excitatory neurons. Exemplary microRNAs that promote PV selective expression include, for example, miR-128, miR-221 and miR-222. In certain embodiments, the application provides polynucleotides comprising at least 1, 2, 3, 4, 5, 6, 7, 8, 9, 10 or more PV selective microRNA binding sites. In one embodiment, the application provides polynucleotides comprising at least 1, 2, 3, 4, 5, 6, 7, 8, 9, 10 or more miR-128 binding sites (SEQ ID NO: 9). In one embodiment, the application provides polynucleotides comprising at least 1, 2, 3, 4, 5, 6, 7, 8, 9, 10 or more miR-221 binding sites (SEQ ID NO: 11). In one embodiment, the application provides polynucleotides comprising at least 1, 2, 3, 4, 5, 6, 7, 8, 9, 10 or more miR-222 binding sites (SEQ ID NO: 13). In one embodiment, the application provides polynucleotides comprising at least 1 miR-128 binding site, at least one miR-221 binding site, and at least one miR-222 binding site. In one embodiment, the application provides polynucleotides comprising at least one miR-128 binding site and at least one miR-222 binding site. In one embodiment, the application provides polynucleotides comprising at least one miR-221 binding site and at least one miR-222 binding site. In an exemplary embodiment, the application provides polynucleotides comprising at least one miR-128 binding site (SEQ ID NO: 9) and at least one miR-221 binding site (SEQ ID NO: 11). In one embodiment, the application provides polynucleotides comprising at least 2 miR-128 binding sites (SEQ ID NO: 9) and at least 2 miR-221 binding sites (SEQ ID NO: 11). In one embodiment, the application provides polynucleotides comprising at least 3 miR-128 binding sites (SEQ ID NO: 9) and at least 3 miR-221 binding sites (SEQ ID NO: 11). In one embodiment, the application provides polynucleotides comprising at least 4 miR-128 binding sites (SEQ ID NO: 9) and at least 4 miR-221 binding sites (SEQ ID NO: 11), In one embodiment, the application provides polynucleotides comprising at least 5 miR-128 binding sites (SEQ ID NO: 9) and at least 5 miR-221 binding sites (SEQ ID NO: 11). In such embodiments, the binding sites may be arranged in any order. For example, for a construct containing 2 miR-128 binding sites and 2 miR-221 binding sites, the binding sites may be arranged in any of the following configurations: miR-128-miR-128-miR-221-miR221, miR-128-miR-221-miR-128-miR-221, miR-128 miR221-miR221-miR-128, miR-221-miR128-miR221-miR128, miR-221-miR128-miR128-miR221, or miR221-miR221-miR128-miR128, In an exemplary embodiment, the polynucleotides provided herein comprise a sequence having 4 miR-128 binding sites (SEQ ID NO: 9) followed by four miR-221 binding sites (SEQ ID NO: 11), e.g., miR-128 miR-128 miR128 miR-128 miR221, miR221-miR-221-miR221. In another exemplary embodiment, the polynucleotides provided herein comprise a sequence having 1 miR-221 sequence (SEQ ID NO: 11), 1 miR-222 sequence (SEQ ID NO: 13) and 1 miR-128 binding site (SEQ ID NO: 9), e.g., miR-221 miR222 miR128. In another exemplary embodiment, the polynucleotides provided, herein comprise a sequence having 2 miR-221 sequences (SEQ ID NO: 11), 2 miR-222 sequences (SEQ ID NO: 13) and 2 miR-128 binding site (SEQ ID NO: 9) arranged in the following order: miR-221-miR222-miR128-miR-221-miR222-miR128.

In polynucleotides having more than one microRNA binding site, the binding sites may be directly adjacent to one another in the polynucleotide sequence (e.g., no linker or intervening sequence between the binding sites) or may be separated from one another by at least 1, 2, 3, 4, 5, 6, 7, 8, 9, 10, 11, 12, 13, 14, 15, 16, 17, 18, 19, 20 or more nucleotides, or from 1-20, 1-15, 1-10, 1-9, 1-8, 1-7, 1-6, 1-5, 1-4, 1-3, or 1-2 nucleotides. In exemplary embodiments, the microRNA binding sites are separated by about 5 nucleotides or by 5 nucleotides. In exemplary embodiments, the sequences separating the microRNA binding sites (as well as the junctions formed between microRNA binding sites, or junctions formed between microRNA binding sites and the sequences separating the microRNA binding sites) are not complementary to any other microRNAs, or any other neuronal microRNAs.

In certain embodiments, the polynucleotides provided herein comprise a microRNA binding site having at least 70%, 75%. 80%, 85%, 90%, 91%, 92%, 93%, 94%. 95%, 96%, 97%, 98%, 99% or 100% identity to SEQ ID NO: 7. In an exemplary embodiment, the polynucleotides provided herein comprise a microRNA binding site comprising SEQ ID NO: 7.

In certain embodiments, the polynucleotides provided herein comprise a microRNA binding site having at least 70%, 75%, 80%, 85%, 90%, 91%, 92%, 93%, 94%, 95%, 96%, 97%, 98%, 99% or 100% identity to SEQ ID NO: 14. In an exemplary embodiment, the polynucleotides provided herein comprise a microRNA binding site comprising SEQ ID NO: 14.

In certain embodiments, the polynucleotides provided herein comprise a microRNA binding site having at least 70%, 75%, 80%, 85%, 90%, 91%, 92%, 93%, 94%, 95%, 96%, 97%, 98%, 99% or 100% identity to SEQ ID NO: 15.

In an exemplary embodiment, the polynucleotides provided herein comprise a microRNA binding site comprising SEQ ID NO: 15.

In certain embodiments, the microRNA binding sites provided herein are located within the 3' untranslated region of an mRNA transcript, e.g., following the translation termination codon TAA, TGA or TAG) and before the polyA tail. The microRNA binding site may be located directly adjacent to the translation termination codon or may be separated from the translation termination codon by at least 1, 2, 3, 4, 5, 6, 7, 8, 9, 10, 11, 12, 13, 14, 15, 16, 17, 18, 19, 20 or more nucleotides, or from 1-20, 1-15, 1-10, 1-9, 1-8, 1-7, 1-6, 1-5, 1-4, 1-3, or 1-2 nucleotides and/or may be located adjacent to the polyA tail or may be separated from the polyA tail by at least 1, 2, 3, 4, 5, 6, 7, 8, 9, 10, 11, 12, 13, 14, 15, 16, 17, 18, 19, 20 or more nucleotides, or from 1-20, 1-15, 1-10, 1-9, 1-8, 1-7, 1-6, 1-5, 1-4, 1-3, or 1-2 nucleotides.

In certain embodiments, a microRNA binding site provided herein results in selective gene expression in a PV cell as compared to off target cell types. In some cases, off target cell types include, but are not limited to, excitatory neurons, non-PV CNS cell-types, and non-neuronal CNS cell types. In certain embodiments, PV selective microRNA binding sites result in selective gene expression in PV neurons over at least one, two, three, four, five, or more non-PV CNS cell types. In some instances, a non-PV CNS cell is an excitatory neuron, a dopaminergic neuron, an astrocyte, a microglia, a motor neuron, a vascular cell, or a non-GABAergic neuron (e.g., a cell that does not express one or more of GAD2, GAD1, NKX2.1, DLX1, DLX5, SST and VIP), a non-PV neuron (e.g., a GABAergic neuron that does not express parvalbumin), or other CNS cells (e.g., CNS cell types that have never expressed any of PV, GAD2, GAD1, NKX2.1, DLX1, DLX5, SST and VIP). In an exemplary embodiment, a PV selective microRNA binding site provided herein result in increased selectivity in gene expression in PV neurons as compared to excitatory neurons (e.g., neurons that express one or more of STAG, Slc17a7, Car12, Syt17, ITPKA, Col6a1, CamKII, Sv2b, INHBA, and/or DKK3) by decreasing expression in the excitatory neurons. In some cases, cell types are distinguished by having a different cell marker, morphology, phenotype, genotype, function, and/or any other means for classifying cell types.

Selectivity of expression driven by a PV selective microRNA binding site can be measured in a number of ways. In one embodiment, selectivity of gene expression in a PV cell over non-PV cells can be measured by comparing the number of PV cells that express a detectable level of a transcript from a gene that contains a PV selective microRNA binding site to the total number of cells that express the gene (e.g., the ratio of PV vs. total cells (PV+non-PV cells) expressing the gene). For example, selectivity for PV neurons can be determined using an immunohistochemistry based colocalization assay using an expression cassette comprising a gene encoding a fluorescent protein (e.g., eGFP) and a PV selective microRNA binding site to measure gene expression and an antibody that identifies PV cells (e.g., an anti-PV antibody that interacts specifically with PV neurons) linked to a second fluorescence label (e.g., red fluorescent protein). Selectivity of expression in PV cells can be calculated by dividing the number of cells that express both PV and eGFP (e.g., PV cells) by the total number of cells that express eGFP (e.g., PV cells and non-PV cells), and multiplying by 100 to convert into a percentage. In another example, selectivity for PV neurons can be determined using an immunohistochemistry based colocalization assay using an expression cassette comprising a gene encoding a fluorescent protein (e.g., eGFP) and a PV selective microRNA binding site to measure gene expression and a first antibody that identifies PV cells (e.g., an anti-PV antibody that interacts specifically with PV neurons) linked to a second fluorescence label (e.g., red fluorescent protein) and a second antibody that identifies excitatory cells (e.g., an anti-CamKII antibody that interacts specifically with excitatory neurons). Selectivity of expression in PV cells can be calculated by dividing the number of cells that express both PV and eGFP (e.g., PV cells) by the number of cells that express eGFP+PV and eGFP+CamKII (e.g., PV cells and excitatory cells), and multiplying by 100 to convert into a percentage. The higher the percentage of PV cells that express the transgene, the more selective the microRNA binding site is for the PV cells. In certain embodiments, a PV selective microRNA binding site provided herein can be highly selective for expression in PV cells. For example, a PV selective microRNA binding site provided herein can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons (e.g., PV neurons/total cells×100 or PV neurons/PV+ excitatory neurons×100).

In some cases, a PV selective microRNA binding site provided herein is short. In some cases, the size of the PV selective microRNA binding site is compatible with the cloning capacity of a vector, e.g., a viral vector or rAAV, such that the combined size of a transgene, a promoter (and optional enhancer) and microRNA binding site does not exceed the cloning capacity of a vector. In some cases, a PV selective microRNA binding site has a length of up to about 500 bp, 400 bp, 300 bp, 250 bp, 225 bp, 215 bp, 210 bp, 200 bp, 150 bp, 140 bp, 135 bp, 130 bp, 125 bp, 120 bp, 115 bp, 110 bp, 100 bp, 90 bp, 80 bp, 75 bp, 70 bp, 65 bp, 60 bp or 50 bp. In some cases, a PV selective microRNA binding site is between about 50-500 bp, 50-400 bp, 50-300 bp, 50-250 bp, 50-200 bp, 50-100 bp, 50-75 bp, 50-70 bp, 100-500 bp, 100-400 bp, 100-300 bp, 100-250 bp, 100-200 bp, 100-150 bp, 100-140 bp, 100-135 bp, 200-500 bp, 200-400 bp, 200-300 bp, or 200-250 bp.

In exemplary embodiments, a polynucleotide provided herein that comprises one or more PV selective microRNA binding sites does not comprise SEQ ID NO: 67.

Expression Cassettes

In another aspect, the application provides expression cassettes comprising a polynucleotide provided herein (e.g., a polynucleotide comprising a sequence encoding an eTF that upregulates SCN1A and/or contains a PV selective microRNA binding site) and one or more regulatory elements. In certain embodiments, the application provides expression cassettes comprising a polynucleotide provided herein (e.g., a polynucleotide comprising a sequence encoding an eTF that upregulates SCN1A and/or contains a PV selective microRNA binding site) and a PV selective promoter.

In certain embodiments, a polynucleotide provided herein (e.g., a polynucleotide comprising a sequence encoding an eTF that upregulates SCN1A and/or contains a PV selective microRNA binding site) is part of an expression cassette comprising one or more regulatory elements in addition to the sequence encoding the eTF. In exemplary embodiments, a polynucleotide provided herein (e.g., a polynucleotide comprising a sequence encoding an eTF that upregulates SCN1A and/or contains a PV selective microRNA binding site) is part of an expression cassette comprising a promoter situated upstream of the transgene sequence so as to be capable of driving expression of the transgene (e.g., an eTF that selectively upregulates SCN1A) in a cell.

In certain embodiments, an expression cassette disclosed herein comprises a polynucleotide provided herein (e.g., a polynucleotide comprising a sequence encoding an eTF that upregulates SCN1A and/or contains a PV selective microRNA binding site) and a constitutive promoter situated upstream of the sequence encoding the transgene so as to be capable of driving expression of the transgene (e.g., an eTF that selectively upregulates SCN1A) in a cell. Examples of constitutive promoters include, a GAD2 promoter, a human synapsin promoter, CBA promoter, a CMV promoter, a minCMV promoter, a TATA box, a super core promoter, or an EF1a promoter, or a combination thereof.

In certain embodiments, an expression cassette disclosed herein comprises a polynucleotide provided herein (e.g., a polynucleotide comprising a sequence encoding an eTF that upregulates SCN1A and/or contains a PV selective microRNA binding site) and a short promoter capable of driving expression of the transgene (e.g., an eTF that selectively upregulates SCN1A) in a cell. In certain embodiments, a short promoter suitable for use in accordance with the nucleic acid molecules described herein comprises less than 500 bp, 450 bp, 400 bp, 350 bp, 300 bp, 250 bp, 225 bp, 200 bp, 175 bp, 150 bp, 145 bp, 140 bp, 135 bp, 130 bp, 125 bp, 120 bp, 115 bp, 110 bp, 105 bp, 100 bp, 95 bp, 90 bp, 85 bp, 80 bp or 75 bp, or from about 80-300 bp, 80-275 bp, 80-250 bp, 80-200 bp, 80-150 bp, 80-125 bp, 80-120 bp, 80-115 bp, 80-110 bp, 80-105 bp, 80-100 bp, 85-300 bp, 85-275 bp, 85-250 bp, 85-200 bp, 85-150 bp, 85-125 bp, 85-120 bp, 85-115 bp, 85-110 bp, 85-105 bp, 85-100 bp, 90-300 bp, 90-275 bp, 90-250 bp, 90-200 bp, 90-150 bp, 90-125 bp, 90-120 bp, 90-115 bp, 90-110 bp, 90-105 bp, 90-100 bp, 95-300 bp, 95-275 bp, 95-250 bp, 95-200 bp, 95-150 bp, 95-125 bp, 95-120 bp, 95-115 bp, 95-110 bp, 95-105 bp, 95-100 bp, 100-300 bp, 100-275 bp, 100-250 bp, 100-200 bp, 100-150 bp, 100-125 bp, 100-120 bp, 100-115 bp, 100-110 bp, or 100-105 bp. In exemplary embodiments, a short promoter suitable for use in accordance with the expression cassettes described herein comprises from about 100-120 bp, about 117 bp, or about 100 bp.

In certain embodiments, an expression cassette disclosed herein comprises a short promoter comprising or consisting of any one of (i) SEQ ID NO: 1; (ii) a variant or functional fragment thereof; or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii) operably linked to a polynucleotide encoding any one of the eTFs that selectively upregulate SCN1A as disclosed herein, and optionally containing a microRNA binding site as disclosed herein. Other examples of short promoter sequence may be found in PCT Publication No. WO 2018/213786.

In certain embodiments, an expression cassette disclosed herein comprises a polynucleotide provided herein (e.g., a polynucleotide comprising a sequence encoding an eTF that upregulates SCN1A and/or contains a PV selective microRNA binding site) and a cell type selective promoter situated upstream of the sequence encoding the transgene (e.g., an eTF that selectively upregulates SCN1A) so as to be capable of driving expression of the transgene selectively in a cell of interest. In certain embodiments, a cell type selective promoter may be selective for (e.g., selectively drive expression in) any cell type of interest, such as, for example, a heart cell, liver cell, muscle cell, bone cell, neuron, or sub populations thereof. In an exemplary embodiment, an expression cassette disclosed herein comprises a polynucleotide encoding an eTF that selectively upregulates SCN1A and a PV selective regulatory element (e.g., a promoter, enhancer, and/or promoter and enhancer) situated upstream of the sequence encoding the eTF so as to be capable of driving expression of the eTF selectively in a PV cell, and optionally a PV selective microRNA binding site. A PV selective regulatory element refers to a regulatory element that specifically modulates gene expression in a PV neuron. In certain embodiments, PV selective regulatory elements enhance expression in a PV neuron relative to one or more other CNS cell types. In certain embodiments, a PV selective regulatory element suppresses transcription and/or translation processes in off target cell-types.

In certain embodiments, a PV selective regulatory element provided herein results in selective gene expression in a PV cell as compared to off target cell types. In some cases, off target cell types include, but are not limited to, excitatory neurons, non-PV CNS cell-types, and non-neuronal CNS cell types. In certain embodiments, PV selective regulatory elements result in selective gene expression in PV neurons over at least one, two, three, four, five, or more non-PV CNS cell types. In some instances, a non-PV CNS cell is an excitatory neuron, a dopaminergic neuron, an astrocyte, a microglia, a motor neuron, a vascular cell, or a non-GABAergic neuron (e.g., a cell that does not express one or more of GAD2, GAD1, NKX2.1, DLX1, DLX5, SST and VIP), a non-PV neuron (e.g., a GABAergic neuron that does not express parvalbumin), or other CNS cells (e.g., CNS cell types that have never expressed any of PV, GAD2, GAD1, NKX2.1, DLX1, DLX5, SST and VIP). In some cases, a PV selective regulatory element provided herein result in increased selectivity in gene expression in PV neurons as compared to non-PV GABAergic cells. In some cases, cell types are distinguished by having a different cell marker, morphology, phenotype, genotype, function, and/or any other means for classifying cell types.

Selectivity of expression driven by a PV selective regulatory element can be measured in a number of ways. In one embodiment, selectivity of gene expression in a PV cell over non-PV cells can be measured by comparing the number of PV cells that express a detectable level of a transcript from a gene that is operably linked to a PV selective regulatory element to the total number of cells that express the gene (e.g., the ratio of PV vs. total cells (PV+non-PV cells) expressing the gene). For example, selectivity for PV neurons can be determined using an immunohistochemistry based colocalization assay using a gene encoding a fluorescent protein (e.g., eGFP) operably linked to a PV selective regulatory element to measure gene expression and an antibody that identifies PV cells (e.g., an anti-PV antibody that interacts specifically with PV neurons) linked to a second fluorescence label (e.g., red fluorescent protein). Selectivity of expression in PV cells can be calculated by dividing the number of cells that express both PV and eGFP (e.g., PV cells) by the total number of cells that express eGFP (e.g., PV cells and non-PV cells), and multiplying by 100 to convert into a percentage. The higher the percentage of PV cells that express the transgene, the more selective the regulatory element is for the PV cells. In certain embodiments, a PV selective regulatory element provided herein can be highly selective for expression in PV cells. For example, a PV selective regulatory element provided herein can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons (e.g., PV neurons/total cells×100).

In some cases, a PV selective regulatory element provided herein is short. In some cases, the size of the PV selective regulatory element is compatible with the cloning capacity of a vector, e.g., a viral vector or rAAV, such that the combined size of a transgene and one or more PV selective regulatory elements does not exceed the cloning capacity of a vector. In some cases, a PV selective regulatory element has a length of up to about 2050 bp, 2000 bp, 1900 bp, 1800 bp, 1700 bp, 1600 bp, 1500 bp, 1400 bp, 1300 bp, 1200 bp, 1100 bp, 1000 bp, 900 bp, 800 bp, 700 bp, 600 bp, 500 bp, 400 bp, 300 bp, 200 bp, or 100 bp. In some cases, a PV selective regulatory element is between about 500-600 bp, 500-700 bp, 500-800 bp, 500-900 bp, 500-1000 bp, 500-1500 bp, 500-2000 bp, or 500-2050 bp.

In certain embodiments, a PV selective regulatory element provided herein comprises or consists of any one of (i) SEQ ID NOs: 2-4; (ii) a variant, functional fragment, or a combination thereof; or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In some cases, a regulatory element comprises any one of SEQ ID NOs: 2-4. Other examples of PV selective regulatory elements may be found in PCT Publication No. WO 2018/187363.

In exemplary embodiments, the application provides expression cassettes comprising a nucleic acid sequence encoding an eTF that selectively upregulates SCN1A under the control of a PV selective regulatory element. In certain embodiments, the application provides expression cassettes comprising a nucleic acid sequence encoding an eTF that selectively upregulates SCN1A comprising a DBD having any one of the following sequences: SEQ ID NOs: 77-98 under the control of a PV selective regulatory element having any one of SEQ ID NOs: 2-4. In certain embodiments, the application provides expression cassettes comprising a nucleic acid sequence encoding an eTF that selectively upregulates SCN1A comprising any one of the following sequences: SEQ ID NOs: 99-131, 205, 207, 209, 213, 217, 219, 221, or 223 under the control of a PV selective regulatory element having any one of SEQ ID NOs: 2-4. In certain embodiments, the application provides expression cassettes comprising a nucleic acid sequence comprising any one of the following sequences: SEQ ID NOs: 67-73 under the control of a PV selective regulatory element having any one of SEQ ID NOs: 2-4. In certain embodiments, the application provides expression cassettes comprising a nucleic acid sequence encoding an eTF that selectively upregulates SCN1A comprising a DBD having any one of the following sequences: SEQ ID NOs: 148-151 under the control of a PV selective regulatory element having any one of SEQ ID NO: 2. In certain embodiments, the application provides expression cassettes comprising a nucleic acid sequence encoding an eTF that selectively upregulates SCN1A comprising any one of the following sequences: SEQ ID NOs: 99-131, 205, 207, 209, 213, 217, 219, 221, or 223 under the control of a PV selective regulatory element having any one of SEQ ID NO: 2. In certain embodiments, the application provides expression cassettes comprising a nucleic acid sequence comprising any one of the following sequences: SEQ ID NOs: 67-76 or 316 under the control of a PV selective regulatory element having any one of SEQ ID NO: 2.

In certain embodiments, the application provides expression cassettes comprising a PV selective microRNA binding site and a promoter and/or enhancer sequence. Any of the promoters described herein may be included in the expression cassette. In an exemplary embodiment, an expression cassette provided herein comprises a PV selective microRNA binding site and a PV selective regulatory element. In certain embodiments, an expression cassette provided herein comprises a PV selective microRNA binding site and a PV selective regulatory element comprising (i) any one of SEQ ID NOs: 2-4; (ii) a variant, functional fragment, or a combination thereof; or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In certain embodiments, an expression cassette provided herein comprises (1) a PV selective microRNA binding site comprising (i) any one of SEQ ID NOs: 7, 14 or 15; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (2) a PV selective regulatory element comprising (i) any one of SEQ ID NOs: 2-4; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In certain embodiments, an expression cassette provided herein comprises (1) a PV selective microRNA binding site comprising (i) SEQ ID NO: 7; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (2) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In one embodiment, an expression cassette provided herein comprises a microRNA binding site comprising SEQ ID NO: 7 and a PV selective regulatory element comprising SEQ ID NO: 2. In certain embodiments, a polynucleotide provided herein comprises (1) a PV selective microRNA binding site comprising (i) SEQ ID NO: 14; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (2) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In one embodiment, an expression cassette provided herein comprises a microRNA binding site comprising SEQ ID NO: 15 and a PV selective regulatory element comprising SEQ ID NO: 2. In certain embodiments, an expression cassette provided herein comprises (1) a PV selective microRNA binding site comprising (i) SEQ ID NO: 15; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (2) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In one embodiment, an expression cassette provided herein comprises a microRNA binding site comprising SEQ ID NO: 15 and a PV selective regulatory element comprising SEQ ID NO: 2.

In certain embodiments, an expression cassette provided herein comprising a PV selective microRNA binding site and a sequence encoding an eTF that upregulates expression of SCN1A as provided herein. In an exemplary embodiment, the application provides an expression cassette comprising a PV selective regulatory element, an eTF that upregulates expression of SCN1A as provided herein, and a PV selective microRNA binding site. In an exemplary embodiment, the application provides an expression cassette comprising (1) a PV selective regulatory element comprising (i) any one of SEQ ID NOs: 2-4; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 77-131, 205, 207, 209, 213, 217, 219, 221, or 223; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) any one of SEQ ID NOs: 7, 14 or 15; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 77 or 127; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 7; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 77 or 127; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 14; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 77 or 127; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 15; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 92 or 106; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 7; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 92 or 106; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 14; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii). In another exemplary embodiment, the application provides an expression cassette comprising (1) a PV selective regulatory element comprising (i) SEQ ID NO: 2; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), (2) a sequence encoding an eTF that upregulates SCN1A comprising (i) any one of SEQ ID NOs: 92 or 106; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii), and (3) a PV selective microRNA binding site comprising (i) SEQ ID NO: 15; (ii) a variant, functional fragment, or a combination thereof of (i); or (iii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of (i) or (ii).

In certain embodiments, an expression cassette provided herein comprising a PV selective regulatory element and a PV selective microRNA binding site is less than 5 kb, 4.9 kb, 4.8 kb, 4.7 kb, 4.6 kb, 4.5 kb, 4.4 kb, 4.3 kb, 4.2 kb, 4.1 kb, 4.0 kb, 3.9 kb, 3.8 kb, 3.7 kb, 3.6 kb, 3.5 kb, 3.4 kb, 3.3 kb, 3.2 kb, 3.1 kb, 3.0 kb, 2.9 kb, 2.8 kb, 2.7 kb, 2.6 kb, 2.5 kb, 2.4 kb, 2.3 kb, 2.2 kb, 2.1 kb, 2.0 kb, 1.9 kb, 1.8 kb, 1.7 kb, 1.6 kb, or 1.5 kb or less, or is from about 1.5-5 kb, 1.5-4.7 kb, 1.5-4.5 kb, 1.5-4.0 kb, 1.5-3.5 kb, 1.5-3.0 kb, 1.5-2.5 kb, 1.5-2.0 kb in size.

In certain embodiments, an expression cassette provided herein may comprise one more additional regulatory elements in an addition to a promoter, such as, for example, sequences associated with transcription initiation or termination, enhancer sequences, and efficient RNA processing signals. Exemplary regulatory elements include, for example, an intron, an enhancer, UTR, stability element, WPRE sequence, a Kozak consensus sequence, posttranslational response element, a microRNA binding site, or a polyadenylation (polyA) sequence, or a combination thereof. Regulatory elements can function to modulate gene expression at the transcriptional phase, post-transcriptional phase, or at the translational phase of gene expression. At the RNA level, regulation can occur at the level of translation (e.g., stability elements that stabilize mRNA for translation), RNA cleavage, RNA splicing, and/or transcriptional termination. In various embodiments, regulatory elements can recruit transcription factors to a coding region that increase gene expression selectivity in a cell type of interest, increases the rate at which RNA transcripts are produced, increase the stability of RNA produced, and/or increase the rate of protein synthesis from RNA transcripts. In an exemplary embodiment, an expression cassette provided herein comprises at least one PV selective microRNA binding site as provided herein.

In certain embodiments, the expression cassettes described herein further comprise a polyA sequence. Suitable polyA sequences include, for example, an artificial polyA that is about 75 bp in length (PA75) (see e.g., WO 2018/126116), the bovine growth hormone polyA, SV40 early polyA signal, SV40 late polyA signal, rabbit beta globin polyA, HSV thymidine kinase polyA, protamine gene polyA, adenovirus 5 EIb polyA, growth hormone polyA, or a PBGD polyA. In exemplary embodiments, a polyA sequence suitable for use in the expression cassettes provided herein is an hGH polyA (SEQ ID NO: 17) or a synthetic polyA (SEQ ID NO: 16). Typically, the polyA sequence is positioned downstream of the polynucleotide encoding the eTF in the expression cassettes described herein.

In certain embodiments, the expression cassettes provided herein further comprise one or more nucleic acid sequences encoding one or more nuclear localization signals (NLS). Any NLS peptide that facilitates import of the protein to which is attached into the cell nucleus may be used. Examples of NLS include, for example, the SV40 large T-antigen NLS, the nucleoplasmin NLS, EGL-13 NLS, c-Myc NLS and TUS-protein NLS. See e.g., C. Dingwall et al., J. Cell Biol. 107: 841-9 (1988); J. P. Makkerh et al., Curr Biol. 6: 1025-7 (1996); and M. Ray et al., Bioconjug. Chem. 26: 1004-7 (2015). The NLS may be located anywhere on the eTF protein sequence, but in preferred embodiments is conjugated to the N-terminus of the eTF or a domain of the eTF. In exemplary embodiments, the nucleic acid cassettes provided herein encode an eTF with an NLS fused to the N-terminus of the eTF. In other embodiments, the nucleic acid cassettes provided herein encode an eTF with a first NLS fused to the N-terminus of the eTF and a second NLS located between the DBD and the TAD domain of the eTF.

Expression Vectors

In certain embodiments, the expression cassettes described herein may be incorporated into an expression vector. Expression vectors may be used to deliver an expression cassette to a target cell via transfection or transduction. A vector may be an integrating or non-integrating vector, referring to the ability of the vector to integrate the expression cassette or transgene into the genome of the host cell. Examples of expression vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs)); episomal vectors; transposons (e.g., PiggyBac); and (b) viral vectors such as retroviral vectors, lentiviral vectors, adenoviral vectors, and adeno-associated viral vectors.

Expression vectors may be linear oligonucleotides or circular plasmids and can be delivered to a cell via various transfection methods, including physical and chemical methods. Physical methods generally refer to methods of delivery employing a physical force to counteract the cell membrane barrier in facilitating intracellular delivery of genetic material. Examples of physical methods include the use of a needle, ballistic DNA, electroporation, sonoporation, photoporation, magnetofection, and hydroporation. Chemical methods generally refer to methods in which chemical carriers deliver a nucleic acid molecule to a cell and may include inorganic particles, lipid-based vectors, polymer-based vectors and peptide-based vectors.

In some embodiments, an expression vector is administered to a target cell using a cationic lipid (e.g., cationic liposome). Various types of lipids have been investigated for gene delivery, such as, for example, a lipid nano emulsion (e.g., which is a dispersion of one immiscible liquid in another stabilized by emulsifying agent) or a solid lipid nanoparticle.

In some embodiments, an expression vector is administered to a target cell using a peptide based delivery vehicle. Peptide based delivery vehicles can have advantages of protecting the genetic material to be delivered, targeting specific cell receptors, disrupting endosomal membranes and delivering genetic material into a nucleus. In some embodiments, an expression vector is administered to a target cell using a polymer based delivery vehicle. Polymer based delivery vehicles may comprise natural proteins, peptides and/or polysaccharides or synthetic polymers. In one embodiment, a polymer based delivery vehicle comprises polyethylenimine (PEI). PEI can condense DNA into positively charged particles which bind to anionic cell surface residues and are brought into the cell via endocytosis. In other embodiments, a polymer based delivery vehicle may comprise poly-L-lysine (PLL), poly (DL-lactic acid) (PLA), poly (DL-lactide-co-glycoside) (PLGA), polyornithine, polyarginine, histones, protamines, dendrimers, chitosans, synthetic amino derivatives of dextran, and/or cationic acrylic polymers. In certain embodiments, polymer based delivery vehicles may comprise a mixture of polymers, such as, for example PEG and PLL.

In certain embodiments, an expression vector may be a viral vector suitable for gene therapy. Preferred characteristics of viral gene therapy vectors or gene delivery vectors may include the ability to be reproducibly and stably propagated and purified to high titers; to mediate targeted delivery (e.g., to deliver the transgene specifically to the tissue or organ of interest without widespread vector dissemination elsewhere); and to mediate gene delivery and transgene expression without inducing harmful side effects.

Several types of viruses, for example the non-pathogenic parvovirus referred to as adeno-associated virus, have been engineered for the purposes of gene therapy by harnessing the viral infection pathway but avoiding the subsequent expression of viral genes that can lead to replication and toxicity. Such viral vectors can be obtained by deleting all, or some, of the coding regions from the viral genome, but leaving intact those sequences (e.g., terminal repeat sequences) that may be necessary for functions such as packaging the vector genome into the virus capsid or the integration of vector nucleic acid (e.g., DNA) into the host chromatin.

In various embodiments, suitable viral vectors include retroviruses (e.g., A-type, B-type, C-type, and D-type viruses), adenovirus, parvovirus (e.g. adeno-associated viruses or AAV), coronavirus, negative strand RNA viruses such as orthomyxovirus (e.g., influenza virus), rhabdovirus (e.g., rabies and vesicular stomatitis virus), paramyxovirus (e. g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Examples of retroviruses include avian leukosis-sarcoma virus, human T-lymphotrophic virus type 1 (HTLV-1), bovine leukemia virus (BLV), lentivirus, and spumavirus. Other viruses include Norwalk virus, togavirus, flavivirus, reoviruses, papovavirus, hepadnavirus, and hepatitis virus, for example. Viral vectors may be classified into two groups according to their ability to integrate into the host genome—integrating and non-integrating. Oncoretroviruses and lentiviruses can integrate into host cellular chromatin while adenoviruses, adeno-associated viruses, and herpes viruses predominantly persist in the cell nucleus as extrachromosomal episomes.

In certain embodiments, a suitable viral vector is a retroviral vector. Retroviruses refer to viruses of the family Retroviridae. Examples of retroviruses include oncoretroviruses, such as murine leukemia virus (MLV), and lentiviruses, such as human immunodeficiency virus 1 (HIV-1). Retroviral genomes are single-stranded (ss) RNAs and comprise various genes that may be provided in cis or trans. For example, retroviral genome may contain cis-acting sequences such as two long terminal repeats (LTR), with elements for gene expression, reverse transcription and integration into the host chromosomes. Other components include the packaging signal (psi or ψ), for the specific RNA packaging into newly formed virions and the polypurine tract (PPT), the site of the initiation of the positive strand DNA synthesis during reverse transcription. In addition, the retroviral genome may comprise gag, pol and env genes. The gag gene encodes the structural proteins, the pol gene encodes the enzymes that accompany the ssRNA and carry out reverse transcription of the viral RNA to DNA, and the env gene encodes the viral envelope. Generally, the gag, pol and env are provided in trans for viral replication and packaging.

In certain embodiments, a retroviral vector provided herein may be a lentiviral vector. At least five serogroups or serotypes of lentiviruses are recognized. Viruses of the different serotypes may differentially infect certain cell types and/or hosts. Lentiviruses, for example, include primate retroviruses and non-primate retroviruses. Primate retroviruses include HIV and simian immunodeficiency virus (SIV). Non-primate retroviruses include feline immunodeficiency virus (FIV), bovine immunodeficiency virus (BIV), caprine arthritis-encephalitis virus (CAEV), equine infectious anemia virus (EIAV) and visnavirus. Lentiviruses or lentivectors may be capable of transducing quiescent cells. As with oncoretrovirus vectors, the design of lentivectors may be based on the separation of cis- and trans-acting sequences.

In certain embodiments, the application provides expression vectors that have been designed for delivery by an optimized therapeutic retroviral vector. The retroviral vector can be a lentivirus comprising a left (5') LTR; sequences which aid packaging and/or nuclear import of the virus; a promoter; optionally one or more additional regulatory elements (such as, for example, an enhancer or polyA sequence); optionally a lentiviral reverse response element (RRE); a construct comprising PV selective regulatory element operably linked to a sequence encoding an eTF; optionally an insulator; and a right (3') retroviral LTR.

In exemplary embodiments, a viral vector provided herein is an adeno-associated virus (AAV). AAV is a small, replication-defective, non-enveloped animal virus that infects humans and some other primate species. AAV is not known to cause human disease and induces a mild immune response. AAV vectors can also infect both dividing and quiescent cells without integrating into the host cell genome.

The AAV genome consists of a linear single stranded DNA which is ~4.7 kb in length. The genome consists of two open reading frames (ORF) flanked by an inverted terminal repeat (ITR) sequence that is about 145 bp in length. The ITR consists of a nucleotide sequence at the 5' end (5' ITR) and a nucleotide sequence located at the 3' end (3' ITR) that contain palindromic sequences. The ITRs function in cis by folding over to form T-shaped hairpin structures by complementary base pairing that function as primers during initiation of DNA replication for second strand synthesis. The two open reading frames encode for rep and cap genes that are involved in replication and packaging of the virion. In an exemplary embodiment, an AAV vector provided herein does not contain the rep or cap genes. Such genes may be provided in trans for producing virions as described further below.

In certain embodiments, an AAV vector may include a stuffer nucleic acid. In some embodiments, the stuffer nucleic acid may encode a green fluorescent protein or antibiotic resistance gene such as kanamycin or ampicillin.

In certain embodiments, the stuffer nucleic acid may be located outside of the ITR sequences (e.g., as compared to the eTF transgene sequence and regulatory sequences, which are located between the 5' and 3' ITR sequences).

Various serotypes of AAV exist, including AAV1, AAV2, AAV3, AAV4, AAV5, AAV6, AAV7, AAV8, AAV9, AAV10, AAV11, AAV12, and AAV13. These serotypes differ in their tropism, or the types of cells they infect. AAVs may comprise the genome and capsids from multiple serotypes (e.g., pseudotypes). For example, an AAV may comprise the genome of serotype 2 (e.g., ITRs) packaged in the capsid from serotype 5 or serotype 9. Pseudotypes may improve transduction efficiency as well as alter tropism.

In some cases, an AAV serotype that can cross the blood brain barrier or infect cells of the CNS is preferred. In some cases, AAV9 or a variant thereof is used to deliver an expression cassette of this disclosure, comprising a PV selective regulatory element operably linked to a transgene encoding an eTF that selectively upregulates SCN1A. In some cases, AAV9 or a variant thereof is used to deliver an expression cassette of this disclosure, comprising a PV selective microRNA binding site. In some cases, AAV9 or a variant thereof is used to deliver an expression cassette of this disclosure, comprising a PV selective regulatory element operably linked to a transgene encoding an eTF that selectively upregulates SCN1A, and a PV selective microRNA binding site In exemplary embodiments, the application provides expression vectors that have been designed for delivery by an AAV. The AAV can be any serotype, for examples, AAV1, AAV2, AAV3, AAV3b, AAV4, AAV5, AAV6, AAV7, AAV8, AAV9, AAV10, AAV11, AAV12, AAV-DJ, or a chimeric, hybrid, or variant AAV. The AAV can also be a self-complementary AAV (scAAV). In certain embodiments, an expression vector designed for delivery by an AAV comprises a 5' ITR and a 3' ITR. In certain embodiments, an expression vector designed for delivery by an AAV comprises a 5' ITR, a promoter, a transgene encoding an eTF, and a 3' ITR. In certain embodiments, an expression vector designed for delivery by an AAV comprises a 5' ITR, an enhancer, a promoter, a transgene encoding an eTF, a polyA sequence, and a 3' ITR.

Host Cells

In another aspect, the invention relates to a host cell comprising an expression cassette or expression vector as disclosed herein. Host cells may be a bacterial cell, a yeast cell, an insect cell or a mammalian cell. In an exemplary embodiment, a host cell refers to any cell line that is susceptible to infection by a virus of interest, and amenable to culture in vitro.

In certain embodiments, a host cell provided herein may be used for ex vivo gene therapy purposes. In such embodiments, the cells are transfected with a nucleic acid molecule or expression vector comprising a PV selective microRNA binding site and/or a sequence encoding an eTF that selectively upregulates SCN1A as disclosed herein and subsequently transplanted into the patient or subject. Transplanted cells can have an autologous, allogenic or heterologous origin. For clinical use, cell isolation will generally be carried out under Good Manufacturing Practices (GMP) conditions. Before transplantation, cell quality and absence of microbial or other contaminants is typically checked and preconditioning, such as with radiation and/or an immunosuppressive treatment, may be carried out. Furthermore, the host cells may be transplanted together with growth factors to stimulate cell proliferation and/or differentiation.

In certain embodiments, a host cell may be used for ex vivo gene therapy. Preferably, said cells are eukaryotic cells such as mammalian cells, these include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. A person skilled in the art will choose the more appropriate cells according to the patient or subject to be transplanted.

In certain embodiments, a host cell provided herein may be a cell with self-renewal and pluripotency properties, such as stem cells or induced pluripotent stem cells. Stem cells are preferably mesenchymal stem cells. Mesenchymal stem cells (MSCs) are capable of differentiating into at least one of an osteoblast, a chondrocyte, an adipocyte, or a myocyte and may be isolated from any type of tissue. Generally, MSCs will be isolated from bone marrow, adipose tissue, umbilical cord, or peripheral blood. Methods for obtaining thereof are well known to a person skilled in the art. Induced pluripotent stem cells (also known as iPS cells or iPSCs) are a type of pluripotent stem cell that can be generated directly from adult cells. Yamanaka et al. induced iPS cells by transferring the Oct3/4, Sox2, Klf4 and c-Myc genes into mouse and human fibroblasts, and forcing the cells to express the genes (WO 2007/069666). Thomson et al. subsequently produced human iPS cells using Nanog and Lin28 in place of Klf4 and c-Myc (WO 2008/118820).

In an exemplary embodiment, a host cell provided herein is a packaging cell. Said cells can be adherent or suspension cells. The packaging cell, and helper vector or virus or DNA construct(s) provide together in trans all the missing functions which are required for the complete replication and packaging of the viral vector.

Preferably, said packaging cells are eukaryotic cells such as mammalian cells, including simian, human, dog and rodent cells. Examples of human cells are PER.C6 cells (WO01/38362), MRC-5 (ATCC CCL-171), WI-38 (ATCC CCL-75), HEK-293 cells (ATCC CRL-1573), HeLa cells (ATCC CCL2), and fetal rhesus lung cells (ATCC CL-160). Examples of non-human primate cells are Vero cells (ATCC CCL81), COS-1 cells (ATCC CRL-1650) or COS-7 cells (ATCC CRL-1651). Examples of dog cells are MDCK cells (ATCC CCL-34). Examples of rodent cells are hamster cells, such as BHK21-F, HKCC cells, or CHO cells.

As an alternative to mammalian sources, cell lines for use in the invention may be derived from avian sources such as chicken, duck, goose, quail or pheasant. Examples of avian cell lines include avian embryonic stem cells (WO01/85938 and WO03/076601), immortalized duck retina cells (WO2005/042728), and avian embryonic stem cell derived cells, including chicken cells (WO2006/108846) or duck cells, such as EB66 cell line (WO2008/129058 & WO2008/142124).

In another embodiment, said host cell are insect cells, such as SF9 cells (ATCC CRL-1711), Sf21 cells (IPLB-Sf21), MG1 cells (BTI-TN-MG1) or High Five™ cells (BTI-TN-5B1-4).

In certain embodiments, the host cells provided herein comprising the recombinant AAV vector/genome of the invention (e.g., comprising a PV selective microRNA binding site and/or a sequence encoding an eTF that selectively upregulates SCN1A) may further comprise one or more additional nucleic acid constructs, such as, for example (i) a nucleic acid construct (e.g., an AAV helper plasmid) that encodes rep and cap genes, but does not carry ITR sequences; and/or (ii) a nucleic acid construct (e.g., a plasmid) providing the adenoviral functions necessary for AAV replication. In an exemplary embodiment, a host cell provided herein comprises: i) an expression vector comprising a PV selective microRNA binding site and/or a sequence encoding an eTF that selectively upregulates SCN1A as provided herein (i.e., the recombinant AAV genome); ii) a nucleic acid construct encoding AAV rep and cap genes which does not carry the ITR sequences; and iii) a nucleic acid construct comprising adenoviral helper genes (as described further below).

In certain embodiments, the rep, cap, and adenoviral helper genes can be combined on a single plasmid (Blouin V et al. J Gene Med. 2004; 6(suppl): S223-S228; Grimm D. et al. Hum. Gene Ther. 2003; 7: 839-850). Thus, in another exemplary embodiment, a host cell provided herein comprises: i) an expression vector comprising a PV selective microRNA binding site and/or a sequence encoding an eTF that selectively upregulates SCN1A as disclosed herein (i.e., the recombinant AAV genome); and ii) a plasmid encoding AAV rep and cap genes which does not carry the ITR sequences and further comprising adenoviral helper genes.

In another embodiment, a host cell provided herein comprises: a) an expression vector comprising a PV selective microRNA binding site and/or a sequence encoding an eTF that selectively upregulates SCN1A as disclosed herein (i.e., the recombinant AAV genome); b) a plasmid encoding AAV rep and cap genes which does not carry the ITR sequences; and c) a plasmid comprising adenoviral helper genes E2a, E4, and VA RNAs; wherein co-transfection is performed in cells, preferably mammalian cells, that constitutively express and transcomplement the adenoviral E1 gene, like HEK-293 cells (ATCC CRL-1573).

In certain embodiments, a host cell suitable for large-scale production of AAV vectors is an insect cells that can be infected with a combination of recombinant baculoviruses (Urabe et al. Hum. Gene Ther. 2002; 13: 1935-1943). For example, SF9 cells may be co-infected with three baculovirus vectors respectively expressing AAV rep, AAV cap and the AAV vector to be packaged. The recombinant baculovirus vectors will provide the viral helper gene functions required for virus replication and/or packaging.

Further guidance for the construction and production of virions for gene therapy according to the invention can be found in: Viral Vectors for Gene Therapy, Methods and Protocols. Series: Methods in Molecular Biology, Vol. 737. Merten and Al-Rubeai (Eds.); 2011 Humana Press (Springer); Gene Therapy. M. Giacca. 2010 Springer-Verlag; Heilbronn R. and Weger S. Viral Vectors for Gene Transfer: Current Status of Gene Therapeutics. In: Drug Delivery, Handbook of Experimental Pharmacology 197; M. Schafer-Korting (Ed.). 2010 Springer-Verlag; pp. 143-170; Adeno-Associated Virus: Methods and Protocols. R. O. Snyder and P. Mollier (Eds). 2011 Humana Press (Springer); Bunning H. et al. Recent developments in adeno-associated virus technology. J. Gene Med. 2008; 10:717-733; and Adenovirus: Methods and Protocols. M. Chillon and A. Bosch (Eds.); Third. Edition. 2014 Humana Press (Springer).

Virions & Methods of Producing Virions

In certain embodiments, the application provides viral particles comprising a viral vector comprising a PV selective microRNA binding site and/or a sequence encoding an eTF that selectively upregulates SCN1A as disclosed herein. The terms "viral particle", and "virion" are used herein interchangeably and relate to an infectious and typically replication-defective virus particle comprising the viral genome (e.g., the viral expression vector) packaged within a capsid and, as the case may be e.g., for retroviruses, a lipidic envelope surrounding the capsid. A "capsid" refers to the structure in which the viral genome is packaged. A capsid consists of several oligomeric structural subunits made of proteins. For example, AAV have an icosahedral capsid formed by the interaction of three capsid proteins: VP1, VP2 and VP3. In one embodiment, a virion provided herein is a recombinant AAV virion or rAAV virion obtained by packaging an AAV vector comprising a PV selective regulatory element and a PV selective microRNA binding site. In another embodiment, a virion provided herein is a recombinant AAV virion or rAAV virion obtained by packaging an AAV vector comprising a PV selective regulatory element operably linked to a sequence encoding an eTF that selectively upregulates SCN1A as described herein in a protein shell. In another embodiment, a virion provided herein is a recombinant AAV virion or rAAV virion obtained by packaging an AAV vector comprising a PV selective regulatory element operably linked to a sequence encoding an eTF that selectively upregulates SCN1A as described herein and a PV selective microRNA binding site in a protein shell.

In certain embodiments, a recombinant AAV virion provided herein may be prepared by encapsidating an AAV genome derived from a particular AAV serotype in a viral particle formed by natural Cap proteins corresponding to an AAV of the same particular serotype. In other embodiments, an AAV viral particle provided herein comprises a viral vector comprising ITR(s) of a given AAV serotype packaged into proteins from a different serotype. See e.g., Bunning H et al. J Gene Med 2008; 10: 717-733. For example, a viral vector having ITRs from a given AAV serotype may be packaged into: a) a viral particle constituted of capsid proteins derived from a same or different AAV serotype (e.g. AAV2 ITRs and AAV9 capsid proteins; AAV2 ITRs and AAV8 capsid proteins; etc.); b) a mosaic viral particle constituted of a mixture of capsid proteins from different AAV serotypes or mutants (e.g. AAV2 ITRs with AAV1 and AAV9 capsid proteins); c) a chimeric viral particle constituted of capsid proteins that have been truncated by domain swapping between different AAV serotypes or variants (e.g. AAV2 ITRs with AAV8 capsid proteins with AAV9 domains); or d) a targeted viral particle engineered to display selective binding domains, enabling stringent interaction with target cell specific receptors (e.g. AAV5 ITRs with AAV9 capsid proteins genetically truncated by insertion of a peptide ligand; or AAV9 capsid proteins non-genetically modified by coupling of a peptide ligand to the capsid surface).

The skilled person will appreciate that an AAV virion provided herein may comprise capsid proteins of any AAV serotype. In one embodiment, the viral particle comprises capsid proteins from an AAV serotype selected from the group consisting of an AAV1, an AAV2, an AAV5, an AAV8, and an AAV9, which are more suitable for delivery to the CNS (M. Hocquemiller et al., Hum Gene Ther 27(7): 478-496 (2016)). In a particular embodiment, the viral particle comprises an expression cassette of the invention wherein the 5'ITR and 3'ITR sequences of the expression cassette are of an AAV2 serotype and the capsid proteins are of an AAV9 serotype.

Numerous methods are known in the art for production of rAAV virions, including transfection, stable cell line production, and infectious hybrid virus production systems which include adenovirus-AAV hybrids, herpesvirus-AAV hybrids (Conway, J E et al., (1997) J. Virology 71(11):8780-8789) and baculovirus-AAV hybrids. rAAV production cultures for the production of rAAV virus particles all require;

1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a transgene (e.g., comprising one or more of: a PV selective microRNA binding site, a sequence encoding an eTF that selectively upregulates SCN1A as described herein, and/or a PV selective promoter) flanked by AAV ITR sequences; and 5) suitable media and media components to support rAAV production.

In various embodiments, the host cells described herein comprise the following three components: (1) a rep gene and a cap gene, (2) genes providing helper functions, and (3) a transgene (e.g., comprising one or more of: a PV selective microRNA binding site, a sequence encoding an eTF that selectively upregulates SCN1A as described herein, and/or a PV selective promoter) flanked by ITRs. The AAV rep gene, AAV cap gene, and genes providing helper functions can be introduced into the cell by incorporating said genes into a vector such as, for example, a plasmid, and introducing said vector into the host cell. The rep, cap and helper function genes can be incorporated into the same plasmid or into different plasmids. In a preferred embodiment, the AAV rep and cap genes are incorporated into one plasmid and the genes providing helper functions are incorporated into another plasmid. The various plasmids for creation of a host cell for virion production (e.g., comprising AAV rep and cap genes, helper functions, or a transgene) can be introduced into the cell by using any suitable method well known in the art. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In certain embodiments, the plasmids providing the rep and cap genes, the helper functions and the transgene flanked by ITRs can be introduced into the cell simultaneously. In another embodiment, the plasmids providing the rep and cap genes and the helper functions can be introduced in the cell before or after the introduction of plasmid comprising the transgene. In an exemplary embodiment, the cells are transfected simultaneously with three plasmids (e.g., a triple transfection method): (1) a plasmid comprising the transgene (e.g., comprising one or more of: a PV selective microRNA binding site, a sequence encoding an eTF that selectively upregulates SCN1A as described herein, and/or a PV selective promoter) flanked by ITRs, (2) a plasmid comprising the AAV rep and cap genes, and (3) a plasmid comprising the genes providing the helper functions. Exemplary host cells may be 293, A549 or HeLa cells.

In other embodiments, one or more of (1) the AAV rep and cap genes, (2) genes providing helper functions, and (3) the transgene (e.g., comprising one or more of: a PV selective microRNA binding site, a sequence encoding an eTF that selectively upregulates SCN1A as described herein, and/or a PV selective promoter) flanked by ITRs, may be carried by the packaging cell, either episomally and/or integrated into the genome of the packaging cell. In one embodiment, host cells may be packaging cells in which the AAV rep and cap genes and helper functions are stably maintained in the host cell and the host cell is transiently transfected with a plasmid containing a transgene (e.g., comprising one or more of: a PV selective microRNA binding site, a sequence encoding an eTF that selectively upregulates SCN1A as described herein, and/or a PV selective promoter) flanked by ITRs. In another embodiment, host cells are packaging cells in which the AAV rep and cap genes are stably maintained in the host cell and the host cell is transiently transfected with a plasmid containing a transgene (e.g., comprising one or more of: a PV selective microRNA binding site, a sequence encoding an eTF that selectively upregulates SCN1A as described herein, and/or a PV selective promoter) flanked by ITRs and a plasmid containing the helper functions. In another embodiment, host cells may be packaging cells in which the helper functions are stably maintained in the host cell and the host cell is transiently transfected with a plasmid containing a transgene (e.g., comprising one or more of: a PV selective microRNA binding site, a sequence encoding an eTF that selectively upregulates SCN1A as described herein, and/or a PV selective promoter) flanked by ITRs and a plasmid containing rep and cap genes. In another embodiment, host cells may be producer cell lines that are stably transfected with rep and cap genes, helper functions and the transgene sequence (e.g., comprising one or more of: a PV selective microRNA binding site, a sequence encoding an eTF that selectively upregulates SCN1A as described herein, and/or a PV selective promoter) flanked by ITRs. Exemplary packaging and producer cells may be derived from 293, A549 or HeLa cells.

In another embodiment, the producer cell line is an insect cell line (typically Sf9 cells) that is infected with baculovirus expression vectors that provide Rep and Cap proteins. This system does not require adenovirus helper genes (Ayuso E, et al., Curr. Gene Ther. 2010, 10:423-436).

The term "cap protein", as used herein, refers to a polypeptide having at least one functional activity of a native AAV Cap protein (e.g. VP1, VP2, VP3). Examples of functional activities of cap proteins include the ability to induce formation of a capsid, facilitate accumulation of single-stranded DNA, facilitate AAV DNA packaging into capsids (i.e. encapsidation), bind to cellular receptors, and facilitate entry of the virion into host cells. In principle, any Cap protein can be used in the context of the present invention.

Cap proteins have been reported to have effects on host tropism, cell, tissue, or organ specificity, receptor usage, infection efficiency, and immunogenicity of AAV viruses. Accordingly, an AAV cap for use in an rAAV may be selected taking into consideration, for example, the subject's species (e.g. human or non-human), the subject's immunological state, the subject's suitability for long or short-term treatment, or a particular therapeutic application (e.g. treatment of a particular disease or disorder, or delivery to particular cells, tissues, or organs). In certain embodiments, the cap protein is derived from the AAV of the group consisting of AAV1, AAV2, AAV5, AAV8, and AAV9 serotypes. In an exemplary embodiment, the cap protein is derived from AAV9.

In some embodiments, an AAV Cap for use in the method of the invention can be generated by mutagenesis (i.e. by insertions, deletions, or substitutions) of one of the aforementioned AAV caps or its encoding nucleic acid. In some embodiments, the AAV cap is at least 70%, 75%, 80%, 85%, 90%, 95%, 98%, or 99% or more similar to one or more of the aforementioned AAV caps.

In some embodiments, the AAV cap is chimeric, comprising domains from two, three, four, or more of the aforementioned AAV caps. In some embodiments, the AAV cap is a mosaic of VP1, VP2, and VP3 monomers originating from two or three different AAV or a recombinant AAV. In some embodiments, a rAAV composition comprises more than one of the aforementioned caps.

In some embodiments, an AAV cap for use in a rAAV virion is engineered to contain a heterologous sequence or other modification. For example, a peptide or protein sequence that confers selective targeting or immune evasion may be engineered into a cap protein. Alternatively or in addition, the cap may be chemically modified so that the surface of the rAAV is polyethylene glycolated (i.e., pegylated), which may facilitate immune evasion. The cap protein may also be mutagenized (e.g., to remove its natural receptor binding, or to mask an immunogenic epitope).

The term "rep protein", as used herein, refers to a polypeptide having at least one functional activity of a native AAV rep protein (e.g. rep 40, 52, 68, 78). Examples of functional activities of a rep protein include any activity associated with the physiological function of the protein, including facilitating replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. In a particular embodiment, AAV rep genes may be from the serotypes AAV1, AAV2, AAV4, AAV5, AAV6, AAV7, AAV8, AAV9, AAV10 or AAVrh10; more preferably from an AAV serotype selected from the group consisting of AAV1, AAV2, AAV5, AAV8, and AAV9.

In some embodiments, an AAV rep protein for use in the method of the invention can be generated by mutagenesis (i.e. by insertions, deletions, or substitutions) of one of the aforementioned AAV reps or its encoding nucleic acid. In some embodiments, the AAV rep is at least 70%, 75%, 80%, 85%, 90%, 95%, 98%, or 99% or more similar to one or more of the aforementioned AAV reps.

The expressions "helper functions" or "helper genes", as used herein, refer to viral proteins upon which AAV is dependent for replication. The helper functions include those proteins required for AAV replication including, without limitation, those proteins involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus E1, E2a, VA, and E4 or herpesvirus UL5, ULB, UL52, and UL29, and herpesvirus polymerase. In a preferred embodiment, the proteins upon which AAV is dependent for replication are derived from adenovirus.

In some embodiments, a viral protein upon which AAV is dependent for replication for use in the method of the invention can be generated by mutagenesis (i.e. by insertions, deletions, or substitutions) of one of the aforementioned viral proteins or its encoding nucleic acid. In some embodiments, the viral protein is at least 70%, 75%, 80%, 85%, 90%, 95%, 98%, or 99% or more similar to one or more of the aforementioned viral proteins.

Methods for assaying the functions of cap proteins, rep proteins and viral proteins upon which AAV is dependent for replication are well known in the art.

Host cells for expressing a transgene of interest (e.g., comprising one or more of: a PV selective microRNA binding site, a sequence encoding an eTF that selectively upregulates SCN1A as described herein, and/or a PV selective promoter) may be grown under conditions adequate for assembly of the AAV virions. In certain embodiments, host cells are grown for a suitable period of time in order to promote the assembly of the AAV virions and the release of virions into the media. Generally, cells may be grown for about 24 hours, about 36 hours, about 48 hours, about 72 hours, about 4 days, about 5 days, about 6 days, about 7 days, about 8 days, about 9 days, or up to about 10 days. After about 10 days (or sooner, depending on the culture conditions and the particular host cell used), the level of production generally decreases significantly. Generally, time of culture is measured from the point of viral production. For example, in the case of AAV, viral production generally begins upon supplying helper virus function in an appropriate host cell as described herein. Generally, cells are harvested about 48 to about 100, preferably about 48 to about 96, preferably about 72 to about 96, preferably about 68 to about 72 hours after helper virus infection (or after viral production begins).

rAAV production cultures can be grown under a variety of conditions (over a wide temperature range, for varying lengths of time, and the like) suitable to the particular host cell being utilized. rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

Suitable media known in the art may be used for the production of rAAV virions. These media include, without limitation, media produced by Hyclone Laboratories and JRH including Modified Eagle Medium (MEM), Dulbecco's Modified Eagle Medium (DMEM), each of which is incorporated herein by reference in its entirety. In certain embodiments, rAAV production culture media may be supplemented with serum or serum-derived recombinant proteins at a level of 0.5%-20% (v/v or w/v). Alternatively, rAAV vectors may be produced in serum-free conditions which may also be referred to as media with no animal-derived products.

After culturing the host cells to allow AAV virion production, the resulting virions may be then be harvested and purified. In certain embodiments, the AAV virions can be obtained from (1) the host cells of the production culture by lysis of the host cells, and/or (2) the culture medium of said cells after a period of time post-transfection, preferably 72 hours. The rAAV virions may be harvested from the spent media from the production culture, provided the cells are cultured under conditions that cause release of rAAV virions into the media from intact cells (see e.g., U.S. Pat. No. 6,566,118). Suitable methods of lysing cells are also known in the art and include for example multiple freeze/thaw cycles, sonication, microfluidization, and treatment with chemicals, such as detergents and/or proteases.

After harvesting, the rAAV virions may be purified. The term "purified" as used herein includes a preparation of rAAV virions devoid of at least some of the other components that may also be present where the rAAV virions naturally occur or are initially prepared from. Thus, for example, purified rAAV virions may be prepared using an isolation technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In certain embodiments, the rAAV production culture harvest may be clarified to remove host cell debris. In some embodiments, the production culture harvest may be clarified using a variety of standard techniques, such as, centrifugation or filtration through a filter of 0.2 μm or greater pore size (e.g., a cellulose acetate filter or a series of depth filters).

In certain embodiments, the rAAV production culture harvest is further treated with Benzonase™ to digest any high molecular weight DNA present in the production culture. In some embodiments, the Benzonase™ digestion is performed under standard conditions, for example, a final concentration of 1-2.5 units/ml of Benzonase™ at a temperature ranging from ambient to 37° C. for a period of 30 minutes to several hours.

In certain embodiments, the rAAV virions may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography. These steps may be used alone, in various combinations, or in different orders. Methods to purify rAAV particles are found, for example, in Xiao et al., (1998) Journal of Virology 72:2224-2232; U.S. Pat. Nos. 6,989,264 and 8,137,948; and WO 2010/148143.

In certain embodiments, purified AAV virions can be dialyzed against PBS, filtered and stored at −80° C. Titers of viral genomes can be determined by quantitative PCR using linearized plasmid DNA as standard curve (see e.g., Lock M, et al., Hum. Gene Ther. 2010; 21:1273-1285).

Pharmaceutical Compositions

In certain embodiments, the application provides compositions comprising a PV selective microRNA binding site and/or a sequence encoding an eTF that selectively upregulates SCN1A and a pharmaceutically acceptable carrier. In other embodiments, the application provides virions comprising a PV selective microRNA binding site and/or a sequence encoding an eTF that selectively upregulates SCN1A and a pharmaceutically acceptable carrier. In exemplary embodiments, such compositions are suitable for gene therapy applications. Pharmaceutical compositions are preferably sterile and stable under conditions of manufacture and storage. Sterile solutions may be accomplished, for example, by filtration through sterile filtration membranes.

Acceptable carriers and excipients in the pharmaceutical compositions are preferably nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the disclosure can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water and physiological saline.

The pharmaceutical compositions of the disclosure may be prepared in microcapsules, such as hydroxylethylcellulose or gelatin-microcapsules and polymethylmethacrylate microcapsules. The pharmaceutical compositions of the disclosure may also be prepared in other drug delivery systems such as liposomes, albumin microspheres, microemulsions, nano-particles, and nanocapsules. The pharmaceutical composition for gene therapy can be in an acceptable diluent, or can comprise a slow release matrix in which the gene delivery vehicle is imbedded.

Pharmaceutical compositions provided herein may be formulated for parenteral administration, subcutaneous administration, intravenous administration, intramuscular administration, intra-arterial administration, intraparenchymal administration, intrathecal administration, intra-cisterna magna administration, intracerebroventricular administration, or intraperitoneal administration. The pharmaceutical composition may also be formulated for, or administered via, nasal, spray, oral, aerosol, rectal, or vaginal administration. In one embodiment, a pharmaceutical composition provided herein is administered to the CNS or cerebral spinal fluid (CSF), i.e. by intraparenchymal injection, intrathecal injection, intra-cisterna magna injection, or intracerebroventricular injection. The tissue target may be specific, for example the CNS, or it may be a combination of several tissues, for example the muscle and CNS tissues. Exemplary tissue or other targets may include liver, skeletal muscle, heart muscle, adipose deposits, kidney, lung, vascular endothelium, epithelial, hematopoietic cells, CNS and/or CSF. In a preferred embodiment, a pharmaceutical composition provided herein comprising a PV selective microRNA binding site and/or an eTF that selectively upregulates SCN1A is administered to the CNS or CSF injection, i.e. by intraparenchymal injection, intrathecal injection, intra-cisterna magna injection, or intracerebroventricular injection. One or more of these methods may be used to administer a pharmaceutical composition of the disclosure.

In certain embodiments, a pharmaceutical composition provided herein comprises an “effective amount” or a “therapeutically effective amount.” As used herein, such amounts refer to an amount effective, at dosages and for periods of time necessary to achieve the desired therapeutic result, such as increasing the level of SCN1A expression and/or decreasing the frequency and/or duration of seizures.

The dosage of the pharmaceutical compositions of the disclosure depends on factors including the route of administration, the disease to be treated, and physical characteristics (e.g., age, weight, general health) of the subject. Dosage may be adjusted to provide the optimum therapeutic response. Typically, a dosage may be an amount that effectively treats the disease without inducing significant toxicity. In one embodiment, an AAV vector provided herein can be administered to the patient for the treatment of an SCN1A deficiency (including for example, Dravet syndrome) in an amount or dose within a range of $5\times10^{11}$ to $1\times10^{14}$ gc/kg (genome copies per kilogram of patient body weight (gc/kg)). In a more particular embodiment, the AAV vector is administered in an amount comprised within a range of about $5\times10^{11}$ gc/kg to about $3\times10^{13}$ gc/kg, or about $1\times10^{12}$ to about $1\times10^{14}$ gc/kg, or about $1\times10^{12}$ to about $1\times10^{13}$ gc/kg, or about $5\times10^{11}$ gc/kg, $1\times10^{12}$ gc/kg, $1.5\times10^{12}$ gc/kg, $2.0\times10^{12}$ gc/kg, $2.5\times10^{12}$ gc/kg, $3\times10^{12}$ gc/kg, $3.5\times10^{12}$ gc/kg, $4\times10^{12}$ gc/kg, $4.5\times10^{12}$ gc/kg, $5\times10^{12}$ gc/kg, $5.5\times10^{12}$ gc/kg, $6\times10^{12}$ gc/kg, $6.5\times10^{12}$ gc/kg, $7\times10^{12}$ gc/kg, $7.5\times10^{12}$ gc/kg, $8\times10^{12}$ gc/kg, $8.5\times10^{12}$ gc/kg, $9\times10^{12}$ gc/kg or $9.5\times10^{12}$ gc/kg. The gc/kg may be determined, for example, by qPCR or digital droplet PCR (ddPCR) (see e.g., M. Lock et al, Hum Gene Ther Methods. 2014 April; 25(2): 115-25). In another embodiment, an AAV vector provided herein can be administered to the patient for the treatment of an SCN1A deficiency (including for example, Dravet syndrome) in an amount or dose within a range of $1\times10^{9}$ to $1\times10^{11}$ iu/kg (infective units of the vector (iu)/subject's or patient's body weight (kg)). In certain embodiments, the pharmaceutical composition may be formed in a unit dose as needed. Such single dosage units may contain about $1\times10^{9}$ gc to about $1\times10^{15}$ gc.

Pharmaceutical compositions of the disclosure may be administered to a subject in need thereof, for example, one or more times (e.g., 1-10 times or more) daily, weekly, monthly, biannually, annually, or as medically necessary. In an exemplary embodiment, a single administration is sufficient. In one embodiment, a pharmaceutical composition comprising an expression cassette encoding a PV selective microRNA binding site and/or an eTF that selectively upregulates SCN1A is suitable for use in human subjects and is administered by intraparenchymal injection, intrathecal injection, intra-cisterna magna injection, or intracerebroventricular injection. In one embodiment, the pharmaceutical composition is delivered via a peripheral vein by bolus injection. In other embodiments, the pharmaceutical composition is delivered via a peripheral vein by infusion over about 10 minutes (±5 minutes), over about 20 minutes (±5 minutes), over about 30 minutes (±5 minutes), over about 60 minutes (±5 minutes), or over about 90 minutes (±10 minutes).

In another aspect, the application further provides a kit comprising a nucleic acid molecule, vector, host cell, virion or pharmaceutical composition as described herein in one or more containers. A kit may include instructions or packaging materials that describe how to administer a nucleic acid molecule, vector, host cell or virion contained within the kit to a patient. Containers of the kit can be of any suitable material, e.g., glass, plastic, metal, etc., and of any suitable size, shape, or configuration. In certain embodiments, the kits may include one or more ampoules or syringes that contain a nucleic acid molecule, vector, host cell, virion or pharmaceutical composition in a suitable liquid or solution form.

Methods of Treatment

In one aspect, the application provides methods for using the eTFs that selectively upregulate SCN1A as disclosed herein. In certain embodiments, the application provides methods for administering an expression cassette, an expression vector, or a viral particle comprising a polynucleotide encoding an eTF that selectively upregulates SCN1A as disclosed herein to upregulate expression of SCN1A in a cell. In various embodiments, an eTF that selectively upregulates SCN1A as disclosed herein may be used to modulate expression of SCN1A in a cell in vitro, in vivo, or ex vivo.

In certain embodiments, the application provides methods for treating a disease or disorder associated with SCN1A by administering an expression cassette, an expression vector, or a viral particle comprising a polynucleotide encoding an eTF that selectively upregulate SCN1A as disclosed herein to a subject in need thereof. In certain embodiments, the disorder is a central nervous system disorder. In exemplary embodiments, the disease or disorder is associated with haploinsufficiency of SCN1A. In certain embodiments, the disorder is epilepsy associated with SCN1A haploinsufficiency. In certain embodiments, the haploinsufficiency is the result of the subject being heterozygous for a loss of function mutation of the SCN1A gene. In certain embodiments, the disorder is epilepsy associated with an insertion, deletion, or substitution in the SCN1A gene. In certain embodiments, the disorder is epilepsy associated with a point mutation in the SCN1A gene. In certain embodiments, a method of treating a disease or disorder comprises administering an expression cassette, an expression vector, or a viral particle comprising a polynucleotide encoding an eTF that selectively upregulates SCN1A as disclosed herein such that under-expression of SCN1A is corrected, brought within a level of a healthy individual, or brought within a normal range as defined by a standard of medical care. In certain embodiments, the methods disclosed herein are used to treat a disease or disorder associated with endogenous SCN1A comprising one or more mutations that results in abnormal expression of SCN1A.

In certain embodiments, the application provides methods for ameliorating a symptom associated with a disease or disorder by administering an expression cassette, an expression vector, or a viral particle comprising a polynucleotide encoding an eTF that selectively upregulates SCN1A as disclosed herein to a subject in need thereof.

In an exemplary embodiment, the application provides methods for treating a disease, disorder or symptom associated with a mutation in SCN1A (e.g., point mutation, substitution, deletion, inversion, etc.), a deficiency in Nav1.1 and/or reduced activity of Nav1.1 by administering to a subject in need thereof an expression cassette, an expression vector, or a viral particle comprising a polynucleotide encoding an eTF that selectively upregulates expression of the SCN1A gene or its protein product Nav1.1. Voltage-gated sodium ion channels are important for the generation and propagation of action potentials in striated muscle and neuronal tissues. Voltage-gated sodium ion channels are heteromeric complexes consisting of a large central pore-forming glycosylated alpha subunit and 2 smaller auxiliary beta subunits. The large alpha subunit Nav1.1 subunit, encoded by the SCN1A gene, is relevant for a variety of diseases or disorders such as Dravet syndrome. Nav1.1 is expressed in neurons, and can be assembled with various beta subunits, including Navβ1 expressed by SCN1B gene.

In certain embodiments, the application provides methods for treating diseases associated with a mutation in SCN1A (e.g., deletion, insertion, inversion, point mutation (e.g., nonsense mutation, missense mutation), etc.) or reduced activity of Nav1.1 using an eTF that selectively upregulates expression of the endogenous SCN1A gene. Diseases and disorders associated with SCN1A mutations include, but are not limited to: Dravet syndrome, Ohtahara syndrome, epilepsy, early infantile epileptic encephalopathy 6 (EIEE6), familial febrile seizures 3A (FEB3A), intractable childhood epilepsy with generalized tonic-clonic seizures (ICEGTC), migraine, familial hemiplegic 3 (FHM3), Panayiotopoulos syndrome, familial atrial fibrillation 13 (ATFB13), generalized epilepsy with febrile seizures plus type 1 (gefs+ type 1), Brugada syndrome, nonspecific cardiac conduction defect, generalized epilepsy with febrile seizures plus, benign familial infantile seizures, early infantile epileptic encephalopathy11 (EIEE11), benign familial infantile epilepsy, neurodegeneration, tauopathies and Alzheimer's disease. In some cases, the neurological condition is Dravet syndrome. Mutations or abnormalities in SCN1A have also been associated with seizure disorders, epilepsy, autism, familial hemiplegic migraine type 3 (FHM3), genetic epilepsy with febrile seizures plus (GEFS+), and effectiveness of certain anti-seizure medications. For instance, ICS5N+5G>A mutation in SCN1A is associated with the maximum safe amount (dose) of the anti-seizure drugs phenytoin and carbamazepine.

In certain embodiments, the application provides a method for treating a subject with, or at risk of developing, Dravet syndrome by administering an expression cassette, expression vector, or viral particle comprising a polynucleotide encoding an eTF that selectively upregulates SCN1A. Dravet syndrome has been characterized by prolonged febrile and non-febrile seizures within the first year of a child's life. This disease progresses to other seizure types like myoclonic and partial seizures, psychomotor delay, and ataxia. It is characterized by cognitive impairment, behavioral disorders, and motor deficits. Behavioral deficits often include hyperactivity and impulsiveness, and in more rare cases, autistic-like behaviors. Dravet syndrome is also associated with sleep disorders including somnolence and insomnia. In many patients, Dravet syndrome is caused by genetic mutations that lead to the production of non-functional proteins. Many challenges exist in treating disorders associated with genetic causes. Thus, most of the existing treatments have been drawn to the prophylactic medical management of seizures and other symptoms.

In 70-90% of patients, Dravet syndrome is caused by nonsense mutations in the SCN1A gene resulting in a premature stop codon and thus a non-functional protein. Typically, a missense mutation in either the S5 or S6 segment of the sodium channel pore results in a loss of channel function and the development of Dravet syndrome. A heterozygous inheritance of an SCN1A mutation, e.g., a nonsense mutation, a missense mutation, deletion, insertion, inversion, etc., is all that is necessary to develop a defective sodium channel; patients with Dravet syndrome will still have one normal copy of the gene. Thus, the disease is characterized as one of haploinsufficiency and thus increasing expression of the functioning copy of SCN1A could restore normal production levels of Nav1.1.

Symptoms associated with Dravet syndrome include seizures, memory defects, developmental delay, poor muscle tone and/or cognitive problems. Treatment with an expression cassette, expression vector, or virial particle described herein can result in an improvement of one or more symptoms, such as a reduction in number, duration, and/or intensity of seizures. Administration of a gene therapy as described herein to a subject at risk of developing Dravet syndrome can prevent the development of or slow the progression of one or more symptoms of Dravet.

In certain embodiments, treatment with an expression cassette, expression vector, or virial particle comprising a polynucleotide encoding an eTF that selectively upregulates SCN1A as described herein reduces seizure duration and/or frequency, e.g., seizures associated with Dravet syndrome, by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, 95% or more as compared to an untreated control or as compared to the level before treatment.

In some Alzheimer's patients, production of amyloid β (Aβ) involving many peptides and proteases that can affect excitability of neurons, causing seizures and downregulation of the Nav1.1 sodium channel in PV neurons. In another embodiment, the application provides methods for treating a subject suffering from Alzheimer's disease by administering an expression cassette, expression vector, or viral particle described herein that comprises a polynucleotide encoding an eTF that selectively upregulates SCN1A. Symptoms associated with Alzheimer's disease include short term memory loss, cognitive difficulties, seizures, and difficulties with language, executive functions, perception (agnosia), and execution of movements (apraxia). Treatment with an expression cassette, expression vector, or viral particle comprising a polynucleotide encoding an eTF that selectively upregulates SCN1A can result in an improvement of one or more Alzheimer's disease symptoms, such as a reduction in progression of memory loss, or the prevention of one or more symptoms. In some cases, the treatment can result in a correction of high gamma power brain activity. The treatment can result in a decrease in seizure frequency and/or seizure severity, or a decrease in high gamma power activity by at least 10%, 20%, 30%, 40%, 50%, 60%, 70% or more as compared to no treatment. In some cases, the treatment can result in an improvement in cognitive function. Learning and/or memory can be improved by at least 10%, 20%, 30%, 40%, 50%, 60%, 70%, 80%, 90%, 100% or more than 100% as compared to no treatment, or before the treatment with a polynucleotide encoding an eTF that selectively upregulates SCN1A as disclosed herein.

In some cases, treatment with an expression cassette, expression vector, or viral particle comprising a polynucleotide encoding an eTF that selectively upregulates SCN1A reduces high gamma power activity (e.g., high gamma power activity associated with Alzheimer's disease) by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

Parkinsonism refers to a collection of signs and symptoms found in Parkinson's disease (PD), including slowness (bradykinesia), stiffness (rigidity), tremor and imbalance (postural instability). In some cases, administration of an expression cassette, expression vector, or viral particle comprising a polynucleotide encoding an eTF that selectively upregulates SCN1A as described herein to a subject at risk of developing or suffering from Parkinson's disease can prevent the development of one or more symptoms thereof or slow down the progression of Parkinson's disease by at least 10%, at least 20%, at least 30%, at least 40%, at least 50%, at least 60%, at least 70%, at least 80%, or at least 90% as compared to no treatment.

In certain embodiments, the application provides methods that can be used to treat a subject who is at risk of developing a disease. The subject can be known to be predisposed to a disease, for example, a neurological disease or a disease associated with epilepsy, seizures and/or encephalopathy. The subject can be predisposed to a disease due to a genetic event, or due to known risk factors. For example, a subject can carry a mutation in SCN1A which is associated with epilepsy (such as, for example, Dravet syndrome). Any mutation in the SCN1A gene that reduces its activity (by reducing expression levels, impairing protein function, or a combination of both) can predispose a subject to a disease, including any one or more of insertions, deletions, inversions, translocations, or substitutions (e.g., point mutations including nonsense mutations and/or missense mutations) in the SCN1A gene. In some cases the subject can be predisposed to a disease such as Alzheimer's disease due to the age of the subject. In some cases, the subject may have an insufficient amount of SCN1A protein and treating a disease associated with SCN1A involves administering an expression cassette, expression vector, or viral particle comprising a polynucleotide encoding an eTF that selectively upregulates endogenous SCN1A as described herein.

In certain embodiments, treatments using an expression cassette, expression vector, or viral particle comprising a polynucleotide encoding an eTF that selectively upregulates endogenous SCN1A provided herein can result in a decrease or cessation of symptoms associated with Dravet or other SCN1A associated disease or disorders, e.g., epilepsy associated with SCN1A haploinsufficiency. For example, treatment can improve learning, memory, cognitive function, and/or motor function; reduce frequency and/or duration of seizures; and/or reduce temperature sensitivity (or increase the temperature threshold for triggering a seizure).

In another aspect, the application provides methods for selective expression of a transgene in PV neurons by administering an expression cassette, an expression vector, or a viral particle comprising at least one PV selective microRNA binding site. In certain embodiments, the application provides methods for selective expression of a transgene in PV neurons of a primate by administering an expression cassette, an expression vector, or a viral particle comprising a transgene and at least one PV selective microRNA binding site. In certain embodiments, the application provides methods for selective expression of a transgene in PV neurons by administering an expression cassette, an expression vector, or a viral particle comprising a PV selective regulatory element operably linked to a transgene and at least one PV selective microRNA binding site. In exemplary embodiments, the transgene comprises a sequence encoding any of the eTFs that selectively upregulate SCN1A as described herein.

In certain embodiments, the application provides a method for gene therapy comprising administering to a subject an expression cassette, an expression vector, or a viral particle comprising a transgene and at least one PV selective microRNA binding site. In certain embodiments, the application provides methods for gene therapy comprising administering to a subject an expression cassette, an expression vector, or a viral particle comprising a PV selective regulatory element operably linked to a transgene and at least one PV selective microRNA binding site. In exemplary embodiments, the transgene comprises a sequence encoding any of the eTFs that selectively upregulate SCN1A as described herein.

In certain embodiments, the application provides a method for treating a disease or disorder comprising administering to an expression cassette, an expression vector, or a viral particle comprising a transgene and at least one PV selective microRNA binding site. In certain embodiments, the application provides methods for treating a disease or disorder comprising administering to a subject an expression cassette, an expression vector, or a viral particle comprising a PV selective regulatory element operably linked to a transgene and at least one PV selective microRNA binding site. In exemplary embodiments, the transgene comprises a sequence encoding any of the eTFs that selectively upregulate SCN1A as described herein. In certain embodiments, the expression cassette, expression vector, or viral particle comprising a transgene and a PV selective microRNA binding site and optionally a PV selective regulatory element may be used to treat a disease or disorder in which PV neurons are implicated. In certain embodiments, the expression cassette, expression vector, or viral particle comprising a transgene and a PV selective microRNA binding site and optionally a PV selective regulatory element are used to treat a neuronal condition. Neuronal diseases or disorders appropriate for treatment include, but are not limited to, Dravet Syndrome, Alzheimer's disease, Parkinson's disease, Huntington's disease, amyotrophic lateral sclerosis (ALS), spinal muscular atrophy (SMA), epilepsy, neurodegenerative disorders, motor disorders, movement disorders, mood disorders, motor neuron diseases, progressive muscular atrophy (PMA), progressive bulbar palsy, pseudobulbar palsy, primary lateral sclerosis, neurological consequences of AIDS, developmental disorders, multiple sclerosis, neurogenetic disorders, stroke, spinal cord injury-, traumatic brain injury, tauopathy, neuronal hypoexcitability and/or seizures. In some embodiments, a viral vector, viral particle or pharmaceutical composition comprising a transgene and a PV selective microRNA binding site and optionally a PV selective regulatory element are used to treat a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis, epilepsy associated with SCN1A haploinsufficiency); and/or neurodegeneration (e.g., Alzheimer's disease, Parkinson's disease). Diseases associated with dysfunctional PV neurons such as those due to loss of function mutations in SCN1A, or Nav1.1 include: Dravet syndrome, Ohtahara syndrome, epilepsy, early infantile epileptic encephalopathy 6 (EIEE6), familial febrile seizures 3A (FEB3A), intractable childhood epilepsy with generalized tonic-clonic seizures (ICEGTC), migraine, familial hemiplegic 3 (FHM3). Panayiotopoulos syndrome, familial atrial fibrillation 13 (ATFB13), generalized epilepsy with febrile seizures plus type 1 (gefs+ type 1), Brugada syndrome, nonspecific cardiac conduction defect, generalized epilepsy with febrile seizures plus, benign familial infantile seizures, early infantile epileptic encephalopathy 11 (EIEE11), benign familial infantile epilepsy, neurodegeneration, tauopathies and Alzheimer's disease.

In certain embodiments, treatment using an expression cassette, an expression vector, or a viral particle comprising a transgene and a PV selective microRNA binding site and optionally a PV selective regulatory element described herein results in improved symptoms associated with a neuronal disease or disorder. For instance, a Parkinson's patient can be monitored symptomatically for improved motor functions indicating positive response to treatment. Administration of a therapy using a method as described herein to a subject at risk of developing a neuronal disorder can prevent the development of or slow the progression of one or more symptoms.

In certain embodiments, an expression cassette, an expression vector, or a viral particle comprising a transgene and a PV selective microRNA binding site and optionally a PV selective regulatory element provided herein can be used to treat a subject who has been diagnosed with a neuronal disease, for example, epilepsy associated with SCN1A haploinsufficiency such as, for example, Dravet syndrome. In various embodiments, any of the neuronal diseases or disorders disclosed herein are caused by a known genetic event (e.g., any of the SCN1A mutations known in the art) or have an unknown cause.

In certain embodiments, an expression cassette, an expression vector, or a viral particle comprising a transgene and a PV selective microRNA binding site and optionally a PV selective regulatory element provided herein can be used to treat a subject who is at risk of developing a disease or disorder. In some embodiments, the subject can be known to be predisposed to a disease, for example, a neuronal disease (e.g. epilepsy associated with SCN1A haploinsufficiency such as, for example, Dravet syndrome). In some embodiments, the subject can be predisposed to a disease due to a genetic event, or due to known risk factors. For example, a subject can carry a mutation in SCN1A which is associated with epilepsy or Dravet syndrome, e.g., an insertion, deletion, inversion, translocation, or substitution (e.g., a point mutation including a nonsense mutation and/or a missense mutation).

In certain embodiments, an expression cassette, an expression vector, or a viral particle comprising a transgene and a PV selective microRNA binding site and optionally a PV selective regulatory element provided herein can be used to reduce one or more symptoms associated with a disease or disorder. For example, symptoms associated with Dravet syndrome include seizures, memory defects, developmental delay, poor muscle tone and/or cognitive problems. Treatment with a viral vector, viral particle or pharmaceutical composition comprising a transgene and a PV selective microRNA binding site and optionally a PV selective regulatory element provided herein can result in an improvement of one or more symptoms, such as a reduction in number, duration, and/or intensity of seizures.

In certain embodiments, the methods described herein are used for increasing expression of a transgene in a PV neuron, gene therapy, or treating a disease or disorder in a primate. In certain embodiments, the primate is a human. In certain embodiments, the primate is a non-human primate. In certain embodiments, the non-human primate is an old world monkey, an orangutan, a gorilla, a chimpanzee, a crab-eating macaque, a rhesus macaque or a pig-tailed macaque.

The terms "subject" and "individual" are used interchangeably herein to refer to a vertebrate, preferably a mammal, more preferably a human. The methods described herein can be useful in human therapeutics, veterinary applications, and/or preclinical studies in animal models of a disease or condition. In various embodiments, a subject that can be treated in accordance with the methods described herein is a mammal, such as, for example, a mouse, rat, hamster, guinea pig, gerbil, cow, sheep, pig, goat, donkey, horse, dog, cat, llama, monkey (e.g., an old world monkey, a marmoset, or a macaque such as a Rhesus macaque, a pig-tailed macaque or a crab-eating macaque (i.e., a cynomolgus monkey)), ape (e.g., an orangutan, gorilla or chimpanzee) or human. In an exemplary embodiment, a subject is a human.

The following tables provide sequences disclosed herein.

TABLE 1

Exemplary engineered transcription factors disclosed herein. Sequences of the regulatory elements (RE) are disclosed below in TABLES 2 and 8. For the RE, when m1 is indicated it means that the m1 microRNA binding site (SEQ ID NO: 7, TABLE 8) is included between the coding region and the polyA tail. Sequences for the DNA binding domains (DBD) are disclosed below in TABLE 3. For the DBD, engineered zinc finger (eZF) indicates that the construct has the formula set forth in SEQ ID NO: 147 (TABLE 10); EGR1 indicates that the DBD is derived from wild-type human EGR1 (SEQ ID NO: 176; TABLE 12); and EGR3 indicates that the DBD is derived from wild-type human EGR3 (SEQ ID NO: 175, TABLE 12). Sequences for the target sites (e.g., the sequences bound by the DBDs) are provided in TABLE 4 below. Sequences for the transcriptional activation domains (TAD) are disclosed below in TABLE 5. For the TAD, (c) indicates that the TAD is located at the c-terminus of the DBD, (n) indicates that the TAD is located at the n-terminus of the DBD, (n/c) means that there is a TAD located at both the n-terminus and c-terminus of the DBD, and 2× CITED4 (n) indicates that there are 2 copies of the CITED4 TAD located at the n-terminus of the DBD. Sequences for the full length engineered transcription factors (DBD + TAD) are provided in TABLE 6 below.

| Construct | RE | DBD | Target Site | TAD (location) | SEQ ID NO (DBD) | SEQ ID NO (DBD + TAD) |
|---|---|---|---|---|---|---|
| 1 | RE 1 | eZF | Z13 | VPR (c) | 89 | 99 |
| 2 | RE 1 | eZF | Z1 | VPR (c) | 77 | 100 |
| 3 | RE 1 | eZF | Z13 | VP64 (c) | 89 | 101 |
| 4 | RE 1 | eZF | Z1 | VP64 (c) | 77 | 102 |
| 5 | RE 1 | EGR1 | Z13 | CITED4 (n/c) | 93 | 103 |
| 6 | RE 1 | EGR1 | Z13 | CITED4 (n) | 93 | 104 |
| 7 | RE 1 | EGR1 | Z1 | CITED4 (n/c) | 92 | 105 |
| 8 | RE 1 | EGR1 | Z1 | CITED4 (n) | 92 | 106 |
| 9 | RE 1 | EGR1 | Z1 | CITED4 (c) | 92 | 107 |
| 10 | RE 1 | EGR1 | Z1 | CITED2 (c) | 92 | 108 |
| 11 | RE 1 | EGR1 | Z1 | CITED2 (n) | 92 | 109 |
| 12 | RE 1 | EGR3 | Z1 | CITED4 (n/c) | 96 | 110 |
| 13 | RE 1 | EGR3 | Z1 | CITED4 (c) | 96 | 111 |
| 14 | RE 1 | EGR3 | Z1 | CITED2 (c) | 96 | 112 |
| 15 | RE 1 | EGR3 | Z1 | CITED2 (n) | 96 | 113 |
| 16 | CBA | EGR3 | Z15 | N/A | 98 | 114 |
| 17 | RE 1 | EGR1 | Z13 | N/A | 93 | 115 |
| 18 | RE 1 | EGR1 | Z15 | N/A | 94 | 116 |
| 19 | RE 1 | EGR1 | Z13 | N/A | 93 | 117 |
| 20 | RE 1 | EGR1 | Z13 | N/A | 93 | 115 |
| 21 | RE 1 | EGR1 | Z1 | N/A | 92 | 118 |
| 22 | CBA | EGR3 | Z13 | N/A | 97 | 119 |
| 23 | RE 1 | EGR1 | Z17 | N/A | 95 | 120 |
| 24 | RE 1 | EGR1 | Z13 | N/A | 93 | 121 |
| 25 | CBA | EGR3 | Z1 | N/A | 96 | 122 |
| 26 | RE 1 | EGR1 | Z1 | N/A | 92 | 123 |

TABLE 1-continued

Exemplary engineered transcription factors disclosed herein. Sequences of the regulatory elements (RE) are disclosed below in TABLES 2 and 8. For the RE, when m1 is indicated it means that the m1 microRNA binding site (SEQ ID NO: 7, TABLE 8) is included between the coding region and the polyA tail. Sequences for the DNA binding domains (DBD) are disclosed below in TABLE 3. For the DBD, engineered zinc finger (eZF) indicates that the construct has the formula set forth in SEQ ID NO: 147 (TABLE 10); EGR1 indicates that the DBD is derived from wild-type human EGR1 (SEQ ID NO: 176; TABLE 12); and EGR3 indicates that the DBD is derived from wild-type human EGR3 (SEQ ID NO: 175, TABLE 12). Sequences for the target sites (e.g., the sequences bound by the DBDs) are provided in TABLE 4 below. Sequences for the transcriptional activation domains (TAD) are disclosed below in TABLE 5. For the TAD, (c) indicates that the TAD is located at the c-terminus of the DBD, (n) indicates that the TAD is located at the n-terminus of the DBD, (n/c) means that there is a TAD located at both the n-terminus and c-terminus of the DBD, and 2× CITED4 (n) indicates that there are 2 copies of the CITED4 TAD located at the n-terminus of the DBD. Sequences for the full length engineered transcription factors (DBD + TAD) are provided in TABLE 6 below.

| Construct | RE | DBD | Target Site | TAD (location) | SEQ ID NO (DBD) | SEQ ID NO (DBD + TAD) |
|---|---|---|---|---|---|---|
| 27 | RE 1 | EGR1 | Z1 | N/A | 92 | 124 |
| 28 | RE 1 | eZF | Z8 | VP64 (c) | 84 | 125 |
| 29 | RE 1 | eZF | Z14 | VP64 (c) | 90 | 126 |
| 30 | CBA | eZF | Z13 | VPR (c) | 89 | 99 |
| 31 | RE 2 (m1) | eZF | Z1 | VP64 (c) | 77 | 102 |
| 32 | RE 2 | eZF | Z1 | VP64 (c) | 77 | 102 |
| 33 | RE 2 | eZF | Z1 | VPR (c) | 77 | 100 |
| 34 | RE 2 | eZF | Z1 | VP64 (c) | 77 | 127 |
| 35 | RE 2 (m1) | eZF | Z1 | VP64 (c) | 77 | 127 |
| 36 | RE 2 | EGR1 | Z1 | CITED4 (n) | 92 | 128 |
| 37 | RE 2 (m1) | EGR1 | Z1 | CITED4 (n) | 92 | 106 |
| 38 | RE 2 (m1) | EGR1 | Z1 | CITED4 (n) | 92 | 129 |
| 39 | RE 2 (m1) | EGR1 | Z1 | CITED4 (n/c) | 92 | 105 |
| 40 | RE 2 (m1) | EGR1 | Z1 | 2× CITED4 (n) | 92 | 130 |
| 41 | RE 2 (m1) | EGR1 | Z1 | 2× CITED4 (n) | 92 | 131 |
| 42 | RE 2 (m2) | eZF | Z1 | VP64 (c) | 77 | 102 |
| 43 | RE 2 (m3) | eZF | Z1 | VP64 (c) | 77 | 102 |
| 44 | RE 2 (m2) | EGR1 | Z1 | CITED4 (n) | 92 | 106 |
| 45 | RE 2 (m3) | EGR1 | Z1 | CITED4 (n) | 92 | 106 |
| 46 | RE 1 | EGR1 | Z1 | CITED4 (n) | 92 | 205 |
| 47 | RE 1 | EGR1 | Z1 | 2× CITED4 (n) | 92 | 207 |
| 48 | RE 1 | EGR1 | Z1 | 2× CITED4 (n) | 92 | 209 |
| 49 | CBA | eZF | Z1 | CREB3 (n) | 77 | 213 |
| 50 | CBA | EGR1 | Z1 | CREB3 (n) | 92 (without C-term Lys) | 217 |
| 51 | CBA | EGR1 | Z13 | CREB3 (n) | 93 (without C-term Lys) | 219 |
| 52 | CBA | eZF | Z1 | CREB3 (n); no TM domain at (c) | 77 | 221 |
| 53 | CBA | EGR1 | Z1 | CREB3 (n); no TM domain at (c) | 92 (without C-term Lys) | 223 |

TABLE 2

Nucleic acid sequences for various regulatory elements (RE) disclosed herein.

| RE | SEQUENCE | SEQ ID NO |
|---|---|---|
| RE 1 | GTGATGCGGTTTTGGCAGTACATCAATGGGCGTGGATAG<br>CGGTTTGACTCACGGGGATTTCCAAGTCTCCACCCCATTG<br>ACGTCAATGGGAGTTTGTTTTGGCACCAAAATCAACGGG<br>ACTTTCCAAAATGTCGTAACAACTCCGCCCCATTGACGCA<br>AATGGGCGGTAGGCGTGTACGGTGGGAGGTCTATATAAG<br>CAGAGCTGGTACCGTGTGTATGCTCAGGGGCTGGGAAAG<br>GAGGGGAGGGAGCTCCGGCTCAG | 1 |
| RE 2 | ggaggaagccatcaactaaactacaatgactgtaagatacaaaattgggaatggtaacatatttt<br>gaagttctgttgacataaagaatcatgatattaatgcccatggaaatgaaagggcgatcaacact<br>atggtttgaaaagggggaaattgtagagcacagatgtgttcgtgtggcagtgtgctgtctctagc<br>aatactcagagaagagagagaacaatgaaattctgattggccccagtgtgagcccagatgagg<br>ttcagctgccaactttctctttcacatcttatgaaagtcatttaagcacaactaactttttttttttttttttt<br>tttttgagacagagtcttgctctgttgcccaggacagagtgcagtagtgactcaatctcggctcac<br>tgcagcctccacctcctaggctcaaacggtcctcctgcatcagcctcccaagtagctggaattac<br>aggagtggcccaccatgcccagctaattttttgtatttttaatagatacgggggtttcaccatatcac<br>ccaggctggtctcgaactcctggcctcaagtgatccacctgcctcggcctcccaaagtgctggg | 2 |

TABLE 2-continued

Nucleic acid sequences for various regulatory elements (RE) disclosed herein.

| RE | SEQUENCE | SEQ ID NO |
|---|---|---|
| | attataggcgtcagccactatgcccaacccgaccaaccttttttaaaataaatatttaaaaaattgg<br>tatttcacatatatactagtatttacatttatccacacaaaacggacgggcctccgctgaaccagtg<br>aggccccagacgtgcgcataaataacccctgcgtgctgcaccacctggggagagggggagg<br>accacggtaaatggagcgagcgcatagcaaaagggacgcggggtccttttctctgccggtgg<br>cactgggtagctgtggccaggtgtggtactttgatggggcccagggctggagctcaaggaag<br>cgtcgcagggtcacagatctggggggaaccccggggaaaagcactgaggcaaaaccgccgc<br>tcgtctcctacaatatatgggagggggaggttgagtacgttctggattactcataagacctttttttt<br>ttccttccgggcgcaaaaccgtgagctggatttataatcgccctataaagctccagaggcggtc<br>aggcacctgcagaggagccccgccgctccgccgactagctgcccccgcgagcaacggcct<br>cgtgatttccccgccgatccggtccccgcctccccactctgcccccgcctaccccggagccgt<br>gcagccgcctctccgaatctctctcttctcctggcgctcgcgtgcgagagggaactagcgaga<br>acgaggaagcagctggaggtgacgccgggcagattacgcctgtcagggccgagccgagcg<br>gatcgctgggcgctgtgcagaggaaaggcgggagtgcccggctcgctgtcgcagagccga<br>ggtgggtaagctagcgaccacctggacttcccagcgcccaaccgtggcttttcagccaggtcc<br>tctcctcccgcggcttctcaaccaaccccatcccagcgccggccacccaacctcccgaaatga<br>gtgcttcctgccccagcagccgaaggcgctactaggaacggtaacctgttacttttccaggggc<br>cgtagtcgacccgctgcccgagttgctgtgcgactgcgcgcgcggggctagagtgcaaggtg<br>actgtggttcttctctggccaagtccgagggagaacgtaaagatatgggccatacccccctctca<br>ccttgtctcaccaaagtccctagtccccggagcagttagcctctttctttccagggaattagccag<br>acacaacaacgggaaccagacaccgaaccagacatgcccgccccgtgcgccctccccgctc<br>gctgcctttcctccctcttgtctctccagagccggatcttcaaggggagcctccgtgcccccggc<br>tgctcagtccctccggtgtgcaggaccccggaagtcctccccgcacagctctcgcttctctttgc<br>agcctgtttctgcgccggaccagtcgaggactctggacagtagaggccccgggacgaccga<br>gctg | |
| RE 3 | TCAACAGGGGGACACTTGGGAAAGAAGGATGGGGACAG<br>AGCCGAGAGGACTGTTACACATTAGAGAAACATCAGTGA<br>CTGTGCCAGCTTTGGGGTAGACTGCACAAAAGCCCTGAG<br>GCAGCACAGGCAGGATCCAGTCTGCTGGTCCCAGGAAGC<br>TAACCGTCTCAGACAGAGCACAAAGCACCGAGACATGTG<br>CCACAAGGCTTGTGTAGAGAGGTCAGAGGACAGCGTACA<br>GGTCCCAGAGATCAAACTCAACCTCACCAGGCTTGGCAG<br>CAAGCCTTTACCAACCCACCCCCACCCCACCCACCCTGCA<br>CGCGCCCCTCTCCCCTCCCCATGGTCTCCCATGGCTATCT<br>CACTTGGCCCTAAAATGTTTAAGGATGACACTGGCTGCTG<br>AGTGGAAATGAGACAGCAGAAGTCAACAGTAGATTTTAG<br>GAAAGCCAGAGAAAAAGGCTTGTGCTGTTTTTAGAAAGC<br>CAAGGGACAAGCTAAGATAGGGCCCAAGTAATGCTAGTA<br>TTTACATTTATCCACACAAAACGGACGGGCCTCCGCTGAA<br>CCAGTGAGGCCCCAGACGTGCGCATAAATAACCCCTGCG<br>TGCTGCACCACCTGGGGAGAGGGGGAGGACCACGGTAAA<br>TGGAGCGAGCGCATAGCAAAAGGGACGCGGGGTCCTTTT<br>CTCTGCCGGTGGCACTGGGTAGCTGTGGCCAGGTGTGGT<br>ACTTTGATGGGGCCCAGGGCTGGAGCTCAAGGAAGCGTC<br>GCAGGGTCACAGATCTGGGGGAACCCCGGGGAAAAGCA<br>CTGAGGCAAAACCGCCGCTCGTCTCCTACAATATATGGG<br>AGGGGGAGGTTGAGTACGTTCTGGATTACTCATAAGACC<br>TTTTTTTTTCCTTCCGGGCGCAAAACCGTGAGCTGGATTT<br>ATAATCGCCCTATAAAGCTCCAGAGGCGGTCAGGCACCT<br>GCAGAGGAGCCCCGCCGCTCCGCCGACTAGCTGCCCCCG<br>CGAGCAACGGCCTCGTGATTTCCCCGCCGATCCGGTCCCC<br>GCCTCCCCACTCTGCCCCCGCCTACCCCGGAGCCGTGCAG<br>CCGCCTCTCCGAATCTCTCTCTTCTCCTGGCGCTCGCGTGC<br>GAGAGGGAACTAGCGAGAACGAGGAAGCAGCTGGAGGT<br>GACGCCGGGCAGATTACGCCTGTCAGGGCCGAGCCGAGC<br>GGATCGCTGGGCGCTGTGCAGAGGAAAGGCGGGAGTGCC<br>CGGCTCGCTGTCGCAGAGCCGAGGTGGGTAAGCTAGCGA<br>CCACCTGGACTTCCCAGCGCCCAACCGTGGCTTTTCAGCC<br>AGGTCCTCTCCTCCCGCGGCTTCTCAACCAACCCCATCCC<br>AGCGCCGGCCACCCAACCTCCCGAAATGAGTGCTTCCTG<br>CCCCAGCAGCCGAAGGCGCTACTAGGAACGGTAACCTGT<br>TACTTTTCCAGGGGCCGTAGTCGACCCGCTGCCCGAGTTG<br>CTGTGCGACTGCGCGCGCGGGGCTAGAGTGCAAGGTGAC<br>TGTGGTTCTTCTCTGGCCAAGTCCGAGGGAGAACGTAAA<br>GATATGGGCCTTTTTCCCCCTCTCACCTTGTCTCACCAAA<br>GTCCCTAGTCCCCGGAGCAGTTAGCCTCTTTCTTTCCAGG<br>GAATTAGCCAGACACAACAACGGGAACCAGACACCGAA<br>CCAGACATGCCCGCCCCGTGCGCCCTCCCCGCTCGCTGCC<br>TTTCCTCCCTCTTGTCTCTCCAGAGCCGGATCTTCAAGGG<br>GAGCCTCCGTGCCCCCGGCTGCTCAGTCCCTCCGGTGTGC<br>AGGACCCCGGAAGTCCTCCCCGCACAGCTCTCGCTTCTCT<br>TTGCAGCCTGTTTCTGCGCCGGACCAGTCGAGGACTCTGG<br>ACAGTAGAGGCCCCGGGACGACCGAGCTG | 3 |

TABLE 2-continued

Nucleic acid sequences for various regulatory elements (RE) disclosed herein.

| RE | SEQUENCE | SEQ ID NO |
|---|---|---|
| RE 4 | GCCCTCTAGGCCACCTGACCAGGTCCCCTCAGTCCCCCCC<br>TTCCCACACTCCCACACTCAGCCCCCCTCCCCCCCCCCG<br>ACCCCTGCAGGATTATCCTGTCTGTGTTCCTGACTCAGCC<br>TGGGAGCCACCTGGGCAGCAGGGGCCAAGGGTGTCCTAG<br>AAGGGACCTGGAGTCCACGCTGGGCCAAGCCTGCCCTTT<br>CTCCCTCTGTCTTCCGTCCCTGCTTGCGGTTCTGCTGAATG<br>TGGTTATTTCTCTGGCTCCTTTTACAGAGAATGCTGCTGCT<br>AATTTTATGTGGAGCTCTGAGGCAGTGTAATTGGAAGCC<br>AGACACCCTGTCAGCAGTGGGCTCCCGTCCTGAGCTGCC<br>ATGCTTCCTGCTCTCCTCCCGTCCCGGCTCCTCATTTCATG<br>CAGCCACCTGTCCCAGGGAGAGAGGAGTCACCCAGGCCC<br>CTCAGTCCGCCCCTTAAATAAGAAAGCCTCCGTTGCTCGG<br>CACACATACCAAGCAGCCGCTGGTGCAATCT | 4 |
| CBA (CMV enhancer + Chicken beta actin promoter) | CGTTACATAACTTACGGTAAATGGCCCGCCTGGCTGACCG<br>CCCAACGACCCCCGCCCATTGACGTCAATAATGACGTAT<br>GTTCCCATAGTAACGCCAATAGGGACTTTCCATTGACGTC<br>AATGGGTGGAGTATTTACGGTAAACTGCCCACTTGGCAG<br>TACATCAAGTGTATCATATGCCAAGTACGCCCCCTATTGA<br>CGTCAATGACGGTAAATGGCCCGCCTGGCATTATGCCCA<br>GTACATGACCTTATGGGACTTTCCTACTTGGCAGTACATC<br>TACGTATTAGTCATCGCTATTACCATGggtcgaggtgagccccacgtt<br>ctgcttcactctccccatctcccccccctccccacccccaattttgtatttatttattttttaattattag<br>tgcagcgatgggggcgggggggggggggggcgcgcgccaggcggggcggggcggggcg<br>aggggcggggcggggcgaggcggagaggtgcggcggcagccaatcagagcggcgcgct<br>ccgaaagtttccttttatggcgaggcggcggcggcggcggccctataaaaagcgaagcgcgc<br>ggcgggcgggagtcgctgcgttgccttcgccccgtgccccgctccgcgccgcctcgcgccg<br>cccgccccggctctgactgaccgcgttactcccacaggtgagcgggcgggacggcccttctc<br>ctccgggctgtaattagcgcttggtttaatgacggctcgtttcttttctgtggctgcgtgaaagcctt<br>aaagggctccgggagggccctttgtgcggggggggagcggctcggggggtgcgtgcgtgtgt<br>gtgtgcgtggggagcgccgcgtgcggcccgcgctgcccggcggctgtgagcgctgcgggc<br>gcggcgcggggctttgtgcgctccgcgtgtgcgcgaggggagcgcggccgggggcggtgc<br>cccgcggtgcgggggggctgcgaggggaacaaaggctgcgtgcggggtgtgtgcgtgggg<br>gggtgagcagggggtgtgggcgcggcggtcgggctgtaacccccccctgcacccccctccc<br>cgagttgctgagcacggcccggcttcgggtgcggggctccgtgcggggcgtggcgcgggg<br>ctcgccgtgccgggcgggggtggcggcaggtgggggtgccgggcggggcggggccgc<br>ctcgggccggggagggctcgggggaggggcgcggcggcccccggagcgccggcggctgt<br>cgaggcgcggcgagccgcagccattgccttttatggtaatcgtgcgagagggcgcagggact<br>tcctttgtcccaaatctggcggagccgaaatctgggaggcgccgccgcaccccctctagcggg<br>cgcgggcgaagcggtgcggcgccggcaggaaggaaatgggcggggagggccttcgtgcg<br>tcgccgcgccgccgtccccttctccatctccagcctcggggctgccgcagggggacggctgc<br>cttcgggggggacggggcagggcggggttcggcttctggcgtgtgaccggcggctctagag<br>cctctgctaaccatgttcatgccttcttctttttcctacagctcctgggcaacgtgctggttgttgtgc<br>tgtctcatcattttggcaaagaatt | 5 |
| EF1 alpha | GAGTAATTCATACAAAAGGACTCGCCCCTGCCTTGGGGA<br>ATCCCAGGGACCGTCGTTAAACTCCCACTAACGTAGAAC<br>CCAGAGATCGCTGCGTTCCCGCCCCCTCACCCGCCCGCTC<br>TCGTCATCACTGAGGTGGAGAAGAGCATGCGTGAGGCTC<br>CGGTGCCCGTCAGTGGGCAGAGCGCACATCGCCCACAGT<br>CCCCGAGAAGTTGGGGGGAGGGGTCGGCAATTGAACCGG<br>TGCCTAGAGAAGGTGGCGCGGGGTAAACTGGGAAAGTGA<br>TGTCGTGTACTGGCTCCGCCTTTTTCCCGAGGGTGGGGGA<br>GAACCGTATATAAGTGCAGTAGTCGCCGTGAACGTTCTTT<br>TTCGCAACGGGTTTGCCGCCAGAACACAGGTAAGTGCCG<br>TGTGTGGTTCCCGCGGGCCTGGCCTCTTTACGGGTTATGG<br>CCCTTGCGTGCCTTGAATTACTTCCACGCCCCTGGCTGCA<br>GTACGTGATTCTTGATCCCGAGCTTCGGGTTGGAAGTGGG<br>TGGGAGAGTTCGAGGCCTTGCGCTTAAGGAGCCCCTTCG<br>CCTCGTGCTTGAGTTGAGGCCTGGCTTGGGCGCTGGGGCC<br>GCCGCGTGCGAATCTGGTGGCACCTTCGCGCCTGTCTCGC<br>TGCTTTCGATAAGTCTCTAGCCATTTAAAATTTTTGATGA<br>CCTGCTGCGACGCTTTTTTTCTGGCAAGATAGTCTTGTAA<br>ATGCGGGCCAAGATCTGCACACTGGTATTTCGGTTTTTGG<br>GGCCGCGGGCGGCGACGGGGCCCGTGCGTCCCAGCGCAC<br>ATGTTCGGCGAGGCGGGGCCTGCGAGCGCGGCCACCGAG<br>AATCGGACGGGGGTAGTCTCAAGCTGGCCGGCCTGCTCT<br>GGTGCCTGGCCTCGCGCCGCCGTGTATCGCCCCGCCCTGG<br>GCGGCAAGGCTGGCCCGGTCGGCACCAGTTGCGTGAGCG<br>GAAAGATGGCCGCTTCCCGGCCCTGCTGCAGGGAGCTCA<br>AAATGGAGGACGCGGCGCTCGGGAGAGCGGGCGGGTGA<br>GTCACCCACACAAAGGAAAAGGGCCTTTCCGTCCTCAGC<br>CGTCGCTTCATGTGACTCCACGGAGTACCGGGCGCCGTCC<br>AGGCACCTCGATTAGTTCTCGAGCTTTTGGAGTACGTCGT | 6 |

TABLE 2-continued

| Nucleic acid sequences for various regulatory elements (RE) disclosed herein. | | |
|---|---|---|
| RE | SEQUENCE | SEQ ID NO |
| | CTTTAGGTTGGGGGGAGGGGTTTTATGCGATGGAGTTTCC CCACACTGAGTGGGTGGAGACTGAAGTTAGGCCAGCTTG GCACTTGATGTAATTCTCCTTGGAATTTGCCCTTTTTGAGT TTGGATCTTGGTTCATTCTCAAGCCTCAGACAGTGGTTCA AAGTTTTTTTCTTCCATTTCAGGTGTCGTGA | |

TABLE 3

Amino acid sequences for exemplary DNA Binding Domains (DBD) provided herein. For the DBD, engineered zinc finger (eZF) indicates that the construct has the formula set forth in SEQ ID NO: 147 (TABLE 10); EGR1 indicates that the DBD is derived from wild-type human EGR1 (SEQ ID NO: 176; TABLE 12); and EGR3 indicates that the DBD is derived from wild-type human EGR3 (SEQ ID NO: 175, TABLE 12). The target sites are the sequences bound by the DBD and are provided in TABLE 4 below.

| DBD/Target site | SEQUENCE | SEQ ID NO |
|---|---|---|
| eZF/z1 | LEPGEKPYKCPECGKSFSRSDNLVRHQRTHTGEKPYKCPEC GKSFSREDNLHTHQRTHTGEKPYKCPECGKSFSRSDELVRH QRTHTGEKPYKCPECGKSFSQSGNLTEHQRTHTGEKPYKC PECGKSFSTSGHLVRHQRTHTGEKPYKCPECGKSFSQNSTL TEHQRTHTGKKTS | 77 |
| eZF/z2 | LEPGEKPYKCPECGKSFSTKNSLTEHQRTHTGEKPYKCPEC GKSFSRADNLTEHQRTHTGEKPYKCPECGKSFSQLAHLRA HQRTHTGEKPYKCPECGKSFSTKNSLTEHQRTHTGEKPYK CPECGKSFSQAGHLASHQRTHTGEKPYKCPECGKSFSTHLD LIRHQRTHTGKKTS | 78 |
| eZF/z3 | LEPGEKPYKCPECGKSFSQAGHLASHQRTHTGEKPYKCPEC GKSFSREDNLHTHQRTHTGEKPYKCPECGKSFSTSGNLTEH QRTHTGEKPYKCPECGKSFSTHLDLIRHQRTHTGEKPYKCP ECGKSFSQKSSLIAHQRTHTGEKPYKCPECGKSFSQAGHLA SHQRTHTGKKTS | 79 |
| eZF/z4 | LEPGEKPYKCPECGKSFSTTGNLTVHQRTHTGEKPYKCPEC GKSFSTSGELVRHQRTHTGEKPYKCPECGKSFSREDNLHTH QRTHTGEKPYKCPECGKSFSTSGNLTEHQRTHTGEKPYKCP ECGKSFSQSSSLVRHQRTHTGEKPYKCPECGKSFSQRANLR AHQRTHTGKKTS | 80 |
| eZF/z5 | LEPGEKPYKCPECGKSFSSRRTCRAHQRTHTGEKPYKCPEC GKSFSTTGALTEHQRTHTGEKPYKCPECGKSFSRSDELVRH QRTHTGEKPYKCPECGKSFSRNDALTEHQRTHTGEKPYKC PECGKSFSQSGDLRRHQRTHTGEKPYKCPECGKSFSTSHSL TEHQRTHTGKKTS | 81 |
| eZF/z6 | LEPGEKPYKCPECGKSFSRKDNLKNHQRTHTGEKPYKCPE CGKSFSDPGALVRHQRTHTGEKPYKCPECGKSFSREDNLH THQRTHTGEKPYKCPECGKSFSDPGALVRHQRTHTGEKPY KCPECGKSFSTSGELVRHQRTHTGEKPYKCPECGKSFSRKD NLKNHQRTHTGKKTS | 82 |
| eZF/z7 | LEPGEKPYKCPECGKSFSSKKALTEHQRTHTGEKPYKCPEC GKSFSSPADLTRHQRTHTGEKPYKCPECGKSFSRSDNLVRH QRTHTGEKPYKCPECGKSFSREDNLHTHQRTHTGEKPYKC PECGKSFSRSDELVRHQRTHTGEKPYKCPECGKSFSQSGNL TEHQRTHTGEKPYKCPECGKSFSTSGHLVRHQRTHTGEKP YKCPECGKSFSQNSTLTEHQRTHTGKKTS | 83 |
| eZF/z8 | LEPGEKPYKCPECGKSFSSPADLTRHQRTHTGEKPYKCPEC GKSFSRSDNLVRHQRTHTGEKPYKCPECGKSFSREDNLHT HQRTHTGEKPYKCPECGKSFSRSDELVRHQRTHTGEKPYK CPECGKSFSQSGNLTEHQRTHTGEKPYKCPECGKSFSTSGH LVRHQRTHTGKKTS | 84 |
| eZF/z9 | LEPGEKPYKCPECGKSFSSKKALTEHQRTHTGEKPYKCPEC GKSFSSPADLTRHQRTHTGEKPYKCPECGKSFSRSDNLVRH QRTHTGEKPYKCPECGKSFSREDNLHTHQRTHTGEKPYKC PECGKSFSRSDELVRHQRTHTGEKPYKCPECGKSFSQSGNL TEHQRTHTGKKTS | 85 |

TABLE 3-continued

Amino acid sequences for exemplary DNA Binding Domains (DBD) provided herein. For the DBD, engineered zinc finger (eZF) indicates that the construct has the formula set forth in SEQ ID NO: 147 (TABLE 10); EGR1 indicates that the DBD is derived from wild-type human EGR1 (SEQ ID NO: 176; TABLE 12); and EGR3 indicates that the DBD is derived from wild-type human EGR3 (SEQ ID NO: 175, TABLE 12). The target sites are the sequences bound by the DBD and are provided in TABLE 4 below.

| DBD/Target site | SEQUENCE | SEQ ID NO |
|---|---|---|
| eZF/z10 | LEPGEKPYKCPECGKSFSDCRDLARHQRTHTGEKPYKCPEC GKSFSRNDALTEHQRTHTGEKPYKCPECGKSFSRNDALTE HQRTHTGEKPYKCPECGKSFSSPADLTRHQRTHTGEKPYK CPECGKSFSDPGNLVRHQRTHTGEKPYKCPECGKSFSQRA HLERHQRTHTGEKPYKCPECGKSFSQSSSLVRHQRTHTGEK PYKCPECGKSFSHRTTLTNHQRTHTGKKTS | 86 |
| eZF/z11 | LEPGEKPYKCPECGKSFSRNDALTEHQRTHTGEKPYKCPEC GKSFSSPADLTRHQRTHTGEKPYKCPECGKSFSDPGNLVRH QRTHTGEKPYKCPECGKSFSQRAHLERHQRTHTGEKPYKC PECGKSFSQSSSLVRHQRTHTGEKPYKCPECGKSFSHRTTL TNHQRTHTGKKTS | 87 |
| eZF/z12 | LEPGEKPYKCPECGKSFSRNDALTEHQRTHTGEKPYKCPEC GKSFSDPGHLVRHQRTHTGEKPYKCPECGKSFSTSGELVRH QRTHTGEKPYKCPECGKSFSTHLDLIRHQRTHTGEKPYKCP ECGKSFSSKKALTEHQRTHTGEKPYKCPECGKSFSQLAHLR AHQRTHTGEKPYKCPECGKSFSRSDHLTNHQRTHTGKKTS | 88 |
| eZF/z13 | LEPGEKPYKCPECGKSFSRSDNLVRHQRTHTGEKPYKCPEC GKSFSHRTTLTNHQRTHTGEKPYKCPECGKSFSREDNLHTH QRTHTGEKPYKCPECGKSFSTSHSLTEHQRTHTGEKPYKCP ECGKSFSQSSSLVRHQRTHTGEKPYKCPECGKSFSREDNLH THQRTHTGKKTS | 89 |
| eZF/z14 | LEPGEKPYKCPECGKSFSDPGALVRHQRTHTGEKPYKCPEC GKSFSRSDNLVRHQRTHTGEKPYKCPECGKSFSQSGDLRR HQRTHTGEKPYKCPECGKSFSTHLDLIRHQRTHTGEKPYKC PECGKSFSTSGNLVRHQRTHTGEKPYKCPECGKSFSRSDNL VRHQRTHTGKKTS | 90 |
| eZF/z15 | LEPGEKPYKCPECGKSFSRRDELNVHQRTHTGEKPYKCPEC GKSFSRSDHLTNHQRTHTGEKPYKCPECGKSFSRSDDLVRH QRTHTGEKPYKCPECGKSFSRSDNLVRHQRTHTGEKPYKC PECGKSFSHRTTLTNHQRTHTGEKPYKCPECGKSFSREDNL HTHQRTHTGEKPYKCPECGKSFSTSHSLTEHQRTHTGEKPY KCPECGKSFSQSSSLVRHQRTHTGEKPYKCPECGKSFSRED NLHTHQRTHTGKKTS | 91 |
| EGR1/z1 | RPYACPVESCDRRFSRSDNLVRHIRIHTGQKPFQCRICMRNF SREDNLHTHIRTHTGEKPFACDICGRKFARSDELVRHTKIHL RQKDRPYACPVESCDRRFSQSGNLTEHIRIHTGQKPFQCRIC MRNFSTSGHLVRHIRTHTGEKPFACDICGRKFAQNSTLTEH TKIHLRQKDK | 92 |
| EGR1/z13 | RPYACPVESCDRRFSRSDNLVRHIRIHTGQKPFQCRICMRNF SHRTTLTNHIRTHTGEKPFACDICGRKFAREDNLHTHTKIHL RQKDRPYACPVESCDRRFSTSHSLTEHIRIHTGQKPFQCRIC MRNFSQSSSLVRHIRTHTGEKPFACDICGRKFAREDNLHTH TKIHLRQKDK | 93 |
| EGR1/z15 | RPYACPVESCDRRFSRRDELNVHIRIHTGQKPFQCRICMRN FSRSDHLTNHIRTHTGEKPFACDICGRKFARSDDLVRHTKIH LRQKDRPYACPVESCDRRFSRSDNLVRHIRIHTGQKPFQCRI CMRNFSHRTTLTNHIRTHTGEKPFACDICGRKFAREDNLHT HTKIHLRQKDRPYACPVESCDRRFSTSHSLTEHIRIHTGQKP FQCRICMRNFSQSSSLVRHIRTHTGEKPFACDICGRKFARED NLHTHTKIHLRQKD | 94 |
| EGr1/z17 | RPYACPVESCDRRFSDPGALVRHIRIHTGQKPFQCRICMRN FSRSDNLVRHIRTHTGEKPFACDICGRKFAQSGDLRRHTKI HLRQKDRPYACPVESCDRRFSTHLDLIRHIRIHTGQKPFQCR ICMRNFSTSGNLVRHIRTHTGEKPFACDICGRKFARSDNLV RHTKIHLRQKDRPYACPVESCDRRFSQSGHLTEHIRIHTGQ KPFQCRICMRNFSERSHLREHIRTHTGEKPFACDICGRKFAQ AGHLASHTKIHLRQKD | 95 |
| EGR3/z1 | RPHACPAEGCDRRFSRSDNLVRHLRIHTGHKPFQCRICMRS FSREDNLHTHIRTHTGEKPFACEFCGRKFARSDELVRHAKI | 96 |

TABLE 3-continued

Amino acid sequences for exemplary DNA Binding Domains (DBD) provided herein. For the DBD, engineered zinc finger (eZF) indicates that the construct has the formula set forth in SEQ ID NO: 147 (TABLE 10); EGR1 indicates that the DBD is derived from wild-type human EGR1 (SEQ ID NO: 176; TABLE 12); and EGR3 indicates that the DBD is derived from wild-type human EGR3 (SEQ ID NO: 175, TABLE 12). The target sites are the sequences bound by the DBD and are provided in TABLE 4 below.

| DBD/Target site | SEQUENCE | SEQ ID NO |
|---|---|---|
| | HLKQKEHACPAEGCDRRFSQSGNLTEHLRIHTGHKPFQCRI CMRSFSTSGHLVRHIRTHTGEKPFACEFCGRKFAQNSTLTE HAKIHLKQKEK | |
| EGR3/z13 | RPHACPAEGCDRRFSRSDNLVRHLRIHTGHKPFQCRICMRS FSHRTTLTNHIRTHTGEKPFACEFCGRKFAREDNLHTHAKI HLKQKEHACPAEGCDRRFSTSHSLTEHLRIHTGHKPFQCRI CMRSFSQSSSLVRHIRTHTGEKPFACEFCGRKFAREDNLHT HAKIHLKQKEK | 97 |
| EGR3/z15 | RPHACPAEGCDRRFSRRDELNVHLRIHTGHKPFQCRICMRS FSRSDHLTNHIRTHTGEKPFACEFCGRKFARSDDLVRHAKI HLKQKEHACPAEGCDRRFSRSDNLVRHLRIHTGHKPFQCRI CMRSFSHRTTLTNHIRTHTGEKPFACEFCGRKFAREDNLHT HAKIHLKQKEHACPAEGCDRRFSTSHSLTEHLRIHTGHKPF QCRICMRSFSQSSSLVRHIRTHTGEKPFACEFCGRKFAREDN LHTHAKIHLKQKEK | 98 |

TABLE 4

Target site sequences and chromosomal location for exemplary target sites bound by DNA binding domains disclosed herein.

| Chr 2 Start Position | Target Site Sequence | Target Site | SEQ ID NO for Target Site Sequence |
|---|---|---|---|
| 166149168 | CTAGGTCAAGTGTAGGAG | z1 | 18 |
| 166149158 | ACTTGACCTAGACAGCCT | z2 | 19 |
| 166073978 | TGAATAACTCATTAGTGA | z3 | 20 |
| 166073933 | AAAGTACATTAGGCTAAT | z4 | 21 |
| 166149199 | CCAGCACTGGTGCTTCGT | z5 | 22 |
| 166149176 | AAGGCTGTCTAGGTCAAG | z6 | 23 |
| 166149168 | CTAGGTCAAGTGTAGGAGACACAC | z7 | 24 |
| 166149165 | GGTCAAGTGTAGGAGACA | z8 | 25 |
| 166149162 | CAAGTGTAGGAGACACAC | z9 | 26 |

TABLE 4-continued

Target site sequences and chromosomal location for exemplary target sites bound by DNA binding domains disclosed herein.

| Chr 2 Start Position | Target Site Sequence | Target Site | SEQ ID NO for Target Site Sequence |
|---|---|---|---|
| 166149160 | AGTGTAGGAGACACACTGCTGGCC | z10 | 27 |
| 166149160 | AGTGTAGGAGACACACTG | z11 | 28 |
| 166149155 | AGGAGACACACTGCTGGCCTG | z12 | 29 |
| 166128025 | TAGGTACCATAGAGTGAG | z13 | 30 |
| 166127991 | GAGGATACTGCAGAGGTC | z14 | 31 |
| 166127999 | TAGGTACCATAGAGTGAGGCGAGGATG | z15 | 32 |
| 166127991 | ATAGAGTGAGGCGAGGATGAAGCCGAG | z16 | 33 |
| 166127974 | TGAAGCCGAGAGGATACTGCAGAGGTC | z17 | 34 |

TABLE 5

Amino acid sequences for exemplary transcriptional activation domains (TADs) disclosed herein.

| TAD | SEQUENCE | SEQ ID NO |
|---|---|---|
| VPR | DALDDFDLDMLGSDALDDFDLDMLGSDALDDFDLDMLGSDA LDDFDLDMLINSRSSGSPKKKRKVGSQYLPDTDDRHRIEEKRK RTYETFKSIMKKSPFSGPTDPRPPPRRIAVPSRSSASVPKPAPQPY PFTSSLSTINYDEFPTMVFPSGQISQASALAPAPPQVLPQAPAPA PAPAMVSALAQAPAPVPVLAPGPPQAVAPPAPKPTQAGEGTLS EALLQLQFDDEDLGALLGNSTDPAVFTDLASVDNSEFQQLLNQ GIPVAPHTTEPMLMEYPEAITRLVTGAQRPPDPAPAPLGAPGLP NGLLSGDEDFSSIADMDFSALLGSGSGSRDSREGMFLPKPEAGS | 132 |

TABLE 5-continued

Amino acid sequences for exemplary transcriptional activation domains (TADs) disclosed herein.

| TAD | SEQUENCE | SEQ ID NO |
|---|---|---|
| | AISDVFEGREVCQPKRIRPFHPPGSPWANRPLPASLAPTPTGPVH EPVGSLTPAPVPQPLDPAPAVTPEASHLLEDPDEETSQAVKALR EMADTVIPQKEEAAICGQMDLSHPPPRGHLDELTTTLESMTEDL NLDSPLTPELNEILDTFLNDECLLHAMHISTGLSIFDTSLF | |
| VP64 | DALDDFDLDMLGSDALDDFDLDMLGSDALDDFDLDMLGSDA LDDFDLDML | 133 |
| CITED2 | MSGLEMADHMMAMNHGRFPDGTNGLHHHPAHRMGMGQFPS PHHHQQQQPQHAFNALMGEHIHYGAGNMNATSGIRHAMGPG TVNGGHPPSALAPAARFNNSQFMGPPVASQGGSLPASMQLQKL NNQYFNHHPYPHNHYMPDLHPAAGHQMNGTNQHFRDCNPKH SGGSSTPGGSGGSSTPGGSGSSSGGGAGSSNSGGGSGSGNMPAS VAHVPAAMLPPNVIDTDFIDEEVLMSLVIEMGLDRIKELPELWL GQNEFDFMTDFVCKQQPSRVSC | 134 |
| CITED4 | ADHLMLAEGYRLVQRPPSAAAAHGPHALRTLPPYAGPGLDSG LRPRGAPLGPPPPRQPGALAYGAFGPPSSFQPFPAVPPPAAGIAH LQPVATPYPGRAAAPPNAPGGPPGPQPAPSAAAPPPPAHALGG MDAELIDEEALTSLELELGLHRVRELPELFLGQSEFDCFSDLGS APPAGSVSC | 135 |
| CREB3 | MELELDAGDQDLLAFLLEESGDLGTAPDEAVRAPLDWALPLSE VPSDWEVDDLLCSLLSPPASLNILSSSNPCLVHHDHTYSLPRET VSMDLESESCRKEGTQMTPQHMEELAEQEIARLVLTDEEKSLL EKEGLILPETLPLTKTEEQILKRVR | 224 |

TABLE 6

Amino acid sequences for exemplary engineered transcription factors (DBD + TAD) disclosed herein.

| CON-STRUCT | SEQUENCE | SEQ ID NO |
|---|---|---|
| 1 | MAPKKKRKVGIHGVPAALEPGEKPYKCPECGKSFS RSDNLVRHQRTHTGEKPYKCPECGKSFSHRTTLTNH QRTHTGEKPYKCPECGKSFSREDNLHTHQRTHTGE KPYKCPECGKSFSTSHSLTEHQRTHTGEKPYKCPEC GKSFSQSSSLVRHQRTHTGEKPYKCPECGKSFSRED NLHTHQRTHTGKKTSKRPAATKKAGQAKKKKGSY PYDVPDYALEEASGSGRADALDDFDLDMLGSDALD DFDLDMLGSDALDDFDLDMLGSDALDDFDLDMLIN SRSSGSPKKKRKVGSQYLPDTDDRHRIEEKRKRTYE TFKSIMKKSPFSGPTDPRPPPRRIAVPSRSSASVPKPA PQPYPFTSSLSTINYDEFPTMVFPSGQISQASALAPAP PQVLPQAPAPAPAPAMVSALAQAPAPVPVLAPGPPQ AVAPPAPKPTQAGEGTLSEALLQLQFDDEDLGALLG NSTDPAVFTDLASVDNSEFQQLLNQGIPVAPHTTEP MLMEYPEAITRLVTGAQRPPDPAPAPLGAPGLPNGL LSGDEDFSSIADMDFSALLGSGSGSRDSREGMFLPK PEAGSAISDVFEGREVCQPKRIRPFHPPGSPWANRPL PASLAPTPTGPVHEPVGSLTPAPVPQPLDPAPAVTPE ASHLLEDPDEETSQAVKALREMADTVIPQKEEAAIC GQMDLSHPPPRGHLDELTTTLESMTEDLNLDSPLTP ELNEILDTFLNDECLLHAMHISTGLSIFDTSLF | 99 |
| 2 | MAPKKKRKVGIHGVPAALEPGEKPYKCPECGKSFS RSDNLVRHQRTHTGEKPYKCPECGKSFSREDNLHT HQRTHTGEKPYKCPECGKSFSRSDELVRHQRTHTGE KPYKCPECGKSFSQSGNLTEHQRTHTGEKPYKCPEC GKSFSTSGHLVRHQRTHTGEKPYKCPECGKSFSQNS TLTEHQRTHTGKKTSKRPAATKKAGQAKKKKGSYP YDVPDYALEEASGSGRADALDDFDLDMLGSDALD DFDLDMLGSDALDDFDLDMLGSDALDDFDLDMLIN SRSSGSPKKKRKVGSQYLPDTDDRHRIEEKRKRTYE TFKSIMKKSPFSGPTDPRPPPRRIAVPSRSSASVPKPA PQPYPFTSSLSTINYDEFPTMVFPSGQISQASALAPAP PQVLPQAPAPAPAPAMVSALAQAPAPVPVLAPGPPQ | 100 |

TABLE 6-continued

Amino acid sequences for exemplary engineered transcription factors (DBD + TAD) disclosed herein.

| CON-STRUCT | SEQUENCE | SEQ ID NO |
|---|---|---|
| | AVAPPAPKPTQAGEGTLSEALLQLQFDDEDLGALLG NSTDPAVFTDLASVDNSEFQQLLNQGIPVAPHTTEP MLMEYPEAITRLVTGAQRPPDPAPAPLGAPGLPNGL LSGDEDFSSIADMDFSALLGSGSGSRDSREGMFLPK PEAGSAISDVFEGREVCQPKRIRPFHPPGSPWANRPL PASLAPTPTGPVHEPVGSLTPAPVPQPLDPAPAVTPE ASHLLEDPDEETSQAVKALREMADTVIPQKEEAAIC GQMDLSHPPPRGHLDELTTTLESMTEDLNLDSPLTP ELNEILDTFLNDECLLHAMHISTGLSIFDTSLF | |
| 3 | MAPKKKRKVGIHGVPAALEPGEKPYKCPECGKSFS RSDNLVRHQRTHTGEKPYKCPECGKSFSHRTTLTNH QRTHTGEKPYKCPECGKSFSREDNLHTHQRTHTGE KPYKCPECGKSFSTSHSLTEHQRTHTGEKPYKCPEC GKSFSQSSSLVRHQRTHTGEKPYKCPECGKSFSRED NLHTHQRTHTGKKTSKRPAATKKAGQAKKKKGSY PYDVPDYALEDALDDFDLDMLGSDALDDFDLDML GSDALDDFDLDMLGSDALDDFDLDML | 101 |
| 4 | MAPKKKRKVGIHGVPAALEPGEKPYKCPECGKSFS RSDNLVRHQRTHTGEKPYKCPECGKSFSREDNLHT HQRTHTGEKPYKCPECGKSFSRSDELVRHQRTHTGE KPYKCPECGKSFSQSGNLTEHQRTHTGEKPYKCPEC GKSFSTSGHLVRHQRTHTGEKPYKCPECGKSFSQNS TLTEHQRTHTGKKTSKRPAATKKAGQAKKKKGSYP YDVPDYALEDALDDFDLDMLGSDALDDFDLDMLG SDALDDFDLDMLGSDALDDFDLDML | 102 |
| 5 | MAADHLMLAEGYRLVQRPPSAAAAHGPHALRTLPP YAGPGLDSGLRPRGAPLGPPPPRQPGALAYGAFGPP SSFQPFPAVPPPAAGIAHLQPVATPYPGRAAAPPNAP GGPPGPQPAPSAAAPPPPAHALGGMDAELIDEEALT SLELELGLHRVRELPELFLGQSEFDCFSDLGSAPPAG SVSCGGSGGGSGQSQLIKPSRMRKYPNRPSKTPPHE | 103 |

TABLE 6-continued

Amino acid sequences for exemplary engineered transcription factors (DBD + TAD) disclosed herein.

| CONSTRUCT | SEQUENCE | SEQ ID NO |
|---|---|---|
| | RPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | |
| 6 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDK | 104 |
| 7 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | 105 |
| 8 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 106 |
| 9 | MQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | 107 |
| 10 | MQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDKLEMSGLEMADHMMAMNHGRFPDGTNGLHHHPAHRMGMGQFPSPHHHQQQ | 108 |

TABLE 6-continued

Amino acid sequences for exemplary engineered transcription factors (DBD + TAD) disclosed herein.

| CONSTRUCT | SEQUENCE | SEQ ID NO |
|---|---|---|
| | QPQHAFNALMGEHIHYGAGNMNATSGIRHAMGPGTVNGGHPPSALAPAARFNNSQFMGPPVASQGGSLPASMQLQKLNNQYFNHHPYPHNHYMPDLHPAAGHQMNGTNQHFRDCNPKHSGGSSTPGGSGGSSTPGGSGSSSGGGAGSSNSGGGSGSGNMPASVAHVPAAMLPPNVIDTDFIDEEVLMSLVIEMGLDRIKELPELWLGQNEFDFMTDFVCKQQPSRVSC | |
| 11 | MSGLEMADHMMAMNHGRFPDGTNGLHHHPAHRMGMGQFPSPHHHQQQQPQHAFNALMGEHIHYGAGNMNATSGVRHAMGPGTVNGGHPPSALAPAARFNNSQFMGPPVASQGGSLPASMQLQKLNNQYFNHHPYPHNHYMPDLHPAAGHQMNGTNQHFRDCNPKHSGGSSTPGGSGGSSTPGGSGSSSGGGAGSSNSGGGSGSGNMPASVAHVPAAMLPPNVIDTDFIDEEVLMSLVIEMGLDRIKELPELWLGQNEFDFMTDFVCKQQPSRVSCQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 109 |
| 12 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGRPHACPAEGCDRRFSRSDNLVRHLRIHTGHKPFQCRICMRSFSREDNLHTHIRTHTGEKPFACEFCGRKFARSDELVRHAKIHLKQKEHACPAEGCDRRFSQSGNLTEHLRIHTGHKPFQCRICMRSFSTSGHLVRHIRTHTGEKPFACEFCGRKFAQNSTLTEHAKIHLKQKEKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | 110 |
| 13 | MRPHACPAEGCDRRFSRSDNLVRHLRIHTGHKPFQCRICMRSFSREDNLHTHIRTHTGEKPFACEFCGRKFARSDELVRHAKIHLKQKEHACPAEGCDRRFSQSGNLTEHLRIHTGHKPFQCRICMRSFSTSGHLVRHIRTHTGEKPFACEFCGRKFAQNSTLTEHAKIHLKQKEKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | 111 |
| 14 | MRPHACPAEGCDRRFSRSDNLVRHLRIHTGHKPFQCRICMRSFSREDNLHTHIRTHTGEKPFACEFCGRKFARSDELVRHAKIHLKQKEHACPAEGCDRRFSQSGNLTEHLRIHTGHKPFQCRICMRSFSTSGHLVRHIRTHTGEKPFACEFCGRKFAQNSTLTEHAKIHLKQKEKKAEKGGAPSASSAPPVSLAPVVTTCALEMSGLEMADHMMAMNHGRFPDGTNGLHHHPAHRMGMGQFPSPHHHQQQQPQHAFNALMGEHIHYGAGNMNATSGIRHAMGPGTVNGGHPPSALAPAARFNNSQFMGPPVASQGGSLPASMQLQKLNNQYFNHHPYPHNHYMPDLHPAAGHQMNGTNQHFRDCNPKHSGGSSTPGGSGGSSTPGGSGSSSGGGAGSSNSGGGSGSGNMPASVAHVPAAMLPPNVIDTDFIDEEVLMSLVIEMGLDRIKELPELWLGQNEFDFMTDFVCKQQPSRVSC | 112 |
| 15 | MSGLEMADHMMAMNHGRFPDGTNGLHHHPAHRMGMGQFPSPHHHQQQQPQHAFNALMGEHIHYGAGNMNATSGVRHAMGPGTVNGGHPPSALAPAARFNNSQFMGPPVASQGGSLPASMQLQKLNNQYFNHHPYPHNHYMPDLHPAAGHQMNGTNQHFRDCNPKHSGGSSTPGGSGGSSTPGGSGSSSGGGAGSSNSGGGSGSGNM | 113 |

TABLE 6-continued

Amino acid sequences for exemplary engineered transcription factors (DBD + TAD) disclosed herein.

| CONSTRUCT | SEQUENCE | SEQ ID NO |
|---|---|---|
| | PASVAHVPAAMLPPNVIDTDFIDEEVLMSLVIEMGLDRIKELPELWLGQNEFDFMTDFVCKQQPSRVSCRPHACPAEGCDRRFSRSDNLVRHLRIHTGHKPFQCRICMRSFSREDNLHTHIRTHTGEKPFACEFCGRKFARSDELVRHAKIHLKQKEHACPAEGCDRRFSQSGNLTEHLRIHTGHKPFQCRICMRSFSTSGHLVRHIRTHTGEKPFACEFCGRKFAQNSTLTEHAKIHLKQKEKKAEKGGAPSASSAPPVSLAPVVTTCA | |
| 16 | MTGKLAEKLPVTMSSLLNQLPDNLYPEEIPSALNLFSGSSDSVVHYNQMATENVMDIGLTNEKPNPELSYSGSFQPAPGNKTVTYLGKFAFDSPSNWCQDNIISLMSAGILGVPPASGALSTQTSTASMVQPPQGDVEAMYPALPPYSNCGDLYSEPVSFHDPQGNPGLAYSPQDYQSAKPALDSNLFPMIPDYNLYHHPNDMGSIPEHKPFQGMDPIRVNPPPITPLETIKAFKDKQIHPGFGSLPQPPLTLKPIRPRKYPNRPSKTPLHERPHACPAEGCDRRFSRRDELNVHLRIHTGHKPFQCRICMRSFSRSDHLTNHIRTHTGEKPFACEFCGRKFARSDDLVRHAKIHLKQKEHACPAEGCDRRFSRSDNLVRHLRIHTGHKPFQCRICMRSFSHRTTLTNHIRTHTGEKPFACEFCGRKFAREDNLHTHAKIHLKQKEHACPAEGCDRRFSTSHSLTEHLRIHTGHKPFQCRICMRSFSQSSSLVRHIRTHTGEKPFACEFCGRKFAREDNLHTHAKIHLKQKEKKAEKGGAPSASSAPPVSLAPVVTTCA | 114 |
| 17 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLFPQQQGDLGLGTPDQKPFQGLESRTQQPSLTPLSTIKAFATQSGSQDLKALNTSYQSQLIKPSRMRKYPNRPSKTPPHERPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDKKADKSVVASSATSSLSSYPSPVATSYPSPVTTSYPSPATTSYPSPVPTSFSSPGSSTYPSPVHSGFPSPSVATTYSSVPPAFPAQVSSFPSSAVTNSFSASTGLSDMTATFSPRTIEIC | 115 |
| 18 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLFPQQQGDLGLGTPDQKPFQGLESRTQQPSLTPLSTIKAFATQSGSQDLKALNTSYQSQLIKPSRMRKYPNRPSKTPPHERPYACPVESCDRRFSRRDELNVHIRIHTGQKPFQCRICMRNFSRSDHLTNHIRTHTGEKPFACDICGRKFARSDDLVRHTKIHLRQKDRPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDKKADKSVVASSATSSLSSYPSPVATSYPSPVTTSYPSPATTSYPSPVPTSFSSPGSSTYPSPVHSGFPSPSVATTYSSVPPAFPAQVSSFPSSAVTNSFSASTGLSDMTATFSPRTIEIC | 116 |
| 19 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLFPQQQGDLGLGTPDQKPFQGLESRTQQPSLTPLSTIKAFATQSGSQDLKALNTSYQSQLIKPSRMRKYPNRPSKTPPHERPYACPVESCDRRFSRSDNLVRHIRIHTGQKPFQCRICMRNFSHRTTLTNHIRTHTGEKPFACDICGRKFAREDNLHTHIRTHTGEKPFACDICGRKFSTSHSLTEHIRIHTGQKPFQCRICMRNFSQSSSLVRHIRTHTGEKPFACDICGRKFAREDNLHTHTKIHLRQKDKKADKSVVASSATSSLSSYPSPVATSYPSPVTTSYPSPATTSYPSPVPTSFSSPGSSTYPSPVHSGFPSPSVATTYSSVPPAFPAQVSSFPSSAVTNSFSASTGLSDMTATFSPRTIEIC | 117 |
| 20 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLFPQQQGDLGLGTPDQKPFQGLESRTQQPSLTPLSTIKAFATQSGSQDLKALNTSYQSQLIKPSRMRKYPNRPSKTPPHERPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDKKADKSVVASSATSSLSSYPSPVATSYPSPVTTSYPSPATTSYPSPVPTSFSSPGSSTYPSPVHSGFPSPSVATTYSSVPPAFPAQVSSFPSSAVTNSFSASTGLSDMTATFSPRTIEIC | 115 |
| 21 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLFPQQQGDLGLGTPDQKPFQGLESRTQQPSLTPLSTIKAFATQSGSQDLKALNTSYQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDKKADKSVVASSATSSLSSYPSPVATSYPSPVTTSYPSPATTSYPSPVPTSFSSPGSSTYPSPVHSGFPSPSVATTYSSVPPAFPAQVSSFPSSAVTNSFSASTGLSDMTATFSPRTIEIC | 118 |
| 22 | MTGKLAEKLPVTMSSLLNQLPDNLYPEEIPSALNLFSGSSDSVVHYNQMATENVMDIGLTNEKPNPELSYSGSFQPAPGNKTVTYLGKFAFDSPSNWCQDNIISLMSAGILGVPPASGALSTQTSTASMVQPPQGDVEAMYPALPPYSNCGDLYSEPVSFHDPQGNPGLAYSPQDYQSAKPALDSNLFPMIPDYNLYHHPNDMGSIPEHKPFQGMDPIRVNPPPITPLETIKAFKDKQIHPGFGSLPQPPLTLKPIRPRKYPNRPSKTPLHERPHACPAEGCDRRFSRSDNLVRHLRIHTGHKPFQCRICMRSFSHRTTLTNHIRTHTGEKPFACEFCGRKFAREDNLHTHAKIHLKQKEHACPAEGCDRRFSTSHSLTEHLRIHTGHKPFQCRICMRSFSQSSSLVRHIRTHTGEKPFACEFCGRKFAREDNLHTHAKIHLKQKEKKAEKGGAPSASSAPPVSLAPVVTTCA | 119 |
| 23 | MAAAKAEMQLMSPLQISDPFGSFPHSPTMDNYPKLEEMMLLSNGAPQFLGAAGAPEGSGSNSSSSSSGGGGGGGGGSNSSSSSSTFNPQADTGEQPYEHLTAESFPDISLNNEKVLVETSYPSQTTRLPPITYTGRFSLEPAPNSGNTLWPEPLFSLVSGLVSMTNPPASSSSAPSPAASSASASQSPPLSCAVPSNDSSPIYSAAPTFPTPNTDIFPEPQSQAFPGSAGTALQYPPPAYPAAKGGFQVPMIPDYLF | 120 |

TABLE 6-continued

Amino acid sequences for exemplary engineered transcription factors (DBD + TAD) disclosed herein.

| CONSTRUCT | SEQUENCE | SEQ ID NO |
|---|---|---|
| | PQQQGDLGLGTPDQKPFQGLESRTQQPSLTPLSTIKA<br>FATQSGSQDLKALNTSYQSQLIKPSRMRKYPNRPSK<br>TPPHERPYACPVESCDRRFSDPGALVRHIRIHTGQKP<br>FQCRICMRNFSRSDNLVRHIRTHTGEKPFACDICGR<br>KFAQSGDLRRHTKIHLRQKDRPYACPVESCDRRFST<br>HLDLIRHIRIHTGQKPFQCRICMRNFSTSGNLVRHIR<br>THTGEKPFACDICGRKFARSDNLVRHTKIHLRQKDR<br>PYACPVESCDRRFSQSGHLTEHIRIHTGQKPFQCRIC<br>MRNFSERSHLREHIRTHTGEKPFACDICGRKFAQAG<br>HLASHTKIHLRQKDKKADKSVVASSATSSLSSYPSP<br>VATSYPSPVTTSYPSPATTSYPSPVPTSFSSPGSSTYP<br>SPVHSGFPSPSVATTYSSVPPAFPAQVSSFPSSAVTNS<br>FSASTGLSDMTATFSPRTIEIC | |
| 24 | MAAAKAEMQLMSPLQISDPFGSFPHSPTMDNYPKL<br>EEMMLLSNGAPQFLGAAGAPEGSGSNSSSSSSGGGG<br>GGGGGSNSSSSSSTFNPQADTGEQPYEHLTAESFPDI<br>SLNNEKVLVETSYPSQTTRLPPITYTGRFSLEPAPNS<br>GNTLWPEPLFSLVSGLVSMTNPPASSSSAPSPAASSA<br>SASQSPPLSCAVPSNDSSPIYSAAPTFPTPNTDIFPEPQ<br>SQAFPGSAGTALQYPPPAYPAAKGGFQVPMIPDYLF<br>PQQQGDLGLGTPDQKPFQGLESRTQQPSLTPLSTIKA<br>FATQSGSQDLKALNTSYQSQLIKPSRMRKYPNRPSK<br>TPPHERPYACPVESCDRRFSRSDNLTRHIRIHTGQKP<br>FQCRICMRNFSHSTTLTNHIRTHTGEKPFACDICGRK<br>FARSDNRKTHIRTHTGEKPFACDICGRKFSTSHSLTE<br>HIRIHTGQKPFQCRICMRNFSQSSSLTRHIRTHTGEKP<br>FACDICGRKFARSDNRKTHTKIHLRQKDKKADKSV<br>VASSATSSLSSYPSPVATSYPSPVTTSYPSPATTSYPS<br>PVPTSFSSPGSSTYPSPVHSGFPSPSVATTYSSVPPAF<br>PAQVSSFPSSAVTNSFSASTGLSDMTATFSPRTIEIC | 121 |
| 25 | MTGKLAEKLPVTMSSLLNQLPDNLYPEEIPSALNLF<br>SGSSDSVVHYNQMATENVMDIGLTNEKPNPELSYS<br>GSFQPAPGNKTVTYLGKFAFDSPSNWCQDNIISLMS<br>AGILGVPPASGALSTQTSTASMVQPPQGDVEAMYP<br>ALPPYSNCGDLYSEPVSFHDPQGNPGLAYSPQDYQS<br>AKPALDSNLFPMIPDYNLYHHPNDMGSIPEHKPFQG<br>MDPIRVNPPPITPLETIKAFKDKQIHPGFGSLPQPPLT<br>LKPIRPRKYPNRPSKTPLHERPHACPAEGCDRRFSRS<br>DNLVRHLRIHTGHKPFQCRICMRSFSREDNLHTHIRT<br>HTGEKPFACEFCGRKFARSDELVRHAKIHLKQKEH<br>ACPAEGCDRRFSQSGNLTEHLRIHTGHKPFQCRICM<br>RSFSTSGHLVRHIRTHTGEKPFACEFCGRKFAQNSTL<br>TEHAKIHLKQKEKKAEKGGAPSASSAPPVSLAPVVT<br>TCA | 122 |
| 26 | MAAAKAEMQLMSPLQISDPFGSFPHSPTMDNYPKL<br>EEMMLLSNGAPQFLGAAGAPEGSGSNSSSSSSGGGG<br>GGGGGSNSSSSSSTFNPQADTGEQPYEHLTAESFPDI<br>SLNNEKVLVETSYPSQTTRLPPITYTGRFSLEPAPNS<br>GNTLWPEPLFSLVSGLVSMTNPPASSSSAPSPAASSA<br>SASQSPPLSCAVPSNDSSPIYSAAPTFPTPNTDIFPEPQ<br>SQAFPGSAGTALQYPPPAYPAAKGGFQVPMIPDYLF<br>PQQQGDLGLGTPDQKPFQGLESRTQQPSLTPLSTIKA<br>FATQSGSQDLKALNTSYQSQLIKPSRMRKYPNRPSK<br>TPPHERPYACPVESCDRRFSRSDNLTRHIRIHTGQKP<br>FQCRICMRNFSRSDNLTTHIRTHTGEKPFACDICGRK<br>FARSDERKRHIRTHTGEKPFACDICGRKFSQSGNLTE<br>HIRIHTGQKPFQCRICMRNFSTSGHLTRHIRTHTGEK<br>PFACDICGRKFAQSSTRKEHTKIHLRQKDKKADKSV<br>VASSATSSLSSYPSPVATSYPSPVTTSYPSPATTSYPS<br>PVPTSFSSPGSSTYPSPVHSGFPSPSVATTYSSVPPAF<br>PAQVSSFPSSAVTNSFSASTGLSDMTATFSPRTIEIC | 123 |
| 27 | MAAAKAEMQLMSPLQISDPFGSFPHSPTMDNYPKL<br>EEMMLLSNGAPQFLGAAGAPEGSGSNSSSSSSGGGG<br>GGGGGSNSSSSSSTFNPQADTGEQPYEHLTAESFPDI<br>SLNNEKVLVETSYPSQTTRLPPITYTGRFSLEPAPNS<br>GNTLWPEPLFSLVSGLVSMTNPPASSSSAPSPAASSA<br>SASQSPPLSCAVPSNDSSPIYSAAPTFPTPNTDIFPEPQ<br>SQAFPGSAGTALQYPPPAYPAAKGGFQVPMIPDYLF | 124 |

TABLE 6-continued

Amino acid sequences for exemplary engineered transcription factors (DBD + TAD) disclosed herein.

| CONSTRUCT | SEQUENCE | SEQ ID NO |
|---|---|---|
| | PQQQGDLGLGTPDQKPFQGLESRTQQPSLTPLSTIKA<br>FATQSGSQDLKALNTSYQSQLIKPSRMRKYPNRPSK<br>TPPHERPYACPVESCDRRFSRSDNLVRHIRIHTGQKP<br>FQCRICMRNFSREDNLHTHIRTHTGEKPFACDICGR<br>KFARSDELVRHIRTHTGEKPFACDICGRKFSQSGNLT<br>EHIRIHTGQKPFQCRICMRNFSTSGHLVRHIRTHTGE<br>KPFACDICGRKFAQNSTLTEHTKIHLRQKDKKADKS<br>VVASSATSSLSSYPSPVATSYPSPVTTSYPSPATTSYP<br>SPVPTSFSSPGSSTYPSPVHSGFPSPSVATTYSSVPPA<br>FPAQVSSFPSSAVTNSFSASTGLSDMTATFSPRTIEIC | |
| 28 | MAPKKKRKVGIHGVPAALEPGEKPYKCPECGKSFSS<br>PADLTRHQRTHTGEKPYKCPECGKSFSRSDNLVRH<br>QRTHTGEKPYKCPECGKSFSREDNLHTHQRTHTGE<br>KPYKCPECGKSFSRSDELVRHQRTHTGEKPYKCPEC<br>GKSFSQSGNLTEHQRTHTGEKPYKCPECGKSFSTSG<br>HLVRHQRTHTGKKTSKRPAATKKAGQAKKKKGSY<br>PYDVPDYALEDALDDFDLDMLGSDALDDFDLDML<br>GSDALDDFDLDMLGSDALDDFDLDML | 125 |
| 29 | MAPKKKRKVGIHGVPAALEPGEKPYKCPECGKSFS<br>DPGALVRHQRTHTGEKPYKCPECGKSFSRSDNLVR<br>HQRTHTGEKPYKCPECGKSFSQSGDLRRHQRTHTG<br>EKPYKCPECGKSFSTHLDLIRHQRTHTGEKPYKCPE<br>CGKSFSTSGNLVRHQRTHTGEKPYKCPECGKSFSRS<br>DNLVRHQRTHTGKKTSKRPAATKKAGQAKKKKGS<br>YPYDVPDYALEDALDDFDLDMLGSDALDDFDLDM<br>LGSDALDDFDLDMLGSDALDDFDLDML | 126 |
| 30 | MAPKKKRKVGIHGVPAALEPGEKPYKCPECGKSFS<br>RSDNLVRHQRTHTGEKPYKCPECGKSFSHRTTLTNH<br>QRTHTGEKPYKCPECGKSFSREDNLHTHQRTHTGE<br>KPYKCPECGKSFSTSHSLTEHQRTHTGEKPYKCPEC<br>GKSFSQSSSLVRHQRTHTGEKPYKCPECGKSFSRED<br>NLHTHQRTHTGKKTSKRPAATKKAGQAKKKKGSY<br>PYDVPDYALEEASGSGRADALDDFDLDMLGSDALD<br>DFDLDMLGSDALDDFDLDMLGSDALDDFDLDMLIN<br>SRSSGSPKKKRKVGSQYLPDTDDRHRIEEKRKRTYE<br>TFKSIMKKSPFSGPTDPRPPPRRIAVPSRSSASVPKPA<br>PQPYPFTSSLSTINYDEFPTMVFPSGQISQASALAPAP<br>PQVLPQAPAPAPAPAMVSALAQAPAPVPVLAPGPPQ<br>AVAPPAPKPTQAGEGTLSEALLQLQFDDEDLGALLG<br>NSTDPAVFTDLASVDNSEFQQLLNQGIPVAPHTTEP<br>MLMEYPEAITRLVTGAQRPPDPAPAPLGAPGLPNGL<br>LSGDEDFSSIADMDFSALLGSGSGSRDSREGMFLPK<br>PEAGSAISDVFEGREVCQPKRIRPFHPPGSPWANRPL<br>PASLAPTPTGPVHEPVGSLTPAPVPQPLDPAPAVTPE<br>ASHLLEDPDEETSQAVKALREMADTVIPQKEEAAIC<br>GQMDLSHPPPRGHLDELTTTLESMTEDLNLDSPLTP<br>ELNEILDTFLNDECLLHAMHISTGLSIFDTSLF | 99 |
| 31 | MAPKKKRKVGIHGVPAALEPGEKPYKCPECGKSFS<br>RSDNLVRHQRTHTGEKPYKCPECGKSFSREDNLHT<br>HQRTHTGEKPYKCPECGKSFSRSDELVRHQRTHTGE<br>KPYKCPECGKSFSQSGNLTEHQRTHTGEKPYKCPEC<br>GKSFSTSGHLVRHQRTHTGEKPYKCPECGKSFSQNS<br>TLTEHQRTHTGKKTSKRPAATKKAGQAKKKKGSYP<br>YDVPDYALEDALDDFDLDMLGSDALDDFDLDMLG<br>SDALDDFDLDMLGSDALDDFDLDML | 102 |
| 32 | MAPKKKRKVGIHGVPAALEPGEKPYKCPECGKSFS<br>RSDNLVRHQRTHTGEKPYKCPECGKSFSREDNLHT<br>HQRTHTGEKPYKCPECGKSFSRSDELVRHQRTHTGE<br>KPYKCPECGKSFSQSGNLTEHQRTHTGEKPYKCPEC<br>GKSFSTSGHLVRHQRTHTGEKPYKCPECGKSFSQNS<br>TLTEHQRTHTGKKTSKRPAATKKAGQAKKKKGSYP<br>YDVPDYALEDALDDFDLDMLGSDALDDFDLDMLG<br>SDALDDFDLDMLGSDALDDFDLDML | 102 |
| 33 | MAPKKKRKVGIHGVPAALEPGEKPYKCPECGKSFS<br>RSDNLVRHQRTHTGEKPYKCPECGKSFSREDNLHT<br>HQRTHTGEKPYKCPECGKSFSRSDELVRHQRTHTGE | 100 |

TABLE 6-continued

Amino acid sequences for exemplary engineered transcription factors (DBD + TAD) disclosed herein.

| CONSTRUCT | SEQUENCE | SEQ ID NO |
|---|---|---|
| | KPYKCPECGKSFSQSGNLTEHQRTHTGEKPYKCPECGKSFSTSGHLVRHQRTHTGEKPYKCPECGKSFSQNSTLTEHQRTHTGKKTSKRPAATKKAGQAKKKKGSYPYDVPDYALEEASGSGRADALDDFDLDMLGSDALDDFDLDMLGSDALDDFDLDMLGSDALDDFDLDMLINSRSSGSPKKKRKVGSQYLPDTDDRHRIEEKRKRTYETFKSIMKKSPFSGPTDPRPPPRRIAVPSRSSASVPKPAPQPYPFTSSLSTINYDEFPTMVFPSGQISQASALAPAPPQVLPQAPAPAPAPAMVSALAQAPAPVPVLAPGPPQAVAPPAPKPTQAGEGTLSEALLQLQFDDEDLGALLGNSTDPAVFTDLASVDNSEFQQLLNQGIPVAPHTTEPMLMEYPEAITRLVTGAQRPPDPAPAPLGAPGLPNGLLSGDEDFSSIADMDFSALLGSGSGSRDSREGMFLPKPEAGSAISDVFEGREVCQPKRIRPFHPPGSPWANRPLPASLAPTPTGPVHEPVGSLTPAPVPQPLDPAPAVTPEASHLLEDPDEETSQAVKALREMADTVIPQKEEAAICGQMDLSHPPPRGHLDELTTTLESMTEDLNLDSPLTPELNEILDTFLNDECLLHAMHISTGLSIFDTSLF | |
| 34 | MAPKKKRKVGIHGVPAALEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNSTLTEHQRTHTGKKTSKRPAATKKAGQAKKKKGSDALDDFDLDMLGSDALDDFDLDMLGSDALDDFDLDMLGSDALDDFDLDML | 127 |
| 35 | MAPKKKRKVGIHGVPAALEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNSTLTEHQRTHTGKKTSKRPAATKKAGQAKKKKGSDALDDFDLDMLGSDALDDFDLDMLGSDALDDFDLDMLGSDALDDFDLDML | 127 |
| 36 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 128 |
| 37 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 106 |
| 38 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 129 |
| 39 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDKLEMADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSC | 105 |
| 40 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 130 |
| 41 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 131 |
| 42 | MAPKKKRKVGIHGVPAALEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNSTLTEHQRTHTGKKTSKRPAATKKAGQAKKKKGSYPYDVPDYALEDALDDFDLDMLGSDALDDFDLDMLGSDALDDFDLDMLGSDALDDFDLDML | 102 |
| 43 | MAPKKKRKVGIHGVPAALEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNS | 102 |

TABLE 6-continued

Amino acid sequences for exemplary engineered transcription factors (DBD + TAD) disclosed herein.

| CONSTRUCT | SEQUENCE | SEQ ID NO |
|---|---|---|
| | TLTEHQRTHTGKKTSKRPAATKKAGQAKKKKGSYPYDVPDYALEDALDDFDLDMLGSDALDDFDLDMLGSDALDDFDLDMLGSDALDDFDLDML | |
| 44 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 106 |
| 45 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 106 |
| 46 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 205 |
| 47 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 207 |
| 48 | MAADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGADHLMLAEGYRLVQRPPSAAAAHGPHALRTLPPYAGPGLDSGLRPRGAPLGPPPPRQPGALAYGAFGPPSSFQPFPAVPPPAAGIAHLQPVATPYPGRAAAPPNAPGGPPGPQPAPSAAAPPPPAHALGGMDAELIDEEALTSLELELGLHRVRELPELFLGQSEFDCFSDLGSAPPAGSVSCGGSGGGSGQSQLIKPSRMRKYPNRPSKTPPHERPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDK | 209 |
| 49 | MELELDAGDQDLLAFLLEESGDLGTAPDEAVRAPLDWALPLSEVPSDWEVDDLLCSLLSPPASLNILSSSNPCLVHHDHTYSLPRETVSMDLESESCRKEGTQMTPQHMEELAEQEIARLVLTDEEKSLLEKEGLILPETLPLTKTEEQILKRVRLEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNSTLTEHQRTHTGKKTSVYVGGLESRVLKYTAQNMELQNKVQLLEEQNLSLLDQLRKLQAMVIEISNKTSSSSTCILVLLVSFCLLLVPAMYSSDTRGSLPAEHGVLSRQLRALPSEDPYQLELPALQSEVPKDSTHQWLDGSDCVLQAPGNTSCLLHYMPQAPSAEPPLEWPFPDLFSEPLCRGPILPLQANLTRKGGWLPTGSPSVILQDRYSG | 213 |
| 50 | MELELDAGDQDLLAFLLEESGDLGTAPDEAVRAPLDWALPLSEVPSDWEVDDLLCSLLSPPASLNILSSSNPCLVHHDHTYSLPRETVSMDLESESCRKEGTQMTPQHMEELAEQEIARLVLTDEEKSLLEKEGLILPETLPLTKTEEQILKRVRRPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGHLVRHIRTHTGEKPFACDICGRKFAQNSTLTEHTKIHLRQKDVYVGGLESRVLKYTAQNMELQNKVQLLEEQNLSLLDQLRKLQAMVIEISNKTSSSSTCILVLLVSFCLLLVPAMYSSDTRGSLPAEHGVLSRQLRALPSEDPYQLELPALQSEVPKDSTHQWLDGSDCVLQAPGNTSCLLHYMPQAPSAEPPLEWPFPDLFSEPLCRGPILPLQANLTRKGGWLPTGSPSVILQDRYSG | 217 |
| 51 | MELELDAGDQDLLAFLLEESGDLGTAPDEAVRAPLDWALPLSEVPSDWEVDDLLCSLLSPPASLNILSSSNPCLVHHDHTYSLPRETVSMDLESESCRKEGTQMTPQHMEELAEQEIARLVLTDEEKSLLEKEGLILPETLPLTKTEEQILKRVRRPYACPVESCDRRFSRSDNLVRHIRIHTGQKPFQCRICMRNFSHRTTLTNHIRTHTGEKPFACDICGRKFAREDNLHTHTKIHLRQKDRPYACPVESCDRRFSTSHSLTEHIRIHTGQKPFQCRICMRNFSQSSSLVRHIRTHTGEKPFACDICGRKFAREDNLHTHTKIHLRQKDVYVGGLESRVLKYTAQNMELQNKVQLLEEQNLSLLDQLRKLQAMVIEISNKTSSSSTCILVLLVSFCLLLVPAMYSSDTRGSLPAEHGVLSRQLRALPSEDPYQLELPALQSEVPKDSTHQWLDGSDCVLQAPGNTSCLLHYMPQAPSAEPPLEWPFPDLFSEPLCRGPILPLQANLTRKGGWLPTGSPSVILQDRYSG | 219 |
| 52 | MELELDAGDQDLLAFLLEESGDLGTAPDEAVRAPLDWALPLSEVPSDWEVDDLLCSLLSPPASLNILSSSNPCLVHHDHTYSLPRETVSMDLESESCRKEGTQMTPQHMEELAEQEIARLVLTDEEKSLLEKEGLILPETLPLTKTEEQILKRVRLEPGEKPYKCPECGKSFSRSDNLVRHQRTHTGEKPYKCPECGKSFSREDNLHTHQRTHTGEKPYKCPECGKSFSRSDELVRHQRTHTGEKPYKCPECGKSFSQSGNLTEHQRTHTGEKPYKCPECGKSFSTSGHLVRHQRTHTGEKPYKCPECGKSFSQNSTLTEHQRTHTGKKTSVYVGGLESRVLKYTAQNMELQNKVQLLEEQNLSLLDQLRKLQAMVIEIS | 221 |
| 53 | MELELDAGDQDLLAFLLEESGDLGTAPDEAVRAPLDWALPLSEVPSDWEVDDLLCSLLSPPASLNILSSSNPCLVHHDHTYSLPRETVSMDLESESCRKEGTQMTPQHMEELAEQEIARLVLTDEEKSLLEKEGLILPETLPLTKTEEQILKRVRRPYACPVESCDRRFSRSDNLVRHIRIHTGQKPFQCRICMRNFSREDNLHTHIRTHTGEKPFACDICGRKFARSDELVRHTKIHLRQKDRPYACPVESCDRRFSQSGNLTEHIRIHTGQKPFQCRICMRNFSTSGH | 223 |

TABLE 6-continued

| Amino acid sequences for exemplary engineered transcription factors (DBD + TAD) disclosed herein. | | |
|---|---|---|
| CON-STRUCT | SEQUENCE | SEQ ID NO |
| | LVRHIRTHTGEKPFACDICGRKFAQNSTLTEHTKIHL<br>RQKDVYVGGLESRVLKYTAQNMELQNKVQLLEEQ<br>NLSLLDQLRKLQAMVIEIS | |

TABLE 7

| Nucleic acid sequences encoding exemplary engineered transcription factors disclosed herein. | | |
|---|---|---|
| CONSTRUCT | SEQUENCE | SEQ ID NO |
| 31 (RE + coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaaggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaactttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaattttgtatttttaatagatacg<br>ggggtttcaccatatcacccaggctggtctcgaactcctggcctcaagtgatcca<br>cctgcctcggcctcccaaagtgctgggattataggcgtcagccactatgcccaac<br>ccgaccaacctttttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagacctttttttttttaccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccccctctcaccttgtctcaccaaagtccctagtccc<br>cggagcagttagcctctactttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT<br>GTGGCAAGAGCTTCTCACAATCAGGGAATCTGA<br>CTGAGCATCAACGAACTCATACCGGGGAAAAAC<br>CTTACAAGTGTCCAGAGTGTGGGAAGAGCTTTTC<br>CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCTACCCA<br>TACGACGTACCAGATTACGCTCTCGAGGACGCGC | 67 |

TABLE 7-continued

Nucleic acid sequences encoding exemplary engineered transcription factors disclosed herein.

| CONSTRUCT | SEQUENCE | SEQ ID NO |
|---|---|---|
| | TGGACGATTTCGATCTCGACATGCTGGGTTCTGA<br>TGCCCTCGATGACTTTGACCTGGATATGTTGGGA<br>AGCGACGCATTGGATGACTTTGATCTGGACATGC<br>TCGGCTCCGATGCTCTGGACGATTTCGATCTCGA<br>TATGTTATAAACTAGTaaagagaccggttcactgtgacagtaaaa<br>gagaccggttcactgtgagaatgaaagagaccggttcactgtgatcggaaaaga<br>gaccggttcactgtgagcggccttgaaacccagcagacaatgtagctcagtaga<br>aacccagcagacaatgtagctgaatggaaacccagcagacaatgtagcttcgg<br>agaaacccagcagacaatgtagctAAGCTTGGGTGGCATCCC<br>TGTGACCCCTCCCCAGTGCCTCTCCTGGCCCTGG<br>AAGTTGCCACTCCAGTGCCCACCAGCCTTGTCCT<br>AATAAAATTAAGTTGCATCATTTTGTCTGACTAG<br>GTGTCCTTCTATAATATTATGGGGTGGAGGGGGG<br>TGGTATGGAGCAAGGGGCAAGTTGGGAAGACAA<br>CCTGTAGGGCCTGCGGGGTCTATTGGGAACCAA<br>GCTGGAGTGCAGTGGCACAATCTTGGCTCACTGC<br>AATCTCCGCCTCCTGGGTTCAAGCGATTCTCCTG<br>CCTCAGCCTCCCGAGTTGTTGGGATTCCAGGCAT<br>GCATGACCAGGCTCAGCTAATTTTTGTTTTTTTGG<br>TAGAGACGGGGTTTCACCATATTGGCCAGGCTGG<br>TCTCCAACTCCTAATCTCAGGTGATCTACCCACC<br>TTGGCCTCCCAAATTGCTGGGATTACAGGCGTGA<br>ACCACTGCTCCCTTCCCTGTCCTT | |
| 32 (RE + coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactactctt<br>tcacatcttatgaaagtcatttaagcacaactaacttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>ggggtttcaccatatcacccaggctggtctcgaactcctggcctcaagtgatcca<br>cctgcctcggcctcccaaagtgctgggattataggcgtcagccactatgcccaac<br>ccgaccaaccttttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccccctctcaccttgtctcaccaaagtccctagtccc<br>cggagcagttagcctctttctttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT<br>GTGGCAAGAGCTTCTCACAATCAGGGAATCTGA<br>CTGAGCATCAACGAACTCATACCGGGAAAAAC<br>CTTACAAGTGTCCAGAGTGTGGGAAGAGCTTTTC | 68 |

TABLE 7-continued

Nucleic acid sequences encoding exemplary engineered transcription factors disclosed herein.

| CONSTRUCT | SEQUENCE | SEQ ID NO |
|---|---|---|
| | CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCTACCCA<br>TACGACGTACCAGATTACGCTCTCGAGGACGCGC<br>TGGACGATTTCGATCTCGACATGCTGGGTTCTGA<br>TGCCCTCGATGACTTTGACCTGGATATGTTGGGA<br>AGCGACGCATTGGATGACTTTGATCTGGACATGC<br>TCGGCTCCGATGCTCTGGACGATTTCGATCTCGA<br>TATGTTATAAACTAGTAAGCTTGGGTGGCATCCC<br>TGTGACCCCTCCCCAGTGCCTCTCCTGGCCCTGG<br>AAGTTGCCACTCCAGTGCCCACCAGCCTTGTCCT<br>AATAAAATTAAGTTGCATCATTTTGTCTGACTAG<br>GTGTCCTTCTATAATATTATGGGGTGGAGGGGGG<br>TGGTATGGAGCAAGGGGCAAGTTGGGAAGACAA<br>CCTGTAGGGCCTGCGGGGTCTATTGGGAACCAA<br>GCTGGAGTGCAGTGGCACAATCTTGGCTCACTGC<br>AATCTCCGCCTCCTGGGTTCAAGCGATTCTCCTG<br>CCTCAGCCTCCCGAGTTGTTGGGATTCCAGGCAT<br>GCATGACCAGGCTCAGCTAATTTTTGTTTTTTTGG<br>TAGAGACGGGGTTTCACCATATTGGCCAGGCTGG<br>TCTCCAACTCCTAATCTCAGGTGATCTACCCACC<br>TTGGCCTCCCAAATTGCTGGGATTACAGGCGTGA<br>ACCACTGCTCCCTTCCCTGTCCTT | |
| 33 (RE + coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaacttttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>ggggtttcaccatatcacccaggctggtctcgaactcctggcctcaagtgatcca<br>cctgcctcggcctcccaaagtgctgggattataggcgtcagccactatgcccaac<br>ccgaccaacctttttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccccctctcaccttgtctcaccaaagtccctagtccc<br>cggagcagttagcctctttctttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT | 69 |

TABLE 7-continued

| Nucleic acid sequences encoding exemplary engineered transcription factors disclosed herein. | | |
|---|---|---|
| CONSTRUCT | SEQUENCE | SEQ ID NO |
| | GTGGCAAGAGCTTCTCACAATCAGGGAATCTGA<br>CTGAGCATCAACGAACTCATACCGGGGAAAAAC<br>CTTACAAGTGTCCAGAGTGTGGGAAGAGCTTTTC<br>CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCTACCCA<br>TACGACGTACCAGATTACGCTCTCGAGGAGGCC<br>AGCGGTTCCGGACGGGCTGACGCATTGGACGAT<br>TTTGATCTGGATATGCTGGGAAGTGACGCCCTCG<br>ATGATTTTGACCTTGACATGCTTGGTTCGGATGC<br>CCTTGATGACTTTGACCTCGACATGCTCGGCAGT<br>GACGCCCTTGATGATTTCGACCTGGACATGCTGA<br>TTAACTCTAGAAGTTCCGGATCTCCGAAAAAGAA<br>ACGCAAAGTTGGTAGCCAGTACCTGCCCGACAC<br>CGACGACCGGCACCGGATCGAGGAAAAGCGGAA<br>GCGGACCTACGAGACATTCAAGAGCATCATGAA<br>GAAGTCCCCCTTCAGCGGCCCCACCGACCCTAGA<br>CCTCCACCTAGAAGAATCGCCGTGCCCAGCAGAT<br>CCAGCGCCAGCGTGCCAAAACCTGCCCCCCAGC<br>CTTACCCCTTCACCAGCAGCCTGAGCACCATCAA<br>CTACGACGAGTTCCCTACCATGGTGTTCCCCAGC<br>GGCCAGATCTCTCAGGCCTCTGCTCTGGCTCCAG<br>CCCCTCCTCAGGTGCTGCCTCAGGCTCCTGCTCC<br>TGCACCAGCTCCAGCCATGGTGTCTGCACTGGCT<br>CAGGCACCAGCACCCGTGCCTGTGCTGGCTCCTG<br>GACCTCCACAGGCTGTGGCTCCACCAGCCCCTAA<br>ACCTACACAGGCCGGCGAGGGCACACTGTCTGA<br>AGCTCTGCTGCAGCTGCAGTTCGACGACGAGGAT<br>CTGGGAGCCCTGCTGGGAAACAGCACCGATCCT<br>GCCGTGTTCACCGACCTGGCCAGCGTGGACAAC<br>AGCGAGTTCCAGCAGCTGCTGAACCAGGGCATC<br>CCTGTGGCCCCTCACACCACCGAGCCCATGCTGA<br>TGGAATACCCCGAGGCCATCACCCGGCTCGTGAC<br>AGGCGCTCAGAGGCCTCCTGATCCAGCTCCTGCC<br>CCTCTGGGAGCACCAGGCCTGCCTAATGGACTGC<br>TGTCTGGCGACGAGGACTTCAGCTCTATCGCCGA<br>TATGGATTTCTCAGCCTTGCTGGGCTCTGGCAGC<br>GGCAGCCGGGATTCCAGGGAAGGGATGTTTTTG<br>CCGAAGCCTGAGGCCGGCTCCGCTATTAGTGACG<br>TGTTTGAGGGCCGCGAGGTGTGCCAGCCAAAAC<br>GAATCCGGCCATTTCATCCTCCAGGAAGTCCATG<br>GGCCAACCGCCCACTCCCCGCCAGCCTCGCACCA<br>ACACCAACCGGTCCAGTACATGAGCCAGTCGGG<br>TCACTGACCCCGGCACCAGTCCCTCAGCCACTGG<br>ATCCAGCGCCCGCAGTGACTCCCGAGGCCAGTC<br>ACCTGTTGGAGGATCCCGATGAAGAGACGAGCC<br>AGGCTGTCAAAGCCCTTCGGGAGATGGCCGATA<br>CTGTGATTCCCCAGAAGGAAGAGGCTGCAATCT<br>GTGGCCAAATGGACCTTTCCCATCCGCCCCCAAG<br>GGGCCATCTGGATGAGCTGACAACCACACTTGA<br>GTCCATGACCGAGGATCTGAACCTGGACTCACCC<br>CTGACCCCGGAATTGAACGAGATTCTGGATACCT<br>TCCTGAACGACGAGTGCCTCTTGCATGCCATGCA<br>TATCAGCACAGGACTGTCCATCTTCGACACATCT<br>CTGTTTTAAACTAGTaataaaagatctttattttcattagatctgtgtgt<br>tggtttttttgtgtg | |
| 34 (RE + coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaacttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>ggggtttcaccatatcacccaggctggtctcgaactcctggcctcaagtgatcca<br>cctgcctcggcctcccaaagtgctgggattataggcgtcagccactatgcccaac<br>ccgaccaaccttttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct | 70 |

TABLE 7-continued

Nucleic acid sequences encoding exemplary engineered transcription factors disclosed herein.

| CONSTRUCT | SEQUENCE | SEQ ID NO |
|---|---|---|
| | ctgccggtggcactgggtagctgtggccaggtgtggtactttgatggggcccag | |
| | ggctggagctcaaggaagcgtcgcagggtcacagatctgggggaaccccgg | |
| | ggaaaagcactgaggcaaaaccgccgctcgtctcctacaatatatgggagggg | |
| | gaggttgagtacgttctggattactcataagaccttttttttttccttccgggcgcaaa | |
| | accgtgagctggatttataatcgccctataaagctccagaggcggtcaggcacct | |
| | gcagaggagccccgccgctccgccgactagctgcccccgcgagcaacggcct | |
| | cgtgatttccccgccgatccggtccccgcctccccactctgcccccgcctacccc | |
| | ggagccgtgcagccgcctctccgaatctctcttctcctggcgctcgcgtgcga | |
| | gagggaactagcgagaacgaggaagcagctggaggtgacgccgggcagatt | |
| | acgcctgtcagggccgagccgagcggatcgctgggcgctgtgcagaggaaa | |
| | ggcgggagtgcccggctcgctgtcgcagagccgaggtgggtaagctagcgac | |
| | cacctggacttcccagcgcccaaccgtggcttttcagccaggtcctctcctcccg | |
| | cggcttctcaaccaaccccatcccagcgccggccacccaacctcccgaaatga | |
| | gtgcttcctgccccagcagccgaaggcgctactaggaacggtaacctgttacttt | |
| | tccaggggccgtagtcgacccgctgcccgagttgctgtgcgactgcgcgcgcg | |
| | gggctagagtgcaaggtgactgtggttcttctctggccaagtccgagggagaac | |
| | gtaaagatatgggccttttttccccctctcaccttgtctcaccaaagtccctagtccc | |
| | cggagcagttagcctctttctttccagggaattagccagacacaacaacgggaac | |
| | cagacaccgaaccagacatgcccgccccgtgcgccctccccgctcgctgccttt | |
| | cctccctcttgtctctccagagccggatcttcaaggggagcctccgtgcccccgg | |
| | ctgctcagtccctccggtgtgcaggaccccggaagtcctccccgcacagctctc | |
| | gcttctctttgcagcctgtttctgcgccggaccagtcgaggactctggacagtaga | |
| | ggccccgggacgaccgagctgGAATTCGCCACCATGGCCCC | |
| | AAAGAAGAAGCGGAAGGTCGGTATCCACGGAGT | |
| | CCCAGCAGCCCTCGAACCAGGTGAAAAACCTTA | |
| | CAAATGTCCTGAATGTGGGAAATCATTCAGTCGC | |
| | AGCGACAACCTGGTGAGACATCAACGCACCCAT | |
| | ACAGGAGAAAAACCTTATAAATGTCCAGAATGT | |
| | GGAAAGTCCTTCTCACGAGAGGATAACTTGCAC | |
| | ACTCATCAACGAACACATACTGGTGAAAAACCA | |
| | TACAAGTGTCCCGAATGTGGTAAAAGTTTTAGCC | |
| | GGAGCGATGAACTTGTCCGACACCAACGAACCC | |
| | ATACAGGCGAGAAGCCTTACAAATGTCCCGAGT | |
| | GTGGCAAGAGCTTCTCACAATCAGGGAATCTGA | |
| | CTGAGCATCAACGAACTCATACCGGGGAAAAAC | |
| | CTTACAAGTGTCCAGAGTGTGGGAAGAGCTTTTC | |
| | CACAAGTGGACATCTGGTACGCCACCAGAGGAC | |
| | ACATACAGGGGAGAAGCCCTACAAATGCCCCGA | |
| | ATGCGGTAAAAGTTTCTCTCAGAATAGTACCCTG | |
| | ACCGAACACCAGCGAACACACACTGGGAAAAAA | |
| | ACGAGTAAAAGGCCGGCGGCCACGAAAAAGGCC | |
| | GGCCAGGCAAAAAAGAAAAAGGGATCCGACGC | |
| | GCTGGACGATTTCGATCTCGACATGCTGGGTTCT | |
| | GATGCCCTCGATGACTTTGACCTGGATATGTTGG | |
| | GAAGCGACGCATTGGATGACTTTGATCTGGACAT | |
| | GCTCGGCTCCGATGCTCTGGACGATTTCGATCTC | |
| | GATATGTTATAAAAGCTTGGGTGGCATCCCTGTG | |
| | ACCCCTCCCCAGTGCCTCTCCTGGCCCTGGAAGT | |
| | TGCCACTCCAGTGCCCACCAGCCTTGTCCTAATA | |
| | AAATTAAGTTGCATCATTTTGTCTGACTAGGTGT | |
| | CCTTCTATAATATTATGGGGTGGAGGGGGGTGGT | |
| | ATGGAGCAAGGGGCAAGTTGGGAAGACAACCTG | |
| | TAGGGCCTGCGGGGTCTATTGGGAACCAAGCTG | |
| | GAGTGCAGTGGCACAATCTTGGCTCACTGCAATC | |
| | TCCGCCTCCTGGGTTCAAGCGATTCTCCTGCCTC | |
| | AGCCTCCCGAGTTGTTGGGATTCCAGGCATGCAT | |
| | GACCAGGCTCAGCTAATTTTTGTTTTTTTGGTAG | |
| | AGACGGGGTTTCACCATATTGGCCAGGCTGGTCT | |
| | CCAACTCCTAATCTCAGGTGATCTACCCACCTTG | |
| | GCCTCCCAAATTGCTGGGATTACAGGCGTGAACC | |
| | ACTGCTCCCTTCCCTGTCCTT | |
| 26 (RE + | ggaggaagccatcaactaaactacaatgactgtaagatacaaaattgggaatggt | 71 |
| coding) | aacatattttgaagttctgttgacataaagaatcatgatattaatgcccatggaaatg | |
| | aaagggcgatcaacactatggtttgaaaagggggaaattgtagagcacagatgt | |
| | gttcgtgtggcagtgtgctgtctctagcaatactcagagaagagagagaacaatg | |
| | aaattctgattggccccagtgtgagcccagatgaggttcagctgccaactttctctt | |
| | tcacatcttatgaaagtcatttaagcacaactaactttttttttttttttttttttttgagaca | |
| | gagtcttgctctgttgcccaggacagagtgcagtagtgactcaatctcggctcact | |
| | gcagcctccacctcctaggctcaaacggtcctcctgcatcagcctcccaagtagc | |
| | tggaattacaggagtggcccaccatgcccagctaatttttgtatttttaatagatacg | |
| | gggtttcaccatatcacccaggctggtctcgaactcctggcctcaagtgatcca | |
| | cctgcctcggcctcccaaagtgctgggattataggcgtcagccactatgcccaac | |
| | ccgaccaacctttttaaaataaatatttaaaaaattggtatttcacatatatactagta | |
| | tttacatttatccacacaaaacggacgggcctccgctgaaccagtgaggcccca | |

TABLE 7-continued

Nucleic acid sequences encoding exemplary engineered transcription factors disclosed herein.

| CONSTRUCT | SEQUENCE | SEQ ID NO |
|---|---|---|
| | gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccctctcaccttgtctcaccaaagtccctagtccc<br>cggagcagttagcctctttctttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT<br>GTGGCAAGAGCTTCTCACAATCAGGGAATCTGA<br>CTGAGCATCAACGAACTCATACCGGGGAAAAAC<br>CTTACAAGTGTCCAGAGTGTGGGAAGAGCTTTTC<br>CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCGACGC<br>GCTGGACGATTTCGATCTCGACATGCTGGGTTCT<br>GATGCCCTCGATGACTTTGACCTGGATATGTTGG<br>GAAGCGACGCATTGGATGACTTTGATCTGGACAT<br>GCTCGGCTCCGATGCTCTGGACGATTTCGATCTC<br>GATATGTTATAAaaagagaccggttcactgtgacagtaaaagagac<br>cggttcactgtgagaatgaaagagaccggttcactgtgatcggaaaagagaccg<br>gttcactgtgagcggccttgaaacccagcagacaatgtagctcagtagaaaccc<br>agcagacaatgtagctgaatggaaacccagcagacaatgtagcttcggagaaa<br>cccagcagacaatgtagctAAGCTTGGGTGGCATCCCTGTG<br>ACCCCTCCCCAGTGCCTCTCCTGGCCCTGGAAGT<br>TGCCACTCCAGTGCCCACCAGCCTTGTCCTAATA<br>AAATTAAGTTGCATCATTTTGTCTGACTAGGTGT<br>CCTTCTATAATATTATGGGGTGGAGGGGGGTGGT<br>ATGGAGCAAGGGGCAAGTTGGGAAGACAACCTG<br>TAGGGCCTGCGGGGTCTATTGGGAACCAAGCTG<br>GAGTGCAGTGGCACAATCTTGGCTCACTGCAATC<br>TCCGCCTCCTGGGTTCAAGCGATTCTCCTGCCTC<br>AGCCTCCCGAGTTGTTGGGATTCCAGGCATGCAT<br>GACCAGGCTCAGCTAATTTTTGTTTTTTTGGTAG<br>AGACGGGGTTTCACCATATTGGCCAGGCTGGTCT<br>CCAACTCCTAATCTCAGGTGATCTACCCACCTTG<br>GCCTCCCAAATTGCTGGGATTACAGGCGTGAACC<br>ACTGCTCCCTTCCCTGTCCTT | |
| 40 (coding) | ATGGCCGCAGATCACCTGATGCTGGCTGAAGGCT<br>ACAGACTGGTGCAGCGGCCTCCATCTGCCGCTGC<br>CGCCCACGGCCCCCACGCCCTGAGAACACTGCCC<br>CCCTACGCCGGCCCTGGTCTTGATAGCGGACTCA<br>GACCTAGAGGCGCCCCTCTGGGCCCTCCACCTCC<br>AAGACAGCCTGGAGCCCTGGCCTACGGCGCCTTC<br>GGCCCTCCTTCTAGCTTCCAGCCCTTCCCCGCCGT | 72 |

TABLE 7-continued

Nucleic acid sequences encoding exemplary engineered transcription factors disclosed herein.

| CONSTRUCT | SEQUENCE | SEQ ID NO |
|---|---|---|
| | GCCTCCTCCAGCcGCTGGCATCGCCCACCTGCAG | |
| | CCTGTGGCCACCCCTTACCCCGGAAGAGCCGCCG | |
| | CCCCTCCAAACGCCCCTGGCGGACCTCCTGGCCC | |
| | CCAGCCTGCTCCAAGCGCCGCTGCCCCTCCACCT | |
| | CCTGCTCATGCCCTGGGCGGCATGGACGCCGAGC | |
| | TGATCGACGAGGAAGCCCTGACCAGCCTGGAAC | |
| | TGGAACTGGGCCTGCACAGAGTGCGGGAACTGC | |
| | CTGAGCTGTTCCTGGGACAGAGCGAGTTCGACTG | |
| | CTTCAGCGACCTGGGCAGCGCCCCTCCTGCCGGC | |
| | TCTGTGTCCTGCgccgaccacctgatgctcgccgagggctaccgcct | |
| | ggtgcagaggccgccgtccgccgccgccgcccatggccctcatgcgctccgg | |
| | actctgccgccgtacgcgggcccgggcctggacagtgggctgaggccgcgg | |
| | ggggctccgctggggccgccgccgccccgccaacccggggccctggcgtac | |
| | ggggccttcgggccgccgtcctccttccagccctttccggccgtgcctccgccg | |
| | gccgcgggcatcgcgcacctgcagcctgtggcgacgccgtaccccggccgc | |
| | gcCgccgcgcccccccaacgctccgggaggcccccccgggcccgcagccggc | |
| | cccaagcgccgcagccccgccgccgcccgcgcacgccctgggcggcatgga | |
| | cgccgaactcatcgacgaggaggcgctgacgtcgctggagctggagctgggg | |
| | ctgcaccgcgtgcgcgagctgcccgagctgttcctgggccagagcgagttcga | |
| | ctgcttctcggacttggggtccgcgccgcccgccggctccgtgagctgccagtc | |
| | ccagctcatcaaacccagccgcatgcgcaagtaccccaaccggcccagcaag | |
| | acgccccccccacgaacgcccttacgcttgcccagtggagtcctgtgatcgccgc | |
| | ttctccCGCAGCGACAACCTGGTGAGAcacatccgcatccac | |
| | acaggccagaagcccttccagtgccgcatctgcatgAGAaacttcagcCG | |
| | AGAGGATAACTTGCACACTcacatccgcacccacacaggcg | |
| | aaaagcccttcgcctgcgacatctgtggaagaaagtttgccCGGAGCGA | |
| | TGAACTTGTCCGAcataccaagatccacttgcggcagaaggaccgc | |
| | ccttacgcttgcccagtggagtcctgtgatcgccgcttctccCAATCAGG | |
| | GAATCTGACTGAGcacatccgcatccacacaggccagaagcccttc | |
| | cagtgccgcatctgcatgAGAaacttcagcACAAGTGGACATCT | |
| | GGTACGCcacatccgcacccacacaggcgaaaagcccttcgcctgcgac | |
| | atctgtggaagaaagtttgccCAGAATAGTACCCTGACCGAA | |
| | cataccaagatccacttgcggcagaaggacaag | |
| 41 (coding) | ATGGCCGCAGATCACCTGATGCTGGCTGAAGGCT | 73 |
| | ACAGACTGGTGCAGCGGCCTCCATCTGCCGCTGC | |
| | CGCCCACGGCCCCCACGCCCTGAGAACACTGCCC | |
| | CCCTACGCCGGCCCTGGTCTTGATAGCGGACTCA | |
| | GACCTAGAGGCGCCCCTCTGGGCCCTCCACCTCC | |
| | AAGACAGCCTGGAGCCCTGGCCTACGGCGCCTTC | |
| | GGCCCTCCTTCTAGCTTCCAGCCCTTCCCCGCCGT | |
| | GCCTCCTCCAGCTGCTGGCATCGCCCACCTGCAG | |
| | CCTGTGGCCACCCCTTACCCCGGAAGAGCCGCCG | |
| | CCCCTCCAAACGCCCCTGGCGGACCTCCTGGCCC | |
| | CCAGCCTGCTCCAAGCGCCGCTGCCCCTCCACCT | |
| | CCTGCTCATGCCCTGGGCGGCATGGACGCCGAGC | |
| | TGATCGACGAGGAAGCCCTGACCAGCCTGGAAC | |
| | TGGAACTGGGCCTGCACAGAGTGCGGGAACTGC | |
| | CTGAGCTGTTCCTGGGACAGAGCGAGTTCGACTG | |
| | CTTCAGCGACCTGGGCAGCGCCCCTCCTGCCGGC | |
| | TCTGTGTCCTGCGGCGGCAGCGGCGGCGGAAGC | |
| | GGCgccgaccacctgatgctcgccgagggctaccgcctggtgcagaggcc | |
| | gccgtccgccgccgccgcccatggccctcatgcgctccggactctgccgccgt | |
| | acgcgggcccgggcctggacagtgggctgaggccgcggggggctccgctgg | |
| | ggccgccgccgccccgccaacccggggccctggcgtacggggccttcgggc | |
| | cgccgtcctccttccagccctttccggccgtgcctccgccggccgcgggcatcg | |
| | cgcacctgcagcctgtggcgacgccgtaccccggccgcgcggccgcgcccc | |
| | ccaacgctccgggaggcccccccgggcccgcagccggccccaagcgccgca | |
| | gccccgccgccgcccgcgcacgccctgggcggcatggacgccgaactcatc | |
| | gacgaggaggcgctgacgtcgctggagctggagctggggctgcaccgcgtgc | |
| | gcgagctgcccgagctgttcctgggccagagcgagttcgactgcttctcggactt | |
| | ggggtccgcgccgcccgccggctccgtgagctgcggtggttctggtggtggtt | |
| | ctggtcagtcccagctcatcaaacccagccgcatgcgcaagtaccccaaccgg | |
| | cccagcaagacgccccccccacgaacgcccttacgcttgcccagtggagtcctgt | |
| | gatcgccgcttctccCGCAGCGACAACCTGGTGAGAcacatc | |
| | cgcatccacacaggccagaagcccttccagtgccgcatctgcatgAGAaact | |
| | tcagcCGAGAGGATAACTTGCACACTcacatccgcacccac | |
| | acaggcgaaaagcccttcgcctgcgacatctgtggaagaaagtttgccCGG | |
| | AGCGATGAACTTGTCCGAcataccaagatccacttgcggcaga | |
| | aggaccgcccttacgcttgcccagtggagtcctgtgatcgccgcttctccCAA | |
| | TCAGGGAATCTGACTGAGcacatccgcatccacacaggccag | |
| | aagcccttccagtgccgcatctgcatgAGAaacttcagcACAAGTGG | |
| | ACATCTGGTACGCcacatccgcacccacacaggcgaaaagcccttc | |
| | gcctgcgacatctgtggaagaaagtttgccCAGAATAGTACCCTG | |
| | ACCGAAcataccaagatccacttgcggcagaaggacaag | |

TABLE 7-continued

Nucleic acid sequences encoding exemplary engineered transcription factors disclosed herein.

| CONSTRUCT | SEQUENCE | SEQ ID NO |
|---|---|---|
| 42 (RE + Coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaacttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>gggtttcaccatatcacccaggctggtctcgaactcctggcctcaagtgatcca<br>cctgcctcggcctcccaaagtgctgggattataggcgtcagccactatgcccaac<br>ccgaccaacctttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtcctttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccccctctcaccttgtctcaccaaagtccctagtccc<br>cggagcagttagcctctttctttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT<br>GTGGCAAGAGCTTCTCACAATCAGGGAATCTGA<br>CTGAGCATCAACGAACTCATACCGGGGAAAAAC<br>CTTACAAGTGTCCAGAGTGTGGGAAGAGCTTTTC<br>CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCTACCCA<br>TACGACGTACCAGATTACGCTCTCGAGGACGCGC<br>TGGACGATTTCGATCTCGACATGCTGGGTTCTGA<br>TGCCCTCGATGACTTTGACCTGGATATGTTGGGA<br>AGCGACGCATTGGATGACTTTGATCTGGACATGC<br>TCGGCTCCGATGCTCTGGACGATTTCGATCTCGA<br>TATGTTATAAACTAGTGAAACCCAGCAGACAAT<br>GTAGCTAGACCCAGTAGCCAGATGTAGCTAAAG<br>AGACCGGTTCACTGTGAAAGCTTGGGTGGCATCC<br>CTGTGACCCCTCCCCAGTGCCTCTCCTGGCCCTG<br>GAAGTTGCCACTCCAGTGCCCACCAGCCTTGTCC<br>TAATAAAATTAAGTTGCATCATTTTGTCTGACTA<br>GGTGTCCTTCTATAATATTATGGGGTGGAGGGGG<br>GTGGTATGGAGCAAGGGGCAAGTTGGGAAGACA<br>ACCTGTAGGGCCTGCGGGGTCTATTGGGAACCA<br>AGCTGGAGTGCAGTGGCACAATCTTGGCTCACTG<br>CAATCTCCGCCTCCTGGGTTCAAGCGATTCTCCT<br>GCCTCAGCCTCCCGAGTTGTTGGGATTCCAGGCA | 74 |

TABLE 7-continued

Nucleic acid sequences encoding exemplary engineered transcription factors disclosed herein.

| CONSTRUCT | SEQUENCE | SEQ ID NO |
|---|---|---|
| | TGCATGACCAGGCTCAGCTAATTTTTGTTTTTTTG<br>GTAGAGACGGGGTTTCACCATATTGGCCAGGCTG<br>GTCTCCAACTCCTAATCTCAGGTGATCTACCCAC<br>CTTGGCCTCCCAAATTGCTGGGATTACAGGCGTG<br>AACCACTGCTCCCTTCCCTGTCCTT | |
| 43 (RE + Coding) | ggaggaagccatcaactaaactacaatgactgtaagatacaaaattgggaatggt<br>aacatatttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaacttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>gggtttcaccatatcacccaggctggtctcgaactcctggcctcaagtgatcca<br>cctgcctcggcctcccaaagtgctgggattataggcgtcagccactatgcccaac<br>ccgaccaacctttttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccccctctcaccttgtctcaccaaagtccctagtccc<br>cggagcagttagcctctactttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCCC<br>AAAGAAGAAGCGGAAGGTCGGTATCCACGGAGT<br>CCCAGCAGCCCTCGAACCAGGTGAAAAACCTTA<br>CAAATGTCCTGAATGTGGGAAATCATTCAGTCGC<br>AGCGACAACCTGGTGAGACATCAACGCACCCAT<br>ACAGGAGAAAAACCTTATAAATGTCCAGAATGT<br>GGAAAGTCCTTCTCACGAGAGGATAACTTGCAC<br>ACTCATCAACGAACACATACTGGTGAAAAACCA<br>TACAAGTGTCCCGAATGTGGTAAAAGTTTTAGCC<br>GGAGCGATGAACTTGTCCGACACCAACGAACCC<br>ATACAGGCGAGAAGCCTTACAAATGTCCCGAGT<br>GTGGCAAGAGCTTCTCACAATCAGGGAATCTGA<br>CTGAGCATCAACGAACTCATACCGGGGAAAAAC<br>CTTACAAGTGTCCAGAGTGTGGGAAGAGCTTTTC<br>CACAAGTGGACATCTGGTACGCCACCAGAGGAC<br>ACATACAGGGGAGAAGCCCTACAAATGCCCCGA<br>ATGCGGTAAAAGTTTCTCTCAGAATAGTACCCTG<br>ACCGAACACCAGCGAACACACACTGGGAAAAAA<br>ACGAGTAAAAGGCCGGCGGCCACGAAAAAGGCC<br>GGCCAGGCAAAAAAGAAAAAGGGATCCTACCCA<br>TACGACGTACCAGATTACGCTCTCGAGGACGCGC<br>TGGACGATTTCGATCTCGACATGCTGGGTTCTGA<br>TGCCCTCGATGACTTTGACCTGGATATGTTGGGA<br>AGCGACGCATTGGATGACTTTGATCTGGACATGC<br>TCGGCTCCGATGCTCTGGACGATTTCGATCTCGA<br>TATGTTATAAACTAGTGAAACCCAGCAGACAAT<br>GTAGCTAGACCCAGTAGCCAGATGTAGCTAAAG<br>AGACCGGTTCACTGTGAGAAACCCAGCAGACAA<br>TGTAGCTAGACCCAGTAGCCAGATGTAGCTAAA<br>GAGACCGGTTCACTGTGAAAGCTTGGGTGGCATC<br>CCTGTGACCCCTCCCCAGTGCCTCTCCTGGCCCT<br>GGAAGTTGCCACTCCAGTGCCCACCAGCCTTGTC | 75 |

TABLE 7-continued

Nucleic acid sequences encoding exemplary engineered transcription factors disclosed herein.

| CONSTRUCT | SEQUENCE | SEQ ID NO |
|---|---|---|
| | CTAATAAAATTAAGTTGCATCATTTTGTCTGACT | |
| | AGGTGTCCTTCTATAATATTATGGGGTGGAGGGG | |
| | GGTGGTATGGAGCAAGGGGCAAGTTGGGAAGAC | |
| | AACCTGTAGGGCCTGCGGGGTCTATTGGGAACC | |
| | AAGCTGGAGTGCAGTGGCACAATCTTGGCTCACT | |
| | GCAATCTCCGCCTCCTGGGTTCAAGCGATTCTCC | |
| | TGCCTCAGCCTCCCGAGTTGTTGGGATTCCAGGC | |
| | ATGCATGACCAGGCTCAGCTAATTTTTGTTTTTTT | |
| | GGTAGAGACGGGGTTTCACCATATTGGCCAGGCT | |
| | GGTCTCCAACTCCTAATCTCAGGTGATCTACCCA | |
| | CCTTGGCCTCCCAAATTGCTGGGATTACAGGCGT | |
| | GAACCACTGCTCCCTTCCCTGTCCTT | |
| 44 (RE + | ggaggaagccatcaactaaactacaatgactgtaagatacaaaattgggaatggt | 76 |
| Coding) | aacatattttgaagttctgttgacataaagaatcatgatattaatgcccatggaaatg | |
| | aaagggcgatcaacactatggtttgaaaaggggggaaattgtagagcacagatgt | |
| | gttcgtgtggcagtgtgctgtctctagcaatactcagagaagagagagagaacaatg | |
| | aaattctgattggccccagtgtgagcccagatgaggttcagctgccaactttctctt | |
| | tcacatcttatgaaagtcatttaagcacaactaactttttttttttttttttttttgagaca | |
| | gagtcttgctctgttgcccaggacagagtgcagtagtgactcaatctcggctcact | |
| | gcagcctccacctcctaggctcaaacggtcctcctgcatcagcctcccaagtagc | |
| | tggaattacaggagtggcccaccatgcccagctaatttttgtatttttaatagatacg | |
| | gggtttcaccatatcacccaggctggtctcgaactcctggcctcaagtgatcca | |
| | cctgcctcggcctcccaaagtgctgggattataggcgtcagccactatgcccaac | |
| | ccgaccaaccttttttaaaataaatatttaaaaaattggtatttcacatatatactagta | |
| | tttacatttatccacacaaaacggacgggcctccgctgaaccagtgaggcccca | |
| | gacgtgcgcataaataacccctgcgtgctgcaccacctggggagagggggag | |
| | gaccacggtaaatggagcgagcgcatagcaaaagggacgcggggtccttttct | |
| | ctgccggtggcactgggtagctgtggccaggtgtggtactttgatggggcccag | |
| | ggctggagctcaaggaagcgtcgcagggtcacagatctgggggaaccccgg | |
| | ggaaaagcactgaggcaaaaccgccgctcgtctcctacaatatatgggagggg | |
| | gaggttgagtacgttctggattactcataagaccttttttttttccttccgggcgcaaa | |
| | accgtgagctggatttataatcgccctataaagctccagaggcggtcaggcacct | |
| | gcagaggagccccgccgctccgccgactagctgcccccgcgagcaacggcct | |
| | cgtgatttccccgccgatccggtccccgcctccccactctgcccccgcctacccc | |
| | ggagccgtgcagccgcctctccgaatctctctcttctcctggcgctcgcgtgcga | |
| | gagggaactagcgagaacgaggaagcagctggaggtgacgccgggcagatt | |
| | acgcctgtcagggccgagccgagcggatcgctgggcgctgtgcagaggaaa | |
| | ggcgggagtgcccggctcgctgtcgcagagccgaggtgggtaagctagcgac | |
| | cacctggacttcccagcgcccaaccgtggcttttcagccaggtcctctcctcccg | |
| | cggcttctcaaccaaccccatcccagcgccggccacccaacctcccgaaatga | |
| | gtgcttcctgccccagcagccgaaggcgctactaggaacggtaacctgttacttt | |
| | tccaggggccgtagtcgacccgctgcccgagttgctgtgcgactgcgcgcgcg | |
| | gggctagagtgcaaggtgactgtggttcttctctggccaagtccgagggagaac | |
| | gtaaagatatgggcctttttcccccctctcaccttgtctcaccaaagtccctagtccc | |
| | cggagcagttagcctctttctttccagggaattagccagacacaacaacgggaac | |
| | cagacaccgaaccagacatgcccgccccgtgcgccctccccgctcgctgccttt | |
| | cctccctcttgtctctccagagccggatcttcaaggggagcctccgtgcccccgg | |
| | ctgctcagtccctccggtgtgcaggaccccggaagtcctccccgcacagctctc | |
| | gcttctctttgcagcctgtttctgcgccggaccagtcgaggactctggacagtaga | |
| | ggccccgggacgaccgagctgGAATTCGCCACCATGGCCgc | |
| | cgaccacctgatgctcgccgagggctaccgcctggtgcagaggccgccgtcc | |
| | gccgccgccgccgcccatggccctcatgcgctccggactctgccgccgtacgcggg | |
| | cccgggcctggacagtgggctgaggccgcggggggctccgctggggccgcc | |
| | gccgccccgccaacccggggccctggcgtacggggccttcgggccgccgtc | |
| | ctccttccagccctttccggccgtgcctccgccggccgcgggcatcgcgcacct | |
| | gcagcctgtggcgacgccgtaccccggccgcgcggccgcgccccccaacgc | |
| | tccgggaggcccccgggcccgcagccggccccaagcgccgcagccccgc | |
| | cgccgcccgcgcacgccctgggcggcatggacgccgaactcatcgacgagg | |
| | aggcgctgacgtcgctggagctggagctggggctgcaccgcgtgcgcgagct | |
| | gcccgagctgttcctgggccagagcgagttcgactgcttctcggacttggggtc | |
| | cgcgccgcccgccggctccgtgagctgcggtggttctggtggtggttctggtca | |
| | gtcccagctcatcaaacccagccgcatgcgcaagtaccccaaccggcccagca | |
| | agacgccccccacgaacgcccttacgcttgcccagtggagtcctgtgatcgcc | |
| | gcttctccCGCAGCGACAACCTGGTGAGAcacatccgcatcc | |
| | acacaggccagaagcccttccagtgccgcatctgcatgAGAaacttcagcC | |
| | GAGAGGATAACTTGCACACTcacatccgcacccacacaggc | |
| | gaaaagcccttcgcctgcgacatctgtggaagaaagtttgccCGGAGCG | |
| | ATGAACTTGTCCGAcataccaagatccacttgcggcagaaggacc | |
| | gcccttacgcttgcccagtggagtcctgtgatcgccgcttctccCAATCAG | |
| | GGAATCTGACTGAGcacatccgcatccacacaggccagaagccct | |
| | tccagtgccgcatctgcatgAGAaacttcagcACAAGTGGACATC | |
| | TGGTACGCcacatccgcacccacacaggcgaaaagcccttcgcctgcg | |
| | acatctgtggaagaaagtttgccCAGAATAGTACCCTGACCG | |
| | AAcataccaagatccacttgcggcagaaggacaagtaaCTCGAGGA | |

TABLE 7-continued

Nucleic acid sequences encoding exemplary engineered transcription factors disclosed herein.

| CONSTRUCT | SEQUENCE | SEQ ID NO |
|---|---|---|
| | AACCCAGCAGACAATGTAGCTAGACCCAGTAGC<br>CAGATGTAGCTAAAGAGACCGGTTCACTGTGAA<br>AGCTTGGGTGGCATCCCTGTGACCCCTCCCCAGT<br>GCCTCTCCTGGCCCTGGAAGTTGCCACTCCAGTG<br>CCCACCAGCCTTGTCCTAATAAAATTAAGTTGCA<br>TCATTTTGTCTGACTAGGTGTCCTTCTATAATATT<br>ATGGGGTGGAGGGGGGTGGTATGGAGCAAGGGG<br>CAAGTTGGGAAGACAACCTGTAGGGCCTGCGGG<br>GTCTATTGGGAACCAAGCTGGAGTGCAGTGGCA<br>CAATCTTGGCTCACTGCAATCTCCGCCTCCTGGG<br>TTCAAGCGATTCTCCTGCCTCAGCCTCCCGAGTT<br>GTTGGGATTCCAGGCATGCATGACCAGGCTCAGC<br>TAATTTTTGTTTTTTTGGTAGAGACGGGGTTTCAC<br>CATATTGGCCAGGCTGGTCTCCAACTCCTAATCT<br>CAGGTGATCTACCCACCTTGGCCTCCCAAATTGC<br>TGGGATTACAGGCGTGAACCACTGCTCCCTTCCC<br>TGTCCTT | |
| 45 (RE + Coding) | ggaggaagccatcaactaaactacaatgactgtaagatacaaaattgggaatggt<br>aacatattttgaagttctgttgacataaagaatcatgatattaatgcccatggaaatg<br>aaagggcgatcaacactatggtttgaaaagggggaaattgtagagcacagatgt<br>gttcgtgtggcagtgtgctgtctctagcaatactcagagaagagagagaacaatg<br>aaattctgattggccccagtgtgagcccagatgaggttcagctgccaactttctctt<br>tcacatcttatgaaagtcatttaagcacaactaacttttttttttttttttttttttgagaca<br>gagtcttgctctgttgcccaggacagagtgcagtagtgactcaatctcggctcact<br>gcagcctccacctcctaggctcaaacggtcctcctgcatcagcctcccaagtagc<br>tggaattacaggagtggcccaccatgcccagctaatttttgtatttttaatagatacg<br>gggtttcaccatatcacccaggctggtctcgaactcctggcctcaagtgatcca<br>cctgcctcggcctcccaaagtgctgggattataggcgtcagccactatgcccaac<br>ccgaccaacctttttaaaataaatatttaaaaaattggtatttcacatatatactagta<br>tttacatttatccacacaaaacggacgggcctccgctgaaccagtgaggcccca<br>gacgtgcgcataaataacccctgcgtgctgcaccacctggggagagggggag<br>gaccacggtaaatggagcgagcgcatagcaaaagggacgcggggtccttttct<br>ctgccggtggcactgggtagctgtggccaggtgtggtactttgatggggcccag<br>ggctggagctcaaggaagcgtcgcagggtcacagatctgggggaaccccgg<br>ggaaaagcactgaggcaaaaccgccgctcgtctcctacaatatatgggagggg<br>gaggttgagtacgttctggattactcataagaccttttttttttccttccgggcgcaaa<br>accgtgagctggatttataatcgccctataaagctccagaggcggtcaggcacct<br>gcagaggagccccgccgctccgccgactagctgcccccgcgagcaacggcct<br>cgtgatttccccgccgatccggtccccgcctccccactctgcccccgcctacccc<br>ggagccgtgcagccgcctctccgaatctctctcttctcctggcgctcgcgtgcga<br>gagggaactagcgagaacgaggaagcagctggaggtgacgccgggcagatt<br>acgcctgtcagggccgagccgagcggatcgctgggcgctgtgcagaggaaa<br>ggcgggagtgcccggctcgctgtcgcagagccgaggtgggtaagctagcgac<br>cacctggacttcccagcgcccaaccgtggcttttcagccaggtcctctcctcccg<br>cggcttctcaaccaaccccatcccagcgccggccacccaacctcccgaaatga<br>gtgcttcctgccccagcagccgaaggcgctactaggaacggtaacctgttacttt<br>tccaggggccgtagtcgacccgctgcccgagttgctgtgcgactgcgcgcgcg<br>gggctagagtgcaaggtgactgtggttcttctctggccaagtccgagggagaac<br>gtaaagatatgggcctttttcccctctcaccttgtctcaccaaagtccctagtccc<br>cggagcagttagcctctttctttccagggaattagccagacacaacaacgggaac<br>cagacaccgaaccagacatgcccgccccgtgcgccctccccgctcgctgccttt<br>cctccctcttgtctctccagagccggatcttcaaggggagcctccgtgcccccgg<br>ctgctcagtccctccggtgtgcaggaccccggaagtcctccccgcacagctctc<br>gcttctctttgcagcctgtttctgcgccggaccagtcgaggactctggacagtaga<br>ggccccgggacgaccgagctgGAATTCGCCACCATGGCCgc<br>cgaccacctgatgctcgccgagggctaccgcctggtgcagaggccgccgtcc<br>gccgccgccgcccatggccctcatgcgctccggactctgccgccgtacgcggg<br>cccgggcctggacagtgggctgaggccgcggggggctccgctggggccgcc<br>gccgccccgccaacccggggccctggcgtacggggccttcgggccgccgtc<br>ctccttccagccctttccggccgtgcctccgccggccgcgggcatcgcgcacct<br>gcagcctgtggcgacgccgtaccccggccgcgcggccgcgcccccaacgc<br>tccgggaggcccccgggcccgcagccggccccaagcgccgcagccccgc<br>cgccgcccgcgcacgccctgggcggcatggacgccgaactcatcgacgagg<br>aggcgctgacgtcgctggagctggagctggggctgcaccgcgtgcgcgagct<br>gcccgagctgttcctgggccagagcgagttcgactgcttctcggacttggggtc<br>cgcgccgcccgccggctccgtgagctgcggtggttctggtggtggttctggtca<br>gtcccagctcatcaaacccagccgcatgcgcaagtaccccaaccggcccagca<br>agacgccccccacgaacgcccttacgcttgcccagtggagtcctgtgatcgcc<br>gcttctccCGCAGCGACAACCTGGTGAGAcacatccgcatcc<br>acacaggccagaagcccttccagtgccgcatctgcatgAGAaacttcagcC<br>GAGAGGATAACTTGCACACTcacatccgcacccacacaggc<br>gaaaagcccttcgcctgcgacatctgtggaagaaagtttgccCGGAGCG<br>ATGAACTTGTCCGAcataccaagatccacttgcggcagaaggacc<br>gcccttacgcttgcccagtggagtcctgtgatcgccgcttctccCAATCAG | 184 |

TABLE 7-continued

Nucleic acid sequences encoding exemplary engineered transcription factors disclosed herein.

| CONSTRUCT | SEQUENCE | SEQ ID NO |
|---|---|---|
| | GGAATCTGACTGAGcacatccgcatccacacaggccagaagccct<br>tccagtgccgcatctgcatgAGAaacttcagcACAAGTGGACATC<br>TGGTACGCcacatccgcacccacacaggcgaaaagcccttcgcctgcg<br>acatctgtggaagaaagtagccCAGAATAGTACCCTGACCG<br>AAcataccaagatccacttgcggcagaaggacaagtaaCTCGAGGA<br>AACCCAGCAGACAATGTAGCTAGACCCAGTAGC<br>CAGATGTAGCTAAAGAGACCGGTTCACTGTGAG<br>AAACCCAGCAGACAATGTAGCTAGACCCAGTAG<br>CCAGATGTAGCTAAAGAGACCGGTTCACTGTGA<br>AAGCTTGGGTGGCATCCCTGTGACCCCTCCCCAG<br>TGCCTCTCCTGGCCCTGGAAGTTGCCACTCCAGT<br>GCCCACCAGCCTTGTCCTAATAAAATTAAGTTGC<br>ATCATTTTGTCTGACTAGGTGTCCTTCTATAATAT<br>TATGGGGTGGAGGGGGGTGGTATGGAGCAAGGG<br>GCAAGTTGGGAAGACAACCTGTAGGGCCTGCGG<br>GGTCTATTGGGAACCAAGCTGGAGTGCAGTGGC<br>ACAATCTTGGCTCACTGCAATCTCCGCCTCCTGG<br>GTTCAAGCGATTCTCCTGCCTCAGCCTCCCGAGT<br>TGTTGGGATTCCAGGCATGCATGACCAGGCTCAG<br>CTAATTTTTGTTTTTTTGGTAGAGACGGGGTTTCA<br>CCATATTGGCCAGGCTGGTCTCCAACTCCTAATC<br>TCAGGTGATCTACCCACCTTGGCCTCCCAAATTG<br>CTGGGATTACAGGCGTGAACCACTGCTCCCTTCC<br>CTGTCCTT | |
| 8 (coding) | ATGGCCgccgaccacctgatgctcgccgagggctaccgcctggtgcaga<br>ggccgccgtccgccgccgccgcccatggccctcatgcgctccggactctgccg<br>ccgtacgcgggcccgggcctggacagtgggctgaggccgcggggggctccg<br>ctggggccgccgccgccccgccaacccggggccctggcgtacggggccttc<br>gggccgccgtcctccttccagccctttccggccgtgcctccgccggccgcggg<br>catcgcgcacctgcagcctgtggcgacgccgtaccccggccgcgcggccgcg<br>cccccaacgctccgggaggcccccgggcccgcagccggccccaagcgcc<br>gcagccccgccgccgcccgcgcacgccctgggcggcatggacgccgaactc<br>atcgacgaggaggcgctgacgtcgctggagctggagctggggctgcaccgcg<br>tgcgcgagctgcccgagctgttcctgggccagagcgagttcgactgcttctcgg<br>acttggggtccgcgccgcccgccggctccgtgagctgcggtggttctggtggtg<br>gttctggtcagtcccagctcatcaaacccagccgcatgcgcaagtaccccaacc<br>ggcccagcaagacgccccccacgaacgcccttacgcttgcccagtggagtcc<br>tgtgatcgccgcttctccCGCAGCGACAACCTGGTGAGAcac<br>atccgcatccacacaggccagaagcccttccagtgccgcatctgcatgAGAa<br>acttcagcCGAGAGGATAACTTGCACACTcacatccgcacc<br>cacacaggcgaaaagcccttcgcctgcgacatctgtggaagaaagtttgccCG<br>GAGCGATGAACTTGTCCGAcataccaagatccacttgcggca<br>gaaggaccgcccttacgcttgcccagtggagtcctgtgatcgccgcttctccCA<br>ATCAGGGAATCTGACTGAGcacatccgcatccacacaggcca<br>gaagcccttccagtgccgcatctgcatgAGAaacttcagcACAAGTG<br>GACATCTGGTACGCcacatccgcacccacacaggcgaaaagccct<br>tcgcctgcgacatctgtggaagaaagtttgccCAGAATAGTACCCT<br>GACCGAAcataccaagatccacttgcggcagaaggacaag | 203 |
| 46 (coding) | ATGGCCgccgaccacctgatgctcgccgagggctaccgcctggtgcaga<br>ggccgccgtccgccgccgccgcccatggccctcatgcgctccggactctgccg<br>ccgtacgcgggcccgggcctggacagtgggctgaggccgcggggggctccg<br>ctggggccgccgccgccccgccaacccggggccctggcgtacggggccttc<br>gggccgccgtcctccttccagccctttccggccgtgcctccgccggccgcggg<br>catcgcgcacctgcagcctgtggcgacgccgtaccccggccgcgcggccgcg<br>cccccaacgctccgggaggcccccgggcccgcagccggccccaagcgcc<br>gcagccccgccgccgcccgcgcacgccctgggcggcatggacgccgaactc<br>atcgacgaggaggcgctgacgtcgctggagctggagctggggctgcaccgcg<br>tgcgcgagctgcccgagctgttcctgggccagagcgagttcgactgcttctcgg<br>acttggggtccgcgccgcccgccggctccgtgagctgcggtggttctggtggtg<br>gttctggtGGTGGCAGCGGGGGAGGTTCTGGTcagtccca<br>gctcatcaaacccagccgcatgcgcaagtaccccaaccggcccagcaagacg<br>cccccccacgaacgcccttacgcttgcccagtggagtcctgtgatcgccgcttct<br>ccCGCAGCGACAACCTGGTGAGAcacatccgcatccacaca<br>ggccagaagcccttccagtgccgcatctgcatgAGAaacttcagcCGAG<br>AGGATAACTTGCACACTcacatccgcacccacacaggcgaaaa<br>gcccttcgcctgcgacatctgtggaagaaagtttgccCGGAGCGATGA<br>ACTTGTCCGAcataccaagatccacttgcggcagaaggaccgccctta<br>cgcttgcccagtggagtcctgtgatcgccgcttctccCAATCAGGGAA<br>TCTGACTGAGcacatccgcatccacacaggccagaagcccttccagtg<br>ccgcatctgcatgAGAaacttcagcACAAGTGGACATCTGGT<br>ACGCcacatccgcacccacacaggcgaaaagcccttcgcctgcgacatctg<br>tggaagaaagtttgccCAGAATAGTACCCTGACCGAAcatac<br>caagatccacttgcggcagaaggacaag | 204 |

TABLE 7-continued

Nucleic acid sequences encoding exemplary engineered transcription factors disclosed herein.

| CONSTRUCT | SEQUENCE | SEQ ID NO |
|---|---|---|
| 47 (coding) | ATGGCCGCAGATCACCTGATGCTGGCTGAAGGCT<br>ACAGACTGGTGCAGCGGCCTCCATCTGCCGCTGC<br>CGCCCACGGCCCCCACGCCCTGAGAACACTGCCC<br>CCCTACGCCGGCCCTGGTCTTGATAGCGGACTCA<br>GACCTAGAGGCGCCCCTCTGGGCCCTCCACCTCC<br>AAGACAGCCTGGAGCCCTGGCCTACGGCGCCTTC<br>GGCCCTCCTTCTAGCTTCCAGCCCTTCCCCGCCGT<br>GCCTCCTCCAGCcGCTGGCATCGCCCACCTGCAG<br>CCTGTGGCCACCCCTTACCCCGGAAGAGCCGCCG<br>CCCCTCCAAACGCCCCTGGCGGACCTCCTGGCCC<br>CCAGCCTGCTCCAAGCGCCGCTGCCCCTCCACCT<br>CCTGCTCATGCCCTGGGCGGCATGGACGCCGAGC<br>TGATCGACGAGGAAGCCCTGACCAGCCTGGAAC<br>TGGAACTGGGCCTGCACAGAGTGCGGGAACTGC<br>CTGAGCTGTTCCTGGGACAGAGCGAGTTCGACTG<br>CTTCAGCGACCTGGGCAGCGCCCCTCCTGCCGGC<br>TCTGTGTCCTGCgccgaccacctgatgctcgccgagggctaccgcct<br>ggtgcagaggccgccgtccgccgccgccgcccatggccctcatgcgctccgg<br>actctgccgccgtacgcgggcccgggcctggacagtgggctgaggccgcgg<br>ggggctccgctggggccgccgccgccccgccaacccggggccctggcgtac<br>ggggccttcgggccgccgtcctccttccagccctttccggccgtgcctccgccg<br>gccgcgggcatcgcgcacctgcagcctgtggcgacgccgtaccccggccgc<br>gcCgccgcgcccccccaacgctccgggaggcccccgggcccgcagccggc<br>cccaagcgccgcagccccgccgccgcccgcgcacgccctgggcggcatgga<br>cgccgaactcatcgacgaggaggcgctgacgtcgctggagctggagctgggg<br>ctgcaccgcgtgcgcgagctgcccgagctgttcctgggccagagcgagttcga<br>ctgcttctcggacttggggtccgcgccgcccgccggctccgtgagctgccagtc<br>ccagctcatcaaacccagccgcatgcgcaagtaccccaaccggcccagcaag<br>acgcccccccacgaacgcccttacgcttgcccagtggagtcctgtgatcgccgc<br>ttctccCGCAGCGACAACCTGGTGAGAcacatccgcatccac<br>acaggccagaagcccttccagtgccgcatctgcatgAGAaacttcagcCG<br>AGAGGATAACTTGCACACTcacatccgcacccacacaggcg<br>aaaagcccttcgcctgcgacatctgtggaagaaagtttgccCGGAGCGA<br>TGAACTTGTCCGAcataccaagatccacttgcggcagaaggaccgc<br>ccttacgcttgcccagtggagtcctgtgatcgccgcttctccCAATCAGG<br>GAATCTGACTGAGcacatccgcatccacacaggccagaagcccttc<br>cagtgccgcatctgcatgAGAaacttcagcACAAGTGGACATCT<br>GGTACGCcacatccgcacccacacaggcgaaaagcccttcgcctgcgac<br>atctgtggaagaaagtttgccCAGAATAGTACCCTGACCGAA<br>cataccaagatccacttgcggcagaaggacaag | 206 |
| 48 (coding) | ATGGCCGCAGATCACCTGATGCTGGCTGAAGGCT<br>ACAGACTGGTGCAGCGGCCTCCATCTGCCGCTGC<br>CGCCCACGGCCCCCACGCCCTGAGAACACTGCCC<br>CCCTACGCCGGCCCTGGTCTTGATAGCGGACTCA<br>GACCTAGAGGCGCCCCTCTGGGCCCTCCACCTCC<br>AAGACAGCCTGGAGCCCTGGCCTACGGCGCCTTC<br>GGCCCTCCTTCTAGCTTCCAGCCCTTCCCCGCCGT<br>GCCTCCTCCAGCTGCTGGCATCGCCCACCTGCAG<br>CCTGTGGCCACCCCTTACCCCGGAAGAGCCGCCG<br>CCCCTCCAAACGCCCCTGGCGGACCTCCTGGCCC<br>CCAGCCTGCTCCAAGCGCCGCTGCCCCTCCACCT<br>CCTGCTCATGCCCTGGGCGGCATGGACGCCGAGC<br>TGATCGACGAGGAAGCCCTGACCAGCCTGGAAC<br>TGGAACTGGGCCTGCACAGAGTGCGGGAACTGC<br>CTGAGCTGTTCCTGGGACAGAGCGAGTTCGACTG<br>CTTCAGCGACCTGGGCAGCGCCCCTCCTGCCGGC<br>TCTGTGTCCTGCGGCGGCAGCGGCGGCGGAAGC<br>GGCgccgaccacctgatgctcgccgagggctaccgcctggtgcagaggcc<br>gccgtccgccgccgccgcccatggccctcatgcgctccggactctgccgccgt<br>acgcgggcccgggcctggacagtgggctgaggccgcggggggctccgctgg<br>ggccgccgccgccccgccaacccggggccctggcgtacggggccttcgggc<br>cgccgtcctccttccagccctttccggccgtgcctccgccggccgcgggcatcg<br>cgcacctgcagcctgtggcgacgccgtaccccggccgcgcggccgcgcccc<br>ccaacgctccgggaggcccccgggcccgcagccggccccaagcgccgca<br>gccccgccgccgcccgcgcacgccctgggcggcatggacgccgaactcatc<br>gacgaggaggcgctgacgtcgctggagctggagctggggctgcaccgcgtgc<br>gcgagctgcccgagctgttcctgggccagagcgagttcgactgcttctcggactt<br>ggggtccgcgccgcccgccggctccgtgagctgcggtggttctggtggtggtt<br>ctggtcagtcccagctcatcaaacccagccgcatgcgcaagtaccccaaccgg<br>cccagcaagacgcccccccacgaacgcccttacgcttgcccagtggagtcctgt<br>gatcgccgcttctccCGCAGCGACAACCTGGTGAGAcacatc<br>cgcatccacacaggccagaagcccttccagtgccgcatctgcatgAGAaact<br>tcagcCGAGAGGATAACTTGCACACTcacatccgcacccac | 208 |

TABLE 7-continued

Nucleic acid sequences encoding exemplary engineered transcription factors disclosed herein.

| CONSTRUCT | SEQUENCE | SEQ ID NO |
|---|---|---|
| | acaggcgaaaagcccttcgcctgcgacatctgtggaagaaagtttgccCGG | |
| | AGCGATGAACTTGTCCGAcataccaagatccacttgcggcaga | |
| | aggaccgcccttacgcttgcccagtggagtcctgtgatcgccgcttctccCAA | |
| | TCAGGGAATCTGACTGAGcacatccgcatccacacaggccag | |
| | aagcccttccagtgccgcatctgcatgAGAaacttcagcACAAGTGG | |
| | ACATCTGGTACGCcacatccgcacccacacaggcgaaaagcccttc | |
| | gcctgcgacatctgtggaagaaagtttgccCAGAATAGTACCCTG | |
| | ACCGAAcataccaagatccacttgcggcagaaggacaag | |
| 49 (coding) | atggagctggaattggatgctggtgaccaagacctgctggccttcctgctagag | 212 |
| | gaaagtggagatttggggacggcacccgatgaggccgtgagggccccactgg | |
| | actgggcgctgccgctttctgaggtGccgagcgactgggaagtagatgatttgc | |
| | tgtgctccctgctgagtcccccagcgtcgttgaacattctcagctcctccaacccc | |
| | tgccttgtccaccatgaccacacctactccctcccacgggaaactgtctctatgga | |
| | tctagagagtgagagctgtagaaaagaggggacccagatgactccacagcata | |
| | tggaggagctggcagagcaggagattgctaggctagtactgacagatgaggag | |
| | aagagtctattggagaaggaggggcttattctgcctgagacacttcctctcactaa | |
| | gacagaggaacaaattctgaaacgtgtgcggCTCGAACCAGGTGA | |
| | AAAACCTTACAAATGTCCTGAATGTGGGAAATC | |
| | ATTCAGTCGCAGCGACAACCTGGTGAGACATCA | |
| | ACGCACCCATACAGGAGAAAAACCTTATAAATG | |
| | TCCAGAATGTGGAAAGTCCTTCTCACGAGAGGAT | |
| | AACTTGCACACTCATCAACGAACACATACTGGTG | |
| | AAAAACCATACAAGTGTCCCGAATGTGGTAAAA | |
| | GTTTTAGCCGGAGCGATGAACTTGTCCGACACCA | |
| | ACGAACCCATACAGGCGAGAAGCCTTACAAATG | |
| | TCCCGAGTGTGGCAAGAGCTTCTCACAATCAGGG | |
| | AATCTGACTGAGCATCAACGAACTCATACCGGG | |
| | GAAAAACCTTACAAGTGTCCAGAGTGTGGGAAG | |
| | AGCTTTTCCACAAGTGGACATCTGGTACGCCACC | |
| | AGAGGACACATACAGGGGAGAAGCCCTACAAAT | |
| | GCCCCGAATGCGGTAAAAGTTTCTCTCAGAATAG | |
| | TACCCTGACCGAACACCAGCGAACACACACTGG | |
| | GAAAAAAACGAGTgtgtaCgttgggggtttagagagcCgggtctt | |
| | gaaatacacagcccagaatatggagcttcagaacaaagtacagcttctggagga | |
| | acagaatttgtcccttctagatcaactgaggaaactccaggccatggtgattgaga | |
| | tCtcaaacaaaaccagcagcagcagcacctgcatcttggtcctGctagtctcctt | |
| | ctgcctcctccttgtacctgctatgtactcctctgacacaaggggggagcctgccag | |
| | ctgagcatggagtgttgtcccgccagcttcgtgccctccccagtgaggaccctta | |
| | ccagctggagctgcctgccctgcagtcagaagtgccgaaagacagcacacacc | |
| | agtggttggacggctcagactgtgtactccaggcccctggcaacacttcctgcct | |
| | gctgcattacatgcctcaggctcccagtgcagagcctcccctggagtggccCtt | |
| | ccctgacctcttctcagagcctctctgccgaggtcccatcctccccctgcaggca | |
| | aatctcacaaggaagggaggatggcttcctactggtagcccctctgtcattttgca | |
| | ggacagatactcaggc | |
| 50 (coding) | atggagctggaattggatgctggtgaccaagacctgctggccttcctgctagag | 216 |
| | gaaagtggagatttggggacggcacccgatgaggccgtgagggccccactgg | |
| | actgggcgctgccgctttctgaggtGccgagcgactgggaagtagatgatttgc | |
| | tgtgctccctgctgagtcccccagcgtcgttgaacattctcagctcctccaacccc | |
| | tgccttgtccaccatgaccacacctactccctcccacgggaaactgtctctatgga | |
| | tctagagagtgagagctgtagaaaagaggggacccagatgactccacagcata | |
| | tggaggagctggcagagcaggagattgctaggctagtactgacagatgaggag | |
| | aagagtctattggagaaggaggggcttattctgcctgagacacttcctctcactaa | |
| | gacagaggaacaaattctgaaacgtgtgcggcgcccttacgcttgcccagtgga | |
| | gtcctgtgatcgccgcttctccCGCAGCGACAACCTGGTGAG | |
| | AcacatccgcatccacacaggccagaagcccttccagtgccgcatctgcatgA | |
| | GAaacttcagcCGAGAGGATAACTTGCACACTcacatccg | |
| | cacccacacaggcgaaaagcccttcgcctgcgacatctgtggaagaaagtttgc | |
| | cCGGAGCGATGAACTTGTCCGAcataccaagatccacttgcg | |
| | gcagaaggaccgcccttacgcttgcccagtggagtcctgtgatcgccgcttctcc | |
| | CAATCAGGGAATCTGACTGAGcacatccgcatccacacagg | |
| | ccagaagcccttccagtgccgcatctgcatgAGAaacttcagcACAAGT | |
| | GGACATCTGGTACGCcacatccgcacccacacaggcgaaaagcc | |
| | cttcgcctgcgacatctgtggaagaaagtttgccCAGAATAGTACCC | |
| | TGACCGAAcataccaagatccacttgcggcagaaggacgtgtaCgttg | |
| | ggggtttagagagcCgggtcttgaaatacacagcccagaatatggagcttcag | |
| | aacaaagtacagcttctggaggaacagaatttgtcccttctagatcaactgagga | |
| | aactccaggccatggtgattgagatCtcaaacaaaaccagcagcagcagcacc | |
| | tgcatcttggtcctGctagtctccttctgcctcctccttgtacctgctatgtactcctc | |
| | tgacacaaggggggagcctgccagctgagcatggagtgttgtcccgccagcttc | |
| | gtgccctccccagtgaggacccttaccagctggagctgcctgccctgcagtcag | |
| | aagtgccgaaagacagcacacaccagtggttggacggctcagactgtgtactcc | |
| | aggcccctggcaacacttcctgcctgctgcattacatgcctcaggctcccagtgc | |
| | agagcctcccctggagtggccCttccctgacctcttctcagagcctctctgccga | |

TABLE 7-continued

Nucleic acid sequences encoding exemplary engineered transcription factors disclosed herein.

| CONSTRUCT | SEQUENCE | SEQ ID NO |
|---|---|---|
| | ggtcccatcctcccccctgcaggcaaatctcacaaggaagggaggatggcttcct<br>actggtagcccctctgtcattttgcaggacagatactcaggc | |
| 51 (coding) | atggagctggaattggatgctggtgaccaagacctgctggccttcctgctagag<br>gaaagtggagatttggggacggcacccgatgaggccgtgagggccccactgg<br>actgggcgctgccgctttctgaggtGccgagcgactgggaagtagatgatttgc<br>tgtgctccctgctgagtcccccagcgtcgttgaacattctcagctcctccaacccc<br>tgccttgtccaccatgaccacacctactccctcccacgggaaactgtctctatgga<br>tctagagagtgagagctgtagaaaagaggggacccagatgactccacagcata<br>tggaggagctggcagagcaggagattgctaggctagtactgacagatgaggag<br>aagagtctattggagaaggaggggcttattctgcctgagacacttcctctcactaa<br>gacagaggaacaaattctgaaacgtgtgcggcgcccttacgcttgcccagtgga<br>gtcctgtgatcgccgcttctcccGCTCAGACAACCTCGTTCGA<br>cacatccgcatccacacaggccagaagcccttccagtgccgcatctgcatgAG<br>AaacttcagcCACCGGACTACACTCACGAACcacatccgca<br>cccacacaggcgaaaagcccttcgcctgcgacatctgtggaagaaagtttgcc<br>AGAGAAGACAATCTCCATACTcataccaagatccacttgcg<br>gcagaaggaccgcccttacgcttgcccagtggagtcctgtgatcgccgcttctcc<br>ACCAGCCATTCTCTCACTGAAcacatccgcatccacacagg<br>ccagaagcccttccagtgccgcatctgcatgAGAaacttcagcCAGTCT<br>AGCTCACTGGTGAGGcacatccgcacccacacaggcgaaaagc<br>ccttcgcctgcgacatctgtggaagaaagtttgccAGGGAGGATAAC<br>CTGCATACGcataccaagatccacttgcggcagaaggacgtgtaCgtt<br>gggggtttagagagcCgggtcttgaaatacacagcccagaatatggagcttca<br>gaacaaagtacagcttctggaggaacagaatttgtcccttctagatcaactgagg<br>aaactccaggccatggtgattgagatCtcaaacaaaaccagcagcagcagcac<br>ctgcatcttggtcctGctagtctccttctgcctcctccttgtacctgctatgtactcct<br>ctgacacaaggggggagcctgccagctgagcatggagtgttgtcccgccagctt<br>cgtgccctccccagtgaggacccttaccagctggagctgcctgccctgcagtca<br>gaagtgccgaaagacagcacacaccagtggttggacggctcagactgtgtact<br>ccaggcccctggcaacacttcctgcctgctgcattacatgcctcaggctcccagt<br>gcagagcctcccctggagtggccCttccctgacctcttctcagagcctctctgcc<br>gaggtcccatcctcccccctgcaggcaaatctcacaaggaagggaggatggcttc<br>ctactggtagcccctctgtcattttgcaggacagatactcaggc | 218 |
| 52 (coding) | atggagctggaattggatgctggtgaccaagacctgctggccttcctgctagag<br>gaaagtggagatttggggacggcacccgatgaggccgtgagggccccactgg<br>actgggcgctgccgctttctgaggtGccgagcgactgggaagtagatgatttgc<br>tgtgctccctgctgagtcccccagcgtcgttgaacattctcagctcctccaacccc<br>tgccttgtccaccatgaccacacctactccctcccacgggaaactgtctctatgga<br>tctagagagtgagagctgtagaaaagaggggacccagatgactccacagcata<br>tggaggagctggcagagcaggagattgctaggctagtactgacagatgaggag<br>aagagtctattggagaaggaggggcttattctgcctgagacacttcctctcactaa<br>gacagaggaacaaattctgaaacgtgtgcggCTCGAACCAGGTGA<br>AAAACCTTACAAATGTCCTGAATGTGGGAAATC<br>ATTCAGTCGCAGCGACAACCTGGTGAGACATCA<br>ACGCACCCATACAGGAGAAAAACCTTATAAATG<br>TCCAGAATGTGGAAAGTCCTTCTCACGAGAGGAT<br>AACTTGCACACTCATCAACGAACACATACTGGTG<br>AAAAACCATACAAGTGTCCCGAATGTGGTAAAA<br>GTTTTAGCCGGAGCGATGAACTTGTCCGACACCA<br>ACGAACCCATACAGGCGAGAAGCCTTACAAATG<br>TCCCGAGTGTGGCAAGAGCTTCTCACAATCAGGG<br>AATCTGACTGAGCATCAACGAACTCATACCGGG<br>GAAAAACCTTACAAGTGTCCAGAGTGTGGGAAG<br>AGCTTTTCCACAAGTGGACATCTGGTACGCCACC<br>AGAGGACACATACAGGGGAGAAGCCCTACAAAT<br>GCCCCGAATGCGGTAAAAGTTTCTCTCAGAATAG<br>TACCCTGACCGAACACCAGCGAACACACACTGG<br>GAAAAAAACGAGTgtgtaCgttgggggtttagagagcCgggtctt<br>gaaatacacagcccagaatatggagcttcagaacaaagtacagcttctggagga<br>acagaatttgtcccttctagatcaactgaggaaactccaggccatggtgattgaga<br>tatca | 220 |
| 53 (coding) | atggagctggaattggatgctggtgaccaagacctgctggccttcctgctagag<br>gaaagtggagatttggggacggcacccgatgaggccgtgagggccccactgg<br>actgggcgctgccgctttctgaggtGccgagcgactgggaagtagatgatttgc<br>tgtgctccctgctgagtcccccagcgtcgttgaacattctcagctcctccaacccc<br>tgccttgtccaccatgaccacacctactccctcccacgggaaactgtctctatgga<br>tctagagagtgagagctgtagaaaagaggggacccagatgactccacagcata<br>tggaggagctggcagagcaggagattgctaggctagtactgacagatgaggag<br>aagagtctattggagaaggaggggcttattctgcctgagacacttcctctcactaa<br>gacagaggaacaaattctgaaacgtgtgcggcgcccttacgcttgcccagtgga<br>gtcctgtgatcgccgcttctcccGCAGCGACAACCTGGTGAG<br>AcacatccgcatccacacaggccagaagcccttccagtgccgcatctgcatgA | 222 |

TABLE 7-continued

Nucleic acid sequences encoding exemplary engineered transcription factors disclosed herein.

| CONSTRUCT | SEQUENCE | SEQ ID NO |
|---|---|---|
| | GAaacttcagcCGAGAGGATAACTTGCACACTcacatccg cacccacacaggcgaaaagcccttcgcctgcgacatctgtggaagaaagtttgc cCGGAGCGATGAACTTGTCCGAcataccaagatccacttgcg gcagaaggaccgcccttacgcttgcccagtggagtcctgtgatcgccgcttctcc CAATCAGGGAATCTGACTGAGcacatccgcatccacacagg ccagaagcccttccagtgccgcatctgcatgAGAaacttcagcACAAGT GGACATCTGGTACGCcacatccgcacccacacaggcgaaaagcc cttcgcctgcgacatctgtggaagaaagtttgccCAGAATAGTACCC TGACCGAAcataccaagatccacttgcggcagaaggacgtgtaCgttg ggggtttagagagcCgggtcttgaaatacacagcccagaatatggagcttcag aacaaagtacagcttctggaggaacagaatttgtcccttctagatcaactgagga aactccaggccatggtgattgagatCtca | |

TABLE 8

Nucleic acid sequences for exemplary MicroRNA and MicroRNA binding sites.

| Description | SEQUENCE | SEQ ID NO |
|---|---|---|
| M1 Binding Site | aaagagaccggttcactgtgacagtaaaagagaccggttcactgtgagaatgaaagag accggttcactgtgatcggaaaagagaccggttcactgtgagcggccttgaaacccagc agacaatgtagctcagtagaaacccagcagacaatgtagctgaatggaaacccagcag acaatgtagcttcggagaaacccagcagacaatgtagct | 7 |
| miR128 Sequence | UCACAGUGAACCGGUCUCUUU | 8 |
| miR128 binding site | AAAGAGACCGGTTCACTGTGA | 9 |
| miR221 sequence | AGCUACAUUGUCUGCUGGGUUUC | 10 |
| miR221 binding site | GAAACCCAGCAGACAATGTAGCT | 11 |
| miR222 sequence | AGCUACAUCUGGCUACUGGGUCU | 12 |
| miR222 binding site | AGACCCAGTAGCCAGATGTAGCT | 13 |
| M2 Binding Site | GAAACCCAGCAGACAATGTAGCTAGACCCAGTAGCC AGATGTAGCTAAAGAGACCGGTTCACTGTGA | 14 |
| M3 Binding Site | GAAACCCAGCAGACAATGTAGCTAGACCCAGTAGCC AGATGTAGCTAAAGAGACCGGTTCACTGTGAGAAAC CCAGCAGACAATGTAGCTAGACCCAGTAGCCAGATG TAGCTAAAGAGACCGGTTCACTGTGA | 15 |

TABLE 9

Different types of zinc finger structures and exemplary zinc finger proteins for generating eTFs.

| ZF type name | SEQ ID NO | ZF structure (wherein each x can independently be any residue) | Exemplary proteins that can serve as the protein platform for an eTF or a DNA binding domain of an eTF disclosed herein |
|---|---|---|---|
| Zinc fingers C2H2-type (ZNF) | 136 | C-x-C-x-H-x-H | KLF4, KLF5, EGR3, ZFP637, SLUG, ZNF750, ZNF281, ZBP89, GLIS1, GLIS3 |
| Ring finger proteins (RNF) | 137 | C-x-C-x-C-x-H-xxx-C-x-C-x-C-x-C | MDM2, BRCA1, ZNF179 |

TABLE 9-continued

Different types of zinc finger structures and exemplary zinc finger proteins for generating eTFs.

| ZF type name | SEQ ID NO | ZF structure (wherein each x can independently be any residue) | Exemplary proteins that can serve as the protein platform for an eTF or a DNA binding domain of an eTF disclosed herein |
|---|---|---|---|
| PHD finger proteins (PHF) | 138 | C-x-C-x-C-x-C-xxx-H-x-C-x-C-x-C | KDM2A, PHF1, ING1 |
| LIM domain containing | 139 | C-x-C-x-H-x-C-x-C-x-C-x-C-x-(C, H, D) | ZNF185, LIMK1, PXN |
| Nuclear hormone receptors (NR) | 140 | C-x-C-x-C-x-C-xxx-C-x-C-x-C-x-C | VDR, ESR1, NR4A1 |
| Zinc fingers CCCH-type (ZC3H) | 141 | C-x-C-x-C-x-H | RC3H1, HELZ, MBNL1, ZFP36, ZFP36L1 |
| Zinc fingers FYVE-type (ZFYVE) | 140 | C-x-C-x-C-x-C-xxx-C-x-C-x-C-x-C | EEA1, HGS, PIKFYVE |
| Zinc fingers CCHC-type (ZCCHC) | 142 | C-x-C-x-H-x-C | CNBP, SF1, LIN28A |
| Zinc fingers DHHC-type (ZDHHC) | 143 | C-x-C-x-H-x-C-xxx-C-x-C-x-H-x-C | ZDHHC2, ZDHHC8, ZDHHC9 |
| Zinc fingers MYND-type (ZMYND) | 144 | C-x-C-x-C-x-C-xxx-C-x-C-x-H-x-C | PDCD2, RUNX1T1, SMYD2, SMYD1 |
| Zinc fingers RANBP2-type (ZRANB) | 145 | C-x-C-x-C-x-C | YAF2, SHARPIN, EWSR1 |
| Zinc fingers ZZ-type (ZZZ) | 145 | C-x-C-x-C-x-C | HERC2, NBR1, CREBBP |
| Zinc fingers C2HC-type (ZC2HC) | 142 | C-x-C-x-H-x-C | IKBKG, L3MBTL1, ZNF746 |
| GATA zinc-finger domain containing (GATAD) | 145 | C-x-C-x-C-x-C | GATA4, GATA6, MTA1 |
| ZF class homeoboxes and pseudogenes | 136 | C-x-C-x-H-x-H | ADNP, ZEB1, ZHX1 |
| THAP domain containing (THAP) | 141 | C-x-C-x-C-x-H | THAP1, THAP4, THAP11 |
| Zinc fingers CXXC-type (CXXC) | 140 | C-x-C-x-C-x-C-xxx-C-x-C-x-C-x-C | CXXCL CXXC5, MBD1, DNMT1 |
| Zinc fingers SWIM-type (ZSWIM) | 141 | C-x-C-x-C-x-H | MAP3K1, ZSWIM5, ZSWIM6 |
| Zinc fingers AN1-type (ZFAND) | 146 | C-x-C-x-C-x-C-xxx-C-x-H-x-H-x-C | ZFAND3, ZFAND6, IGHMBP2 |
| Zinc fingers 3CxxC-type (Z3CXXC) | 142 | C-x-C-x-H-x-C | ZAR1, RTP1, RTP4 |

TABLE 9-continued

Different types of zinc finger structures and exemplary zinc finger proteins for generating eTFs.

| ZF type name | SEQ ID NO | ZF structure (wherein each x can independently be any residue) | Exemplary proteins that can serve as the protein platform for an eTF or a DNA binding domain of an eTF disclosed herein |
|---|---|---|---|
| Zinc fingers CW-type (ZCW) | 145 | C-x-C-x-C-x-C | MORC1, ZCWPW1, KDM1B |
| Zinc fingers GRF-type (ZGRF) | 145 | C-x-C-x-C-x-C | TTF2, NEIL3, TOP3A |
| Zinc fingers MIZ-type (ZMIZ) | 142 | C-x-C-x-H-x-C | PIAS1, PIAS3, PIAS4 |
| Zinc fingers BED-type (ZBED) | 136 | C-x-C-x-H-x-H | ZBED1, ZBED4, ZBED6 |
| Zinc fingers HIT-type (ZNHIT) | 144 | C-x-C-x-C-x-C-xxx-C-x-C-x-H-x-C | ZNHIT3, DDX59, INO80B |
| Zinc fingers MYM-type (ZMYM) | 145 | C-x-C-x-C-x-C | ZMYM2, ZMYM3, ZMYM4 |
| Zinc fingers matrin-type (ZMAT) | 136 | C-x-C-x-H-x-H | ZNF638, ZMAT1, ZMAT3, ZMAT5 |
| Zinc fingers C2H2C-type | 136 | C-x-C-x-H-x-H | MYT1, MYT1L, ST18 |
| Zinc fingers DBF-type (ZDBF) | 136 | C-x-C-x-H-x-H | DBF4, DBF4B, ZDBF2 |
| Zinc fingers PARP-type | 142 | C-x-C-x-H-x-C | LIG3, PARP1 |

TABLE 10

Amino acid sequences for exemplary zinc finger DNA binding domains.

| DBD/Target site | SEQUENCE | SEQ ID NO |
|---|---|---|
| eZF | LEPGEKP - [YKCPECGKSFS X HQRTH TGEKP]n - YKCPECGKSFS X HQRTH - TGKKTS, wherein n is an integer from 1-15, and each X is a recognition sequence capable of binding to 3 bp of target sequence | 147 |
| Z1 Target Site | RSDNLVR x REDNLHT x RSDELVR x QSGNLTE x TSGHLVR x QNSTLTE, wherein each x is a linker comprising 1-50 amino acid residues | 148 |
| Z13 Target Site | RSDNLVR x HRTTLTN x REDNLHT x TSHSLTE x QSSSLVR x REDNLHT, wherein each x is a linker comprising 1-50 amino acid residues | 149 |
| Z14 Target Site | DPGALVR x RSDNLVR x QSGDLRR x THLDLIR x TSGNLVR x RSDNLVR, wherein each x is a linker comprising 1-50 amino acid residues | 150 |
| Z15 Target Site | RRDELNV x RSDHLTN x RSDDLVR x RSDNLVR x HRTTLTN x REDNLHT x TSHSLTE x QSSSLVR x REDNLHT, wherein each x is a linker comprising 1-50 amino acid residues | 151 |

TABLE 11

Amino acid sequences for exemplary zinc finger recognition sequences disclosed herein.

| SEQUENCE | SEQ ID NO |
|---|---|
| RSDNLVR | 152 |
| REDNLHT | 153 |
| RSDELVR | 154 |
| QSGNLTE | 155 |
| TSGHLVR | 156 |
| QNSTLTE | 157 |
| DPGALVR | 158 |
| HRTTLTN | 159 |

TABLE 11-continued

Amino acid sequences for exemplary zinc finger recognition sequences disclosed herein.

| SEQUENCE | SEQ ID NO |
|---|---|
| QSGDLRR | 160 |
| TSHSLTE | 161 |
| THLDLIR | 162 |
| QSSSLVR | 163 |
| TSGNLVR | 164 |
| RRDELNV | 165 |
| RSDDLVR | 166 |
| RSDHLTN | 167 |

TABLE 12

Other nucleotide and amino acid sequence disclosed herein.

| Description | SEQUENCE | SEQ ID NO |
|---|---|---|
| EGR1 NLS Domain | LIKPSRMRKYPNRPSK | 168 |
| SV40 NLS | PKKKRKV | 169 |
| Nucleoplasmin NLS | KRPAATKKAGQAKKKK | 170 |
| HA Tag | YPYDVPDYA | 171 |
| spA (synthetic polyA) | AATAAAAGATCTTTATTTTCATTAGATCTGTGTGTTGG TTTTTTGTGTGCGGACCGCACGTG | 16 |
| hGH (human growth hormone polyA) | GGGTGGCATCCCTGTGACCCCTCCCCAGTGCCTCTCCT GGCCCTGGAAGTTGCCACTCCAGTGCCCACCAGCCTT GTCCTAATAAAATTAAGTTGCATCATTTTGTCTGACTA GGTGTCCTTCTATAATATTATGGGGTGGAGGGGGGTG GTATGGAGCAAGGGGCAAGTTGGGAAGACAACCTGT AGGGCCTGCGGGGTCTATTGGGAACCAAGCTGGAGTG CAGTGGCACAATCTTGGCTCACTGCAATCTCCGCCTCC TGGGTTCAAGCGATTCTCCTGCCTCAGCCTCCCGAGTT GTTGGGATTCCAGGCATGCATGACCAGGCTCAGCTAA TTTTTGTTTTTTTGGTAGAGACGGGGTTTCACCATATT GGCCAGGCTGGTCTCCAACTCCTAATCTCAGGTGATCT ACCCACCTTGGCCTCCCAAATTGCTGGGATTACAGGC GTGAACCACTGCTCCCTTCCCTGTCCTT | 17 |
| SCN1A protein | MEQTVLVPPGPDSFNFFTRESLAAIERRIAEEKAKNPKPD KKDDDENGPKPNSDLEAGKNLPFIYGDIPPEMVSEPLED LDPYYINKKTFIVLNKGKAIFRFSATSALYILTPFNPLRKI AIKILVHSLFSMLIMCTILTNCVFMTMSNPPDWTKNVEY TFTGIYTFESLIKIIARGFCLEDFTFLRDPWNWLDFTVITF AYVTEFVDLGNVSALRTFRVLRALKTISVIPGLKTIVGAL IQSVKKLSDVMILTVFCLSVFALIGLQLFMGNLRNKCIQ WPPTNASLEEHSIEKNITVNYNGTLINETVFEFDWKSYIQ DSRYHYFLEGFLDALLCGNSSDAGQCPEGYMCVKAGRN PNYGYTSFDTFSWAFLSLFRLMTQDFWENLYQLTLRAA GKTYMIFFVLVIFLGSFYLINLILAVVAMAYEEQNQATLE EAEQKEAEFQQMIEQLKKQQEAAQQAATATASEHSREP SAAGRLSDSSSEASKLSSKSAKERRNRRKKRKQKEQSGG EEKDEDEFQKSESEDSIRRKGFRFSIEGNRLTYEKRYSSP HQSLLSIRGSLFSPRRNSRTSLFSFRGRAKDVGSENDFAD DEHSTFEDNESRRDSLFVPRRHGERRNSNLSQTSRSSRM LAVFPANGKMHSTVDCNGVVSLVGGPSVPTSPVGQLLP EVIIDKPATDDNGTTTETEMRKRRSSSFHVSMDFLEDPSQ RQRAMSIASILTNTVEELEESRQKCPPCWYKFSNIFLIWD CSPYWLKVKHVVNLVVMDPFVDLAITICIVLNTLFMAM EHYPMTDHFNNVLTVGNLVFTGIFTAEMFLKIIAMDPYY | 172 |

TABLE 12-continued

Other nucleotide and amino acid sequence disclosed herein.

| Description | SEQUENCE | SEQ ID NO |
|---|---|---|
| | YFQEGWNIFDGFIVTLSLVELGLANVEGLSVLRSFRLLRV<br>FKLAKSWPTLNMLIKIIGNSVGALGNLTLVLAIIVFIFAVV<br>GMQLFGKSYKDCVCKIASDCQLPRWHMNDFFHSFLIVF<br>RVLCGEWIETMWDCMEVAGQAMCLTVFMMVMVIGNL<br>VVLNLFLALLLSSFSADNLAATDDDNEMNNLQIAVDRM<br>HKGVAYVKRKIYEFIQQSFIRKQKILDEIKPLDDLNNKKD<br>SCMSNHTAEIGKDLDYLKDVNGTTSGIGTGSSVEKYIIDE<br>SDYMSFINNPSLTVTVPIAVGESDFENLNTEDFSSESDLEE<br>SKEKLNESSSSSEGSTVDIGAPVEEQPVVEPEETLEPEACF<br>TEGCVQRFKCCQINVEEGRGKQWWNLRRTCFRIVEHNW<br>FETFIVFMILLSSGALAFEDIYIDQRKTIKTMLEYADKVFT<br>YIFILEMLLKWVAYGYQTYFTNAWCWLDFLIVDVSLVS<br>LTANALGYSELGAIKSLRTLRALRPLRALSRFEGMRVVV<br>NALLGAIPSIMNVLLVCLIFWLIFSIMGVNLFAGKFYHCI<br>NTTTGDRFDIEDVNNHTDCLKLIERNETARWKNVKVNF<br>DNVGFGYLSLLQVATFKGWMDIMYAAVDSRNVELQPK<br>YEESLYMYLYFVIFIIFGSFFTLNLFIGVIIDNFNQQKKKFG<br>GQDIFMTEEQKKYYNAMKKLGSKKPQKPIPRPGNKFQG<br>MVFDFVTRQVFDISIMILICLNMVTMMVETDDQSEYVTT<br>ILSRINLVFIVLFTGECVLKLISLRHYYFTIGWNIFDFVVVI<br>LSIVGMFLAELIEKYFVSPTLFRVIRLARIGRILRLIKGAK<br>GIRTLLFALMMSLPALFNIGLLLFLVMFIYAIFGMSNFAY<br>VKREVGIDDMFNFETFGNSMICLFQITTSAGWDGLLAPIL<br>NSKPPDCDPNKVNPGSSVKGDCGNPSVGIFFFVSYIIISFL<br>VVVNMYIAVILENFSVATEESAEPLSEDDFEMFYEVWEK<br>FDPDATQFMEFEKLSQFAAALEPPLNLPQPNKLQLIAMD<br>LPMVSGDRIHCLDILFAFTKRVLGESGEMDALRIQMEER<br>FMASNPSKVSYQPITTTLKRKQEEVSAVIIQRAYRRHLLK<br>RTVKQASFTYNKNKIKGGANLLIKEDMIIDRINENSITEK<br>TDLTMSTAACPPSYDRVTKPIVEKHEQEGKDEKAKGK | |
| dCAS protein | KRNYILGLAIGITSVGYGIIDYETRDVIDAGVRLFKEANV<br>ENNEGRRSKRGARRLKRRRRHRIQRVKKLLFDYNLLTD<br>HSELSGINPYEARVKGLSQKLSEEEFSAALLHLAKRRGV<br>HNVNEVEEDTGNELSTKEQISRNSKALEEKYVAELQLER<br>LKKDGEVRGSINRFKTSDYVKEAKQLLKVQKAYHQLDQ<br>SFIDTYIDLLETRRTYYEGPGEGSPFGWKDIKEWYEMLM<br>GHCTYFPEELRSVKYAYNADLYNALNDLNNLVITRDEN<br>EKLEYYEKFQIIENVFKQKKKPTLKQIAKEILVNEEDIKG<br>YRVTSTGKPEFTNLKVYHDIKDITARKEIIENAELLDQIA<br>KILTIYQSSEDIQEELTNLNSELTQEEIEQISNLKGYTGTH<br>NLSLKAINLILDELWHTNDNQIAIFNRLKLVPKKVDLSQQ<br>KEIPTTLVDDFILSPVVKRSFIQSIKVINAIIKKYGLPNDIIIE<br>LAREKNSKDAQKMINEMQKRNRQTNERIEEIIRTTGKEN<br>AKYLIEKIKLHDMQEGKCLYSLEAIPLEDLLNNPFNYEV<br>DHIIPRSVSFDNSFNNKVLVKQEEASKKGNRTPFQYLSSS<br>DSKISYETFKKHILNLAKGKGRISKTKKEYLLEERDINRF<br>SVQKDFINRNLVDTRYATRGLMNLLRSYFRVNNLDVKV<br>KSINGGFTSFLRRKWKFKKERNKGYKHHAEDALIIANAD<br>FIFKEWKKLDKAKKVMENQMFEEKQAESMPEIETEQEY<br>KEIFITPHQIKHIKDFKDYKYSHRVDKKPNRELINDTLYS<br>TRKDDKGNTLIVNNLNGLYDKDNDKLKKLINKSPEKLL<br>MYHHDPQTYQKLKLIMEQYGDEKNPLYKYYEETGNYL<br>TKYSKKDNGPVIKKIKYYGNKLNAHLDITDDYPNSRNK<br>VVKLSLKPYRFDVYLDNGVYKFVTVKNLDVIKKENYYE<br>VNSKCYEEAKKLKKISNQAEFIASFYNNDLIKINGELYRV<br>IGVNNDLLNRIEVNMIDITYREYLENMNDKRPPRIIKTIAS<br>KTQSIKKYSTDILGNLYEVKSKKHPQIIKKG | 173 |
| dCAS9-VP64 construct | MAPKKKRKVGIHGVPAAKRNYILGLAIGITSVGYGIIDYE<br>TRDVIDAGVRLFKEANVENNEGRRSKRGARRLKRRRRH<br>RIQRVKKLLFDYNLLTDHSELSGINPYEARVKGLSQKLSE<br>EEFSAALLHLAKRRGVHNVNEVEEDTGNELSTKEQISRN<br>SKALEEKYVAELQLERLKKDGEVRGSINRFKTSDYVKEA<br>KQLLKVQKAYHQLDQSFIDTYIDLLETRRTYYEGPGEGS<br>PFGWKDIKEWYEMLMGHCTYFPEELRSVKYAYNADLY<br>NALNDLNNLVITRDENEKLEYYEKFQIIENVFKQKKKPT<br>LKQIAKEILVNEEDIKGYRVTSTGKPEFTNLKVYHDIKDI<br>TARKEIIENAELLDQIAKILTIYQSSEDIQEELTNLNSELTQ<br>EEIEQISNLKGYTGTHNLSLKAINLILDELWHTNDNQIAIF<br>NRLKLVPKKVDLSQQKEIPTTLVDDFILSPVVKRSFIQSIK<br>VINAIIKKYGLPNDIIIELAREKNSKDAQKMINEMQKRNR<br>QTNERIEEIIRTTGKENAKYLIEKIKLHDMQEGKCLYSLE<br>AIPLEDLLNNPFNYEVDHIIPRSVSFDNSFNNKVLVKQEE<br>ASKKGNRTPFQYLSSSDSKISYETFKKHILNLAKGKGRIS | 174 |

TABLE 12-continued

Other nucleotide and amino acid sequence disclosed herein.

| Description | SEQUENCE | SEQ ID NO |
|---|---|---|
| | KTKKEYLLEERDINRFSVQKDFINRNLVDTRYATRGLMN LLRSYFRVNNLDVKVKSINGGFTSFLRRKWKFKKERNK GYKHHAEDALIIANADFIFKEWKKLDKAKKVMENQMFE EKQAESMPEIETEQEYKEIFITPHQIKHIKDFKDYKYSHR VDKKPNRELINDTLYSTRKDDKGNTLIVNNLNGLYDKD NDKLKKLINKSPEKLLMYHHDPQTYQKLKLIMEQYGDE KNPLYKYYEETGNYLTKYSKKDNGPVIKKIKYYGNKLN AHLDITDDYPNSRNKVVKLSLKPYRFDVYLDNGVYKFV TVKNLDVIKKENYYEVNSKCYEEAKKLKKISNQAEFIAS FYNNDLIKINGELYRVIGVNNDLLNRIEVNMIDITYREYL ENMNDKRPPRIIKTIASKTQSIKKYSTDILGNLYEVKSKK HPQIIKKGKRPAATKKAGQAKKKKGSYPYDVPDYALED ALDDFDLDMLGSDALDDFDLDMLGSDALDDFDLDMLG SDALDDFDLDML | |
| WT EGR3 Protein (human) | MTGKLAEKLPVTMSSLLNQLPDNLYPEEIPSALNLFSGSS DSVVHYNQMATENVMDIGLTNEKPNPELSYSGSFQPAP GNKTVTYLGKFAFDSPSNWCQDNIISLMSAGILGVPPAS GALSTQTSTASMVQPPQGDVEAMYPALPPYSNCGDLYS EPVSFHDPQGNPGLAYSPQDYQSAKPALDSNLFPMIPDY NLYHHPNDMGSIPEHKPFQGMDPIRVNPPPITPLETIKAF KDKQIHPGFGSLPQPPLTLKPIRPRKYPNRPSKTPLHERPH ACPAEGCDRRFSRSDELTRHLRIHTGHKPFQCRICMRSFS RSDHLTTHIRTHTGEKPFACEFCGRKFARSDERKRHAKI HLKQKEKKAEKGGAPSASSAPPVSLAPVVTTCA | 175 |
| WT EGR1 Protein (human) | MAAAKAEMQLMSPLQISDPFGSFPHSPTMDNYPKLEEM MLLSNGAPQFLGAAGAPEGSGSNSSSSSSGGGGGGGG SNSSSSSSTFNPQADTGEQPYEHLTAESFPDISLNNEKVL VETSYPSQTTRLPPITYTGRFSLEPAPNSGNTLWPEPLFSL VSGLVSMTNPPASSSSAPSPAASSASASQSPPLSCAVPSN DSSPIYSAAPTFPTPNTDIFPEPQSQAFPGSAGTALQYPPP AYPAAKGGFQVPMIPDYLFPQQQGDLGLGTPDQKPFQG LESRTQQPSLTPLSTIKAFATQSGSQDLKALNTSYQSQLI KPSRMRKYPNRPSKTPPHERPYACPVESCDRRFSRSDEL TRHIRIHTGQKPFQCRICMRNFSRSDHLTTHIRTHTGEKP FACDICGRKFARSDERKRHTKIHLRQKDKKADKSVVASS ATSSLSSYPSPVATSYPSPVTTSYPSPATTSYPSPVPTSFSS PGSSTYPSPVHSGFPSPSVATTYSSVPPAFPAQVSSFPSSA VTNSFSASTGLSDMTATFSPRTIEIC | 176 |
| Linker | GGSGGGSG | 177 |
| Linker | GGSGGGSGGGSGGGSG | 178 |
| Linker | [GGGS]n | 179 |
| Linker | [GGGGS]n | 180 |
| Linker | [GGSG]n | 181 |
| Recognition site for WT EGR1 or EGR3 | GCG(T/G)GGGCG | 182 |
| sgRNA scaffold | GTTTTAGTACTCTGGAAACAGAATCTACTAAAACAAG GCAAAATGCCGTGTTTATCTCGTCAACTTGTTGGCGAG A | 183 |
| Human CREB3 coding sequence | atggagctggaattggatgctggtgaccaagacctgctggccttcctgctagaggaaagt ggagatttggggacggcacccgatgaggccgtgagggccccactggactgggcgctg ccgctttctgaggtGccgagcgactgggaagtagatgatttgctgtgctccctgctgagtc ccccagcgtcgttgaacattctcagctcctccaacccctgccttgtccaccatgaccacac ctactccctcccacgggaaactgtctctatggatctagagagtgagagctgtagaaaaga ggggacccagatgactccacagcatatggaggagctggcagagcaggagattgctagg ctagtactgacagatgaggagaagagtctattggagaaggaggggcttattctgcctgag acacttcctctcactaagacagaggaacaaattctgaaacgtgtgcggaggaagattcga aataaaagatctgctcaagagagccgcaggaaaaagaaggtgtaCgttgggggtttaga gagcCgggtcttgaaatacacagcccagaatatggagcttcagaacaaagtacagcttct ggaggaacagaatttgtcccttctagatcaactgaggaaactccaggccatggtgattgag atCtcaaacaaaaccagcagcagcagcacctgcatcttggtcctGctagtctccttctgc ctcctccttgtacctgctatgtactcctctgacacaagggggagcctgccagctgagcatg gagtgttgtcccgccagcttcgtgccctccccagtgaggacccttaccagctggagctgc ctgccctgcagtcagaagtgccgaaagacagcacacaccagtggttggacggctcaga ctgtgtactccaggcccctggcaacacttcctgcctgctgcattacatgcctcaggctccca | 210 |

TABLE 12-continued

Other nucleotide and amino acid sequence disclosed herein.

| Description | SEQUENCE | SEQ ID NO |
|---|---|---|
| | gtgcagagcctcccctggagtggccCttccctgacctcttctcagagcctctctgccgag gtcccatcctccccctgcaggcaaatctcacaaggaagggaggatggcttcctactggta gcccctctgtcattttgcaggacagatactcaggc | |
| Human CREB3 AA sequence | MELELDAGDQDLLAFLLEESGDLGTAPDEAVRAPLDWA LPLSEVPSDWEVDDLLCSLLSPPASLNILSSSNPCLVHHD HTYSLPRETVSMDLESESCRKEGTQMTPQHMEELAEQEI ARLVLTDEEKSLLEKEGLILPETLPLTKTEEQILKRVRRKI RNKRSAQESRRKKKVYVGGLESRVLKYTAQNMELQNK VQLLEEQNLSLLDQLRKLQAMVIEISNKTSSSSTCILVLL VSFCLLLVPAMYSSDTRGSLPAEHGVLSRQLRALPSEDP YQLELPALQSEVPKDSTHQWLDGSDCVLQAPGNTSCLL HYMPQAPSAEPPLEWPFPDLFSEPLCRGPILPLQANLTRK GGWLPTGSPSVILQDRYSG | 211 |
| Human CREB3 C-terminal domain with transmembrane region | VYVGGLESRVLKYTAQNMELQNKVQLLEEQNLSLLDQL RKLQAMVIEISNKTSSSSTCILVLLVSFCLLLVPAMYSSD TRGSLPAEHGVLSRQLRALPSEDPYQLELPALQSEVPKD STHQWLDGSDCVLQAPGNTSCLLHYMPQAPSAEPPLEW PFPDLFSEPLCRGPILPLQANLTRKGGWLPTGSPSVILQD RYSG | 225 |
| Human CREB3 C-terminal domain without transmembrane region | VYVGGLESRVLKYTAQNMELQNKVQLLEEQNLSLLDQL RKLQAMVIEIS | 226 |
| CREB3-TRE coding sequence | atggagctggaattggatgctggtgaccaagacctgctggccttcctgctagaggaaagt ggagatttggggacggcacccgatgaggccgtgagggccccactggactgggcgctg ccgctttctgaggtGccgagcgactgggaagtagatgatttgctgtgctccctgctgagtc cccagcgtcgttgaacattctcagctcctccaacccctgccttgtccaccatgaccacac ctactccctcccacgggaaactgtctctatggatctagagagtgagagctgtagaaaaga ggggacccagatgactccacagcatatggaggagctggcagagcaggagattgctagg ctagtactgacagatgaggagaagagtctattggagaaggaggggcttattctgcctgag acacttcctctcactaagacagaggaacaaattctgaaacgtgtgcggCTTGAGCC CGGAGAGAAGCCGTACAAGTGCCCTGAGTGCGGCAA GTCTTTTAGCAGAAGAGACGAACTTAATGTCCACCAG CGAACGCATACTGGTGAAAAGCCCTATAAATGTCCTG AATGTGGGAAATCATTCTCCAGCCGCAGAACCTGTAG GGCTCACCAGCGAACACACACCGGCGAAAAACCATA CAAATGTCCAGAATGCGGGAAATCCTTTTCTCAGTCAT CCAACTTGGTGAGACATCAACGCACGCACACTGGAGA AAAGCCTTACAAATGCCCGGAATGTGGAAAGTCTTTT TCCCAATTGGCCCATTTGCGAGCCCATCAGAGGACTC ACACGGGCGAGAAACCTTACAAATGCCCGGAATGCGG GAAATCTTTTTCAACGAGTGGCAACCTCGTAAGACAC CAAAGAACGCATACAGGCGAAAAGCCATATAAGTGTC CTGAGTGTGGTAAATCATTCTCACACAGGACCACCCT GACAAATCACCAGCGCACGCACACCGGCAAGAAGAC AAGCgtgtaCgttgggggtttagagagcCgggtcttgaaatacacagcccagaatat ggagcttcagaacaaagtacagcttctggaggaacagaatttgtcccttctagatcaactg aggaaactccaggccatggtgattgagatCtcaaacaaaaccagcagcagcagcacct gcatcttggtcctGctagtctccttctgcctcctccttgtacctgctatgtactcctctgacac aagggggagcctgccagctgagcatggagtgttgtcccgccagcttcgtgccctcccca gtgaggaccccttaccagctggagctgcctgccctgcagtcagaagtgccgaaagacagc acacaccagtggttggacggctcagactgtgtactccaggcccctggcaacacttcctgc ctgctgcattacatgcctcaggctcccagtgcagagcctcccctggagtggcccCttccct gacctcttctcagagcctctctgccgaggtcccatcctccccctgcaggcaaatctcacaa ggaagggaggatggcttcctactggtagcccctctgtcattttgcaggacagatactcagg c | 214 |
| CREB3-TRE | MELELDAGDQDLLAFLLEESGDLGTAPDEAVRAPLDWA LPLSEVPSDWEVDDLLCSLLSPPASLNILSSSNPCLVHHD HTYSLPRETVSMDLESESCRKEGTQMTPQHMEELAEQEI ARLVLTDEEKSLLEKEGLILPETLPLTKTEEQILKRVRLEP GEKPYKCPECGKSFSRRDELNVHQRTHTGEKPYKCPEC GKSFSSRRTCRAHQRTHTGEKPYKCPECGKSFSQSSNLV RHQRTHTGEKPYKCPECGKSFSQLAHLRAHQRTHTGEK PYKCPECGKSFSTSGNLVRHQRTHTGEKPYKCPECGKSF SHRTTLTNHQRTHTGKKTSVYVGGLESRVLKYTAQNME LQNKVQLLEEQNLSLLDQLRKLQAMVIEISNKTSSSSTCI LVLLVSFCLLLVPAMYSSDTRGSLPAEHGVLSRQLRALP | 215 |

TABLE 12-continued

Other nucleotide and amino acid sequence disclosed herein.

| Description | SEQUENCE | SEQ ID NO |
|---|---|---|
| | SEDPYQLELPALQSEVPKDSTHQWLDGSDCVLQAPGNTS CLLHYMPQAPSAEPPLEWPFPDLFSEPLCRGPILPLQANL TRKGGWLPTGSPSVILQDRYSG | |

EXAMPLES

The following examples are included to further describe some aspects of the present disclosure, and should not be used to limit the scope of the invention.

Example 1

Identification of Target Regions Capable of Upregulating SCN1A Using SCN1A Specific Transcriptional Activators In order to identify regions of the genome capable of upregulating endogenous SCN1A expression, various engineered transcription factors (either zinc finger nucleases or gRNA/daCas9 constructs) were designed that targeted various regions of the genome as set forth in Tables 4 and 13 above. For gRNA/daCas9 constructs, the gRNA had the same sequence as the target region because the gRNA was designed to target the complementary genomic strand. The dCas9 protein was a dCAS9-VP64 construct (SEQ ID NO: 174).

HEK293 cells were cultured per standard methods, and transfected (FugeneHD, Promega) with 3 ug plasmid carrying an engineered transcription factor or control construct per well of a 6-well plate. Cells were transfected with plasmids expressing the constructs indicated in TABLE 13 below. 48 h following transfection, cells were collected and RNA was isolated (Qiagen RNeasy Mini kit), and DNase treated. RNA (3 ug) was reverse transcribed using OligoDT primers (Superscript IV, Invitrogen). cDNA samples were analyzed by qPCR using Phusion Polymerase (New England Biolabs) and SYBR Green I: (30 s at 98° C., 40×[10 sec at 98° C., 15 sec at 66° C., 15 sec at 72° C.]). Primers against SCN1A (5'-TGTCTCGGCATTGAGAACATTC-3' (SEQ ID NO: 185); 5'-ATTGGTGGGAGGCCATTGTAT-3' (SEQ ID NO: 186)) were used to quantify levels of endogenous SCN1A transcript, and relative levels of SCN1A expression were determined by the delta-delta Ct method with GAPDH as a reference gene (5'-ACCACAGTCCATGCCATCAC'-3' (SEQ ID NO: 187); 5'-TCCACCACCCTGTTGCTGTA-3' (SEQ ID NO: 188)). Data are presented as fold changes relative to the control condition.

The results are shown in FIG. 1 and in TABLE 13 below as fold change of SCN1A transcription relative to control conditions (e.g., EGFP-KASH reporter construct). TABLE 13 reports values for constructs that led to at least a 1.5 fold increase in transcription relative to the control conditions.

TABLE 13

Effect of different genomic target sites and corresponding eTFs had on transcription. CON indicates the zinc finger Construct that was used in the experiment (see TABLE 1). For the gRNA constructs, the target site and the gRNA sequence are the same since the gRNAs were designed to target the complementary DNA strand.

| CON | Chr 2 Start Position | Target Sequence | Target Site from FIG. 1 | SEQ ID NO for Target Site | Mean | Ttest |
|---|---|---|---|---|---|---|
| 4 | 166149168 | ctaggtcaagtgtaggag | z1 | 18 | 5.12090848 | 0.0096628 |
| 28 | 166149165 | GGTCAAGTGTAGGAGACA | z8 | 25 | 1.52068773 | 0.62403349 |
| 3 | 166128025 | taggtaccatagagtgag | z13 | 30 | 25.4730028 | 0.14942042 |
| 29 | 166127991 | gaggatactgcagaggtc | z14 | 31 | 8.6766618 | 0.16432794 |
| | 166149176 | aaggctgtctaggtcaagtgt | g9 | 35 | 1.36378425 | 0.18753821 |
| | 166149118 | tgttcctccagattaacactt | g10 | 36 | 1.63040825 | 0.46710683 |
| | 166128002 | gatgaagccgagaggatactg | g11 | 37 | 18.7579211 | 0.13148732 |
| | 166128037 | gctgatttgtattaggtacca | g12 | 38 | 22.4892633 | 0.09291316 |
| | 166177299 | AGAAAGCTGATACAGATACAA | g15 | 39 | 1.7542842 | 0.34519408 |
| | 166178880 | ggtacgggcaaagatttcttg | g17 | 40 | 1.36801947 | 0.48762102 |
| | 166177299 | AGAAAGCTGATACAGATACAA | g19 | 41 | 1.45636874 | 0.44464045 |
| | 166177369 | ACACAATGAGCCACCTACAAG | g20 | 42 | 1.31187425 | 0.42605224 |
| | 166177362 | GTGGCTCATTGTGTGTGTGCC | g22 | 43 | 1.25217773 | 0.26572657 |

TABLE 13-continued

Effect of different genomic target sites and corresponding eTFs had on transcription. CON indicates the zinc finger Construct that was used in the experiment (see TABLE 1). For the gRNA constructs, the target site and the gRNA sequence are the same since the gRNAs were designed to target the complementary DNA strand.

| CON | Chr 2 Start Position | Target Sequence | Target Site from FIG. 1 | SEQ ID NO for Target Site | Mean | Ttest |
|---|---|---|---|---|---|---|
| | 166155264 | CATATCCCTGCAGGTTCAGAA | g24 | 44 | 1.75688991 | 0.28984533 |
| | 166155099 | agagagagagagagagagaga | g25 | 45 | 2.05701745 | 0.42409102 |
| | 166155393 | TTCTCAGTTTTGAAATTAAAA | g26 | 46 | 1.64498972 | 0.21705582 |
| | 166155255 | TGGATTCTCTTCTGAACCTGC | g27 | 47 | 2.27026665 | 0.43195546 |
| | 166148361 | TGCTGAGGCAGGACACAGTGT | g29 | 48 | 2.4290169 | 0.30364553 |
| | 166148843 | ATCATCTGTAACCATCAAGGA | g30 | 49 | 2.58328006 | 0.0748197 |
| | 166148565 | TCCTGCCTACTTAGTTTCAAG | g31 | 50 | 1.97097781 | 0.25980859 |
| | 166148953 | ATTACAGTTCTGTCAGCATGC | g32 | 51 | 1.34500323 | 0.32186367 |
| | 166149373 | TGGTCTCATTCTTTTTGTGGG | g33 | 52 | 1.71471378 | 0.32104302 |
| | 166142239 | CGATATTTTCATGGATTCCTT | g34 | 53 | 1.7735976 | 0.21954265 |
| | 166142391 | CTGACACTTACTTTGTCTAAA | g35 | 54 | 1.95513108 | 0.02069095 |
| | 166142219 | AAAACTGGAACCGCATTCCCA | g36 | 55 | 2.08698135 | 0.0454403 |
| | 166142396 | ACAAAGTAAGTGTCAGTGTGG | g37 | 56 | 1.30739959 | 0.72725347 |
| | 166142344 | ATAATAGTTGTGTCTTTATAA | g38 | 57 | 1.55783618 | 0.29846459 |
| | 166141162 | TGTACAAGCAGGGCTGCAAAG | g39 | 58 | 1.4663605 | 0.02946062 |
| | 166140590 | GTTAACAAATACACTAAACAC | g40 | 59 | 1.37399196 | 0.33638238 |
| | 166140928 | ttcaacaagctcccaagaagt | g42 | 60 | 1.46929899 | 0.24465271 |
| | 166141090 | ATGTTCAAGGTGCAGAAGGAA | g43 | 61 | 2.04547409 | 0.09880194 |
| | 165990246 | TGTTTGCTCAAACGTGCACCA | g44 | 62 | 2.13402102 | 0.25583999 |
| | 165989684 | AAATAAGACATGAAAACAAGA | g45 | 63 | 1.27016182 | 0.32368695 |
| | 165990193 | AAATATGTACCACAAGAAATG | g46 | 64 | 2.29522738 | 0.41829497 |
| | 165990076 | TATCTGGTTTCTCTCACTGCT | g47 | 65 | 1.44542116 | 0.0947106 |
| | 165989571 | ATTGCAAAGCATAATTTGGAT | g48 | 66 | 1.42246971 | 0.18117243 |

Example 2

Figure 2A:
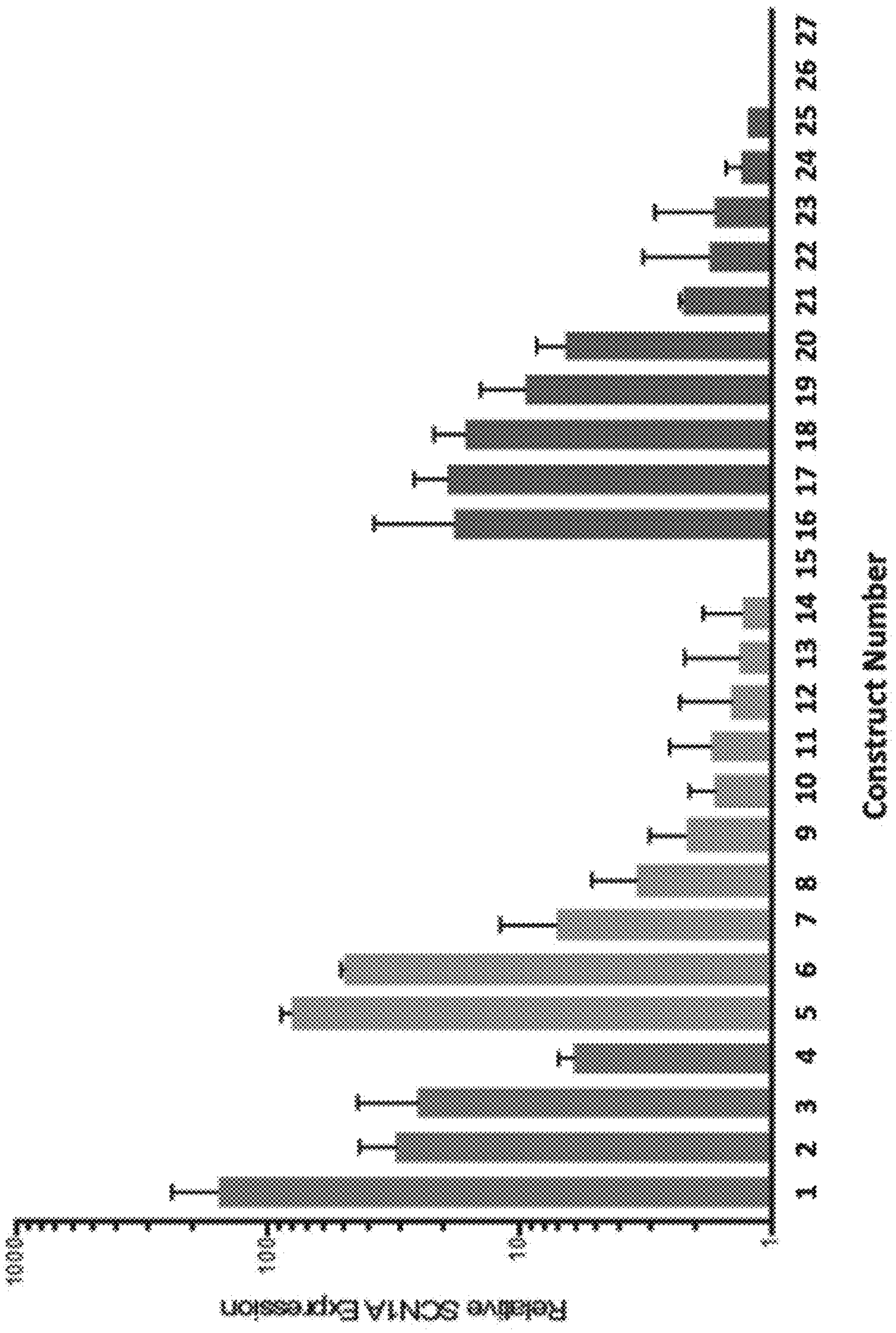
FIG. 2A, FIG. 2B, and FIG. 2C illustrate the relative expression of endogenous SCN1A in HEK293 cells using SCN1A-specific transcriptional activators (see TABLE 1). Data are presented as fold change relative to control conditions, and shown on a $Log_{10}$ scale.
Figure 2B:
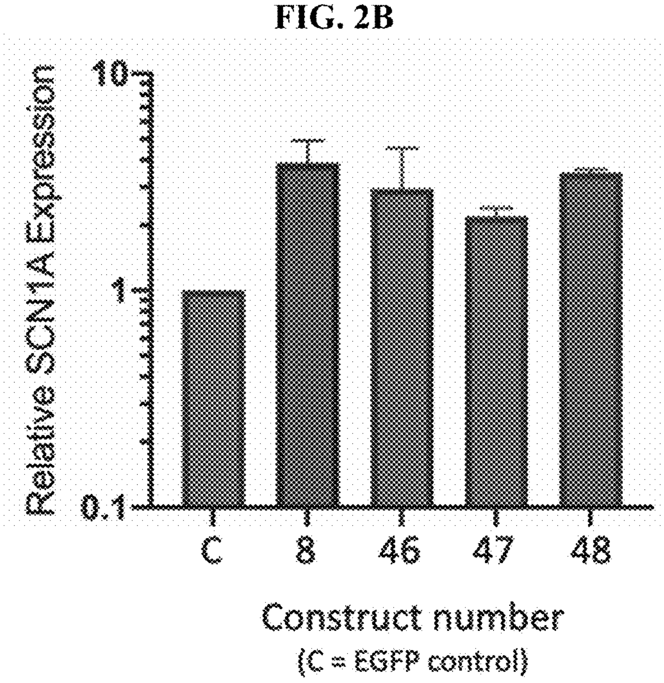
Figure 2C:
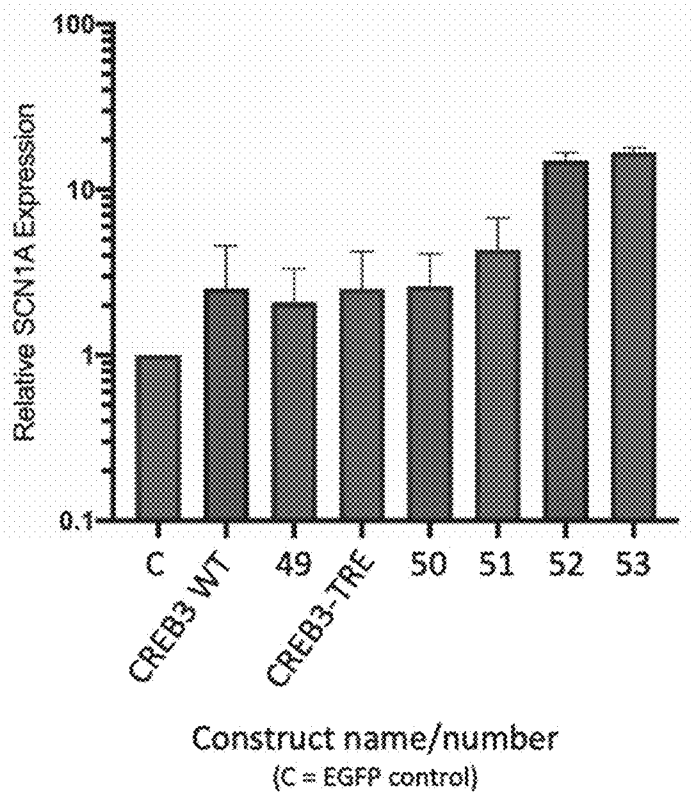

Upregulation of Endogenous SCN1A in HEK293 Cells Using SCN1A Specific Transcription Factors HEK293 cells were cultured per standard methods and plated into 6-well plates. Cells in each well were transfected (FugeneHD, Promega) with 3 ug of a plasmid carrying either a single engineered transcription factor construct, a WT human CREB3 (SEQ ID NO: 211), or an EGFP control construct. The engineered transcription factor constructs tested included: Constructs 1-27 and 46-53 (TABLE 1) and a plasmid expressing CREB3-TRE (SEQ ID NO: 215; CREB3 with the bZIP DNA binding domain replaced with the TET promoter-targeted synthetic ZF domain) (each tested separately). 48 h following transfection, cells were collected and RNA was isolated (Qiagen RNeasy Mini kit), and DNase treated. RNA (3 ug) was reverse transcribed using OligoDT primers (Superscript IV, Invitrogen). cDNA samples were analyzed by qPCR using Phusion Polymerase (New England Biolabs) and SYBR Green I: (30 s at 98° C., 40×[10 sec at 98° C., 15 sec at 66° C., 15 sec at 72° C.]). Primers against SCN1A (5'-TGTCTCGGCATTGAGAA-CATTC-3' (SEQ ID NO: 185); 5'-ATTGGTGGGAGGC-CATTGTAT-3' (SEQ ID NO: 186)) were used to quantify levels of endogenous SCN1A transcript, and relative levels of SCN1A expression were determined by the delta-delta Ct method with GAPDH as a reference gene (5'-AC-CACAGTCCATGCCATCAC'3' (SEQ ID NO: 187); 5'-TC-CACCACCCTGTTGCTGTA-3' (SEQ ID NO: 188)). Data are presented as fold changes relative to the control condition (see FIG. 2A, FIG. 2B and FIG. 2C). The control construct consisted of EGFP expressed under the control of RE 1 (SEQ ID NO: 1). Delivery of engineered transcription factors induced varying degrees of upregulation in endogenous SCN1A transcript with respect to the EGFP condition.

Example 3

Figure 3A:
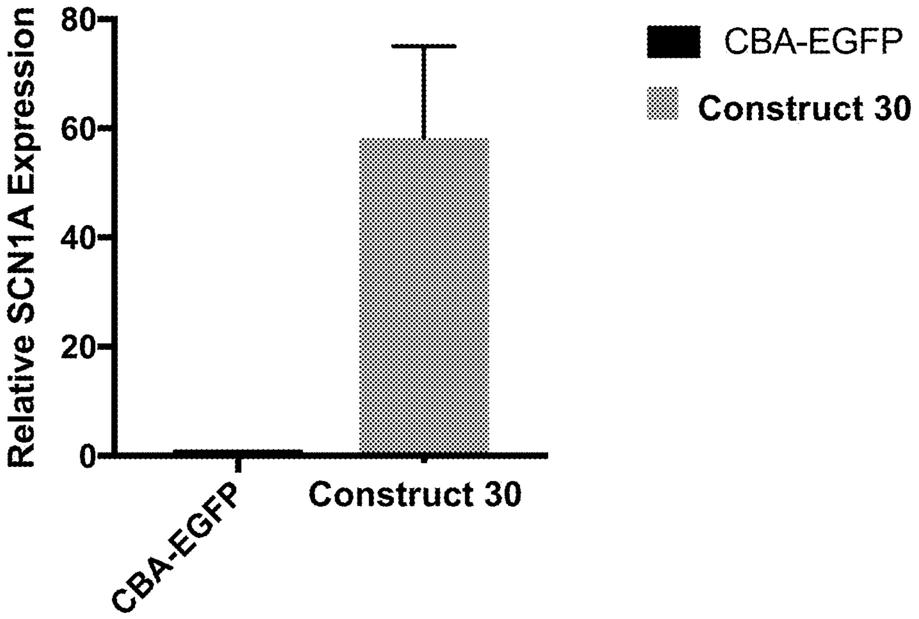
FIG. 3A illustrates the relative expression of endogenous SCN1A in GABA neurons using an SCN1A-specific transcriptional activator (Construct 30). Data are presented as fold change relative to control conditions (CBA-EGFP).
Figure 3B:
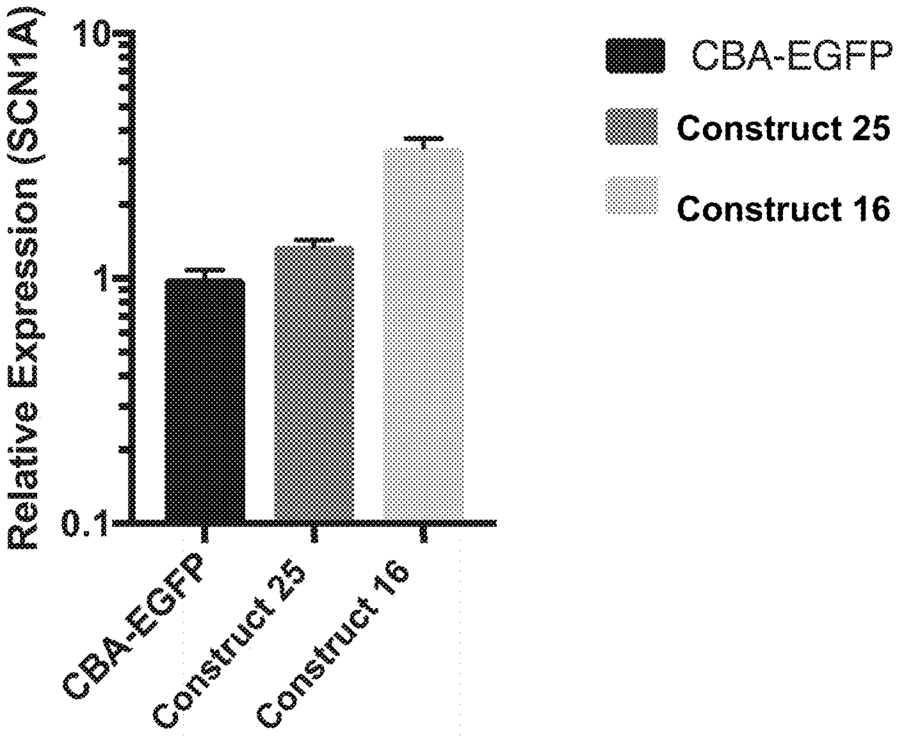
FIG. 3B illustrates the relative expression of endogenous SCN1A in GABA neurons using SCN1A-specific transcriptional activators (Constructs 25 and 16). Data are presented as fold change relative to control conditions (CBA-EGFP) in $Log_{10}$.

Upregulation of Endogenous SCN1A in GABA Neurons Using SCN1A Specific Transcription Factors iCell GABA neurons (Cellular Dynamics) were plated in a 6-well plate (~1 E6 cells/well) and maintained per manufacturer's recommended protocol. 72 h following plating, recombinant AAV (serotype AAV-DJ) expressing EGFP or an activator Construct 30 in FIG. 3A or Construct 25 or Construct 16 in FIG. 3B) under the control of a ubiquitous promoter (CBA promoter) was added to the culture media at approximately 2 E11 genome copies/well. One week (FIG. 3A) or two weeks (FIG. 3B) following infection, RNA was isolated from cultured cells (Qiagen RNeasy Mini kit), and DNase treated. Recovered RNA was reverse transcribed using OligoDT primers (Superscript IV, Invitrogen). cDNA samples were analyzed by qPCR using Phusion Polymerase (New England Biolabs) and SYBR Green I: (30 s at 98° C., 40×[10 sec at 98° C., 15 sec at 66° C., 15 sec at 72° C.]). Primers against SCN1A (5'-TGTCTCGGCATTGAGAACATTC-3' (SEQ ID NO: 185); 5'-ATTGGTGGGAGGCCATTGTAT-3' (SEQ ID NO: 186)) were used to quantify levels of endogenous SCN1A transcript, and relative levels of SCN1A expression were determined by the delta-delta Ct method with GAPDH as a reference gene (5'-ACCACAGTCCATGCCATCAC'3' (SEQ ID NO: 187); 5'-TCCACCACCCTGTTGCTGTA-3' (SEQ ID NO: 188)). Data are presented as fold changes relative to the control condition (see FIG. 3A and FIG. 3B). AAV-driven expression of engineered transcription factors produced significant upregulation of endogenous SCN1A transcript in cultured iPS-derived GABA neurons.

Example 4

Specific Upregulation of Endogenous SCN1A in GABA Neurons Using an SCN1A Specific Transcription Factor iCell GABA neurons (Cellular Dynamics) were plated in a 6-well plate (~1 E6 cells/well) and maintained per manufacturer's recommended protocol. 72 h following plating, recombinant AAV (serotype AAV-DJ) expressing EGFP or activator (Construct 30), which comprises a zinc finger DBD fused to a VPR TAD driven by a CBA promoter) under the control of a CBA promoter was added to the culture media at approximately 2 E11 genome copies/well.

Figure 4:
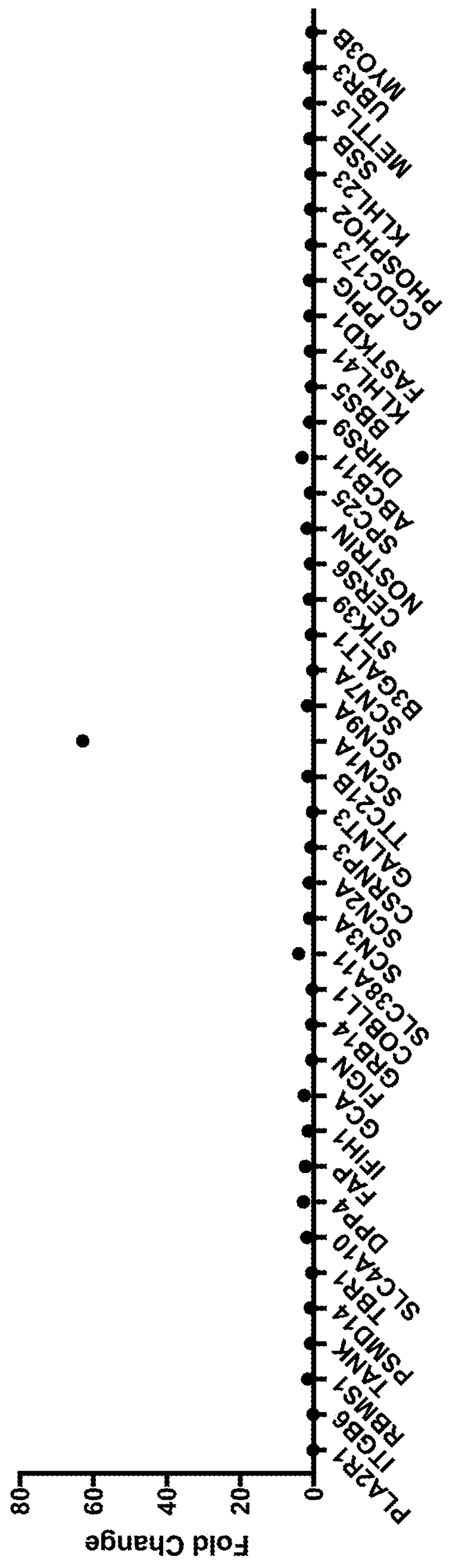
FIG. 4 illustrates the relative expression of endogenous SCN1A and the 40 nearest neighboring genes driven by an SCN1A specific transcription factor (Construct 30). Data are presented as fold change relative to control conditions (CBA-EGFP-KASH) in $Log_{10}$.

One week following infection, RNA was isolated from cultured cells (Qiagen RNeasy Mini kit), and DNase treated. RNAseq libraries were prepared from the recovered RNA, using the TruSeq Stranded mRNA library kit (Illumina) and sequenced on an Illumina NextSeq (2×75 cycle paired end sequencing). Sequencing reads were aligned to human genome (RNASTAR) and differential expression analysis was performed with DESeq2. Data are presented as fold change with respect to control (AAVDJ-CBA-EGFP) samples (see FIG. 4). Results are shown in TABLE 14 and FIG. 4 illustrates the relative expression of endogenous SCN1A and the 40 nearest neighboring gene transcripts presented as fold changes relative to the control condition. Construct 30, as described in TABLE 1, was able to specifically increase expression of the SCN1A gene, or the Nav1.1 protein, as compared to the other genes examined. This indicated the target site recognized by the transcriptional activator of Construct 30 was specific for the SCN1A gene, thus resulting in an increase in SCN1A gene expression in GABA neurons.

TABLE 14

Effects on transcription of endogenous SCN1A and the 40 nearest neighbor genes in GABA neurons treated with an SCN1A specific transcription factor (Construct 30).

| Gene Name | Chr 2 Start | Chr 2 End | Chr Strand | Fold Change vs. Control |
|---|---|---|---|---|
| PLA2R1 | 160788518 | 160919121 | − | 0.16367458 |
| ITGB6 | 160956176 | 161128399 | − | 0.20679884 |
| RBMS1 | 161128661 | 161350305 | − | 1.63514667 |
| TANK | 161993418 | 162092732 | + | 0.90946407 |
| PSMD14 | 162164548 | 162268228 | + | 0.92699237 |
| TBR1 | 162272604 | 162282381 | + | 0.53199642 |
| SLC4A10 | 162280842 | 162841792 | + | 1.89407328 |
| DPP4 | 162848750 | 162931052 | − | 2.82345284 |
| FAP | 163027193 | 163101661 | − | 2.26977379 |
| IFIH1 | 163123588 | 163175213 | − | 1.46146481 |
| GCA | 163175349 | 163228105 | + | 2.58702426 |
| FIGN | 164449905 | 164592522 | − | 0.46785861 |
| GRB14 | 165349321 | 165478358 | − | 0.5631965 |
| COBLL1 | 165510133 | 165700189 | − | 0.43199257 |
| SLC38A11 | 165752695 | 165812035 | − | 4.06730119 |
| SCN3A | 165944031 | 166060577 | − | 1.0807866 |
| SCN2A | 166095911 | 166248818 | + | 1.24475196 |
| CSRNP3 | 166326156 | 166545917 | + | 0.82971233 |
| GALNT3 | 166604100 | 166651192 | − | 0.33804418 |
| TTC21B | 166713984 | 166810353 | − | 1.58661143 |
| SCN1A | 166845669 | 166984523 | − | 62.9552975 |
| SCN9A | 167051694 | 167232503 | − | 1.71659087 |
| SCN7A | 167260082 | 167350757 | − | 0.29331967 |
| B3GALT1 | 168675181 | 168730551 | + | 0.64436013 |
| STK39 | 168810529 | 169104651 | − | 1.19821739 |
| CERS6 | 169312371 | 169631644 | + | 0.86828378 |
| NOSTRIN | 169643048 | 169722024 | + | 1.82142718 |
| SPC25 | 169690641 | 169769881 | − | 0.86880697 |
| ABCB11 | 169779447 | 169887832 | − | 3.1441368 |
| DHRS9 | 169921298 | 169952677 | + | 1.10381777 |
| BBS5 | 170335687 | 170382432 | + | 0.65476347 |
| KLHL41 | 170366211 | 170382772 | + | 0.87373377 |
| FASTKD1 | 170386258 | 170430385 | − | 1.02786927 |
| PPIG | 170440849 | 170497916 | + | 1.09866236 |
| CCDC173 | 170501934 | 170550943 | − | 0.67290779 |
| PHOSPHO2 | 170550974 | 170558218 | + | 0.91339152 |
| KLHL23 | 170550997 | 170633499 | + | 0.73926347 |
| SSB | 170648442 | 170668574 | + | 1.00631994 |
| METTL5 | 170666590 | 170681441 | − | 1.21271497 |
| UBR3 | 170683967 | 170940641 | + | 1.21350908 |
| MYO3B | 171034654 | 171511681 | + | 0.52839217 |

Example 5

Expression of SCN1A from an Expression Cassette In Vivo

To test the expression of transcriptional activators of SCN1A in vivo, recombinant AAV9 vectors were generated by Vector Biolabs (Malvern, PA). Male C57Bl/6 mice (N=5 per group, 7-8 weeks old) were infused bilaterally with 1.5 ul of purified AAV vector into the dorsal hippocampus (AP−2.0 mm, lateral ±1.5, DV−1.4 mm from dura) and ventral hippocampus (AP−3.1 mm, lateral ±2.8, DV−3.8 mm from dura), for a total of 4 injection sites. AAV was delivered at a rate of 0.3 ul/minute with a 4 m rest period following each injection. Four weeks after treatment, mice were euthanized and hippocampal tissue was dissected. For each group, tissue from both the left and right hippocampus tissue was collected pooled for homogenization in most animals (N=4), except for one animal, where only the left hippocampus was collected and homogenized. RNA was isolated from the homogenate (Qiagen RNeasy Mini kit), and DNase treated. RNA (3 μg) was reverse transcribed using OligoDT primers (Superscript IV, Invitrogen). cDNA samples were analyzed by qPCR for expression of mouse SCN1A using Phusion Polymerase (New England Biolabs) and SYBR Green I: 30 s at 98° C., 40×[10 sec at 98° C., 15 sec at 64° C., 15 sec at 72° C.]. Primers against mouse SCN1A (5'-CAAAAAAGCCACAAAAGCCT-3' (SEQ ID NO: 189); 5'-TTAGCTCCGCAAGAAACATC-3' (SEQ ID NO: 190)) were used to quantify levels of endogenous SCN1A transcript, and relative levels of SCN1A expression in vivo were determined by the delta-delta Ct method with GAPDH as a reference gene (5'-ACCACAGTCCATGC-CATCAC'3' (SEQ ID NO: 187); 5'-TCCAC-CACCCTGTTGCTGTA-3' (SEQ ID NO: 188))

Figure 5A:
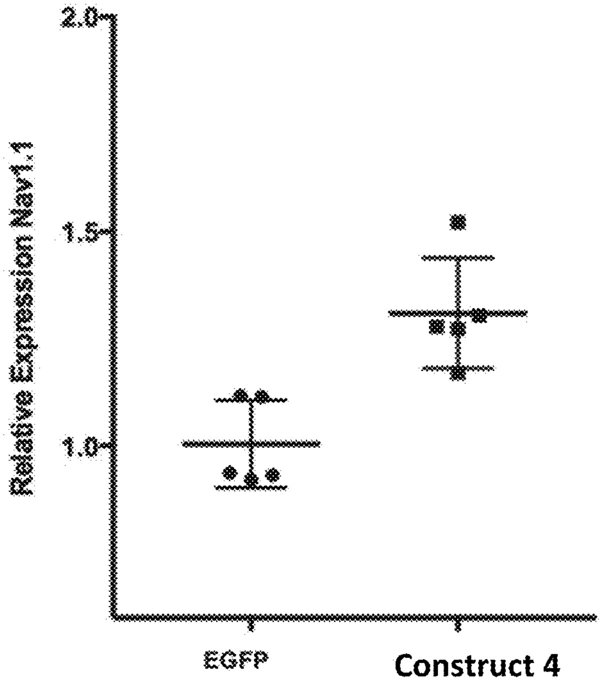
FIG. 5A and FIG. 5B illustrate expression of a SCN1A-specific transcriptional activator in vivo as compared to a control expression cassette which expressed eGFP.
Figure 5B:
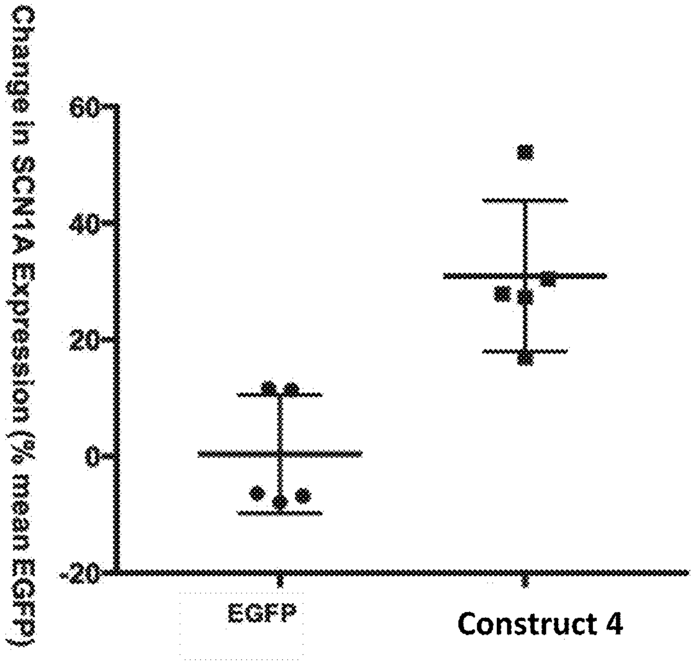

FIG. 5A and FIG. 5B illustrate the mean results of five animals, each injected with an AAV9 construct. The eGFP control construct comprised an eGFP reporter transgene. Construct 4 (see TABLE 1) comprised a transcriptional activator that recognized a target sequence comprising SEQ ID NO: 18, as described in TABLE 1 above. FIG. 5A illustrates the relative expression of SCN1A in vivo. FIG. 5B illustrates the change in SCN1A expression in vivo as a percentage of mean eGFP expression. These results indicated the SCN1A transcriptional activator of expression cassette A resulted in approximately 20%-30% upregulation of SCN1A expression in vivo.

Such expression cassettes can be adapted for use in humans to treat Dravet syndrome, epilepsy, seizures, Alzheimer's disease, Parkinson's disease, and/or any other diseases or conditions associated with a deficiency and/or impaired activity of SCN1A.

Example 6

Hyperthermic Seizure (HTS) Assay in Mouse Models of Dravet Syndrome

A. Heterozygous Scn1a Knockout Mouse Model

Treatment of Dravet syndrome and/or symptoms thereof using the expression cassettes was tested in the Scn1a$^{tm1Kea}$ mouse line. This mouse line is an established mouse model for Dravet syndrome. Scn1a$^{tm1Kea}$ mouse lines do not require CRE recombinase. The Scn1a$^{tm1Kea}$ mouse (available from the Jackson Laboratory; described in Hawkins et al., Scientific Reports, vol. 7: 15327 (2017)) comprises a deletion of the first coding exon of SCN1A. Mice homozygous for the SCN1A knockout allele are characterized by tremors, ataxia, seizures, and die by postnatal day 16. Heterozygous mice on the C57BL/6 background develop spontaneous seizures and a large percentage die within weeks. Such a mouse strain can be used to study safety and efficacy of treatment of epilepsy and Dravet syndrome. See Miller et al., Genes Brain Behav. 2014 February; 13(2):163-72 for additional information.

To test the efficacy of transcriptional activators in the Scn1a$^{tm1Kea}$ mouse line, litters of pups produced from male Scn1a+/− crossed with female C57Bl/6J breeding were dosed with AAV vector via bilateral ICV at P1. Mice were dosed with Constructs 31-34 (TABLE 1). Mice were left undisturbed with their dam until weening at P18 and then again left undisturbed until P26-P28 when the hyperthermic seizure (HTS) assay was initiated. Separate litters of dosed P1 mice were weened at P18 and observed for mortality daily. Hyperthermia seizure induction was performed in P26-P28 heterozygous (HET) and WT Scn1a mice in a mixed 129Stac X C57BL/6 background. Prior to the assay mice had a lubricated rectal temperature probe (Ret-4) inserted and connected to a temperature control module (TCAT 2DF, Physitemp) that was connected in series with a heating lamp (HL-1). Mice were then placed into a large glass beaker and briefly allowed to equilibrate to the environment. Following this, body temperature was increased by ~0.5° C. every 2 minutes until the onset of the first tonic-clonic seizure accompanied by loss of posture or until 43° C. was reached. If a mouse experienced a seizure with loss of posture the experiment was ended and the internal body temperature of the mouse was recorded. If no seizure with loss of posture was detected over the full course of the experiment, that mouse was considered seizure free and the assay concluded. Tissue samples were obtained from the mice at P1 and genotyping of the mice was performed during the course of the experiment using real-time PCR. The genotyping was unblinded after the assay had been completed and the status of the mice as HET or WT was correlated to the data obtained. Data was plotted in a Kaplan-Meier survival curve and significance determined by the Mantel-Cox test. Results are shown in TABLE 15 and TABLE 16 and FIGS. 6A-E.

TABLE 15

Summary of conditions used in Example 6.

| Construct | Dosage (gc/mouse) |
|---|---|
| Construct 31 (FIG. 6A & 6E)) | 6.0E+10 |
| Construct 32 (FIG 6B, 6D, 6E) | 3.1E+11 |
| Construct 33 (FIG. 6C) | 5.8E+10 |
| Construct 34 (FIG. 6D) | 4.9E+13 |

TABLE 16

Summary of results of hyperthermic seizure assay.

| eTF Construct (FIG.) | # Control Animals (PBS treated) | # Treated Animals | % Seizure Free at 42.6° C. | P Value |
|---|---|---|---|---|
| EGFP reporter | 16 | N/A | 44% | |
| Construct 31 (FIG. 6A & 6E)) | 16 | 18 | 95 | P < 0.0001 |
| Construct 32 (FIG 6B, 6D, 6E) | 16 | 21 | 76 | P < 0.05 |
| Construct 33 (FIG. 6C) | 16 | 14 | 93 | P < 0.001 |
| Construct 34 (FIG. 6D) | 16 | 12 | 83 | P < 0.05 |

Figure 6A:
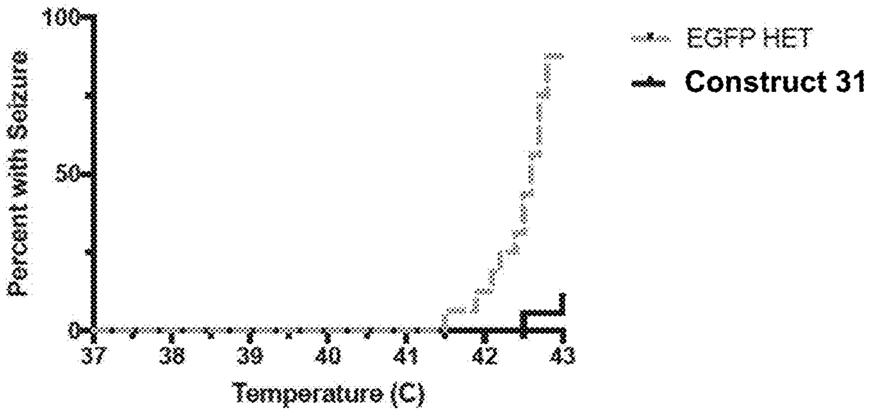
FIG. 6A, FIG. 6B, FIG. 6C, FIG. 6D, FIG. 6E, FIG. 6F, and FIG. 6G illustrate the effect on hyperthermic seizures in the $Scn1a^{tm1Kea}$ knockout mouse model of Dravet syndrome using various SCN1A specific transcription factors as compared to a control. P1 Scn1a+/−mice (heterozygous; HET) were infused with either AAV9-EGFP or an AAV9 vector expressing an SCN1A specific transcription factor (one of Constructs 31-34, 42 and 43). At P26-P28 infused mice were run through the hyperthermia induced seizure assay and the internal temperature at which they experienced a tonic-clonic seizure was recorded.
Figure 6B:
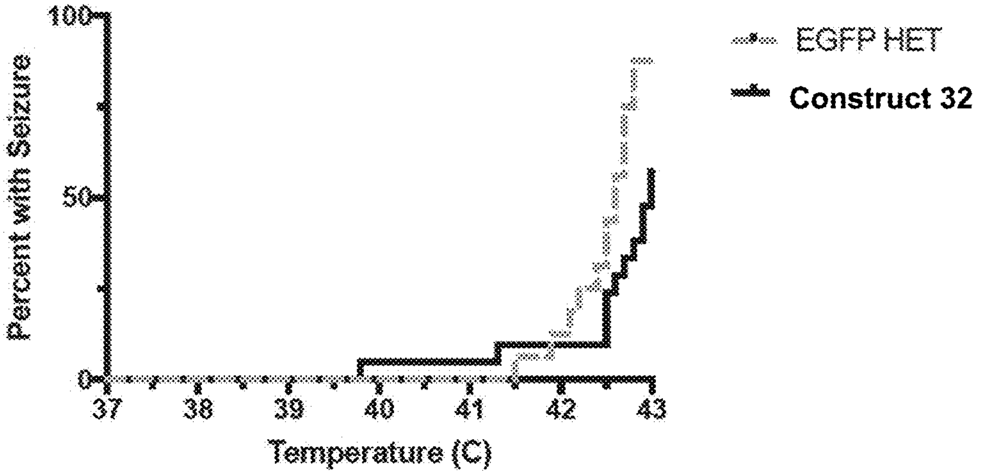
Figure 6C:
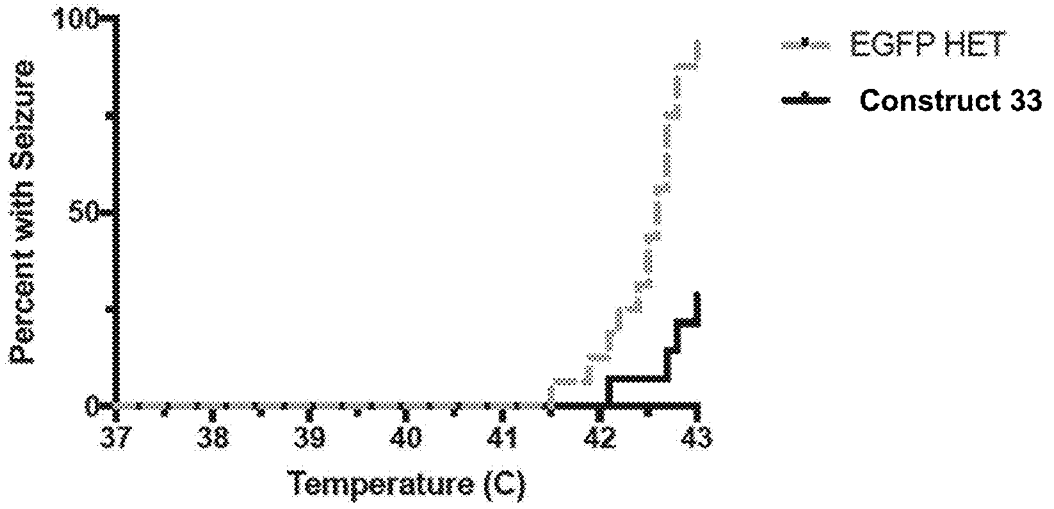
Figure 6D:
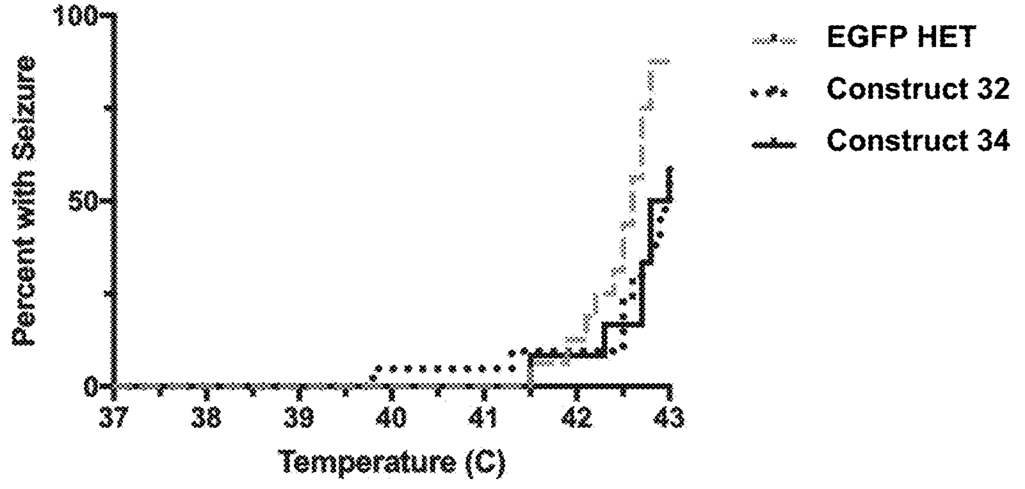
Figure 6E:
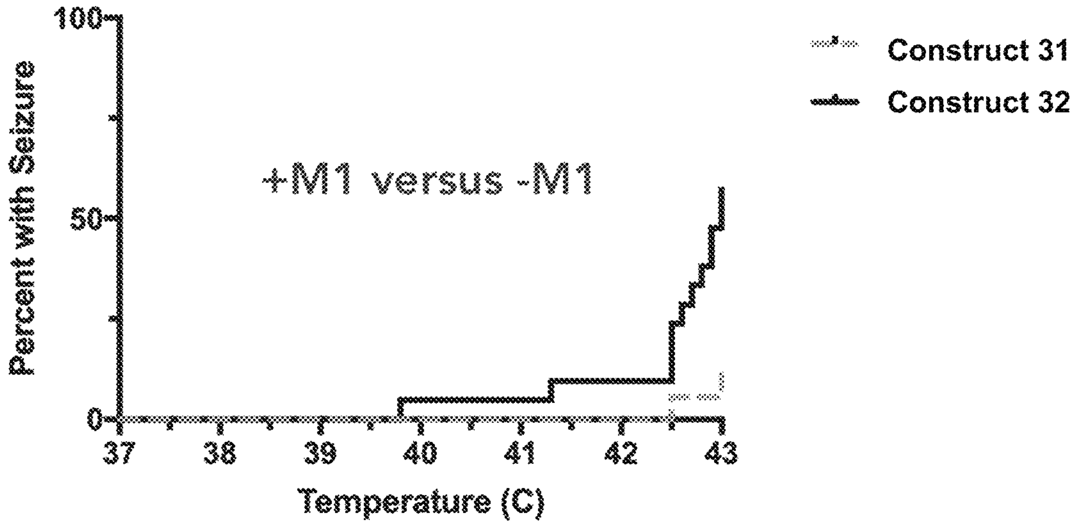
Figure 6F:
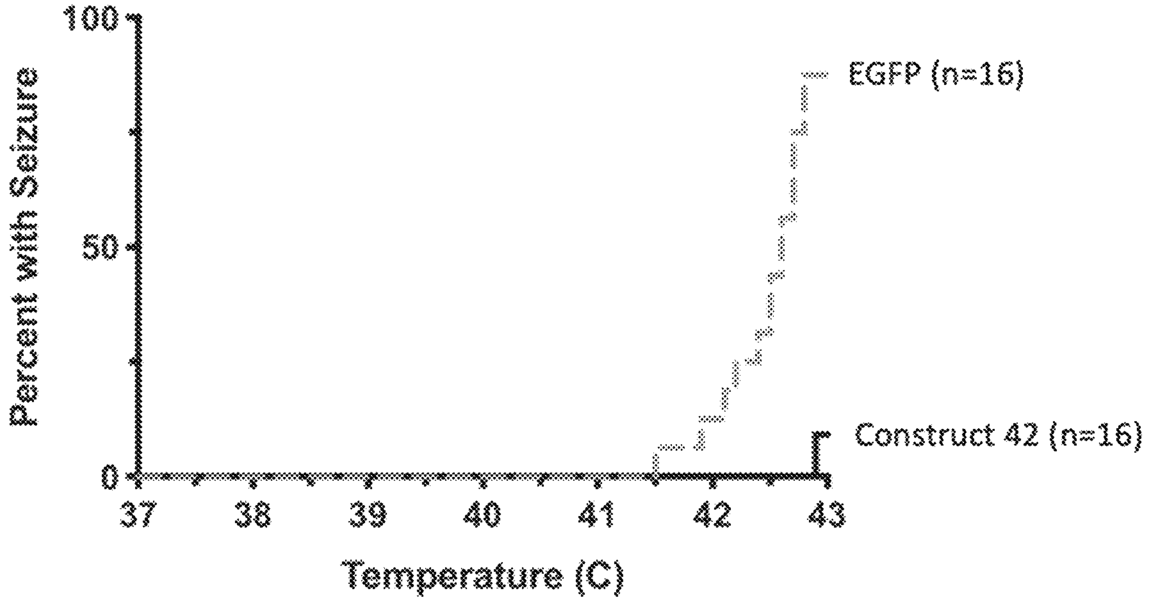
Figure 6G:
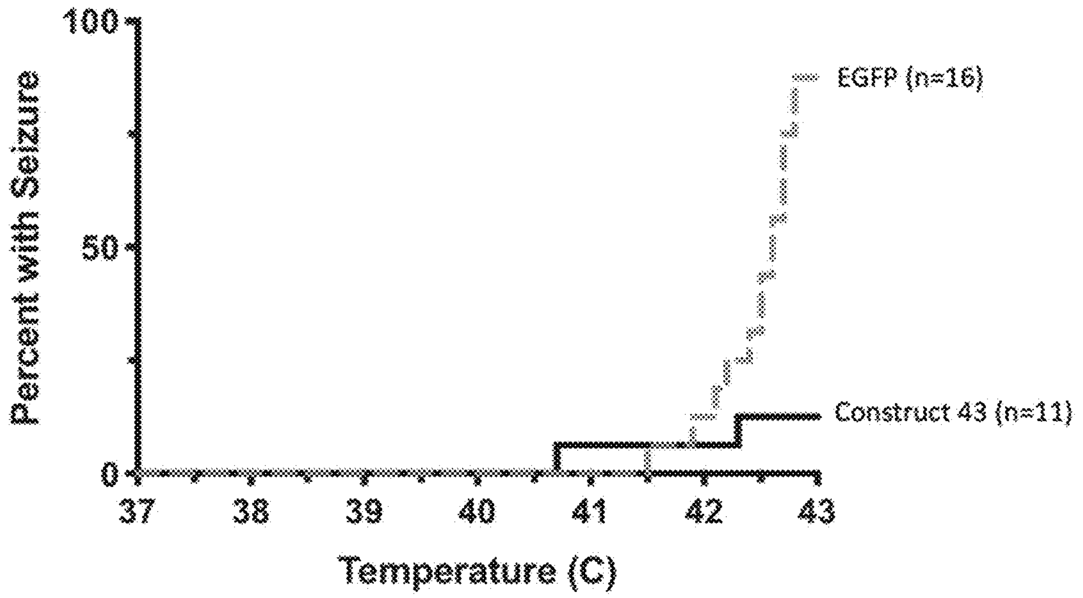

Additional experiments were conducted in Scn1a$^{tm1Kea}$ mice as described above to test Constructs 42 and 43 for their effect on seizures in the I-ITS assay. In these experiments, Construct 42 was dosed at 9×10$^{10}$ gc/mouse via bilateral ICV at P1 and Construct 43 was dosed at 6×10$^{10}$ gc/mouse via bilateral ICV at P1 or P5. Results are shown in FIG. 6F (Construct 42) and FIG. 6G (Construct 43), Both constructs showed a significant reduction in seizures as compared to EGFP controls (P<0.0001 for both Construct 42 and 43).

B. Heterozygous Scn1a$^{RX}$ Mutant Mouse Model

Treatment of Dravet syndrome and/or symptoms thereof using an expression cassette of the present disclosure was tested in the Scn1a$^{RX}$ mouse line. This mouse line is an established mouse model for Dravet syndrome. Scn1a$^{RX}$ mouse lines do not require CRE recombinase. The Scn1a$^{RX}$ mouse (available from the Jackson Laboratory; described in Ogiwara et al., J. Neuroscience, vol. 27: 5903-5914 (2007)) comprises a loss of function single base nonsense mutation of the in exon 21 of the SCN1A gene (CgG to TgA; R1407X). Heterozygous mice on the C57BL/6 background develop spontaneous seizures and a large percentage die within weeks.

Figure 6H:
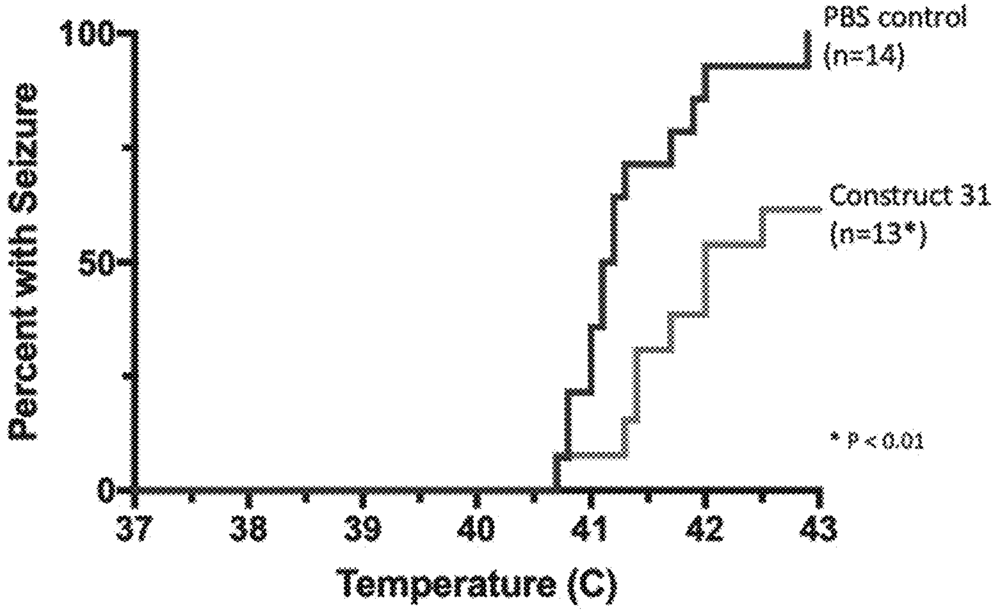
FIG. 6H illustrates the effect on hyperthermic seizures in the $Scn1a^{RX}$ mutant mouse model of Dravet syndrome using Construct 31 (compared to PBS injected control).

To test the efficacy of transcriptional activators in the Scn1a$^{RX}$ mouse line, litters of pups produced from male and IVF crossing of Scn1a$^{RX/+}$ sperm with female C57Bl/6J ova with embryos implanted into CD-1 dams were dosed with AAV vector (Construct 31) at $5.1\times10^{10}$ genome copies (gc)/mouse or PBS control via bilateral ICV at P1. Mice were left undisturbed with their dam until weening at P18 and then again left undisturbed until P26-P28 when the HTS assay was initiated. Separate litters of dosed P1 mice were weened at P18 and observed for mortality daily. Hyperthermia seizure induction was performed in P26-P28 heterozygous (HET) and WT Scn1a mice in a C57BL/6 background. Prior to the assay mice had a lubricated rectal temperature probe (Ret-4) inserted and connected to a temperature control module (TCAT 2DF, Physitemp) that was connected in series with a heating lamp (HL-1). Mice were then placed into a large glass beaker and briefly allowed to equilibrate to the environment. Following this, body temperature was increased by ~0.5° C. every 2 minutes until the onset of the first tonic-clonic seizure accompanied by loss of posture or until 43° C. was reached. If a mouse experienced a seizure with loss of posture the experiment was ended and the internal body temperature of the mouse was recorded. If no seizure with loss of posture was detected over the full course of the experiment, that mouse was considered seizure free and the assay concluded. Tissue samples were obtained from the mice at P1 and genotyping of the mice was performed during the course of the experiment using real-time PCR. The genotyping was unblinded after the assay had been completed and the status of the mice as HET or WT was correlated to the data obtained. None of the WT Scna1 mice tested experienced a seizure. Data for the Construct 31 treated (n=13) and PBS control treated (n=14) HET mice was plotted in a Kaplan-Meier survival curve and significance determined by the Mantel-Cox test. As shown in FIG. 6H, Construct 31 treated HET mice show a significant reduction in hyperthermia seizure induction over PBS control treated HET mice (P<0.01).

Example 7

Survival Assay in Mouse Model of Dravet Syndrome

A. Heterozygous Scn1a Knockout Mouse Model

To test the efficacy of transcriptional activators in the Scn1a$^{tm1Kea}$ mouse line, litters of pups produced from male Scn1a+/− crossed with female C57Bl/6J breeding were dosed with AAV vector via bilateral ICV at P1. Mice were left undisturbed with their dam until weaning. Observation of the health status of Scn1a+/−mice was performed daily following weaning at P18. Mice that were found dead in their home cage of any cause had the date recorded. Data was plotted in a Kaplan-Meier survival curve and significance determined by the Mantel-Cox test.

Results are shown in TABLE 17 and FIGS. 7A-D.

TABLE 17

Summary of conditions and results for survival assay.

| SEQ ID | Dosage (gc/mouse) | # Control Animals (PBS treated) | # Treated Animals | % Survival at P100 (*at P83) | P Value |
|---|---|---|---|---|---|
| PBS | N/A | 53 | N/A | 49% | |
| Construct 33 (FIG. 7C & 7D) | 5.8E+10 | 53 | 29 | 76% | P < 0.05 |
| Construct 31 (FIG. 7B & 7D) | 6.0E+10 | 53 | 34 | 97% | P < 0.0001 |

B. Heterozygous Scn1a$^{RX}$ Mutant Mouse Model

To test the efficacy of transcriptional activators in the Scn1a' mouse line, litters of pups produced from male and IVF crossing of Scn1a$^{RX}$ sperm with female C57Bl/6J ova with embryos implanted into CD-1 dams were dosed with AAV vector (Construct 31) at $5.1\times10^{10}$ genome copies (gc)/mouse or PBS control via bilateral ICV at P1. Mice were left undisturbed with their dam until weaning. Observation of the health status of Scn1a$^{RX/+}$ mice was performed daily following weaning at P18. Mice that were found dead in their home cage of any cause had the date recorded. Data for Construct 31 treated (n=27) and control treated (n=18) was plotted in a Kaplan-Meier survival curve and significance determined by the Mantel-Cox test.

Figure 7A:
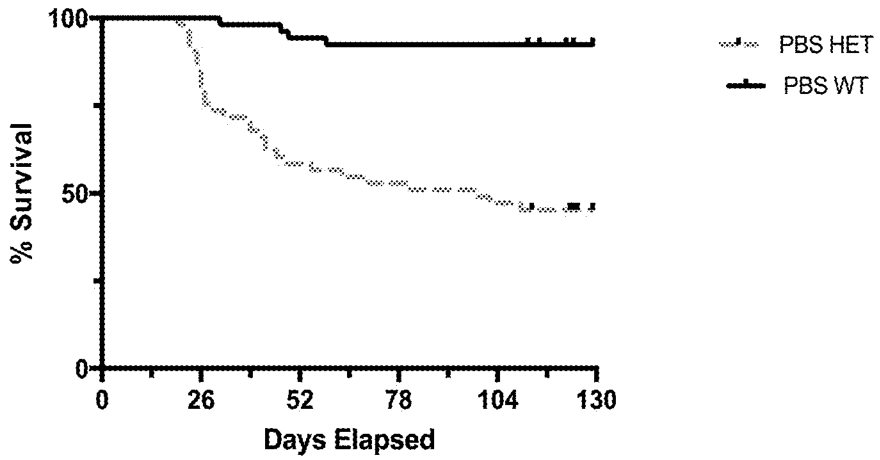
FIG. 7A, FIG. 7B, FIG. 7C, and FIG. 7D illustrate survival in the $Scn1a^{tm1Kea}$ knockout mouse model of Dravet syndrome under various conditions.
Figure 7B:
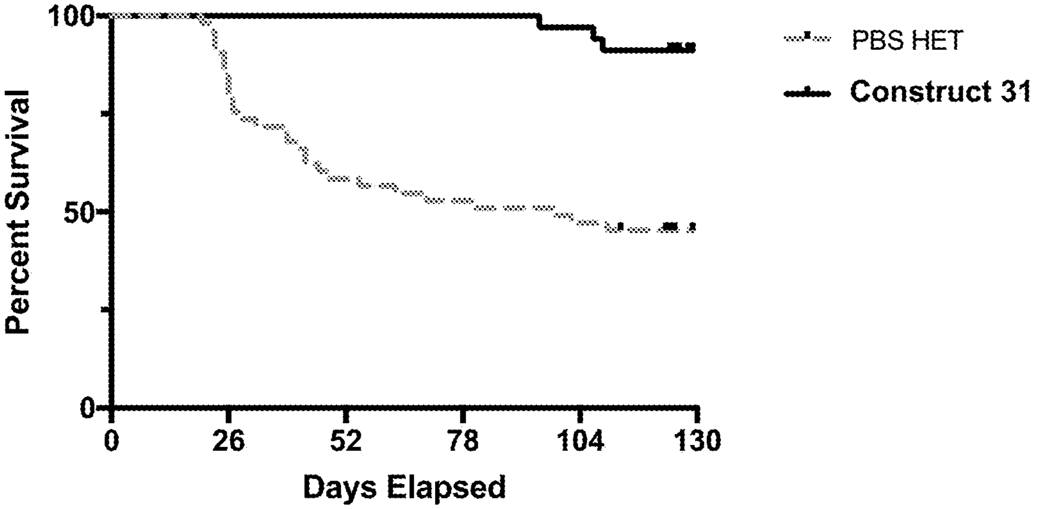
Figure 7C:
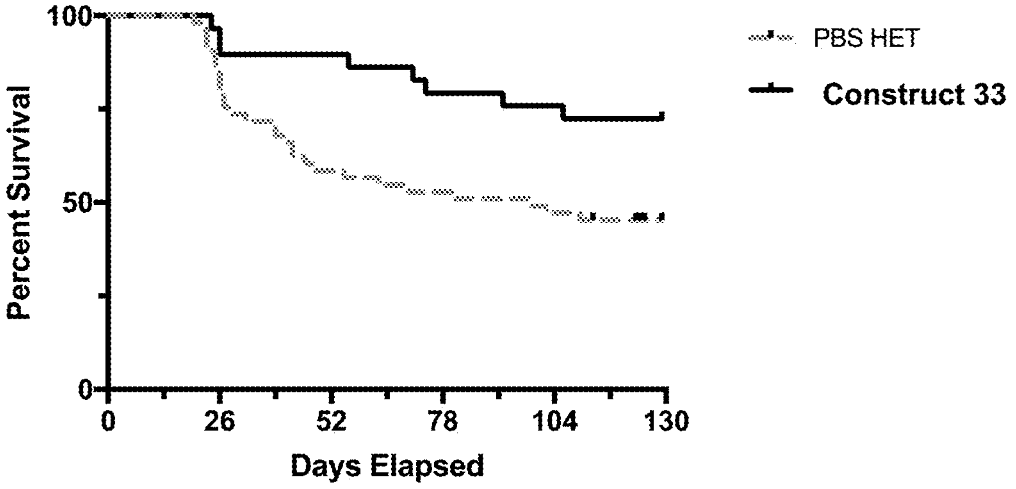
Figure 7D:
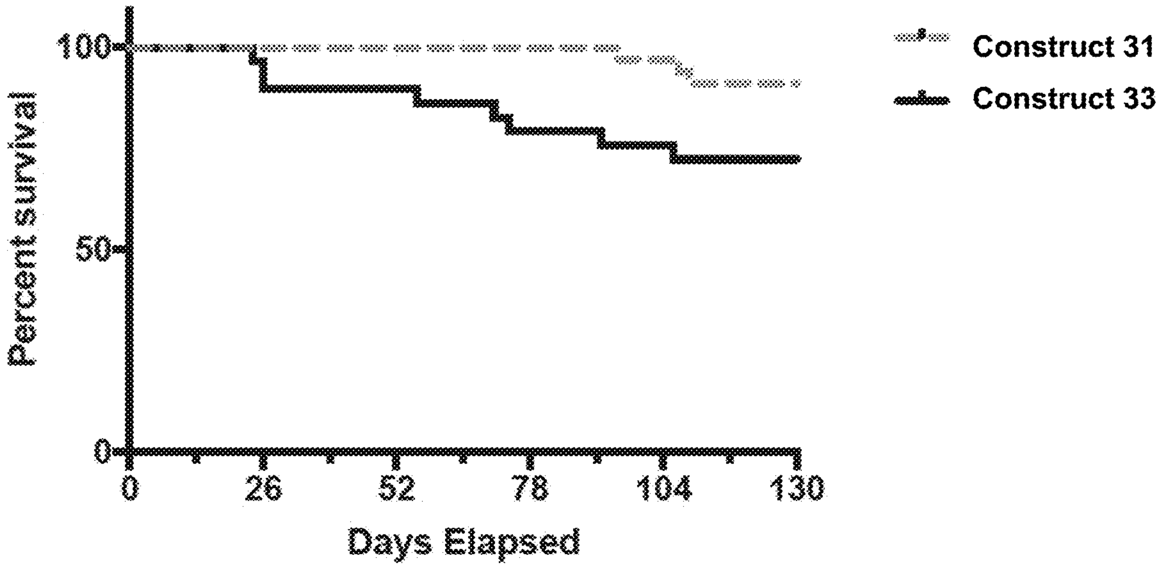
Figure 7E:
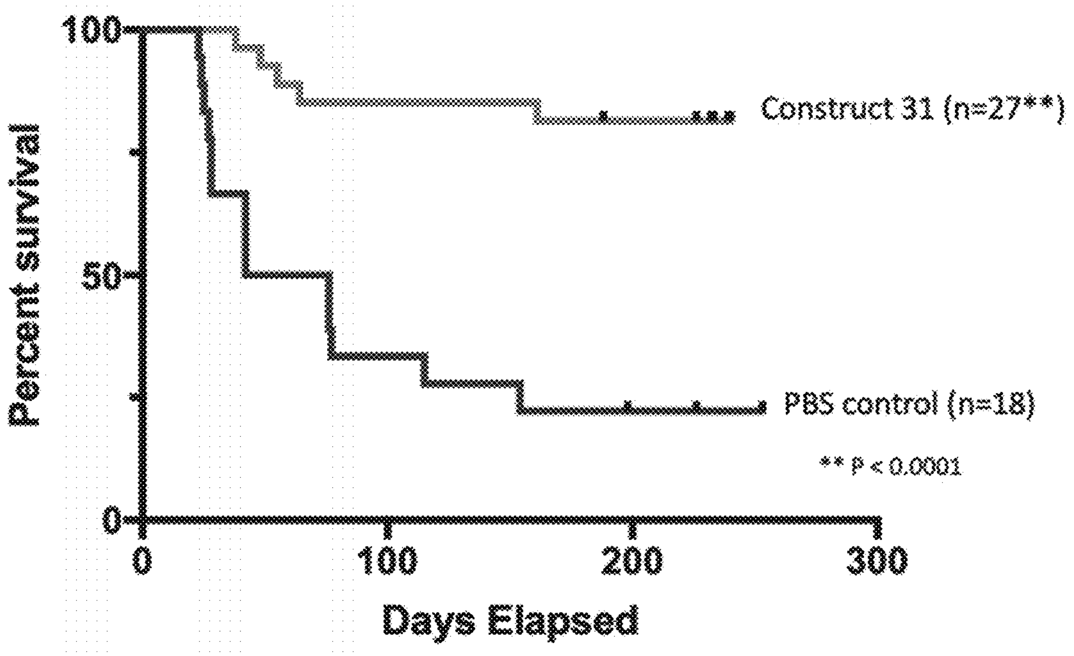
FIG. 7E illustrates survival in the $Scn1a^{RX}$ mutant mouse model of Dravet syndrome using Construct 31 (compared to PBS injected control).

As shown in FIG. 7E, Construct 31 treated Scn1a$^{RX/+}$ mice had increased survival over PBS control treated Scn1a$^{RX/+}$ mice (P<0.0001).

Example 8

SCN1A Transcription Levels in Non-Human Primates Following Treatment with AAV Encoding SCN1A Specific Transcription Factor The study used male cynomolgus macaques (*Macaca fascicularis*) between ages 2 and 3. Animals were prescreened for cross-reactive antibody to AAV9 prior to enrollment in the study by a cell-based neutralizing antibody assay. AAV9 expressing an SCN1A specific transcription factor (Construct 33) or a control was diluted in PBS and injected intraparenchymally at 1.2 E12 gc/animal. Three different stereotaxic coordinates in each hemisphere, six injection sites per animal, were identified for the injections. 10 ul volume was injected per site. Injections in the right hemisphere were symmetrical to those in the left. Two untreated animals were used as a control.

To assess Scn1A mRNA expression, reverse transcription followed by qPCR method was conducted. At necropsy, 28 days post dosing, tissues sections from various regions of the brain (frontal cortex, parietal cortex, temporal cortex, occipital cortex, hippocampus, medulla, cerebellum; 200 mg each) from control and treated animals were collected in RNAlater and then frozen. Briefly, 30 mg of tissue was dissected, RNA extracted (with Qiagen Rneasy Lipid tissue mini kit, catalog #1023539), converted to cDNA by reverse transcription (using Applied Biosystems high capacity cDNA Reverse Transcription kit, catalog #4368814) and qPCR performed using primer/probe set for Scn1A and housekeeping gene GAPDH (Applied Biosystems, catalog #Rh02621745-gI FAM).

Primer/probe sets for SCN1A are given below.

TABLE 18

| Primer Sequences used in Example 8. | | | |
|---|---|---|---|
| Gene | SEQ ID NO | Sequence (5'-3') | Note |
| Scn1A | 191 | CCATGGAACTGGCTCGATTTCAC | F-primer |
| | 192 | ATTGGTGGGAGGCCACTGTAT | R-primer |
| ' | 193 | AGGCCTGAAAACCATTGTGGGAGCCCT | Probe (FAM) |

Gene expression of Scn1A in each test sample was determined by relative quantitation (RQ) using the comparative Ct (ΔCt) method. This method measures Ct difference (ΔCt) between target gene and housekeeping gene, then compares ΔCt values of treatment samples to control samples.

ΔCt=Ct average of Target gene−Ct average of housekeeping gene

ΔΔCt=ΔCt of treatment sample−ΔCt control sample

Relative expression (treatment sample)=$2^{-\Delta\Delta Ct}$

Figure 8:
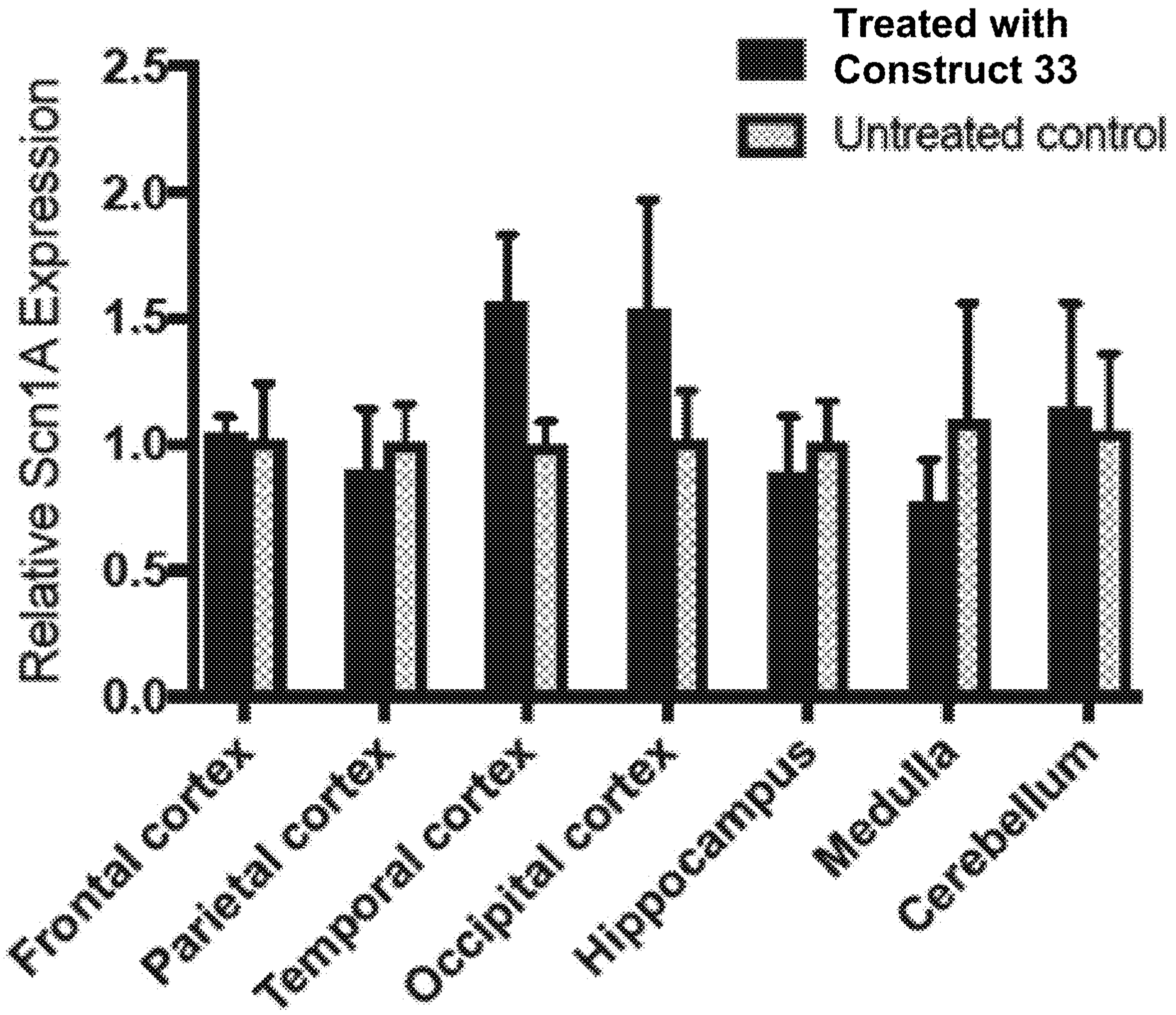
FIG. 8 illustrates relative Scn1A mRNA expression in different brain tissues following intraparenchymal delivery of an AAV9 vector encoding an SCN1A specific transcription factor (Construct 33), administered to two cynomolgus macaques at $1.2\times10^{12}$ gc/animal, normalized to two untreated control animal. All animals were sacrificed 28 days after injection and Scn1A mRNA was quantified in the tissue samples by Taqman PCR. Data is reported as normalized expression of target mRNA in different tissue sections from the brain. Similar results were recorded with a different set of Scn1a gene derived primers/probe as well.
Figure 9A:
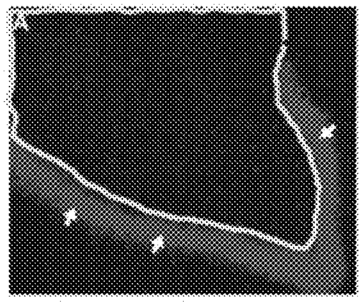
FIGS. 9A-9F shows the pattern of expression of EGFP in marmoset hippocampus dentate gyrus region following treatment with AAV9 vectors comprising an EGFP transgene under the control of EF1a promoter, RE 2 promoter (SEQ ID NO: 2), or RE 2 promoter (SEQ ID NO: 2) with an ml microRNA binding site (SEQ ID NO: 7) located between the EGFP coding region and polyA site. A representative region of the dentate gyrus region of the hippocampus is shown for each vector treatment. The top row shows the cell nuclei stained with DAPI and the bottom row shows the GFP positive regions stained with an anti-GFP antibody.
Figure 9B:
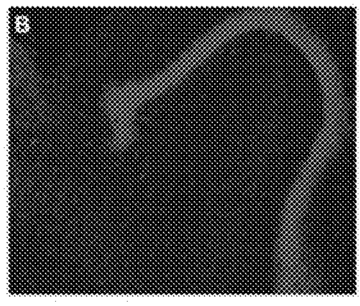
Figure 9C:
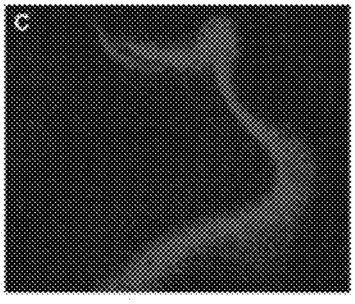
Figure 9D:
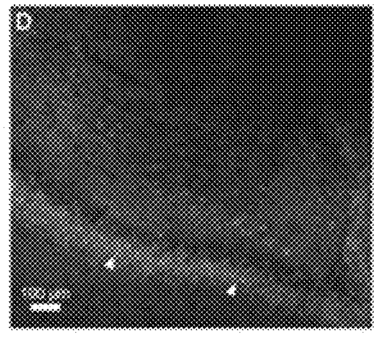
Figure 9E:
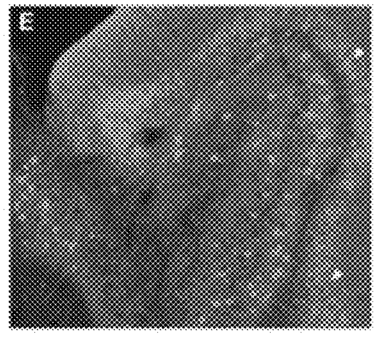
Figure 9F:
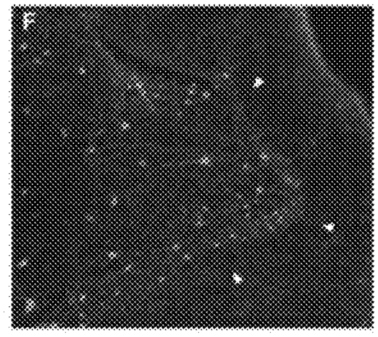
Figures 10A, 10B, 10C, 10D, 10E, 10F, 10G, 10H, 10I, 10J, 10K, 10L:
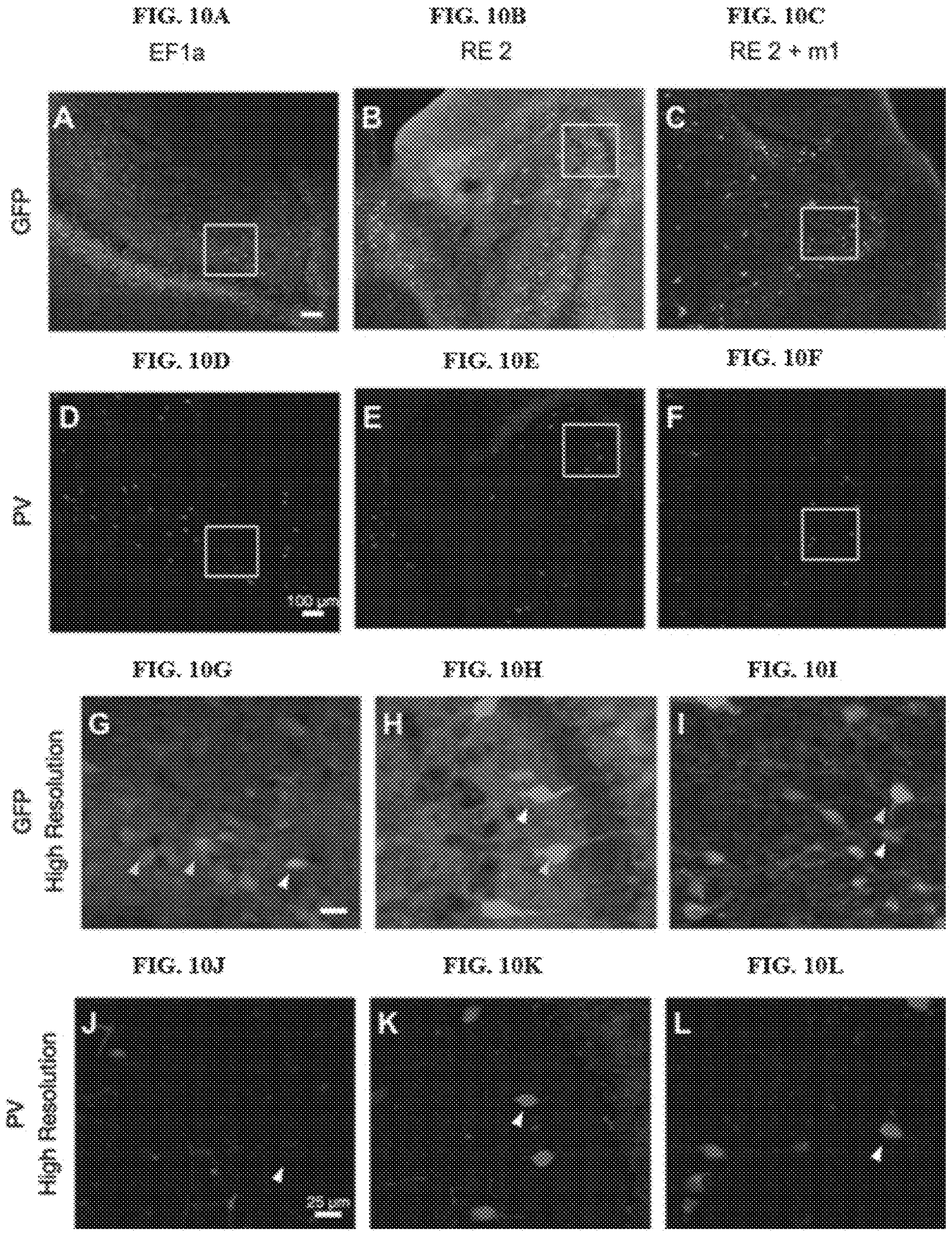
FIGS. 10A-10L shows that the pattern of expression of EGFP in marmoset hippocampus dentate gyrus region following treatment with AAV9 vectors comprising an EGFP transgene under the control of EF1a promoter, RE 2 promoter (SEQ ID NO: 2), or RE 2 promoter (SEQ ID NO: 2) with an ml microRNA binding site (SEQ ID NO: 7) located between the EGFP coding region and polyA site is primarily localized to parvalbumin (PV) positive cells in the RE 2 and RE 2+ml treated animals. A representative region of the dentate gyrus region of the hippocampus is shown for each vector treatment. The top row shows the GFP positive regions and the next row down shows the same regions stained with the inhibitory interneuron marker for PV. The boxed region in FIGS. 10A-10F is shown at a higher magnification in FIGS. 10G-10L. GFP expression driven by RE 2 and RE 2+ml is primarily co-localized with the inhibitory interneuron marker PV (FIGS. 10H and 10K, 10I and 10L white arrowheads), whereas in EG-EF1a GFP expression is not as readily localized to PV positive cells (FIGS. 10G and 10J white arrowheads). In addition, the GFP positive cells have distinctly interneuron morphology of highly branching cells with a pyramidal cell body in RE 2 and RE 2+ml treated animals (FIGS. 10H and 10I yellow arrowheads) as compared to a less distinct cell body morphology in the EF1a treated animals (FIG. 10G yellow arrowheads).

Data is reported as normalized expression of target mRNA in different tissue sections from the brain (see FIG. 8). As illustrated in FIG. 8, sites in the brain proximal to the intraparenchymal injection sites showed the highest levels of SCN1A transcript expression.

Example 9

Selective Transgene Expression in PV Neurons in Non-Human Primates Following Treatment with AAV Having PV Selective Promoter and MicroRNA Binding Site The study used six marmosets (*Callithrix jacchus*) that were prescreened for cross-reactive antibody to AAV9 prior to enrollment in the study. Two monkeys were treated with AAV9 containing an EGFP transgene under the control of the EF1alpha promoter, two monkeys were treated with AAV9 containing an EGFP transgene under the control of RE 2 (SEQ ID NO: 2), and two monkeys were treated with AAV9 containing an EGFP transgene under the control of RE 2 (SEQ ID NO: 2) and also containing a microRNA binding site (SEQ ID NO: 7) located between the coding region of EGFP and the polyA tail. The AAV9 vectors were diluted in PBS and the animals were treated with three intracerebral injections (2 uL each) into the hippocampus/entorhinal cortex of each hemisphere for a total of 6 injection sites per animal. The two animals treated with the AAV9 vector containing EF1alpha-EGFP each received a total dose of 5.8 E+11 gc/animal, the two animals treated with the AAV9 vector containing RE 2-EGFP each received a total dose of 3.0 E+11 gc/animal, and the two animal treated with the AAV9 vector containing RE 2+ml-EGFP each received a total dose of 2.3 E+11 gc/animal.

Immunohistochemistry was used to assess parvalbumin (PV) selective expression. At necropsy, 28 days post dosing, tissues sections from various regions of the brain were collected. Floating Marmoset brain sections (35 um) were fixed in 4% paraformaldehyde, blocked with buffer (PBS, 3% BSA, 3% Donkey Serum, 0.3% Triton-X 100, 0.2% Tween-20) and then stained with anti-GFP (Abcam ab290) followed by a secondary antibody conjugated to Alexa-488 (Thermo A21206). This was followed by anti-PV antibody (Swant) and secondary antibody conjugated to Alexa-647 (Thermo A31571) and 4',6-diamidino-2-phenylindole (DAPI). Sections were mounted and imaged using a PerkinElmer Vectra3.

Results are shown in FIGS. 9A-9F and 10A-10L.

Example 10 eTF$^{SCN1A}$ Biodistribution

The objective of this study was to compare the biodistribution of eTF$^{SCN1A}$ in the central nervous system (CNS) of juvenile cynomolgus macaque monkeys when administered at a dose of 4.8 E+13 via unilateral intracerebroventricular (ICV) injection. Each animal was injected with AAV9 containing an expression cassette encoding eTF$^{SCN1A}$ under the control of a GABA selective regulatory element (RE$^{GABA}$-eTF$^{SCN1A}$), The AAV9 particles were formulated in PBS f 0,001% pluronic acid and administered at a dose of 4.8 E+13 or 8 E+13 vg/animal. A volume of 2 ml of formulated viral particles was administered to each animal. The study design is set forth in TABLE 19.

Twenty-four month old cynomolgus macaque monkeys were grouped as indicated in TABLE 19. Prior to initiation of the study, blood samples from the animals were tested for levels of neutralizing antibody titer to AAV9 using the NAb titer assay described above. Animals with low or negative results for antibodies were selected for the study. Samples were administered via ICV injection using standard surgical procedures. Thawed dosing material was briefly stored on wet ice and warmed to room temperature just prior to dosing. The animals were anesthetized, prepared for surgery, and mounted in a MRI compatible stereotaxic frame (Kopf). A baseline MRI was performed to establish target coordinates. An incision was made and a single hole was drilled through the skull over the target location. A 3 mL BD syringe attached to a 36" micro-bore extension set was prepared with sample and placed in an infusion pump. The extension line was primed. The dura was opened, and the dosing needle was advanced to a depth of 13.0 to 18.1 mm from the pia. Contrast media injection and fluoroscopy was used to confirm placement of the spinal needle into the right lateral ventricle. The 3.0" 22 g Quinke BD spinal huber point needle was filled with contrast to determine placement prior to attaching the primed extension line and syringe. Pump settings were 0.1 mL/minute for 19 to 20 minutes. Buffer was pushed by hand post dose to clear the extension line. The needle remained in place for 1 to 2 minutes post completion of infusion and then the needle was withdrawn. The vehicle and test article were administered once on day 1 and the subjects were maintained for a 27- or 29-day recovery period.

TABLE 19

| Biodistribution Study Design | | | |
|---|---|---|---|
| Group | Gender | ID | Dose (VG/animal) |
| Group 1 | M | 21001 | |
| (Buffer Control) | F | 11501 | |
| Group 2 | M | 2001 | 4.8E+13 |
| (RE$^{GABA}$-eTF$^{SCN1A}$) | F | 2501 | 4.8E+13 |
| | M | 3001 | 4.8E+13 |
| | M | 3002 | 8E+13 |

Following dosing, animals were routinely monitored throughout the duration of the study and blood samples were periodically withdrawn. eTF$^{SCN1A}$ administration was not associated with any unexpected mortality, clinical findings, or macroscopic observations. AAV9-RE$^{GABA}$-eTF$^{SCN1A}$ treated animals survived until scheduled necropsy at day 28±2 days. No clinical or behavioral signs, increases in body temperature, or body weight reduction were observed during daily or weekly physical examinations. Transient elevation in liver transaminases (ALT and AST) in AAV9-RE$^{GABA}$-eTF$^{SCN1A}$ treated animals were observed, but were fully resolved by the end of study without immunomodulation, and no concomitant increase in serum bilirubin or alkaline phosphatases was noted. No other measured clinical chemistry endpoint was remarkable. No microscopic observations were reported in the liver histopathology studies. CSF leukocytes were elevated in terminal collection relative to pre-treatment values but comparable between control and AAV9-RE$^{GABA}$-eTF$^{SCN1A}$ treated animals. No AAV9-RE$^{GABA}$-eTF$^{SCN1A}$ associated pleocytosis was observed. Macro-observations and detailed micro-histopathology examination of non-neuronal tissues across all animals were unremarkable. Tissues included major peripheral organs (i.e. heart, lungs, spleen, liver and gonads). Macro-observations and detailed micro-histopathology of neuronal tissues did not show any notable findings. Tissues included brain, spinal cord, and associated dorsal root ganglia (from cervical, thoracic and lumbar region). Studies were conducted by three independent pathologists including one at a specialized neuropathology site.

ICV administration of AAV9 did not prevent post-dose immune response in the serum, as anti-AAV9 capsid neutralizing antibodies were observed four weeks post-dose. However, neutralizing anti-AAV9 antibody levels in the CSF remained unchanged and comparable to pre-dose levels (TABLE 20).

TABLE 20

AAV9 serum NAb titer

| Subject Number | AAV9 Serum NAb Titer: Pre-Screen | AAV9 Serum NAb Titer: At Injection | AAV9 Serum NAb Titer: 4-Weeks Post Injection | AAV9 CSF NAb Titer: At Injection | AAV9 CSF NAb Titer: 4-Weeks Post Injection |
|---|---|---|---|---|---|
| 21001 | 1:5 | <1:5 | <1:5 | <1:5 | <1:5 |
| 11501 | <1:5 | <1:5 | <1:5 | <1:5 | <1:5 |
| 2001 | <1:5 | <1:5 | 1:405 | <1:5 | 1:5 |
| 2501 | <1:5 | <1:5 | 1:135 | <1:5 | 1:5 |
| 3001 | <1:5 | <1:5 | 1:1215 | <1:5 | <1:5 |
| 3002 | <1:5 | <1:5 | 1:135 | <1:5 | <1:5 |

Samples were collected 27-29 days post-dose from major organs (heart ventricles, liver lobes, king cardiac lobes, kidneys, spleen, pancreas, and cervical lymph nodes) during schedule necroscopy. Punches were collected via eight millimeter punch and further processed as discussed below.

Example 11

Biodistribution of eTF$^{SCN1A}$ in the Brain ddPCR was used to measure eTF$^{SCN1A}$ biodistribution in the brain. Samples from various regions of cynomolgus macaque brain tissue (FC: Frontal cortex; PC: parietal cortex; TC: temporal cortex; Hip: hippocampus; Med: medulla; OC: occipital cortex) were measured for vector copy number to assess biodistribution of eTF$^{SCN1A}$ under the control of a GABA selective regulatory element (RE$^{GABA}$-eTF$^{SCN1A}$) when administered in AAV9 by unilateral ICY, Tissue DNA was isolated with DNeasy Blood c Tissues kits (Qiagen). DNA quantity was determined and normalized using UV spectrophotometer. 20 nanograms of tissue DNA was added to a 20 microliter reaction along with ddPCR Super Mix for Probes (no dUTP) (Bio-Rad) and TaqMan primers and probes directed against regions of the eTF$^{SCN1A}$ sequence. Droplets were generated and templates were amplified using automated droplet generator and thermo cycler (Bio-Rad). After the PCR step, the plate was loaded and read by QX2000 Droplet Reader to determine vector copy number in tissues. Monkey Albumin (MfAlb) gene served as an internal control for normalizing genomic DNA content and was amplified in the same reaction. Primers and probes for eTF$^{SCN1A}$ and MfAlb are set forth in TABLE 21.

TABLE 21

Primers and probes for eTF$^{SCN1A}$ and MfAlb

Figure 11:
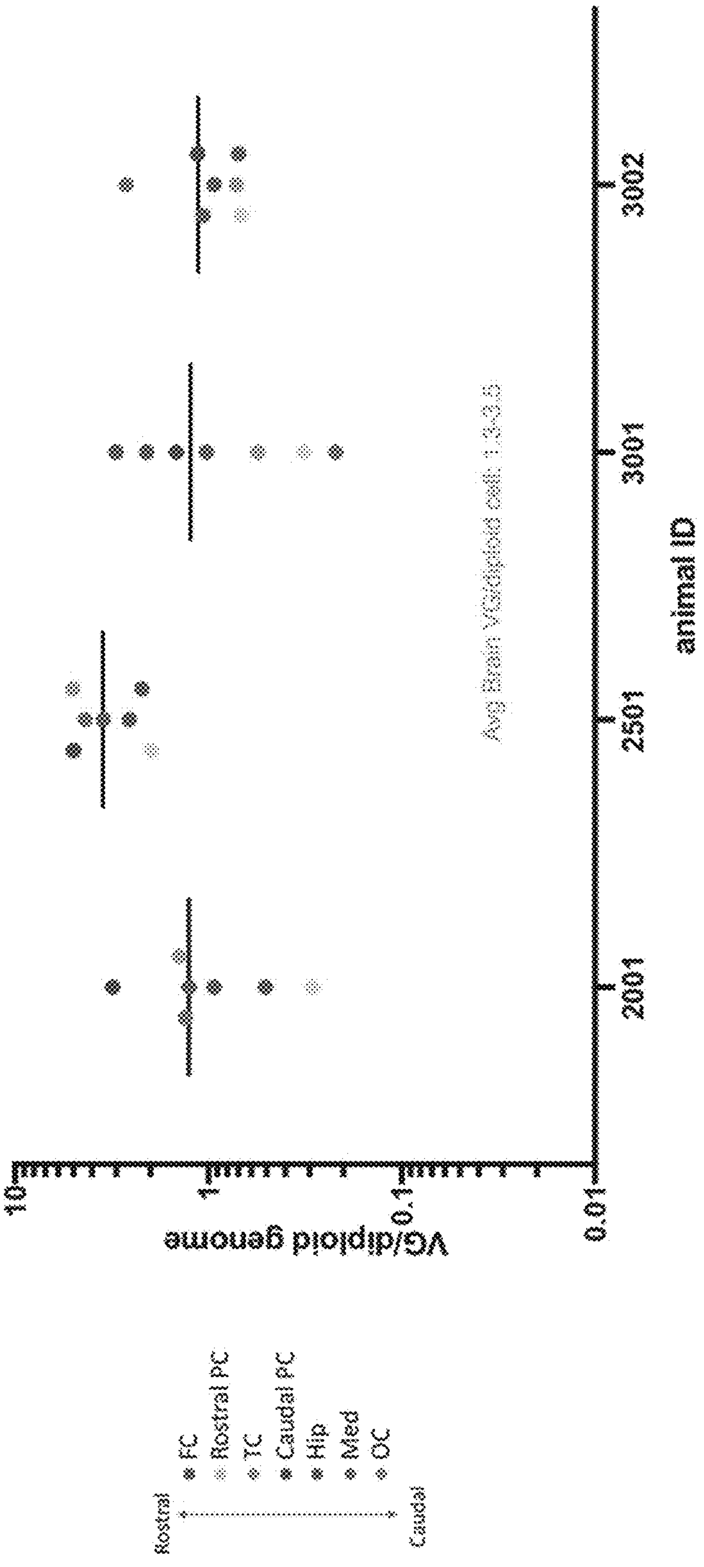
FIG. 11 shows the VG/diploid genome in frontal cortex (FC). Rostral parietal cortex (Rostral PC), temporal cortex (TC), Caudal parietal cortex (Caudal PC), hippocampus (Hip), medulla (Med), and occipital cortex (OC) tissue samples for animals treated with AAV9-RE$^{GABA}$-eTF$^{SCN1A}$ administered at 4.8 E+13 or 8 E+13 vg/animal via unilateral intracerebroventricular (ICV) administration (Example 10 and Example 11). Each data point represents the VG/diploid genome for the tissue sample and the horizontal bars represent the average VG/diploid genome for all tissue samples for each animal.

| Primers/ probe Name | | Sequence (5'-3') |
|---|---|---|
| eTF$^{SCN1A}$ | eTF$^{SCN1A}$ Forward primer | GAATGTGGGAAATCATTCAGTCGC (SEQ ID NO: 194) |
| | eTF$^{SCN1A}$ Reverse primer | GCAAGTTATCCTCTCGTGAGAAGG (SEQ ID NO: 195) |
| | eTF$^{SCN1A}$ probe | GCGACAACCTGGTGAGACATCAACGCACC (SEQ ID NO: 196) |
| MfAlbumin | MfAlb Forward primer | GCTGTTATCTCTTGTGGGCTGT (SEQD ID NO: 197) |
| | MfAlb Reverse primer | AAACTCATGGGAGCTGCCGGTT (SEQ ID NO: 198) |
| | MfAlb probe | CCACACAAATCTCTCCCTGGCATTG (SEQ ID NO: 199) |

eTF$^{SCN1A}$ was broadly distributed throughout the brain when dosed at 4.8 E+13 viral genomes per animal with an average of 1.3-3.5 VG/diploid genome (FIG. 11) In addition, when comparing gene transfer throughout the brain of RE$^{GABA}$-eTF$^{SCN1A}$ dosed at 4.8 E+13 viral genomes per animal to gene transfer throughout the brain of eGFP dosed via ICV at various doses, an increase in VG/diploid genome was observed with increasing doses. This indicated that gene transfer in the brain occurred in a dose-dependent manner when administered in AAV9 via ICV.

Example 12 eTF$^{SCN1A}$ Transcription in the Brain

Figure 12:
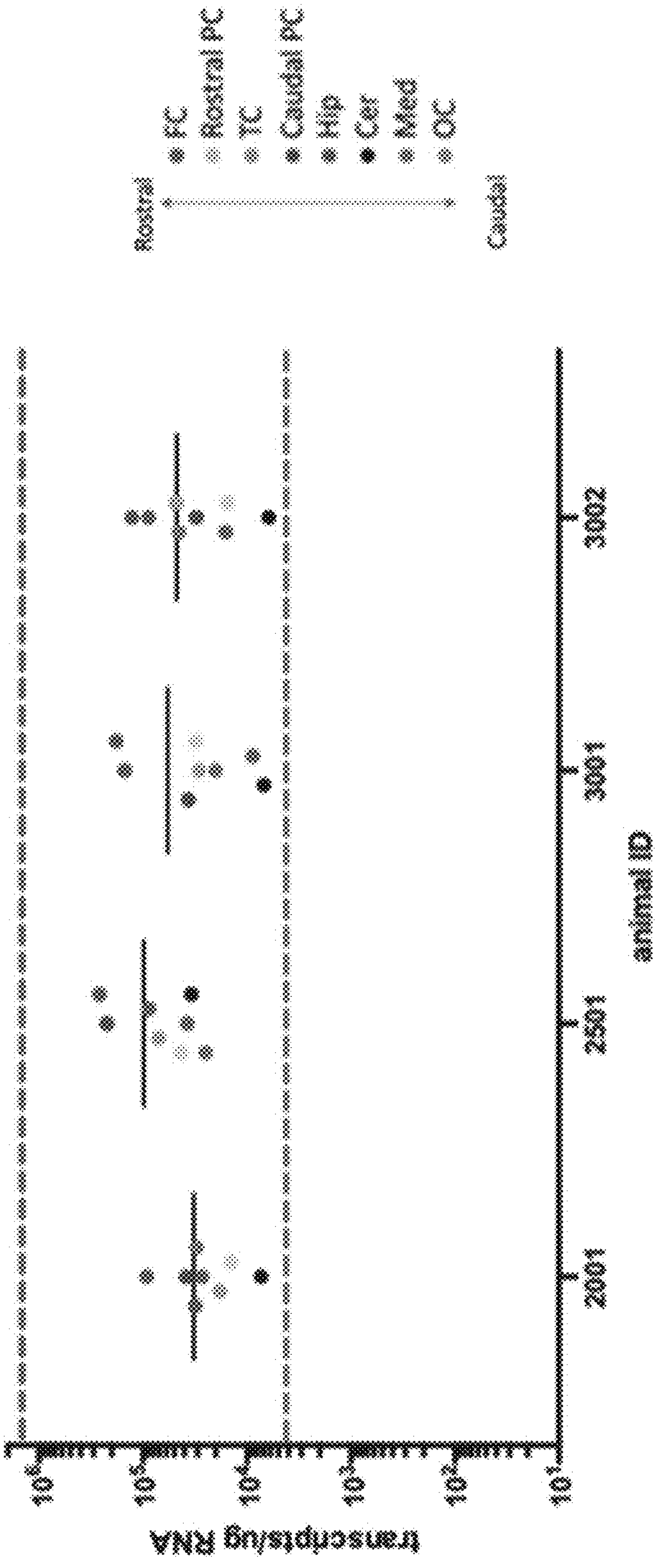
FIG. 12 shows the transcripts/μg RNA in frontal cortex (FC), Rostral parietal cortex (Rostral PC), temporal cortex (TC), Caudal parietal cortex (Caudal PC), hippocampus (Hip), medulla (Med), and occipital cortex (OC) tissue samples for animals treated with AAV9-RE$^{GABA}$-eTF$^{SCN1A}$ administered at 4.8 E+13 or 8 E+13 vg/animal via unilateral intracerebroventricular (ICV) administration (Example 10 and Example 11). Each data point represents the VG/diploid genome for the tissue sample and the horizontal bars represent the average VG/diploid genome for all tissue samples for each animal. Average transcripts for ARFGAP2 were 1.85 E+6/μg RNA, and are indicated by the dashed upper boundary line. The detection limit is indicated by the dashed lower boundary line.

Transcription of eTF$^{SCN1A}$ under the control of a GABA selective regulatory element, RE$^{GABA}$ (RE$^{GABA}$-eTF$^{SCN1A}$), was assessed by measuring eTF$^{SCN1A}$ mRNA using a ddPCR-based gene expression assay. Tissue RNA was isolated with RNeasy Plus Mini kits (Qiagen) or RNeasy Lipid Tissue Mini kits (Qiagen) for brain tissues. RNA quantity was determined and normalized using UV spectrophotometer and RNA quality (RIN) was checked using Bioanalyzer RNA Chip. One microgram of tissue RNA was used for DNase treatment and cDNA synthesis with SuperScript VILO cDNA synthesis kit with ezDNase™ Enzyme kits (Thermo Fisher). 50 micrograms of RNA was converted to cDNA, cDNA was added to a 20 microliter reaction along with ddPCR Super Mix for Probes (no dUTP) (Bio-Rad) and TaqMan primers and probes directed against regions of eTF$^{SCN1A}$ sequence (TABLE 22). Droplets were generated and templates were amplified using automated droplet generator and thermo cycler (Bio-Rad). After PCR amplification, the plate was loaded and read by QX2000 Droplet Reader to provide gene expression levels in tissues. The monkey gene ARFGAP2 (MfARFGAP2) (Thermo Fisher Scientific) served as an endogenous control for normalizing gene expression levels and was amplified in the same reaction. Average transcripts for ARFGAP2 were 1.85 E+6/ug RNA (FIG. 12, upper boundary). Limit of detection indicated by lower boundary.

eTF$^{SCN1A}$ mRNA was observed throughout the brain in all animals, indicating that the GABA-selective promoter, RE$^{GABA}$, was transcriptionally active in the brain tissue for all AAV9-RE$^{GABA}$-eTF$^{SCN1A}$ treated macaques (FIG. 12). FC: Frontal cortex; PC: parietal cortex; TC: temporal cortex; Hip: hippocampus; Med: medulla; OC: occipital cortex.

TABLE 22

TaqMan primers and probes directed against regions of eTF$^{SCN1A}$ sequence

| Primers/ probe Name | Description | Sequence (5'-3') |
|---|---|---|
| eTF$^{SCN1A}$ | eTF$^{SCN1A}$ Forward primer | GAATGTGGGAAATCATTCAGTCGC (SEQ ID NO: 200) |
| | eTF$^{SCN1A}$ Reverse primer | GCAAGTTATCCTCTCGTGAGAAGG (SEQ ID NO: 201) |
| | eTF$^{SCN1A}$ probe | GCGACAACCTGGTGAGACATCAACGCACC (SEQ ID NO: 202) |
| MfARFGAP2 | Forward, Reverse Primers, Probe | Thermo Fisher (Cat#: 4448491) |

Example 13 eTF$^{SCN1A}$ Biodistribution and Transcription in Peripheral Tissues

Figure 13:
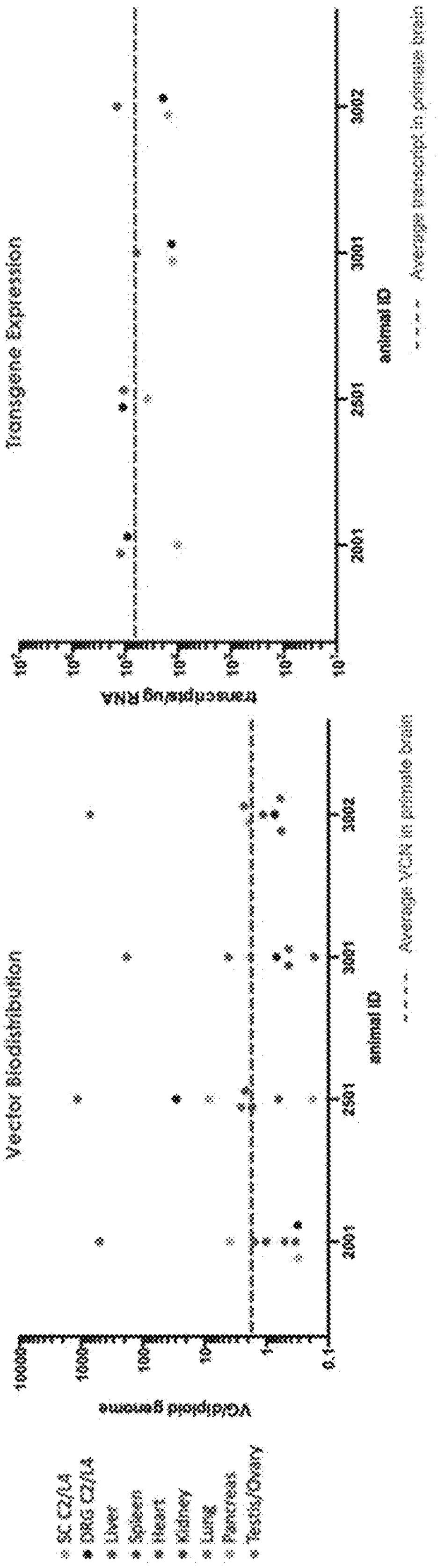
FIG. 13 shows vector biodistribution (VG/diploid genome) and transgene expression (transcripts/μg RNA) in peripheral tissue samples outside of the brain. The peripheral tissue samples shown are spinal cord C2/L4 (SC C2/L4), dorsal root ganglion C2/L4 (DRG C2/L4), liver, spleen, heart, kidney, lung, pancreas, and testis/ovary. Average VCN (vector biodistribution) and transcript (transgene expression) in the primate brain is indicated by a dashed line.

Vector copy number was further measured in various organs to evaluate transduction of RE$^{GABA}$-eTF$^{SCN1A}$ in tissues throughout the body when administered in AAV9 by unilateral ICV. Transcript levels of eTF$^{SCN1A}$ were also measured by ddPCR to assess transcriptional activity eTF$^{SCN1A}$ under the control of the GABA-selective regulatory element RE$^{GABA}$ in tissues throughout the body when administered in AAV9 by unilateral ICV. Both methods were performed as generally described above. RE$^{GABA}$-eTF$^{SCN1A}$ transduction and transcription of eTF$^{SCN1A}$ in the spinal cord (SC) and dorsal root ganglion (DRG) were comparable to levels observed in the brain. With the exception of the liver, RE$^{GABA}$-eTF$^{SCN1A}$ transduction was lower in peripheral tissues outside of the brain (FIG. 13). Transduction of RE$^{GABA}$-eTF$^{SCN1A}$ in the liver was higher than in the brain. Transcription of eTF$^{SCN1A}$ was undetected in peripheral tissues, including the heart, lungs and gonads. However, eTF$^{SCN1A}$ transcript levels in the liver were comparable to the levels of eTF$^{SCN1A}$ measured in the brain. Furthermore, eTF$^{SCN1A}$ transcription in the liver is extremely low when normalized to the number of vector copies present (approximately 1000-fold lower compared to transcription of eTF$^{SCN1A}$ in the brain). Overall, this demonstrated that transcription of eTF$^{SCN1A}$ under the control of the GABA-selective regulatory element RE$^{GABA}$ is restricted to the CNS.

What is claimed is:

1. A polynucleotide comprising a nucleic acid sequence encoding an engineered DNA binding protein comprising a zinc finger DNA binding domain, wherein the zinc finger DNA binding domain comprises an amino acid sequence comprising SEQ ID NO: 148.

2. The polynucleotide of claim 1, wherein the zinc finger DNA binding domain comprises an amino acid sequence selected from the group consisting of: SEQ ID NO:77, SEQ ID NO:92, and SEQ ID NO:96.

3. The polynucleotide of claim 1, wherein the engineered DNA binding protein is an engineered transcription factor comprising a transcription activation domain.

4. The polynucleotide of claim 3, wherein the transcription activation domain is derived from VPR, VP64, VP16, VP128, p65, p300, CITED2, CITED4, EGR1, or EGR3, or any functional fragment or variant thereof.

5. The polynucleotide of claim 3, wherein the transcription activation domain comprises an amino acid sequence selected from the group consisting of: SEQ ID NO: 132, SEQ ID NO: 133, SEQ ID NO: 134, SEQ ID NO: 135, and SEQ ID NO:224.

6. The polynucleotide of claim 3, wherein the zinc finger DNA binding domain comprises SEQ ID NO:77, and wherein the engineered transcription factor comprises an amino acid sequence selected from the group consisting of: SEQ ID NO:100, SEQ ID NO:102, SEQ ID NO: 127, SEQ ID NO:213, and SEQ ID NO:221.

7. The polynucleotide of claim 3, wherein the zinc finger DNA binding domain comprises SEQ ID NO:92, and wherein the engineered transcription factor comprises an amino acid sequence selected from the group consisting of: SEQ ID NO:105, SEQ ID NO:106, SEQ ID NO:107, SEQ ID NO:108, SEQ ID NO:109, SEQ ID NO:118, SEQ ID NO:128, SEQ ID NO: 129, SEQ ID NO: 130, and SEQ ID NO: 131.

8. The polynucleotide of claim 3, wherein the zinc finger DNA binding domain comprises SEQ ID NO:96, and wherein the engineered transcription factor comprises an amino acid sequence selected from the group consisting of SEQ ID NO:110, SEQ ID NO:111, SEQ ID NO:112, SEQ ID NO:113, and SEQ ID NO: 122.

9. The polynucleotide of claim 6, wherein the engineered transcription factor comprises SEQ ID NO:127.

10. The polynucleotide of claim 1, further comprising a regulatory element operably linked to the nucleic acid sequence encoding the engineered DNA binding protein to form an expression cassette.

11. The polynucleotide of claim 10, wherein the regulatory element comprises a GAD2 promoter, a human synapsin promoter, a CBA promoter, a CMV promoter, a minimal CMV (minCMV) promoter, a TATA box, a super core promoter, or an EF1α promoter, or a combination thereof.

12. The polynucleotide of claim 10, wherein the regulatory element is a parvalbumin (PV) neuron selective regulatory element.

13. The polynucleotide of claim 12, wherein the PV neuron selective regulatory element comprises a sequence selected from SEQ ID NOS: 1-4.

14. The polynucleotide of claim 13, wherein the PV neuron selective regulatory element comprises SEQ ID NO:2.

15. The polynucleotide of claim 12, wherein the expression cassette further comprises a microRNA binding site that inhibits expression of the engineered DNA binding protein in excitatory neurons.

16. The polynucleotide of claim 15, wherein the microRNA binding site comprises a sequence selected from the group consisting of: SEQ ID NO:9, SEQ ID NO:11, and SEQ ID NO:13.

17. The polynucleotide of claim 15, wherein the microRNA binding site comprises a sequence having at least 90% identity to any one of SEQ ID NO:7, SEQ ID NO: 14, or SEQ ID NO: 15.

18. The polynucleotide of claim 17, wherein the microRNA binding site comprises a sequence having at least 97% identity to SEQ ID NO:7.

19. The polynucleotide of claim 18, wherein the microRNA binding site comprises SEQ ID NO: 7.

20. The polynucleotide of claim 10, wherein the expression cassette comprises a nucleotide sequence having at least 90% identity to a sequence selected from the group consisting of: SEQ ID NO:67, SEQ ID NO:68, SEQ ID NO:69, SEQ ID NO:70, SEQ ID NO:71, SEQ ID NO:74, SEQ ID NO:75, SEQ ID NO:76, and SEQ ID NO: 184.

21. The polynucleotide of claim 20, wherein the expression cassette comprises a nucleotide sequence having at least 97% identity to a sequence selected from the group consisting of: SEQ ID NO:67, SEQ ID NO:68, SEQ ID NO:69, SEQ ID NO:70, SEQ ID NO:71, SEQ ID NO:74, SEQ ID NO:75, SEQ ID NO:76, and SEQ ID NO:184.

22. The polynucleotide of claim 21, wherein the expression cassette comprises a nucleotide sequence selected from the group consisting of: SEQ ID NO:67, SEQ ID NO:68, SEQ ID NO:69, SEQ ID NO:70, SEQ ID NO:71, SEQ ID NO:74, SEQ ID NO: 75, SEQ ID NO:76, and SEQ ID NO: 184.

23. The polynucleotide of claim 22, wherein the expression cassette comprises SEQ ID NO: 71.

24. An expression vector comprising the polynucleotide of claim 10.

25. The expression vector of claim 24, wherein the expression vector is a viral vector.

26. The expression vector of claim 25, wherein the viral vector is an adeno-associated virus (AAV) vector.

27. The expression vector of claim 26, wherein the AAV vector has a serotype selected from the group consisting of: AAV1, AAV2, AAV3, AAV4, AAV5, AAV6, AAV7, AAV8, AAV9, AAV10, AAV11, AAV12, rh10, avian AAV, bovine AAV, canine AAV, equine AAV, primate AAV, non-primate AAV, ovine AAV, scAAV, scAAV1, scAAV2, scAAV5, scAAV8, or scAAV9, and hybrids thereof.

28. The expression vector of claim 26, wherein the expression cassette further comprises a 5' AAV inverted terminal repeat (ITR) sequence and a 3' AAV ITR sequence.

29. The expression vector of claim 28, wherein the 5' AAV ITR sequence and the 3' AAV ITR sequence are each independently selected from ITR sequences derived from AAV1, AAV2, AAV5, AAV8, or AAV9.

30. The expression vector of claim 26, wherein the expression cassette comprises a nucleic acid sequence having at least 90% sequence identity to a sequence selected from the group consisting of: SEQ ID NO:67, SEQ ID NO:68, SEQ ID NO:69, SEQ ID NO:70, SEQ ID NO: 71, SEQ ID NO:74, SEQ ID NO:75, SEQ ID NO:76, and SEQ ID NO:184.

31. The expression vector of claim 30, wherein the expression cassette comprises a nucleotide sequence having at least 97% identity to a sequence selected from the group consisting of: SEQ ID NO:67, SEQ ID NO:68, SEQ ID NO:69, SEQ ID NO:70, SEQ ID NO:71, SEQ ID NO:74, SEQ ID NO:75, SEQ ID NO:76, and SEQ ID NO: 184.

32. The expression vector of claim 31, wherein the expression cassette comprises a nucleotide sequence selected from the group consisting of: SEQ ID NO:67, SEQ ID NO:68, SEQ ID NO:69, SEQ ID NO:70, SEQ ID NO:71, SEQ ID NO: 74, SEQ ID NO: 75, SEQ ID NO:76, and SEQ ID NO: 184.

33. The expression vector of claim 32, wherein the expression cassette comprises SEQ ID NO:71.

34. The expression vector of claim 33, wherein the AAV vector has an AAV9 serotype.

35. The expression vector of claim 34, wherein the expression cassette further comprises a 5' AAV2 ITR sequence and a 3' AAV2 ITR sequence.

36. A composition comprising the polynucleotide of claim 10 and one or more pharmaceutically acceptable carriers.

37. The composition of claim 36, wherein the zinc finger DNA binding domain comprises an amino acid sequence selected from the group consisting of: SEQ ID NO: 77, SEQ ID NO:92, and SEQ ID NO:96.

38. The composition of claim 37, wherein the engineered DNA binding protein is an engineered transcription factor comprising a transcription activation domain.

39. The composition of claim 38, wherein the transcription activation domain is derived from VPR, VP64, VP16, VP128, p65, p300, CITED2, CITED4, EGR1, or EGR3, or any functional fragment or variant thereof.

40. The composition of claim 38, wherein the transcription activation domain comprises an amino acid sequence selected from the group consisting of: SEQ ID NO: 132, SEQ ID NO: 133, SEQ ID NO: 134, SEQ ID NO: 135, and SEQ ID NO:224.

41. The composition of claim 38, wherein the engineered transcription factor comprises an amino acid sequence selected from the group consisting of: SEQ ID NO: 100, SEQ ID NO:102, SEQ ID NO:105, SEQ ID NO: 106, SEQ ID NO: 107, SEQ ID NO: 108, SEQ ID NO: 109, SEQ ID NO:110, SEQ ID NO: 111, SEQ ID NO: 112, SEQ ID NO: 113, SEQ ID NO: 118, SEQ ID NO: 122, SEQ ID NO: 127, SEQ ID NO: 128, SEQ ID NO: 129, SEQ ID NO: 130, SEQ ID NO: 131, SEQ ID NO:213, and SEQ ID NO:221.

42. The composition of claim 41, wherein the engineered transcription factor comprises SEQ ID NO: 127.

43. The composition of claim 36, wherein the regulatory element is a PV neuron selective regulatory element.

44. The composition of claim 43, wherein the expression cassette further comprises a microRNA binding site that inhibits expression of the engineered DNA binding protein in excitatory neurons.

45. The composition of claim 44, wherein the PV neuron selective regulatory element comprises SEQ ID NO:2 and the microRNA binding site comprises SEQ ID NO:7.

46. The composition of claim 44, wherein the expression cassette comprises a sequence having at least 97% identity to SEQ ID NO:71.

47. The composition of claim 46, wherein the expression cassette comprises SEQ ID NO:71.

48. The composition of claim 47, wherein the expression cassette is incorporated into an adeno-associated virus (AAV) vector.

49. The composition of claim 48, wherein the AAV vector has an AAV9 serotype.

50. The composition of claim 49, wherein the expression cassette further comprises a 5' AAV2 ITR sequence and a 3' AAV2 ITR sequence.

51. A non-naturally occurring transcription factor comprising a DNA binding domain and a transcription activation domain, wherein the DNA binding domain comprises SEQ ID NO:148.

52. The non-naturally occurring transcription factor of claim 51, wherein the DNA binding domain comprises an amino acid sequence having at least 90% identity to SEQ ID NO:77, SEQ ID NO:92, or SEQ ID NO:96.

53. The non-naturally occurring transcription factor of claim 52, wherein the DNA binding domain comprises an amino acid sequence selected from the group consisting of: SEQ ID NO:77, SEQ ID NO:92, and SEQ ID NO:96.

54. The non-naturally occurring transcription factor of claim 51, wherein the transcription activation domain comprises a VPR, VP64, VP16, VP128, p300, CITED2, or CITED4 transcription activation domain.

55. The non-naturally occurring transcription factor of claim 51, wherein the transcription activation domain comprises an amino acid sequence having at least 90% identity to a sequence selected from the group consisting of: SEQ ID NO: 132, SEQ ID NO: 133, SEQ ID NO: 134, SEQ ID NO: 135, and SEQ ID NO:224.

56. The non-naturally occurring transcription factor of claim 51, wherein the non-naturally occurring transcription factor comprises an amino acid sequence having at least 90% sequence identity to a sequence selected from the group consisting of: SEQ ID NO:100, SEQ ID NO:102, SEQ ID NO:105, SEQ ID NO:106, SEQ ID NO:107, SEQ ID NO: 108, SEQ ID NO: 109, SEQ ID NO: 110, SEQ ID NO:111, SEQ ID NO:112, SEQ ID NO:113, SEQ ID NO:118, SEQ ID NO: 122, SEQ ID NO: 127, SEQ ID NO: 128, SEQ ID NO: 129, SEQ ID NO: 130, SEQ ID NO: 131, SEQ ID NO:213, and SEQ ID NO: 221.

57. The non-naturally occurring transcription factor of claim 56, wherein the non-naturally occurring transcription factor comprises SEQ ID NO:127.

58. A cell comprising the polynucleotide of claim 1.

59. The cell of claim 58, wherein the zinc finger DNA binding domain comprises SEQ ID NO:77, SEQ ID NO:92, or SEQ ID NO:96.

60. The cell of claim 58, wherein the engineered DNA binding protein is an engineered transcription factor comprising a transcription activation domain.

61. The cell of claim 60, wherein the transcription activation domain comprises a VPR, VP64, VP16, VP128, p300, CITED2, or CITED4 sequence.

62. The cell of claim 61, wherein the engineered transcription factor comprises an amino acid sequence having at least 95% identity to a sequence selected from the group consisting of: SEQ ID NO:100, SEQ ID NO:102, SEQ ID NO: 105, SEQ ID NO: 106, SEQ ID NO: 107, SEQ ID NO:

108, SEQ ID NO: 109, SEQ ID NO:110, SEQ ID NO: 111, SEQ ID NO:112, SEQ ID NO:113, SEQ ID NO:118, SEQ ID NO: 122, SEQ ID NO: 127, SEQ ID NO:128, SEQ ID NO: 129, SEQ ID NO: 130, SEQ ID NO: 131, SEQ ID NO: 213, and SEQ ID NO:221.

63. The cell of claim 58, wherein the polynucleotide further comprises a regulatory element operably linked to the nucleic acid sequence encoding the engineered DNA binding protein to form an expression cassette.

64. The cell of claim 63, wherein the regulatory element promotes PV neuron selective expression of the engineered transcription factor.

65. The cell of claim 64, wherein the PV neuron selective regulatory element comprises SEQ ID NO:2.

66. The cell of claim 63, wherein the polynucleotide further comprises a microRNA binding site that inhibits expression of the engineered DNA binding protein in excitatory neurons.

67. The cell of claim 66, wherein the microRNA binding site comprises SEQ ID NO:7.

68. The cell of claim 63, wherein the expression cassette comprises a nucleotide sequence having at least 90% identity to SEQ ID NO:71.

69. The cell of claim 63, wherein the expression cassette is flanked by a 5' AAV ITR and a 3' AAV ITR.

70. The cell of claim 69, further comprising an AAV rep gene, an AAV cap gene, and adenoviral helper genes.

71. The cell of claim 70, wherein the cell is a 293 cell, an A549 cell or a HeLa cell.

* * * * *